United States Patent
Aharoni et al.

(10) Patent No.: US 12,129,475 B2
(45) Date of Patent: Oct. 29, 2024

(54) GLYCOALKALOID METABOLISM ENYZYMES (GAMES) AND USES THEREOF

(71) Applicants: YEDA RESEARCH AND DEVELOPMENT CO. LTD., Rehovot (IL); Yissum Research Development Company of The Hebrew University of Jerusalem Ltd., Jerusalem (IL)

(72) Inventors: Asaph Aharoni, Tel Aviv (IL); Prashant Sonawane, Rehovot (IL); Pablo D. Cardenas, Rehovot (IL); Burdman Saul, Rehovot (IL)

(73) Assignee: YEDA RESEARCH AND DEVELOPMENT CO. LTD., Rehovot (IL)

(*) Notice: Subject to any disclaimer, the term of this patent is extended or adjusted under 35 U.S.C. 154(b) by 585 days.

(21) Appl. No.: 16/484,200

(22) PCT Filed: Feb. 8, 2018

(86) PCT No.: PCT/IL2018/050142
§ 371 (c)(1),
(2) Date: Aug. 7, 2019

(87) PCT Pub. No.: WO2018/146678
PCT Pub. Date: Aug. 16, 2018

(65) Prior Publication Data
US 2019/0367940 A1    Dec. 5, 2019

(30) Foreign Application Priority Data
Feb. 9, 2017 (IL) .......................... 250538

(51) Int. Cl.
C12N 15/82 (2006.01)
C12N 9/02 (2006.01)
C12N 9/04 (2006.01)

(52) U.S. Cl.
CPC ....... *C12N 15/8279* (2013.01); *C12N 9/0006* (2013.01); *C12N 9/0071* (2013.01); *C12N 15/8218* (2013.01); *C12N 15/8243* (2013.01)

(58) Field of Classification Search
None
See application file for complete search history.

(56) References Cited

U.S. PATENT DOCUMENTS

| | | | |
|---|---|---|---|
| 4,987,071 A | 1/1991 | Cech et al. | |
| 5,959,180 A | 9/1999 | Mochs et al. | |
| 6,326,174 B1 | 12/2001 | Joyce et al. | |
| 7,375,259 B1 | 5/2008 | Mccue et al. | |
| 7,439,419 B1 | 10/2008 | Mccue et al. | |
| 2005/0108791 A1 | 5/2005 | Edgerton | |
| 2009/0070895 A1 | 3/2009 | Rae et al. | |
| 2009/0070897 A1 | 3/2009 | Goldman et al. | |
| 2011/0265221 A1 | 10/2011 | Abad et al. | |
| 2012/0159676 A1 | 6/2012 | Umemoto et al. | |
| 2013/0167271 A1 | 6/2013 | Umemoto et al. | |

FOREIGN PATENT DOCUMENTS

| | | |
|---|---|---|
| EP | 3012323 | 4/2016 |
| WO | WO 2000/066716 | 11/2000 |
| WO | WO 2011/061656 A1 | 4/2011 |
| WO | WO 2012/095843 A1 | 7/2012 |
| WO | WO 2014/195944 A1 | 12/2014 |

OTHER PUBLICATIONS

Fofani et al., 2007, International Journal of Plant Genomics, 2007:1-13.*
Cardenas et al., 2019, Nature Communications, 10:1-13.*
Arnqvist et al. "Reduction of cholesterol and glycoalkaloid levels in transgenic potato plants by overexpression of a type 1 sterol methyltransferase cDNA" Plant Physiology. Apr. 1, 2003;131(4):1792-9.
Belhaj "Plant genome editing made easy: targeted mutagenesis in model and crop plants using the CRISPR/Cas system. Plant methods" Oct. 11, 2013;9(1):1.
Cárdenas et al. "GAME9 regulates the biosynthesis of steroidal alkaloids and upstream isoprenoids in the plant mevalonate pathway" Nature communications. Feb. 15, 2016:7:10654.
Cárdenas et al. "The bitter side of the nightshades: Genomics drives discovery in Solanaceae steroidal alkaloid metabolism" Phytochemistry. May 1, 2015:113:24-32.
Casamitjana-Martinez et al. "Root-specific CLE19 overexpression and the sol1/2 suppressors implicate a CLV-like pathway in the control of *Arabidopsis* root meristem maintenance" Current Biology. Aug. 19, 2003;13(16):1435-41.
Chen et al. "Short-chain dehydrogenase/reductase catalyzing the final step of noscapine biosynthesis is localized to laticifers in opium poppy" The Plant Journal. Jan. 2014;77(2):173-84.

(Continued)

*Primary Examiner* — Jason Deveau Rosen
(74) *Attorney, Agent, or Firm* — Mark S. Cohen; Pearl Cohen; ZEDEK LATZER BARATZ LLP

(57) ABSTRACT

Disclosed herein are genetically modified plants having altered biological activity of 3-β-hydroxysteroid dehydrogenase/isomerase (GAME25), or 2-oxoglutarate-dependent dioxygenase (GAME31), or a combination thereof, wherein the genetically modified plants have an altered content of at least one cholesterol derived compound selected from the group including a steroidal alkaloid or a glycosylated derivative thereof and an unsaturated or saturated steroidal saponin or a glycoside derivative thereof. Further disclosed herein are genetically modified plants having altered expression of a gene encoding a 3-β-hydroxysteroid dehydrogenase/isomerase (GAME25), or a 2-oxoglutarate-dependent dioxygenase (GAME31), or a combination thereof, wherein the genetically modified plant has an altered content of at least one cholesterol derived compound selected from the group including a steroidal alkaloid or a glycosylated derivative thereof and an unsaturated or saturated steroidal saponin or a glycoside derivative thereof. Methods of producing these genetically modified plants are also disclosed.

9 Claims, 68 Drawing Sheets
Specification includes a Sequence Listing.

(56) References Cited

OTHER PUBLICATIONS

Chitwood et al. "A quantitative genetic basis for leaf morphology in a set of precisely defined tomato introgression lines" The Plant Cell. Jul. 1, 2013;25(7):2465-81.
Database NCBI "Predicted: ethylene-responsive transcription factor 1-like [Solanum lycopersicum]" GeneBank accession No. XP_004229751. URL: http:www.ncbi.nlm.nih.gov/protein/460367786?report=genbank&log$=prottop&blast_rank=2&RID=ZUTPRBJX01R. originally accessed Nov. 23, 2016.
Database NCBI "Predicted: transcription factor BIM2-like [Solanum lycopersicum]" GeneBank accession No. XP_004234703.1. URL: http:www.ncbi.nlm.nih.gov/protein/460377857?report=genbank&log$=prottop&blast_rank=1&RID=TE9A3KF01R. originally accessed Mar. 12, 2013.
Database UniProt [Online], Oct. 1, 2000 (Oct. 1, 2000), "SubName: Full=Putative alcohol dehydrogenase {EC0:0000313:EMBL:CAB91875.I, EC0:0000313:Ensembl1Plants:Solyc01g073640.2 1} ;", XP00' 2779764, retrieved from EBI accession No. UNIPROT:Q9LEG3 Database accession No. Q9LEG3.
Database Protein [Online], Dec. 23, 2015 (Dec. 23, 2015), "Predicted short-chain dehydrogenase reductase 3b-like (xanthoxin dehydrogenase)", XP002779765, retrieved from NCBI Database accession No. XP 015062676.
Database UniProt [Online] Apr. 3, 2013 (Apr. 3, 2013), "SubName: Full =Uncharacterized protein {EC0:0000313:Ensembl1Plants:PGSC0003DMT4000 79897};", XP002779766, retrieved from EB! accession No. UNIPROT:M1D2N5 Database accession No. M1D2N5.
Database NCBI [online], Apr. 15, 2005 (Apr. 15, 2005), Lycopersicon esculentum mRNA for putative alcohol dehydrogenase (yfe37 gene) GenBank:AJ277945.1, https://www.ncbi.nlm.nih.gov/nuccore/7981381.
Database NCBI [online], Nov. 22, 2016 (Nov. 22, 2016), Predicted: probable 2-oxoglutarate-dependent dioxygenase AOP1 isoform X1 [Solanum lycopersicum], NCBI Reference Sequence: XP_004233541.1, https://www.ncbi.nlm.nih.gov/protein/460375495?report=genbank.&log$=protalign&blast_rank=1&RID=UWXRDWSA016.
De Carolis et al. "2-Oxoglutarate-dependent dioxygenase and related enzymes: biochemical characterization" Phytochemistry. Aug. 10, 1994;36(5):1093-107.
De Carolis et al. "Isolation and characterization of a 2-oxoglutarate dependent dioxygenase involved in the second-to-last step in vindoline biosynthesis" Plant physiology. Nov. 1, 1990;94(3):1323-9.
Dinesh-Kumar et al. "Virus-induced gene silencing" In Plant Functional Genomics 2003 (pp. 287-293). Humana Press.
Eckert et al. "DNA polymerase fidelity and the polymerase chain reaction" Genome Research. Aug. 1, 1991;1(1):17-24.
Eich, Eckart. "Solanaceae and Convolvulaceae: Secondary metabolites: Biosynthesis, chemotaxonomy, biological and economic significance" (a handbook), pp. 414, 416, 420, 422, 434, 441-445. Springer Science & Business Media, 2008.
Eshed et al. "An introgression line population of Lycopersicon pennellii in the cultivated tomato enables the identification and fine mapping of yield-associated QTL" Genetics. Nov. 1, 1995:141(3):1147-62.
Estornell et al. "A multisite gateway-based toolkit for targeted gene expression and hairpin RNA silencing in tomato fruits" Plant biotechnology journal. Apr. 2009;7(3):298-309.
Expósito-Rodríguez et al. "Selection of internal control genes for quantitative real-time RT-PCR studies during tomato development process" BMC plant biology. Dec. 2008;8(1):131.
Fernandez, A. I., Viron, N., Alhagdow, M., Karimi, M., Jones, M., Amsellem, Z., . . . & May, S. (2009). Flexible tools for gene expression and silencing in tomato. *Plant Physiology*, 151(4), 1729-1740.
Fernandez-Pozo et al. "The Sol Genomics Network (SGN)—from genotype to phenotype to breeding" Nucleic acids research. Nov. 26, 2014;43(D1):D1036-41.

Finsterbusch et al. "Δ5-3β-Hydroxysteroid dehydrogenase from Digitalis lanata Ehrh.—a multifunctional enzyme in steroid metabolism?" Planta. Oct. 1, 1999;209(4):478-86.
Fire et al. Potent and specific genetic interference by double-stranded RNA in Caenorhabditis elegans. nature. Feb. 1998;391(6669):806.
Friedman et al. "Potato glycoalkaloids: chemistry, analysis, safety, and plant physiology" Critical Reviews in Plant Sciences. Jan. 1, 1997;16(1):55-132.
Friedman M. "Tomato glycoalkaloids: role in the plant and in the diet. Journal of agricultural and food chemistry" Oct. 9, 2002,50(21):5751-80.
Friedman M. "Potato glycoalkaloids and metabolites: roles in the plant and in the diet" Journal of Agricultural and Food Chemistry. Nov. 15, 2006;54(23):8655-81.
Friedman et al. "Dehydrotomatine content in tomatoes" Journal of agricultural and food chemistry. Nov. 16, 1998;46(11):4571-6.
Friedman et al. "Anticarcinogenic effects of glycoalkaloids from potatoes against human cervical, liver, lymphoma, and stomach cancer cells" Journal of agricultural and food chemistry. Jul. 27, 2005;53(15):6162-9.
Gantasala et al. "Selection and validation of reference genes for quantitative gene expression studies by real-time PCR in eggplant (*Solanum melongena* L)" BMC research notes. Dec. 2013;6(1):312.
Gatto et al. "Activity of extracts from wild edible herbs against postharvest fungal diseases of fruit and vegetables" Postharvest Biology and Technology. Jul. 1, 2011;61(1):72-82.
Gavidia et al. "Plant progesterone 5B-reductase is not homologous to the animal enzyme. Molecular evolutionary characterization of P5βR from Digitalis purpurea" Phytochemistry. Mar. 1, 2007;68(6):853-64.
Ginzberg et al. "Potato steroidal glycoalkaloids: biosynthesis and genetic manipulation" Potato Research. Feb. 1, 2009;52(1):1-5.
Guo et al. "par-1, a gene required for establishing polarity in C. elegans embryos, encodes a putative Ser/Thr kinase that is asymmetrically distributed" Cell. May 19, 1995;81(4):611-20.
Heim et al. "The basic helix-loop-helix transcription factor family in plants: a genome-wide study of protein structure and functional diversity" Molecular biology and evolution. May 1, 2003;20(5). 735-47.
Heinig et al. "Analysis of steroidal alkaloids and saponins in Solanaceae plant extracts using UPLC-qTOF mass spectrometry" In Plant Isoprenoids 2014 (pp. 171-185). Humana Press, New York, NY.
Herl et al. "Δ5-3β-Hydroxysteroid dehydrogenase (3βHSD) from Digitalis lanata. Heterologous expression and characterisation of the recombinant enzyme" Planta medica. Jun. 2007;73(07):704-10.
Herl et al. "Molecular cloning and heterologous expression of progesterone 5β-reductase from Digitalis lanata Ehrh" Phytochemistry. Feb. 1, 2006:67(3):225-31.
Higuchi R. Recombinant PCR. PCR Protocols: A Guide to Methods and Applications. 1990:177-83 (Ch. 22).
Ingelbrecht et al. Different 3'end regions strongly influence the level of gene expression in plant cells. The Plant Cell. Jul. 1, 1989;1(7):671-80.
International search Report for PCT Application No. PCT/IL2018/050142 issued Jul. 10, 2018.
Itkin et al. "Biosynthesis of antinutritional alkaloids in solanaceous crops is mediated by clustered genes. Science" Jul. 12, 2013;341(6142):175-9.
Itkin et al. "Glycoalkaloid Metabolism1 is required for steroidal alkaloid glycosylation and prevention of phytotoxicity in tomato" The Plant Cell. Dec. 1, 2011;23(12):4507-25.
Kai et al. Scopoletin is biosynthesized via ortho-hydroxylation of feruloyl CoA by a 2-oxoglutarate-dependent dioxygenase in *Arabidopsis thaliana*. The Plant Journal. Sep. 2008;55(6):989-99.
Kallberg et al. "Short-chain dehydrogenases/reductases (SDRs) Coenzyme-based functional assignments in completed genomes" European Journal of Biochemistry. Sep. 2002;269(18):4409-17.
Karimi M. et al. "Gateway™ vectors for Agrobacterium-mediated plant transformation" Trends Plant Sci. 2002, 7, 193-195.

(56) References Cited

OTHER PUBLICATIONS

Kavanagh et al. "Medium-and short-chain dehydrogenase/reductase gene and protein families" Cellular and Molecular Life Sciences. Dec. 1, 2008:65(24):3895.

Kawai et al. "Evolution and diversity of the 2-oxoglutarate-dependent dioxygenase superfamily in plants" The Plant Journal. Apr. 2014;78(2):328-43.

Kitaoka et al. "Investigating inducible short-chain alcohol dehydrogenases/reductases clarifies rice oryzalexin biosynthesis" The Plant Journal. Oct. 2016;88(2):271-9.

Kundu S. Distribution and prediction of catalytic domains in 2-oxoglutarate dependent dioxygenases. BMC research notes. Dec. 2012;5(1):410.

Laurila et al. "Formation of parental-type and novel glycoalkaloids in somatic hybrids between Solanum brevidens and S. tuberosum" Plant Science. Aug. 16, 1996;118(2):145-55.

Li et al. "ESI-QqTOF-MS/MS and APCI-IT-MS/MS analysis of steroid saponins from the rhizomes of Dioscorea panthaica". Journal of Mass Spectrometry. Jan. 1, 2006;41(1):1-22.

Lin et al. "Putative genes involved in salkosaponin biosynthesis in *Bupleurum* species" International journal of molecular sciences. Jun. 2013;14(6):12806-26.

McCue et al. "Metabolic compensation of steroidal glycoalkaloid biosynthesis in transgenic potato tubers: using reverse genetics to confirm the in vivo enzyme function of a steroidal alkaloid galactosyltransferase" Plant Science. Jan. 1, 2005;168(1):267-73.

McKibbin et al. "Production of high-starch, low-glucose potatoes through over-expression of the metabolic regulator SnRK1" Plant biotechnology journal. Jul. 2006;4(4):409-18.

Meitinger et al. "Purification of Δ5-3-ketosteroid isomerase from Digitalis lanata" Phytochemistry. Jan. 1, 2015;109:6-13.

Meitinger et al. "The catalytic mechanism of the 3-ketosteroid isomerase of Digitalis lanata involves an intramolecular proton transfer and the activity is not associated with the 3β-hydroxysteroid dehydrogenase activity" Tetrahedron Letters. Apr. 16, 2016;57(14):1567-71.

Milner et al. "Bioactivities of glycoalkaloids and their aglycones from *Solanum* species" Journal of Agricultural and Food Chemistry. Mar. 14, 2011;59(8):3454-84.

Mintz-Oron S, Mandel T, Rogachev I, Feldberg L, Lotan O, Yativ M, Wang Z, Jetter R, Venger I, Adato A, Aharoni A. Gene expression and metabolism in tomato fruit surface tissues. Plant Physiology. Jun. 1, 2008;147(2):823-51.

Moummou H, Kallberg Y, Tonfack LB, Persson B, Van Der Rest B. The plant short-chain dehydrogenase (SDR) superfamily: genome-wide inventory and diversification patterns. BMC plant biology. Dec. 2012;12(1):219.

Ofner et al. "Solanum pennellii backcross inbred lines (BIL s) link small genomic bins with tomato traits" The Plant Journal. Jul. 2016;87(2):151-60.

Okamoto et al. "A short-chain dehydrogenase involved in terpene metabolism from Zingiber zerumbet" The FEBS journal. Aug. 2011:278(16):2892-900.

Orzaez e al. "A visual reporter system for virus-induced gene silencing in tomato fruit based on anthocyanin accumulation". Plant physiology. Jul. 1, 2009;150(3):1122-34.

Ringer et al. "Monoterpene metabolism. Cloning, expression, and characterization of (−)-isopiperitenol/(−)-carveol dehydrogenase of peppermint and spearmint" Plant physiology. Mar. 1, 2005;137(3):863-72.

Robinson et al. "Integrative genomics viewer" Nature biotechnology. Jan. 1, 2011:29(1):24-6.

Rocha-Sosa et al. "Both developmental and metabolic signals activate the promoter of a class I patatin gene". The EMBO journal. Jan. 1989;8(1):23.

Roddick JG. "The acetyicholinesterase-inhibitory activity of steroidal glycoalkaloids and their aglycones" Phytochemistry. Jan. 1, 1989;28(10):2631-4.

Roddick JG. "Steroidal glycoalkaloids: nature and consequences of bioactivity" In Saponins used in traditional and modern medicine 1996 (pp. 277-295). Springer, Boston, MA.

Schilmiller et al. "Mass spectrometry screening reveals widespread diversity in trichome specialized metabolites of tomato chromosomal substitution lines" The Plant Journal. May 2010;62(3):391-403.

Schwahn et al. "Metabolomics-assisted refinement of the pathways of steroidal glycoalkaloid biosynthesis in the tomato clade" Journal of integrative plant biology. Sep. 2014;56(9):864-75.

Shannon et al. "Cytoscape: a software environment for integrated models of biomolecular interaction networks" Genome research. Nov. 1, 2003;13(11):2498-504.

Sievers et al. "Fast, scalable generation of high-quality protein multiple sequence alignments using Clustal Omega. Molecular systems biology" Jan. 1, 2011;7(1), Article No. 539.

Sonawane et al. "Plant cholesterol biosynthetic pathway overlaps with phytosterol metabolism" Nature plants. Jan. 2017;3(1):16205.

Tamura et al. "MEGA6: molecular evolutionary genetics analysis version 6.0" Molecular biology and evolution. Oct. 16, 2013;30(12):2725-9.

Tonfack et al. "The plant SDR superfamily: Involvement in primary and secondary metabolism" Current Topics in Plant Biology. (2011) 12. 41-53.

Trapnell et al. "Differential gene and transcript expression analysis of RNA-seq experiments with TopHat and Cufflinks" Nature protocols. Mar. 2012;7(3):562.

Umemoto et al. "Two cytochrome P450 monooxygenases catalyze early hydroxylation steps in the potato steroid glycoalkaloid biosynthetic pathway" Plant physiology. Aug. 1, 2016;171(4):2458-67.

Unger et al. "Applications of the Restriction Free (RF) cloning procedure for molecular manipulations and protein expression" Journal of structural biology. Oct. 1, 2010;172(1):34-44.

Unger et al. "Recombinant protein expression in the baculovirus-infected insect cell system" In Chemical Genomics and Proteomics 2012 (pp. 187-199). Humana Press.

Wu et al. A new liquid chromatography-mass spectrometry-based strategy to integrate chemistry, morphology, and evolution of eggplant (*Solanum*) species. Journal of Chromatography A. Nov. 1, 2013;1314:154-72.

Yang et al. "Isolation and functional analysis of a strong specific promoter in photosynthetic tissues" Science in China Series C: Life Sciences. Dec. 1, 2003:46(6):651-60.

EP Application No. EP22209230.6 Search Report dated May 3, 2023.

Database Genbank Predicted: "probable 2-oxoglutarate-dependent dioxygenase AOP1 [Solanum tuberosum]", NOBI Reference Sequence: XP_006354215.1, Jan. 5, 2016, 1 page.

Database UniProt/TrEMBL, Anonymous: "Uncharacterized protein [Solanum tuberosum]", XP09304014, Sep. 7, 2016, 2 pages.

Database GenPept, "Anonymous: Predicted: probable 2-oxoglutarate-dependent dioxygenase AOP1.2 [Solanum tuberosum]", XP09304014, Jan. 5, 2016, 1 page.

Database UniProt/TrEMBL, Anonymous: "Uncharacterized protein [Solanum tuberosum]", XP093040139, Jun. 8, 2016, 1 page.

Cardenas et al., (2019). Pathways to defense metabolites and evading fruit bitterness in genus *Solanum* evolved through 2-oxoglutarate-dependent dioxygenases. Nature Communications, 10(1), 13 pages.

Szamanski et al., (2020). Analysis of wild tomato introgression lines elucidates the genetic basis of transcriptome and metabolome variation underlying fruit traits and pathogen response. *Nature Genetics*, 52(10), 30 pages.

* cited by examiner

```
SEQ ID NO: 15  S.tuberosum     MANKLRLEGKVAI TGAASGI EASARLFAEHGARIVVADIQDELGLKVVESIGADKASY
SEQ ID NO: 3   S.lycopersicum  MANKLRLEGKVAI TGAASGI EASARLFAEHGARIVVADIQDELGQKVVDSIGSDKASY
SEQ ID NO: 12  S.pennellii     MANKLRLEGKVAI TGAASGI EASARLFVEHGARVVVADIQDELGQKVVDSIGADKASY
                                                   *
SEQ ID NO: 15  S.tuberosum     RHCDVTDEKQVEDTVAYTVEKYGTLDIMFSNVGTLNFCSVLDMDVMFDKTMAINARGSA
SEQ ID NO: 3   S.lycopersicum  RHCDVTDEKQVEETVAYAVEKYGTLDIMFSNVGTLNFCSVLMDVLAFIETMAINVRGSA
SEQ ID NO: 12  S.pennellii     RHCDVTDEKQVEETVAYAVEKYGTLDIMFSNVGTLNFCSVLMDVMAFIETMAINVRGSA SEQ ID NO: 15  S.tuberosum     LAVKHAAPFMVDKKIRGSTICNASIDGIVAGATSLA IASK AVVGIVKAAARDLGPYGI
SEQ ID NO: 3   S.lycopersicum  LAVKHAAKVMVDKKIRGSTICNASLEGILAGAASLA IASK AVVGIIKAAAFELGPHGI
SEQ ID NO: 12  S.pennellii     LAVKHAAKVMVTDKKITRGSTICNASLEGTLAGAASLA IASK AVVGIIKAAAFELGPHGI SEQ ID NO: 15  S.tuberosum     RVNGVSPYGIATPLVCKAYGIDAGFIEAAIYGNGNLKGVRLSTMHVAQSALFLASDESAY
SEQ ID NO: 3   S.lycopersicum  RVNGVSPYGIATPLVTLAYGIDAALLEEAIYGNGHLKGVKLSTMHVAQSALFLASDESAY
SEQ ID NO: 12  S.pennellii     RVNGVSPYGIATPLVCKAYGIDAALLERAIYGNGHLKGVKLSTMHVAQSALFLASDESAY SEQ ID NO: 15  S.tuberosum     TSGQMLAVDGGLSSTLRVQ
SEQ ID NO: 3   S.lycopersicum  TSGQMLAVDGGLSSIIKLQ
SEQ ID NO: 12  S.pennellii     TSGQMLAVDGGLSSIIKLQ
```

FIGURE 5

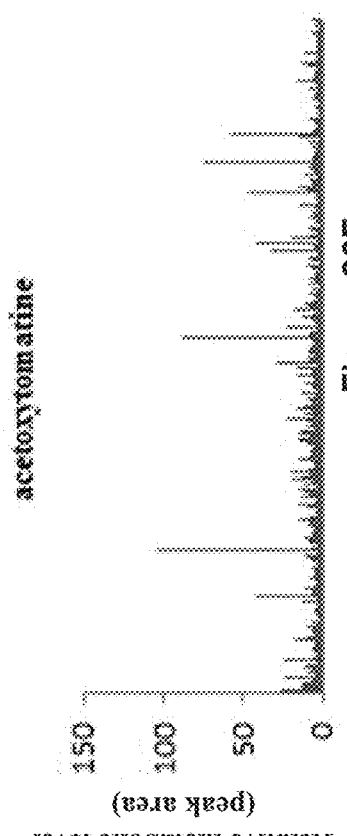
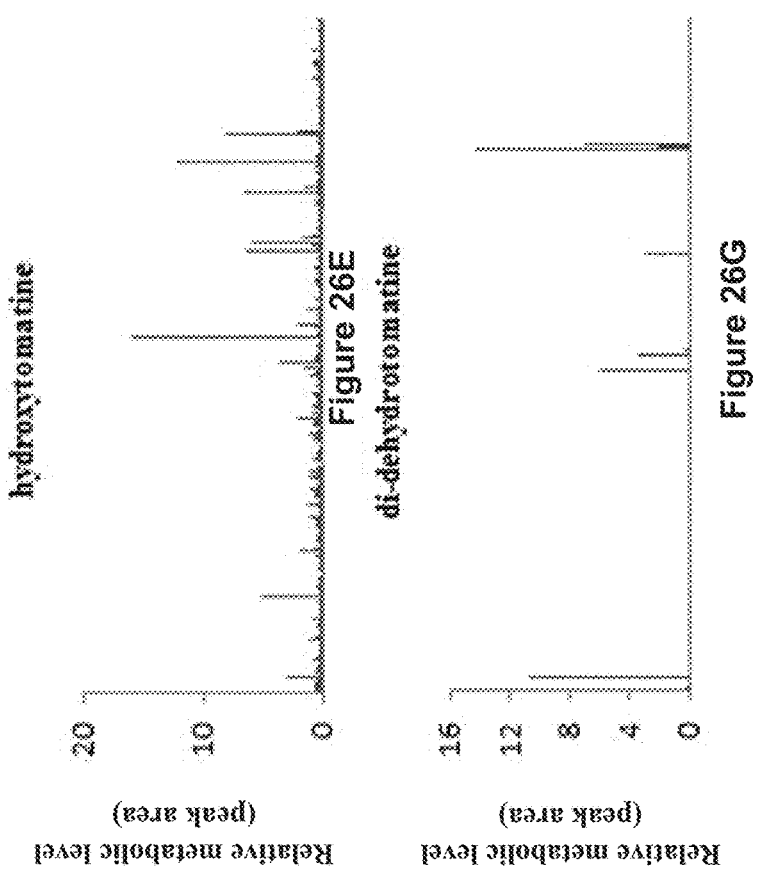

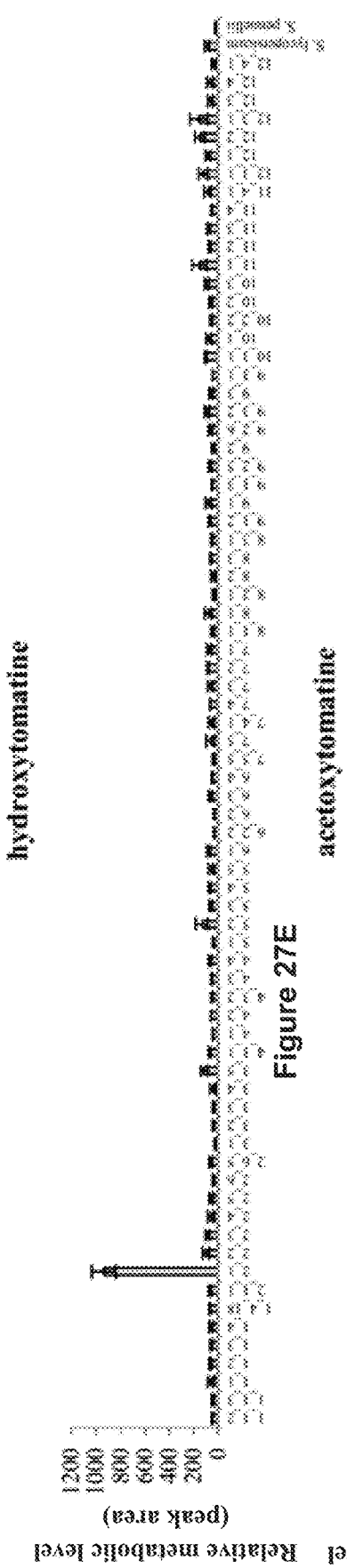
Figure 27E hydroxytomatine
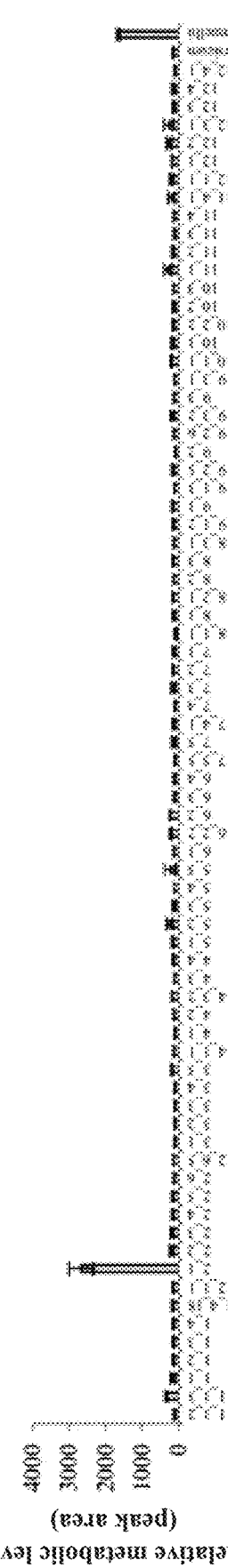
Figure 27F acetoxytomatine
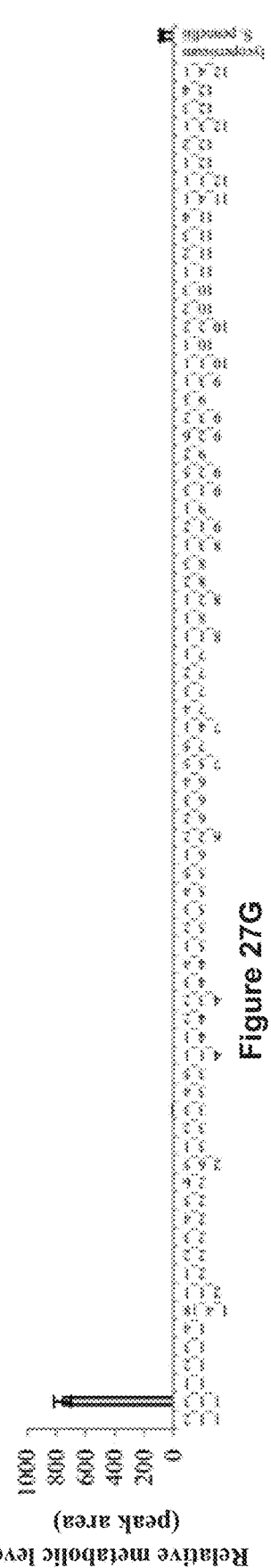
Figure 27G di-dehydrotomatine

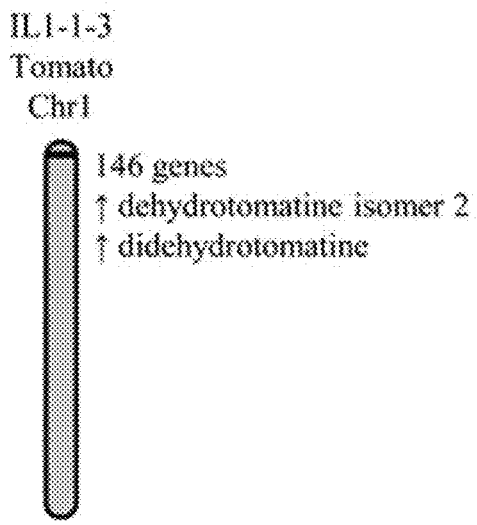
Figure 28A
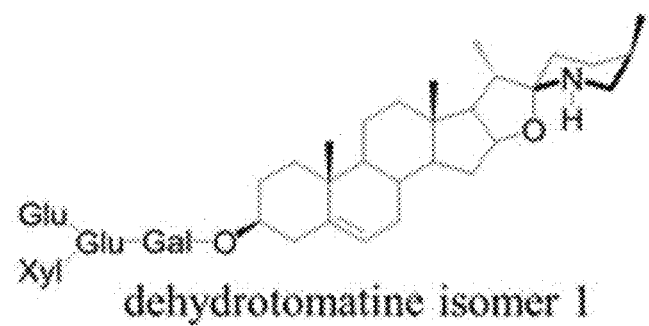
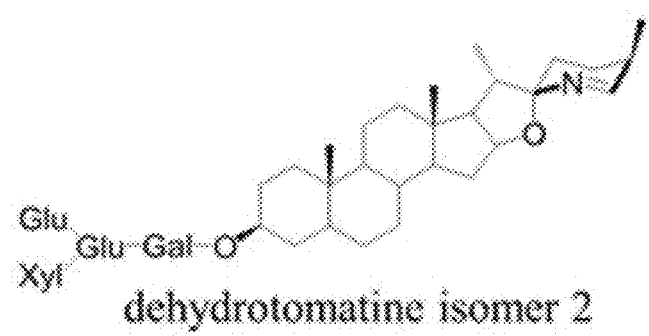
Figure 28B

| Region in chromosome 1 linked to content of dehydrotomatine isomer 2 | |
|---|---|
| Sixlyc01g0073930 | Sel1 domain protein repeat-containing protein (AHRD V1 *-*- A8GBQ0_CHICK); contains Interpro domain(s) IPR011990 Tetratricopeptide-like helical |
| Sixlyc01g0073940 | Alanine aminotransferase 2 (AHRD V1 **** A8IKE5_SOYBN); contains Interpro domain(s) IPR004839 Aminotransferase, class I and II |
| Sixlyc01g0073950 | Peroxidase 1 (AHRD V1 *-*- B6TU73_MAIZE); contains Interpro domain(s) IPR000823 Plant peroxidase |
| Sixlyc01g0073960 | RLK, Receptor like protein, putative resistance protein with an antifungal domain |
| Sixlyc01g0073970 | RLK, Receptor like protein, putative resistance protein with an antifungal domain |
| Sixlyc01g0073980 | RLK, Receptor like protein, putative resistance protein with an antifungal domain |
| Sixlyc01g0073990 | RLK, Receptor like protein, putative resistance protein with an antifungal domain |
| Sixlyc01g0098000 | ADP-ribosylation factor (AHRD V1 **-* Q76ME3_WHEAT); contains Interpro domain(s) IPR006688 ADP-ribosylation factor |
| Sixlyc01g0098010 | Os04g0327550 protein (Fragment) (AHRD V1 *-*- C7J7J3_ORYSJ); contains Interpro domain(s) IPR003863 Protein of unknown function DUF220 |
| Sixlyc01g0098020 | Equilibrative nucleoside transporter 1 (AHRD V1 **-* Q4W6L4_ORYSJ) |
| Sixlyc01g0098030 | Unknown Protein (AHRD V1) |
| Sixlyc01g0098040 | S-locus F-box-like protein, x (Fragment) (AHRD V1 *** B9F0G3_PETIN); contains Interpro domain(s) IPR006527 F-box associated |
| Sixlyc01g0098050 | Leaf senescence protein-like (AHRD V1 ***- Q67V91_ORYSJ); contains Interpro domain(s) IPR004233 Protein of unknown function DUF231, plant |
| Sixlyc01g0098060 | Phosphoglycerate mutase (AHRD V1 *-- A4TBN9_MYCGI); contains Interpro domain(s) IPR003156 Ribonuclease H |
| Sixlyc01g0098070 | Alpha/beta superfamily hydrolase (AHRD V1 *-- D8CIF5_9SYNE); contains Interpro domain(s) IPR010763 Protein of unknown function DUF1380 |
| Sixlyc01g0098080 | Ribosomal protein S27 (AHRD V1 ***- Q3HVK9_SOLTU); contains Interpro domain(s) IPR000592 Ribosomal protein S27e |
| Sixlyc01g0098090 | Ribosomal protein S27 (AHRD V1 ***- Q3HVK9_SOLTU); contains Interpro domain(s) IPR000592 Ribosomal protein S27e |
| Sixlyc01g0098100 | Transferase transferring glycosyl groups (AHRD V1 **-* D7MH74_ARALY) |
| Sixlyc01g0098110 | Cytochrome P450 |
| Sixlyc01g0098120 | Histone acetyltransferase (AHRD V1 **** B9RG17_RICCO); contains Interpro domain(s) IPR009255 Transcriptional coactivation |
| Sixlyc01g0098130 | BHP domain-containing protein 1B (AHRD V1 *-- DHP1B_HUMAN); contains Interpro domain(s) IPR008659 Protein of unknown function DUF847 |
| Sixlyc01g0098140 | Receptor kinase (AHRD V1 **** B8XA87_GOSRA); contains Interpro domain(s) IPR002290 Serine/threonine protein kinase |
| Sixlyc01g0098150 | Unknown Protein (AHRD V1) |
| Sixlyc01g0098160 | Tetratricopeptide repeat-containing protein (AHRD V1 *** EFL8H9_ARALY); contains Interpro domain(s) IPR011990 Tetratricopeptide-like helical |
| Sixlyc01g0098170 | Zinc finger CCCH domain-containing protein 17 (AHRD V1 ***- C8H7_ARATH); contains Interpro domain(s) IPR000571 Zinc finger, CCCH-type |
| Sixlyc01g0098180 | DNA-binding protein (Fragment) (AHRD V1 **-* Q42851_ARATH); contains Interpro domain(s) IPR005516 Remorin, C-terminal region |
| Sixlyc01g0098190 | Os05g0354100 protein (Fragment) (AHRD V1 **-* Q8DJB8_ORYSJ) |
| Sixlyc01g0098200 | Os05g0354100 protein (Fragment) (AHRD V1 *** Q8DJB8_ORYSJ) |
| Sixlyc01g0098210 | Unknown Protein (AHRD V1) |
| Sixlyc01g0098220 | Arabinogalactan protein (AHRD V1 ***- B6SST2_MAIZE) |
| Sixlyc01g0098230 | TCP family transcription factor (AHRD V1 ***- A6MCZ2_9ORYZ); contains Interpro domain(s) IPR005333 Transcription factor, TCP |

| Gene ID | Description |
|---|---|
| Solyc01g089270 | Unknown Protein (AHRD V1) |
| Solyc01g089280 | Serine/threonine-protein phosphatase (AHRD V1 ****- D7LGI6_ARALY); contains Interpro domain(s) IPR015391 Serine/threonine protein phosphatase, BSU1 |
| Solyc01g089290 | Polyribonucleotide 5'hairpin-hydroxyl-kinase Clp1 (AHRD V1 ****- CLP1_CHICK); contains Interpro domain(s) IPR018855 Pre-mRNA cleavage complex II Clp1 |
| Solyc01g089300 | Serine/threonine kinase (AHRD V1 **-* C4QNE1_SCHMA); contains Interpro domain(s) IPR002290 Serine/threonine protein kinase |
| Solyc01g089310 | Sterol reductase (AHRD V1 **** A8IAG7_CHLRE); contains Interpro domain(s) IPR001171 Ergosterol biosynthesis ERG4/ERG24 |
| Solyc01g089320 | U-box domain-containing protein 24 (AHRD V1 ***- D7LAS1_ARALY); contains Interpro domain(s) IPR003613 U box domain |
| Solyc01g089330 | U-box domain-containing protein family-like (AHRD V1 ***- D7LI34_ARALY); contains Interpro domain(s) IPR003613 U box domain |
| Solyc01g089340 | Calmodulin-binding protein family-like (AHRD V1 ***- Q6YXT2_ORYSJ); contains Interpro domain(s) IPR003448 IQ calmodulin-binding region |
| Solyc01g089350 | CCR4-NOT transcription complex subunit 7 (AHRD V1 ***- B4FG48_MAIZE); contains Interpro domain(s) IPR006941 Ribonuclease CAF1 |
| Solyc01g089360 | CCR4-NOT transcription complex subunit 7 (AHRD V1 ***- B4FG48_MAIZE); contains Interpro domain(s) IPR006941 Ribonuclease CAF1 |
| Solyc01g089370 | Cytochrome P450 |
| Solyc01g089380 | Nicalin (AHRD V1 ***- B4FZF8_MAIZE); contains Interpro domain(s) IPR008710 Nicastrin |
| Solyc01g089390 | mRNA decapping enzyme (AHRD V1 *-*- Q45XB8_XENLA); contains Interpro domain(s) IPR010334 Dcp1-like decapping |

Region in chromosome 2 linked to content of hydroxytomatine

| Gene ID | Description |
|---|---|
| Solyc02g062360 | Histone-lysine N-methyltransferase NSD3 (AHRD V1 *--- NSD3_HUMAN); contains Interpro domain(s) IPR018144 Plus-3 domain, subgroup |
| Solyc02g062370 | Zinc finger CCCH domain-containing protein 19 (AHRD V1 *-*- C3H19_ARATH); contains Interpro domain(s) IPR013169 GYF |
| Solyc02g062380 | GATA transcription factor 9 (AHRD V1 *-*- B6STZ1_MAIZE); contains Interpro domain(s) IPR000679 Zinc finger, GATA-type |
| Solyc02g062390 | Unknown Protein (AHRD V1); contains Interpro domain(s) IPR008167 Dehydrin |
| Solyc02g062400 | Short interbands related sequence 5 (AHRD V1 *-*- DZKC76_BRARP); contains Interpro domain(s) IPR007818 Protein of unknown function DUF702 |
| Solyc02g062410 | Nuclear movement protein nudc (AHRD V1 ***- Q57KI6_AEDAE); contains Interpro domain(s) IPR017447 CS |
| Solyc02g062420 | Transmembrane protein 222 (Fragment) (AHRD V1 **-- Q5SSC2_HUMAN); contains Interpro domain(s) IPR020849 Protein of unknown function DUF778 |
| Solyc02g062430 | D-lactate dehydrogenase 2 mitochondrial (AHRD V1 *** ASDXM0_LODEL); contains Interpro domain(s) IPR004113 FAD-linked oxidase, C-terminal |
| Solyc02g062440 | Unknown Protein (AHRD V1); contains Interpro domain(s) IPR018666 Zinc finger, GRF-type |
| Solyc02g062460 | 2-oxoglutarate-dependent dioxygenase (AHRD V1 **** B9GL08_POPTR); contains Interpro domain(s) IPR005123 Oxoglutarate and iron-dependent oxygenase |
| Solyc02g062470 | 2-oxoglutarate-dependent dioxygenase (Fragment) (AHRD V1 ***- Q9AJ20_ARABA) |
| Solyc02g062480 | Transposon Ty1-A Gag-Pol polyprotein (AHRD V1 *-*- YA15B_YEAST); contains Interpro domain(s) IPR001584 Integrase, catalytic core |
| Solyc02g062490 | 2-oxoglutarate-dependent dioxygenase (Fragment) (AHRD V1 ***- Q9AJ20_ARABA) |
| Solyc02g062500 | 2-oxoglutarate-dependent dioxygenase (AHRD V1 **** B9GL08_POPTR); contains Interpro domain(s) IPR005123 Oxoglutarate and iron-dependent oxygenase |
| Solyc02g062510 | Peroxidase (AHRD V1 ***- Q6ZA68_9EOSR); contains Interpro domain(s) IPR002316 Haem peroxidase, plant/fungal/bacterial |
| Solyc02g062520 | Pseudouridine synthase family protein (AHRD V1 ***- D7LU41_ARALY); contains Interpro domain(s) IPR006223 Pseudouridine synthase, RluC/RluD |
| Solyc02g062530 | Os03g0852400 protein (Fragment) (AHRD V1 ***- Q0DLQ0_ORYSJ) |

Figure 29B

A: Full reaction
B: No ascorbic acid
C: No ketoglutaric acid
D: No FeSO₄
E: No substrate
F: No GAME31
G: Denatured GAME31

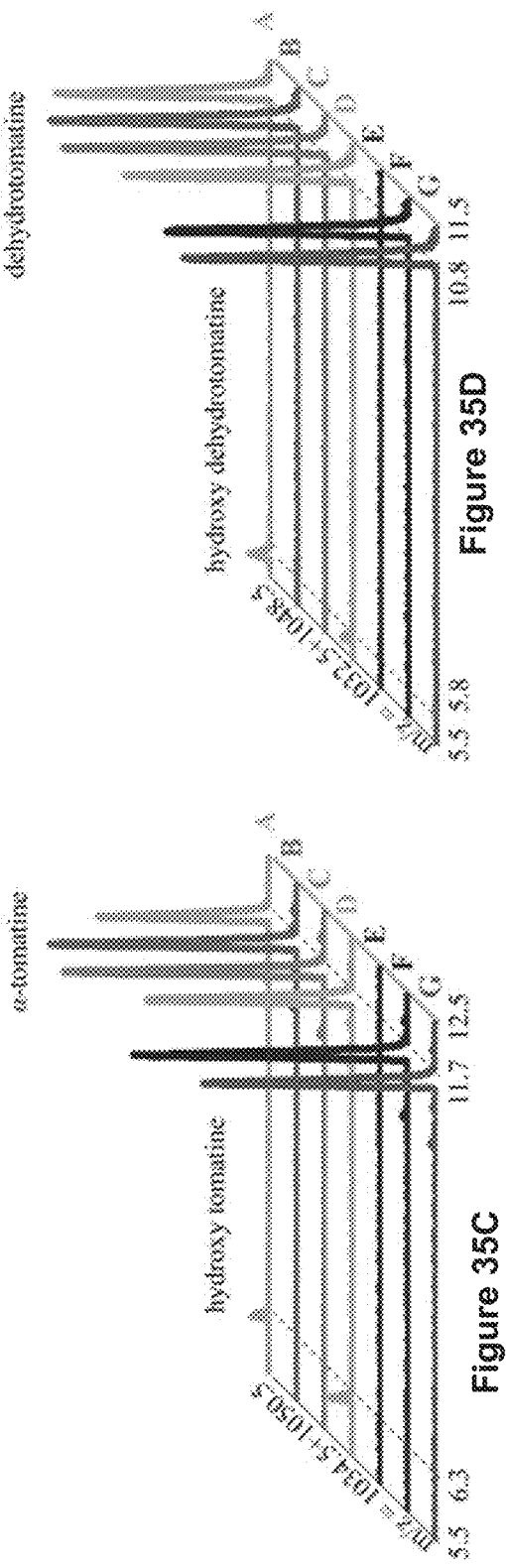

SEQUENCE LISTING

<160> NUMBER OF SEQ ID NOS: 107

<210> SEQ ID NO 1
<211> LENGTH: 1468
<212> TYPE: DNA
<213> ORGANISM: Solanum lycopersicum

<400> SEQUENCE: 1

| | | | | | |
|---|---|---|---|---|---|
| gtgatatatt | tcaaaaaata | attaaaatac | atatatattg | catacataat | tcacttttaa | 60 |
| tacatattgc | agatttaact | taaacattgt | tataaatggt | gataaataaa | aaaatcgtta | 120 |
| aaattagtaa | ttattcatta | aactgcatct | atttatgtaa | tttttccaat | taaaaatcta | 180 |
| ttatttttt | tcaatccaat | ccaaacaggc | tctaaagcat | caatgttttt | gaaattacca | 240 |
| aaatagcctc | ggttgttaag | cgcttccttc | tatatattag | tgaattcaaa | ctacagtcgg | 300 |
| tacaaaggaa | gttatttact | cttataatgg | caaataagct | caggtatagc | atagttagta | 360 |
| tttgtttaaa | ttaatggtgc | taatcagtac | attaatttat | tttctcaaaa | ttgtgtaatt | 420 |
| acatataatt | aaatgtgttt | aatcaaatgt | ttttcttttt | tatatgcatc | gatcctgtag | 480 |
| gttggagggc | aaagtagcta | taattaccgg | tgctgctagt | ggcattggag | aagcaagtgc | 540 |
| tagattgttc | gttgaacatg | gtgctcgtgt | cgtcgtcgcc | gatattcaag | atgaacttgg | 600 |
| tcaaaaagta | gttgattcta | tcggatctga | caaagccagc | taccggcact | gcgacgttac | 660 |
| agacgagaag | caagttgagg | aaaccgtagc | ttacgcggta | gagaaatacg | gtactcttga | 720 |
| cattatgttt | agtaatgtcg | ggacgctgaa | tttctgcagc | gtcctcgaca | tggacgtgct | 780 |
| ggccttcgat | gagaccatgg | ccatcaacgt | acgcggatcc | gcgttagcgg | ttaagcacgc | 840 |
| ggctaaagtt | atggttgata | agaaaattcg | gggatctatt | atatgtaacg | cgagtttaga | 900 |
| agggatttta | gctggggccg | cttcgctcgc | ctacattgcg | tcaaagcacg | cagtggtagg | 960 |
| cattataaaa | gcggccgcac | gtgaactggg | tccacatggg | ataagggtga | atggggtgtc | 1020 |
| gccctatgga | atagcgacgc | cccttgtgac | taaggcgtat | ggactggatg | cggctctatt | 1080 |
| ggaagaagca | atttacggta | atggacactt | gaaaggagtt | aagttgagca | cgatgcatgt | 1140 |
| agcacaatca | gcactttttt | tggcgtctga | tgaatctgct | tatacaagtg | gtcaaaattt | 1200 |
| agctgttgat | ggtggactaa | gttctatttt | gaagctacaa | taaattgtca | cgctatttgt | 1260 |
| gttggcgtgc | tgtggcgtgg | gccttaatcc | tcactctctt | gtgtctgtac | ttctgtttca | 1320 |
| tctcgtttcg | tttcaaattt | tcaacttaat | aatactctca | tattttatgc | gatattttc | 1380 |
| agatttatac | taagttttttt | atagatattt | taaacgttgt | gacttaaaaa | gatataaatt | 1440 |
| tcattttttt | aaaattaaaa | attttatg | | | | 1468 |

<210> SEQ ID NO 2
<211> LENGTH: 780
<212> TYPE: DNA
<213> ORGANISM: Artificial Sequence
<220> FEATURE:
<223> OTHER INFORMATION: GAME25 CDS of Solanum Lycopersicum

<400> SEQUENCE: 2

| | | | | | |
|---|---|---|---|---|---|
| atggcaaata | agctcaggtt | ggagggcaaa | gtagctataa | ttaccggtgc | tgctagtggc | 60 |
| attggagaag | caagtgctag | attgttcgtt | gaacatggtg | ctcgtgtcgt | cgtcgccgat | 120 |
| attcaagatg | aacttggtca | aaaagtagtt | gattctatcg | gatctgacaa | agccagctac | 180 |
| cggcactgcg | acgttacaga | cgagaagcaa | gttgaggaaa | ccgtagctta | cgcggtagag | 240 |
| aaatacggta | ctcttgacat | tatgtttagt | aatgtcggga | cgctgaattt | ctgcagcgtc | 300 |

-continued

```
ctcgacatgg acgtgctggc cttcgatgag accatggcca tcaacgtacg cggatccgcg    360
ttagcggtta agcacgcggc taaagttatg gttgataaga aaattcgggg atctattata    420
tgtaacgcga gtttagaagg gattttagct ggggccgctt cgctcgccta cattgcgtca    480
aagcacgcag tggtaggcat tataaaagcg gccgcacgtg aactgggtcc acatgggata    540
agggtgaatg gggtgtcgcc ctatggaata gcgacgcccc ttgtgactaa ggcgtatgga    600
ctggatgcgg ctctattgga agaagcaatt tacggtaatg gacacttgaa aggagttaag    660
ttgagcacga tgcatgtagc acaatcagca ctttttttgg cgtctgatga atctgcttat    720
acaagtggtc aaaatttagc tgttgatggt ggactaagtt ctatttttgaa gctacaataa    780
```

<210> SEQ ID NO 3
<211> LENGTH: 259
<212> TYPE: PRT
<213> ORGANISM: Solanum lycopersicum

<400> SEQUENCE: 3

```
Met Ala Asn Lys Leu Arg Leu Glu Gly Lys Val Ala Ile Ile Thr Gly
 1               5                  10                  15

Ala Ala Ser Gly Ile Gly Glu Ala Ser Ala Arg Leu Phe Val Glu His
                20                  25                  30

Gly Ala Arg Val Val Val Ala Asp Ile Gln Asp Glu Leu Gly Gln Lys
            35                  40                  45

Val Val Asp Ser Ile Gly Ser Asp Lys Ala Ser Tyr Arg His Cys Asp
        50                  55                  60

Val Thr Asp Glu Lys Gln Val Glu Glu Thr Val Ala Tyr Ala Val Glu
    65                  70                  75                  80

Lys Tyr Gly Thr Leu Asp Ile Met Phe Ser Asn Val Gly Thr Leu Asn
                85                  90                  95

Phe Cys Ser Val Leu Asp Met Asp Val Leu Ala Phe Asp Glu Thr Met
            100                 105                 110

Ala Ile Asn Val Arg Gly Ser Ala Leu Ala Val Lys His Ala Ala Lys
        115                 120                 125

Val Met Val Asp Lys Lys Ile Arg Gly Ser Ile Ile Cys Asn Ala Ser
    130                 135                 140

Leu Glu Gly Ile Leu Ala Gly Ala Ala Ser Leu Ala Tyr Ile Ala Ser
145                 150                 155                 160

Lys His Ala Val Val Gly Ile Ile Lys Ala Ala Ala Arg Glu Leu Gly
                165                 170                 175

Pro His Gly Ile Arg Val Asn Gly Val Ser Pro Tyr Gly Ile Ala Thr
            180                 185                 190

Pro Leu Val Thr Lys Ala Tyr Gly Leu Asp Ala Ala Leu Leu Glu Glu
        195                 200                 205

Ala Ile Tyr Gly Asn Gly His Leu Lys Gly Val Lys Leu Ser Thr Met
    210                 215                 220

His Val Ala Gln Ser Ala Leu Phe Leu Ala Ser Asp Glu Ser Ala Tyr
225                 230                 235                 240

Thr Ser Gly Gln Asn Leu Ala Val Asp Gly Gly Leu Ser Ser Ile Leu
                245                 250                 255

Lys Leu Gln
```

<210> SEQ ID NO 4
<211> LENGTH: 24
<212> TYPE: DNA

```
<213> ORGANISM: Artificial Sequence
<220> FEATURE:
<223> OTHER INFORMATION: GAME25 qRT Forward primer

<400> SEQUENCE: 4
gaagcaattt acggtaatgg acac                                              24

<210> SEQ ID NO 5
<211> LENGTH: 23
<212> TYPE: DNA
<213> ORGANISM: Artificial Sequence
<220> FEATURE:
<223> OTHER INFORMATION: GAME25 qRT Reverse primer

<400> SEQUENCE: 5
gaacttagtc caccatcaac agc                                               23

<210> SEQ ID NO 6
<211> LENGTH: 30
<212> TYPE: DNA
<213> ORGANISM: Artificial Sequence
<220> FEATURE:
<223> OTHER INFORMATION: GAME25 RNAi Forward primer

<400> SEQUENCE: 6
gcggccgcat tgtcacgcta tttgtgttgg                                        30

<210> SEQ ID NO 7
<211> LENGTH: 36
<212> TYPE: DNA
<213> ORGANISM: Artificial Sequence
<220> FEATURE:
<223> OTHER INFORMATION: GAME25 RNAi Reverse primer

<400> SEQUENCE: 7
ggcgcgccga aatttatatc tttttaagtc acaacg                                 36

<210> SEQ ID NO 8
<211> LENGTH: 199
<212> TYPE: DNA
<213> ORGANISM: Artificial Sequence
<220> FEATURE:
<223> OTHER INFORMATION: GAME25-RNAi construct

<400> SEQUENCE: 8
attgtcacgc tatttgtgtt ggcgtgctgt ggcgtgggcc ttaatcctca ctctcttgtg       60
tctgtacttc tgtttcatct cgtttcgttt caaattttca acttaataat actctctcat      120
tttatgcgat atttttcaga tttatactaa gttttttata gatattttaa acgttgtgac      180
ttaaaaagat ataaatttc                                                   199

<210> SEQ ID NO 9
<211> LENGTH: 28
<212> TYPE: DNA
<213> ORGANISM: Artificial Sequence
<220> FEATURE:
<223> OTHER INFORMATION: GAME25 baculo Forward primer

<400> SEQUENCE: 9
cccgggatgg caaataagct caggttgg                                          28

<210> SEQ ID NO 10
<211> LENGTH: 66
<212> TYPE: DNA
<213> ORGANISM: Artificial Sequence
```

```
<220> FEATURE:
<223> OTHER INFORMATION: GAME25 baculo Reverese primer

<400> SEQUENCE: 10
tctagattac agatcttctt cagaaataag ttttttgttct tgtagcttca aaatagaact    60
tagtcc                                                                66

<210> SEQ ID NO 11
<211> LENGTH: 780
<212> TYPE: DNA
<213> ORGANISM: Artificial Sequence
<220> FEATURE:
<223> OTHER INFORMATION: GAME25 CDS of Solanum pennellii

<400> SEQUENCE: 11
atggcaaata agctcaggtt ggagggcaaa gtagctataa ttactggtgc tgctagtggc    60
attggagagg caagtgctag attgttcgtt gaacatggtg ctcgtgtcgt cgtcgccgat   120
attcaagatg aacttggtca aaaagtagtt gattctatcg gagctgacaa agccagctac   180
cggcactgcg acgttacaga cgagaagcaa gttgaggaaa ccgtagccta cgcggtagag   240
aaatacggta ctcttgacat tatgtttagt aatgtcggga cgctgaattt ctgcagcgtc   300
ctcgacatgg acgtgatggc cttcgatgag acgatggcca tcaacgtacg tggatccgcg   360
ctagcggtta agcacgcggc taaagttatg gttgataaga aaattcgggg atctattata   420
tgtaacgcga gtttagaggg gatttttagct ggggccgctt cgcttgccta cattgcgtca   480
aagcacgcag tcgtaggcat aataaaagcg gccgcacgtg aactgggtcc acatgggata   540
agggtgaatg gggtgtcgcc atatggaata gcgacgcccc tggtgtgtaa ggcgtatgga   600
ctggatgcgg ctctattgga agaagcaatt tatggtaatg gacacttgaa aggtgttaag   660
ttgagcacga tgcatgtagc acaatcagca cttttttttgg cgtctgatga atctgcttac   720
acaagtggtc aaaatttagc tgttgatggt ggactaagtt ctattttgaa gctacaataa   780

<210> SEQ ID NO 12
<211> LENGTH: 259
<212> TYPE: PRT
<213> ORGANISM: Solanum pennellii

<400> SEQUENCE: 12

Met Ala Asn Lys Leu Arg Leu Glu Gly Lys Val Ala Ile Ile Thr Gly
1               5                   10                  15

Ala Ala Ser Gly Ile Gly Glu Ala Ser Ala Arg Leu Phe Val Glu His
            20                  25                  30

Gly Ala Arg Val Val Val Ala Asp Ile Gln Asp Glu Leu Gly Gln Lys
        35                  40                  45

Val Val Asp Ser Ile Gly Ala Asp Lys Ala Ser Tyr Arg His Cys Asp
    50                  55                  60

Val Thr Asp Glu Lys Gln Val Glu Glu Thr Val Ala Tyr Ala Val Glu
65                  70                  75                  80

Lys Tyr Gly Thr Leu Asp Ile Met Phe Ser Asn Val Gly Thr Leu Asn
                85                  90                  95

Phe Cys Ser Val Leu Asp Met Asp Val Met Ala Phe Asp Glu Thr Met
            100                 105                 110

Ala Ile Asn Val Arg Gly Ser Ala Leu Ala Val Lys His Ala Ala Lys
        115                 120                 125

Val Met Val Asp Lys Lys Ile Arg Gly Ser Ile Ile Cys Asn Ala Ser
    130                 135                 140
```

Leu Glu Gly Ile Leu Ala Gly Ala Ala Ser Leu Ala Tyr Ile Ala Ser
145                 150                 155                 160

Lys His Ala Val Val Gly Ile Ile Lys Ala Ala Arg Glu Leu Gly
            165                 170                 175

Pro His Gly Ile Arg Val Asn Gly Val Ser Pro Tyr Gly Ile Ala Thr
            180                 185                 190

Pro Leu Val Cys Lys Ala Tyr Gly Leu Asp Ala Ala Leu Leu Glu Glu
        195                 200                 205

Ala Ile Tyr Gly Asn Gly His Leu Lys Gly Val Lys Leu Ser Thr Met
210                 215                 220

His Val Ala Gln Ser Ala Leu Phe Leu Ala Ser Asp Glu Ser Ala Tyr
225                 230                 235                 240

Thr Ser Gly Gln Asn Leu Ala Val Asp Gly Gly Leu Ser Ser Ile Leu
            245                 250                 255

Lys Leu Gln

<210> SEQ ID NO 13
<211> LENGTH: 1080
<212> TYPE: DNA
<213> ORGANISM: Solanum tubersoum

<400> SEQUENCE: 13
aaaaaattta acatacagtt gctgcaaagg aagctaccta ctcgtataat ggcaaataag      60
ctcaggtact taattagtac attaatttct ttctttcttt tctcaaattg tatatgagaa     120
ttaaatgtgt attttagct ttaatcaaat gttttgtgg tatattatat gcatcgtgta      180
ggttggaggg caaagtggct ataattacag gtgctgcaag tggcattgga gaagcaagtg     240
ctagattgtt cgccgaacat ggtgctcgta ttgtcgtagc cgatattcaa gatgaacttg     300
gtctgaaagt agttgaatct atcggagctg acaaagccag ctaccgacac tgcgacgtta     360
cagacgagaa gcaagttgag gataccgtag cttacacggt agagaaatac ggtactcttg     420
acatcatgtt tagtaatgtt gggacgctga attttgcag cgtcctggac atggacgtga     480
tggtcttcga taagacgatg gccatcaacg cacgaggatc cgcgttagcg gtcaagcacg     540
cggctagatt tatggttgat aagaaaattc ggggatccat tatatgcaac gcgagtttag     600
atggtattgt agctgggggcc acttcgcttg cctacattgc gtcaaagcac gcagttgtag     660
gcattgtgaa agcggccgca cgtgacctag gtccatacgg gataagggtg aatgggggtgt     720 cgccatatgg aatagcgacg cccctggtgt gcaaagcgta tgggttggat gcgggtccat     780
tggaagcagc aatatatgga aatggaaact gaaaggtgt taggttgagc acgatgcatg     840
tagcacaatc agcactttc ttggcgtctg atgaatctgc ttacacaagt ggtcaaaatt     900
tagctgttga tggtggactt agttctattt tgaaggtaca atagattgtc actctattgt     960
gctggtgtgc tgtgatgtgt gcattagttc tattttgaag ctacaataat tcctttgtca    1020
tgtagtactg tttatcttgt ttcatttcga attttcaact taaataatat tctctcacag    1080

<210> SEQ ID NO 14
<211> LENGTH: 780
<212> TYPE: DNA
<213> ORGANISM: Artificial Sequence
<220> FEATURE:
<223> OTHER INFORMATION: CDS of GAME25 of Solanum tubersoum

<400> SEQUENCE: 14
atggcaaata agctcaggtt ggagggcaaa gtggctataa ttacaggtgc tgcaagtggc      60

```
attggagaag caagtgctag attgttcgcc gaacatggtg ctcgtattgt cgtagccgat    120
attcaagatg aacttggtct gaaagtagtt gaatctatcg gagctgacaa agccagctac    180
cgacactgcg acgttacaga cgagaagcaa gttgaggata ccgtagctta cacggtagag    240
aaatacggta ctcttgacat catgtttagt aatgttggga cgctgaattt ttgcagcgtc    300
ctggacatgg acgtgatggt cttcgataag acgatggcca tcaacgcacg aggatccgcg    360
ttagcggtca agcacgcggc tagatttatg gttgataaga aaattcgggg atccattata    420
tgcaacgcga gtttagatgg tattgtagct ggggccactt cgcttgccta cattgcgtca    480
aagcacgcag ttgtaggcat tgtgaaagcg gccgcacgtg acctaggtcc atacgggata    540
agggtgaatg gggtgtcgcc atatggaata gcgacgcccc tggtgtgcaa agcgtatggg    600
ttggatgcgg gtccattgga agcagcaata tatggaaatg gaaacttgaa aggtgttagg    660
ttgagcacga tgcatgtagc acaatcagca cttttcttgg cgtctgatga atctgcttac    720
acaagtggtc aaaatttagc tgttgatggt ggacttagtt ctattttgaa ggtacaatag    780
```

<210> SEQ ID NO 15
<211> LENGTH: 259
<212> TYPE: PRT
<213> ORGANISM: Solanum tubersoum

<400> SEQUENCE: 15

```
Met Ala Asn Lys Leu Arg Leu Glu Gly Lys Val Ala Ile Ile Thr Gly
1               5                   10                  15

Ala Ala Ser Gly Ile Gly Glu Ala Ser Ala Arg Leu Phe Ala Glu His
            20                  25                  30

Gly Ala Arg Ile Val Val Ala Asp Ile Gln Asp Glu Leu Gly Leu Lys
        35                  40                  45

Val Val Glu Ser Ile Gly Ala Asp Lys Ala Ser Tyr Arg His Cys Asp
    50                  55                  60

Val Thr Asp Glu Lys Gln Val Glu Asp Thr Val Ala Tyr Thr Val Glu
65                  70                  75                  80

Lys Tyr Gly Thr Leu Asp Ile Met Phe Ser Asn Val Gly Thr Leu Asn
                85                  90                  95

Phe Cys Ser Val Leu Asp Met Asp Val Met Val Phe Asp Lys Thr Met
            100                 105                 110

Ala Ile Asn Ala Arg Gly Ser Ala Leu Ala Val Lys His Ala Ala Arg
        115                 120                 125

Phe Met Val Asp Lys Lys Ile Arg Gly Ser Ile Ile Cys Asn Ala Ser
    130                 135                 140

Leu Asp Gly Ile Val Ala Gly Ala Thr Ser Leu Ala Tyr Ile Ala Ser
145                 150                 155                 160

Lys His Ala Val Val Gly Ile Val Lys Ala Ala Ala Arg Asp Leu Gly
                165                 170                 175

Pro Tyr Gly Ile Arg Val Asn Gly Val Ser Pro Tyr Gly Ile Ala Thr
            180                 185                 190

Pro Leu Val Cys Lys Ala Tyr Gly Leu Asp Ala Gly Pro Leu Glu Ala
        195                 200                 205

Ala Ile Tyr Gly Asn Gly Asn Leu Lys Gly Val Arg Leu Ser Thr Met
    210                 215                 220

His Val Ala Gln Ser Ala Leu Phe Leu Ala Ser Asp Glu Ser Ala Tyr
225                 230                 235                 240

Thr Ser Gly Gln Asn Leu Ala Val Asp Gly Gly Leu Ser Ser Ile Leu
```

245                 250                 255
Lys Val Gln

<210> SEQ ID NO 16
<211> LENGTH: 2552
<212> TYPE: DNA
<213> ORGANISM: Solanum lycopersycum

<400> SEQUENCE: 16

| | | | | | |
|---|---|---|---|---|---|
| tgactataat | tgatactcaa | tctgttgaaa | tataatgaac | caattcttat | caaaacacag | 60 |
| tggagtacaa | gtaatcacgt | tggttcctat | gaaatggttc | atctatttcc | cattatatat | 120 |
| aggctactta | tttcctcacc | tataaagtaa | aaaactttct | agtgttttct | tctttctttt | 180 |
| gttttttct | ctttgctcat | attctaaaaa | tatttcatca | atggcatcta | tcaaatcagt | 240 |
| taaagttcct | actatagatt | tttccaatta | tcaagagcta | aaaccaaaca | ctccactatg | 300 |
| ggaatccaca | aaaattcaag | ttttgaagc | tttacaagaa | tatggttgtt | ttgaagcaat | 360 |
| atatgataaa | gtttcaaagg | aaattagaga | ggaaacattt | gatatgtcaa | agaaatatt | 420 |
| tgaatttcct | ttagagacta | aagtgaaaaa | tatctcagaa | aaaccaatgc | atggctatat | 480 |
| ggggatgatt | ccacaattgc | cattgtatga | gagtttgtgt | attcctgatt | tgcttaatcc | 540 |
| tcaaagtctt | gaaaaatttt | ctaatatctt | ttggcctcag | ggtaatcaac | atttctggta | 600 |
| tgtttacttt | tatttctttt | tcattttgt | tttcttatta | tctttaaatt | ttgttctagt | 660 |
| ggaactgttc | aaaagctact | atctttagaa | ataataattt | ttattagctt | agttgattga | 720 |
| ttatgcgata | ttattaatag | cttaaaaaaa | taatttttat | tagcttagaa | ataataattt | 780 |
| ttattaactt | agttgattga | ctatgcgata | ttattaatag | cttaaaagag | cttagttgat | 840 |
| cagactacga | agtaaaaata | aaaagagacg | gaagtctgtg | tctcgcatct | atttttatt | 900 |
| gcaccgttta | aactaaataa | aatatagaca | acaacatcaa | atatttggt | aggaagacac | 960 |
| gatttattca | acagaaatat | agacaacaac | attaaagtat | ttggtacatg | aaatcactat | 1020 |
| ccataagtg | acagttcgtt | ggccttctca | tttttataa | aataaataga | aacacaagag | 1080 |
| ttgtctcaag | tgaaaaaatt | gaattatgtt | caaccttctt | catatgttta | tactaatatt | 1140 |
| acatgagcgt | taattttgc | agcaatttga | taaaatctta | ttctaatcca | cttgtggaat | 1200 |
| tggatgggat | gttgaaaagg | atgatttcgg | agaatttggg | attgaaaaat | cacattgatg | 1260 |
| aattattgaa | tgccaattac | ttcctattta | gatttacaca | ttataaggga | tcatcaattg | 1320 |
| ctagtggaga | tgaaaataat | aaagctgctg | gattgggtgg | ccacacggat | ggtaacttct | 1380 |
| tgacttttat | atcgcaaaat | caagttaatg | gattgcaaat | caacaaaaat | ggagaatgga | 1440 |
| ttgatgtgat | tatttcacca | aattcttacg | ttgttttggc | cggtgattcc | ttcaaagtaa | 1500 |
| gtattttaag | ttttgaacta | gtgttactta | tcttgttggg | aactgttttg | tttgattttt | 1560 |
| aaaagaaaaa | atattaaatg | atcaaaaaaa | ttataatatc | ttttttgttt | taaggttaaa | 1620 |
| taaattgatt | taaaaatttc | attttaatt | aaaagagggt | agtaaaatgc | ttaaaaagct | 1680 |
| aaaataattt | agtgtgaaat | atattatttt | attatcattc | taatcaaaat | ttctggtcac | 1740 |
| accttatagc | ataggggttt | cagagggccc | cgagatattt | tgttttgatc | ttatatttct | 1800 |
| cgaatctatg | aaaatgttat | tccactagtg | tttatattat | tttctgaaat | gcatattttt | 1860 |
| gaatgatttg | atatatgctc | aatatttca | tgcaaaactg | aaaatgaatt | ttggtattat | 1920 |
| tgaccgtatt | tgtattgttt | tactctccaa | aaatattatc | gatcgcatct | atctttgtat | 1980 |
| ttatacaggc | ttggacaaat | ggtcgattgc | attcacctct | ccacagagta | acaatgtccg | 2040 |

```
gacaaaatga tagactctcc attcaattgt tttcattatc aaagccaggt cacttcatcc   2100
aggcaccaaa agaactagta gatgaagaac acccattact cttcaagcca tttgaaattc   2160
ttgaattatt caagtatggt accacagaag ctggctatac agctcctcca agtgatcttt   2220
tcaagattta ttgtggtgtt tgatatgcta attgttgaat ttccgcttca acaagcaact   2280
tttctaatga gtttcatctt gttttttaa gtagtatgca ttttatgttt gaattgttgc    2340
agttggcaat tcatgtttaa tttgttttg ttttttgag aaaatatttc caatgggttt     2400
cgttggaaat tcgtcttgtt tttttttc aagtagtgta catcttattt ttggattgtt     2460
gatgttgagc gctaatgttt aatttgtttg tgttttgaag aggatgatta tactctttaa   2520
gaggattcac cgtaatcttt tagtattatt tg                                 2552

<210> SEQ ID NO 17
<211> LENGTH: 1495
<212> TYPE: DNA
<213> ORGANISM: Artificial Sequence
<220> FEATURE:
<223> OTHER INFORMATION: cDNA of GAME31 of Solanum lycopersycum

<400> SEQUENCE: 17
tgactataat tgatactcaa tctgttgaaa tataatgaac caattcttat caaaacacag     60
tggagtacaa gtaatcacgt tggttcctat gaaatggttc atctatttcc cattatatat    120
aggctactta tttcctcacc tataaagtaa aaaactttct agtgttttct tctttctttt    180 gttttttct ctttgctcat attctaaaaa tatttcatca atggcatcta tcaaatcagt     240
taaagttcct actatagatt tttccaatta tcaagagcta aaaccaaaca ctccactatg    300
ggaatccaca aaaattcaag ttttgaagc tttacaagaa tatggttgtt ttgaagcaat    360
atatgataaa gtttcaaagg aaattagaga ggaaacattt gatatgtcaa aagaaatatt   420
tgaatttcct ttagagacta aagtgaaaaa tatctcagaa aaaccaatgc atggctatat   480
ggggatgatt ccacaattgc cattgtatga gagtttgtgt attcctgatt tgcttaatcc    540
tcaaagtctt gaaaaattt ctaatatctt ttggcctcag ggtaatcaac atttctgcaa    600
tttgataaaa tcttattcta atccacttgt ggaattggat gggatgttga aaggatgat    660 ttcggagaat ttgggattga aaaatcacat tgatgaatta ttgaatgcca attacttcct   720
atttagattt acacattata agggatcatc aattgctagt ggagatgaaa ataataaagc   780
tgctggattg ggtggccaca cggatggtaa cttcttgact tttatatcgc aaaatcaagt   840
taatggattg caaatcaaca aaaatggaga atggattgat gtgattattt caccaaattc   900
ttacgttgtt ttggccggtg attccttcaa agcttggaca aatggtcgat gcattcacc    960 tctccacaga gtaacaatgt ccggacaaaa tgatagactc tccattcaat tgttttcatt  1020
atcaaagcca ggtcacttca tccaggcacc aaaagaacta gtagatgaag aacacccatt  1080
actcttcaag ccatttgaaa ttcttgaatt attcaagtat ggtaccacag aagctggcta  1140
tacagctcct ccaagtgatc tttttcaagat ttattgtggt gtttgatatg ctaattgttg  1200
aatttccgct tcaacaagca actttttcta atgagtttcat cttgtttttt taagtagtat  1260
gcattttatg tttgaattgt tgcagttggc aattcatgtt taatttgttt tgttttttt   1320 gagaaaatat ttccaatggg tttcgttgga aattcgtctt gttttttt tcaagtagt     1380 gtacatctta tttttggatt gttgatgttg agcgctaatg tttaatttgt tgtgttttg   1440 aagaggatga ttatactctt taagaggatt caccgtaatc ttttagtatt atttg        1495
```

<210> SEQ ID NO 18
<211> LENGTH: 321
<212> TYPE: PRT
<213> ORGANISM: Solanum lycopersycum

<400> SEQUENCE: 18

Met Ala Ser Ile Lys Ser Val Lys Val Pro Thr Ile Asp Phe Ser Asn
1               5                   10                  15
Tyr Gln Glu Leu Lys Pro Asn Thr Pro Leu Trp Glu Ser Thr Lys Ile
            20                  25                  30
Gln Val Phe Glu Ala Leu Gln Glu Tyr Gly Cys Phe Glu Ala Ile Tyr
        35                  40                  45
Asp Lys Val Ser Lys Glu Ile Arg Glu Thr Phe Asp Met Ser Lys
    50                  55                  60
Glu Ile Phe Glu Phe Pro Leu Glu Thr Lys Val Lys Asn Ile Ser Glu
65                  70                  75                  80
Lys Pro Met His Gly Tyr Met Gly Met Ile Pro Gln Leu Pro Leu Tyr
                85                  90                  95
Glu Ser Leu Cys Ile Pro Asp Leu Leu Asn Pro Gln Ser Leu Glu Lys
            100                 105                 110
Phe Ser Asn Ile Phe Trp Pro Gln Gly Asn Gln His Phe Cys Asn Leu
        115                 120                 125
Ile Lys Ser Tyr Ser Asn Pro Leu Val Glu Leu Asp Gly Met Leu Lys
    130                 135                 140
Arg Met Ile Ser Glu Asn Leu Gly Leu Lys Asn His Ile Asp Glu Leu
145                 150                 155                 160
Leu Asn Ala Asn Tyr Phe Leu Phe Arg Phe Thr His Tyr Lys Gly Ser
                165                 170                 175
Ser Ile Ala Ser Gly Asp Glu Asn Asn Lys Ala Ala Gly Leu Gly Gly
            180                 185                 190
His Thr Asp Gly Asn Phe Leu Thr Phe Ile Ser Gln Asn Gln Val Asn
        195                 200                 205
Gly Leu Gln Ile Asn Lys Asn Gly Glu Trp Ile Asp Val Ile Ile Ser
    210                 215                 220
Pro Asn Ser Tyr Val Val Leu Ala Gly Asp Ser Phe Lys Ala Trp Thr
225                 230                 235                 240
Asn Gly Arg Leu His Ser Pro Leu His Arg Val Thr Met Ser Gly Gln
                245                 250                 255
Asn Asp Arg Leu Ser Ile Gln Leu Phe Ser Leu Ser Lys Pro Gly His
            260                 265                 270
Phe Ile Gln Ala Pro Lys Glu Leu Val Asp Glu His Pro Leu Leu
        275                 280                 285
Phe Lys Pro Phe Glu Ile Glu Leu Phe Lys Tyr Gly Thr Thr Glu
    290                 295                 300
Ala Gly Tyr Thr Ala Pro Pro Ser Asp Leu Phe Lys Ile Tyr Cys Gly
305                 310                 315                 320
Val

<210> SEQ ID NO 19
<211> LENGTH: 462
<212> TYPE: DNA
<213> ORGANISM: Solanum lycoperscum

<400> SEQUENCE: 19
atggcatcta ccaaattagt taaagttccc acaatagatt tttcaaatca tcaagatcta         60

```
aaaccaaaca ctccactatg ggaatccaaa aaaattcaag tttttgaagc tttgcaagaa      120
tatggttgtt ttgaagcaat ttatgataaa gttccaaaag atattagaga ggaaacattt      180
agtatttcaa aagaaatatt tgaatttcct ttagagacta aattgaaaaa tatttcagaa      240
aaaccaacgc atggatatat gggaatgatt ccacaattgc cattgtatga gagtttgtgt      300
attcctgatt tgcttaatcc taaaagtctt caaagttttg ctaatatctt ttggcctcag      360
ggtaaccaac atttctggta tgtttactta tgtttttatt tcgccctagc agaagtgttc      420
aaaagtacga cattagaaat tcttagtgac ttaattgatt ga                        462
```

<210> SEQ ID NO 20
<211> LENGTH: 462
<212> TYPE: DNA
<213> ORGANISM: Artificial Sequence
<220> FEATURE:
<223> OTHER INFORMATION: cDNA of GAME31-like 1 of Solanum lycopersycum

<400> SEQUENCE: 20

```
atggcatcta ccaaattagt taaagttccc acaatagatt tttcaaatca tcaagatcta       60
aaaccaaaca ctccactatg ggaatccaaa aaaattcaag tttttgaagc tttgcaagaa      120
tatggttgtt ttgaagcaat ttatgataaa gttccaaaag atattagaga ggaaacattt      180
agtatttcaa aagaaatatt tgaatttcct ttagagacta aattgaaaaa tatttcagaa      240
aaaccaacgc atggatatat gggaatgatt ccacaattgc cattgtatga gagtttgtgt      300
attcctgatt tgcttaatcc taaaagtctt caaagttttg ctaatatctt ttggcctcag      360
ggtaaccaac atttctggta tgtttactta tgtttttatt tcgccctagc agaagtgttc      420
aaaagtacga cattagaaat tcttagtgac ttaattgatt ga                        462
```

<210> SEQ ID NO 21
<211> LENGTH: 153
<212> TYPE: PRT
<213> ORGANISM: Solanum lycopersycum

<400> SEQUENCE: 21

Met Ala Ser Thr Lys Leu Val Lys Val Pro Thr Ile Asp Phe Ser Asn
1               5                   10                  15

His Gln Asp Leu Lys Pro Asn Thr Pro Leu Trp Glu Ser Lys Lys Ile
            20                  25                  30

Gln Val Phe Glu Ala Leu Gln Glu Tyr Gly Cys Phe Glu Ala Ile Tyr
        35                  40                  45

Asp Lys Val Pro Lys Asp Ile Arg Glu Glu Thr Phe Ser Ile Ser Lys
    50                  55                  60

Glu Ile Phe Glu Phe Pro Leu Glu Thr Lys Leu Lys Asn Ile Ser Glu
65                  70                  75                  80

Lys Pro Thr His Gly Tyr Met Gly Met Ile Pro Gln Leu Pro Leu Tyr
                85                  90                  95

Glu Ser Leu Cys Ile Pro Asp Leu Leu Asn Pro Lys Ser Leu Gln Ser
            100                 105                 110

Phe Ala Asn Ile Phe Trp Pro Gln Gly Asn Gln His Phe Trp Tyr Val
        115                 120                 125

Tyr Leu Cys Phe Tyr Phe Ala Leu Ala Glu Val Phe Lys Ser Thr Thr
    130                 135                 140

Leu Glu Ile Leu Ser Asp Leu Ile Asp
145                 150

<210> SEQ ID NO 22
<211> LENGTH: 1113
<212> TYPE: DNA
<213> ORGANISM: Solanum lycopersycum

<400> SEQUENCE: 22

| | | | | | |
|---|---|---|---|---|---|
| tgagatgttg | aaaaggatga | tttcggagaa | tttgggatta | aaaaatcaca | ttgatgaatt | 60 |
| attgaatgcc | aattacatcc | tatttagatt | tacacagtat | aagggatcat | caattgctag | 120 |
| tggagatgaa | aataataaag | cagctggatt | gggtggccac | acagatggta | acttcttgtc | 180 |
| tattatatca | caaaatgaag | ttaatggatt | gcaaatcaac | aaaaatggag | agtggattga | 240 |
| tgtcaacatt | tcgccaaatt | cttatgttgt | tttatccggt | gattccttca | cagtaagtgt | 300 |
| taagttttga | gctagtgtta | ttatcttgtt | gggaactgtg | ttgtttgatt | ttctaaaggg | 360 |
| ataatgctaa | atgacaagaa | actcaaaaaa | tcaataagat | atttgttgaa | tcttacgtct | 420 |
| ctaaatatat | tatcatgcta | gtgttaatta | tttcccgaaa | tgcatatttt | tgaagaatct | 480 |
| gacatactga | gtgatattct | ggaagagtcc | aaccaagaca | ctttgttgaa | actacatgct | 540 |
| caatattttc | atgcaaaact | gaaaatgaat | cttgatattt | gttgaccta | tgttgctcta | 600 |
| ttctccaaaa | atactactgc | gactatcttt | gtatttatgc | aggcatggac | aaatggccga | 660 |
| ttgcattctc | ctgttcatag | agttgaaatg | cccagaggaa | gtgatagata | ttccattcaa | 720 |
| ttattttcat | tatcaaaacc | aggtcacttc | atcgaggcac | caaaagaaat | ggtggatgaa | 780 |
| gaacacctt | tgcttttcaa | gccatttgaa | attcttggat | tacttgggta | tggtgccaca | 840 |
| gaagctggct | atacaactcc | tcccagtgat | cttttcaagg | catattgcgg | tgtctgatat | 900 |
| gctaattgcg | aatttccatt | tctattagaa | taaagttagt | atttatgaga | tttttgttgg | 960 |
| taattcatgt | ttaattggtt | tgtgtttttt | tggaaaatat | ttctaatgtg | ttccgttgga | 1020 |
| aattcgtgtg | catcttatgt | ttggattgtt | ggtattggga | attcatgttt | aatttgtttg | 1080 |
| tgttcttggg | caaataataa | atttgaagcg | gat | | | 1113 |

<210> SEQ ID NO 23
<211> LENGTH: 547
<212> TYPE: DNA
<213> ORGANISM: Artificial Sequence
<220> FEATURE:
<223> OTHER INFORMATION: cDNA of GAME31-like 2 of Solanum lycopersycum

<400> SEQUENCE: 23

| | | | | | |
|---|---|---|---|---|---|
| tgagatgttg | aaaaggatga | tttcggagaa | tttgggatta | aaaaatcaca | ttgatgaatt | 60 |
| attgaatgcc | aattacatcc | tatttagatt | tacacagtat | aagggatcat | caattgctag | 120 |
| tggagatgaa | aataataaag | cagctggatt | gggtggccac | acagatggta | acttcttgtc | 180 |
| tattatatca | caaaatgaag | ttaatggatt | gcaaatcaac | aaaaatggag | agtggattga | 240 |
| tgtcaacatt | tcgccaaatt | cttatgttgt | tttatccggt | gattccttca | cagcatggac | 300 |
| aaatggccga | ttgcattctc | ctgttcatag | agttgaaatg | cccagaggaa | gtgatagata | 360 |
| ttccattcaa | ttattttcat | tatcaaaacc | aggtcacttc | atcgaggcac | caaaagaaat | 420 |
| ggtggatgaa | gaacacctt | tgcttttcaa | gccatttgaa | attcttggat | tacttgggta | 480 |
| tggtgccaca | gaagctggct | atacaactcc | tcccagtgat | cttttcaagg | catattgcgg | 540 |
| tgtctga | | | | | | 547 |

<210> SEQ ID NO 24
<211> LENGTH: 181

<212> TYPE: PRT
<213> ORGANISM: Solanum lycopersycum

<400> SEQUENCE: 24

```
Glu Met Leu Lys Arg Met Ile Ser Glu Asn Leu Gly Leu Lys Asn His
1               5                   10                  15
Ile Asp Glu Leu Leu Asn Ala Asn Tyr Ile Leu Phe Arg Phe Thr Gln
            20                  25                  30
Tyr Lys Gly Ser Ser Ile Ala Ser Gly Asp Glu Asn Asn Lys Ala Ala
        35                  40                  45
Gly Leu Gly Gly His Thr Asp Gly Asn Phe Leu Ser Ile Ile Ser Gln
    50                  55                  60
Asn Glu Val Asn Gly Leu Gln Ile Asn Lys Asn Gly Glu Trp Ile Asp
65                  70                  75                  80
Val Asn Ile Ser Pro Asn Ser Tyr Val Val Leu Ser Gly Asp Ser Phe
                85                  90                  95
Thr Ala Trp Thr Asn Gly Arg Leu His Ser Pro Val His Arg Val Glu
            100                 105                 110
Met Pro Arg Gly Ser Asp Arg Tyr Ser Ile Gln Leu Phe Ser Leu Ser
        115                 120                 125
Lys Pro Gly His Phe Ile Glu Ala Pro Lys Glu Met Val Asp Glu Glu
    130                 135                 140
His Pro Leu Leu Phe Lys Pro Phe Glu Ile Leu Gly Leu Leu Gly Tyr
145                 150                 155                 160
Gly Ala Thr Glu Ala Gly Tyr Thr Thr Pro Pro Ser Asp Leu Phe Lys
                165                 170                 175
Ala Tyr Cys Gly Val
            180
```

<210> SEQ ID NO 25
<211> LENGTH: 4148
<212> TYPE: DNA
<213> ORGANISM: Solanum lycopersycum

<400> SEQUENCE: 25

| | |
|---|---|
| tgactagaaa tagacataaa accctgtact ttttgacaca catgtaatag cactttctct | 60 |
| atctaatacg caactcttta ttaatttttgc gtaaattttg agctatttcc cattatatat | 120 |
| aggctactta tttcctcacc tcttaagtaa aaaactttca agtgtttctt ctttctttta | 180 |
| tttctctttg ttcacatatt ctaaaaatat ttcatcaatg gcatctatca aatcagttaa | 240 |
| agttcctact atagattttt ccaattatca agagctaaaa ccaaacactc cactatggga | 300 |
| atccacaaaa attcaagttt ttgaagcttt tcaagaatat ggttgttttg aagcaatata | 360 |
| tgataaagtt ccaaatgaaa ttagagagga aacatttgat atgtcaaaag aaatatttga | 420 |
| atttccttta gatactaaag tgaaaaatat ttcagaaaaa ccaatgcatg gatatatggg | 480 |
| aatgattcca caattgccat tgtatgagag tttgtgtatt cctgatttgc ttaatcctca | 540 |
| aagtcttcaa aattttgcta atatcttttg gcctcagggt aatcaacatt tctggtatgt | 600 |
| ctatttcact gttttcatct tttttatttt cttactatca ttatctttaa atttaagaaa | 660 |
| aaacgataaa tatatcccta aatataaatg gtatgcagat attctccatc atattttgg | 720 |
| gacatatatt tttaccgttc aaaaattaaa gcatatatac catttttatac taatggatat | 780 |
| agacgtgtca taatcttatc taccgcccca acattggatc gatggataag attgtgccaa | 840 |
| gtttcctaat ttaaccattc gttagagtga agggcagaaa ttttcgactt tttaaatgtc | 900 |

```
agggacatca atgtcccaaa agtatgacgg aggaaaaata taacgaaaaa tatgtgcata    960
ctatttacga tcgtttgaaa aaatatttgt cttttttcct tttaaatttt ggcctaatga   1020
aagtgttcaa aaagtataac attagagatt cccagtaaat tgattaacta tttgaccatt   1080
caatagtttt atggaataag ttaattttt ctttgagaaa acaaaatag gagattataa     1140
atggaagttt ccttctcgaa tctattcatt agcacacccc taaacaaaca aaagtgccga   1200
taacgttaaa atatttggta tgaagtctcg atctactcaa taaaaacaaa taaattaata   1260
ggagacaata gacagtatct ttctcgaatc aatttcgaat ttatttcttt tatcacattg   1320
ttaataaaat gaaaattatc aacaacatca gaatatttgg tatgtgtcac gatctaataa   1380
ttgtagaaat cgagatataa atacgatttg agaaatcaaa gattgtattg atgaaaaata   1440
atgttaagtt acaaggtttt tatatggaga gaattgtaga gttctaagtt aactataata   1500
aaatactatt acaatacata ttactattat aataataata ataatgcaaa tcctagtcgt   1560
aatataattc taatcgactt caactagtac aataagtaaa taagtagcac tgcgtctaat   1620
cctagtatga atctaactcg tcagtcagtt ccgctttccc attttgttt tcactatcct    1680
agttttaaaa ataaaataaa atataagact tagttaacgt aaatatggcc tcatttgttt   1740
gtatttaatt gggggtctaa atcttaatca atcagattcg cctcattcag tatgtttgtt   1800
tttttatgac tgaatcttaa ttatttagat ttaattcatt aagtttgttt gttttatttt   1860
cttagaagtc tcttaacgag tctgaataca tctgagttaa tcagatctgt aatacactct   1920
taagaccatt cagactcaaa agtaattcct atcttaattc aactacatca caaaaactca   1980
taaaagttttt tttcttatta aattaatgtt aattacatgc ttacccgtta taatttcctt  2040
tattttacta acttaatata cgtcctttac tttcataaat taatcaatat atttgaattg   2100
ataaacactt catgatataa tatttagcac gattctagaa acaagaaag tattgattag    2160
ttgatcgata acaataacaa atctgcatta taaaataaaa tgctttcata aacattatat   2220
tactactcta tataaactat tttacattgc attatattag attatcaaag ttttttgagtg  2280
caaaaaagaa tagtcatata ttagtgatgt aacttaatgt taaattctta atagataaat   2340
catatgacct attcatgata agaatgtcca aaaattttatt ttccatataa aaaattattt   2400
tactaaaatg aggttttttat aattttttgt tgatacatcg tttaatttca tatgtacatt   2460
caaatattaa aaacgaatta tctcaataat ccagttttca tattcagaga aaataccttaa  2520
atattaaaat gtttattcag atttacatat ctagatctta atgcatattt taatatttag   2580
atgtatattc agattcagac gttttgatct taatagaaac aaataaggcc taagtgaaag   2640
aatggtatca acttgaaatg tttctaaatc tgttcaacct tctttatatg tttataaaca   2700
ttatatgtgt attttttttt tgcagcaatt tggtaaagtc ttattctaat ccacttgtgg   2760
aattggatga gattttgaaa aggatgattt cggagaattt gagattaaaa attcacattg   2820
atgaattgtt gaatgccaat tatttcctat ttagatttac acattacaag ggatcatcaa   2880
ttactggtgg agatgagaat aacaaagttg ctggattggg tggccacaca gatggtaact   2940
tcttgacttt tatatcgcaa aatcaagtca atggattgca atcaacaaa atggagaat     3000
ggattgatgt gaatatttca ccaaattctt atgttgtttt ggctggtgat ccttcaaag    3060
taagtgttaa gttttgaatt attgttatta tcttgttggg aactgtttg tttgattttt    3120
aaaagaaaaa tgctaaatgg tcacaaattt ttaaagtcaa taatattttt tttgttttaa   3180
ggtaaataaa ttgataaaaa aagaattcat ttttaattaa aagatattga aattaaaagg   3240
gtaaaaatac tttaaacata gtgtgaatta tgttatttta tcattctaat caaaatttgt   3300
```

```
ggccaatatt gttacacctt ataggattta tcaaaaaaac atagttttca gaggctcaag    3360
atatttgttg gatcttatgt ttctcgaatc tctgaaaatg ttgttccgct tgtgttgaat    3420
gtattatttt ctgaaatgta tattttttgaa gaatttgata tattaatgat atgctcaata    3480
ttttcatgca aaacggaaaa tgaattttgg tattattgac cctatttgta ttgttctact    3540
ctccaaaaat attatcgatc acgtctatct ttgtatttat acaggcttgg acaaatggtc    3600
gattgcattc tcctcttcac agagtaacaa tgtccggaga aaatgataga ctctccattc    3660
aattattttc attatcaaaa ccaggtcact tcatcgaggc accaaaagaa ctagtggatg    3720
aagaacaccc tttactcttc aagccatttg aaattattgg attatttgag tatggtacca    3780
cagaagctgg ctatacagct cctccaagtg atcttctcaa gagttattgc ggtgtttgat    3840
atgctaattg cgaatttccg cttcagcaac caacttttct aataagtttc gtctgaaatt    3900
cgtgttgttt taattattat gcattttatg tttgaattgt tgtagttggc aattcatgtt    3960
taatttgttt gtgtttttt ttttgagaaa atattgcatt gggtttcatt ggaaatttgt    4020 gtttttttaaa aagtagtgtg catcttatgt ttggattgtt ggtgttgaga attcattttt    4080
aatttgtttt tttttttggg caaataatga atttaaaatt gttgatttta ctctttagtg    4140
gaaatgat                                                             4148

<210> SEQ ID NO 26
<211> LENGTH: 1345
<212> TYPE: DNA
<213> ORGANISM: Artificial Sequence
<220> FEATURE:
<223> OTHER INFORMATION: cDNA of GAME31-like 3 of Solanum lycopersycum

<400> SEQUENCE: 26
tgactagaaa tagacataaa acctgtact ttttgacaca catgtaatag cactttctct      60
atctaatacg caactcttta ttaattttgc gtaaattttg agctatttcc cattatatat     120
aggctactta tttcctcacc tcttaagtaa aaaactttca agtgtttctt ctttcttta      180 tttctctttg ttcacatatt ctaaaaatat ttcatcaatg gcatctatca aatcagttaa     240
agttcctact atagattttt ccaattatca agagctaaaa ccaaacactc cactatggga     300
atccacaaaa attcaagttt ttgaagcttt tcaagaatat ggttgttttg aagcaatata     360
tgataaagtt ccaaatgaaa ttagagagga acatttgat atgtcaaaag aaatatttga     420 atttcccttta gatactaaag tgaaaaatat ttcagaaaaa ccaatgcatg gatatatggg    480
aatgattcca caattgccat tgtatgagag tttgtgtatt cctgatttgc ttaatcctca    540
aagtcttcaa aattttgcta atatctttg gcctcagggt aatcaacatt tctgcaattt     600
ggtaaagtct tattctaatc cacttgtgga attggatgag attttgaaaa ggatgatttc    660
ggagaatttg agattaaaaa ttcacattga tgaattgttg aatgccaatt atttcctatt    720
tagatttaca cattacaagg gatcatcaat tactggtgga gatgagaata caaaagttgc    780
tggattgggt ggccacacag atggtaactt cttgactttt atatcgcaaa atcaagtcaa    840
tggattgcaa atcaacaaaa atggagaatg gattgatgtg aatatttcac caaattctta    900
tgttgttttg gctggtgatt ccttcaaagc ttggacaaat ggtcgattgc attctcctct    960
tcacagagta acaatgtccg gagaaaatga tagactctcc attcaattat tttcattatc   1020
aaaaccaggt cacttcatcg aggcaccaaa agaactagtg gatgaagaac acctttact   1080 cttcaagcca tttgaaatta ttggattatt tgagtatggt accacagaag ctggctatac   1140
```

```
agctcctcca agtgatcttc tcaagagtta ttgcggtgtt tgatatgcta attgcgaatt    1200
tccgcttcag caaccaactt ttctaataag tttcgtctga aattcgtgtt gttttaatta    1260
ttatgcattt tatgtttgaa ttgttgtagt tggcaattca tgtttaattt gtttgtgttt    1320 ttttttttc tttagtggaa atgat                                           1345
```

<210> SEQ ID NO 27
<211> LENGTH: 321
<212> TYPE: PRT
<213> ORGANISM: Solanum lycopersycum

<400> SEQUENCE: 27

```
Met Ala Ser Ile Lys Ser Val Lys Val Pro Thr Ile Asp Phe Ser Asn
1               5                   10                  15

Tyr Gln Glu Leu Lys Pro Asn Thr Pro Leu Trp Glu Ser Thr Lys Ile
            20                  25                  30

Gln Val Phe Glu Ala Phe Gln Glu Tyr Gly Cys Phe Glu Ala Ile Tyr
        35                  40                  45

Asp Lys Val Pro Asn Glu Ile Arg Glu Thr Phe Asp Met Ser Lys
    50                  55                  60

Glu Ile Phe Glu Phe Pro Leu Asp Thr Lys Val Lys Asn Ile Ser Glu
65                  70                  75                  80

Lys Pro Met His Gly Tyr Met Gly Met Ile Pro Gln Leu Pro Leu Tyr
                85                  90                  95

Glu Ser Leu Cys Ile Pro Asp Leu Leu Asn Pro Gln Ser Leu Gln Asn
            100                 105                 110

Phe Ala Asn Ile Phe Trp Pro Gln Gly Asn Gln His Phe Cys Asn Leu
        115                 120                 125

Val Lys Ser Tyr Ser Asn Pro Leu Val Glu Leu Asp Glu Ile Leu Lys
    130                 135                 140

Arg Met Ile Ser Glu Asn Leu Arg Leu Lys Ile His Ile Asp Glu Leu
145                 150                 155                 160

Leu Asn Ala Asn Tyr Phe Leu Phe Arg Phe Thr His Tyr Lys Gly Ser
                165                 170                 175

Ser Ile Thr Gly Gly Asp Glu Asn Asn Lys Val Ala Gly Leu Gly Gly
            180                 185                 190

His Thr Asp Gly Asn Phe Leu Thr Phe Ile Ser Gln Asn Gln Val Asn
        195                 200                 205

Gly Leu Gln Ile Asn Lys Asn Gly Glu Trp Ile Asp Val Asn Ile Ser
    210                 215                 220

Pro Asn Ser Tyr Val Val Leu Ala Gly Asp Ser Phe Lys Ala Trp Thr
225                 230                 235                 240

Asn Gly Arg Leu His Ser Pro Leu His Arg Val Thr Met Ser Gly Glu
                245                 250                 255

Asn Asp Arg Leu Ser Ile Gln Leu Phe Ser Leu Ser Lys Pro Gly His
            260                 265                 270

Phe Ile Glu Ala Pro Lys Glu Leu Val Asp Glu His Pro Leu Leu
        275                 280                 285

Phe Lys Pro Phe Glu Ile Ile Gly Leu Phe Glu Tyr Gly Thr Thr Glu
    290                 295                 300

Ala Gly Tyr Thr Ala Pro Pro Ser Asp Leu Leu Lys Ser Tyr Cys Gly
305                 310                 315                 320

Val
```

<210> SEQ ID NO 28
<211> LENGTH: 963
<212> TYPE: DNA
<213> ORGANISM: Artificial Sequence
<220> FEATURE:
<223> OTHER INFORMATION: CDS of GAME31

<400> SEQUENCE: 28

```
atgggatcta ccaaatcaat taaagttccc actatcgatt tttccaacca tcaagatcta    60
aaaccaaaca ctccacaatg ggaatccaca aaagatcaag ttttgaagc ttttcaagaa   120
tttggttgtt ttgaagcaat atatgataaa gtgccaaatg aaattagaaa gggcatgttt   180
gatgtttcaa agaaatatt tgaatttccc ctagagacca aattgaaaaa cttatcagac   240
aaaccattac atggctacat ggggatgatt ccaaacttgc ctttgtatga gagtttgtgt   300
attcctgatt tgcttaatcc tcaaagtctt caaaattttg aaaatatctt ttggccacat   360
ggaaatcctg attttgcaa tttggtaaaa tgttactcaa atccacttgt ggaattggat   420
gaaatgttga gaggatgat tttggagaaa ttgggagtag aaaatcagat tgatgagtta   480
ttggatccca atatgtcct atttagattt acacactaca agggtcatc accaactaat   540
ggagataaaa atactaaaag tgagggacta ggtggccaca ctgatggtaa cttcttgact   600
tttatagcac aaaatcaagt aagtggattg caaattaata aaaatggaga gtggattgat   660
gtcaacatct caccaaattc ttttgctgtt tgtctgctg attccttcaa agcatggaca   720
aatggtcgat tgcattctcc aattcacaga gtaacaatgg ctggagaaaa tgatagattc   780
tccattcaat tattttcact atccaaacca ggtcacttca tagaggcccc aaaagaactt   840
gtggatgaac aacaccccttt actcttcaaa ccatatgaaa tgcttggatt atttaagtat   900
gttacttcac aaagtggata tggagctcct ggtgatgctt tcaaggctta ttgtggtgtt   960
tga                                                                963
```

<210> SEQ ID NO 29
<211> LENGTH: 320
<212> TYPE: PRT
<213> ORGANISM: Solanum melongena

<400> SEQUENCE: 29

```
Met Gly Ser Thr Lys Ser Ile Lys Val Pro Thr Ile Asp Phe Ser Asn
1               5                   10                  15

His Gln Asp Leu Lys Pro Asn Thr Pro Gln Trp Glu Ser Thr Lys Asp
            20                  25                  30

Gln Val Phe Glu Ala Phe Gln Glu Phe Gly Cys Phe Glu Ala Ile Tyr
        35                  40                  45

Asp Lys Val Pro Asn Glu Ile Arg Lys Gly Met Phe Asp Val Ser Lys
    50                  55                  60

Glu Ile Phe Glu Phe Pro Leu Glu Thr Lys Leu Lys Asn Leu Ser Asp
65                  70                  75                  80

Lys Pro Leu His Gly Tyr Met Gly Met Ile Pro Asn Leu Pro Leu Tyr
                85                  90                  95

Glu Ser Leu Cys Ile Pro Asp Leu Leu Asn Pro Gln Ser Leu Gln Asn
            100                 105                 110

Phe Glu Asn Ile Phe Trp Pro His Gly Asn Pro Asp Phe Cys Asn Leu
        115                 120                 125

Val Lys Cys Tyr Ser Asn Pro Leu Val Glu Leu Asp Glu Met Leu Lys
    130                 135                 140

Arg Met Ile Leu Glu Lys Leu Gly Val Glu Asn Gln Ile Asp Glu Leu
```

```
                    145                 150                 155                 160
Leu Asp Pro Lys Tyr Val Leu Phe Arg Phe Thr His Tyr Lys Gly Ser
                165                 170                 175

Ser Pro Thr Asn Gly Asp Lys Asn Thr Lys Ser Glu Gly Leu Gly Gly
                180                 185                 190

His Thr Asp Gly Asn Phe Leu Thr Phe Ile Ala Gln Asn Gln Val Ser
                195                 200                 205

Gly Leu Gln Ile Asn Lys Asn Gly Glu Trp Ile Asp Val Asn Ile Ser
                210                 215                 220

Pro Asn Ser Phe Ala Val Leu Ser Ala Asp Ser Phe Lys Ala Trp Thr
225                 230                 235                 240

Asn Gly Arg Leu His Ser Pro Ile His Arg Val Thr Met Ala Gly Glu
                245                 250                 255

Asn Asp Arg Phe Ser Ile Gln Leu Phe Ser Leu Ser Lys Pro Gly His
                260                 265                 270

Phe Ile Glu Ala Pro Lys Glu Leu Val Asp Glu Gln His Pro Leu Leu
                275                 280                 285

Phe Lys Pro Tyr Glu Met Leu Gly Leu Phe Lys Tyr Val Thr Ser Gln
                290                 295                 300

Ser Gly Tyr Gly Ala Pro Gly Asp Ala Phe Lys Ala Tyr Cys Gly Val
305                 310                 315                 320

<210> SEQ ID NO 30
<211> LENGTH: 2345
<212> TYPE: DNA
<213> ORGANISM: Solanum tuberosum

<400> SEQUENCE: 30
gaaactttga agtctttctt gtttcctaaa tattcctcaa atggcatcta ccaaagttac    60
gattcccacc atagatttt gcgattctga gcttaaacca aacactccac aatgggaatc    120
aacaaaagtt caagttttg aagccttaca agaatttggt tgttttgaag caatatataa    180
caaagttcca aatgaaatta gagagggcat gtttgatact ttaaaagaag tatttgattt    240
tccactgccc aaattgatag aatatagaga gaaaccctt catatatatg atgggcaaat    300
tccaagtgta ccactctttg gtagtgtgta ctctgctgat ttggtcctcc caaatagtgt    360
tgaaacattt gccaataccc tttggtctca tggaaaccct aattttaggt atgcattact    420
tcttttcat taattatagg gagtcacgat agtgtaagat gcattaaaag gagaaacgtt    480
tcctagtaga attgtttcta ttcctagggc tagaatcagg aacctttagt taaattaata    540
gagataatat tcattccatc actaaaggtg aaaattaagt atcttatatt gtccataaat    600
tttatataga agagatgtga gaattaataa aataaaaatt aaaaactcac gagtaaacaa    660
aataattata tctaatttat attaataaag aagagtattt gattattata ttaagtcaaa    720
tgataagcta ataaatcaat attaacaatc taatcacatg atttatataa aattggttat    780
gggtatggga agggagggag ggaagtacat ttcattgagg aacaatgcaa tagttagaca    840
ggatttaaca tacttgaaca agatatcata atctaaaatg attaaaaata atttttttaat   900
attatctaca catcgcgcga atatatatat atatatatat taagtgtatt tcttaaataa    960
tattgtatta ctatttatat aaattttgta tgttttaatt ttgcagcaat gtggcaaagt   1020
cctacttcaa gcaacttatg gaattaaatg acatggttaa aaagatggtt ttggagagtc   1080
ttgggctaaa aaattacatt gatgaattct tgaattccaa tgtttatatg tcaagattta   1140
ctaattacaa ggtaattaaa ggtgaaaatg agaataaatc aggattacct tcccacacag   1200
```

| atagttccta cttgaccata attaaacaaa atcaaaatgg attgcaagtt ctctacaaaa | 1260 |
| atggagagtg gattgagctc aatcgtcaaa atggactgca agttctctac aaaaatggag | 1320 |
| agtggattga gctcaatcat acttcaccaa attcctatat tgttttatca gaagatgttt | 1380 |
| ttatggtaag ttattattta ttttttatta cagaagtcaa aaatacacct aaactttta | 1440 |
| tttatatgta ttttgacgc ttaactcttt atttttttgt gtgtaggggt ggtttgttgc | 1500 |
| tatagtagag gagaataaaa gaaatagatt tttttgtat gattgattat tcaagcccaa | 1560 |
| ctagaagcta agattagagg agttttgaag caacgaaaaa aaatgttgtg tgtgatttat | 1620 |
| agatattgat gcaggctcga tccgtgaaag aaatcactaa tatttatatt agattagatc | 1680 |
| gtttacctaa ctaaacatcc cttgaagtac tgccctttct ccaaaccata tgtgaacgtc | 1740 |
| aaatatttta tgcatcaacc tgtcttttt tatttggccc caactaactt caatccacat | 1800 |
| aaattattaa atcttgatat tagttggaat aacatatctc ttttctgaga aattgaaaat | 1860 |
| aatgccagaa ctatcataat ctttttttaa aaaaattgtc ttgttattat cttattaatt | 1920 |
| taaaattttc tttcttcaga ggaaatttaa gtcaatcttt ttgttcctta attattaatt | 1980 |
| aaacaaataa attcttatac atactttta tgtgttgatg ctatgaatta attatacagg | 2040 |
| catggacaaa tgatagattg acatctgctc aacacagggt tgtaacaaca ggagacaaag | 2100 |
| aaagattctc tattcaagtt ttttccttc caaatccaga ttacactgtg aaggtcccac | 2160 |
| aagaattagt ggatgaagaa caccctttaa tgtacaagcc ttttaagatg tctgaatata | 2220 |
| ataaatatat tatgttaggt gctaaaaatg gattgggtgt caagaattat tgtggtcttt | 2280 |
| aaaaatttag tagctatgaa aatttattta tgtattgttt tgatgaataa aatgtatcag | 2340 |
| atggc | 2345 |

<210> SEQ ID NO 31
<211> LENGTH: 963
<212> TYPE: DNA
<213> ORGANISM: Artificial Sequence
<220> FEATURE:
<223> OTHER INFORMATION: cDNA of GAME31of Solanum tuberosum

<400> SEQUENCE: 31

| atggcatcta ccaaagttaa gattcccacc atagattttt ctaatctaga actaaaacca | 60 |
| aacactccac tatgggaatc cacaaaagtt caagttttg aagctttaaa agaatatggt | 120 |
| tgttttgaag caacatatga taaaattcca aatgaaatta gagagggtat ttttggtatt | 180 |
| acaaaagaaa tatttcaatt tcctttagag accaaagtga aaaattattc agatataaca | 240 |
| ttacatggct atgtaggaat gattccacac ttgccatttt atgagagttt gtgtattcct | 300 |
| gatttgctta atcctcaaaa tgttgaaact tttgctaata tcttttggcc tcatggtaat | 360 |
| cctgatttct gcaatttggt aaaagcttac tcaaatccac ttatggaatt ggatgaaatg | 420 |
| ttgaaaaaga tgattttgga gaatttggga ttagaaaatc atattgatga attgctggat | 480 |
| attaattata tgagatttag atttacacat tacaagggat catcaattat tagtggagat | 540 |
| catgaaaata tattaaaaca agatggattg aatggccaca cagatggtaa cttcttgact | 600 |
| tttatatcac aaaatcaagt caatggtttg caaatcaaca aaaatggaga gtggattgat | 660 |
| gtcaatattt caccaaattc ttatgttgtt ttgtctggtg attcattcaa agcatggaca | 720 |
| aatggtcgat tgcattctcc catccacaag gtaaaaatat ttggtgaaag tgatagattc | 780 |
| tcaattcaat tattttcatt ctcaaaacca ggtcacttta taaaggcccc aaaagaactt | 840 |

```
gtggatgaag aacaccctttt actcttcaag ccatttgaaa tggttggatt atctgagtat    900
gttacttccc aagctggcta tgcagctccc agtgatgctt tcaaggctta ttgtggtctt    960
tga                                                                  963
```

<210> SEQ ID NO 32
<211> LENGTH: 320
<212> TYPE: PRT
<213> ORGANISM: Solanum tuberosum

<400> SEQUENCE: 32

```
Met Ala Ser Thr Lys Val Lys Ile Pro Thr Ile Asp Phe Ser Asn Leu
1               5                   10                  15

Glu Leu Lys Pro Asn Thr Pro Leu Trp Glu Ser Thr Lys Val Gln Val
            20                  25                  30

Phe Glu Ala Leu Lys Glu Tyr Gly Cys Phe Glu Ala Thr Tyr Asp Lys
        35                  40                  45

Ile Pro Asn Glu Ile Arg Glu Gly Ile Phe Gly Ile Thr Lys Glu Ile
    50                  55                  60

Phe Gln Phe Pro Leu Glu Thr Lys Val Lys Asn Tyr Ser Asp Ile Thr
65                  70                  75                  80

Leu His Gly Tyr Val Gly Met Ile Pro His Leu Pro Phe Tyr Glu Ser
                85                  90                  95

Leu Cys Ile Pro Asp Leu Leu Asn Pro Gln Asn Val Glu Thr Phe Ala
            100                 105                 110

Asn Ile Phe Trp Pro His Gly Asn Pro Asp Phe Cys Asn Leu Val Lys
        115                 120                 125

Ala Tyr Ser Asn Pro Leu Met Glu Leu Asp Glu Met Leu Lys Lys Met
    130                 135                 140

Ile Leu Glu Asn Leu Gly Leu Glu Asn His Ile Asp Glu Leu Leu Asp
145                 150                 155                 160

Ile Asn Tyr Met Arg Phe Arg Phe Thr His Tyr Lys Gly Ser Ser Ile
                165                 170                 175

Ile Ser Gly Asp His Glu Asn Asn Ile Lys Gln Asp Gly Leu Asn Gly
            180                 185                 190

His Thr Asp Gly Asn Phe Leu Thr Phe Ile Ser Gln Asn Gln Val Asn
        195                 200                 205

Gly Leu Gln Ile Asn Lys Asn Gly Glu Trp Ile Asp Val Asn Ile Ser
    210                 215                 220

Pro Asn Ser Tyr Val Val Leu Ser Gly Asp Ser Phe Lys Ala Trp Thr
225                 230                 235                 240

Asn Gly Arg Leu His Ser Pro Ile His Lys Val Lys Ile Phe Gly Glu
                245                 250                 255

Ser Asp Arg Phe Ser Ile Gln Leu Phe Ser Phe Ser Lys Pro Gly His
            260                 265                 270

Phe Ile Lys Ala Pro Lys Glu Leu Val Asp Glu His Pro Leu Leu
        275                 280                 285

Phe Lys Pro Phe Glu Met Val Gly Leu Ser Glu Tyr Val Thr Ser Gln
    290                 295                 300

Ala Gly Tyr Ala Ala Pro Ser Asp Ala Phe Lys Ala Tyr Cys Gly Leu
305                 310                 315                 320
```

<210> SEQ ID NO 33
<211> LENGTH: 2345
<212> TYPE: DNA
<213> ORGANISM: Solanum tuberosum

<400> SEQUENCE: 33

```
gaaactttga agtctttctt gtttcctaaa tattcctcaa atggcatcta ccaaagttac    60
gattcccacc atagatttt gcgattctga gcttaaacca aacactccac aatgggaatc   120
aacaaaagtt caagttttg aagccttaca agaatttggt tgttttgaag caatatataa   180
caaagttcca aatgaaatta gagagggcat gtttgatact ttaaaagaag tatttgattt   240
tccactgccc aaattgatag aatatagaga gaaacccttt catatatatg atgggcaaat   300
tccaagtgta ccactctttg gtagtgtgta ctctgctgat ttggtcctcc caaatagtgt   360
tgaaacattt gccaatacct tttggtctca tggaaaccct aatttaggt atgcattact   420
tcttttcat taattatagg gagtcacgat agtgtaagat gcattaaaag gagaaacgtt   480
tcctagtaga attgtttcta ttcctagggc tagaatcagg aacctttagt taaattaata   540
gagataatat tcattccatc actaaaggtg aaaattaagt atcttatatt gtccataaat   600
tttatataga agagatgtga gaattaataa aataaaaatt aaaaactcac gagtaaacaa   660
aataattata tctaatttat attaataaag aagagtattt gattattata ttaagtcaaa   720
tgataagcta ataaatcaat attaacaatc taatcacatg atttatataa aattggttat   780
gggtatggga agggagggag ggaagtacat tcattgagg aacaatgcaa tagttagaca   840
ggatttaaca tacttgaaca agatatcata atctaaaatg attaaaaata attttttaat   900
attatctaca catcgcgcga atatatatat atatatatat taagtgtatt tcttaaataa   960
tattgtatta ctatttatat aaattttgta tgttttaatt ttgcagcaat gtggcaaagt  1020
cctacttcaa gcaacttatg gaattaaatg acatggttaa aaagatggtt ttggagagtc  1080
ttgggctaaa aaattacatt gatgaattct tgaattccaa tgtttatatg tcaagattta  1140
ctaattacaa ggtaattaaa ggtgaaaatg agaataaatc aggattaccct tcccacacag  1200
atagttccta cttgaccata attaaacaaa atcaaaatgg attgcaagtt ctctacaaaa  1260
atggagagtg gattgagctc aatcgtcaaa atggactgca agttctctac aaaaatggag  1320
agtggattga gctcaatcat acttcaccaa attcctatat tgttttatca gaagatgttt  1380
ttatggtaag ttattattta ttttttatta cagaagtcaa aaatacacct aaactttta  1440
tttatatgta ttttttgacgc ttaactcttt attttttgt gtgtagggt ggtttgttgc  1500
tatagtagag gagaataaaa gaaatagatt ttttttgtat gattgattat tcaagcccaa  1560
ctagaagcta agattagagg agttttgaag caacgaaaaa aaatgttgtg tgtgatttat  1620
agatattgat gcaggctcga tccgtgaaag aaatcactaa tatttatatt agattagatc  1680
gtttacctaa ctaaacatcc cttgaagtac tgcccttct ccaaaccata tgtgaacgtc  1740
aaatatttta tgcatcaacc tgtctttttt tatttggccc caactaactt caatccacat  1800
aaattattaa atcttgatat tagttggaat aacatatctc ttttctgaga aattgaaaat  1860
aatgccagaa ctatcataat ctttttttaa aaaattgtc ttgttattat cttattaatt  1920
taaaattttc tttcttcaga ggaaatttaa gtcaatcttt ttgttcctta attattaatt  1980
aaacaaataa attcttatac atacttttta tgtgttgatg ctatgaatta attatacagg  2040
catggacaaa tgatagattg acatctgctc aacacagggt tgtaacaaca ggagacaaag  2100
aaagattctc tattcaagtt ttttcctttc caaatccaga ttacactgtg aaggtcccac  2160
aagaattagt ggatgaagaa caccctttaa tgtacaagcc ttttaagatg tctgaatata  2220
ataaatatat tatgttaggt gctaaaaatg gattgggtgt caagaattat tgtggtctttt  2280
```

```
aaaaatttag tagctatgaa aatttattta tgtattgttt tgatgaataa aatgtatcag    2340
atggc                                                                2345
```

<210> SEQ ID NO 34
<211> LENGTH: 990
<212> TYPE: DNA
<213> ORGANISM: Artificial Sequence
<220> FEATURE:
<223> OTHER INFORMATION: cDNA of GAME31-like1of Solanum tuberosum

<400> SEQUENCE: 34

```
atggcatcta ccaaagttac gattcccacc atagattttt gcgattctga gcttaaacca     60
aacactccac aatgggaatc aacaaaagtt caagtttttg aagccttaca agaatttggt    120
tgttttgaag caatatataa caaagttcca aatgaaatta gagagggcat gtttgatact    180
ttaaaagaag tatttgattt tccactgccc aaattgatag aatatagaga gaacccttt    240 catatatatg atgggcaaat tccaagtgta ccactctttg gtagtgtgta ctctgctgat    300
ttggtcctcc caaatagtgt tgaaacattt gccaatacct tttggtctca tggaaacccct   360 aattttagca atgtggcaaa gtcctacttc aagcaactta tggaattaaa tgacatggtt    420
aaaaagatgg ttttggagag tcttgggcta aaaaattaca ttgatgaatt cttgaattcc   480
aatgtttata tgtcaagatt tactaattac aaggtaatta aggtgaaaa tgagaataaa    540 tcaggattac cttcccacac agatagttcc tacttgacca taattaaaca aaatcaaaat    600
ggattgcaag ttctctacaa aaatggagag tggattgagc tcaatcgtca aaatggactg    660
caagttctct acaaaaatgg agagtggatt gagctcaatc atacttcacc aaattcctat   720
attgttttat cagaagatgt ttttatggca tggacaaatg atagattgac atctgctcaa    780
cacagggttg taacaacagg agacaaagaa agattctcta ttcaagtttt ttcctttcca    840
aatccagatt acactgtgaa ggtcccacaa gaattagtgg atgaagaaca ccctttaatg    900
tacaagccct ttaagatgtc tgaatataat aaatatatta tgttaggtgc taaaaatgga    960
ttgggtgtca agaattattg tggtctttaa                                     990
```

<210> SEQ ID NO 35
<211> LENGTH: 329
<212> TYPE: PRT
<213> ORGANISM: Solanum tuberosum

<400> SEQUENCE: 35

```
Met Ala Ser Thr Lys Val Thr Ile Pro Thr Ile Asp Phe Cys Asp Ser
1               5                   10                  15

Glu Leu Lys Pro Asn Thr Pro Gln Trp Glu Ser Thr Lys Val Gln Val
            20                  25                  30

Phe Glu Ala Leu Gln Glu Phe Gly Cys Phe Glu Ala Ile Tyr Asn Lys
        35                  40                  45

Val Pro Asn Glu Ile Arg Glu Gly Met Phe Asp Thr Leu Lys Glu Val
    50                  55                  60

Phe Asp Phe Pro Leu Pro Lys Leu Ile Glu Tyr Arg Glu Lys Pro Phe
65                  70                  75                  80

His Ile Tyr Asp Gly Gln Ile Pro Ser Val Pro Leu Phe Gly Ser Val
                85                  90                  95

Tyr Ser Ala Asp Leu Val Leu Pro Asn Ser Val Glu Thr Phe Ala Asn
            100                 105                 110

Thr Phe Trp Ser His Gly Asn Pro Asn Phe Ser Asn Val Ala Lys Ser
        115                 120                 125
```

```
Tyr Phe Lys Gln Leu Met Glu Leu Asn Asp Met Val Lys Met Val
        130                 135                 140
Leu Glu Ser Leu Gly Leu Lys Asn Tyr Ile Asp Glu Phe Leu Asn Ser
145                 150                 155                 160
Asn Val Tyr Met Ser Arg Phe Thr Asn Tyr Lys Val Ile Lys Gly Glu
                165                 170                 175
Asn Glu Asn Lys Ser Gly Leu Pro Ser His Thr Asp Ser Ser Tyr Leu
            180                 185                 190
Thr Ile Ile Lys Gln Asn Gln Asn Gly Leu Gln Val Leu Tyr Lys Asn
            195                 200                 205
Gly Glu Trp Ile Glu Leu Asn Arg Gln Asn Gly Leu Gln Val Leu Tyr
210                 215                 220
Lys Asn Gly Glu Trp Ile Glu Leu Asn His Thr Ser Pro Asn Ser Tyr
225                 230                 235                 240
Ile Val Leu Ser Glu Asp Val Phe Met Ala Trp Thr Asn Asp Arg Leu
                245                 250                 255
Thr Ser Ala Gln His Arg Val Val Thr Thr Gly Asp Lys Glu Arg Phe
                260                 265                 270
Ser Ile Gln Val Phe Ser Phe Pro Asn Pro Asp Tyr Thr Val Lys Val
            275                 280                 285
Pro Gln Glu Leu Val Asp Glu Glu His Pro Leu Met Tyr Lys Pro Phe
290                 295                 300
Lys Met Ser Glu Tyr Asn Lys Tyr Ile Met Leu Gly Ala Lys Asn Gly
305                 310                 315                 320
Leu Gly Val Lys Asn Tyr Cys Gly Leu
                325

<210> SEQ ID NO 36
<211> LENGTH: 1897
<212> TYPE: DNA
<213> ORGANISM: Solanum tuberosum

<400> SEQUENCE: 36
ttattatttg cacaaaaaat acaaacaaag catgaattcc catcgaaatt actcactgtt      60
acaacaattc aaacataaga tacacactac taaagaaaca cgaatttcga caagcattct     120
gttagaaatc ccatatatac ttacagtatt ctaacaagaa cgttcataaa aaaatcacgt     180
ttttttattc tagcatatat aaaacaaaga actctaaagc taaagataca cactattata     240
aaaacacgaa ttccaaatga aatccattgg aaatgatgaa acattttcg atgaatattc      300
tgttagaaat cccaaatata ctaacagtac tctgacaaaa atgttcatta gaaattcacg     360
tttatcatat caaagaccac aataagcctt gaaagcatca ctgggagctg catagccagc     420
ttgggaagta acatactcag ataatccaac catttcaaat ggcttgaaga gtaaagggtg     480
ttcttcatcc acaagttctt tggggccctt tataaagtga cctggttttg agaatgaaaa     540
taattgaatt gagaatctat cactttcacc aaatattttt accttgtgga tgggagaatg     600
caatcgacca tttgtccatg cctgtataaa ttcacgtcgt cagtgcataa aactcaaaca     660
catttatttg aaggatccaa catttttaga gattcaaaaa gcatagactc caacaaatat     720
caaaattcat ttttcagttt tgcatgaaaa tattaaatat gtaggtagtt ccatttaata     780
ttcgagaaac ataggttaat ccaacaaat atgaagattc attttcaatt ttgcatcaag      840
atattaaacc taaattttgt ttggtatatt ccaaccttgg aaatattctt cacaaatatc     900
gttaggtatg cgtcagatcc tctaaaatct atattttgtt tttgaaggtg caataataat     960
```

```
attttttgaag agttcgagta acatggattt caacaaagta atatgactag ctaaaaaaat    1020
aaaatgagta acacttactt tgaatgaatc accagacaaa acaacataag aatttggtga    1080
aatattgaca tcaatccact ctccattttt gttgatttgc aaaccattga cttgattttg    1140
tgatataaaa gtcaagaagt taccatctgt gtggccattc aatccatctt gtttaatatt    1200
attttcatga tctccactaa taattgatga tcccttgtaa tgtgtaaatc taaatctcat    1260
ataattaata tccagcaatt catcaatatg attttctaat cccaaattct ccaaaatcat    1320 cttttttcaac atttcatcca attccataag tggatttgag taagctttta ccaaattgct    1380
gcaaaaattt atcactatct caaaaataac tttctcgcta ctccacgact ctaatcaatg    1440
cacaaaataa ttttatttta aaaaataaaa taaagtagac ataccagaaa tcaggattac    1500
catgaggcca aaagtatatta gcaaaagttt caacattttg aggattaagc aaatcaggaa    1560
tacacaaact ctcataaaat ggcaagtgtg gaatcattcc tacatagcca tgtaatgtta    1620
tatctgaata attttttcact ttggtctcta aaggaaattg aaatatttct tttgtaatac    1680
caaaaatacc ctctctaatt tcatttggaa ttttatcata tgttgcttca aaacaaccat    1740
attcttttaa agcttcaaaa acttgaactt tgtggattc ccatagtgga gtgtttggtt    1800
ttagttctag attagaaaaa tctatggtgg gaatcttaac tttggtagat gccatttgaa    1860
agaaacaaag aaggaattaa agacttcaca atgtgaa                             1897

<210> SEQ ID NO 37
<211> LENGTH: 339
<212> TYPE: DNA
<213> ORGANISM: Artificial Sequence
<220> FEATURE:
<223> OTHER INFORMATION: cDNA of GAME31-like2of Solanum tuberosum

<400> SEQUENCE: 37
atgattccac acttgccatt ttatgggagt ttgtgtattc ctgatttgct taatcctcaa      60
aatgttgaaa cttttgctaa tatcttttgg cctcatggta atcctgattt ctgcaatttg     120
gtaaaagctt actcaaatcc acttatgaa ttggatgaat tgttgaaaag gatgattttg     180
gagaatttgg gattagaaaa tcatattgat gaattgttgg atcctaatta tatgagattt     240
agatttacac attacaaggg atcatcaatt attagtggag atcatgaaaa taatattaaa     300
catgatggat tgaatgccac acagatggta gcttcttga                            339

<210> SEQ ID NO 38
<211> LENGTH: 112
<212> TYPE: PRT
<213> ORGANISM: Solanum tuberosum

<400> SEQUENCE: 38

Met Ile Pro His Leu Pro Phe Tyr Gly Ser Leu Cys Ile Pro Asp Leu
1               5                   10                  15

Leu Asn Pro Gln Asn Val Glu Thr Phe Ala Asn Ile Phe Trp Pro His
            20                  25                  30

Gly Asn Pro Asp Phe Cys Asn Leu Val Lys Ala Tyr Ser Asn Pro Leu
        35                  40                  45

Met Glu Leu Asp Glu Leu Leu Lys Arg Met Ile Leu Glu Asn Leu Gly
    50                  55                  60

Leu Glu Asn His Ile Asp Glu Leu Leu Asp Pro Asn Tyr Met Arg Phe
65                  70                  75                  80

Arg Phe Thr His Tyr Lys Gly Ser Ser Ile Ile Ser Gly Asp His Glu
```

```
                    85                  90                  95
Asn Asn Ile Lys His Asp Gly Leu Asn Ala Thr Gln Met Val Ala Ser
            100                 105                 110

<210> SEQ ID NO 39
<211> LENGTH: 3623
<212> TYPE: DNA
<213> ORGANISM: Solanum tuberosum
<220> FEATURE:
<221> NAME/KEY: misc_feature
<222> LOCATION: (677)..(1284)
<223> OTHER INFORMATION: n is a, c, g, or t
<220> FEATURE:
<221> NAME/KEY: misc_feature
<222> LOCATION: (1884)..(1901)
<223> OTHER INFORMATION: n is a, c, g, or t

<400> SEQUENCE: 39
attttttaat aaaaataata cagtacaata cattacaata caacgcaaca caatacaata     60
cgttatgtaa tcatatgcaa taaccattca aatataaatt ttcaaccacc catacatacg    120
atacatttta ttcataaaga aaatacacat atataaattt tcataccota caaaaatttt    180
aaagaccaca ataattcttg agattaattc catttttatc acctgacata gtttatttat    240
gaaattcaag caagttaaaa ggcttgaaga gtaaagggtg gtcttcatcc actaattctt    300
ttggggtcct tcacagtata atctggatgt ggtatggaaa ataattgaat agataatcta    360
tctttgtctc ctgttggtac tactctgtgt tcagcagatg tcaaactatt atttgtccat    420
gcctgtataa atccacaaca tcgacacata aaaagcatta gtgatttctt tcacagagaa    480
agggcagcac ctcaagggga tgttaggaaa acaatctaat ctaatagaaa atattagtga    540
tttttttctcg atcaagcccg catcgtaatc tatatatcac atacaaacaa tcttatcgtt    600
acttcaaaac tgctctgatc ttagcttcta gttgggctta ataatcaac catacaaaaa    660
aaatctctat ttctttnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnnnnnnnn nnnnnnnnnn nnnnnnnnnn nnnnnnnnnn   1260
nnnnnnnnnn nnnnnnnnnn nnnnggtgtg tttggtacga aggaaaatat ttctggaaa    1320
atgttttta atttcccatg tttggttgac tttaattatt tggaaaatgt tttccaaatc    1380
aacttatttt cctcaaattt aaggaaaatg atttccctta aaattaagg aaaacatttt    1440
cgaaacttct acttcatcct taaattataa tattttttta ccctactac caaaccagcc    1500
cgccaccoct gtcaaatttt attttattta aaaaattact tttgaaaaat atttcagggt   1560
cggaagtttg gctggggtcc taggtcagat ctctaggtcg gattttgaac ggtcatcaag   1620
gtcatgtcct agttcgggtg ttagggtcgg gtcctagatt gattattggg attgattttc    1680
gagttaaaag ttatttttcct aaagagtatt ttctagtctt aagcgaaaaa taaaagatat   1740
```

| | |
|---|---|
| tttctggaaa aaaaattcat tcaccaacca aacattaaaa aatagtttct actcatcaac | 1800 |
| taaatatgag aaaataagtt agaaatccac ttgttttcca agaaaacatt ttccttcata | 1860 |
| ccaaacacac ccttaatata tatnnnnnnn nnnnnnnnnn nttatatatg tatagatagc | 1920 |
| tagtatacat actcgagcga tgtgcggaaa atattaatat gttatttta atcttacccc | 1980 |
| tacccatgcc cctacccgac cttccccatt caaaaaaata aattaaaatt tttaaaattt | 2040 |
| caaatatatt tttatcacta ccaccaaact agctcccccg cccccctccc ctcaaacata | 2100 |
| aaaaaaaaaa attaaaatta tttttgaaaa atttttaaat cttaaatttt ttttacctca | 2160 |
| ccaaccccta ccaccctac tcccttcccc ctcattttta atttcccatg tttggttgac | 2220 |
| tttaatgatt tggaaaatgt tttccaaatc aacttatttt cctcaaattt aaggaaaatg | 2280 |
| attatcctaa aagttatttt cctaaagagt attttctagt ctcaagagaa aataaaagat | 2340 |
| attttttcag aaaataattt tcattcacca accaaacatg agaaaataag ttagaaatcc | 2400 |
| acttgttttc caagaaaaca ttttccttca taccaaacac accccttaata tataatgtat | 2460 |
| atatacctag tatacatact cgcgtgatgt gtgaaaaata ttttaaatgtt attttaaatc | 2520 |
| attttagatt gtgatatctt gttcgagcat gttaaatcac gtccaactat tgcattgtta | 2580 |
| ctcaatgaaa tgtactcccc tccatcectt cacataccog taaccaattc tatatgaata | 2640 |
| gcgacaatga atcatgtgat tagattgtta gtattgattt tattagctta tcacttggat | 2700 |
| ataattatta aatactcttc taattaatat aaattagata tatttattt gtttactcgt | 2760 |
| gagttcttaa ttttattt attaatgatc acatctcttt tatataaaat gtatggacaa | 2820 |
| taagatactt aattttcacc tttagtgatg gaatgaatat tatctctata atttaactaa | 2880 |
| agattcatga ttctagccttt aggaataaaa acaattctag taggaaacgt ttctccttt | 2940 |
| aatgtgtctt acactatcgt gactccatat tattaatctg aatcccaaaa taaataccga | 3000 |
| atacataatg aaaaaaaaa aatctcctac aaatatatga gcaagaataa ttggtgtact | 3060 |
| aacatgacta aaactaaatg atatcaccta cataaatctt attcttccaa atatcattaa | 3120 |
| tgaaaatga ctttcataat accgagcaca ttatatgtaa ttaaaagaag taatacatac | 3180 |
| ctaaagttag ggtttccatc agaccaaaag gtattggcaa atgttcaat actatttggg | 3240 |
| aggaccaaat cagcagagct cacactacca tagagtggta tacttggaat tttcccatca | 3300 |
| tatatatgaa agggttttc tctatattct atcaatttgg acaatggaaa atcaaatact | 3360 |
| tcttttaaat tatcaaacat gccctctcta atttcatttg gaactttgtc atatattgct | 3420 |
| tcaaacaac caaattcttt taaggcttca aaaacttgaa cttttgttga ttcccattgt | 3480 |
| ggagtgttg gttttagctc aagattgcaa aaatctatgg tgggaatctt acctttagta | 3540 |
| gatgccattg atgaataaat taaaagaga ggaaatagaa agaaataaag aaggagaaat | 3600 |
| actttacaat atgaaaatta aag | 3623 |

<210> SEQ ID NO 40
<211> LENGTH: 432
<212> TYPE: DNA
<213> ORGANISM: Artificial Sequence
<220> FEATURE:
<223> OTHER INFORMATION: cDNA of GAME31-like3of Solanum tuberosum

<400> SEQUENCE: 40

| | |
|---|---|
| atggcatcta ctaaaggtaa gattcccacc atagattttt gcaatcttga gctaaaacca | 60 |
| aacactccac aatgggaatc aacaaaagtt caagttttg aagccttaaa agaatttggt | 120 |
| tgttttgaag caatatatga caaagttcca aatgaaatta gagagggcat gtttgataat | 180 |

```
ttaaaagaag tatttgattt tccattgtcc aaattgatag aatatagaga aaaacccttt    240
catatatatg atgggaaaat tccaagtata ccactctatg gtagtgtgag ctctgctgat    300
ttggtcctcc caaatagtgt tgaaacattt gccaatacct tttggtctga tggaaaccct    360
aactttaggt atgtattact tcttttaatt atatataatg tgcttggtat tatgaaagtc    420
atttttcatt aa                                                        432

<210> SEQ ID NO 41
<211> LENGTH: 143
<212> TYPE: PRT
<213> ORGANISM: Solanum tuberosum

<400> SEQUENCE: 41

Met Ala Ser Thr Lys Gly Lys Ile Pro Thr Ile Asp Phe Cys Asn Leu
1               5                   10                  15

Glu Leu Lys Pro Asn Thr Pro Gln Trp Glu Ser Thr Lys Val Gln Val
            20                  25                  30

Phe Glu Ala Leu Lys Glu Phe Gly Cys Phe Glu Ala Ile Tyr Asp Lys
        35                  40                  45

Val Pro Asn Glu Ile Arg Glu Gly Met Phe Asp Asn Leu Lys Glu Val
    50                  55                  60

Phe Asp Phe Pro Leu Ser Lys Leu Ile Glu Tyr Arg Glu Lys Pro Phe
65                  70                  75                  80

His Ile Tyr Asp Gly Lys Ile Pro Ser Ile Pro Leu Tyr Gly Ser Val
                85                  90                  95

Ser Ser Ala Asp Leu Val Leu Pro Asn Ser Val Glu Thr Phe Ala Asn
            100                 105                 110

Thr Phe Trp Ser Asp Gly Asn Pro Asn Phe Arg Tyr Val Leu Leu Leu
        115                 120                 125

Leu Ile Ile Tyr Asn Val Leu Gly Ile Met Lys Val Ile Phe His
    130                 135                 140

<210> SEQ ID NO 42
<211> LENGTH: 2345
<212> TYPE: DNA
<213> ORGANISM: Solanum tuberosum

<400> SEQUENCE: 42
gaaactttga agtctttctt gtttcctaaa tattcctcaa atggcatcta ccaaagttac     60
gattcccacc atagatttt gcgattctga gcttaaacca aacactccac aatgggaatc    120
aacaaaagtt caagttttg aagccttaca agaatttggt tgttttgaag caatatataa    180
caaagttcca aatgaaatta gagagggcat gtttgatact ttaaaagaag tatttgattt    240
tccactgccc aaattgatag aatatagaga gaaacccttt catatatatg atgggcaaat    300
tccaagtgta ccactctttg gtagtgtgta ctctgctgat ttggtcctcc caaatagtgt    360
tgaaacattt gccaatacct tttggtctca tggaaaccct aatttaggt atgcattact    420 tcttttcat taattatagg gagtcacgat agtgtaagat gcattaaaag gagaaacgtt    480
tcctagtaga attgtttcta ttcctagggc tagaatcagg aacctttagt taaattaata    540
gagataatat tcattccatc actaaaggtg aaaattaagt atcttatatt gtccataaat    600
tttatataga agagatgtga gaattaataa aataaaaatt aaaaactcac gagtaaacaa    660
aataattata tctaatttat attaataaag aagagtattt gattattata ttaagtcaaa    720
tgataagcta ataaatcaat attaacaatc taatcacatg atttatataa aattggttat    780
```

| | |
|---|---|
| gggtatggga agggagggag ggaagtacat ttcattgagg aacaatgcaa tagttagaca | 840 |
| ggatttaaca tacttgaaca agatatcata atctaaaatg attaaaaata attttttaat | 900 |
| attatctaca catcgcgcga atatatatat atatatatat taagtgtatt tcttaaataa | 960 |
| tattgtatta ctatttatat aaattttgta tgttttaatt ttgcagcaat gtggcaaagt | 1020 |
| cctacttcaa gcaacttatg gaattaaatg acatggttaa aaagatggtt ttggagagtc | 1080 |
| ttgggctaaa aaattacatt gatgaattct tgaattccaa tgtttatatg tcaagattta | 1140 |
| ctaattacaa ggtaattaaa ggtgaaaatg agaataaatc aggattacct tcccacacag | 1200 |
| atagttccta cttgaccata attaaacaaa atcaaaatgg attgcaagtt ctctacaaaa | 1260 |
| atggagagtg gattgagctc aatcgtcaaa atggactgca agttctctac aaaaatggag | 1320 |
| agtggattga gctcaatcat acttcaccaa attcctatat tgttttatca gaagatgttt | 1380 |
| ttatggtaag ttattattta ttttttatta cagaagtcaa aaatacacct aaactttta | 1440 |
| tttatatgta tttttgacgc ttaactcttt attttttgt gtgtaggggt ggtttgttgc | 1500 |
| tatagtagag gagaataaaa gaaatagatt ttttttgtat gattgattat tcaagcccaa | 1560 |
| ctagaagcta agattagagg agttttgaag caacgaaaaa aaatgttgtg tgtgattat | 1620 |
| agatattgat gcaggctcga tccgtgaaag aaatcactaa tatttatatt agattagatc | 1680 |
| gtttacctaa ctaaacatcc cttgaagtac tgccctttct ccaaaccata tgtgaacgtc | 1740 |
| aaatatttta tgcatcaacc tgtctttttt tatttggccc caactaactt caatccacat | 1800 |
| aaattattaa atcttgatat tagttggaat aacatatctc ttttctgaga aattgaaaat | 1860 |
| aatgccagaa ctatcataat cttttttaa aaaaattgtc ttgttattat cttattaatt | 1920 |
| taaaattttc tttcttcaga ggaaatttaa gtcaatcttt ttgttcctta attattaatt | 1980 |
| aaacaaataa attcttatac atacttttta tgtgttgatg ctatgaatta attatacagg | 2040 |
| catggacaaa tgatagattg acatctgctc aacacagggt tgtaacaaca ggagacaaag | 2100 |
| aaagattctc tattcaagtt ttttcctttc caaatccaga ttacactgtg aaggtcccac | 2160 |
| aagaattagt ggatgaagaa caccctttaa tgtacaagcc ttttaagatg tctgaatata | 2220 |
| ataaatatat tatgttaggt gctaaaaatg gattgggtgt caagaattat tgtggtcttt | 2280 |
| aaaaatttag tagctatgaa aatttattta tgtattgttt tgatgaataa aatgtatcag | 2340 |
| atggc | 2345 |

<210> SEQ ID NO 43
<211> LENGTH: 852
<212> TYPE: DNA
<213> ORGANISM: Artificial Sequence
<220> FEATURE:
<223> OTHER INFORMATION: cDNA of GAME31-like4of Solanum tuberosum

<400> SEQUENCE: 43

| | |
|---|---|
| atggcatcta ccaaagttac gattcccacc atagattttt gcgattctga gcttaaacca | 60 |
| aacactccac aatgggaatc aacaaaagtt caagtttttg aagccttaca agaatttggt | 120 |
| tgttttgaag caatatataa caaagttcca aatgaaatta gagagggcat gtttgatact | 180 |
| ttaaaagaag tatttgattt tccactgccc aaattgatag aatatagaga gaaccctttt | 240 |
| catatatatg atgggcaaat tccaagtgta ccactctttg gtagtgtgta ctctgctgat | 300 |
| ttggtcctcc caaatagtgt tgaaacattt gccatacct tttggtctca tggaaaccct | 360 |
| aattttagca atgtggcaaa gtcctacttc aagcaactta tggaattgaa tgacatggtg | 420 |

| gaaaagatgg | ttttggagag | tcttgggcta | aaaaattaca | ctgatgaatt | cttgaattcc | 480 |
| aatgtttata | tgtcaagatt | tactaattac | aaggtaatta | aaggtgaaaa | tgagaataaa | 540 |
| tcagcattac | cttcacacac | agatagttcc | tacttgacca | taattaaaca | aaatcaaaat | 600 |
| ggattgcaag | catggacaaa | tgatagattg | acatctgctc | aacacagggt | tgtaacaaca | 660 |
| ggagacaaag | atagattctc | tgttcaatta | ttttccctcc | taaatccaga | ttatactgtg | 720 |
| aaggtcccaa | aagaattagt | ggatgaagaa | caccctttaa | tgtacaagcc | ttttaagatg | 780 |
| cctgaatata | ataaatatct | tatgttaggt | gctaaaaatg | gattgggtgt | caagaattat | 840 |
| tgtggtcttt | aa | | | | | 852 |

<210> SEQ ID NO 44
<211> LENGTH: 168
<212> TYPE: PRT
<213> ORGANISM: Solanum tuberosum

<400> SEQUENCE: 44

Met Ile Ser Cys Ser Gly Leu Lys Asn Tyr Ile Asp Glu Phe Leu Asn
1               5                   10                  15
Ser Asn Val Phe Met Ser Arg Phe Thr Asn Tyr Arg Val Ile Lys Gly
            20                  25                  30
Glu Asn Glu Asn Lys Ser Ala Leu Pro Ser His Thr Asp Ser Ser Tyr
        35                  40                  45
Leu Thr Ile Ile Lys Gln Asn Gln Asn Gly Leu Gln Val Leu Tyr Lys
    50                  55                  60
Asn Gly Glu Trp Ile Glu Leu Asn His Thr Ser Pro Asn Ser Tyr Ile
65                  70                  75                  80
Val Leu Ser Glu Asp Val Phe Met Ala Trp Thr Asn Asp Arg Leu Thr
                85                  90                  95
Ser Ala Gln His Arg Val Val Thr Thr Gly Asp Lys Asp Arg Phe Ser
            100                 105                 110
Ile Gln Val Phe Ser Phe Pro Asn Pro Asp Tyr Thr Val Lys Val Pro
        115                 120                 125
Gln Glu Leu Val Asp Glu Glu His Pro Leu Met Phe Lys Pro Phe Lys
    130                 135                 140
Leu Pro Glu Phe Asn Lys Tyr Ile Lys Leu Gly Ala Lys Asn Gly Pro
145                 150                 155                 160
Gly Leu Lys Asn Tyr Cys Gly Phe
                165

<210> SEQ ID NO 45
<211> LENGTH: 2345
<212> TYPE: DNA
<213> ORGANISM: Solanum tuberosum

<400> SEQUENCE: 45

| gaaactttga | agtctttctt | gtttcctaaa | tattcctcaa | atggcatcta | ccaaagttac | 60 |
| gattcccacc | atagattttt | gcgattctga | gcttaaacca | acactccac | aatgggaatc | 120 |
| aacaaaagtt | caagttttg | aagccttaca | agaatttggt | tgttttgaag | caatatataa | 180 |
| caaagttcca | atgaaatta | gagagggcat | gtttgatact | ttaaaagaag | tatttgattt | 240 |
| tccactgccc | aaattgatag | aatatagaga | gaaacccttt | catatatatg | atgggcaaat | 300 |
| tccaagtgta | ccactctttg | gtagtgtgta | ctctgctgat | ttggtcctcc | caaatagtgt | 360 |
| tgaaacattt | gccaatacct | tttggtctca | tggaaaccct | aattttaggt | atgcattact | 420 |

-continued

```
tcttttcat taattatagg gagtcacgat agtgtaagat gcattaaaag gagaaacgtt      480
tcctagtaga attgtttcta ttcctagggc tagaatcagg aacctttagt taaattaata      540
gagataatat tcattccatc actaaaggtg aaaattaagt atcttatatt gtccataaat      600
tttatataga agagatgtga gaattaataa aataaaaatt aaaaactcac gagtaaacaa      660
aataattata tctaatttat attaataaag aagagtattt gattattata ttaagtcaaa      720
tgataagcta ataaatcaat attaacaatc taatcacatg atttatataa aattggttat      780
gggtatggga agggagggag ggaagtacat tcattgagg aacaatgcaa tagttagaca      840
ggatttaaca tacttgaaca agatatcata atctaaaatg attaaaaata attttttaat      900
attatctaca catcgcgcga atatatatat atatatatat taagtgtatt tcttaaataa      960
tattgtatta ctatttatat aaattttgta tgttttaatt ttgcagcaat gtggcaaagt     1020
cctacttcaa gcaacttatg gaattaaatg acatggttaa aaagatggtt ttggagagtc     1080
ttgggctaaa aaattacatt gatgaattct tgaattccaa tgtttatatg tcaagattta     1140
ctaattacaa ggtaattaaa ggtgaaaatg agaataaatc aggattacct tcccacacag     1200
atagttccta cttgaccata attaaacaaa atcaaaatgg attgcaagtt ctctacaaaa     1260
atggagagtg gattgagctc aatcgtcaaa atggactgca agttctctac aaaaatggag     1320
agtggattga gctcaatcat acttcaccaa attcctatat tgttttatca gaagatgttt     1380
ttatggtaag ttattattta ttttttatta cagaagtcaa aaatacacct aaactttta      1440 tttatatgta ttttgacgc ttaactcttt atttttttgt gtgtaggggt ggtttgttgc     1500
tatagtagag gagaataaaa gaaatagatt ttttttgtat gattgattat tcaagcccaa     1560
ctagaagcta agattagagg agttttgaag caacgaaaaa aaatgttgtg tgtgatttat     1620
agatattgat gcaggctcga tccgtgaaag aaatcactaa tatttatatt agattagatc     1680
gtttacctaa ctaaacatcc cttgaagtac tgccctttct ccaaaccata tgtgaacgtc     1740
aaatatttta tgcatcaacc tgtctttttt tatttggccc caactaactt caatccacat     1800
aaattattaa atcttgatat tagttggaat aacatatctc ttttctgaga aattgaaaat     1860
aatgccagaa ctatcataat cttttttaa aaaaattgtc ttgttattat cttattaatt     1920
taaaattttc tttcttcaga ggaaatttaa gtcaatcttt ttgttccttc attattaatt     1980
aaacaaataa attcttatac atactttta tgtgttgatg ctatgaatta attatacagg     2040
catggacaaa tgatagattg acatctgctc aacacagggt tgtaacaaca ggagacaaag     2100
aaagattctc tattcaagtt ttttcctttc caaatccaga ttacactgtg aaggtcccac     2160
aagaattagt ggatgaagaa cacccttaa tgtacaagcc ttttaagatg tctgaatata     2220
ataaatatat tatgttaggt gctaaaaatg gattgggtgt caagaattat tgtggtcttt     2280
aaaaatttag tagctatgaa aatttattta tgtattgttt tgatgaataa aatgtatcag     2340
atggc                                                                 2345
```

<210> SEQ ID NO 46
<211> LENGTH: 507
<212> TYPE: DNA
<213> ORGANISM: Artificial Sequence
<220> FEATURE:
<223> OTHER INFORMATION: cDNA of GAME31-like5of Solanum tuberosum

<400> SEQUENCE: 46

```
atgatatctt gttctgggct aaaaaattac attgatgaat tcttgaattc caatgttttt       60
atgtcaagat ttactaatta cagggtaatt aaaggtgaaa atgagaataa atcagcacta      120
```

```
ccttcccaca cagatagttc ctacttgacc ataattaaac aaaatcaaaa tggattgcaa        180
gttctctaca aaaatggaga gtggattgag ctcaatcata cttcaccaaa ttcctatatt        240
gttttatcag aagatgtttt tatggcatgg acaaatgata gattgacatc tgctcaacac        300
agggttgtaa caacaggaga caaagataga ttctctattc aagttttttc ctttccaaat        360
ccagattaca ctgtgaaggt cccacaagaa ttagtggatg aagaacaccc tttaatgttc        420
aagcctttta agttgcctga atttaataaa tatattaagt taggtgctaa aaatggaccg        480
ggtctcaaga attattgtgg tttttaa                                           507
```

```
<210> SEQ ID NO 47
<211> LENGTH: 168
<212> TYPE: PRT
<213> ORGANISM: Solanum tuberosum

<400> SEQUENCE: 47

Met Ile Ser Cys Ser Gly Leu Lys Asn Tyr Ile Asp Glu Phe Leu Asn
1               5                   10                  15

Ser Asn Val Phe Met Ser Arg Phe Thr Asn Tyr Arg Val Ile Lys Gly
            20                  25                  30

Glu Asn Glu Asn Lys Ser Ala Leu Pro Ser His Thr Asp Ser Ser Tyr
        35                  40                  45

Leu Thr Ile Ile Lys Gln Asn Gln Asn Gly Leu Gln Val Leu Tyr Lys
    50                  55                  60

Asn Gly Glu Trp Ile Glu Leu Asn His Thr Ser Pro Asn Ser Tyr Ile
65                  70                  75                  80

Val Leu Ser Glu Asp Val Phe Met Ala Trp Thr Asn Asp Arg Leu Thr
                85                  90                  95

Ser Ala Gln His Arg Val Val Thr Thr Gly Asp Lys Asp Arg Phe Ser
            100                 105                 110

Ile Gln Val Phe Ser Phe Pro Asn Pro Asp Tyr Thr Val Lys Val Pro
        115                 120                 125

Gln Glu Leu Val Asp Glu Glu His Pro Leu Met Phe Lys Pro Phe Lys
    130                 135                 140

Leu Pro Glu Phe Asn Lys Tyr Ile Lys Leu Gly Ala Lys Asn Gly Pro
145                 150                 155                 160

Gly Leu Lys Asn Tyr Cys Gly Phe
                165
```

```
<210> SEQ ID NO 48
<211> LENGTH: 2762
<212> TYPE: DNA
<213> ORGANISM: Solanum tuberosum

<400> SEQUENCE: 48
cactaatata tttttaataa aaacaataca gtacaataca ttacaataca acgcaacaca         60
acacaataca atacgttatg aaatcatatg caataaccac acaaatataa attttcaacc        120
acccatgcat acgatacatt gtattcataa agaaaataca cataaataaa taccctacta        180
aattttaaaa gaccacaata attcttgaga ttaattcaat ttttattacc tgacatagtt        240
tatttatgaa attcaagcaa gttaaaaggc ttgaagagta agggtggtct tcatccacta        300
attattttgg ggccttcaca gcaaaatctt gatttgggaa aggaaaataa ttgaatagat        360
agtctatctt tgtctcctgt tgttactact ctgtgttcag cagatgtcaa actatcattt        420
gtccatgcct gtataaatcc acaacatcga cacataaaaa gtattagtga tttcttttca        480
```

```
cagagaaagg gcaacacctc aagggatgtt aggaaaacaa tctaatctaa tacaaaatat    540
tagtgatttt ttctcgatca agcccgcatc gtaatctata aatcacatac aaacaatctt    600
atcgttactt caaaactgct ctgatcttag cttctagttg ggcttgaata atcaaccata    660
caaaaaaatc tctatttctt ttattctcct cttctatagc atcaacccac ccctcacac    720 acaaaataat aaagagttaa gcgtcaaaaa tacacataaa taaataattt aggtgtattt    780
tttaccttga tactcaaaaa taaataataa cttaccctga aagcatctgc tgataaaaca    840
atataggaat ttggtgttgt attattgagc tctatccact ctccatttt gtagagaact     900 tgcaatccat tttgattttg tttaattata gtcaagtagc cactatctgt gtggggaggt    960
aattctgatc tattctcatc ttcacccttta attaccttgt aattagtaaa tcttgacaca   1020
aaaacattgg aattcaagat ttcatcaatg taatttgttt tcccaagact ctccaaaacc    1080 atttttcca ccatgtcatt caattccata agttgcttga agtaggactt tgccacattg     1140
ctgccaaatt aaaacataca aaacttatat aatggtaatg caatattgtg atattactca    1200
aaattatgta agaaatacac ttagggtgtg tttggtacga aggaaaatat tttctagaaa    1260 atgttttta atttcccatg tttggttgac tttaatgatt tggaaaatgt tttccaaatc     1320
aacttatttt cctcaaattt aaggaaaatg attatcctaa aagttatttt cctaaagagt    1380
attttctagt cttaagtgaa aaataagtta gaaatccact tgttttccaa gaaaacattt    1440
tccttcatac caaacacacc cttaatatat aatgtatata tacctagtat acatactcgc    1500
gcgatgtgtg aaaaatattt aaatgttatt ttaatcattt tagattgtga tatcttgttc    1560
gagcatgtta aatcatgtcc aactattgca ttgttactca atgaaatgta ctcccctcca    1620
tcccttcaca tacccgtaac caattctata tgaatagcga tgtgtgaaaa atatttaaat    1680
gttattttta atcatttag attgtgatat cttgttcgag catgttaaat catgtccaac    1740
tattgcattg ttactcaatg aaatgtactc ccctccatcc cttcacatac ccgtaaccaa    1800
ttctatatga atagcgacaa tgaatcatgt gattagattg ttaatattga ttttattagc    1860
ttatcacttg gatataatta ttaaatactc ttctaattaa tataaattag atatatttat    1920
tttgtttact cgtgagttct taattttat tttattaatg atcacatctc ttttatataa     1980
aatgtatgga caataagata cttaattttc acctttagtg atggaatgaa tattatctct    2040
ataatttaac taaagattcc tgattctagc cttaggaata aaaacaattc tagtaggaaa    2100
cgtttctcct tttaatgtgt cttacactat cgtgactcca tattattaaa tctgaaatcc    2160
caaaaataaa taccgaatac ataatgaaaa aaaaaaaatc tcctacaaaa tatatgagca    2220 agataattg gtgtactaac atgactaaac taaatgatat cacctacata aatcttattc      2280
tttcaaatat cattaatgaa aaataacttt cataataccg aacacattat atataattaa    2340
aagaagtaat acatacctaa agttagggtt tccatcagac caaaaggtat tggcaaatgt    2400
ttcaacacta tttgggagga ccaaatcagc agagctcaca ctaccataga gtggtatact    2460
tggaatttgc ccatcatata aatggggttt ttctctatat tctatcaatt tggacactgg    2520
aaaatcaaat acttctttta aagtatcaaa catgccctct ctaatttcat ttggaacttt    2580
gtcatatatt gcttcaaaac aaccaaattc ttttaaggct tcaaaaactt gaactttgt    2640 tgattcccat tgtggagtgt ttggttttag ctcaagattg caaaaatcta tggtgggaat    2700
cttaactttg gtagatgcca ttgatgaata aattaaatag agaggaaata gaaagaaata    2760
aa                                                                  2762
```

<210> SEQ ID NO 49
<211> LENGTH: 828
<212> TYPE: DNA
<213> ORGANISM: Artificial Sequence
<220> FEATURE:
<223> OTHER INFORMATION: cDNA of GAME31-like6 of Solanum tuberosum

<400> SEQUENCE: 49

```
atggcatcta ccaaagttaa gattcccacc atagatttt gcaatcttga gctaaaacca      60
aacactccac aatgggaatc aacaaaagtt caagttttg aagccttaaa agaatttggt     120
tgttttgaag caatatatga caaagttcca atgaaatta gagagggcat gtttgatact     180
ttaaaagaag tatttgattt ccagtgtcc aaattgatag aatatagaga aaaccccat      240
ttatatgatg ggcaaattcc aagtatacca ctctatggta gtgtgagctc tgctgatttg     300
gtcctcccaa atagtgttga acatttgcc aatacctttt ggtctgatgg aaaccctaac     360
tttagcaatg tggcaaagtc ctacttcaag caacttatgg aattgaatga catggtggaa     420
aaaatggttt tggagagtct tgggaaaaca aattacattg atgaaatctt gaattccaat     480
gtttttgtgt caagatttac taattacaag gtaattaaag gtgaagatga aatagatca      540
gaattacctc cccacacaga tagtggctac ttgactataa ttaaacaaaa tcaaaatgga     600
ttgcaagttc tctacaaaaa tggagagtgg atagagctca ataatacaac accaaattcc     660
tatattgttt tatcagcaga tgctttcagg gcatggacaa atgatagttt gacatctgct     720
gaacacagag tagtaacaac aggagacaaa gatagactat ctattcaatt attttccttt     780
cccaaatcaa gattttgctg tgaaggcccc aaaataatta gtggatga                 828
```

<210> SEQ ID NO 50
<211> LENGTH: 275
<212> TYPE: PRT
<213> ORGANISM: Solanum tuberosum

<400> SEQUENCE: 50

```
Met Ala Ser Thr Lys Val Lys Ile Pro Thr Ile Asp Phe Cys Asn Leu
1               5                   10                  15

Glu Leu Lys Pro Asn Thr Pro Gln Trp Glu Ser Thr Lys Val Gln Val
            20                  25                  30

Phe Glu Ala Leu Lys Glu Phe Gly Cys Phe Glu Ala Ile Tyr Asp Lys
        35                  40                  45

Val Pro Asn Glu Ile Arg Glu Gly Met Phe Asp Thr Leu Lys Glu Val
    50                  55                  60

Phe Asp Phe Pro Val Ser Lys Leu Ile Glu Tyr Arg Glu Lys Pro His
65                  70                  75                  80

Leu Tyr Asp Gly Gln Ile Pro Ser Ile Pro Leu Tyr Gly Ser Val Ser
                85                  90                  95

Ser Ala Asp Leu Val Leu Pro Asn Ser Val Glu Thr Phe Ala Asn Thr
            100                 105                 110

Phe Trp Ser Asp Gly Asn Pro Asn Phe Ser Asn Val Ala Lys Ser Tyr
        115                 120                 125

Phe Lys Gln Leu Met Glu Leu Asn Asp Met Val Glu Lys Met Val Leu
    130                 135                 140

Glu Ser Leu Gly Lys Thr Asn Tyr Ile Asp Glu Ile Leu Asn Ser Asn
145                 150                 155                 160

Val Phe Val Ser Arg Phe Thr Asn Tyr Lys Val Ile Lys Gly Glu Asp
                165                 170                 175
```

```
Glu Asn Arg Ser Glu Leu Pro Pro His Thr Asp Ser Gly Tyr Leu Thr
            180                 185                 190

Ile Ile Lys Gln Asn Gln Asn Gly Leu Gln Val Leu Tyr Lys Asn Gly
        195                 200                 205

Glu Trp Ile Glu Leu Asn Asn Thr Thr Pro Asn Ser Tyr Ile Val Leu
    210                 215                 220

Ser Ala Asp Ala Phe Arg Ala Trp Thr Asn Asp Ser Leu Thr Ser Ala
225                 230                 235                 240

Glu His Arg Val Val Thr Thr Gly Asp Lys Asp Arg Leu Ser Ile Gln
                245                 250                 255

Leu Phe Ser Phe Pro Lys Ser Arg Phe Cys Cys Glu Gly Pro Lys Ile
            260                 265                 270

Ile Ser Gly
        275

<210> SEQ ID NO 51
<211> LENGTH: 1429
<212> TYPE: DNA
<213> ORGANISM: Solanum tuberosum

<400> SEQUENCE: 51
gcagcaatgt ggcaaagtcc tacttcaagc aacttatgga attgaatggc atggtggaaa      60
agatggtttt ggagagtctt gggctaaaaa attacattga tgaattcttg aattccaatg     120
tttatatgtc aagatttact aattacaagg taattaaagg tgaaatgag  aataaatcag     180
gattaccttc ccacacagat agttcctact tgaccataat taaacaaaat caaaatggat     240
tgcaagttct tctacaaaaa tggagagtgg attgagctca atcatacctc accaaattcc     300
tatattgttt tatcagcaga tgctcttatg gtaagttatt atttattttt gattacagca     360
gtcaaaaata cgcctaaact tctaatttat atgtattttt gacgctttaa ctcattatta     420
tttttgtgt gtgggtggt tgttgctat agtagaggag aataaagaa atagagattt     480
tttttgtatg attgattatt caagcccaac tagaagctaa gattagagga gttttcaacc     540
aacgaaaaaa atgtttgtgt gtgatttata tatcatgatg caggctcaat ccgtaaaaga     600
aatcactaat atttgtatta gattagattg tttacctaac taacatccct tgaagtgttg     660
cccttctcc aaaccctatg tgaacgtcaa atattttatg catcaacctg tcttattta     720
tttgacctca actaacttca atccacaaaa aatattaaat cttgatatta tttggaataa     780
cgtatctctt tttctggaaa attgaaaatg ataccagaac tatcataata atttttaaa     840
ttgtcttgtt attatcttat taattaaa ttttcattct ccataggaaa tttaagtcaa     900
tcttttgtt ccttaattat taattaaaca ataaattct tatacatact ttttatgtgt     960
tgatgatatg aattaattat acaggcatgg acaaatgata gattgacatc tgctcaacat    1020
agggttgtaa caacaggaga caaagataga ttctctgttc aattattttc cctcgtaaat    1080
ccagattata ctttgaaggt cccaaaagaa ttagtggatg aagaacaccc tttaatgtac    1140
aagccttta agatgcctga atataataaa tatcttatgt taggtgctaa aaatggattg    1200
ggtgtcaaga attattgtgg tcttaaaaa tttagtagct atgaaaattt atttatgtat    1260
tgttttgatg aataaaatgt atcagatggc tggttgaata ctttgaattt atatttggat    1320
ggttattacg tatgattgcg taaagtattg tattgtatt tattttgttg tgttgttttg    1380
tattgtgttg cgttgtatat attgttttga tgaataaaat atatgagtg                1429

<210> SEQ ID NO 52
```

```
<211> LENGTH: 339
<212> TYPE: DNA
<213> ORGANISM: Artificial Sequence
<220> FEATURE:
<223> OTHER INFORMATION: cDNA of GAME31-like7 of Solanum tuberosum

<400> SEQUENCE: 52
atggattgca agttcttcta caaaaatgga gagtggattg agctcaatca tacctcacca        60
aattcctata ttgttttatc agcagatgct cttatggcat ggacaaatga tagattgaca       120
tctgctcaac atagggttgt aacaacagga gacaaagata gattctctgt tcaattattt       180
tccctcgtaa atccagatta tactttgaag gtcccaaaag aattagtgga tgaagaacac       240
cctttaatgt acaagccttt taagatgcct gaatataata aatatcttat gttaggtgct       300
aaaaatggat tgggtgtcaa gaattattgt ggtctttaa                              339
```

```
<210> SEQ ID NO 53
<211> LENGTH: 112
<212> TYPE: PRT
<213> ORGANISM: Solanum tuberosum

<400> SEQUENCE: 53

Met Asp Cys Lys Phe Phe Tyr Lys Asn Gly Glu Trp Ile Glu Leu Asn
 1               5                  10                  15

His Thr Ser Pro Asn Ser Tyr Ile Val Leu Ser Ala Asp Ala Leu Met
            20                  25                  30

Ala Trp Thr Asn Asp Arg Leu Thr Ser Ala Gln His Arg Val Val Thr
        35                  40                  45

Thr Gly Asp Lys Asp Arg Phe Ser Val Gln Leu Phe Ser Leu Val Asn
    50                  55                  60

Pro Asp Tyr Thr Leu Lys Val Pro Lys Glu Leu Val Asp Glu Glu His
65                  70                  75                  80

Pro Leu Met Tyr Lys Pro Phe Lys Met Pro Glu Tyr Asn Lys Tyr Leu
                85                  90                  95

Met Leu Gly Ala Lys Asn Gly Leu Gly Val Lys Asn Tyr Cys Gly Leu
            100                 105                 110
```

```
<210> SEQ ID NO 54
<211> LENGTH: 55
<212> TYPE: DNA
<213> ORGANISM: Artificial Sequence
<220> FEATURE:
<223> OTHER INFORMATION: RF-Tomato-GAME31-Forward Primer

<400> SEQUENCE: 54
tccgcgggtg aaaacctgta cttccagggt gcatctatca aatcagttaa agttc            55
```

```
<210> SEQ ID NO 55
<211> LENGTH: 57
<212> TYPE: DNA
<213> ORGANISM: Artificial Sequence
<220> FEATURE:
<223> OTHER INFORMATION: RF-Tomato-GAME31-Reverse Primer

<400> SEQUENCE: 55
gtggtggtgc tcgagtgcgg ccgcaagctt tcaaacacca cataaatct tgaaaag           57
```

```
<210> SEQ ID NO 56
<211> LENGTH: 55
<212> TYPE: DNA
<213> ORGANISM: Artificial Sequence
<220> FEATURE:
```

```
<223> OTHER INFORMATION: RF-Eggplant-GAME31-Forward Primer

<400> SEQUENCE: 56
tccgcgggtg aaaacctgta cttccagggt ggatctacca aatcaattaa agttc        55

<210> SEQ ID NO 57
<211> LENGTH: 51
<212> TYPE: DNA
<213> ORGANISM: Artificial Sequence
<220> FEATURE:
<223> OTHER INFORMATION: RF-Eggplant-GAME31-Reverse Primer

<400> SEQUENCE: 57
gtggtggtgc tcgagtgcgg ccgcaagctt tcaaacacca caataagcct t            51

<210> SEQ ID NO 58
<211> LENGTH: 149
<212> TYPE: DNA
<213> ORGANISM: Artificial Sequence
<220> FEATURE:
<223> OTHER INFORMATION: SlGAME31-RNAi

<400> SEQUENCE: 58
gggtttcgtt ggaaattcgt cttgtttttt tttttcaagt agtgtacatc ttattttggg   60
attgttgatg ttgagcgcta atgtttaatt tgtttgtgtt ttgaagagga tgattatact   120
ctttaagagg attcaccgta atcttttag                                     149

<210> SEQ ID NO 59
<211> LENGTH: 966
<212> TYPE: DNA
<213> ORGANISM: Artificial Sequence
<220> FEATURE:
<223> OTHER INFORMATION: SlGAME31-Cosup

<400> SEQUENCE: 59
atggcatcta tcaaatcagt taaagttcct actatagatt tttccaatta tcaagagcta   60
aaaccaaaca ctccactatg ggaatccaca aaaattcaag ttttttgaagc tttacaagaa  120 tatggttgtt ttgaagcaat atatgataaa gtttcaaagg aaattagaga ggaaacattt   180
gatatgtcaa agaaatatt tgaatttcct ttagagacta aagtgaaaaa tatctcagaa    240
aaaccaatgc atggctatat ggggatgatt ccacaattgc cattgtatga gagtttgtgt   300
attcctgatt tgcttaatcc tcaaagtctt gaaaaatttt ctaatatctt ttggcctcag   360
ggtaatcaac atttctgcaa tttgataaaa tcttattcta atccacttgt ggaattggat   420
gggatgttga aaaggatgat ttcggagaat ttgggattga aaaatcacat tgatgaatta   480
ttgaatgcca attacttcct atttagattt acacattata agggatcatc aattgctagt   540
ggagatgaaa ataataaagc tgctggattg ggtggccaca cggatggtaa cttcttgact   600
tttatatcgc aaaatcaagt taatggattg caaatcaaca aaaatggaga atggattgat   660
gtgattattt caccaaattc ttacgttgtt ttggccggtg attccttcaa agcttggaca   720
aatggtcgat tgcattcacc tctccacaga gtaacaatgt ccggacaaaa tgatagactc   780
tccattcaat tgttttcatt atcaaagcca ggtcacttca tccaggcacc aaaagaacta   840
gtagatgaag aacacccatt actcttcaag ccatttgaaa ttcttgaatt attcaagtat   900
ggtaccacag aagctggcta tacagctcct ccaagtgatc ttttcaagat ttattgtggt   960
gtttga                                                             966
```

```
<210> SEQ ID NO 60
<211> LENGTH: 29
<212> TYPE: DNA
<213> ORGANISM: Artificial Sequence
<220> FEATURE:
<223> OTHER INFORMATION: qRT-PCR forward primer

<400> SEQUENCE: 60
agtacaagta atcacgttgg ttcctatga                                29

<210> SEQ ID NO 61
<211> LENGTH: 34
<212> TYPE: DNA
<213> ORGANISM: Artificial Sequence
<220> FEATURE:
<223> OTHER INFORMATION: qRT-PCR reverse primer

<400> SEQUENCE: 61
cactagaaag tttttactt tataggtgag gaaa                           34

<210> SEQ ID NO 62
<211> LENGTH: 35
<212> TYPE: DNA
<213> ORGANISM: Artificial Sequence
<220> FEATURE:
<223> OTHER INFORMATION: Cloning SlGAME31 for RNAi forward primer

<400> SEQUENCE: 62
aaaaagcggc cgcgggtttc gttggaaatt cgtct                         35

<210> SEQ ID NO 63
<211> LENGTH: 38
<212> TYPE: DNA
<213> ORGANISM: Artificial Sequence
<220> FEATURE:
<223> OTHER INFORMATION: Cloning SlGAME31 for RNAi reverse primer

<400> SEQUENCE: 63
aaaaaggcgc gccctaaaag attacggtga atcctctt                      38

<210> SEQ ID NO 64
<211> LENGTH: 55
<212> TYPE: DNA
<213> ORGANISM: Artificial Sequence
<220> FEATURE:
<223> OTHER INFORMATION: Cloning SlGAME31 for Cosupression forward
      primer

<400> SEQUENCE: 64
ggggacaagt ttgtacaaaa aagcaggcta tggcatctat caaatcagtt aaagt   55

<210> SEQ ID NO 65
<211> LENGTH: 54
<212> TYPE: DNA
<213> ORGANISM: Artificial Sequence
<220> FEATURE:
<223> OTHER INFORMATION: Cloning SlGAME31 for Cosupression reverse
      primer

<400> SEQUENCE: 65
ggggaccact ttgtacaaga aagctgggtt caaacaccac aataaatctt gaaa    54

<210> SEQ ID NO 66
<211> LENGTH: 259
<212> TYPE: PRT
<213> ORGANISM: S. lycopersicum
```

-continued

```
<400> SEQUENCE: 66

Met Ala Ser Lys Leu Arg Leu Glu Gly Lys Val Ala Ile Ile Thr Gly
1               5                   10                  15

Gly Ala Ser Gly Ile Gly Glu Ala Ser Ala Arg Leu Phe Val Gln His
            20                  25                  30

Gly Ala Arg Val Val Ala Asp Ile Gln Asp Glu Leu Gly Leu Gln
        35                  40                  45

Val Val Gln Ser Ile Gly Ile His Lys Ala Thr Tyr Arg His Cys Asp
    50                  55                  60

Val Thr Asp Glu Lys Gln Val Glu Asp Thr Val Ala Tyr Ala Val Gln
65                  70                  75                  80

Lys Tyr Ala Thr Leu Asp Ile Met Phe Ser Asn Val Gly Thr Leu Asn
                85                  90                  95

Phe Cys Ser Val Leu Asp Met Asp Met Thr Ala Phe Asp Glu Thr Met
            100                 105                 110

Thr Val Asn Val Arg Gly Ser Ala Leu Ala Val Lys His Ala Ala Arg
        115                 120                 125

Val Met Val Asp Lys Lys Ile Arg Gly Ser Ile Ile Cys Asn Val Ser
    130                 135                 140

Leu Glu Gly Ile Leu Ala Gly Ala Ala Ser Leu Ala Tyr Ile Ala Ser
145                 150                 155                 160

Lys His Ala Val Val Gly Ile Val Lys Ala Ala Arg Glu Leu Gly
                165                 170                 175

Pro Tyr Gly Ile Arg Val Asn Gly Val Ser Pro Tyr Gly Ile Ala Thr
            180                 185                 190

Pro Leu Val Cys Lys Ala Tyr Gly Leu Asp Ala Ala Pro Leu Glu Ala
        195                 200                 205

Ala Ile Asn Gly Asn Ala Asn Leu Lys Gly Val Thr Leu Ser Thr Met
    210                 215                 220

His Val Ala Gln Ser Ala Leu Phe Leu Ala Ser Asp Glu Ser Ala Tyr
225                 230                 235                 240

Thr Ser Gly Gln Asn Leu Ala Val Asp Gly Leu Ser Ser Ile Leu
                245                 250                 255

Lys Leu Gln

<210> SEQ ID NO 67
<211> LENGTH: 259
<212> TYPE: PRT
<213> ORGANISM: S. pennellii

<400> SEQUENCE: 67

Met Ala Ser Lys Leu Arg Leu Glu Gly Lys Val Ala Ile Ile Thr Gly
1               5                   10                  15

Gly Ala Ser Gly Ile Gly Glu Ala Ser Ala Arg Leu Phe Val Gln His
            20                  25                  30

Gly Ala Arg Val Val Ala Asp Ile Gln Asp Glu Leu Gly Leu Gln
        35                  40                  45

Val Val Gln Ser Ile Gly Ile His Lys Ala Thr Tyr Arg His Cys Asp
    50                  55                  60

Val Thr Asp Glu Lys Gln Val Glu Asp Thr Val Ala Tyr Ala Val Gln
65                  70                  75                  80

Lys Tyr Ala Thr Leu Asp Val Met Phe Ser Asn Val Gly Thr Leu Asn
                85                  90                  95

Phe Cys Ser Val Leu Asp Met Asp Met Thr Ala Phe Asp Glu Thr Met
```

```
                    100                 105                 110
Thr Val Asn Val Arg Gly Ser Ala Leu Ala Val Lys His Ala Ala Arg
            115                 120                 125
Val Met Val Asp Lys Lys Ile Arg Gly Ser Ile Ile Cys Asn Val Ser
        130                 135                 140
Leu Glu Gly Ile Leu Ala Gly Ala Ala Ser Leu Ala Tyr Ile Ala Ser
145                 150                 155                 160
Lys His Ala Val Val Gly Ile Val Lys Ala Ala Arg Glu Leu Gly
                165                 170                 175
Pro Tyr Gly Ile Arg Val Asn Gly Val Ser Pro Tyr Gly Ile Ala Thr
            180                 185                 190
Pro Leu Val Cys Lys Ala Tyr Gly Leu Asp Ala Ala Pro Leu Glu Ala
        195                 200                 205
Ala Ile Asn Gly Asn Ala Asn Leu Lys Gly Val Thr Leu Ser Thr Met
        210                 215                 220
His Val Ala Gln Ser Ala Leu Phe Leu Ala Ser Asp Glu Ser Ala Tyr
225                 230                 235                 240
Thr Ser Gly Gln Asn Leu Ala Val Asp Gly Gly Leu Ser Ser Ile Leu
            245                 250                 255
Lys Leu Gln

<210> SEQ ID NO 68
<211> LENGTH: 236
<212> TYPE: PRT
<213> ORGANISM: C. annuum

<400> SEQUENCE: 68

Leu Glu Gly Lys Val Ala Val Ile Thr Gly Ala Ala Ser Gly Ile Gly
1               5                   10                  15
Glu Ala Ser Ala Arg Leu Phe Val Glu His Gly Ala Arg Val Val Ile
            20                  25                  30
Ala Asp Ile Gln Asp Glu Leu Gly Leu Gln Ile Ala Ala Ser Ile Gly
        35                  40                  45
Thr Asp Lys Ala Ser Tyr Ile His Cys Asp Val Thr Asp Glu Lys Gln
    50                  55                  60
Val Glu Glu Ala Val Ala Tyr Ala Val Glu Asn Ser Val Leu Asp Leu
65                  70                  75                  80
Asp Val Lys Ala Phe Asp Glu Thr Met Val Ile Asn Ala Arg Gly Ser
                85                  90                  95
Ala Val Ala Val Lys His Ala Ala Arg Val Met Val Glu Lys Lys Ile
            100                 105                 110
Arg Gly Ser Ile Ile Cys Thr Ala Ser Leu Glu Gly Ile Leu Ala Gly
        115                 120                 125
Ala Ala Ser Leu Ala Tyr Val Ser Ser Lys His Ala Val Val Gly Leu
        130                 135                 140
Val Lys Ala Ala Arg Glu Leu Gly Val His Gly Ile Arg Val Asn
145                 150                 155                 160
Gly Val Ser Pro Tyr Gly Ile Ala Thr Pro Leu Val Cys Lys Ala Tyr
            165                 170                 175
Gly Leu Asp Ala Gly Pro Leu Glu Thr Ala Ile Tyr Gly Asn Ala His
                180                 185                 190
Leu Lys Gly Val Thr Leu Ser Thr Met His Val Ala Gln Ala Ala Leu
            195                 200                 205
Phe Leu Ala Ser Asp Glu Ser Ala Tyr Ile Ser Gly Gln Asn Leu Ala
```

```
                    210                 215                 220
Val Asp Gly Gly Leu Ser Ser Ile Leu Lys Leu Glu
225                 230                 235
```

<210> SEQ ID NO 69
<211> LENGTH: 261
<212> TYPE: PRT
<213> ORGANISM: N. benthamiana

<400> SEQUENCE: 69

```
Met Ala Asn Lys Leu Arg Leu Glu Gly Lys Val Ala Val Ile Thr Gly
1               5                   10                  15
Gly Ala Ser Gly Ile Gly Glu Ala Thr Ala Arg Leu Phe Val Glu His
                20                  25                  30
Gly Ala Arg Val Val Ile Ala Asp Ile Gln Asp Glu Leu Gly Leu Gln
            35                  40                  45
Val Val Ala Ser Ile Gly Thr Asp Lys Ala Ser Tyr Arg His Cys Asp
50                  55                  60
Val Thr Asp Glu Asn Lys Val Glu Glu Thr Val Ala Tyr Ala Val Glu
65                  70                  75                  80
Lys Tyr Gly Thr Leu Asp Ile Met Phe Ser Asn Val Gly Thr Leu Asn
                85                  90                  95
Phe Cys Ser Val Leu Asp Ile Asp Val Thr Ala Phe Asp Lys Thr Met
            100                 105                 110
Ala Leu Asn Val Arg Gly Thr Ala Leu Ala Val Lys His Ala Ala Arg
        115                 120                 125
Val Met Val Ala Lys Gln Val Lys Gly Ser Ile Ile Cys Asn Ala Ser
130                 135                 140
Ile Glu Ala Ile Leu Ala Gly Ala Ala Ser Leu Ala Tyr Val Ala Ser
145                 150                 155                 160
Lys His Ala Val Gly Ile Val Lys Ala Ala Ala Arg Glu Leu Gly
                165                 170                 175
Leu His Gly Ile Arg Val Asn Gly Val Ser Pro Tyr Gly Ile Ala Thr
            180                 185                 190
Pro Leu Val Cys Lys Ala Tyr Gly Cys Glu Asp Ala Ala Ser Leu Glu
        195                 200                 205
Ala Gly Ile Ser Val Asn Ala His Leu Lys Gly Val Thr Leu Ser Thr
    210                 215                 220
Glu His Ile Ala Gln Ala Ala Leu Phe Leu Ala Ser Asp Glu Ser Ala
225                 230                 235                 240
Tyr Ile Ser Gly His Asn Leu Ala Val Asp Gly Leu Thr Ser Met
                245                 250                 255
Leu Lys Leu Ser Tyr
            260
```

<210> SEQ ID NO 70
<211> LENGTH: 258
<212> TYPE: PRT
<213> ORGANISM: S. melongena

<400> SEQUENCE: 70

```
Met Ala Asn Lys Leu Lys Leu Glu Gly Lys Val Ala Val Ile Thr Gly
1               5                   10                  15
Gly Ala Ser Gly Ile Gly Glu Glu Ser Ala Arg Leu Phe Val Glu His
                20                  25                  30
Gly Ala Arg Val Val Ile Ala Asp Ile Gln Asp Asp Leu Gly Leu Glu
```

```
                35                  40                  45
Val Val Thr Ser Ile Gly Ala Asp Lys Ala Cys Tyr Arg His Cys Asp
 50                  55                  60

Val Ser Glu Glu Lys Gln Val Lys Glu Thr Val Ala Tyr Ala Val Glu
 65                  70                  75                  80

Lys Tyr Gly Thr Leu Asp Ile Met Phe Ser Asn Ala Gly Thr Leu Gly
                 85                  90                  95

Thr Leu Gly Ser Val Leu Glu Met Asp Met Thr Ala Phe Asp Met Thr
                100                 105                 110

Met Ala Val Asn Met Arg Gly Ser Ala Leu Ala Val Lys His Ala Ala
                115                 120                 125

Arg Val Met Val Ala Asn Lys Ile Arg Gly Ser Ile Ile Cys Thr Ala
130                 135                 140

Ser Val Glu Ala Ile Leu Ala Gly Ala Ala Pro Leu Ala Tyr Val Ala
145                 150                 155                 160

Ser Lys His Ala Ile Leu Gly Val Met Lys Ala Ala Arg Glu Leu
                165                 170                 175

Gly Gln Tyr Gly Ile Arg Val Asn Cys Val Ser Pro Tyr Gly Ile Ala
                180                 185                 190

Thr Pro Leu Val Cys Lys Ala Tyr His Ser Asp Ala Gly Ser Leu Glu
                195                 200                 205

Ala Ser Ile Tyr Glu Arg Ala His Leu Lys Gly Ile Thr Leu Ser Thr
210                 215                 220

Lys His Ile Ala Asn Ala Ser Leu Phe Leu Ala Ser Asp Glu Ser Ala
225                 230                 235                 240

Tyr Val Ser Gly His Asn Leu Ala Val Asp Gly Ala Leu Ser Ser Ile
                245                 250                 255

Met Ser

<210> SEQ ID NO 71
<211> LENGTH: 263
<212> TYPE: PRT
<213> ORGANISM: C. annuum

<400> SEQUENCE: 71

Met Ile Phe Phe Phe Cys Gly Thr Arg Leu Glu Gly Lys Ile Ala Ile
 1               5                  10                  15

Ile Thr Gly Ala Ala Ser Gly Ile Gly Glu Ala Ser Ala Arg Leu Phe
                20                  25                  30

Val Glu His Gly Ala His Val Ile Ile Ala Asp Ile Gln Asp Glu Leu
                35                  40                  45

Gly Leu Gln Val Val Ser Ser Ile Gly Thr Asp Lys Ala Cys Tyr Arg
 50                  55                  60

His Cys Asp Val Thr Asp Glu Lys Gln Val Glu Thr Val Ala Tyr
 65                  70                  75                  80

Ala Val Glu Lys Tyr Gly Thr Leu Asp Ile Met Phe Ser Asn Ala Gly
                 85                  90                  95

Met Leu Gly Thr Phe Gly Ser Leu Leu Asp Met Asp Val Lys Glu Phe
                100                 105                 110

Asp Leu Thr Ile Ala Val Asn Thr Arg Gly Ala Ala Leu Ala Val Lys
                115                 120                 125

His Ala Ala Arg Val Met Val Ala Lys Asn Ile Arg Gly Ser Ile Ile
130                 135                 140

Cys Thr Ala Ser Val Glu Ser Ile Leu Ala Gly Ala Ala Pro Leu Ala
```

```
                145                 150                 155                 160
Tyr Ile Ala Ser Lys His Gly Ile Leu Gly Val Val Lys Ala Ala
                165                 170                 175

Arg Glu Leu Gly Lys Asn Gly Ile Arg Val Asn Cys Val Ser Pro Phe
                180                 185                 190

Gly Ile Ala Thr Pro Met Val Cys Lys Ser Tyr Gly Glu Ala Ser
                195                 200                 205

Tyr Ile Glu Thr Ser Val Gly Gly His Ala Asn Leu Lys Gly Val Ser
210                 215                 220

Leu Thr Thr Lys His Ile Ala Glu Ala Ala Leu Phe Leu Ala Ser Glu
225                 230                 235                 240

Glu Ser Ala Tyr Ile Ser Gly Gln Asn Leu Ala Val Asp Gly Gly Leu
                245                 250                 255

Ser Ala Ile Met Arg Leu Asp
                260

<210> SEQ ID NO 72
<211> LENGTH: 260
<212> TYPE: PRT
<213> ORGANISM: S. melongena

<400> SEQUENCE: 72

Met Ala Asn Lys Leu Arg Leu Glu Gly Lys Val Ala Val Ile Thr Gly
1               5                   10                  15

Gly Ala Ser Gly Ile Gly Glu Ala Ser Ala Arg Leu Phe Val Glu His
                20                  25                  30

Gly Ala Arg Val Val Ile Ala Asp Ile Gln Asp Glu Leu Ser Leu Gln
            35                  40                  45

Val Val Ser Ser Ile Gly Gly Asp Lys Ala Cys Tyr Arg Arg Cys Asp
50                  55                  60

Val Ser Asp Glu Lys Gln Val Glu Glu Thr Val Ala Tyr Ala Val Glu
65                  70                  75                  80

Lys Tyr Gly Thr Leu Asp Ile Met Phe Ser Asn Ala Gly Ile Leu Gly
                85                  90                  95

Ser Phe Gly Ser Leu Leu Glu Met Asp Met Thr Ala Phe Asp Arg Ile
                100                 105                 110

Met Ala Val Asn Thr Arg Gly Ala Ala Leu Ala Val Lys His Ala Ala
            115                 120                 125

Arg Val Met Val Ala Asn Lys Ile Arg Gly Ser Ile Ile Cys Thr Ala
130                 135                 140

Ser Val Glu Ala Ile Leu Ala Gly Glu Ala Ser Leu Ala Tyr Ile Ala
145                 150                 155                 160

Ser Lys His Ala Ile Leu Gly Val Val Lys Ala Ala Arg Asp Leu
                165                 170                 175

Gly Gln Tyr Gly Ile Arg Val Asn Cys Val Ser Pro Tyr Gly Ile Ala
            180                 185                 190

Thr Pro Met Val Cys Lys Ser Ile Gly Ala Asp Ala Thr Ile Glu
            195                 200                 205

Ala Arg Ile Cys Gly Asn Ala Asn Leu Lys Gly Val Ser Leu Asn Thr
            210                 215                 220

Lys His Ile Ala Glu Ala Ala Leu Phe Leu Gly Ser Asp Glu Ser Ala
225                 230                 235                 240

Tyr Val Ser Ala His Asn Leu Ala Val Asp Gly Gly Leu Ser Ser Ile
                245                 250                 255
```

Met Lys Leu Asn
         260

<210> SEQ ID NO 73
<211> LENGTH: 262
<212> TYPE: PRT
<213> ORGANISM: S. tuberosum

<400> SEQUENCE: 73

Met Ala Asn Lys Leu Arg Leu Glu Gly Lys Val Ala Val Ile Thr Gly
1               5                   10                  15

Gly Ala Ser Gly Ile Gly Glu Ala Thr Ala Arg Leu Phe Val Glu His
            20                  25                  30

Gly Ala His Val Val Ile Ala Asp Ile Gln Asp Glu Leu Ala Leu Gln
        35                  40                  45

Val Val Ser Ser Ile Gly Ser Asp Asn Val Cys Tyr Arg Arg Cys Asp
50                  55                  60

Val Thr Asp Glu Lys Gln Val Asp Glu Thr Val Ala Phe Ala Val Gln
65                  70                  75                  80

Lys Tyr Gly Thr Leu Asp Ile Met Phe Ser Asn Ala Gly Ile Leu Gly
                85                  90                  95

Ser Ser Gly Ser Leu Leu Glu Met Asp Met Ala Val Phe Asp Arg Thr
            100                 105                 110

Met Ala Val Asn Thr Arg Gly Ala Ala Leu Ala Val Lys His Ala Ala
        115                 120                 125

Lys Val Met Val Ala Lys Lys Ile Arg Gly Ser Ile Ile Cys Thr Ala
    130                 135                 140

Ser Val Glu Ser Ile Leu Ala Gly Ala Ala Ser Leu Ala Tyr Ile Ala
145                 150                 155                 160

Ser Lys His Ala Val Leu Gly Val Val Lys Ala Ala Arg Glu Leu
                165                 170                 175

Gly Gln His Gly Ile Arg Val Asn Cys Val Ser Pro Phe Gly Val Ala
            180                 185                 190

Thr Pro Met Val Cys Lys Ser Phe Gly Ala Asp Ala Ala Met Glu
        195                 200                 205

Ala Thr Ile Arg Gly Asn Ala Asn Leu Lys Gly Val Ser Leu Thr Thr
    210                 215                 220

Met His Ile Ala Glu Ala Ala Leu Phe Leu Ala Ser Asp Glu Ser Ala
225                 230                 235                 240

Tyr Ile Ser Ala His Asn Leu Ala Ile Asp Gly Gly Leu Ser Ser Ile
                245                 250                 255

Met Lys Ile Asn Val Asn
         260

<210> SEQ ID NO 74
<211> LENGTH: 260
<212> TYPE: PRT
<213> ORGANISM: S. lycopersicum

<400> SEQUENCE: 74

Met Ala Asn Lys Leu Arg Leu Glu Gly Lys Val Ala Val Ile Thr Gly
1               5                   10                  15

Gly Ala Ser Gly Ile Gly Glu Ala Ala Ala Arg Leu Phe Val Glu His
            20                  25                  30

Gly Ala Arg Val Val Ile Ala Asp Ile Gln Asp Glu Leu Ala Leu Gln
        35                  40                  45

```
Val Ala Ser Ser Ile Gly Ser Asp Asn Val Cys Tyr Gln Arg Cys Asp
    50                  55                  60

Val Ser Asp Glu Lys Gln Val Asn Glu Thr Val Ala Phe Ala Val Glu
65                  70                  75                  80

Lys Tyr Gly Thr Leu Asp Ile Met Phe Ser Asn Ala Gly Ile Leu Asn
                85                  90                  95

Pro Phe Glu Ser Ile Leu Glu Met Asp Met Thr Val Phe Asp Arg Thr
            100                 105                 110

Ile Ala Val Asn Ala Arg Gly Ala Ala Leu Ala Val Lys His Ala Ala
            115                 120                 125

Arg Val Met Val Ala Asn Lys Ile Arg Gly Ser Ile Ile Cys Thr Ala
    130                 135                 140

Ser Val Glu Ser Ile Leu Ala Gly Ala Ala Pro Leu Ala Tyr Ile Ala
145                 150                 155                 160

Ser Lys His Ala Val Leu Gly Val Val Lys Ala Ala Arg Glu Leu
                165                 170                 175

Gly Gln His Gly Ile Arg Val Asn Cys Val Ser Pro Phe Gly Ile Ala
            180                 185                 190

Thr Pro Met Val Cys Lys Ser Phe Gly Ala Asp Ala Ala Ile Glu
    195                 200                 205

Ala Lys Ile Cys Gly Asn Ala Asn Leu Lys Gly Val Ser Leu Thr Thr
    210                 215                 220

Met His Ile Ala Glu Ala Leu Phe Leu Ala Ser Asp Glu Ser Ala
225                 230                 235                 240

Tyr Ile Ser Ala Gln Asn Leu Ala Val Asp Gly Gly Leu Ser Ser Met
            245                 250                 255

Met Lys Leu Met
            260

<210> SEQ ID NO 75
<211> LENGTH: 260
<212> TYPE: PRT
<213> ORGANISM: S. pennellii

<400> SEQUENCE: 75

Met Ala Asn Lys Leu Arg Leu Glu Gly Lys Val Ala Val Ile Thr Gly
1               5                   10                  15

Gly Ala Ser Gly Ile Gly Glu Ala Ala Ala Arg Leu Phe Val Glu His
            20                  25                  30

Gly Ala Arg Val Val Ile Ala Asp Ile Gln Asp Glu Leu Ala Leu Gln
        35                  40                  45

Val Ala Ser Ser Ile Gly Ser Val Asn Val Cys Cys Arg Arg Cys Asp
    50                  55                  60

Val Ser Asp Glu Lys Gln Val Asn Glu Thr Val Ala Phe Ala Val Glu
65                  70                  75                  80

Lys Tyr Gly Thr Leu Asp Ile Met Phe Ser Asn Ala Gly Ile Leu Asn
                85                  90                  95

Pro Phe Glu Ser Ile Leu Glu Met Asp Met Thr Val Phe Asp Arg Thr
            100                 105                 110

Ile Ala Val Asn Ala Arg Gly Ala Ala Leu Ala Val Lys His Ala Ala
            115                 120                 125

Arg Val Met Val Ala Asn Lys Ile Arg Gly Ser Ile Ile Cys Thr Ala
    130                 135                 140

Ser Val Glu Ser Ile Leu Ala Gly Ala Ala Pro Leu Ala Tyr Ile Ala
145                 150                 155                 160
```

```
Ser Lys His Ala Val Leu Gly Val Val Lys Ala Ala Arg Glu Leu
            165                 170                 175

Gly Gln His Gly Ile Arg Val Asn Cys Val Ser Pro Phe Gly Ile Ala
            180                 185                 190

Thr Pro Met Val Cys Lys Ser Phe Gly Ala Asp Ala Ala Ile Glu
            195                 200                 205

Ala Lys Ile Cys Gly Asn Ala Asn Leu Lys Gly Val Ser Leu Thr Thr
            210                 215                 220

Met His Ile Ala Glu Ala Ala Leu Phe Leu Ala Ser Asp Glu Ser Ala
225                 230                 235                 240

Tyr Ile Ser Ala Gln Asn Leu Ala Val Asp Gly Gly Leu Ser Ser Met
            245                 250                 255

Met Lys Leu Met
            260

<210> SEQ ID NO 76
<211> LENGTH: 260
<212> TYPE: PRT
<213> ORGANISM: N. benthamiana

<400> SEQUENCE: 76

Met Ala Asn Lys Arg Arg Leu Glu Gly Lys Val Ala Val Ile Thr Gly
1               5                   10                  15

Ala Ala Ser Gly Ile Gly Glu Ala Thr Ala Arg Leu Phe Val Glu His
            20                  25                  30

Gly Ala Arg Val Val Ile Ala Asp Ile Gln Asp Glu Leu Gly His Gln
            35                  40                  45

Val Val Ala Ser Ile Gly Thr Asp Lys Ala Ser Tyr Arg His Cys Asp
50                  55                  60

Val Thr Asp Glu Lys Gln Val Glu Asp Thr Val Val Tyr Thr Val Glu
65                  70                  75                  80

Lys Tyr Gly Thr Leu Asp Ile Met Phe Ser Asn Ala Gly Thr Ile Gly
            85                  90                  95

Thr Leu Gly Ser Ile Leu Asp Met Asp Met Thr Val Phe Asp Arg Thr
            100                 105                 110

Met Ala Ile Asn Ala Arg Gly Ser Ala Leu Ala Val Lys His Ala Ala
            115                 120                 125

Arg Val Met Val Thr Lys Lys Ile Gln Gly Ser Ile Ile Cys Thr Ala
            130                 135                 140

Ser Leu Glu Ala Thr Leu Ala Gly Ala Ala Pro Leu Ala Tyr Val Thr
145                 150                 155                 160

Ser Lys His Ala Ile Leu Gly Val Val Lys Ala Ala Ala Arg Glu Leu
            165                 170                 175

Gly Gln His Gly Ile Arg Val Asn Cys Val Ser Pro Tyr Gly Ile Ala
            180                 185                 190

Thr Pro Met Val Cys Lys Thr Phe Gly Gly Asp Ala Ala Pro Ile Glu
            195                 200                 205

Ala Ser Ile Ser Gly Asn Ala Asn Leu Lys Gly Ile Thr Leu Ser Thr
            210                 215                 220

Lys His Ile Ala Glu Ala Ala Leu Phe Leu Ala Ser Asp Glu Ser Ala
225                 230                 235                 240

Tyr Val Ser Ala His Asn Leu Ala Val Asp Gly Gly Leu Ser Ser Ile
            245                 250                 255

Met Lys Leu Asp
```

<210> SEQ ID NO 77
<211> LENGTH: 241
<212> TYPE: PRT
<213> ORGANISM: N. benthamiana

<400> SEQUENCE: 77

Met Ala Asn Lys Leu Arg Leu Glu Gly Lys Val Ala Val Ile Thr Gly
1               5                   10                  15

Ala Ala Ser Gly Ile Gly Glu Ala Thr Ala Arg Leu Phe Val Glu His
            20                  25                  30

Gly Ala Arg Val Val Ile Ala Asp Ile Gln Asp Glu Leu Gly His Gln
        35                  40                  45

Val Val Ala Ser Ile Gly Thr Asp Lys Ala Ser Tyr Arg His Cys Asp
50                  55                  60

Val Thr Asp Glu Lys Gln Val Glu Asp Thr Val Val Tyr Ala Val Glu
65                  70                  75                  80

Lys Tyr Gly Thr Leu Asp Ile Met Phe Ser Asn Ala Gly Thr Ile Gly
                85                  90                  95

Thr Leu Ser Ser Ile Leu Asp Met Asp Met Thr Val Phe Asp Arg Thr
            100                 105                 110

Met Ala Ile Asn Ala Arg Gly Ser Ala Leu Ala Val Lys His Ala Ala
        115                 120                 125

Arg Ile Met Val Thr Lys Lys Ile Gln Gly Ser Ile Ile Cys Thr Ala
130                 135                 140

Ser Leu Glu Ala Ile Leu Ala Gly Ala Ala Pro Leu Ala Tyr Val Ala
145                 150                 155                 160

Ser Lys His Ala Ile Leu Gly Val Val Lys Ala Ala Arg Glu Leu
                165                 170                 175

Gly Gln His Gly Ile Arg Val Asn Cys Val Ser Pro Tyr Gly Ile Ala
            180                 185                 190

Thr Pro Met Val Cys Lys Thr Phe Gly Gly Asp Ala Ala Pro Ile Glu
        195                 200                 205

Ala Ser Ile Ser Gly Asn Ala Asn Leu Lys Gly Ile Thr Leu Ser Thr
    210                 215                 220

Lys His Ile Ala Glu Ala Ala Leu Phe Leu Ala Ser Asp Glu Ser Ala
225                 230                 235                 240

Tyr

<210> SEQ ID NO 78
<211> LENGTH: 257
<212> TYPE: PRT
<213> ORGANISM: A. thaliana

<400> SEQUENCE: 78

Met Ser Gly Lys Arg Leu Asp Gly Lys Ile Val Ile Thr Gly Gly
1               5                   10                  15

Ala Ser Gly Ile Gly Ala Glu Ser Val Arg Leu Phe Thr Glu His Gly
            20                  25                  30

Ala Arg Val Val Ile Val Asp Val Gln Asp Glu Leu Gly Gln Asn Val
        35                  40                  45

Ala Val Ser Ile Gly Glu Asp Lys Ala Ser Tyr Tyr His Cys Asp Val
    50                  55                  60

Thr Asn Glu Thr Glu Val Glu Asn Ala Val Lys Phe Thr Val Glu Lys
65                  70                  75                  80

```
Tyr Gly Lys Leu Asp Val Leu Phe Ser Asn Ala Gly Val Ile Glu Pro
                85                  90                  95

Phe Val Ser Ile Leu Asp Leu Asn Leu Asn Glu Leu Asp Arg Thr Ile
            100                 105                 110

Ala Ile Asn Leu Arg Gly Thr Ala Ala Phe Ile Lys His Ala Ala Arg
        115                 120                 125

Ala Met Val Glu Lys Gly Ile Arg Gly Ser Ile Val Cys Thr Thr Ser
    130                 135                 140

Val Ala Ala Glu Ile Ala Gly Thr Ala Pro His Gly Tyr Thr Thr Ser
145                 150                 155                 160

Lys His Gly Leu Leu Gly Leu Ile Lys Ser Ala Ser Gly Gly Leu Gly
                165                 170                 175

Lys Tyr Gly Ile Arg Val Asn Gly Val Ala Pro Phe Gly Val Ala Thr
            180                 185                 190

Pro Leu Val Cys Asn Gly Phe Lys Met Glu Pro Asn Val Val Glu Gln
        195                 200                 205

Asn Thr Ser Ala Ser Ala Asn Leu Lys Gly Ile Val Leu Lys Ala Arg
    210                 215                 220

His Val Ala Glu Ala Ala Leu Phe Leu Ala Ser Asp Glu Ser Ala Tyr
225                 230                 235                 240

Val Ser Gly Gln Asn Leu Ala Val Asp Gly Gly Tyr Ser Val Val Lys
                245                 250                 255

Pro

<210> SEQ ID NO 79
<211> LENGTH: 266
<212> TYPE: PRT
<213> ORGANISM: M. truncatula

<400> SEQUENCE: 79

Met Ser Arg Lys Arg Leu Glu Gly Lys Val Ala Ile Val Thr Gly Gly
1               5                   10                  15

Ala Ser Gly Ile Gly Ala Glu Thr Ala Lys Thr Phe Val Glu Asn Gly
            20                  25                  30

Ala Phe Val Val Ile Ala Asp Ile Asn Asp Glu Leu Gly His Gln Val
        35                  40                  45

Ala Thr Ser Ile Gly Leu Asp Lys Val Ser Tyr His His Cys Asp Val
    50                  55                  60

Arg Asp Glu Lys Gln Val Glu Glu Thr Val Ala Phe Ala Leu Glu Lys
65                  70                  75                  80

Tyr Gly Thr Leu Asp Ile Met Phe Ser Asn Ala Gly Ile Glu Gly Gly
                85                  90                  95

Met Ser Ser Ser Ile Leu Glu Phe Asp Leu Asn Glu Phe Asp Asn Thr
            100                 105                 110

Met Ala Ile Asn Val Arg Gly Ser Leu Ala Ala Ile Lys His Ala Ala
        115                 120                 125

Arg Phe Met Val Glu Arg Lys Ile Arg Gly Ser Ile Ile Cys Thr Ala
    130                 135                 140

Ser Val Ala Ala Ser Val Ala Gly Asn Arg Gly His Asp Tyr Val Thr
145                 150                 155                 160

Ser Lys His Gly Leu Leu Gly Leu Val Arg Ser Thr Cys Gly Glu Leu
                165                 170                 175

Gly Ala Tyr Gly Ile Arg Val Asn Ser Ile Ser Pro Tyr Gly Val Ala
            180                 185                 190
```

```
Thr Pro Leu Ala Cys Arg Ala Leu Asn Met Glu Met Ser Lys Val Glu
            195                 200                 205

Ala Asn Met Lys Asp Ser Ala Asn Leu Lys Gly Ile Thr Leu Lys Ala
    210                 215                 220

Thr His Ile Ala Glu Ala Ala Leu Phe Leu Ala Ser Glu Ser Ala
225                 230                 235                 240

Tyr Ile Ser Gly His Asn Leu Val Val Asp Gly Gly Phe Ser Val Ile
                245                 250                 255

Asn Ser Cys Val Pro Thr Thr Ile Lys Lys
            260                 265

<210> SEQ ID NO 80
<211> LENGTH: 266
<212> TYPE: PRT
<213> ORGANISM: C. annuum

<400> SEQUENCE: 80

Met Ala Val Val Met Gln Lys Leu Lys Gly Lys Val Ala Ile Val Thr
1               5                   10                  15

Gly Gly Ala Ser Gly Ile Gly Glu Ala Thr Val Arg Leu Phe Ala Glu
            20                  25                  30

His Gly Ala Arg Ala Val Val Ile Ala Asp Ile Gln Asp Glu Lys Gly
        35                  40                  45

Arg Ala Val Ala Glu Ser Ile Pro Leu Gln Val Cys Ser Tyr Val His
50                  55                  60

Cys Asp Val Ser Asp Glu Asn Gln Val Lys Gly Leu Val Asp Trp Thr
65                  70                  75                  80

Val Lys Lys Tyr Gly Gln Leu Asp Ile Met Phe Ser Asn Ala Gly Thr
                85                  90                  95

Val Gly Asn Ser Gly Gln Lys Val Leu Asp Leu Asp Leu Ser Glu Phe
            100                 105                 110

Asp Arg Val Ile Arg Val Asn Ala Arg Gly Met Ala Ala Cys Val Lys
        115                 120                 125

His Ala Ala Arg Ala Met Val Glu Gln Gly Gly Arg Gly Ser Ile Ile
130                 135                 140

Cys Thr Gly Ser Val Gly Ala Ser Lys Gly Ala Ala Trp Arg Thr Asp
145                 150                 155                 160

Tyr Thr Met Ser Lys His Ala Val Leu Gly Leu Val Thr Ser Ala Ser
                165                 170                 175

Arg Gln Leu Gly Lys Tyr Gly Ile Arg Val Asn Ser Ile Ser Pro Ser
            180                 185                 190

Ala Val Met Thr Pro Leu Met Ser Ser Ala Glu Ala Glu Thr Ser Met
        195                 200                 205

Lys Val Leu Lys Met Tyr Gly Pro Leu Thr Ser Leu Lys Gly Ile Thr
210                 215                 220

Leu Thr Val Lys His Leu Ala Asp Ala Val Leu Phe Leu Ala Ser Asp
225                 230                 235                 240

Asp Ser Ala Phe Val Asn Gly His Asp Leu Leu Val Asp Gly Gly Leu
                245                 250                 255

Leu His Leu Pro Asp Pro Met Ser Ser Leu
            260                 265

<210> SEQ ID NO 81
<211> LENGTH: 266
<212> TYPE: PRT
```

<213> ORGANISM: S. tuberosum

<400> SEQUENCE: 81

```
Met Ala Glu Val Thr Gln Lys Leu Lys Gly Lys Val Ala Ile Val Thr
1               5                   10                  15

Gly Gly Ala Ser Gly Ile Gly Glu Ala Thr Ala Arg Leu Phe Ala Gln
            20                  25                  30

His Gly Ala Arg Ala Val Val Ile Ala Asp Ile Gln Asp Gly Lys Gly
        35                  40                  45

Arg Ala Val Ala Val Ser Ile Pro Ser Gln Ile Cys Ser Tyr Val Gln
    50                  55                  60

Cys Asp Val Ser Asp Glu Asn Gln Val Lys Ala Met Val Asp Trp Thr
65                  70                  75                  80

Val Gln Lys Tyr Gly Gln Leu Asp Ile Met Phe Ser Asn Ala Gly Val
                85                  90                  95

Val Gly Asn Ser Gly Gln Lys Val Leu Asp Leu Asp Leu Ser Glu Phe
            100                 105                 110

Asp Arg Val Met Asn Val Asn Ala Arg Gly Met Ala Ala Cys Val Lys
        115                 120                 125

His Ala Ala Arg Ala Met Val Asp Lys Arg Val Arg Gly Ser Ile Ile
    130                 135                 140

Cys Thr Gly Ser Ile Gly Ala Ser Arg Gly Gly Ala Trp Arg Thr Asp
145                 150                 155                 160

Tyr Ile Met Ser Lys His Ala Val Leu Gly Leu Val Arg Ser Ala Cys
                165                 170                 175

Arg Gln Leu Gly Glu Tyr Gly Ile Arg Val Asn Ser Ile Ser Pro Ser
            180                 185                 190

Ala Val Met Thr Pro Leu Met Ile Ser Ala Glu Pro Glu Val Ser Met
        195                 200                 205

Lys Ser Leu Lys Arg Tyr Gly Pro Gln Thr Ser Leu Lys Gly Ile Thr
    210                 215                 220

Leu Thr Val Lys His Leu Ala Glu Ala Ala Leu Phe Leu Ala Ser Asp
225                 230                 235                 240

Asp Ser Ala Phe Ser Ser Arg Ser Asn Glu Phe Ile Val Lys Gln Arg
                245                 250                 255

Glu Gln Pro Asn Leu Ser Leu Phe Phe Phe
            260                 265
```

<210> SEQ ID NO 82
<211> LENGTH: 266
<212> TYPE: PRT
<213> ORGANISM: S. melongena

<400> SEQUENCE: 82

```
Met Ser Ala Ile Thr Gln Lys Leu Asn Gly Lys Val Ala Ile Val Thr
1               5                   10                  15

Gly Gly Ala Ser Gly Ile Gly Glu Ala Thr Val Arg Leu Phe Ala Gln
            20                  25                  30

His Gly Ala Arg Ala Val Val Ile Ala Asp Ile Gln Asp Glu Lys Gly
        35                  40                  45

Arg Ala Val Ala Gln Ser Ile Pro Ser Gln Ile Cys Ile Tyr Val Lys
    50                  55                  60

Cys Asp Val Ser Asp Glu Asn Gln Val Lys Ser Met Val Asp Trp Thr
65                  70                  75                  80

Val Gln Gln Tyr Gly Gln Leu Asp Ile Met Phe Ser Asn Ala Gly Thr
```

```
                85                  90                  95
Val Gly Asn Ser Gly Gln Lys Ile Leu Asp Leu Asp Leu Ser Glu Phe
                100                 105                 110

Asp Arg Val Met Asn Val Asn Ala Arg Gly Met Ala Ala Cys Val Lys
            115                 120                 125

His Ala Arg Ala Met Val Glu Lys Arg Val Arg Gly Ser Ile Ile
        130                 135                 140

Cys Thr Gly Ser Ile Ala Ala Ser Arg Ala Gly Ala Trp Arg Thr Asp
145                 150                 155                 160

Tyr Ala Met Ser Lys His Ala Val Leu Gly Leu Met Arg Ser Ala Ser
                165                 170                 175

Arg Gln Leu Gly Glu Tyr Gly Ile Arg Val Asn Ser Ile Ser Pro Ser
                180                 185                 190

Ala Val Met Thr Pro Leu Met Ile Ser Ala Glu Ala Glu Ala Ser Met
                195                 200                 205

Arg Val Leu Lys Met Tyr Gly Ser Val Thr Ser Leu Lys Gly Ile Thr
            210                 215                 220

Leu Thr Val Lys His Leu Ala Asp Ala Val Leu Phe Leu Ala Ser Asp
225                 230                 235                 240

Asp Ser Val Phe Val Ser Gly His Asp Leu Ala Val Asp Gly Gly Leu
                245                 250                 255

Ile Ser Leu Pro Asp Pro Met Ser Ser Leu
                260                 265

<210> SEQ ID NO 83
<211> LENGTH: 302
<212> TYPE: PRT
<213> ORGANISM: O. sativa

<400> SEQUENCE: 83

Met Phe Thr Ala Met His Arg Ile Leu Ser Arg Gly Arg Arg Thr Pro
1               5                   10                  15

Ala Ala Ser Ser Ser Ser Val Thr Ala Phe Ala Thr Ala Ser Asp Ser
                20                  25                  30

Gln Arg Leu Ala Gly Lys Val Ala Val Ile Thr Gly Gly Ala Ser Gly
            35                  40                  45

Ile Gly Arg Ala Thr Ala Glu Glu Phe Val Arg Asn Gly Ala Lys Val
50                  55                  60

Ile Leu Ala Asp Val Gln Asp Asp Leu Gly His Ala Val Ala Ala Glu
65                  70                  75                  80

Leu Gly Ala Asp Ala Ala Ser Tyr Ala Arg Cys Asp Val Thr Asp Glu
                85                  90                  95

Ala Gln Val Ala Ala Val Asp Leu Ala Val Ala Arg His Gly Arg
            100                 105                 110

Leu Asp Val Val Phe Asn Asn Ala Gly Ile Pro Gly Asp Leu Thr Pro
        115                 120                 125

Thr Pro Val Gly Ala Leu Asp Leu Ala Asp Phe Asp Arg Val Met Ala
        130                 135                 140

Val Asn Thr Arg Ala Val Val Ala Gly Val Lys His Ala Ala Arg Val
145                 150                 155                 160

Met Val Pro Arg Arg Gly Ser Ile Ile Cys Thr Ala Ser Thr Ala
                165                 170                 175

Gly Val Ile Gly Gly Val Ala Val Pro His Tyr Ser Val Ser Lys Ala
            180                 185                 190
```

Ala Val Leu Gly Leu Val Arg Ala Val Ala Gly Glu Met Ala Arg Ser
            195                 200                 205

Gly Val Arg Val Asn Ala Ile Ser Pro Asn Tyr Ile Trp Thr Pro Met
210                 215                 220

Ala Ala Val Ala Phe Ala Arg Trp Tyr Pro Ser Arg Ser Ala Asp Asp
225                 230                 235                 240

His Arg Arg Ile Val Glu Asn Asp Ile Asn Glu Met Asp Gly Val Thr
            245                 250                 255

Leu Glu Ala Glu Asp Val Ala Arg Ala Val Phe Leu Ala Ser Asp
            260                 265                 270

Glu Ala Lys Tyr Val Asn Gly His Asn Leu Val Asp Gly Gly Tyr
        275                 280                 285

Thr Val Gly Lys Val Pro Asn Met Pro Val Pro Asp Gly His
    290                 295                 300

<210> SEQ ID NO 84
<211> LENGTH: 300
<212> TYPE: PRT
<213> ORGANISM: O. sativa

<400> SEQUENCE: 84

Met Phe Arg Ala Ala Gln Leu Leu Arg Glu Thr Asn Arg Ala Leu
1               5                   10                  15

Gly Ala Ala Thr Ser Pro Ala Gly Phe Val Ser Gly Phe Ser Thr Ala
            20                  25                  30

Ser Asn Ser Ala Gln Arg Leu Ala Gly Lys Val Ala Val Ile Thr Gly
        35                  40                  45

Gly Ala Ser Gly Ile Gly Lys Ala Thr Ala Lys Glu Phe Ile Glu Asn
50                  55                  60

Gly Ala Lys Val Ile Met Ala Asp Val Gln Asp Leu Gly His Ser
65                  70                  75                  80

Thr Ala Ala Glu Leu Gly Pro Asp Ala Ser Tyr Thr Arg Cys Asp Val
            85                  90                  95

Thr Asp Glu Ala Gln Val Ala Ala Ala Val Asp Leu Ala Val Lys Arg
        100                 105                 110

His Gly His Leu Asp Ile Leu Tyr Asn Asn Ala Gly Val Met Gly Ala
    115                 120                 125

Met Pro Gln Asp Asp Met Ala Ser Val Asp Leu Ala Asn Phe Asp Arg
        130                 135                 140

Met Met Ala Ile Asn Ala Arg Ala Ala Leu Val Gly Ile Lys His Ala
145                 150                 155                 160

Ala Arg Val Met Ser Pro Arg Arg Ser Gly Val Ile Leu Cys Thr Ala
            165                 170                 175

Ser Asp Thr Gly Val Met Pro Met Pro Asn Ile Ala Leu Tyr Ala Val
        180                 185                 190

Ser Lys Ala Thr Thr Ile Ala Ile Val Arg Ala Ala Glu Pro Leu
    195                 200                 205

Ser Arg His Gly Leu Arg Val Asn Ala Ile Ser Pro His Gly Thr Arg
        210                 215                 220

Thr Pro Met Ala Met His Val Leu Ser Gln Met Tyr Pro Gly Val Ser
225                 230                 235                 240

Lys Asp Asp Leu Glu Lys Met Ala Asp Ala Met Asp Ala Gly Glu
            245                 250                 255

Val Met Glu Pro Lys Tyr Val Ala Arg Ala Ala Leu Tyr Leu Ala Ser
        260                 265                 270

```
Asp Glu Ala Lys Tyr Val Asn Gly His Asn Leu Val Val Asp Gly Gly
            275                 280                 285

Phe Thr Ser His Lys Gly Ser Asp Thr Arg Leu Asn
    290                 295                 300
```

<210> SEQ ID NO 85
<211> LENGTH: 285
<212> TYPE: PRT
<213> ORGANISM: A. thaliana

<400> SEQUENCE: 85

```
Met Ser Thr Asn Thr Glu Ser Ser Tyr Ser Ser Leu Pro Ser Gln
1               5                   10                  15

Arg Leu Gly Lys Val Ala Leu Ile Thr Gly Gly Ala Thr Gly Ile
                20                  25                  30

Gly Glu Ser Ile Val Arg Leu Phe His Lys His Gly Ala Lys Val Cys
            35                  40                  45

Ile Val Asp Leu Gln Asp Leu Gly Gly Val Cys Lys Ser Leu
        50                  55                  60

Leu Arg Gly Glu Ser Lys Glu Thr Ala Phe Phe Ile His Gly Asp Val
65                  70                  75                  80

Arg Val Glu Asp Asp Ile Ser Asn Ala Val Asp Phe Ala Val Lys Asn
                85                  90                  95

Phe Gly Thr Leu Asp Ile Leu Ile Asn Asn Ala Gly Leu Cys Gly Ala
                100                 105                 110

Pro Cys Pro Asp Ile Arg Asn Tyr Ser Leu Ser Glu Phe Glu Met Thr
                115                 120                 125

Phe Asp Val Asn Val Lys Gly Ala Phe Leu Ser Met Lys His Ala Ala
    130                 135                 140

Arg Val Met Ile Pro Glu Lys Lys Gly Ser Ile Val Ser Leu Cys Ser
145                 150                 155                 160

Val Gly Gly Val Val Gly Gly Val Gly Pro His Ser Tyr Val Gly Ser
                165                 170                 175

Lys His Ala Val Leu Gly Leu Thr Arg Ser Val Ala Ala Glu Leu Gly
                180                 185                 190

Gln His Gly Ile Arg Val Asn Cys Val Ser Pro Tyr Ala Val Ala Thr
            195                 200                 205

Lys Leu Ala Leu Ala His Leu Pro Glu Glu Arg Thr Glu Asp Ala
    210                 215                 220

Phe Val Gly Phe Arg Asn Phe Ala Ala Ala Asn Ala Asn Leu Lys Gly
225                 230                 235                 240

Val Glu Leu Thr Val Asp Asp Val Ala Asn Ala Val Leu Phe Leu Ala
                245                 250                 255

Ser Asp Asp Ser Arg Tyr Ile Ser Gly Asp Asn Leu Met Ile Asp Gly
                260                 265                 270

Gly Phe Thr Cys Thr Asn His Ser Phe Lys Val Phe Arg
                275                 280                 285
```

<210> SEQ ID NO 86
<211> LENGTH: 275
<212> TYPE: PRT
<213> ORGANISM: O. sativa

<400> SEQUENCE: 86

```
Met Ala Gly Ser Ser Tyr Gly Asp Val His Glu Ser Ala Arg Lys Leu
1               5                   10                  15
```

```
Val Gly Lys Val Ala Leu Ile Thr Gly Gly Ala Ser Gly Ile Gly Glu
             20                  25                  30

Cys Thr Ala Arg Leu Phe Val Lys His Gly Ala Gln Val Val Ala
             35                  40                  45

Asp Ile Gln Asp Glu Ala Gly Ala Arg Leu Cys Ala Glu Leu Gly Ser
 50                  55                  60

Ala Thr Ala Ser Tyr Val Arg Cys Asp Val Thr Ser Glu Asp Asp Val
 65                  70                  75                  80

Ala Ala Ala Val Asp His Ala Val Ala Arg Tyr Gly Lys Leu Asp Val
                 85                  90                  95

Met Phe Asn Asn Ala Gly Ile Gly Gly Ala Ala Cys His Ser Ile Leu
                100                 105                 110

Glu Ser Thr Lys Ala Asp Phe Asp Arg Val Leu Ala Val Asn Leu Thr
            115                 120                 125

Gly Pro Phe Leu Gly Thr Lys His Ala Ala Arg Val Met Val Ala Ala
130                 135                 140

Gly Arg Gly Gly Cys Ile Ile Gly Thr Ala Ser Leu Ala Ser Ala Val
145                 150                 155                 160

Ala Gly Thr Ala Ser His Ala Tyr Thr Cys Ala Lys Arg Ala Leu Val
                165                 170                 175

Gly Leu Thr Glu Asn Ala Ala Ala Glu Leu Gly Arg His Gly Ile Arg
                180                 185                 190

Val Asn Cys Val Ser Pro Ala Ala Ala Thr Pro Leu Ala Thr Gly
            195                 200                 205

Tyr Val Gly Leu Glu Gly Glu Ala Phe Glu Ala Ala Met Glu Ala Val
            210                 215                 220

Ala Asn Leu Lys Gly Val Arg Leu Arg Val Glu Asp Ile Ala Ala Ala
225                 230                 235                 240

Val Leu Phe Leu Ala Ser Asp Asp Ala Arg Tyr Val Ser Gly His Asn
                245                 250                 255

Leu Leu Ile Asp Gly Gly Cys Ser Ile Val Asn Pro Ser Phe Gly Ile
                260                 265                 270

Phe Lys Asp
            275

<210> SEQ ID NO 87
<211> LENGTH: 274
<212> TYPE: PRT
<213> ORGANISM: O. sativa

<400> SEQUENCE: 87

Met Ala Ala Gly Ser Ser His Val Ser Ala Asp Ala Arg Lys Leu Val
 1               5                  10                  15

Gly Lys Val Ala Val Ile Thr Gly Gly Ala Ser Gly Ile Gly Ala Cys
             20                  25                  30

Thr Ala Arg Leu Phe Val Lys His Gly Ala Arg Val Val Ala Asp
             35                  40                  45

Ile Gln Asp Glu Leu Gly Ala Ser Leu Val Ala Glu Leu Gly Pro Asp
 50                  55                  60

Ala Ser Ser Tyr Val His Cys Asp Val Thr Asn Glu Gly Asp Val Ala
 65                  70                  75                  80

Ala Ala Val Asp His Ala Val Ala Arg Phe Gly Lys Leu Asp Val Met
                 85                  90                  95

Phe Asn Asn Ala Gly Val Ser Gly Pro Pro Cys Phe Arg Met Ser Glu
```

```
            100                 105                 110
Cys Thr Lys Glu Asp Phe Glu Arg Val Leu Ala Val Asn Leu Val Gly
            115                 120                 125

Pro Phe Leu Gly Thr Lys His Ala Ala Arg Val Met Ala Pro Ala Arg
130                 135                 140

Arg Gly Ser Ile Ile Ser Thr Ala Ser Leu Ser Ser Ser Val Ser Gly
145                 150                 155                 160

Ala Ala Ser His Ala Tyr Thr Thr Ser Lys His Ala Leu Val Gly Phe
                165                 170                 175

Thr Glu Asn Ala Ala Gly Glu Leu Gly Arg His Gly Ile Arg Val Asn
            180                 185                 190

Cys Val Ser Pro Ala Gly Val Ala Thr Pro Leu Ala Arg Ala Ala Met
            195                 200                 205

Gly Met Asp Asp Glu Ala Ile Glu Ala Ile Met Ala Asn Ser Ala Asn
            210                 215                 220

Leu Lys Gly Ala Gly Ala Leu Lys Ala Asp Asp Ile Ala Ala Ala Ala
225                 230                 235                 240

Leu Phe Leu Ala Ser Asp Asp Gly Arg Tyr Val Ser Gly Gln Asn Leu
                245                 250                 255

Arg Val Asp Gly Gly Leu Ser Val Val Asn Ser Ser Phe Gly Phe Phe
            260                 265                 270

Arg Asp

<210> SEQ ID NO 88
<211> LENGTH: 274
<212> TYPE: PRT
<213> ORGANISM: O. sativa

<400> SEQUENCE: 88

Met Ala Gly Ser Ser His Val Ser Ala Asp Ala Arg Lys Leu Val Gly
1               5                   10                  15

Lys Val Ala Val Ile Thr Gly Gly Ala Ser Gly Ile Gly Ala Cys Thr
            20                  25                  30

Ala Arg Leu Phe Val Lys His Gly Ala Arg Val Val Val Ala Asp Ile
            35                  40                  45

Gln Asp Glu Leu Gly Ala Ser Leu Val Ala Glu Leu Gly Pro Asp Ala
        50                  55                  60

Ser Ser Tyr Val His Cys Asp Val Thr Asn Glu Gly Asp Val Ala Ala
65                  70                  75                  80

Ala Val Asp His Ala Val Ala Thr Phe Gly Lys Leu Asp Val Met Phe
                85                  90                  95

Asn Asn Ala Gly Val Thr Gly Pro Pro Cys Phe Arg Ile Thr Glu Ser
            100                 105                 110

Thr Lys Glu Asp Phe Glu Arg Val Leu Ala Val Asn Leu Ile Gly Pro
            115                 120                 125

Phe Leu Gly Thr Lys His Ala Ala Arg Val Met Ala Pro Ala Arg Arg
130                 135                 140

Gly Ser Ile Ile Ser Thr Ala Ser Leu Ser Ser Ser Val Ser Gly Thr
145                 150                 155                 160

Ala Ser His Ala Tyr Thr Thr Ser Lys Arg Ala Leu Val Gly Phe Thr
                165                 170                 175

Glu Asn Ala Ala Gly Glu Leu Gly Arg His Gly Ile Arg Val Asn Cys
            180                 185                 190

Val Ser Pro Ala Ala Val Ala Thr Pro Leu Ala Arg Ala Ala Met Gly
```

```
                195                 200                 205
Met Asp Met Asp Asp Glu Thr Ile Glu Ala Ile Met Glu Lys Ser Ala
    210                 215                 220

Asn Leu Lys Gly Val Gly Leu Lys Val Asp Asp Ile Ala Ala Ala Ala
225                 230                 235                 240

Leu Phe Leu Ala Ser Asp Asp Gly Arg Tyr Val Ser Gly Gln Asn Leu
                245                 250                 255

Arg Val Asp Gly Val Ser Val Val Asn Ser Ser Phe Gly Phe Phe
                260                 265                 270

Arg Asp

<210> SEQ ID NO 89
<211> LENGTH: 349
<212> TYPE: PRT
<213> ORGANISM: A. thaliana

<400> SEQUENCE: 89

Met Glu Leu Ile Asn Asp Phe Leu Asn Leu Thr Ala Pro Phe Phe Thr
1               5                   10                  15

Phe Phe Gly Leu Cys Phe Phe Leu Pro Pro Phe Tyr Phe Phe Lys Phe
                20                  25                  30

Leu Gln Ser Ile Phe Ser Thr Ile Phe Ser Glu Asn Leu Tyr Gly Lys
            35                  40                  45

Val Val Leu Ile Thr Gly Ala Ser Ser Gly Ile Gly Glu Gln Leu Ala
        50                  55                  60

Tyr Glu Tyr Ala Cys Arg Gly Ala Cys Leu Ala Leu Thr Ala Arg Arg
65                  70                  75                  80

Lys Asn Arg Leu Glu Glu Val Ala Glu Ile Ala Arg Glu Leu Gly Ser
                85                  90                  95

Pro Asn Val Val Thr Val His Ala Asp Val Ser Lys Pro Asp Asp Cys
                100                 105                 110

Arg Arg Ile Val Asp Asp Thr Ile Thr His Phe Gly Arg Leu Asp His
            115                 120                 125

Leu Val Asn Asn Ala Gly Met Thr Gln Ile Ser Met Phe Glu Asn Ile
130                 135                 140

Glu Asp Ile Thr Arg Thr Lys Ala Val Leu Asp Thr Asn Phe Trp Gly
145                 150                 155                 160

Ser Val Tyr Thr Thr Arg Ala Ala Leu Pro Tyr Leu Arg Gln Ser Asn
                165                 170                 175

Gly Lys Ile Val Ala Met Ser Ser Ala Ala Trp Leu Thr Ala Pro
                180                 185                 190

Arg Met Ser Phe Tyr Asn Ala Ser Lys Ala Ala Leu Leu Ser Phe Phe
                195                 200                 205

Glu Thr Met Arg Ile Glu Leu Gly Gly Asp Val His Ile Thr Ile Val
    210                 215                 220

Thr Pro Gly Tyr Ile Glu Ser Glu Leu Thr Gln Gly Lys Tyr Phe Ser
225                 230                 235                 240

Gly Glu Gly Glu Leu Ile Val Asn Gln Asp Met Arg Asp Val Gln Val
                245                 250                 255

Gly Pro Phe Pro Val Ala Ser Ala Ser Gly Cys Ala Lys Ser Ile Val
                260                 265                 270

Asn Gly Val Cys Arg Lys Gln Arg Tyr Val Thr Glu Pro Ser Trp Phe
                275                 280                 285

Lys Val Thr Tyr Leu Trp Lys Val Leu Cys Pro Glu Leu Ile Glu Trp
```

-continued

```
             290                 295                 300

Gly Cys Arg Leu Leu Tyr Met Thr Gly Thr Gly Met Ser Glu Asp Thr
305                 310                 315                 320

Ala Leu Asn Lys Arg Ile Met Asp Ile Pro Gly Val Arg Ser Thr Leu
                325                 330                 335

Tyr Pro Glu Ser Ile Arg Thr Pro Glu Ile Lys Ser Asp
            340                 345
```

<210> SEQ ID NO 90
<211> LENGTH: 264
<212> TYPE: PRT
<213> ORGANISM: A. thaliana

<400> SEQUENCE: 90

```
Met Glu Thr Asp Lys Arg Trp Ser Leu Ala Gly Lys Thr Ala Leu Val
1               5                   10                  15

Thr Gly Gly Thr Arg Gly Ile Gly Arg Ala Val Val Glu Glu Leu Ala
                20                  25                  30

Lys Phe Gly Ala Lys Val His Thr Cys Ser Arg Asn Gln Glu Glu Leu
            35                  40                  45

Asn Ala Cys Leu Asn Asp Trp Lys Ala Asn Gly Leu Val Val Ser Gly
50                  55                  60

Ser Val Cys Asp Ala Ser Val Arg Asp Gln Arg Glu Lys Leu Ile Gln
65                  70                  75                  80

Glu Ala Ser Ser Ala Phe Ser Gly Lys Leu Asn Ile Leu Ile Asn Asn
                85                  90                  95

Val Gly Thr Asn Val Arg Lys Pro Thr Val Glu Tyr Ser Glu Glu
                100                 105                 110

Tyr Ala Lys Ile Met Ser Thr Asn Leu Glu Ser Ala Phe His Leu Ser
            115                 120                 125

Gln Ile Ala His Pro Leu Leu Lys Ala Ser Gly Val Gly Ser Ile Val
130                 135                 140

Phe Ile Ser Ser Val Ala Gly Leu Val His Leu Ser Ser Gly Ser Ile
145                 150                 155                 160

Tyr Gly Ala Thr Lys Gly Ala Leu Asn Gln Leu Thr Arg Asn Leu Ala
                165                 170                 175

Cys Glu Trp Ala Ser Asp Asn Ile Arg Thr Asn Cys Val Ala Pro Trp
            180                 185                 190

Tyr Ile Lys Thr Ser Leu Val Glu Thr Leu Leu Glu Lys Lys Glu Phe
        195                 200                 205

Val Glu Ala Val Val Ser Arg Thr Pro Leu Gly Arg Val Gly Glu Pro
210                 215                 220

Glu Glu Val Ser Ser Leu Val Ala Phe Leu Cys Leu Pro Ala Ser Ser
225                 230                 235                 240

Tyr Ile Thr Gly Gln Val Ile Ser Val Asp Gly Gly Phe Thr Val Asn
                245                 250                 255

Gly Phe Ser Tyr Ala Met Lys Pro
            260
```

<210> SEQ ID NO 91
<211> LENGTH: 310
<212> TYPE: PRT
<213> ORGANISM: Z. mays

<400> SEQUENCE: 91

Met Asp Ala Ala Ala Ala Ala Ser Pro Thr Ser Lys Arg Ile Ala

```
                1               5              10              15
        Leu Val Thr Gly Gly Asn Lys Gly Ile Gly Leu Glu Thr Cys Arg Gln
                       20              25              30

Leu Ala Ser Arg Gly Val Arg Val Leu Thr Ala Arg Asn Glu Ala
                       35              40              45

Arg Gly Leu Glu Ala Val Glu Arg Val Arg Cys Ala Arg Gly Asp Ala
         50              55              60

Glu Val Tyr Phe His Gln Leu Asp Val Thr Asp Pro Cys Ser Ala Ala
         65              70              75              80

Arg Leu Ala Asp Phe Val Arg Asp Gln Phe Gly Arg Leu Asp Ile Leu
                       85              90              95

Ile Asn Asn Ala Gly Ile Ser Gly Val His Arg Asp Pro Val Leu Ser
                      100             105             110

Ala Ala Val Lys Asp Lys Val Asp Gly Met Asp Val Asn Gln Arg Val
                      115             120             125

Glu Trp Met Lys Glu Asn Ser Lys Glu Thr Tyr Glu Glu Ala Val Gln
                130             135             140

Cys Met Lys Thr Asn Tyr Tyr Gly Ala Lys Leu Val Thr Glu Ala Leu
        145             150             155             160

Leu Pro Leu Leu Gln Leu Ser Ser Gly Arg Ile Val Asn Val Ser
                      165             170             175

Ser Gly Phe Gly Leu Leu Arg Asn Phe Asn Ser Glu Asp Leu Arg Lys
                      180             185             190

Glu Phe Glu Asp Ile Asp Asn Leu Thr Glu Ser Arg Leu Glu Glu Leu
                      195             200             205

Met Asp Lys Phe Leu Glu Asp Phe Lys Ala Asn Leu Val Glu Glu His
                      210             215             220

Gly Trp Pro Thr Gly Gly Ser Ser Ala Tyr Lys Val Val Lys Ala Ala
        225             230             235             240

Leu Asn Ala Tyr Thr Arg Ile Leu Ala Lys Lys Tyr Pro Thr Leu Arg
                      245             250             255

Ile Asn Cys Leu Thr Pro Gly Tyr Val Lys Thr Asp Ile Ser Met His
                      260             265             270

Met Gly Val Leu Thr Leu Glu Glu Gly Ala Arg Asn Pro Val Lys Val
                      275             280             285

Ala Leu Leu Pro Asp Asp Gly Pro Thr Gly Ala Tyr Phe Asp Leu Asn
                      290             295             300

Gly Glu Ala Ser Phe Val
        305                 310

<210> SEQ ID NO 92
        <211> LENGTH: 303
        <212> TYPE: PRT
        <213> ORGANISM: A. thaliana

<400> SEQUENCE: 92

Met Ala Glu Glu Thr Pro Arg Leu Phe Asn Gly Phe Cys Arg Tyr Ala
        1               5              10              15

Val Val Thr Gly Ala Asn Arg Gly Ile Gly Phe Glu Ile Cys Arg Gln
                       20              25              30

Leu Ala Ser Glu Gly Ile Arg Val Val Leu Thr Ser Arg Asp Glu Asn
                       35              40              45

Arg Gly Leu Glu Ala Val Glu Thr Leu Lys Lys Glu Leu Glu Ile Ser
         50              55              60
```

```
Asp Gln Ser Leu Leu Phe His Gln Leu Asp Val Ala Asp Pro Ala Ser
 65                  70                  75                  80

Ile Thr Ser Leu Ala Glu Phe Val Lys Thr Gln Phe Gly Lys Leu Asp
                 85                  90                  95

Ile Leu Val Asn Asn Ala Gly Ile Gly Gly Ile Ile Thr Asp Ala Glu
            100                 105                 110

Ala Leu Arg Ala Gly Ala Gly Lys Glu Gly Phe Lys Trp Asp Glu Ile
        115                 120                 125

Ile Thr Glu Thr Tyr Glu Leu Thr Glu Glu Cys Ile Lys Ile Asn Tyr
    130                 135                 140

Tyr Gly Pro Lys Arg Met Cys Glu Ala Phe Ile Pro Leu Leu Lys Leu
145                 150                 155                 160

Ser Asp Ser Pro Arg Ile Val Asn Val Ser Ser Met Gly Gln Leu
                165                 170                 175

Lys Asn Val Leu Asn Glu Trp Ala Lys Gly Ile Leu Ser Asp Ala Glu
            180                 185                 190

Asn Leu Thr Glu Glu Arg Ile Asp Gln Val Ile Asn Gln Leu Leu Asn
        195                 200                 205

Asp Phe Lys Glu Gly Thr Val Lys Glu Lys Asn Trp Ala Lys Phe Met
    210                 215                 220

Ser Ala Tyr Val Val Ser Lys Ala Ser Leu Asn Gly Tyr Thr Arg Val
225                 230                 235                 240

Leu Ala Lys Lys His Pro Glu Phe Arg Val Asn Ala Val Cys Pro Gly
                245                 250                 255

Phe Val Lys Thr Asp Met Asn Phe Lys Thr Gly Val Leu Ser Val Glu
            260                 265                 270

Glu Gly Ala Ser Ser Pro Val Arg Leu Ala Leu Leu Pro His Gln Glu
        275                 280                 285

Thr Pro Ser Gly Cys Phe Phe Ser Arg Lys Gln Val Ser Glu Phe
    290                 295                 300

<210> SEQ ID NO 93
<211> LENGTH: 311
<212> TYPE: PRT
<213> ORGANISM: P. bracteatum

<400> SEQUENCE: 93

Met Pro Glu Thr Cys Pro Asn Thr Val Thr Lys Met Arg Cys Ala Val
  1               5                  10                  15

Val Thr Gly Gly Asn Lys Gly Ile Gly Phe Glu Ile Cys Lys Gln Leu
             20                  25                  30

Ser Ser Ser Gly Ile Met Val Val Leu Thr Cys Arg Asp Val Thr Arg
         35                  40                  45

Gly Leu Glu Ala Val Glu Lys Leu Lys Asn Ser Asn His Glu Asn Val
     50                  55                  60

Val Phe His Gln Leu Asp Val Thr Asp Pro Ile Thr Thr Met Ser Ser
 65                  70                  75                  80

Leu Ala Asp Phe Ile Lys Ala Arg Phe Gly Lys Leu Asp Ile Leu Val
                 85                  90                  95

Asn Asn Ala Gly Val Ala Gly Phe Ser Val Asp Ala Asp Arg Phe Lys
            100                 105                 110

Ala Met Ile Ser Asp Ile Gly Glu Asp Ser Glu Glu Val Val Lys Ile
        115                 120                 125

Tyr Glu Lys Pro Glu Ala Gln Glu Leu Met Ser Glu Thr Tyr Glu Leu
    130                 135                 140
```

```
Ala Glu Glu Cys Leu Lys Ile Asn Tyr Tyr Gly Val Lys Ser Val Thr
145                 150                 155                 160

Glu Val Leu Leu Pro Leu Leu Gln Leu Ser Asp Ser Pro Arg Ile Val
                165                 170                 175

Asn Val Ser Ser Ser Thr Gly Ser Leu Lys Tyr Val Ser Asn Glu Thr
            180                 185                 190

Ala Leu Glu Ile Leu Gly Asp Gly Asp Ala Leu Thr Glu Glu Arg Ile
        195                 200                 205

Asp Met Val Val Asn Met Leu Leu Lys Asp Phe Lys Glu Asn Leu Ile
    210                 215                 220

Glu Thr Asn Gly Trp Pro Ser Phe Gly Ala Ala Tyr Thr Thr Ser Lys
225                 230                 235                 240

Ala Cys Leu Asn Ala Tyr Thr Arg Val Leu Ala Lys Lys Ile Pro Lys
                245                 250                 255

Phe Gln Val Asn Cys Val Cys Pro Gly Leu Val Lys Thr Glu Met Asn
            260                 265                 270

Tyr Gly Ile Gly Asn Tyr Thr Ala Asp Glu Gly Ala Lys His Val Val
        275                 280                 285

Arg Ile Ala Leu Phe Pro Asp Asp Gly Pro Ser Gly Phe Phe Tyr Asp
290                 295                 300

Cys Ser Glu Leu Ser Ala Phe
305                 310

<210> SEQ ID NO 94
<211> LENGTH: 343
<212> TYPE: PRT
<213> ORGANISM: Z. mays

<400> SEQUENCE: 94

Met Ser Thr Gly Gly Arg Lys Met Arg Thr Ala Cys Val Thr Gly Gly
1               5                   10                  15

Asn Gly Tyr Ile Ala Ser Ala Leu Ile Lys Val Leu Leu Glu Lys Gly
            20                  25                  30

Tyr Ala Val Lys Thr Thr Val Arg Asn Pro Asp Asp Met Glu Lys Asn
        35                  40                  45

Ser His Leu Lys Asp Leu Gln Ala Leu Gly Ser Leu Glu Val Phe Arg
    50                  55                  60

Ala Asp Leu Asp Glu Asp Gly Ser Phe Asp Asp Ala Val Ala Gly Cys
65                  70                  75                  80

Asp Tyr Ala Phe Leu Val Ala Ala Pro Val Asn Leu His Thr Lys Asn
                85                  90                  95

Pro Glu Glu Glu Met Ile Glu Pro Ala Val Arg Gly Thr Leu Asn Val
            100                 105                 110

Met Arg Ser Cys Val Lys Ala Gly Thr Val Arg Arg Val Val Leu Thr
        115                 120                 125

Ser Ser Ala Ala Ala Val Thr Thr Arg Pro Gln Leu Gln Gly Asp Gly
    130                 135                 140

His Val Leu Asp Glu Glu Ser Trp Ser Asp Val Glu Tyr Leu Arg Ala
145                 150                 155                 160

His Lys Pro Ala Gly Pro Trp Gly Tyr Pro Val Ser Lys Val Leu Leu
                165                 170                 175

Glu Lys Glu Ala Ser Arg Phe Ala Glu Glu His Gly Ile Gly Leu Val
            180                 185                 190

Thr Val Cys Pro Gly Leu Thr Val Gly Ala Ala Pro Ala Pro Thr Ala
```

```
              195                 200                 205
Arg Thr Ser Val Pro Asn Cys Leu Ser Leu Leu Ser Gly Asp Glu Ala
    210                 215                 220

Ala Phe Ala Val Leu Asp Ala Ile Glu Ser Ala Thr Gly Cys Leu Pro
225                 230                 235                 240

Leu Val His Val Asp Asp Val Cys Arg Ala Glu Leu Phe Ala Ala Glu
                245                 250                 255

Glu Gly Ala Ala Ala Arg Arg Tyr Val Cys Cys Gly Leu Asn Thr Thr
            260                 265                 270

Val Ala Glu Leu Ala Arg Phe Leu Ala Asp Lys Tyr Pro Gln Tyr Gly
        275                 280                 285

Val Lys Thr Asn Leu Leu Ser Gly Glu Arg Leu Glu Lys Pro Arg Val
    290                 295                 300

Cys Leu Ser Ser Ala Lys Leu Val Lys Glu Gly Phe Glu Phe Arg Tyr
305                 310                 315                 320

Arg Thr Leu Asp Asp Ile Tyr Asp Asp Met Val Glu Tyr Gly Lys Ala
                325                 330                 335

Leu Gly Ile Leu Pro Asp Leu
            340

<210> SEQ ID NO 95
<211> LENGTH: 340
<212> TYPE: PRT
<213> ORGANISM: A. thaliana

<400> SEQUENCE: 95

Met Asp Gln Thr Leu Thr His Thr Gly Ser Lys Lys Ala Cys Val Ile
1               5                   10                  15

Gly Gly Thr Gly Asn Leu Ala Ser Ile Leu Ile Lys His Leu Leu Gln
            20                  25                  30

Ser Gly Tyr Lys Val Asn Thr Thr Val Arg Asp Pro Glu Asn Glu Lys
        35                  40                  45

Lys Ile Ala His Leu Arg Lys Leu Gln Glu Leu Gly Asp Leu Lys Ile
    50                  55                  60

Phe Lys Ala Asp Leu Thr Asp Glu Asp Ser Phe Glu Ser Ser Phe Ser
65                  70                  75                  80

Gly Cys Glu Tyr Ile Phe His Val Ala Thr Pro Ile Asn Phe Lys Ser
                85                  90                  95

Glu Asp Pro Glu Lys Asp Met Ile Lys Pro Ala Ile Gln Gly Val Ile
            100                 105                 110

Asn Val Leu Lys Ser Cys Leu Lys Ser Lys Ser Val Lys Arg Val Ile
        115                 120                 125

Tyr Thr Ser Ser Ala Ala Ala Val Ser Ile Asn Asn Leu Ser Gly Thr
    130                 135                 140

Gly Ile Val Met Asn Glu Glu Asn Trp Thr Asp Val Glu Phe Leu Thr
145                 150                 155                 160

Glu Glu Lys Pro Phe Asn Trp Gly Tyr Pro Ile Ser Lys Val Leu Ala
                165                 170                 175

Glu Lys Thr Ala Trp Glu Phe Ala Lys Glu Asn Lys Ile Asn Leu Val
            180                 185                 190

Thr Val Ile Pro Ala Leu Ile Ala Gly Asn Ser Leu Leu Ser Asp Pro
        195                 200                 205

Pro Ser Ser Leu Ser Leu Ser Met Ser Phe Ile Thr Gly Lys Glu Met
    210                 215                 220
```

His Val Thr Gly Leu Lys Glu Met Gln Lys Leu Ser Gly Ser Ile Ser
225                 230                 235                 240

Phe Val His Val Asp Asp Leu Ala Arg Ala His Leu Phe Leu Ala Glu
            245                 250                 255

Lys Glu Thr Ala Ser Gly Arg Tyr Ile Cys Cys Ala Tyr Asn Thr Ser
            260                 265                 270

Val Pro Glu Ile Ala Asp Phe Leu Ile Gln Arg Tyr Pro Lys Tyr Asn
        275                 280                 285

Val Leu Ser Glu Phe Glu Gly Leu Ser Ile Pro Lys Leu Thr Leu
        290                 295                 300

Ser Ser Gln Lys Leu Ile Asn Glu Gly Phe Arg Phe Glu Tyr Gly Ile
305                 310                 315                 320

Asn Glu Met Tyr Asp Gln Met Ile Glu Tyr Phe Glu Ser Lys Gly Leu
                325                 330                 335

Ile Lys Ala Lys
            340

<210> SEQ ID NO 96
<211> LENGTH: 348
<212> TYPE: PRT
<213> ORGANISM: P. somniferum

<400> SEQUENCE: 96

Met His Gly Gln Lys Asn Ile Ser Glu Arg Tyr Gln Lys Phe Lys Glu
1               5                   10                  15

Met Glu Gly Thr Gly Lys Ile Val Cys Val Thr Gly Gly Ala Gly Tyr
                20                  25                  30

Leu Ala Ser Trp Leu Ile Met Arg Leu Leu Glu Arg Gly Tyr Ser Val
            35                  40                  45

Arg Thr Thr Val Arg Ser Asp Pro Lys Phe Arg Glu Asp Val Ser His
    50                  55                  60

Leu Lys Ala Leu Pro Glu Ala Thr Glu Lys Leu Gln Ile Phe Glu Ala
65                  70                  75                  80

Asp Leu Glu Asn Pro Glu Ser Phe Asp Asp Ala Ile Asn Gly Cys Val
                85                  90                  95

Gly Val Phe Leu Val Ala Gln Gly Met Asn Phe Ala Glu Glu Tyr Thr
            100                 105                 110

Leu Glu Lys Ile Ile Lys Thr Cys Val Glu Gly Thr Leu Arg Ile Leu
        115                 120                 125

Gln Ser Cys Leu Lys Ser Lys Thr Val Lys Lys Val Val Tyr Thr Ser
    130                 135                 140

Ser Ala Asp Ala Ala Met Met Ile Ser Asn Leu Lys Ala Val Lys Glu
145                 150                 155                 160

Ile Asp Glu Thr Ile Trp Ser Glu Val Asp Asn Phe Ile Ser Lys Pro
                165                 170                 175

Glu Gln Val Ile Pro Gly Leu Pro Ser Tyr Val Val Ser Lys Val Leu
            180                 185                 190

Thr Glu Arg Ala Cys Leu Lys Phe Ser Glu Glu His Gly Leu Asp Val
        195                 200                 205

Val Thr Ile Leu Pro Pro Leu Val Val Gly Pro Phe Ile Thr Pro His
    210                 215                 220

Pro Pro Pro Ser Val Ser Ile Ala Leu Ser Ile Ile Ser Gly Asp Val
225                 230                 235                 240

Ser Met Met Leu Gly Val Arg Leu Glu Asn Ala Val His Ile Asp Asp
                245                 250                 255

```
Val Ala Leu Ala His Ile Phe Val Phe Glu Cys Glu Lys Ala Lys Gly
            260                 265                 270

Arg His Ile Cys Ser Ser Val Asp Phe Pro Met His Asp Leu Pro Lys
            275                 280                 285

Phe Ile Ser Glu Asn Tyr Pro Glu Phe Asn Val Pro Thr Asp Leu Leu
            290                 295                 300

Lys Asp Ile Glu Glu Gln Pro Val His Leu Ser Ser Asp Lys Leu
305                 310                 315                 320

Leu Ser Met Gly Phe Gln Phe Lys Tyr Asp Phe Ala Glu Ile Phe Gly
                    325                 330                 335

Asp Ala Ile Arg Cys Ala Lys Glu Lys Gly Phe Leu
                340                 345

<210> SEQ ID NO 97
<211> LENGTH: 360
<212> TYPE: PRT
<213> ORGANISM: A. thaliana

<400> SEQUENCE: 97

Met Val Arg Glu Glu Glu Asp Asp Asn Asn Gly Gly Gly Gly Glu
1               5                   10                  15

Arg Lys Leu Pro Val Ala Asp Glu Thr Val Pro Ser Leu Leu Asp Gly
                20                  25                  30

Thr Gly Leu Val Cys Val Thr Gly Thr Gly Phe Val Ala Ser Trp
            35                  40                  45

Leu Ile Met Arg Leu Leu Gln Arg Gly Tyr Ser Val Arg Ala Thr Val
50                  55                  60

Arg Thr Asn Pro Glu Gly Asn Lys Lys Asp Ile Ser Tyr Leu Thr Glu
65                  70                  75                  80

Leu Pro Phe Ala Ser Glu Arg Leu Gln Ile Phe Thr Ala Asp Leu Asn
                85                  90                  95

Glu Pro Glu Ser Phe Lys Pro Ala Ile Glu Gly Cys Lys Ala Val Phe
            100                 105                 110

His Val Ala His Pro Met Asp Pro Asn Ser Asn Glu Thr Glu Glu Thr
            115                 120                 125

Val Thr Lys Arg Thr Val Gln Gly Leu Met Gly Ile Leu Lys Ser Cys
130                 135                 140

Leu Asp Ala Lys Thr Val Lys Arg Phe Phe Tyr Thr Ser Ser Ala Val
145                 150                 155                 160

Thr Val Phe Tyr Ser Gly Lys Asn Gly Gly Gly Gly Glu Val Asp
                165                 170                 175

Glu Ser Val Trp Ser Asp Val Glu Val Phe Arg Asn Gln Lys Glu Lys
            180                 185                 190

Arg Val Ser Ser Ser Tyr Val Ser Lys Met Ala Ala Glu Thr Ala
            195                 200                 205

Ala Leu Glu Phe Gly Gly Lys Asn Gly Leu Glu Val Val Thr Leu Val
            210                 215                 220

Ile Pro Leu Val Val Gly Pro Phe Ile Ser Pro Ser Leu Pro Ser Ser
225                 230                 235                 240

Val Phe Ile Ser Leu Ala Met Leu Phe Gly Asn Tyr Lys Glu Lys Tyr
                245                 250                 255

Leu Phe Asp Thr Tyr Asn Met Val His Ile Asp Asp Val Ala Arg Ala
            260                 265                 270

Met Ile Leu Leu Leu Glu Lys Pro Val Ala Lys Gly Arg Tyr Ile Cys
```

```
                275                 280                 285
Ser Ser Val Glu Met Lys Ile Asp Glu Val Phe Glu Phe Leu Ser Thr
    290                 295                 300
Lys Phe Pro Gln Phe Gln Leu Pro Ser Ile Asp Leu Lys Asn Tyr Lys
305                 310                 315                 320
Val Glu Lys Arg Met Ser Leu Ser Ser Lys Leu Arg Ser Glu Gly
                325                 330                 335
Phe Glu Phe Lys Tyr Gly Ala Glu Ile Phe Gly Gly Ala Ile Arg
                340                 345                 350
Ser Cys Gln Ala Arg Gly Phe Leu
                355                 360

<210> SEQ ID NO 98
<211> LENGTH: 323
<212> TYPE: PRT
<213> ORGANISM: Homo sapiens

<400> SEQUENCE: 98

Met Asp Pro Lys Tyr Gln Arg Val Glu Leu Asn Asp Gly His Phe Met
1               5                   10                  15
Pro Val Leu Gly Phe Gly Thr Tyr Ala Pro Glu Val Pro Arg Asn
                20                  25                  30
Arg Ala Val Glu Val Thr Lys Leu Ala Ile Glu Ala Gly Phe Arg His
                35                  40                  45
Ile Asp Ser Ala Tyr Leu Tyr Asn Asn Glu Glu Gln Val Gly Leu Ala
    50                  55                  60
Ile Arg Ser Lys Ile Ala Asp Gly Ser Val Lys Arg Glu Asp Ile Phe
65                  70                  75                  80
Tyr Thr Ser Lys Leu Trp Cys Thr Phe Phe Gln Pro Gln Met Val Gln
                85                  90                  95
Pro Ala Leu Glu Ser Ser Leu Lys Lys Leu Gln Leu Asp Tyr Val Asp
                100                 105                 110
Leu Tyr Leu Leu His Phe Pro Met Ala Leu Lys Pro Gly Glu Thr Pro
                115                 120                 125
Leu Pro Lys Asp Glu Asn Gly Lys Val Ile Phe Asp Thr Val Asp Leu
                130                 135                 140
Ser Ala Thr Trp Glu Val Met Glu Lys Cys Lys Asp Ala Gly Leu Ala
145                 150                 155                 160
Lys Ser Ile Gly Val Ser Asn Phe Asn Cys Arg Gln Leu Glu Met Ile
                165                 170                 175
Leu Asn Lys Pro Gly Leu Lys Tyr Lys Pro Val Cys Asn Gln Val Glu
                180                 185                 190
Cys His Pro Tyr Leu Asn Gln Ser Lys Leu Leu Asp Phe Cys Lys Ser
                195                 200                 205
Lys Asp Ile Val Leu Val Ala His Ser Ala Leu Gly Thr Gln Arg His
                210                 215                 220
Lys Leu Trp Val Asp Pro Asn Ser Pro Val Leu Leu Glu Asp Pro Val
225                 230                 235                 240
Leu Cys Ala Leu Ala Lys Lys His Lys Arg Thr Pro Ala Leu Ile Ala
                245                 250                 255
Leu Arg Tyr Gln Leu Gln Arg Gly Val Val Val Leu Ala Lys Ser Tyr
                260                 265                 270
Asn Glu Gln Arg Ile Arg Glu Asn Ile Gln Val Phe Glu Phe Gln Leu
                275                 280                 285
```

```
Thr Ser Glu Asp Met Lys Val Leu Asp Gly Leu Asn Arg Asn Tyr Arg
    290                 295                 300
Tyr Val Val Met Asp Phe Leu Met Asp His Pro Asp Tyr Pro Phe Ser
305                 310                 315                 320
Asp Glu Tyr
```

<210> SEQ ID NO 99
<211> LENGTH: 323
<212> TYPE: PRT
<213> ORGANISM: Mus musculus

<400> SEQUENCE: 99

```
Met Asp Ser Lys Gln Gln Thr Val Arg Leu Ser Asp Gly His Phe Ile
1               5                   10                  15
Pro Ile Leu Gly Phe Gly Thr Tyr Ala Pro Gln Glu Val Pro Lys Ser
            20                  25                  30
Lys Ala Thr Glu Ala Thr Lys Ile Ala Ile Asp Ala Gly Phe Arg His
        35                  40                  45
Ile Asp Ser Ala Ser Met Tyr Gln Asn Glu Lys Glu Val Gly Leu Ala
    50                  55                  60
Ile Arg Ser Lys Ile Ala Asp Gly Thr Val Lys Arg Glu Asp Ile Phe
65                  70                  75                  80
Tyr Thr Ser Lys Val Trp Cys Thr Phe His Arg Pro Glu Leu Val Arg
                85                  90                  95
Val Cys Leu Glu Gln Ser Leu Lys Gln Leu Gln Leu Asp Tyr Val Asp
            100                 105                 110
Leu Tyr Leu Ile His Phe Pro Met Ala Met Lys Pro Gly Glu Asn Tyr
        115                 120                 125
Leu Pro Lys Asp Glu Asn Gly Lys Leu Ile Tyr Asp Ala Val Asp Ile
    130                 135                 140
Cys Asp Thr Trp Glu Ala Met Glu Lys Cys Lys Asp Ala Gly Leu Ala
145                 150                 155                 160
Lys Ser Ile Gly Val Ser Asn Phe Asn Arg Arg Gln Leu Glu Lys Ile
                165                 170                 175
Leu Lys Lys Pro Gly Leu Lys Tyr Lys Pro Val Cys Asn Gln Val Glu
            180                 185                 190
Cys His Pro Tyr Leu Asn Gln Gly Lys Leu Leu Asp Phe Cys Arg Ser
        195                 200                 205
Lys Asp Ile Val Leu Val Ala Tyr Ser Ala Leu Gly Ser His Arg Glu
    210                 215                 220
Lys Gln Trp Val Asp Gln Ser Ser Pro Val Leu Leu Asp Asn Pro Val
225                 230                 235                 240
Leu Gly Ser Met Ala Lys Lys Tyr Asn Arg Thr Pro Ala Leu Ile Ala
                245                 250                 255
Leu Arg Tyr Gln Leu Gln Arg Gly Val Val Val Leu Ala Lys Ser Phe
            260                 265                 270
Ser Glu Lys Arg Ile Lys Glu Asn Met Gln Val Phe Glu Phe Gln Leu
        275                 280                 285
Thr Ser Glu Asp Met Lys Val Leu Asp Leu Asn Lys Asn Ile Arg
    290                 295                 300
Tyr Ile Ser Gly Ser Ser Phe Lys Asp His Pro Asp Phe Pro Phe Trp
305                 310                 315                 320
Asp Glu Tyr
```

-continued

```
<210> SEQ ID NO 100
<211> LENGTH: 317
<212> TYPE: PRT
<213> ORGANISM: S. lycopersicum

<400> SEQUENCE: 100
```

Met Ala Glu Ala Thr Glu Met Pro Tyr Ile Glu Leu Asn Thr Gly Phe
1               5                   10                  15

Ser Ile Pro Ala Val Gly Leu Gly Thr Trp Gln Ser Asp Pro Gly Val
            20                  25                  30

Val Gly Lys Ala Val Glu Thr Ala Ile Lys Met Gly Tyr Arg His Ile
        35                  40                  45

Asp Cys Ala Gln Ile Tyr Lys Asn Glu Lys Glu Ile Gly Glu Val Leu
    50                  55                  60

Ser Arg Leu Phe Lys Asp Gly Val Val Lys Arg Glu Leu Phe Ile
65                  70                  75                  80

Thr Ser Lys Leu Trp Asn Thr Asn His Ala Pro Glu Asp Val Pro Val
                85                  90                  95

Ala Leu Asp Lys Thr Leu Gln Asp Leu Gln Leu Glu Tyr Val Asp Leu
            100                 105                 110

Tyr Leu Ile His Trp Pro Val Ser Met Lys Pro Gly Ser Val Asp Phe
        115                 120                 125

Lys Pro Glu Asn Leu Met Pro Thr Asn Ile Pro Arg Ile Trp Glu Ala
130                 135                 140

Met Glu Lys Val Tyr Asp Ser Gly Lys Ala Arg Val Ile Gly Val Ser
145                 150                 155                 160

Asn Phe Ser Thr Lys Lys Leu Glu Asp Leu Leu Gln Val Ala Arg Thr
                165                 170                 175

Pro Pro Ala Val Asn Gln Val Glu Cys His Pro Ser Trp Gln Gln Ala
            180                 185                 190

Lys Leu Arg Glu Leu Cys Lys Ser Asn Asn Val His Leu Ser Ala Tyr
        195                 200                 205

Ser Pro Leu Gly Ser Pro Gly Thr Thr Trp Leu Lys Ser Asp Val Leu
    210                 215                 220

Lys Gln Pro Ala Val Ile Ser Val Ala Glu Lys Leu Gly Lys Thr Pro
225                 230                 235                 240

Ala Gln Val Cys Leu Arg Trp Gly Ile Gln Met Gly Gln Ser Val Leu
                245                 250                 255

Pro Lys Ser Thr His Glu Ala Arg Ile Lys Glu Asn Leu Asp Val Leu
            260                 265                 270

Asn Trp Ser Ile Pro Asp Asp Leu Ala Lys Phe Ser Glu Ile Pro
        275                 280                 285

Gln Ala Arg Leu Leu Lys Gly Ala Ser Phe Ala His Glu Thr His Gly
    290                 295                 300

Gln Tyr Arg Thr Leu Glu Glu Leu Trp Asp Gly Glu Ile
305                 310                 315

```
<210> SEQ ID NO 101
<211> LENGTH: 331
<212> TYPE: PRT
<213> ORGANISM: S. lycopersicum

<400> SEQUENCE: 101
```

Met Thr Met Asn Leu Ile Lys Gln Met Leu Val Pro Asn Val Asn Leu
1               5                   10                  15

Asn Ser Gly His Lys Met Pro Leu Ile Gly Met Gly Thr Ala Pro Ser 20                  25                  30
Leu Pro Glu His Asp Gln Leu Val Ser Thr Leu Ile Asp Ala Ile Glu
            35                  40                  45

Ile Gly Tyr Arg His Phe Asp Thr Ala Ala Val Tyr Gly Ser Glu Glu
    50                  55                  60

Ala Leu Gly Gln Ala Val Val Glu Ala Ile Gln Arg Gly Leu Ile Lys
65                  70                  75                  80

Ser Arg Glu Gln Val Phe Ile Thr Ser Lys Leu Trp Cys Thr Glu Thr
                85                  90                  95

His Arg His Leu Val Leu Pro Ala Leu Lys Arg Thr Leu Gly Arg Leu
            100                 105                 110

Lys Met Asp Tyr Leu Asp Leu Tyr Leu Ile His Leu Pro Val Thr Met
        115                 120                 125

Lys Lys Lys Val Asn Ser Lys Asp Asp Glu Met Arg Val Asp Lys Glu
    130                 135                 140

Asp Ile Ile Pro Phe Asp Met Arg Gly Thr Trp Glu Ala Met Glu Glu
145                 150                 155                 160

Cys Cys Arg Leu Gly Leu Ala Lys Ser Ile Gly Val Ser Asn Phe Thr
                165                 170                 175

Cys Thr Lys Ile Ser Gln Ile Leu His Tyr Ala Thr Ile Leu Pro Ala
            180                 185                 190

Val Asn Gln Val Glu Met His Val Ala Trp Arg Gln Glu Lys Met Leu
        195                 200                 205

Glu Phe Cys Lys Glu Lys Gly Ile His Val Ser Ala Trp Ser Pro Leu
    210                 215                 220

Gly Ala Asn Gly Leu Thr Pro Trp Gly Ile His Ser Val Met Glu Ser
225                 230                 235                 240

Pro Val Leu Lys Asp Ile Ala Ile His Lys Arg Lys Ser Val Ala Gln
                245                 250                 255

Val Ala Leu Arg Trp Val Tyr Glu Gln Gly Ala Ser Val Ile Val Lys
            260                 265                 270

Ser Phe Asn Lys Glu Arg Met Lys Glu Asn Leu Gln Ile Leu Asp Trp
        275                 280                 285

Glu Leu Ser Asn Glu Glu Ile Ala Gln Ile Gln Glu Ile Pro Pro Cys
    290                 295                 300

Thr Gly Phe Asn Val Asp Met Val Leu Val His Pro Asn Gly Pro Tyr
305                 310                 315                 320

Lys Ser Ala Asn Gln Phe Trp Asp Gly Glu Ile
                325                 330

<210> SEQ ID NO 102
<211> LENGTH: 312
<212> TYPE: PRT
<213> ORGANISM: M. truncatula

<400> SEQUENCE: 102

Met Gly Ser Val Glu Ile Pro Thr Lys Val Leu Thr Asn Thr Ser Ser
1               5                   10                  15

Gln Leu Lys Met Pro Val Val Gly Met Gly Ser Ala Pro Asp Phe Thr
            20                  25                  30

Cys Lys Lys Asp Thr Lys Asp Ala Ile Ile Glu Ala Ile Lys Gln Gly
        35                  40                  45

Tyr Arg His Phe Asp Thr Ala Ala Ala Tyr Gly Ser Glu Gln Ala Leu
    50                  55                  60

Gly Glu Ala Leu Lys Glu Ala Ile Glu Leu Gly Leu Val Thr Arg Gln
65                  70                  75                  80

Asp Leu Phe Val Thr Ser Lys Leu Trp Val Thr Glu Asn His Pro His
                85                  90                  95

Leu Val Ile Pro Ala Leu Gln Lys Ser Leu Lys Thr Leu Gln Leu Asp
            100                 105                 110

Tyr Leu Asp Leu Tyr Leu Ile His Trp Pro Leu Ser Ser Gln Pro Gly
        115                 120                 125

Lys Phe Thr Phe Pro Ile Asp Val Ala Asp Leu Leu Pro Phe Asp Val
    130                 135                 140

Lys Gly Val Trp Glu Ser Met Glu Gly Leu Lys Leu Gly Leu Thr
145                 150                 155                 160

Lys Ala Ile Gly Val Ser Asn Phe Ser Val Lys Leu Glu Asn Leu
                165                 170                 175

Leu Ser Val Ala Thr Ile Leu Pro Ala Val Asn Gln Val Glu Met Asn
            180                 185                 190

Leu Ala Trp Gln Gln Lys Lys Leu Arg Glu Phe Cys Asn Ala Asn Gly
        195                 200                 205

Ile Val Leu Thr Ala Phe Ser Pro Leu Arg Lys Gly Ala Ser Arg Gly
    210                 215                 220

Pro Asn Glu Val Met Glu Asn Asp Met Leu Lys Glu Ile Ala Asp Ala
225                 230                 235                 240

His Gly Lys Ser Val Ala Gln Ile Ser Leu Arg Trp Leu Tyr Glu Gln
                245                 250                 255

Gly Val Thr Phe Val Pro Lys Ser Tyr Asp Lys Glu Arg Met Asn Gln
            260                 265                 270

Asn Leu Cys Ile Phe Asp Trp Ser Leu Thr Lys Glu Asp His Glu Lys
        275                 280                 285

Ile Asp Gln Ile Lys Gln Asn Arg Leu Ile Pro Gly Pro Thr Lys Pro
    290                 295                 300

Gly Leu Asn Asp Leu Tyr Asp Asp
305                 310

<210> SEQ ID NO 103
<211> LENGTH: 321
<212> TYPE: PRT
<213> ORGANISM: P. somniferum

<400> SEQUENCE: 103

Met Glu Ser Asn Gly Val Pro Met Ile Thr Leu Ser Ser Gly Ile Arg
1               5                   10                  15

Met Pro Ala Leu Gly Met Gly Thr Ala Glu Thr Met Val Lys Gly Thr
            20                  25                  30

Glu Arg Glu Lys Leu Ala Phe Leu Lys Ala Ile Glu Val Gly Tyr Arg
        35                  40                  45

His Phe Asp Thr Ala Ala Ala Tyr Gln Thr Glu Glu Cys Leu Gly Glu
    50                  55                  60

Ala Ile Ala Glu Ala Leu Gln Leu Gly Leu Ile Lys Ser Arg Asp Glu
65                  70                  75                  80

Leu Phe Ile Thr Ser Lys Leu Trp Cys Ala Asp Ala His Ala Asp Leu
                85                  90                  95

Val Leu Pro Ala Leu Gln Asn Ser Leu Arg Asn Leu Lys Leu Asp Tyr
            100                 105                 110

Leu Asp Leu Tyr Leu Ile His His Pro Val Ser Leu Lys Pro Gly Lys
        115                 120                 125

Phe Val Asn Glu Ile Pro Lys Asp His Ile Leu Pro Met Asp Tyr Lys
    130                 135                 140

Ser Val Trp Ala Ala Met Glu Glu Cys Gln Thr Leu Gly Phe Thr Arg
145                 150                 155                 160

Ala Ile Gly Val Cys Asn Phe Ser Cys Lys Arg Leu Gln Glu Leu Met
                165                 170                 175

Glu Thr Ala Asn Ser Pro Pro Val Val Asn Gln Val Glu Met Ser Pro
            180                 185                 190

Thr Leu His Gln Lys Asn Leu Arg Glu Tyr Cys Lys Ala Asn Asn Ile
        195                 200                 205

Met Ile Thr Ala His Ser Val Leu Gly Ala Val Gly Ala Ala Trp Gly
    210                 215                 220

Thr Asn Ala Val Met His Ser Lys Val Leu His Gln Ile Ala Val Ala
225                 230                 235                 240

Arg Gly Lys Ser Val Ala Gln Val Ser Met Arg Trp Val Tyr Gln Gln
                245                 250                 255

Gly Ala Ser Leu Val Val Lys Ser Phe Asn Glu Ala Arg Met Lys Glu
            260                 265                 270

Asn Leu Lys Ile Phe Asp Trp Glu Leu Thr Ala Glu Asp Met Glu Lys
        275                 280                 285

Ile Ser Glu Ile Pro Gln Ser Arg Thr Ser Ser Ala Ala Phe Leu Leu
    290                 295                 300

Ser Pro Thr Gly Pro Phe Lys Thr Glu Glu Glu Phe Trp Asp Glu Lys
305                 310                 315                 320

Asp

<210> SEQ ID NO 104
<211> LENGTH: 320
<212> TYPE: PRT
<213> ORGANISM: A. thaliana

<400> SEQUENCE: 104

Met Ser Ala Leu Thr Phe Pro Ile Gly Ser Val His His Leu Met Pro
1               5                   10                  15

Val Leu Ala Leu Gly Thr Ala Ala Ser Pro Pro Glu Pro Ile Val
                20                  25                  30

Leu Lys Arg Thr Val Leu Glu Ala Ile Lys Leu Gly Tyr Arg His Phe
            35                  40                  45

Asp Thr Ser Pro Arg Tyr Gln Thr Glu Glu Pro Leu Gly Glu Ala Leu
    50                  55                  60

Ala Glu Ala Val Ser Leu Gly Leu Ile Gln Ser Arg Ser Glu Leu Phe
65                  70                  75                  80

Val Thr Ser Lys Leu Trp Cys Ala Asp Ala His Gly Gly Leu Val Val
                85                  90                  95

Pro Ala Ile Gln Arg Ser Leu Glu Thr Leu Lys Leu Asp Tyr Leu Asp
            100                 105                 110

Leu Tyr Leu Ile His Trp Pro Val Ser Ser Lys Pro Gly Lys Tyr Lys
    115                 120                 125

Phe Pro Ile Glu Glu Asp Phe Leu Pro Met Asp Tyr Glu Thr Val
    130                 135                 140

Trp Ser Glu Met Glu Glu Cys Gln Arg Leu Gly Val Ala Lys Cys Ile
145                 150                 155                 160

Gly Val Ser Asn Phe Ser Cys Lys Lys Leu Gln His Ile Leu Ser Ile
                165                 170                 175

```
Ala Lys Ile Pro Pro Ser Val Asn Gln Val Glu Met Ser Pro Val Trp
            180                 185                 190

Gln Gln Arg Lys Leu Arg Glu Leu Cys Lys Ser Lys Gly Ile Val Val
        195                 200                 205

Thr Ala Tyr Ser Val Leu Gly Ser Arg Gly Ala Phe Trp Gly Thr His
    210                 215                 220

Lys Ile Met Glu Ser Asp Val Leu Lys Glu Ile Ala Glu Ala Lys Gly
225                 230                 235                 240

Lys Thr Val Ala Gln Val Ser Met Arg Trp Ala Tyr Glu Glu Gly Val
            245                 250                 255

Ser Met Val Val Lys Ser Phe Arg Lys Asp Arg Leu Glu Glu Asn Leu
        260                 265                 270

Lys Ile Phe Asp Trp Ser Leu Thr Glu Glu Lys Gln Arg Ile Ser
    275                 280                 285

Thr Glu Ile Ser Gln Ser Arg Ile Val Asp Gly Glu Val Tyr Ile Ser
    290                 295                 300

Glu Lys Gly Pro Ile Lys Ser Val Thr Glu Met Trp Asp Gly Glu Ile
305                 310                 315                 320

<210> SEQ ID NO 105
<211> LENGTH: 259
<212> TYPE: PRT
<213> ORGANISM: D. lanata

<400> SEQUENCE: 105

Met Ser Ser Lys Pro Arg Leu Glu Gly Lys Val Ala Ile Ile Thr Gly
1               5                   10                  15

Ala Ala Ser Gly Ile Gly Glu Glu Thr Ala Arg Leu Phe Val Glu His
            20                  25                  30

Gly Ala Ser Val Val Ala Asp Val Gln Asp Glu Leu Gly Arg Gln
        35                  40                  45

Val Val Ala Ser Val Asn Ser Asp Asp Lys Ile Ser Tyr Tyr His Cys
    50                  55                  60

Asp Val Arg Asp Glu Lys Gln Val Ala Ala Thr Val Arg Tyr Ala Val
65                  70                  75                  80

Glu Lys Tyr Gly Arg Leu Asp Ile Met Leu Ser Asn Ala Gly Val Phe
            85                  90                  95

Gly Ala Leu Met Thr Asn Val Ile Asp Leu Asp Met Val Asp Phe Glu
            100                 105                 110

Asn Val Leu Ala Thr Asn Val Arg Gly Val Ala Asn Thr Ile Lys His
        115                 120                 125

Ala Ala Arg Ala Met Val Glu Gly Lys Val Lys Gly Ser Ile Ile Cys
    130                 135                 140

Thr Ala Ser Val Ser Ala Ser Leu Gly Gly Met Gly Pro Pro Ala Tyr
145                 150                 155                 160

Thr Ala Ser Lys His Ala Val Leu Gly Leu Val Lys Gly Ala Cys Ala
            165                 170                 175

Glu Leu Gly Val His Gly Ile Arg Val Asn Ser Val Ala Pro Tyr Gly
        180                 185                 190

Val Ala Thr Pro Met Pro Cys Ser Ala Tyr Gly Met Thr Pro Ser Gln
    195                 200                 205

Met Glu Glu Ala Asn Asn Ser Arg Ala Asn Leu Lys Gly Val Val Leu
    210                 215                 220

Lys Ala Lys His Val Ala Glu Ala Ala Leu Phe Leu Ala Ser Asp Glu
```

```
225                 230                 235                 240
Ser Ala Tyr Val Ser Gly Gln Asn Leu Ala Val Asp Gly Gly Phe Thr
                245                 250                 255

Val Val Arg

<210> SEQ ID NO 106
<211> LENGTH: 33
<212> TYPE: DNA
<213> ORGANISM: Artificial Sequence
<220> FEATURE:
<223> OTHER INFORMATION: GAME25 silencing construct for S. pennellii
      forward primer

<400> SEQUENCE: 106
gcggccgcat tgtcactcta ttgtgttggc gtg                                   33

<210> SEQ ID NO 107
<211> LENGTH: 36
<212> TYPE: DNA
<213> ORGANISM: Artificial Sequence
<220> FEATURE:
<223> OTHER INFORMATION: GAME25 silencing construct for S. pennellii
      reverse primer

<400> SEQUENCE: 107
ggcgcgccta aatttatatc ttttcaagtc acaatg                                36
```

GLYCOALKALOID METABOLISM ENYZYMES (GAMES) AND USES THEREOF

CROSS-REFERENCE TO RELATED APPLICATIONS

This application is a National Phase Application of PCT International Application Number PCT/IL2018/050142, International filing date Feb. 8, 2018, which claims the benefit of Israeli Patent Application Number 250538 filed Feb. 9, 2017, which are hereby incorporated by reference in their entirety herein.

SEQUENCE LISTING STATEMENT

The instant application contains a Sequence Listing which has been submitted electronically in ASCII format and is hereby incorporated by reference in its entirety. Said ASCII copy, created on Feb. 6, 2018, is named P-80579-PC_ST25-UPDATE-06FEB18.txt and is 199,976 bytes in size.

FIELD OF THE DISCLOSURE

Identification and use of key genes in the biosynthesis of steroidal alkaloids to genetically modified plants, wherein the genetically modified plants have an altered content of steroidal alkaloids and glycosylated derivatives thereof. Genetically modified plants described comprise Solanaceae crop plants, including those with reduced content of anti-nutritional steroidal glycoalkaloids.

BACKGROUND

The plant kingdom produces hundreds of thousands of different small compounds that are often genus or family specific. These molecules, referred to as secondary metabolites, are not vital to cells that produce them, but contribute to the overall fitness of the organisms. Steroidal alkaloids are one example of secondary metabolites. They are low molecular weight nitrogen-containing organic compounds, typically with a heterocyclic structure. Steroidal alkaloid biosynthesis in plants is tightly controlled during development and in response to stress and pathogens.

Consisting of a C-27 cholestane skeleton and a heterocyclic nitrogen component, steroidal alkaloids (SAs) were suggested to be synthesized in the cytosol from cholesterol. Conversion of cholesterol to the alkamine SA should require several hydroxylation, oxidation and transamination reactions (Eich E. 2008. Solanaceae and Convolvulaceae—secondary metabolites: biosynthesis, chemotaxonomy, biological and economic significance: a handbook. Berlin: Springer), and in most cases further glycosylation to form steroidal glycoalkaloids (SGAs) (Arnqvist L. et al. 2003. Plant Physiol 131:1792-1799). The oligosaccharide moiety components of SGAs directly conjugate to the hydroxyl group at C-3/3 of the alkamine steroidal skeleton (aglycone). The oligosaccharide moiety includes D-glucose, D-galactose, L-rhamnose, D-xylose, and L-arabinose, the first two monosaccharides being the predominant units.

SGA biosynthesis depends on genes encoding UDP-glycosyltransferases (UGTs) that add to the aglycone various sugar moieties (McCue K F et al., 2005. Plant Sci. 168:267-273; Itkin M et al., 2011. Plant Cell 23:4507-4525). The tomato GLYCOALKALOID METABOLISM 1 (GAME1) glycosyltransferase, a homolog of the potato SGT1 (McCue et al., 2005, supra), catalyzes galactosylation of the alkamine tomatidine (Itkin et al., 2011, supra).

SAs play a role in protecting plants against a broad range of pathogens and are thus referred to as phytoanticipins (antimicrobial compounds). SGAs are also known to contribute to plant resistance towards a wide range of pathogens, pests, and predators, including bacteria, fungi, oomycetes, viruses, insects and animals many SGAs are harmful to a variety of organisms including mammals and humans. When present in edible plant parts, these harmful SGAs are referred to as anti-nutritional substances. These SGAs cause gastrointestinal and neurological disorders and, at high concentrations, may be lethal to humans. For this reason, total SGA levels exceeding 200 mg per kilogram fresh weight of edible tuber are deemed unsafe for human consumption.

Thus, SGA are well known anti-nutritional secondary metabolites produced by numerous members of Solanaceae family (e.g. potato, tomato, eggplant). Well-known examples of SGA anti-nutritional secondary metabolite compounds include α-tomatine and dehydrotomatine in tomato (*Solanum lycopersicum*), α-chaconine and α-solanine in potato (*Solanum tuberosum*), and α-solamargine and α-solasonine in aubergine (*Solanum melongena*).

In tomato, α-tomatine and dehydrotomatine represent the major SGAs accumulating predominantly in green tissues; young and mature leaves, flower buds, skin and seeds of immature and mature green fruit. Dehydrotomatidine (i.e. tomatidenol) is the first SA aglycone formed in SGA biosynthesis which could further be hydrogenated at the C-5 position to form tomatidine (FIGS. 1A-1C). Both aglycones are further glycosylated (tetra-saccharide moiety i.e. lycotetrose) to produce dehydrotomatine and α-tomatine respectively (FIGS. 1A-1C). Thus, the SGA pathway branches at dehydrotomatidine for either formation of tomatidine derived SGAs or glycosylated dehydrotomatine derivatives (FIGS. 1A-1C). Notably, dehydrotomatidine and tomatidine are only different in their structures by the presence or absence of the double bond at the C-5 position. The conversion of dehydrotomatidine to tomatidine was hypothesized in the past as a single reaction catalyzed by a hypothetical hydrogenase. In most tomato plant tissues, the relative portion of dehydrotomatine as compared to α-tomatine ranges from ~2.5-~10%. As tomato fruit matures and reaches to the red stage, the entire pool of α-tomatine and dehydrotomatine is largely being converted to esculeosides (major SGAs) and dehydroesculeosides (minor SGAs), respectively (FIGS. 1A-1C).

In cultivated potato, α-chaconine and α-solanine are the major SGAs sharing the same aglycone, solanidine (in which a C-5,6 double bond is present) and possess chacotriose and solatriose moieties, respectively. As there is no demissidine or demissine detected in cultivated potatoes, it was suggested that a hydrogenase enzyme able to convert solanidine to demissidine is lacking in these species. Several wild potato species (e.g. *S. demissum, S. chacoense, S. commersonii*) and their somatic hybrids (*S. brevidens×S. tuberosum*), predicted to contain an active hydrogenase, do produce demissidine or its glycosylated form, demissine being one of their major SGAs (FIGS. 2A-2B). In eggplant, α-solamargine and α-solasonine are the most abundant SGAs derived from the solasodine aglycone (in which a C-5,6 double bond is present); while some wild *solanum* species, e.g. *S. dulcamara* produce soladulcidine or its glycosylated forms, soladulcine A and β-soladulcine (C-5,6 double bond is absent), as major SGAs from the solasodine aglycone (FIGS. 3A-3C).

In addition to SGAs, many *Solanum* species also produce cholesterol-derived unsaturated or saturated steroidal saponins. Unsaturated and saturated steroidal saponins are widespread in the plant kingdom, especially among monocots, e.g. the Agavaceae, Asparagaceae, Dioscoreaceae and Liliaceae families. Similar to SGAs, steroidal saponins are highly diverse in structures and could be either saturated (e.g. sarasapogenin) or unsaturated (e.g. diosgenin) in the C-5,6 position.

Cholesterol, the main sterol produced by all animals, serves as a key building block in the biosynthesis of SGAs. An array of tomato and potato GLYCOALKALOIDMETABOLISM (GAME) genes participating in core SGA biosynthesis starting from cholesterol were reported in recent years. The tomato SGAs biosynthetic pathway can be divided into two main parts. In the first, the SA aglycone is formed from cholesterol by the likely action of the GAME6, GAME8, GAME11, GAME4 and GAME12 enzymes. The second part results in the generation of SGA through the action of UDP-glycosyltransferases (UGTs): GAME1, GAME2, GAME17 and GAME18 in tomato, and STEROL ALKALOID GLYCOSYL TRANSFERASE1 (SGT1), SGT2 and SGT3 in potato.

The formation of unsaturated steroidal saponin aglycone is also a main step in steroidal saponin biosynthesis pathway (FIG. 3A). The aglycone of steroidal saponin is either a spirostanol (closed ring) or a furostanol (open ring). Both these saponin aglycones (e.g. diosgenin) undergoes either glycosylation to form unsaturated saponin glycosides (e.g. dioscin) or hydrogenation at C-5,6 position to form saturated saponin aglycones (e.g. sarasapogenin). These saturated saponin aglycones are further glycosylated to produce downstream saturated saponin glycosides (e.g. parillin) (FIG. 3A). Therefore, like SGAs, unsaturated and saturated aglycone forms of steroidal saponin metabolites also primarily contribute for their structural diversity. Notably, dehydrotomatidine/tomatidine, solanidine/demissidine, solasodine/soladulcidine SA aglycones and unsaturated/saturated steroidal saponin aglycones are only different in their structures by the presence or absence of the double bond at the C-5,6 position. However, the biosynthetic basis of the formation of saturated steroidal alkaloid and steroidal saponin aglycones from their unsaturated forms in Solanaceae or in any other plant families remains unclear till date. In fact, the conversion of dehydrotomatidine to tomatidine in tomato, and solanidine to demissidine in wild potato species by elimination of the C-5,6 double bond was hypothesized for decades to be carried out in a single reaction catalyzed by a hypothetical hydrogenase enzyme.

There is an ongoing attempt to elucidate the biosynthesis pathway of steroidal alkaloids and to control their production. It would be advantageous to both the farmer and the consumer to have a Solanaceae plant wherein the levels of SGA present would provide the necessary plant resistance to pathogens and predators, while the fruits, tubers and vegetables had reduced anti-nutritional secondary metabolites. The ability to manipulate the synthesis of the SGAs may provide the means to develop, through classical breeding or genetic engineering, crops with modified levels and composition of SGAs, conferring the plant with a preexisting chemical barrier against a broad range of pathogens and insects. At the same time, anti-nutritional compounds (e.g., chaconine and solanine from potato) would be removed.

Disclosed herein are newly identified genes present in Solanaceae family members encoding enzymes active in the steroidal glycoalkaloids metabolic pathway, whose manipulation may provide just such a balance between plant resistance and decreased anti-nutritional secondary metabolites. For example, in tomato plants genes encoding enzymes active in the conversion of dehydrotomatidine to tomatidine and from α-tomatine to hydroxytomatine have been identified, whose manipulation within tomato plants may provide just such a balance between tomato plant resistance during growth and fruit development, and decreased anti-nutritional secondary metabolites present in resultant tomatoes.

SUMMARY

In one aspect, provided herein is a genetically modified plant comprising an altered content of at least one cholesterol derived compound selected from the group comprising a steroidal alkaloid or a glycosylated derivative thereof, and an unsaturated or saturated steroidal saponin or a glycoside derivative thereof, said plant comprising at least one cell having an altered biological activity of at least one enzyme selected from the group comprising a 3-β-hydroxysteroid dehydrogenase/isomerase (GAME25) and a 2-oxoglutarate-dependent dioxygenase (GAME31), or a combination thereof; or an altered expression of at least one gene selected from the group comprising a gene encoding a 3-β-hydroxysteroid dehydrogenase/isomerase (GAME25) and a gene encoding a 2-oxoglutarate-dependent dioxygenase (GAME31), or a combination thereof; or a combination thereof of an altered biological activity of at least one enzyme selected from the group comprising a 3-β-hydroxysteroid dehydrogenase/isomerase (GAME25) and a 2-oxoglutarate-dependent dioxygenase (GAME31), or a combination thereof, and an altered expression of at least one gene selected from the group comprising a gene encoding a 3-β-hydroxysteroid dehydrogenase/isomerase (GAME25) and a gene encoding a 2-oxoglutarate-dependent dioxygenase (GAME31), or a combination thereof; wherein the at least one cell of said genetically modified plant has an altered content of at least one cholesterol derived compound selected from the group comprising a steroidal alkaloid or a glycosylated derivative thereof and an unsaturated or saturated steroidal saponin or a glycoside derivative thereof compared to a corresponding unmodified plant.

In a related aspect, the amino acid sequence of 3-β-hydroxysteroid dehydrogenase/isomerase (GAME25) comprises the amino acid sequence set forth in any one of SEQ ID NO: 3, SEQ ID NO: 12, and SEQ ID NO: 15, or a protein homologue thereof, wherein said protein homologue is at least 80% homologous to any of SEQ ID NO: 3, SEQ ID NO: 12, and SEQ ID NO: 15.

In a related aspect, 3-β-hydroxysteroid dehydrogenase/isomerase (GAME25) is encoded by a gene comprising the polynucleotide sequence set forth in any one of SEQ ID NO: 1, SEQ ID NO: 2, SEQ ID NO: 11, SEQ ID NO: 13, and SEQ ID NO: 14, or a gene homologue thereof, wherein said gene homologue is at least 80% homologous to any of SEQ ID NO: 1, SEQ ID NO: 2, SEQ ID NO: 11, SEQ ID NO: 13, and SEQ ID NO: 14.

In a related aspect, the amino acid sequence of 2-oxoglutarate-dependent dioxygenase (GAME31) comprises the amino acid sequence set forth in any one of SEQ ID NO: 18, SEQ ID NO: 21, SEQ ID NO: 24, SEQ ID NO: 27, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, and SEQ ID NO: 53, or a protein homologue thereof, wherein said protein homologue is at least 80% homologous to any of SEQ ID NO: 18, SEQ ID NO: 21, SEQ ID NO: 24, SEQ ID NO: 27, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, and SEQ ID NO: 53.

In a related aspect, 2-oxoglutarate-dependent dioxygenase (GAME31) is encoded by a gene comprising the polynucleotide sequence set forth in any one of SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, or SEQ ID NO: 52, or a nucleic acid sequence having at least 80% identity to any of SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, or SEQ ID NO: 52.

In a related aspect, altered expression comprises a reduced or inhibited expression of said GAME25 gene, or GAME31 gene, or a combination thereof compared to its expression in a corresponding unmodified plant; or an increased expression of said GAME25 gene, or GAME31 gene, or a combination thereof compared to its expression in a corresponding unmodified plant; or a combination of reduced or inhibited expression of one of said GAME25 gene or said GAME31 gene, and increased expression the other of said GAME25 gene or said GAME31 gene of compared to their expression in a corresponding unmodified plant and increased expression of.

In a related aspect, altered biological activity comprises increased enzyme activity of said 3-β-hydroxysteroid dehydrogenase/isomerase (GAME25) or said 2-oxoglutarate-dependent dioxygenase (GAME31), or the combination thereof; or increased stability of said 3-β-hydroxysteroid dehydrogenase/isomerase (GAME25) or said 2-oxoglutarate-dependent dioxygenase (GAME31), or the combination thereof; or decreased enzyme activity of said 3-β-hydroxysteroid dehydrogenase/isomerase (GAME25) or said 2-oxoglutarate-dependent dioxygenase (GAME31), or the combination thereof; or decreased stability of said 3-β-hydroxysteroid dehydrogenase/isomerase (GAME25) or said 2-oxoglutarate-dependent dioxygenase (GAME31), or the combination thereof; compared to the biological activity in an unmodified plant.

In a related aspect, the expression of the at least one gene or combination thereof in said genetically modified plant is altered, said altering comprises mutagenizing the at least one gene, said mutation present within a coding region of said at least one gene, or a regulatory sequence of said at least one gene, or a combination thereof.

In a related aspect, mutagenesis comprises one or more point mutations, a site-directed point mutagenesis, random point mutagenesis, genome editing, mutagenesis using uracil-containing templates, oligonucleotide-directed mutagenesis, phosphorothioate-modified DNA mutagenesis, mutagenesis using gapped duplex DNA, point mismatch repair mutagenesis, mutagenesis using a repair-deficient host strains, restriction-selection and restriction-purification, deletion mutagenesis, mutagenesis by total gene synthesis, mutagenesis during double-strand break repair, mutagenesis by chimeric constructs, mutagenesis by a CRISPR/Cas system, mutagenesis by a zinc-finger nucleases (ZFN) system, mutagenesis by a transcription activator-like effector nucleases (TALEN) system, or any combination thereof.

In a related aspect, the plant is a Solanaceae crop plant. In a related aspect, a Solanaceae crop plant is selected from the group comprising a cultivated tomato plant, a wild-tomato plant, a cultivated potato plant, a wild-potato plant, an aubergine plant, a chili pepper plant, a bell pepper plant, and a bittersweet plant.

In a related aspect, altered content of at least one cholesterol derived compound selected from the group comprising a steroidal alkaloid or a glycosylated derivative thereof and an unsaturated or saturated steroidal saponin or a glycoside derivative thereof comprises a reduced content of at least one steroidal alkaloid or a glycosylated derivative thereof compared to said corresponding unmodified plant, or an increased content of at least one steroidal alkaloid or a glycosylated derivative thereof compared to said corresponding unmodified plant, or a reduced content of at least one unsaturated or saturated steroidal saponin or a glycosylated derivative thereof compared to said corresponding unmodified plant, or an increased content of at least one unsaturated or saturated steroidal saponin or a glycosylated derivative thereof compared to said corresponding unmodified plant, or a combination of a reduced content of at least one steroidal alkaloid or a glycosylated derivative thereof, and an increased content of at least one steroidal alkaloid or a glycosylated derivative thereof, or an appearance of at least one steroidal alkaloid or a glycosylated derivative thereof compared to said corresponding unmodified plant that does not contain said at least one steroidal alkaloid or a glycosylated derivative thereof; or an appearance of at least one unsaturated or saturated steroidal saponin or a glycosylated derivative thereof compared to said corresponding unmodified plant that does not contain said at least one unsaturated or saturated steroidal saponin or a glycosylated derivative thereof; or any combination thereof, compared to said corresponding unmodified plant.

In a related aspect, the reduced content of at least one steroidal alkaloid or a glycosylated derivative thereof comprises reduced content of at least one anti-nutritional steroidal alkaloid or a glycosylated derivative thereof, or reduced content of at least one toxic steroidal alkaloid or a glycosylated derivative thereof, or a combination thereof. In a related aspect, the increased content of at least one steroidal alkaloid or a glycosylated derivative thereof results in increased plant resistance to at least one plant pathogen, pest, or predator, or any combination thereof, and optionally generates precursor molecules for steroidal alkaloid molecules that provide resistance to at least one plant pathogen, pest, or predator, or any combination thereof.

In a related aspect, the at least one steroidal alkaloid or glycosylated derivative thereof is selected from the group comprising tomatidine, α-tomatine, α-tomatine isomer (1 and 2), α-tomatine isomer 1, α-tomatine isomer 2, hydroxytomatine, acetoxytomatine, dehydrotomatidine, dehydrotomatine, dehydrotomatine isomer 1, dehydrotomatine+4-hexose, acetoxy-hydroxytomatine, acetoxy-hydroxy-dehydrotomatine, tomatidine+4 hexose, esculeosides, esculeoside A, esculeoside A+hexose, esculeoside B, acetoxyesculeoside B, demissidine, demissine, dehydrosolasodine, hydroxy-dehydrotomatine, acetoxy-hydroxy-dehydrotomatine, dehydroesculeosides, dehydroesculeoside A, dehydroesculeoside A+hexose, leptinine I, leptinine II, leptine I, leptine II, lycoperosides, soladulcidine, β-soladulcine, soladulcine A, solanidine, α-solanine, α-chaconine, solasodine, α-solasonine, α-solamargine, hydroxysolasonine, and hydroxysolamargine, or any derivatives thereof, or any combination thereof.

In a related aspect, the at least one unsaturated or saturated steroidal saponin or glycosylated derivative thereof is selected from the group comprising dioscin, diosgenin, parillin, and sarasapogenin. In a related aspect, the plant is a potato plant and said at least one steroidal alkaloid or glycosylated derivative thereof is selected from the group comprising α-solanine, α-chaconine, leptinine I, leptinine II, leptine I, and leptine II. In a related aspect, the plant is a tomato plant and said at least one steroidal alkaloid or glycosylated derivative thereof is selected from the group comprising α-tomatine, α-tomatine isomer (1 and 2), α-tomatine isomer 2, hydroxytomatine, acetoxytomatine, dehydrotomatidine, dehydrotomatine, dehydrotomatine isomer 1, dehydrotomatine+4-hexose, esculeosides, lycoperoside, or any derivatives thereof, or any combination thereof.

In a related aspect, the plant is an eggplant plant and said at least one steroidal alkaloid or glycosylated derivative thereof is selected from the group comprising soladulcidine, β-soladulcine, soladulcine A, or any derivatives thereof, and said unsaturated or saturated steroidal saponin or glycosylated derivative thereof is selected from the group comprising dioscin, diosgenin, parillin, and sarasapogenin, or any derivatives thereof, or any combination thereof. In a related aspect, the genetically modified plant is a transgenic plant comprising said at least one cell comprising at least one silencing molecule targeted to a gene selected from the group comprising GAME25 and GAME31, or a combination thereof.

In a related aspect, the silencing molecule is selected from the group comprising an RNA interference molecule and an antisense molecule. In a related aspect, the silencing molecule comprises a polynucleotide having a nucleic acid sequence substantially complementary to a region of the GAME25 gene or a complementary sequence thereof. In a related aspect, the nucleic acid sequence comprises the nucleic acid sequence set forth in SEQ ID NO: 8, or a fragment thereof. In a related aspect, the silencing molecule comprises a polynucleotide having a nucleic acid sequence substantially complementary to a region of the GAME31 gene or a complementary sequence thereof. In a related aspect, the nucleic acid sequence is set forth in any one of SEQ ID NO: 58 or SEQ ID NO: 59.

In a related aspect, the at least one cell having altered biological activity, or altered expression, or a combination thereof, is selected from the group consisting of leaf cell, a young leaf cell, a mature leaf cell, a bud cell, a petal cell, a flower cell, a stem cell, a shoot cell, a peel cell, a root cell, a fruit cell, a tuber cell, and a vegetable cell. In a related aspect, the fruit is a green fruit, a breaker fruit, or a red ripe fruit.

In one aspect, provided herein is a method of reducing the content of at least one cholesterol derived compound selected from the group comprising a steroidal alkaloid or a glycosylated derivative thereof and an unsaturated or saturated steroidal saponin or a glycoside derivative thereof in a plant, said method comprising transforming at least one plant cell within said plant with at least one silencing molecule targeted to a nucleic acid sequence encoding at least one protein selected from the group comprising 3-β-hydroxysteroid dehydrogenase/isomerase (GAME25), 2-oxoglutarate-dependent dioxygenase (GAME31), or any combination thereof; or transforming at least one plant cell within said plant with at least one polynucleotide sequence encoding at least one protein selected from the group comprising 3-β-hydroxysteroid dehydrogenase/isomerase (GAME25), or a 2-oxoglutarate-dependent dioxygenase (GAME31), or any combination thereof, wherein said at least one polynucleotide sequence comprises a mutation in a coding region or a regulatory region; or a combination thereof; thereby producing a plant with a reduced content of said at least one cholesterol derived compound selected from the group comprising a steroidal alkaloid or a glycosylated derivative thereof and an unsaturated or saturated steroidal saponin or a glycoside derivative thereof compared to a corresponding non-transformed plant.

In a related aspect, the at least one steroidal alkaloid or a glycosylated derivative thereof comprises α-tomatine, α-tomatine isomer (1 and 2), hydroxytomatine, or acetoxytomatine, and said at least one unsaturated or saturated steroidal saponin or glycosylated derivative thereof comprises a sarasapogenin or any combination thereof. In a related aspect, the further at least one steroidal alkaloid or a glycosylated derivative thereof is increased, said at least one steroidal alkaloid or a glycosylated derivative thereof comprising a dehydrotomatine, a dehydrotomatine isomer 1, or a dehydrotomatidine+4-hexose, and said at least one unsaturated or saturated steroidal saponin or glycosylated derivative thereof comprises a diosgenin, or any combination thereof.

In one aspect, provided herein is a method of enhancing the content of at least one cholesterol derived compound selected from the group comprising a steroidal alkaloid or a glycosylated derivative thereof and an unsaturated or saturated steroidal saponin or a glycoside derivative thereof in a plant, comprising transforming at least one plant cell within said plant with a nucleic acid sequence encoding 3-β-hydroxysteroid dehydrogenase/isomerase (GAME25), 2-oxoglutarate-dependent dioxygenase (GAME31), or a combination thereof, wherein said transforming results in overexpression of said GAME25, GAME31, or a combination thereof; or transforming at least one plant cell with at least one polynucleotide sequence encoding at least one protein selected from the group comprising 3-β-hydroxysteroid dehydrogenase/isomerase (GAME25), or a 2-oxoglutarate-dependent dioxygenase (GAME31), or any combination thereof, wherein said at least one polynucleotide sequence comprises a mutation in a coding region or a regulatory region; thereby producing a plant with an enhanced content of said at least cholesterol derived compound selected from the group comprising a steroidal alkaloid or a glycosylated derivative thereof and an unsaturated or saturated steroidal saponin or a glycoside derivative thereof compared to a corresponding non-transformed plant.

In a related aspect, the at least one steroidal alkaloid or a glycosylated derivative thereof comprises a α-tomatine, α-tomatine isomer (1 and 2), hydroxytomatine, acetoxytomatine, soladulcidine, β-soladulcine, soladulcine A, an unsaturated or saturated steroidal saponin, a leptin, or a leptinine, and said unsaturated or saturated steroidal saponin or glycosylated derivative thereof comprises a sarasapogenin, or any combination thereof.

In one aspect, provided herein is a method of producing beneficial steroidal derivatives, said method comprising the steps of: incubating a recombinant plant 3-β-hydroxysteroid dehydrogenase/isomerase (GAME25), or 2-oxoglutarate-dependent dioxygenase (GAME31), or a combination thereof, with selected precursor molecules under biosynthetic conditions; and collecting and isolating the steroidal derivatives from the biosynthetic medium.

In one aspect, provided herein is a recombinant protein having the amino acid sequence set forth in SEQ ID NO: 3, SEQ ID NO: 12, or SEQ ID NO: 15, or protein homologue thereof, wherein said protein homolog is at least 50% homologous to any of SEQ ID NO: 3, SEQ ID NO: 12, or SEQ ID NO: 15 and has the same catalytic function as the protein encoded by SEQ ID NO: 3, SEQ ID NO: 12, or SEQ ID NO: 15, for the production of a steroidal derivative comprising a steroidal alkaloid or a glycosylated derivative thereof, an unsaturated or saturated steroidal saponin or a glycoside derivative thereof, or a biosynthetic product thereof.

In one aspect, provided herein is the use of a recombinant protein having the amino acid sequence set forth in SEQ ID NO: 18, SEQ ID NO: 21, SEQ ID NO: 24, SEQ ID NO: 27, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50 or SEQ ID NO: 53, or protein homologue thereof, wherein said protein homolog is at least 50% homologous to any of SEQ ID NO: 18, SEQ ID NO: 21, SEQ ID NO: 24, SEQ ID NO: 27, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50 or SEQ ID NO: 53 and has the same catalytic function as the protein encoded by SEQ ID NO: 18, SEQ ID NO: 21, SEQ ID NO: 24, SEQ ID NO: 27, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50 or SEQ ID NO: 53, for the production of a steroidal derivative comprising a steroidal alkaloid or a glycosylated derivative thereof, an unsaturated or saturated steroidal saponin or a glycoside derivative thereof, or a biosynthetic product thereof.

In one aspect, provided herein is the use of a plant nucleic acid sequence encoding a 3-β-hydroxysteroid dehydrogenase/isomerase (GAME25) enzyme, said nucleic acid comprising the sequence set forth in SEQ ID NO: 1, SEQ ID NO: 2, SEQ ID NO: 11, SEQ ID NO: 13, or SEQ ID NO: 14or a nucleic acid sequence having a sequence which is at least 50% identical to SEQ ID NO: 1, SEQ ID NO: 2, SEQ ID NO: 11, SEQ ID NO: 13, or SEQ ID NO: 14, wherein said encoded enzyme has the same catalytic function as the protein encoded by SEQ ID NO: 1, SEQ ID NO: 2, SEQ ID NO: 11, SEQ ID NO: 13, or SEQ ID NO: 14, or a plant 2-oxoglutarate-dependent dioxygenase (GAME31) enzyme, said nucleic acid comprising the sequence set forth in SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, and SEQ ID NO: 52 or a nucleic acid sequence having a sequence which is at least 50% identical to SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, and SEQ ID NO: 52, wherein said encoded enzyme has the same catalytic function as the protein encoded by SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, and SEQ ID NO: 52, or a combination of a plant nucleic acid encoding 3-β-hydroxysteroid dehydrogenase/isomerase (GAME25) and a plant nucleic acid encoding 2-oxoglutarate-dependent dioxygenase (GAME31), for the production of a recombinant cell capable of biosynthesis of a steroidal alkaloid or a glycosylated derivative thereof or an unsaturated or saturated steroidal saponin or a glycosylated derivative thereof, wherein said cell comprises a non-plant cell.

In one aspect, provided herein is a method for breeding a plant having altered content of at least one cholesterol derived compound selected from the group comprising a steroidal alkaloid or a glycosylated derivative thereof and an unsaturated or saturated steroidal saponin or a glycoside derivative thereof; said method comprising: providing a first plant, wherein the expression level of a polynucleotide encoding a 3-β-hydroxysteroid dehydrogenase/isomerase (GAME25), a 2-oxoglutarate-dependent dioxygenase (GAME31), or a combination thereof is in a pre-determined range of values, or a biological activity of a 3-β-hydroxysteroid dehydrogenase/isomerase (GAME25), a 2-oxoglutarate-dependent dioxygenase (GAME31), or a combination thereof, is in a pre-determined range of values; providing a second plant; crossing said first and second plants to generate an offspring plant; and selecting an offspring plant that has a significantly different content of at least one cholesterol derived compound selected from the group comprising a steroidal alkaloid or a glycosylated derivative thereof and an unsaturated or saturated steroidal saponin or a glycoside derivative thereof, compared to said second plant.

In a related aspect, the pre-determined value of expression comprises under-expression or over-expression or said pre-determine value of biological activity comprises increases enzyme activity, or decreased enzyme activity, or increased stability, or decreased stability of said 3-β-hydroxysteroid dehydrogenase/isomerase (GAME25) or 2-oxoglutarate-dependent dioxygenase (GAME31), or the combination thereof.

In one aspect, provided herein is a method for breeding a plant having an altered expression of at least one gene selected from the group comprising a gene encoding 3-β-hydroxysteroid dehydrogenase/isomerase (GAME25), a gene encoding a 2-oxoglutarate-dependent dioxygenase (GAME31), or a combination thereof, said method comprising: providing a first transformed plant, wherein said first transformed plant is transformed with an expression vector comprising a polynucleotide comprising at least one silencing molecule targeted to a nucleic acid sequence encoding at least one protein selected from the group comprising a3-β-hydroxysteroid dehydrogenase/isomerase (GAME25) and a 2-oxoglutarate-dependent dioxygenase (GAME31), or a combination thereof, wherein said at least one silencing molecule is operably linked to a promoter; or providing a first transformed plant, wherein said first transformed plant is transformed with an expression vector comprising at least one polynucleotide which overexpresses at least one protein selected from the group comprising a 3-β-hydroxysteroid dehydrogenase/isomerase (GAME25), a 2-oxoglutarate-dependent dioxygenase (GAME31), or a combination thereof; or providing a first transformed plant, wherein said first transformed plant is transformed with an expression vector comprising at least one polynucleotide which comprises a mutation in a gene encoding at least one protein selected from the group comprising a 3-β-hydroxysteroid dehydrogenase/isomerase (GAME25), a 2-oxoglutarate-dependent dioxygenase (GAME31), or a combination thereof; providing a second non-transformed plant; crossing said first transformed plant with a second plant to generate a hybrid plant, wherein the hybrid plant comprises the expression vector; and selecting a hybrid plant that has an altered expression of said at least one gene selected from the group comprising a gene encoding 3-β-hydroxysteroid dehydrogenase/isomerase (GAME25), a gene encoding a 2-oxoglutarate-dependent dioxygenase (GAME31), or a combination thereof compared to a corresponding unmodified plant; and wherein optionally, said plant comprises an altered content of at least one cholesterol derived compound selected from the group comprising a steroidal alkaloid or a glycosylated derivative thereof and an unsaturated or saturated steroidal saponin or a glycoside derivative thereof, compared to a corresponding unmodified plant.

In a related aspect, the at least one silencing molecule or said overexpressing polynucleotide is operably linked to a constitutive promoter, an inducible promoter, a tissue-specific promoter, or a developmental-stage specific promoter. In a related aspect, the at least one polynucleotide comprising a mutation is operably linked to a constitutive promoter, an inducible promoter, a tissue-specific promoter, or a developmental-stage specific promoter. In a related aspect, the expression level and/or biological activity of the 3-β-hydroxysteroid dehydrogenase/isomerase (GAME25), or the 2-oxoglutarate-dependent dioxygenase (GAME31), or a combination thereof, provide a biological marker for a plant comprising altered content of at least one cholesterol derived compound selected from the group comprising a steroidal alkaloid or a glycosylated derivative thereof and an unsaturated or saturated steroidal saponin or a glycoside derivative thereof.

In a related aspect, the altered content comprises reduced content of an anti-nutritional or toxic steroidal alkaloid or a glycosylated derivative thereof. In a related aspect, the altered content comprises increased content of a steroidal alkaloid or a glycosylated derivative thereof that provides resistance to a plant pathogen, pest, or predator.

In some aspects, provided herein is a method for selecting plant progenitors, said method comprising a step of determining the expression level of a gene encoding a 3-β-hydroxysteroid dehydrogenase/isomerase (GAME25), or a 2-oxoglutarate-dependent dioxygenase (GAME31), or a combination thereof, wherein expression levels of said GAME25 gene, or said GAME31 gene, or the combination thereof, is predictive of altered content of at least one cholesterol derived compound selected from the group comprising a steroidal alkaloid or a glycosylated derivative thereof and an unsaturated or saturated steroidal saponin or a glycoside derivative thereof in an offspring plant; or determining the biological activity of a 3-β-hydroxysteroid dehydrogenase/isomerase (GAME25), or a 2-oxoglutarate-dependent dioxygenase (GAME31), or a combination thereof, wherein biological activity of said GAME25 enzyme, or said GAME31 enzyme, or the combination thereof, is predictive of altered content of at least one cholesterol derived compound selected from the group comprising a steroidal alkaloid or a glycosylated derivative thereof and an unsaturated or saturated steroidal saponin or a glycoside derivative thereof in an offspring plant.

In some aspects, provided herein is a method for determining the capacity of a plant to produce at least one cholesterol derived compound selected from the group comprising a steroidal alkaloid or a glycosylated derivative thereof and an unsaturated or saturated steroidal saponin or a glycoside derivative thereof in at least a part of said plant, said method comprising a step of measuring the expression level of GAME25, or GAME31, or a combination thereof, in at least a part of said plant; or measuring the biological activity of a 3-β-hydroxysteroid dehydrogenase/isomerase (GAME25), or a 2-oxoglutarate-dependent dioxygenase (GAME31), or a combination thereof, in at least a part of said plant; or a combination thereof.

BRIEF DESCRIPTION OF THE DRAWINGS

The following drawings form part of the present specification and are included to further demonstrate certain embodiments of the present disclosure, the compositions and formulations described herein may be better understood by reference to one or more of these drawings in combination with the detailed description of specific embodiments presented herein.

FIG. 1A shows a schematic representation of the main steps of SGA biosynthesis in tomato. FIG. 1B shows a schematic representation of SGA biosynthesis in tomato illustrating also the molecular structure of the compounds generated. FIG. 1C shows a further schematic representation of SGA biosynthesis in tomato illustrating also the molecular structure of the compounds generated. α-tomatine derived saturated SGAs are shown in black color and dehydrotomatine-derived unsaturated SGAs are shown in red color.

FIG. 2A shows a schematic representation of the main steps of SGA biosynthesis in potato. FIG. 2B shows a schematic representation of SGA biosynthesis in potato illustrating also the molecular structure of the compounds generated.

FIG. 3A shows biosynthetic pathway of steroidal saponins and their glycosides. First, cholesterol is converted to either unsaturated furostanol type saponin aglycone or spirostanol type saponin aglycone. Both these unsaturated aglycones are further glycosylated by GTs (glycosyltransferases) to form their unsaturated saponin glycosides respectively. Alternatively, both unsaturated saponin aglycones are further hydrogenated at C-5,6 position to form their saturated saponin aglycone forms. Similar to unsaturated ones, these saturated aglycone forms also undergoes glycosylation to form diverse saturated saponin glycosides. The enzymatic conversion responsible for formation of saturated saponin aglycone from unsaturated ones is unknown till date in any well-known steroidal saponin producing plant species. FIG. 3B shows a schematic representation of the main steps of SGA biosynthesis in eggplant. FIG. 3C shows a schematic representation of SGA biosynthesis in eggplant illustrating also the molecular structure of the compounds generated. In eggplant SGA biosynthesis, cholesterol is first converted to solasodine, unsaturated SA aglycone. Solasodine is further glycosylated by SGT (STEROL ALKALOID GLYCOSYL TRANSFERASE) enzymes to produce unsaturated α-solasonine and α-solamargine SGAs in cultivated eggplant. Cultivated eggplant is deficient in GAME25 gene and therefore lacks saturated SGAs. In contrary, some *Solanum* species, e.g. *S. dulcamara* produce saturated soladulcidine alkaloid aglycone and further its glycosylated derivatives soladulcine A and β-soladulcine from the solasodine aglycone. This suggests the presence of GAME25 homolog in those *Solanum* species. The formation of saturated alkaloid aglycone in any known *Solanum* species remains unclear till date.

FIG. 4A GAME25 normalized expression level among various tomato tissue types and developmental stages (from RNA-Seq data). Briefly, RNA-Seq transcriptome data was obtained from different tomato tissues and organs (flesh, peel, roots, young leaf, flower buds and young flower petals) and five developmental stages for peel and flesh tissues (19 experiments in total). FIG. 4B shows expression of GAME25 in four stages of fruit development of different wild tomato species (normalized RNA-seq data). IG: immature green, MG: mature green, BR: breaker, R: ripe. FPKM: Fragments Per Kilobase of transcript per Million mapped reads.

FIG. 5 shows the alignment of tomato, *S. pennellii* and potato GAME25 proteins investigated in this study. GAME25 is a classical SDR family member protein possessing TGxxxGxG cofactor binding and the YxxxK catalytic motifs (marked in boxes). The Asp (D) residue at 40th position indicating preference for NAD+ over NADP+ was shown in asterisk.

FIG. 11A shows reduced levels of saturated α-tomatine and its downstream derivatives in green fruit of GAME25-silenced tomato compared to wild-type. FIG. 11B shows levels of less abundant SGAs in GAME25 silenced tomato green fruits. FIG. 11C shows increased levels of unsaturated dehydrotomatine and its downstream SGAs in green fruit of GAME25-silenced tomato lines compared to wild-type. FIG. 11D shows increased dehydrotomatine derived SGA levels in breaker fruits of GAME25i lines compared to wild-type breaker fruits. FIG. 11E shows levels of less abundant SGAs in GAME25 silenced tomato breaker fruits. FIG. 11F shows increased α-tomatine derived SGA levels in breaker fruits of GAME25i lines compared to wild-type breaker fruits. FIG. 11G shows substantial reduction in levels of esculeoside A, major saturated SGA in red stage fruit, in GAME25-silenced red ripe fruit. α-tomatine and its derived saturated SGAs were not detected in GAME25-silenced red ripe fruit. FIG. 11H shows a massive increase in levels of unsaturated dehydroesculeoside A in GAME25-silenced red fruit compared to wild-type red fruits. FIG. 11I shows levels of less abundant SGAs in GAME25 silenced tomato red fruits. Asterisks indicate significant changes from wild-type samples as calculated by a Student's t-test (*P-value <0.05; P-value <0.01; *P-value <0.001).

FIG. 13A shows GAME25 expression in leaves, green and red fruit of transgenic tomato lines overexpressing the tomato GAME25 gene (GAME25-Ox) as determined by quantitative Real Time-PCR (qRT-PCR). FIG. 13B shows levels of α-tomatine, and FIG. 13C shows levels of additional SGAs in leaves of GAME25-Ox tomato lines as compared to wild-type ones. FIGS. 13D-13E show levels of α-tomatine, dehydrotomatine and additional SGAs in breaker (FIG. 13D) and red (FIG. 13E) fruit of GAME25-Ox lines as compared to wild-type fruit. Overexpression of GAME25 resulted in accumulation of either α-tomatine or its derived SGAs (e.g. acetoxy- or acetoxyhydroxytomatine) in leaves and fruit tissues. The values indicate means of three biological replicates±standard error. Student's t-test was used to assess the significance of the difference between transgenic and wild-type tissues (*P-value <0.05; P-value <0.01; *P-value <0.001). #91, #92 and #93 represent three independent GAME25-Ox tomato transgenes. LC-MS was used for metabolite analysis.

FIG. 16A Solasonine (m/z 884.5076) and β-soladulcine (m/z 886.5131). FIG. 16B Solmargine (m/z 868.5106) and soladulcine A (m/z 870.5265). FIG. 16C malonyl-solamargine (m/z 954.5066) and saturated malonyl-solamargine (m/z 956.5238). FIG. 16D steroidal saponin (m/z 1031.5396) and saturated steroidal saponin (m/z 1033.5608). FIG. 16E steroidal saponin (m/z 1117.5479) and saturated steroidal saponin (m/z 1119.5586). FIG. 16F shows a comparison of mass fragmentation of steroidal alkaloid and steroidal saponin aglycones; Upper panel: Overlays of mass spectra of saturated SA aglycones (red) and unsaturated SA aglycones (black), lower panel: Overlays of mass spectra of saturated steroidal saponin aglycones (red) and unsaturated steroidal saponin aglycones (black). Characteristic fragment structures are shown, fragments after loss of the side chain of steroidal alkaloids or saponins are identical, m/z 253.19 & 271.21 (blue) for unsaturated compounds and m/z 255.21 & 273.22 (red) for saturated compounds.

FIG. 17A shows GAME25 gene expression (qRT-PCR) in GAME25-Ox lines in potato. Line #11, #12 and #13 are independent GAME25-Ox transgenic lines. FIGS. 17B-17C show levels of α-solanine and α-chaconine in leaves (FIG. 17B) and tuber peel (FIG. 17C) of GAME25-Ox lines as determined by LC-MS. Values represent mean±standard error (n=3). Student's t-test was used to assess whether the transgenic lines significantly differ from wild-type plants (*P-value <0.05; P-value <0.01; *P-value <0.001). #13 transgenic plants did not produce tubers.

FIG. 18A shows tomato GAME25 protein. FIG. 18B shows potato GAME25 protein. M: Molecular weight protein marker.

FIGS. 19A-19B show an overlay of extracted ion chromatograms of m/z 412.32 Da, $[M+H^+]^+$ (mass of the GAME25 reaction product and the control reaction (sf9 cells microsomes) obtained with dehydrotomatidine as a substrate and tomato GAME25. FIGS. 19C-19D show the mass spectra and structures of the detected product (upper panel) and substrate (lower panel) of potato GAME25 enzymatic reaction with dehydrotomatidine as a substrate. FIG. 19E shows the mass fragmentation spectrum of the GAME25 enzymatic reaction product (with dehydrotomatidine as substrate) including the interpretation of the detected mass fragments. The fragmentation pattern corresponds to the proposed structure of the GAME25 product obtained with tomato GAME25. FIGS. 19F-19G shows an overlay of extracted ion chromatograms of m/z 396.32 Da, $[M+H^+]^+$ (mass of the GAME25 reaction product) and the control reaction (sf9 cells microsomes) with solanidine as a substrate and tomato GAME25. FIGS. 19H-19I shows the mass spectra and structures of the detected product (upper panel) and substrate (lower panel) of the potato GAME25 enzymatic reaction with solanidine as a substrate. FIG. 19J shows chromatograms of the potato GAME25 enzymatic reaction (upper panel), control reaction (middle panel), both with solanidine as substrate, and the solanid-4-en-3-one authentic standard injection (lower panel). The newly formed product (at RT 23.2 min.) co-elutes with solanid-4-en-3one. FIG. 19K shows an overlay of extracted ion chromatograms of potato GAME25 enzyme reaction product [m/z 412.32 Da, [M+H+]+] and the control reaction (sf9 cells microsomes) with solasodine as a substrate. FIG. 19L shows the mass spectra and structures of the detected product (upper panel) and substrate (lower panel) of potato GAME25 enzymatic reaction with solasodine as a substrate.

FIG. 20A shows an overlay of extracted ion chromatograms of m/z 412.32 Da, [M+H+]+, mass of product of GAME25 of enzyme reaction and control (reaction mixture without GAME25) using Solasodine as a substrate. FIG. 20B shows the mass spectra and structures of detected product (upper panel) and substrate (lower panel) of GAME25 enzymatic reaction with Solasodine as substrate. FIG. 20C shows the structures of fragments detected in MS-MS analysis of product of GAME25 (tomato) using Solasodine as a substrate. FIG. 20D shows MSMS spectrum of product of GAME25 (tomato) with Solasodine as a substrate.

FIG. 21A shows the expression of recombinant GAME25 and GAME35 proteins in E. coli BL21 (DE3) cells analyzed on SDS-PAGE. FIG. 21B and FIG. 21C show Western blot analysis of His-tagged recombinant GAME25 and GAME35 proteins. M: Molecular weight protein marker, W: Whole cell extract, El: Imidazole eluted fractions from Ni-NTA column, pET28: Empty pET28 vector transformed into BL21(DE3) cells was used as negative control. Recombinant proteins are marked with red arrows.

FIG. 22A shows chromatograms of the GAME25 enzymatic reaction using solanidine as substrate, control reaction (empty pET28 vector transformed into BL21(DE3) cells) and the solanid-4-en-3-one authentic standard injection (lower panel). GAME25 efficiently converted solanidine to the solanid-4-en-3-one product. FIG. 22B shows GAME35 enzyme reaction using solanid-4-en-3-one as substrate. GAME35 did not show any enzyme activity with solanid-4-en-3-one as a substrate.

FIG. 23A shows the inhibition area of C. gloeosporioides mycelial growth resulting from addition of leaf extracts of GAME25i plants compared to wild-type leaf extracts. FIG. 23B shows a representative image of the C. gloeosporioides mycelial growth inhibition after application of leaf extracts from GAME25i plants. FIG. 23C shows the inhibition area of Botrytis cinereal mycelial growth resulting from addition of leaf extracts of GAME25i plants compared to wild-type leaf extracts. FIG. 23D shows a representative image of the Botrytis cinereal mycelial growth inhibition after application of leaf extracts from GAME25i plants. FIG. 23E shows the percentage of C. gloeosporioides conidia germination resulting from addition of leaf extracts of GAME25i plants compared to wild-type leaf extracts. FIGS. 23F-G show representative images of C. gloeosporioides conidia germination in the presence of a GAME25i leaf extract (FIG. 23F) and wild-type leaf extract (FIG. 23G). FIG. 23H shows the percentage of Botrytis cinereal conidia germination resulting from addition of leaf extracts of GAME25i plants compared to wild-type leaf extracts. FIGS. 23I-J show representative images of Botrytis cinerea conidia germination in the presence of a GAME25i leaf extract (FIG. 23I) and wild-type leaf extract (FIG. 23J). FIGS. 23A, 23C, 23E and 23H indicate show means±standard error (n=15). This 15 process replicates were obtained from three separate experiment repetitions. Asterisks indicate significant changes from wild-type samples as calculated by a Student's t-test (*P-value <0.05; P-value <0.01; *P-value <0.001).

FIG. 24A shows an overlay of extracted ion chromatograms of m/z 415.32 (M+H$^+$ of Diosgenin substrate) and 413.31 (M+H$^+$ of detected reaction product), red: reaction with recombinant GAME25 protein from tomato, produced in E. coli, black: control reaction with E. coli protein extract (empty vector). GAME25 converts Diosgenin quantitatively to the putative product Diosgen-4-en-3-one. FIG. 24B shows mass fragmentation spectra of Diosgenin substrate (lower panel) and reaction product (upper panel) with explanation of characteristic fragments for Diosgenin and Diosgen-4-en-3-one, loss of the side chain leads to fragments m/z 271.21 and 269.19 respectively, followed by a neutral loss of water resulting in fragments m/z 253.19 and 251.18. Abbreviations: E. coli: Escherichia coli, EIC: extracted ion chromatogram, m/z mass to charge, M: molecular mass.

FIGS. 26A-26G show variation in SGA levels in the BIL/IL populations. The SGA content in leaf tissues was determined by leaf-dipping method and further analysis by UPLC-qTOF-MS. In all figures, the x-axis represents all 671 lines from the populations and the Y axis represents relative peak abundance. FIG. 26A shows levels of α-tomatine isomer 1. FIG. 26B shows levels of α-tomatine isomer 2. FIG. 26C shows levels of dehydrotomatine isomer 1. FIG. 26D shows levels of dehydrotomatine isomer 2. FIG. 26E shows levels of hydroxytomatine FIG. 26F shows levels of acetoxytomatine. FIG. 26G shows levels of di-dehydrotomatine. While α-tomatine (isomer 1 and 2) and dehydrotomatine (isomer 1) were present in most of the lines, other SGAs were either absent of present predominantly in few tomato lines.

FIGS. 27A-27G show the SGA levels in the IL populations. The SGA content was determined from ground-tissue extracts by UPLC-qTOF-MS. The peak areas were determined by target analysis using the TargetLynx software Values represent mean±s.d. (n=3). FIG. 27A shows levels of α-tomatine isomer 1. FIG. 27B shows levels of α-tomatine isomer 2. FIG. 27C shows levels of dehydrotomatine isomer 1. FIG. 27D shows levels of dehydrotomatine isomer 2. FIG. 27E shows levels of hydroxytomatine. FIG. 27F shows levels of acetoxytomatine. FIG. 27G shows levels of di-dehydrotomatine.

FIGS. 28A and 28B present a region in tomato chromosome 1 linked to the accumulation of dehydrotomatine isomer 2. FIG. 28A presents the schematic representation of chromosome 1 showing the region in IL 1-1-1 controlling the content of dehydrotomatine isomer 2. FIG. 28B presents the suggested structures of the two isomers of dehydrotomatine (Schilmiler et al., (2010) Mass spectrometry screening reveals widespread diversity in trichome specialized metabolites of tomato chromosomal substitution lines. Plant J. 62: 391-403).

FIGS. 29A and 29B present in tabular form a detailed list of genes present in the regions linked to SGA content in the BIL/IL populations. The table presented in FIG. 29A lists the genes in chromosome 1 region linked to content of dehydrotomatine isomer 2. The Table presented in FIG. 29B lists the genes in chromosome 2 region linked to content of hydroxytomatine and acetoxytomatine.

FIG. 30A presents a schematic representation of chromosome 2 showing the region controlling the content of hydroxytomatine and acetoxytomatine in the BIL/IL populations. FIG. 30B schematically shows that out of the 17 genes in the region, four correspond to 2-oxoglutarate-dependent dioxygenases, named in this study SlGAME31 and SlGAME31-like genes. SlGAME31 and SlGAME31-like3 are full length coding sequences, while SlGAME31-like1 and SlGAME31-like2 are partial. FIG. 30C presents the predicted reaction catalyzed by GAME31, from α-tomatine to hydroxytomatine (position pointed by red arrow) and downstream pathway to esculeosides.

FIG. 31A presents a normalized expression profile of SlGAME31 and SlGAME31-like genes in RNA-Seq data from vegetative apex of the ILs (Chitwood et al., (2013) A quantitative genetic basis for leaf morphology in a set of precisely defined tomato introgression lines. Plant Cell 25: 2465-2481). SlGAME31 showed about 4.6-fold increased expression in IL2-1 (marked by *) in comparison with the other ILs, while SlGAME31-like genes showed very low expression levels across the population (<15 normalized Reads Per Million, RPM). FIG. 31B presents a normalized expression profile (from RNA-Seq dataset previously reported (Cárdenas et al., (2016) Nat. Commun. 7, 10654) of SlGAME31 in different tomato (cv. Microtom) tissue types and developmental stages. SlGAME31 showed an expression pattern correlating with fruit ripening, being lower in immature stages of fruit and other tissues (leaf, buds, petals and root). SlGAME31-like3 was slightly expressed while SlGAME31-like1 and SlGAME31-like2 genes were not detected in this dataset. IG: immature green; MG: mature green; Br: breaker; Or: orange; RR: red ripe. FPKM: Fragments Per Kilobase of transcript per Million mapped reads.

FIG. 32A shows that the sequence homology searches identified SmGAME31, encoding a 2-oxoglutarate-dependent dioxygenase in chromosome 1 of eggplant, as the closest homolog of the tomato GAME31. SmGAME31 is predicted to catalyze the hydroxylation of α-solamargine to hydrosolamargine. FIG. 32B shows that in potato, a tandem gene cluster of 8 homologs of SlGAME31 was identified, and which spanned ~205 Kbp. At the protein level, StGAME31 displayed 54% identity to StGAME31-like1, 94% to StGAME31-like2, 67% to StGAME31-like3, 51% StGAME31-like4 and StGAME31-like5, 58% to StGAME31-like6 and 54% identity to StGAME31-like7. GAME31 in potato is predicted to hydroxylate α-chaconine and α-solanine, precursors of leptinine I and II, respectively. These later compounds can be further acetylated to produce leptine I and II, respectively.

FIGS. 35A-35D show the hydroxylation of SA/SGAs by SmGAME31. Enzymatic reactions were performed with the same set of SA/SGAs as for SlGAME31. Hydroxylated derivatives were obtained for: α-solamargine (FIG. 35A), solasodine (FIG. 35B), α-tomatine (FIG. 35C), and dehydrotomatine (FIG. 35D). The enzymatic reaction was carried out in multiple conditions (A-G-see box) and formation of hydroxy-derivatives were assessed by UPLC-qTOF-MS. For each compound, its m/z and the m/z of its hydroxylated derivatives are shown. The x-axes show the retention time (RT).

FIG. 36C presents a schematic representation of the SGA biosynthetic pathway. FIG. 36D shows changes in SGAs when SlGAME31 is downregulated.

DETAILED DESCRIPTION

Figure 1A:
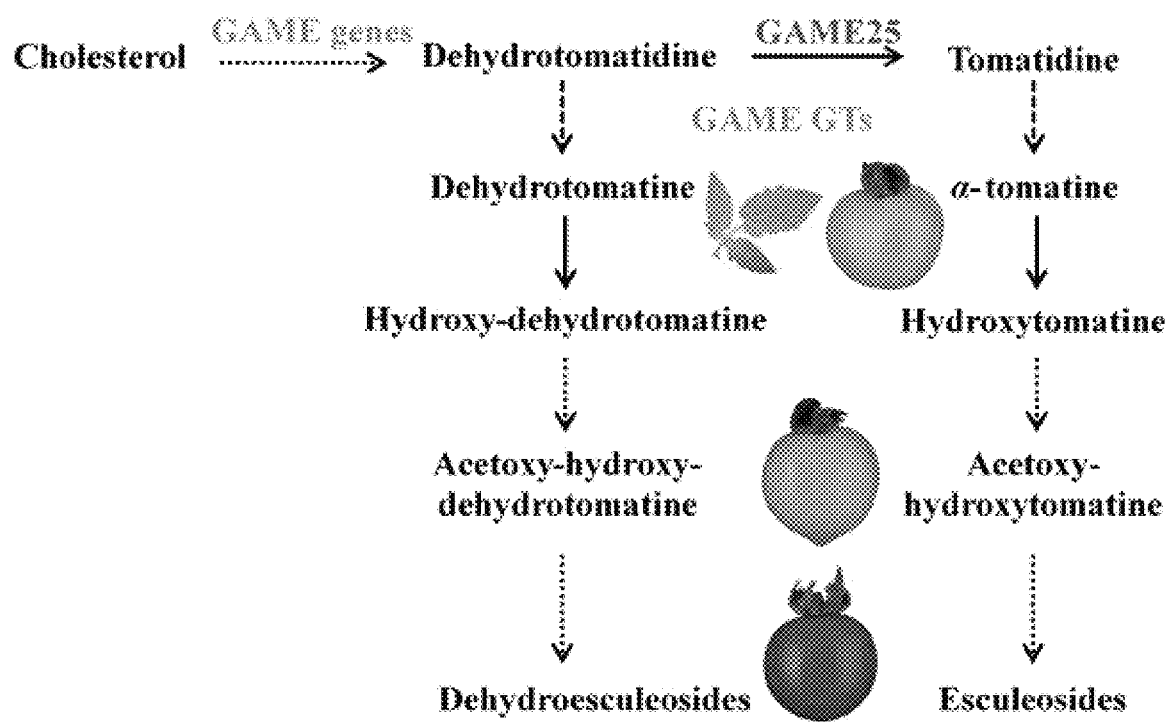
FIGS. 1A-1C together provide an overview of Steroidal Glycoalkaloid (SGA) biosynthesis in tomato. SGA biosynthesis starts with the conversion of cholesterol to unsaturated dehyrotomatidine (tomatidenol), the first SA aglycone in the green stage of fruit development. This occurs through the action of GAME enzymes (GAME-6, 8, 11, 4, 12). Dehydrotomatidine is further converted to saturated tomatidine, another steroidal alkaloid aglycone. Both dehydrotomatidine and tomatidine are glycosylated by various UGTs (GAME-1, 17, 18, 2) to form dehydrotomatine and α-tomatine respectively. The presence or absence of C-5,6 double bond is the only difference between dehydrotomatidine and tomatidine steroidal alkaloid aglycones structure. This difference in the C-5,6 double bond at steroidal aglycones level further creates a vast structural diversity of SGAs (either unsaturated or saturated derivatives) during tomato fruit development and ripening stages (see all structures). α-tomatine and dehydrotomatine are major SGAs in green tomato fruit. Subsequently, hydroxy- and/or acetoxy-derivatives of α-tomatine and dehydrotomatine accumulate in the breaker tomato fruit. In red fruit, esculeosides and lycoperosides are the most abundant SGAs. α-tomatine derived saturated SGAs are highly abundant compared to dehydrotomatine-derived unsaturated SGAs throughout tomato fruit development and ripening. The conversion of dehydrotomatidine to tomatidine was previously predicted as a single step reaction by the action of a hypothetical hydrogenase.

In the following detailed description, numerous specific details are set forth in order to provide a thorough understanding of the genetically modified plants and methods presented herein. However, it will be understood by those skilled in the art that these genetically modified plants and methods may be practiced without these specific details. In other instances, well-known methods, procedures, and components have not been described in detail so as not to obscure the formulations and compositions disclosed herein.

Genetically Modified Plants

Disclosed herein are genetically modified plants, wherein expression of key genes in the steroidal glycoalkaloids metabolic pathway (biosynthesis pathway of steroidal alkaloids and glycosylated derivatives thereof) have been altered. Altering the expression of these genes results in concomitant alteration in the steroidal alkaloid profile. Changing the production level of steroidal alkaloid can result in improved plants comprising elevated content of steroidal alkaloids having increased resistance to pathogens, or plants having a reduced content of these secondary compounds in the plant edible parts and thus producing improved crops, wherein the improved crop has reduced or eliminated anti-nutritional content. Alternatively, or additionally, controlling the expression of genes disclosed herein may be used for the production of desired steroidal alkaloids for further use, for example in the pharmaceutical industry. In particular, disclosed herein are the means and methods for producing crop plants of the Solanaceae family that are devoid of toxic amounts of deleterious steroidal alkaloids typically present in edible parts of these plants. The plants disclosed herein are thus of significant nutritional and commercial value.

The Examples presented below demonstrate that unexpectedly by modifying the expression of a gene within the steroidal glycoalkaloid metabolic pathway, the level of at least one steroidal alkaloid, and/or at least one steroidal glycoalkaloid may be altered. For example, silencing of a single gene within the steroidal glycoalkaloid metabolic pathway, for example GAME25 in a tomato plant, resulted in significant reduction in the amount of α-tomatine concurrent with a significant accumulation of dehydrotomatine and its isomers.

In one embodiment, disclosed herein is a genetically modified plant comprising at least one cell having an altered expression of at least one gene selected from the group comprising a gene encoding a 3-β-hydroxysteroid dehydrogenase/isomerase (GAME25) and a gene encoding a 2-oxoglutarate-dependent dioxygenase (GAME31), or a combination thereof, wherein the genetically modified plant has an altered content of at least one cholesterol derived compound selected from the group comprising a steroidal alkaloid or a glycosylated derivative thereof and an unsaturated or saturated steroidal saponin or a glycoside derivative thereof compared to a corresponding unmodified plant.

In some embodiments, disclosed herein is a genetically modified plant comprising an altered content of at least one cholesterol derived compound selected from the group comprising a steroidal alkaloid or a glycosylated derivative thereof and an unsaturated or saturated steroidal saponin or a glycoside derivative thereof, said plant comprising at least one cell having
   an altered biological activity of at least one enzyme selected from the group comprising a 3-β-hydroxysteroid dehydrogenase/isomerase (GAME25) and a 2-oxoglutarate-dependent dioxygenase (GAME31), or a combination thereof; or
   an altered expression of at least one gene selected from the group comprising a gene encoding a 3-β-hydroxysteroid dehydrogenase/isomerase (GAME25) and a gene encoding a 2-oxoglutarate-dependent dioxygenase (GAME31), or a combination thereof; or
   a combination thereof of an altered biological activity of at least one enzyme selected from the group comprising a 3-β-hydroxysteroid dehydrogenase/isomerase (GAME25) and a 2-oxoglutarate-dependent dioxygenase (GAME31), or a combination thereof, and an altered expression of at least one gene selected from the group comprising a gene encoding a 3-β-hydroxysteroid dehydrogenase/isomerase (GAME25) and a gene encoding a 2-oxoglutarate-dependent dioxygenase (GAME31), or a combination thereof; wherein the at least one cell of said genetically modified plant has an altered content of at least one cholesterol derived compound selected from the group comprising a steroidal alkaloid or a glycosylated derivative thereof and an unsaturated or saturated steroidal saponin or a glycoside derivative thereof compared to a corresponding unmodified plant.

One of ordinary skill in the art would appreciate that the term "gene" may encompass a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene. The fragments may range in size from a few nucleotides to the entire gene sequence minus one nucleotide. Thus, "a nucleic acid sequence comprising at least a part of a gene" may comprise fragments of the gene or the entire gene.

The skilled artisan would appreciate that the term "gene" optionally also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

In one embodiment, a gene comprises DNA sequence comprising upstream and downstream regions, as well as the coding region, which comprises exons and any intervening introns of the gene. In some embodiments, upstream and downstream regions comprise non-coding regulatory regions. In some embodiments, upstream and downstream regions comprise regulatory sequences, for example but not limited to promoters, enhancers, and silencers. Non-limiting examples of regulatory sequences include, but are not limited to, AGGA box, TATA box, Inr, DPE, ZmUbi1, PvUbi1, PvUbi2, CaMV, 35S, OsAct1, zE19, E8, TA29, A9, pDJ3S, B33, PAT1, alcA, G-box, ABRE, DRE, and PCNA. Regulatory regions, may in some embodiments, increase or decrease the expression of specific genes within a plant described herein.

In another embodiment, a gene comprises the coding regions of the gene, which comprises exons and any intervening introns of the gene. In another embodiment, a gene comprises its regulatory sequences. In another embodiment, a gene comprises the gene promoter. In another embodiment, a gene comprises its enhancer regions. In another embodiment, a gene comprises 5' non-coding sequences. In another embodiment, a gene comprises 3' non-coding sequences.

In one embodiment, the skilled artisan would appreciate that DNA comprises a gene, which may include upstream and downstream sequences, as well as the coding region of the gene. In another embodiment, DNA comprises a cDNA (complementary DNA). One of ordinary skill in the art would appreciate that cDNA may encompass synthetic DNA reverse transcribed from RNA through the action of a reverse transcriptase. The cDNA may be single stranded or double stranded and can include strands that have either or both of a sequence that is substantially identical to a part of the RNA sequence or a complement to a part of the RNA sequence. Further, cDNA may include upstream and downstream regulatory sequences. In still another embodiment, DNA comprises CDS (complete coding sequence). One of ordinary skill in the art would appreciate that CDS may encompass a DNA sequence, which encodes a full-length protein or polypeptide. A CDS typically begins with a start codon ("ATG") and ends at (or one before) the first in-frame stop codon ("TAA", "TAG", or "TGA"). The skilled artisan would recognize that a cDNA, in one embodiment, comprises a CDS.

As used herein, the terms "polynucleotide", "polynucleotide sequence", "nucleic acid sequence", and "isolated polynucleotide" may be used interchangeably herein, having all the same qualities and meanings. These terms encompass nucleotide sequences and the like. A polynucleotide may be a polymer of RNA or DNA or hybrid thereof, that is single- or double-stranded, linear or branched, and that optionally contains synthetic, non-natural or altered nucleotide bases. The terms also encompass RNA/DNA hybrids.

One of ordinary skill in the art would appreciate that a genetically modified plant may encompass a plant comprising at least one cell genetically modified by man. In some embodiments, the genetic modification includes modification of an endogenous gene(s), for example by introducing mutation(s) deletions, insertions, transposable element(s) and the like into an endogenous polynucleotide or gene of interest. Additionally, or alternatively, in some embodiments, the genetic modification includes transforming at least one plant cell with a heterologous polynucleotide or multiple heterologous polynucleotides. The skilled artisan would appreciate that a genetically modified plant comprising transforming at least one plant cell with a heterologous polynucleotide or multiple heterologous polynucleotides may in certain embodiments be termed a "transgenic plant".

A skilled artisan would appreciate that a comparison of a "genetically modified plant" to a "corresponding unmodified plant" as used herein encompasses comparing a plant comprising at least one genetically modified cell and to a plant of the same type lacking the modification.

The skilled artisan would appreciate that the term "transgenic" when used in reference to a plant as disclosed herein encompasses a plant that contains at least one heterologous transcribable polynucleotide in one or more of its cells. The term "transgenic material" encompasses broadly a plant or a part thereof, including at least one cell, multiple cells or tissues that contain at least one heterologous polynucleotide in at least one of cell. Thus, comparison of a "transgenic plant" and a "corresponding non transgenic plant", or of a "genetically modified plant comprising at least one cell having altered expression, wherein said plant comprising at least one cell comprising a heterologous transcribable polynucleotide" and a "corresponding un modified plant" encompasses comparison of the "transgenic plant" or "genetically modified plant" to a plant of the same type lacking said heterologous transcribable polynucleotide. A skilled artisan would appreciate that, in some embodiments, a "transcribable polynucleotide" comprises a polynucleotide that can be transcribed into an RNA molecule by an RNA polymerase.

One of ordinary skill in the art would appreciate that the terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

Transformation of a cell may be stable or transient. The skilled artisan would appreciate that the term "transient transformation" or "transiently transformed" may encompass the introduction of one or more exogenous polynucleotides into a cell in the absence of integration of the exogenous polynucleotide into the host cell's genome. In contrast, the term "stable transformation" or "stably transformed" may encompass the introduction and integration of one or more exogenous polynucleotides into the genome of a cell. The skilled artisan would therefore appreciate that the term "stable transformant" may encompass a cell which has stably integrated one or more exogenous polynucleotides into the genomic or organellar DNA. It is to be understood that an organism or its cell transformed with the nucleic acids, constructs and/or vectors as disclosed herein can be transiently as well as stably transformed.

The skilled artisan would appreciate that the term "construct" may encompass an artificially assembled or isolated nucleic acid molecule which includes the polynucleotide of interest. In general, a construct may include the polynucleotide or polynucleotides of interest, a marker gene which in some cases can also be a gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

The skilled artisan would appreciate that the term "expression" may encompass the production of a functional end-product e.g., an mRNA or a protein.

Figure 1B:
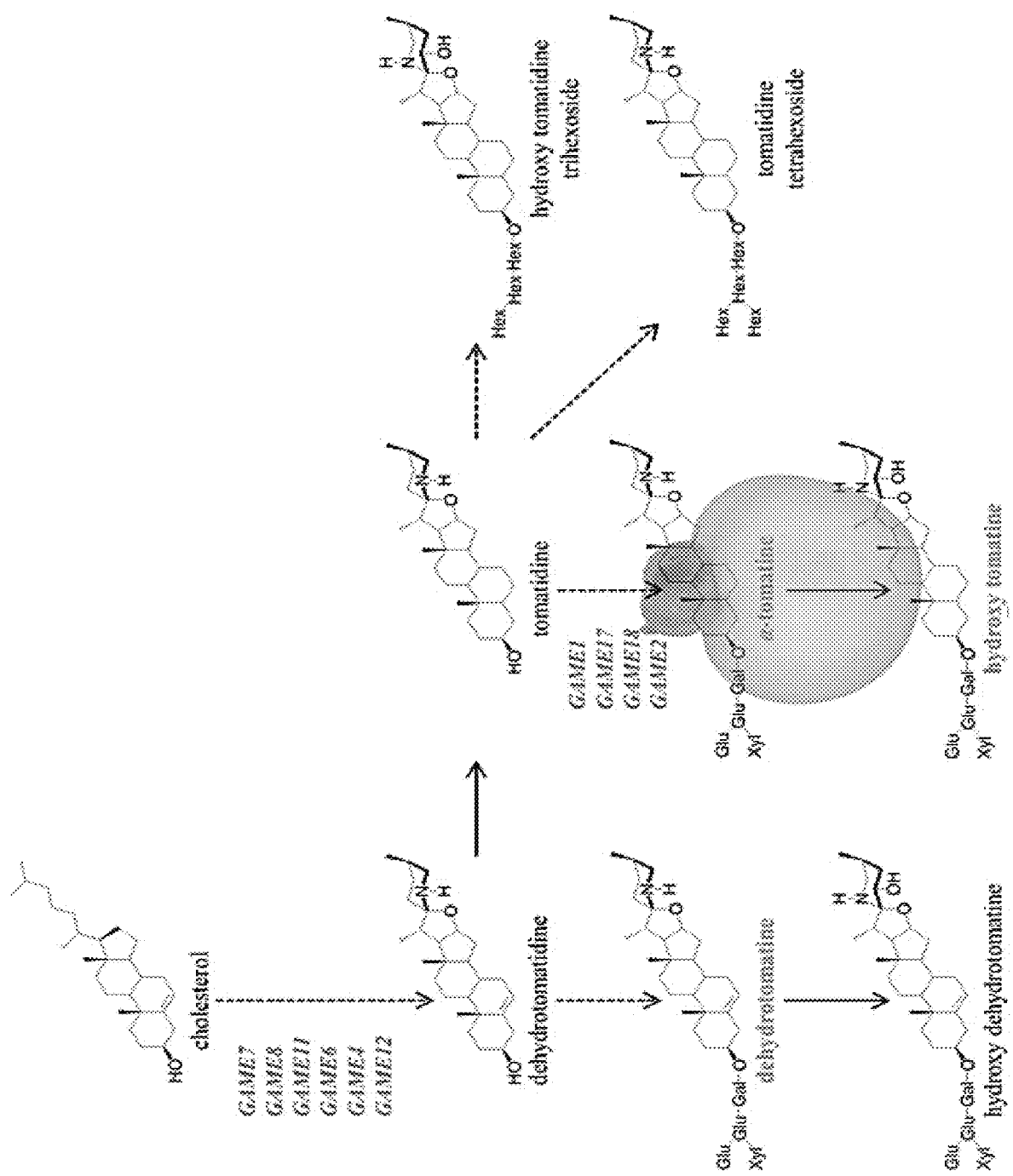
Figure 1B:
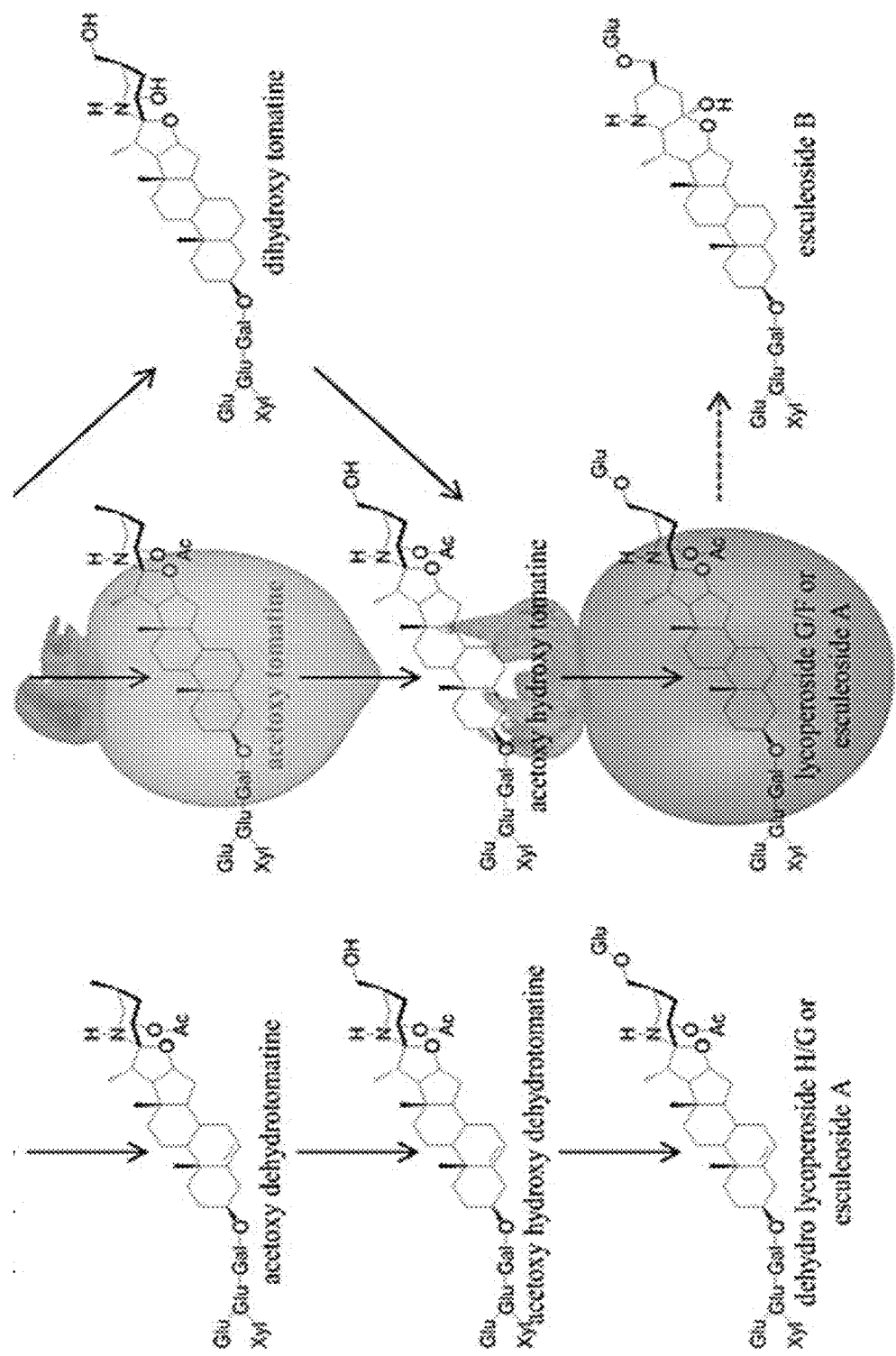
Figure 1C:
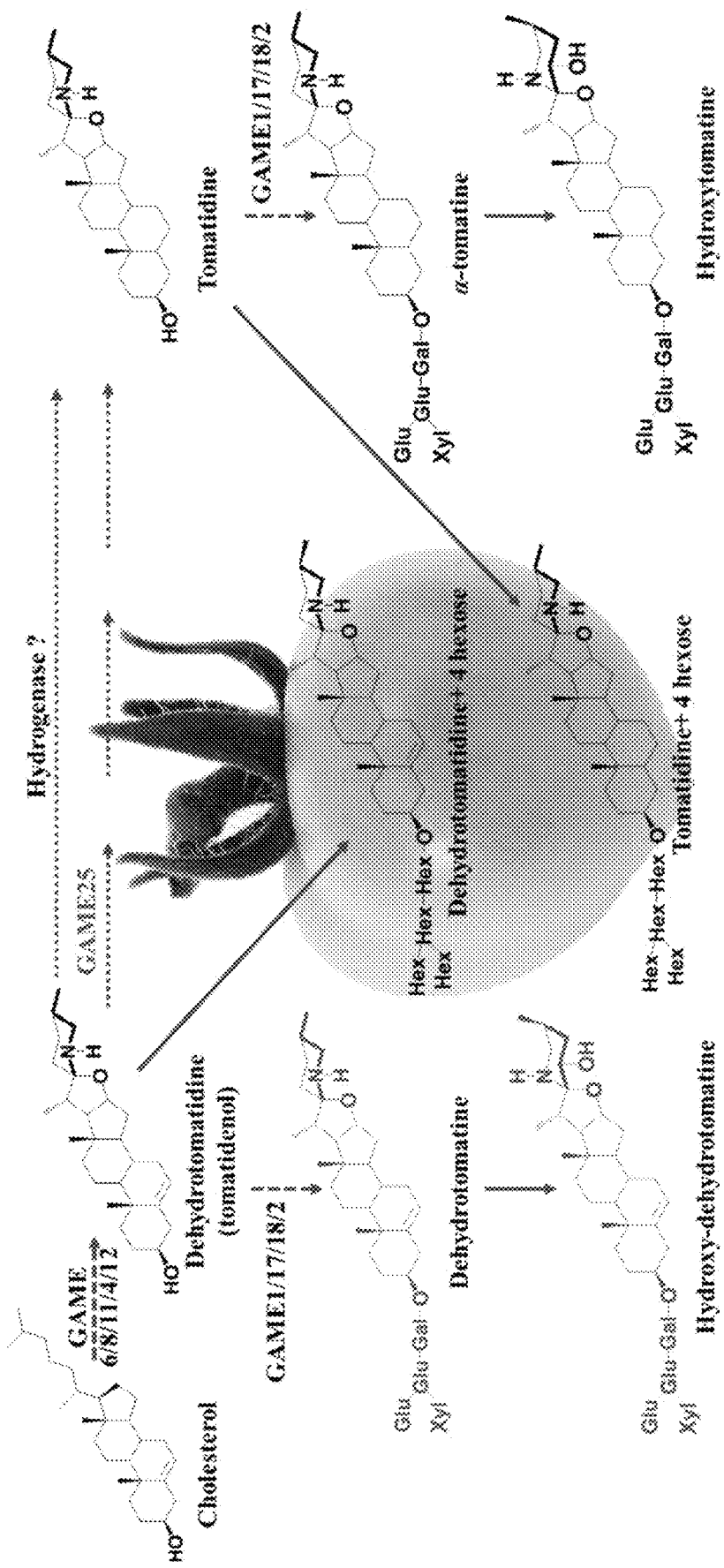
Figure 1C:
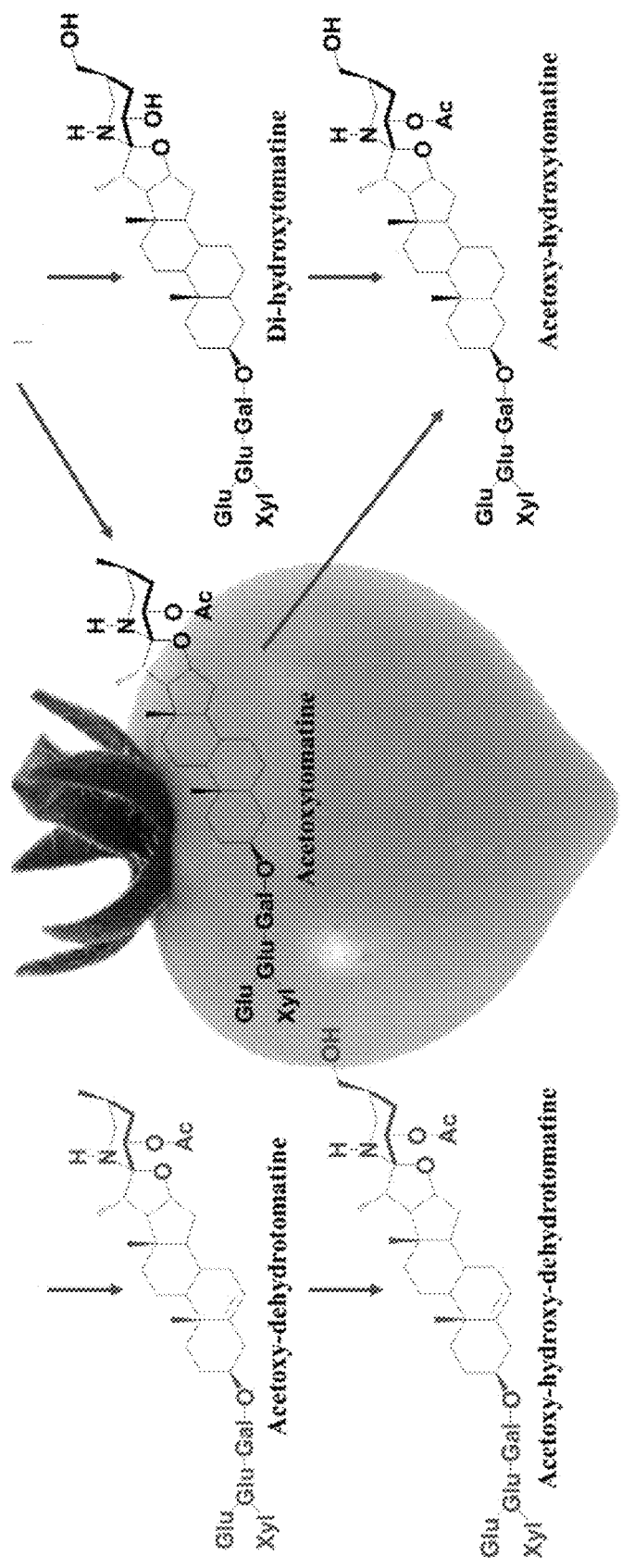
Figure 1C:
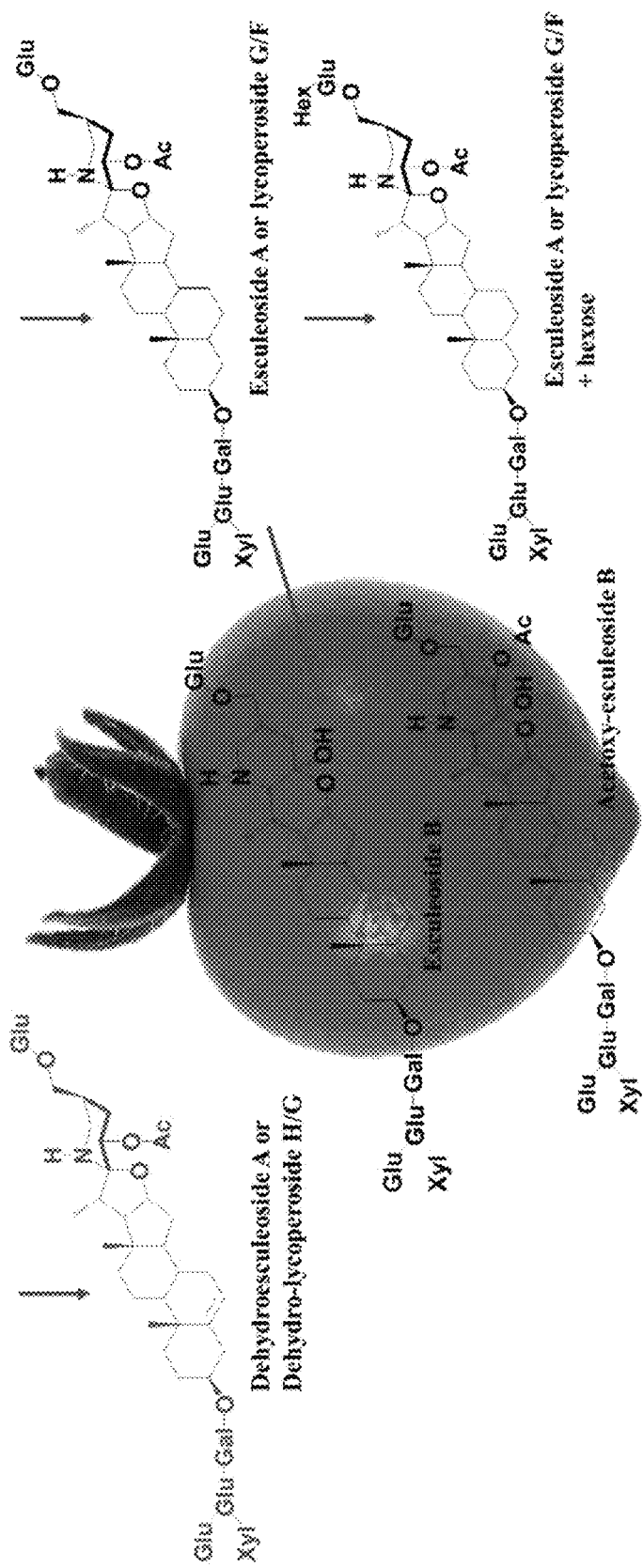

The enzymes encoded by GAME25 and GAME31 are involved in particular steps of cholesterol metabolism (FIGS. 1A-1C, FIGS. 2A-2B, FIGS. 3A-3C). For example, a tomato GAME25 gene (SEQ ID NO: 1) encodes a side chain reductase enzyme, 3-β-hydroxysteroid dehydrogenase/isomerase, (GAME25; SEQ ID NO: 3), which in tomato catalyzes the first step in the multi-step conversion of dehydrotomatidine to tomatidine (FIGS. 1A-1C).

Figure 2A:
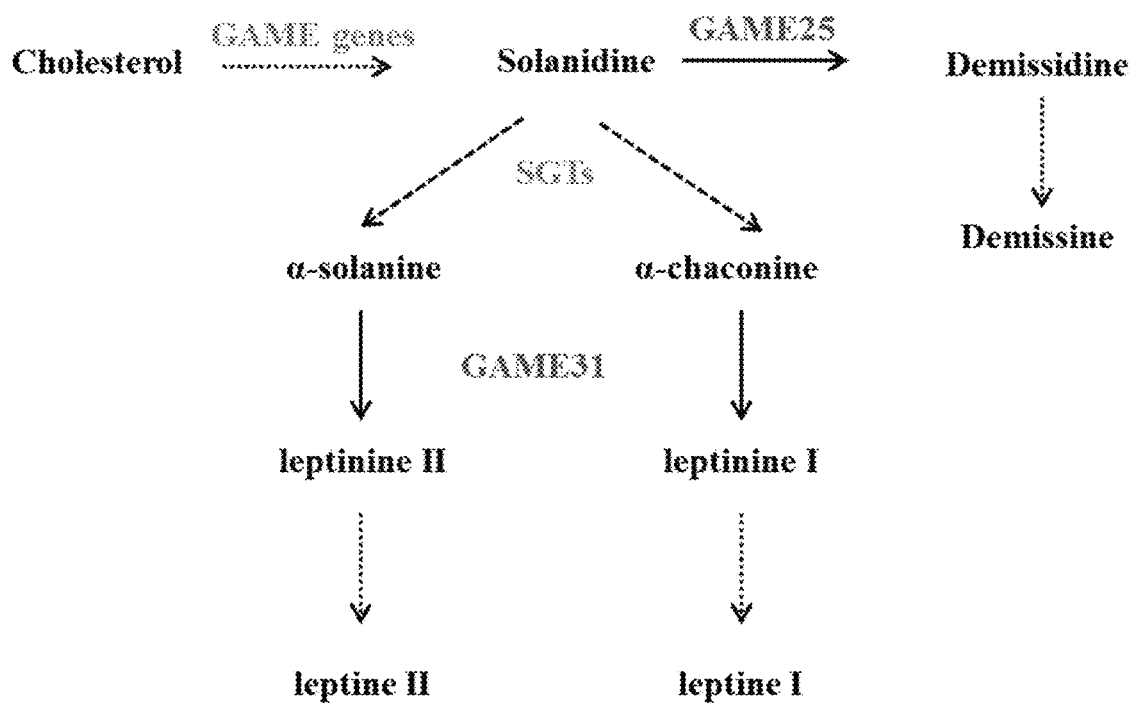
FIGS. 2A-2B provide an overview of SGA biosynthesis in potato. Cholesterol is first converted to the aglycone solanidine in potato. Solanidine is further glycosylated by SGT enzymes to produce α-solanine and α-chaconine in cultivated potato. Some wild potato species (e.g. *S. chacoense* and *S. demissum* etc.) produce demissidine or its glycosylated form demissine from the solanidine aglycone. The enzymatic conversion of solanidine to demissidine in wild potato plants was hypothesized previously to be carried out in a single reaction catalyzed by a hypothetical hydrogenase GAME. GTs—GAME Glycosyltransferase. SGT—Sterol alkaloid Glycosyltransferase. Dotted arrows represent multiple glycosyltransferase enzymatic steps between the compounds shown. Solid arrows represent a single enzymatic step between compounds.
Figure 2B:
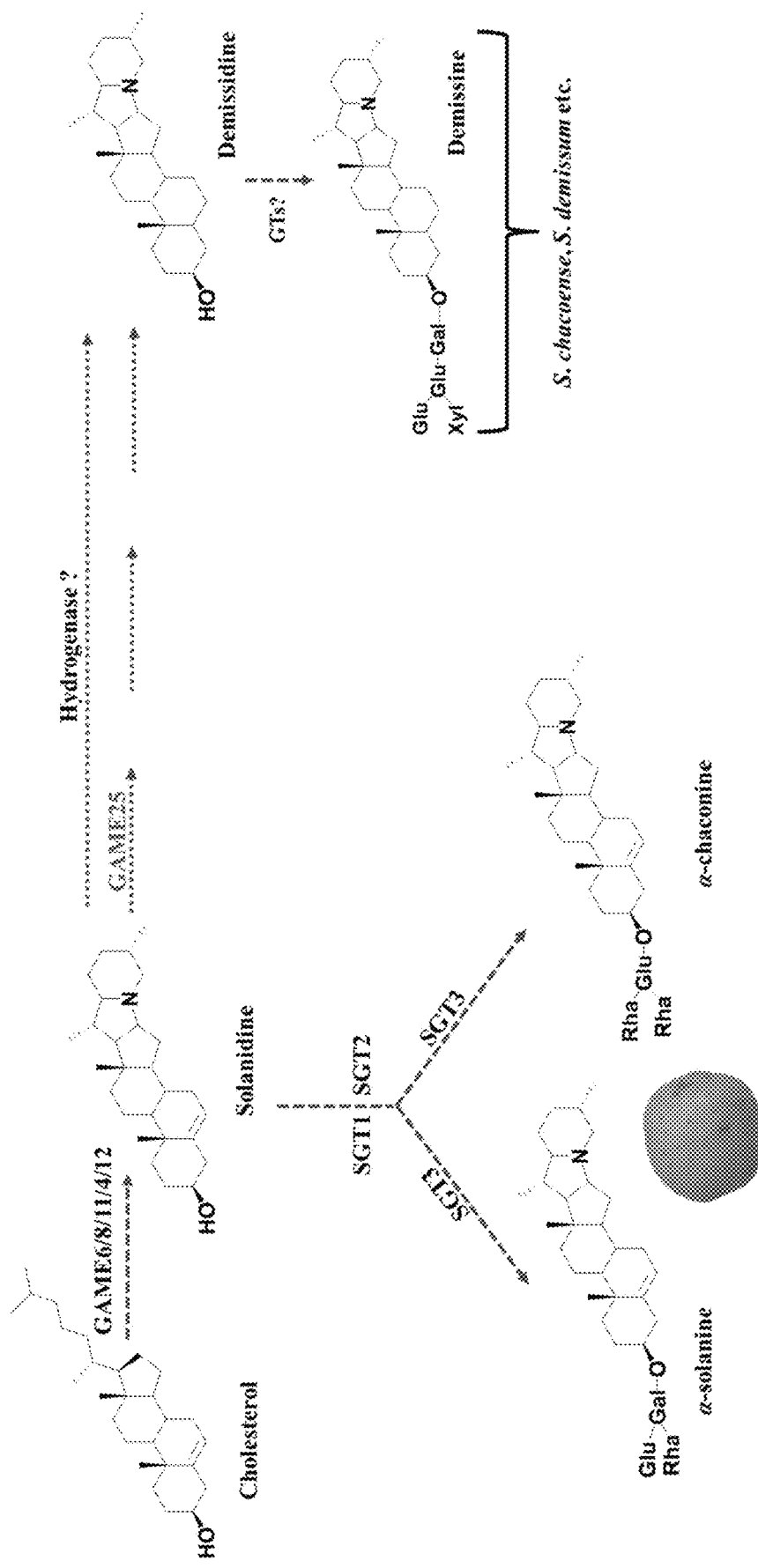

A homologue of the GAME25 gene was identified in potato (SEQ ID NO: 13), wherein the encoded enzyme (SEQ ID NO: 15) may catalyze the first step in the conversion of solanidine to demissidine (FIGS. 2A-2B).

In some embodiments, a tomato plant comprises a cultivated tomato plant. In some embodiments, a cultivated tomato plant comprises a *Solanum lycopersicum* (*S. lycopersicum*) species of tomato plant. In some embodiment, a tomato plant comprises a wild tomato plant. In some embodiments, a wild tomato plant comprises a *Solanum pennellii* (*S. pennellii*) species.

In one embodiment, a tomato GAME25 gene comprises the nucleic acid sequence of SEQ ID NO: 1. In another embodiment, a tomato GAME25 gene consists of the nucleic acid sequence of SEQ ID NO: 1. In another embodiment, SEQ ID NO: 1 comprises or consists of the following nucleic acid sequence:

```
                                             (SEQ ID NO: 1)
GTGATATATTTCAAAAAATAATTAAAATACATATATATTGCATACATAAT

TCACTTTTAATACATATTGCAGATTTAACTTAAACATTGTTATAAATGGT

GATAAATAAAAAAATCGTTAAAATTAGTAATTATTCATTAAACTGCATCT
```

-continued

```
ATTTATGTAATTTTTCCAATTAAAAATCTATTATTTTTTTCAATCCAAT

CCAAACAGGCTCTAAAGCATCAATGTTTTTGAAATTACCAAAATAGCCTC

GGTTGTTAAGCGCTTCCTTCTATATATTAGTGAATTCAAACTACAGTCGG

TACAAAGGAAGTTATTTACTCTTATAATGGCAAATAAGCTCAGGTATAGC

ATAGTTAGTATTTGTTTAAATTAATGGTGCTAATCAGTACATTAATTTAT

TTTCTCAAAATTGTGTAATTACATATAATTAAATGTGTTTAATCAAATGT

TTTTCTTTTTTATATGCATCGATCCTGTAGGTTGGAGGGCAAAGTAGCTA

TAATTACCGGTGCTGCTAGTGGCATTGGAGAAGCAAGTGCTAGATTGTTC

GTTGAACATGGTGCTCGTGTCGTCGTCGCCGATATTCAAGATGAACTTGG

TCAAAAAGTAGTTGATTCTATCGGATCTGACAAAGCCAGCTACCGGCACT

GCGACGTTACAGACGAGAAGCAAGTTGAGGAAACCGTAGCTTACGCGGTA

GAGAAATACGGTACTCTTGACATTATGTTTAGTAATGTCGGGACGCTGAA

TTTCTGCAGCGTCCTCGACATGGACGTGCTGGCCTTCGATGAGACCATGG

CCATCAACGTACGCGGATCCGCGTTAGCGGTTAAGCACGCGGCTAAAGTT

ATGGTTGATAAGAAAATTCGGGGATCTATTATATGTAACGCGAGTTTAGA

AGGGATTTTAGCTGGGGCCGCTTCGCTCGCCTACATTGCGTCAAAGCACG

CAGTGGTAGGCATTATAAAAGCGGCCGCACGTGAACTGGGTCCACATGGG

ATAAGGGTGAATGGGGTGTCGCCCTATGGAATAGCGACGCCCCTTGTGAC

TAAGGCGTATGGACTGGATGCGGCTCTATTGGAAGAAGCAATTTACGGTA

ATGGACACTTGAAAGGAGTTAAGTTGAGCACGATGCATGTAGCACAATCA

GCACTTTTTTGGCGTCTGATGAATCTGCTTATACAAGTGGTCAAAATTT

AGCTGTTGATGGTGGACTAAGTTCTATTTTGAAGCTACAATAAATTGTCA

CGCTATTTGTGTTGGCGTGCTGTGGCGTGGGCCTTAATCCTCACTCTCTT

GTGTCTGTACTTCTGTTTCATCTCGTTTCGTTTCAAATTTTCAACTTAAT

AATACTCTCATATTTTATGCGATATTTTTCAGATTTATACTAAGTTTTTT

ATAGATATTTTAAACGTTGTGACTTAAAAAGATATAAATTTCATTTTTTT

AAAATTAAAAATTTTATG.
```

In one embodiment, a potato comprises a cultivated potato plant or a wild potato plant.

In some embodiments, a potato plant comprises a cultivated potato plant. In some embodiments, a cultivated potato plant comprises a *Solanum tuberosum* (*S. tuberosum*) species of potato plant. In some embodiment, a potato plant comprises a wild potato plant. In some embodiments, a wild potato plant comprises a *Solanum pennellii* (*S. pennellii*) species.

In another embodiment, a potato GAME25 gene comprises the nucleic acid sequence of SEQ ID NO: 13. In another embodiment, a potato GAME25 gene consists of the nucleic acid sequence of SEQ ID NO: 13. In another embodiment, SEQ ID NO: 13 comprises or consists of the following nucleic acid sequence:

```
                                        (SEQ ID NO: 13)
AAAAAATTTAACATACAGTTGCTGCAAAGGAAGCTACCTACTCGTATAAT

GGCAAATAAGCTCAGGTACTTAATTAGTACATTAATTTCTTTCTTTCTTT

TCTCAAATTGTATATGAGAATTAAATGTGTATTTTTAGCTTTAATCAAAT

GTTTTTGTGGTATATTATATGCATCGTGTAGGTTGGAGGGCAAAGTGGCT

ATAATTACAGGTGCTGCAAGTGGCATTGGAGAAGCAAGTGCTAGATTGTT

CGCCGAACATGGTGCTCGTATTGTCGTAGCCGATATTCAAGATGAACTTG

GTCTGAAAGTAGTTGAATCTATCGGAGCTGACAAAGCCAGCTACCGACAC

TGCGACGTTACAGACGAGAAGCAAGTTGAGGATACCGTAGCTTACACGGT

AGAGAAATACGGTACTCTTGACATCATGTTTAGTAATGTTGGGACGCTGA

ATTTTTGCAGCGTCCTGGACATGGACGTGATGGTCTTCGATAAGACGATG

GCCATCAACGCACGAGGATCCGCGTTAGCGGTCAAGCACGCGGCTAGATT

TATGGTTGATAAGAAAATTCGGGGATCCATTATATGCAACGCGAGTTTAG

ATGGTATTGTAGCTGGGGCCACTTCGCTTGCCTACATTGCGTCAAAGCAC

GCAGTTGTAGGCATTGTGAAAGCGGCCGCACGTGACCTAGGTCCATACGG

GATAAGGGTGAATGGGGTGTCGCCATATGGAATAGCGACGCCCCTGGTGT

GCAAAGCGTATGGGTTGGATGCGGGTCCATTGGAAGCAGCAATATATGGA

AATGGAAACTTGAAAGGTGTTAGGTTGAGCACGATGCATGTAGCACAATC

AGCACTTTTCTTGGCGTCTGATGAATCTGCTTACACAAGTGGTCAAAATT

TAGCTGTTGATGGTGGACTTAGTTCTATTTTGAAGGTACAATAGATTGTC

ACTCTATTGTGCTGGTGTGCTGTGATGTGTGCATTAGTTCTATTTTGAAG

CTACAATAATTCCTTTGTCATGTAGTACTGTTTATCTTGTTTCATTTCGA

ATTTTCAACTTAAATAATATTCTCTCACAG.
```

In one embodiment, a tomato GAME25 cDNA comprises the nucleic acid sequence of SEQ ID NO: 2. In another embodiment, a tomato GAME25 cDNA consists of the nucleic acid sequence of SEQ ID NO: 2. In another embodiment, SEQ ID NO: 2 comprises or consists of the following nucleic acid sequence:

```
                                        (SEQ ID NO: 2)
ATGGCAAATAAGCTCAGGTTGGAGGGCAAAGTAGCTATAATTACCGGTGC

TGCTAGTGGCATTGGAGAAGCAAGTGCTAGATTGTTCGTTGAACATGGTG

CTCGTGTCGTCGTCGCCGATATTCAAGATGAACTTGGTCAAAAAGTAGTT

GATTCTATCGGATCTGACAAAGCCAGCTACCGGCACTGCGACGTTACAGA

CGAGAAGCAAGTTGAGGAAACCGTAGCTTACGCGGTAGAGAAATACGGTA

CTCTTGACATTATGTTTAGTAATGTCGGGACGCTGAATTTCTGCAGCGTC

CTCGACATGGACGTGCTGGCCTTCGATGAGACCATGGCCATCAACGTACG

CGGATCCGCGTTAGCGGTTAAGCACGCGGCTAAAGTTATGGTTGATAAGA

AAATTCGGGGATCTATTATATGTAACGCGAGTTTAGAAGGGATTTTAGCT

GGGGCCGCTTCGCTCGCCTACATTGCGTCAAAGCACGCAGTGGTAGGCAT

TATAAAAGCGGCCGCACGTGAACTGGGTCCACATGGGATAAGGGTGAATG

GGGTGTCGCCCTATGGAATAGCGACGCCCCTTGTGACTAAGGCGTATGGA

CTGGATGCGGCTCTATTGGAAGAAGCAATTTACGGTAATGGACACTTGAA

AGGAGTTAAGTTGAGCACGATGCATGTAGCACAATCAGCACTTTTTTGG

CGTCTGATGAATCTGCTTATACAAGTGGTCAAAATTTAGCTGTTGATGGT

GGACTAAGTTCTATTTTGAAGCTACAATAA.
```

In another embodiment, a tomato GAME25 cDNA comprises the nucleic acid sequence of SEQ ID NO: 11. In another embodiment, a tomato GAME25 cDNA consists of the nucleic acid sequence of SEQ ID NO: 11. In another embodiment, SEQ ID NO: 11 comprises or consists of the following nucleic acid sequence:

(SEQ ID NO: 11)
ATGGCAAATAAGCTCAGGTTGGAGGGCAAAGTAGCTATAATTACTGGTGC

TGCTAGTGGCATTGGAGAGGCAAGTGCTAGATTGTTCGTTGAACATGGTG

CTCGTGTCGTCGTCGCCGATATTCAAGATGAACTTGGTCAAAAGTAGTT

GATTCTATCGGAGCTGACAAAGCCAGCTACCGGCACTGCGACGTTACAGA

CGAGAAGCAAGTTGAGGAAACCGTAGCCTACGCGGTAGAGAAATACGGTA

CTCTTGACATTATGTTTAGTAATGTCGGGACGCTGAATTTCTGCAGCGTC

CTCGACATGGACGTGATGGCCTTCGATGAGACGATGGCCATCAACGTACG

TGGATCCGCGCTAGCGGTTAAGCACGCGGCTAAAGTTATGGTTGATAAGA

AAATTCGGGGATCTATTATATGTAACGCGAGTTTAGAGGGGATTTTAGCT

GGGGCCGCTTCGCTTGCCTACATTGCGTCAAAGCACGCAGTCGTAGGCAT

AATAAAAGCGGCCGCACGTGAACTGGGTCCACATGGGATAAGGGTGAATG

GGGTGTCGCCATATGGAATAGCGACGCCCTGGTGTGTAAGGCGTATGGA

CTGGATGCGGCTCTATTGGAAGAAGCAATTTATGGTAATGGACACTTGAA

AGGTGTTAAGTTGAGCACGATGCATGTAGCACAATCAGCACTTTTTTGG

CGTCTGATGAATCTGCTTACACAAGTGGTCAAAATTTAGCTGTTGATGGT

GGACTAAGTTCTATTTTGAAGCTACAATAA.

In another embodiment, a potato GAME25 cDNA comprises the nucleic acid sequence of SEQ ID NO: 14. In another embodiment, a potato GAME25 cDNA consists of the nucleic acid sequence of SEQ ID NO: 14. In another embodiment, SEQ ID NO: 14 comprises or consists of the following nucleic acid sequence:

(SEQ ID NO: 14)
ATGGCAAATAAGCTCAGGTTGGAGGGCAAAGTGGCTATAATTACAGGTGC

TGCAAGTGGCATTGGAGAAGCAAGTGCTAGATTGTTCGCCGAACATGGTG

CTCGTATTGTCGTAGCCGATATTCAAGATGAACTTGGTCTGAAAGTAGTT

GAATCTATCGGAGCTGACAAAGCCAGCTACCGACACTGCGACGTTACAGA

CGAGAAGCAAGTTGAGGATACCGTAGCTTACACGGTAGAGAAATACGGTA

CTCTTGACATCATGTTTAGTAATGTTGGGACGCTGAATTTTTGCAGCGTC

CTGGACATGGACGTGATGGTCTTCGATAAGACGATGGCCATCAACGCACG

AGGATCCGCGTTAGCGGTCAAGCACGCGGCTAGATTTATGGTTGATAAGA

AAATTCGGGGATCCATTATATGCAACGCGAGTTTAGATGGTATTGTAGCT

GGGGCCACTTCGCTTGCCTACATTGCGTCAAAGCACGCAGTTGTAGGCAT

TGTGAAAGCGGCCGCACGTGACCTAGGTCCATACGGGATAAGGGTGAATG

GGGTGTCGCCATATGGAATAGCGACGCCCTGGTGTGCAAAGCGTATGGG

TTGGATGCGGGTCCATTGGAAGCAGCAATATATGGAAATGGAAACTTGAA

AGGTGTTAGGTTGAGCACGATGCATGTAGCACAATCAGCACTTTTCTTGG

CGTCTGATGAATCTGCTTACACAAGTGGTCAAAATTTAGCTGTTGATGGT

GGACTTAGTTCTATTTTGAAGGTACAATAG.

In one embodiment, a tomato GAME25 polypeptide comprises the amino acid sequence set forth in SEQ ID NO: 3. In another embodiment, a tomato GAME25 polypeptide consists of the amino acid sequence set forth in SEQ ID NO: 3. In another embodiment, SEQ ID NO: 3 comprises or consists of the following amino acid sequence:

(SEQ ID NO: 3)
MANKLRLEGKVAIITGAASGIGEASARLFVEHGARVVVADIQDELGQKVV

DSIGSDKASYRHCDVTDEKQVEETVAYAVEKYGTLDIMFSNVGTLNFCSV

LDMDVLAFDETMAINVRGSALAVKHAAKVMVDKKIRGSIICNASLEGILA

GAASLAYIASKHAVVGIIKAAARELGPHGIRVNGVSPYGIATPLVTKAYG

LDAALLEEAIYGNGHLKGVKLSTMHVAQSALFLASDESAYTSGQNLAVDG

GLSSILKLQ.

In another embodiment, a tomato GAME25 polypeptide comprises the amino acid sequence set forth in SEQ ID NO: 12. In another embodiment, a tomato GAME25 polypeptide consists of the amino acid sequence set forth in SEQ ID NO: 12. In another embodiment, SEQ ID NO: 12 comprises or consists of the following amino acid sequence:

(SEQ ID NO: 12)
MANKLRLEGKVAIITGAASGIGEASARLFVEHGARVVVADIQDELGQKVV

DSIGADKASYRHCDVTDEKQVEETVAYAVEKYGTLDIMFSNVGTLNFCSV

LDMDVMAFDETMAINVRGSALAVKHAAKVMVDKKIRGSIICNASLEGILA

GAASLAYIASKHAVVGIIKAAARELGPHGIRVNGVSPYGIATPLVCKAYG

LDAALLEEAIYGNGHLKGVKLSTMHVAQSALFLASDESAYTSGQNLAVDG

GLSSILKLQ.

In another embodiment, a potato GAME25 polypeptide comprises the amino acid sequence set forth in SEQ ID NO: 15. In another embodiment, a potato GAME25 polypeptide consists of the amino acid sequence set forth in SEQ ID NO: 15. In another embodiment, SEQ ID NO: 15 comprises or consists of the following amino acid sequence:

(SEQ ID NO: 15)
MANKLRLEGKVAIITGAASGIGEASARLFAEHGARIVVADIQDELGLKVV

ESIGADKASYRHCDVTDEKQVEDTVAYTVEKYGTLDIMFSNVGTLNFCSV

LDMDVMVFDKTMAINARGSALAVKHAARFMVDKKIRGSIICNASLDGIVA

GATSLAYIASKHAVVGIVKAAARDLGPYGIRVNGVSPYGIATPLVCKAYG

LDAGPLEAAIYGNGNLKGVRLSTMHVAQSALFLASDESAYTSGQNLAVDG

GLSSILKVQ.

In one embodiment, a GLYCOALKALOID METABOLISM 25 (GAME25) polypeptide comprises a 3-β-hydroxysteroid dehydrogenase/isomerase enzyme activity. In another embodiment, a 3-β-hydroxysteroid dehydrogenase/isomerase (GAME25) enzyme comprises the amino acid sequence set forth in any one of SEQ ID NO: 3, SEQ ID NO: 12, and SEQ ID NO: 15, or a protein homologue thereof, wherein said protein homologue is at least 80% homologous to any of SEQ ID NO: 3, SEQ ID NO: 12, and SEQ ID NO: 15.

One of ordinary skill in the art would recognize that a 3-β-hydroxysteroid dehydrogenase/isomerase is a side chain reductase enzyme. In one embodiment, homologues of the GAME25 enzyme comprise a 3-β-hydroxysteroid dehydrogenase/isomerase enzyme activity. In some embodiments, a homologue also encompasses deletion, insertion, or substitution variants, including an amino acid substitution, thereof and biologically active polypeptide fragments thereof. In one embodiment, the variant comprises conservative substitutions, or deletions, insertions, or substitutions that do not significantly alter the three dimensional structure of the GAME25 enzyme. In another embodiment, the deletion, insertion, or substitution does not alter the function of interest of the GAME25 enzyme, which in one embodiment wherein said plant is a tomato plant is a first step in the multi-step conversion of dehydrotomatidine to tomatidine. In another embodiment, the deletion, insertion, or substitution does not alter the function of interest of the GAME25 enzyme, which in another embodiment wherein said plant is a potato plant is a first step in the multi-step conversion of solanidine to demissidine.

In some embodiments, when a genetically modified plant is a tomato plant, the altered at least one steroidal alkaloid or a glycosylated derivative thereof is selected from the group comprising α-tomatine, α-tomatine isomer (1 and 2), α-tomatine isomer 2, hydroxytomatine, acetoxytomatine, dehydrotomatidine, dehydrotomatine, dehydrotomatine isomer 1, dehydrotomatine+4-hexose, or any derivatives thereof, or any combination thereof. In some embodiments, when a genetically modified plant is an eggplant plant, the altered at least one steroidal alkaloid or a glycosylated derivative thereof is selected from the group comprising β-soldulcine, soladulcine A, and the unsaturated or saturated steroidal saponin or glycosylated derivative thereof is selected from dioscin, diosgenin, parillin, sarasapogenin, or any derivatives thereof, or any combination thereof.

In another embodiment, the disclosure includes a homologue of a GAME25 enzyme. In another embodiment, the disclosure includes a homologue of a GAME25 enzyme having a 3-β-hydroxysteroid dehydrogenase/isomerase enzyme activity. In another embodiment, homologues comprise polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to a GAME25 enzyme as determined using BlastP software of the National Center of Biotechnology Information (NCBI) using default parameters.

In another embodiment, the amino acid sequence of a GAME25 enzyme homologue is at least 70% homologous to a GAME25 amino acid sequence or a peptide thereof, described herein. In another embodiment, the amino acid sequence of a GAME25 enzyme homologue is at least 80% homologous a GAME25 amino acid sequence or a peptide thereof, described herein. In another embodiment, the amino acid sequence of a GAME25 enzyme homologue is at least 90% homologous a GAME25 amino acid sequence or a peptide thereof, described herein. In another embodiment, the amino acid sequence of a GAME25 enzyme homologue is at least 95% homologous a GAME25 amino acid sequence or a peptide thereof, described herein. In another embodiment, the amino acid sequence of a GAME25 enzyme homologue is at least 98% homologous a GAME25 amino acid sequence or a peptide thereof, described herein.

A skilled artisan would appreciate that the terms "polypeptides", "polypeptide", "enzyme" or grammatical equivalents thereof, may be used interchangeably to encompass amino acid sequences or proteins and may encompass polymers of amino acids of any length. These polypeptides may in some embodiments include proteins which have been modified post-translationally by reactions such as glycosylation, phosphorylation, acetylation or protein processing. The structure of the polypeptide may be modified, for example, by substitutions, deletions or insertions of amino acids and fusion with other proteins while retaining its biological activity.

In some embodiment, homologues of GAME25 enzyme are produced in plants, wherein said plants comprise a cultivated tomato plant, a wild tomato plant, a cultivated potato plant, a wild potato plant, or a bittersweet plant.

In another embodiment, a 3-β-hydroxysteroid dehydrogenase/isomerase comprises the amino acid sequence set forth in any one of SEQ ID NO: 3, SEQ ID NO: 12, or SEQ ID NO: 15.

In one embodiment, the 3-β-hydroxysteroid dehydrogenase/isomerase (GAME25) polypeptide is encoded by a gene comprising the nucleotide sequence set forth in any one of SEQ ID NO: 1, SEQ ID NO. 13, or a gene homologue thereof, wherein said gene homologue is at least 80% homologous to any of SEQ ID NO: 1, SEQ ID NO. 13. In another embodiment, the 3-β-hydroxysteroid dehydrogenase/isomerase (GAME25) polypeptide is encoded by a cDNA comprising the nucleotide sequence set forth in any one of SEQ ID NO: 2, SEQ ID NO: 11, or SEQ ID NO. 14, or a gene homologue thereof, wherein said gene homologue is at least 80% homologous to any of SEQ ID NO: 2, SEQ ID NO: 11, or SEQ ID NO. 14.

In another embodiment, the 3-β-hydroxysteroid dehydrogenase/isomerase is encoded by a gene comprising the nucleotide sequence set forth in SEQ ID NO: 1, SEQ ID NO. 13. In another embodiment, a 3-β-hydroxysteroid dehydrogenase/isomerase (GAME25) is encoded by the nucleic acid sequence set forth in any one of SEQ ID NO: 2, SEQ ID NO: 11, or SEQ ID NO. 14, or a polynucleotide homologue thereof, wherein said polynucleotide homologue is at least 80% homologous to any of SEQ ID NO: 2, SEQ ID NO: 11, or SEQ ID NO. 14. In another embodiment, a 3-β-hydroxysteroid dehydrogenase/isomerase (GAME25) is encoded by the nucleic acid sequence set forth in any one of SEQ ID NO: 1, SEQ ID NO: 2, SEQ ID NO: 11, SEQ ID NO: 13, or SEQ ID NO. 14, or a polynucleotide homologue thereof, wherein said polynucleotide homologue is at least 80% homologous to any of SEQ ID NO: 1, SEQ ID NO: 2, SEQ ID NO: 11, SEQ ID NO: 13, or SEQ ID NO. 14.

In some embodiments, said 3-β-hydroxysteroid dehydrogenase/isomerase (GAME25) is encoded by a gene comprising the polynucleotide sequence set forth in any one of SEQ ID NO: 1, SEQ ID NO: 2, SEQ ID NO: 11, SEQ ID NO: 13, and SEQ ID NO: 14, or a gene homologue thereof, wherein said gene homologue is at least 80% homologous to any of SEQ ID NO: 1, SEQ ID NO: 2, SEQ ID NO: 11, SEQ ID NO: 13, and SEQ ID NO: 14.

A skilled artisan would appreciate that a "homologue" of a nucleic acid sequence as disclosed herein, for example a homologue of a gene sequence or a homologue of a cDNA sequence, comprises a percent homology with a corresponding nucleic acid sequence disclosed herein.

Homology is, in some embodiment, determined by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

In one embodiment, homologues of a GAME25 gene or a GAME25 cDNA encode a polypeptide comprising a 3-β-hydroxysteroid dehydrogenase/isomerase enzyme activity. In some embodiments, a homologue also encompasses deletion, insertion, or substitution variants, thereof, and biologically active polynucleotide fragments thereof. In one embodiment, the variant comprises conservative substitutions, or deletions, insertions, or substitutions that do not significantly alter the three dimensional structure of the encoded GAME25 enzyme. In another embodiment, the deletion, insertion, or substitution does not alter the function of interest of the encoded GAME25 enzyme, which in one embodiment wherein said plant is a tomato plant, is a first step in the multi-step conversion of dehydrotomatidine to tomatidine. In another embodiment, the deletion, insertion, or substitution does not alter the function of interest of the encoded GAME25 enzyme, which in another embodiment wherein said plant is a potato plant, is a first step in the multi-step conversion of solanidine to demissidine.

In another embodiment, the disclosure includes a homologue of a GAME25 gene. In another embodiment, the disclosure includes a homologue of a GAME25 cDNA. In another embodiment, the disclosure includes a homologue of a GAME25 gene encoding an enzyme having a 3-β-hydroxysteroid dehydrogenase/isomerase enzyme activity. In another embodiment, the disclosure includes a homologue of a GAME25 cDNA encoding an enzyme having a 3-β-hydroxysteroid dehydrogenase/isomerase enzyme activity. In another embodiment, homologues comprise a polynucleotide sequence which is at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to a GAME25 gene nucleic acid sequence.

In one embodiment, the phrase "a polynucleotide sequence" encompasses a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

In one embodiment, a "complementary polynucleotide sequence" encompasses a sequence, which results from reverse transcription of messenger RNA using a reverse transcriptase or any other RNA-dependent DNA polymerase. In one embodiment, the sequence can be subsequently amplified in vivo or in vitro using a DNA polymerase.

In one embodiment, a "genomic polynucleotide sequence" encompasses a sequence derived (isolated) from a chromosome and thus it represents a contiguous portion of a chromosome.

In one embodiment, a "composite polynucleotide sequence" encompasses a sequence, which is at least partially complementary and at least partially genomic. In one embodiment, a composite sequence can include some exonal sequences required to encode the polypeptide disclosed herein, as well as some intronic sequences interposing therebetween. In one embodiment, the intronic sequences can be of any source, including of other genes, and typically will include conserved splicing signal sequences. In one embodiment, intronic sequences include cis-acting expression regulatory elements.

In another embodiment, the nucleic sequence of a GAME25 gene homologue is at least 70% homologous to a GAME25 nucleic acid sequence or a fragment thereof, described herein. In another embodiment, the nucleic sequence of a GAME25 gene homologue is at least 80% homologous to a GAME25 nucleic acid sequence or a fragment thereof, described herein. In another embodiment, the nucleic sequence of a GAME25 gene homologue is at least 90% homologous to a GAME25 nucleic acid sequence or a fragment thereof, described herein. In another embodiment, the nucleic sequence of a GAME25 gene homologue is at least 95% homologous to a GAME25 nucleic acid sequence or a fragment thereof, described herein. In another embodiment, the nucleic sequence of a GAME25 gene homologue is at least 98% homologous to a GAME25 nucleic acid sequence or a fragment thereof, described herein.

In another embodiment, the nucleic sequence of a GAME25 cDNA homologue is at least 70% homologous to a GAME25 nucleic acid sequence or a fragment thereof, described herein. In another embodiment, the nucleic sequence of a GAME25 cDNA homologue is at least 80% homologous to a GAME25 nucleic acid sequence or a fragment thereof, described herein. In another embodiment, the nucleic sequence of a GAME25 cDNA homologue is at least 90% homologous to a GAME25 nucleic acid sequence or a fragment thereof, described herein. In another embodiment, the nucleic sequence of a GAME25 cDNA homologue is at least 95% homologous to a GAME25 nucleic acid sequence or a fragment thereof, described herein. In another embodiment, the nucleic sequence of a GAME25 cDNA homologue is at least 98% homologous to a GAME25 nucleic acid sequence or a fragment thereof, described herein.

In one embodiment, homologues of a GAME25 gene are expressed in plants, wherein said plants comprise cultivated tomato, wild tomato, cultivated potato, wild potato, aubergine, sweet or chili pepper plants, or bittersweet plants. In one embodiment, homologues of a GAME25 cDNA are expressed in plants, wherein said plants comprise cultivated tomato, wild tomato, cultivated potato, wild potato, aubergine, sweet or chili pepper plants, or bittersweet plants.

In one embodiment, a GLYCOALKALOID METABOLISM 31 (GAME31) polypeptide comprises a 2-oxoglutarate-dependent dioxygenase enzyme activity. In one embodiment, a GAME31 polypeptide is encoded by a GAME31 gene. In another embodiment, a GAME31 polypeptide is encoded by a GAME31 cDNA.

In one embodiment, a tomato GAME31 gene comprises the nucleic acid sequence of SEQ ID NO: 16. In another embodiment, a tomato GAME31 gene consists of the nucleic acid sequence of SEQ ID NO: 16. In another embodiment, SEQ ID NO: 16 comprises or consists of the following nucleic acid sequence:

```
                                      (SEQ ID NO: 16)
TGACTATAATTGATACTCAATCTGTTGAAATATAATGAACCAATTCTTAT

CAAAACACAGTGGAGTACAAGTAATCACGTTGGTTCCTATGAAATGGTTC

ATCTATTTCCCATTATATATAGGCTACTTATTTCCTCACCTATAAAGTAA

AAAACTTTCTAGTGTTTTCTTCTTTCTTTTGTTTTTTTCTCTTTGCTCAT

ATTCTAAAAATATTTCATCAATGGCATCTATCAAATCAGTTAAAGTTCCT

ACTATAGATTTTTCCAATTATCAAGAGCTAAAACCAAACACTCCACTATG
```

```
GGAATCCACAAAAATTCAAGTTTTTGAAGCTTTACAAGAATATGGTTGTT

TTGAAGCAATATATGATAAAGTTTCAAAGGAAATTAGAGAGGAAACATTT

GATATGTCAAAAGAAATATTTGAATTTCCTTTAGAGACTAAAGTGAAAAA

TATCTCAGAAAAACCAATGCATGGCTATATGGGGATGATTCCACAATTGC

CATTGTATGAGAGTTTGTGTATTCCTGATTTGCTTAATCCTCAAAGTCTT

GAAAAATTTTCTAATATCTTTTGGCCTCAGGGTAATCAACATTTCTGGTA

TGTTTACTTTTATTTCTTTTTCATTTTTGTTTTCTTATTATCTTTAAATT

TTGTTCTAGTGGAACTGTTCAAAAGCTACTATCTTTAGAAATAATAATTT

TTATTAGCTTAGTTGATTGATTATGCGATATTATTAATAGCTTAAAAAAA

TAATTTTTATTAGCTTAGAAATAATAATTTTTATTAACTTAGTTGATTGA

CTATGCGATATTATTAATAGCTTAAAAGAGCTTAGTTGATCAGACTACGA

AAGTAAAATAAAAAGAGACGGAAGTCTGTGTCTCGCATCTATTTTTTATT

GCACCGTTTAAACTAAATAAAATATAGACAACAACATCAAAATATTTGGT

AGGAAGACACGATTTATTCAACAGAAATATAGACAACAACATTAAAGTAT

TTGGTACATGAAATCACTATCCAATAAGTGACAGTTCGTTGGCCTTCTCA

TTTTTTATAAAATAAATAGAAACACAAGAGTTGTCTCAAGTGAAAAAATT

GAATTATGTTCAACCTTCTTCATATGTTTATACTAATATTACATGAGCGT

TAATTTTTGCAGCAATTTGATAAAATCTTATTCTAATCCACTTGTGGAAT

TGGATGGGATGTTGAAAAGGATGATTTCGGAGAATTTGGGATTGAAAAAT

CACATTGATGAATTATTGAATGCCAATTACTTCCTATTTAGATTTACACA

TTATAAGGGATCATCAATTGCTAGTGGAGATGAAAATAATAAAGCTGCTG

GATTGGGTGGCCACACGGATGGTAACTTCTTGACTTTTATATCGCAAAAT

CAAGTTAATGGATTGCAAATCAACAAAAATGGAGAATGGATTGATGTGAT

TATTTCACCAAATTCTTACGTTGTTTTGGCCGGTGATTCCTTCAAAGTAA

GTATTTAAGTTTTGAACTAGTGTTACTTATCTTGTTGGGAACTGTTTTG

TTTGATTTTTAAAAGAAAAAATATTAAATGATCAAAAAATTATAATATC

TTTTTTGTTTTAAGGTTAAATAAATTGATTTAAAAATTTCATTTTTAATT

AAAAGAGGGTAGTAAAATGCTTAAAAAGCTAAAATAATTTAGTGTGAAAT

ATATTATTTTATTATCATTCTAATCAAAATTTCTGGTCACACCTTATAGC

ATAGGGGTTTCAGAGGGCCCCGAGATATTTGTTTTGATCTTATATTTCT

CGAATCTATGAAAATGTTATTCCACTAGTGTTTATATTATTTTCTGAAAT

GCATATTTTTGAATGATTTGATATATGCTCAATATTTTCATGCAAAACTG

AAAATGAATTTTGGTATTATTGACCGTATTTGTATTGTTTTACTCTCCAA

AAATATTATCGATCGCATCTATCTTTGTATTTATACAGGCTTGGACAAAT

GGTCGATTGCATTCACCTCTCCACAGAGTAACAATGTCCGGACAAAATGA

TAGACTCTCCATTCAATTGTTTTCATTATCAAAGCCAGGTCACTTCATCC

AGGCACCAAAAGAACTAGTAGATGAAGAACACCCATTACTCTTCAAGCCA

TTTGAAATTCTTGAATTATTCAAGTATGGTACCACAGAAGCTGGCTATAC

AGCTCCTCCAAGTGATCTTTTCAAGATTTATTGTGGTGTTTGATATGCTA

ATTGTTGAATTTCCGCTTCAACAAGCAACTTTTCTAATGAGTTTCATCTT

GTTTTTTTAAGTAGTATGCATTTTATGTTTGAATTGTTGCAGTTGGCAAT

TCATGTTTAATTTGTTTTTGTTTTTTTGAGAAAATATTTCCAATGGGTTT

CGTTGGAAATTCGTCTTGTTTTTTTTTTCAAGTAGTGTACATCTTATTT

TTGGATTGTTGATGTTGAGCGCTAATGTTTAATTTGTTTGTGTTTTGAAG

AGGATGATTATACTCTTTAAGAGGATTCACCGTAATCTTTTAGTATTATT

TG.
```

The start codon (ATG) for SEQ ID NO: 16 starts at nucleotide 221 of SEQ ID NO: 16. The coding sequence present within SEQ ID NO: 16 ends at nucleotide 2243. Therefore, the skilled artisan would recognize that the coding sequence comprised in SEQ ID NO: 16 is found between nucleotides 221-2243.

In one embodiment, a tomato GAME31-like gene comprises the nucleic acid sequence of SEQ ID NO: 19. In another embodiment, a tomato GAME31-like gene consists of the nucleic acid sequence of SEQ ID NO: 19. In another embodiment, SEQ ID NO: 19 comprises or consists of the following nucleic acid sequence:

```
                                (SEQ ID NO: 19; SlGAME31-like1)
ATGGCATCTACCAAATTAGTTAAAGTTCCCACAATAGATTTTTCAAATCA

TCAAGATCTAAAACCAAACACTCCACTATGGGAATCCAAAAAAATTCAAG

TTTTTGAAGCTTTGCAAGAATATGGTTGTTTTGAAGCAATTTATGATAAA

GTTCCAAAAGATATTAGAGAGGAAACATTTAGTATTTCAAAAGAAATATT

TGAATTTCCTTTAGAGACTAAATTGAAAAATATTTCAGAAAAACCAACGC

ATGGATATATGGGAATGATTCCACAATTGCCATTGTATGAGAGTTTGTGT

ATTCCTGATTTGCTTAATCCTAAAAGTCTTCAAAGTTTTGCTAATATCTT

TTGGCCTCAGGGTAACCAACATTTCTGGTATGTTTACTTATGTTTTTATT

TCGCCCTAGCAGAAGTGTTCAAAAGTACGACATTAGAAATTCTTAGTGAC

TTAATTGATTGA
```

In one embodiment, a tomato GAME31-like gene comprises the nucleic acid sequence of SEQ ID NO: 22. In another embodiment, a tomato GAME31-like gene consists of the nucleic acid sequence of SEQ ID NO: 22. In another embodiment, SEQ ID NO: 22 comprises or consists of the following nucleic acid sequence:

```
                                (SEQ ID NO: 22; SlGAME31-like2)
TGAGATGTTGAAAAGGATGATTTCGGAGAATTTGGGATTAAAAAATCACA

TTGATGAATTATTGAATGCCAATTACATCCTATTTAGATTTACACAGTAT

AAGGGATCATCAATTGCTAGTGGAGATGAAAATAATAAAGCAGCTGGATT

GGGTGGCCACACAGATGGTAACTTCTTGTCTATTATATCACAAAATGAAG

TTAATGGATTGCAAATCAACAAAAATGGAGAGTGGATTGATGTCAACATT

TCGCCAAATTCTTATGTTGTTTTATCCGGTGATTCCTTCACAGTAAGTGT

TAAGTTTTGAGCTAGTGTTATTATCTTGTTGGGAACTGTGTTGTTTGATT

TTCTAAAGGGATAATGCTAAATGACAAGAAACTCAAAAAATCAATAAGAT

ATTTGTTGAATCTTACGTCTCTAAATATATTATCATGCTAGTGTTAATTA

TTTCCCGAAATGCATATTTTTGAAGAATCTGACATACTGAGTGATATTCT
```

```
GGAAGAGTCCAACCAAGACACTTTGTTGAAACTACATGCTCAATATTTTC
ATGCAAAACTGAAAATGAATCTTGATATTTGTTGACCCTATGTTGCTCTA
TTCTCCAAAAATACTACTGCGACTATCTTTGTATTTATGCAGGCATGGAC
AAATGGCCGATTGCATTCTCCTGTTCATAGAGTTGAAATGCCCAGAGGAA
GTGATAGATATTCCATTCAATTATTTTCATTATCAAACCAGGTCACTTC
ATCGAGGCACCAAAAGAAATGGTGGATGAAGAACACCCTTTGCTTTTCAA
GCCATTTGAAATTCTTGGATTACTTGGGTATGGTGCCACAGAAGCTGGCT
ATACAACTCCTCCCAGTGATCTTTTCAAGGCATATTGCGGTGTCTGATAT
GCTAATTGCGAATTTCCATTTCTATTAGAATAAAGTTAGTATTTATGAGA
TTTTTGTTGGTAATTCATGTTTAATTGGTTTGTGTTTTTTTGGAAAATAT
TTCTAATGTGTTCCGTTGGAAATTCGTGTGCATCTTATGTTTGGATTGTT
GGTATTGGGAATTCATGTTTAATTTGTTTGTGTTCTTGGGCAAATAATAA
ATTTGAAGCGGAT.
```

In one embodiment, a tomato GAME31-like gene comprises the nucleic acid sequence of SEQ ID NO: 25. In another embodiment, a tomato GAME31-like gene consists of the nucleic acid sequence of SEQ ID NO: 25. In another embodiment, SEQ ID NO: 25 comprises or consists of the following nucleic acid sequence:

```
TGACTAGAAATAGACATAAAACCCTGTACTTTTTGACACACATGTAATAG
CACTTTCTCTATCTAATACGCAACTCTTTATTAATTTTGCGTAAATTTTG
AGCTATTTCCCATTATATATAGGCTACTTATTTCCTCACCTCTTAAGTAA
AAAACTTTCAAGTGTTTCTTCTTTCTTTTATTTCTCTTTGTTCACATATT
CTAAAAATATTTCATCAATGGCATCTATCAAATCAGTTAAAGTTCCTACT
ATAGATTTTTCCAATTATCAAGAGCTAAAACCAAACACTCCACTATGGGA
ATCCACAAAAATTCAAGTTTTTGAAGCTTTTCAAGATATGGTTGTTTTG
AAGCAATATATGATAAAGTTCCAAATGAAATTAGAGAGGAAACATTTGAT
ATGTCAAAAGAAATATTTGAATTTCCTTTAGATACTAAAGTGAAAAATAT
TTCAGAAAAACCAATGCATGGATATATGGGAATGATTCCACAATTGCCAT
TGTATGAGAGTTTGTGTATTCCTGATTGCTTAATCCTCAAAGTCTTCAA
AATTTTGCTAATATCTTTTGGCCTCAGGGTAATCAACATTTCTGGTATGT
CTATTTCACTGTTTTCATCTTTTTTATTTTCTTACTATCATTATCTTTAA
ATTTAAGAAAAACGATAAATATATCCTTAAATATAAATGGTATGCAGAT
ATTCTCCATCATATTTTTGGGACATATATTTTTACCGTTCAAAAATTAAA
GCATATATACCATTTTATACTAATGGATATAGACGTGTCATAATCTTATC
TACCGCCCCAACATTGGATCGATGGATAAGATTGTGCCAAGTTTCCTAAT
TTAACCATTCGTTAGAGTGAAGGGCAGAAATTTTCGACTTTTTAAATGTC
AGGGACATCAATGTCCCAAAAGTATGACGGAGGAAAAATATAACGAAAAA
TATGTGCATACTATTTACGATCGTTTGAAAAAATATTTGTCTTTTTTCCT
TTTAAATTTTGGCCTAATGAAAGTGTTCAAAAAGTATAACATTAGAGATT
CCCAGTAAATTGATTAACTATTTGACCATTCAATAGTTTTATGGAATAAG
TTAATTTTTTCTTTGAGAAAAACAAAATAGGAGATTATAAATGGAAGTTT
CCTTCTCGAATCTATTCATTAGCACACCCCTAAACAAACAAAAGTGCCGA
TAACGTTAAAATATTTGGTATGAAGTCTCGATCTACTCAATAAAAACAAA
TAAATTAATAGGAGACAATAGACAGTATCTTTCTCGAATCAATTTCGAAT
TTATTTCTTTTATCACATTGTTAATAAAATGAAAATTATCAACAACATCA
GAATATTTGGTATGTGTCACGATCTAATAATTGTAGAAATCGAGATATAA
ATACGATTTGAGAAATCAAAGATTGTATTGATGAAAAATAATGTTAAGTT
ACAAGGTTTTTATATGGAGAGAATTGTAGAGTTCTAAGTTAACTATAATA
AAATACTATTACAATACATATTACTATTATAATAATAATAATAATGCAAA
TCCTAGTCGTAATATAATTCTAATCGACTTCAACTAGTACAATAAGTAAA
TAAGTAGCACTGCGTCTAATCCTAGTATGAATCTAACTCGTCAGTCAGTT
CCGCTTTCCCATTTTTGTTTTCACTATCCTAGTTTTAAAAATAAAATAAA
ATATAAGACTTAGTTAACGTAAATATGGCCTCATTTGTTTGTATTTAATT
GGGGGTCTAAATCTTAATCAATCAGATTCGCCTCATTCAGTATGTTTGTT
TTTTTATGACTGAATCTTAATTATTTAGATTTAATTCATTAAGTTTGTTT
GTTTTATTTTCTTAGAAGTCTCTTAACGAGTCTGAATACATCTGAGTTAA
TCAGATCTGTAATACACTCTTAAGACCATTCAGACTCAAAAGTAATTCCT
ATCTTAATTCAACTACATCACAAAAACTCATAAAAGTTTTTTTCTTATTA
AATTAATGTTAATTACATGCTTACCCGTTATAATTTCCTTTATTTTACTA
ACTTAATATACGTCCTTTACTTTCATAAATTAATCAATATATTTGAATTG
ATAAACACTTCATGATATAATATTTAGCACGATTCTAGAAAACAAGAAAG
TATTGATTAGTTGATCGATAACAATAACAAATCTGCATTATAAAATAAAA
TGCTTTCATAAACATTATATTACTACTCTATATAAACTATTTTACATTGC
ATTATATTAGATTATCAAAGTTTTTGAGTGCAAAAAAGAATAGTCATATA
TTAGTGATGTAACTTAATGTTAAATTCTTAATAGATAAATCATATGACCT
ATTCATGATAAGAATGTCCAAAAATTTATTTTCCATATAAAAAATTATTT
TACTAAAATGAGGTTTTTATAATTTTTTGTTGATACATCGTTTAATTTCA
TATGTACATTCAAATATTAAAAACGAATTATCTCAATAATCCAGTTTTCA
TATTCAGAGAAATACCTTAATATTAAAATGTTTATTCAGATTTACATAT
CTAGATCTTAATGCATATTTTAATATTTAGATGTATATTCAGATTCAGAC
GTTTTGATCTTAATAGAAACAAATAAGGCCTAAGTGAAAGAATGGTATCA
ACTTGAAATGTTTCTAAATCTGTTCAACCTTCTTTATATGTTTATAAACA
TTATATGTGTATTTTTTTTTGCAGCAATTTGGTAAAGTCTTATTCTAAT
CCACTTGTGGAATTGGATGAGATTTTGAAAAGGATGATTTCGGAGAATTT
GAGATTAAAAATTCACATTGATGAATTGTTGAATGCCAATTATTTCCTAT
TTAGATTTACACATTACAAGGGATCATCAATTACTGGTGGAGATGAGAAT
AACAAAGTTGCTGGATTGGGTGGCCACACAGATGGTAACTTCTTGACTTT
TATATCGCAAAATCAAGTCAATGGATTGCAAATCAACAAAAATGGAGAAT
GGATTGATGTGAATATTTCACCAAATTCTTATGTTGTTTTGGCTGGTGAT
TCCTTCAAAGTAAGTGTTAAGTTTTGAATTATTGTTATTATCTTGTTGGG
AACTGTTTTGTTTGATTTTTAAAAGAAAAATGCTAAATGGTCACAAATTT
```

```
TTAAAGTCAATAATATTTTTTTGTTTTAAGGTAAATAAATTGATAAAAA
AAGAATTCATTTTTAATTAAAAGATATTGAAATTAAAAGGGTAAAAATAC
TTTAAACATAGTGTGAATTATGTTATTTTATCATTCTAATCAAAATTTGT
GGCCAATATTGTTACACCTTATAGGATTTATCAAAAAAACATAGTTTTCA
GAGGCTCAAGATATTTGTTGGATCTTATGTTTCTCGAATCTCTGAAAATG
TTGTTCCGCTTGTGTTGAATGTATTATTTTCTGAAATGTATATTTTTGAA
GAATTTGATATATTAATGATATGCTCAATATTTTCATGCAAAACGGAAAA
TGAATTTTGGTATTATTGACCCTATTTGTATTGTTCTACTCTCCAAAAT
ATTATCGATCACGTCTATCTTTGTATTTATACAGGCTTGGACAAATGGTC
GATTGCATTCTCCTCTTCACAGAGTAACAATGTCCGGAGAAAATGATAGA
CTCTCCATTCAATTATTTTCATTATCAAAACCAGGTCACTTCATCGAGGC
ACCAAAAGAACTAGTGGATGAAGAACACCCTTTACTCTTCAAGCCATTTG
AAATTATTGGATTATTTGAGTATGGTACCACAGAAGCTGGCTATACAGCT
CCTCCAAGTGATCTTCTCAAGAGTTATTGCGGTGTTTGATATGCTAATTG
CGAATTTCCGCTTCAGCAACCAACTTTTCTAATAAGTTTCGTCTGAAATT
CGTGTTGTTTTAATTATTATGCATTTTATGTTTGAATTGTTGTAGTTGGC
AATTCATGTTTAATTTGTTTGTGTTTTTTTTTTGAGAAAATATTGCATT
GGGTTTCATTGGAAATTTGTGTTTTTAAAAAGTAGTGTGCATCTTATGT
TTGGATTGTTGGTGTTGAGAATTCATTTTTAATTTGTTTTTTTTTTGGG
CAAATAATGAATTTAAAATTGTTGATTTTACTCTTTAGTGGAAATGAT
                                (SEQ ID NO: 25; S1GAME31-like3).
```

The start codon (ATG) for SEQ ID NO: 25 starts at nucleotide 218. The coding sequence present within SEQ ID NO: 25 ends at nucleotide 1182. Therefore, the skilled artisan would recognize that the CDS comprised in SEQ ID NO: 25 comprises nucleotides 21-1182.

In another embodiment, a potato GAME31 gene comprises the nucleic acid sequence of SEQ ID NO: 30. In another embodiment, a potato GAME31 gene consists of the nucleic acid sequence of SEQ ID NO: 30. In another embodiment, SEQ ID NO: 30 comprises or consists of the following nucleic acid sequence:

```
                                          (SEQ ID NO: 30)
GAAACTTTGAAGTCTTTCTTGTTTCCTAAATATTCCTCAAATGGCATC
TACCAAAGTTACGATTCCCACCATAGATTTTTGCGATTCTGAGCTTAAAC
CAAACACTCCACAATGGGAATCAACAAAAGTTCAAGTTTTTGAAGCCTTA
CAAGAATTTGGTTGTTTTGAAGCAATATATAACAAAGTTCCAAATGAAAT
TAGAGAGGGCATGTTTGATACTTTAAAAGAAGTATTTGATTTTCCACTGC
CCAAATTGATAGAATATAGAGAGAAACCCTTTCATATATATGATGGGCAA
ATTCCAAGTGTACCACTCTTTGGTAGTGTGTACTCTGCTGATTTGGTCCT
CCCAAATAGTGTTGAAACATTTGCCAATACCTTTTGGTCTCATGGAAACC
CTAATTTTAGGTATGCATTACTTCTTTTTCATTAATTATAGGGAGTCACG
ATAGTGTAAGATGCATTAAAAGGAGAAACGTTTCCTAGTAGAATTGTTTC
TATTCCTAGGGCTAGAATCAGGAACCTTTAGTTAAATTAATAGAGATAAT
ATTCATTCCATCACTAAAGGTGAAAATTAAGTATCTTATATTGTCCATAA
ATTTTATATAGAAGAGATGTGAGAATTAATAAAATAAAAATTAAAAACTC
ACGAGTAAACAAAATAATTATATCTAATTTATATTAATAAAGAAGAGTAT
TTGATTATTATATTAAGTCAAATGATAAGCTAATAAATCAATATTAACAA
TCTAATCACATGATTTATATAAAATTGGTTATGGGTATGGGAAGGGAGGG
AGGGAAGTACATTTCATTGAGGAACAATGCAATAGTTAGACAGGATTTAA
CATACTTGAACAAGATATCATAATCTAAAATGATTAAAAATAATTTTTTA
ATATTATCTACACATCGCGCGAATATATATATATATATATATTAAGTGTA
TTTCTTAAATAATATTGTATTACTATTTATATAAATTTTGTATGTTTTAA
TTTTGCAGCAATGTGGCAAAGTCCTACTTCAAGCAACTTATGGAATTAAA
TGACATGGTTAAAAAGATGGTTTTGGAGAGTCTTGGGCTAAAAAATTACA
TTGATGAATTCTTGAATTCCAATGTTTATATGTCAAGATTTACTAATTAC
AAGGTAATTAAAGGTGAAAATGAGAATAAATCAGGATTACCTTCCCACAC
AGATAGTTCCTACTTGACCATAATTAAACAAAATCAAAATGGATTGCAAG
TTCTCTACAAAAATGGAGAGTGGATTGAGCTCAATCGTCAAAATGGACTG
CAAGTTCTCTACAAAAATGGAGAGTGGATTGAGCTCAATCATACTTCACC
AAATTCCTATATTGTTTATCAGAAGATGTTTTTATGGTAAGTTATTATT
TATTTTTTATTACAGAAGTCAAAAATACACCTAAACTTTTTATTTATATG
TATTTTTGACGCTTAACTCTTTATTTTTTTGTGTGTAGGGGTGGTTTGTT
GCTATAGTAGGAGAATAAAAGAAATAGATTTTTTTGTATGATTGATT
ATTCAAGCCCAACTAGAAGCTAAGATTAGAGGAGTTTTGAAGCAACGAAA
AAAAATGTTGTGTGATTTATAGATATTGATGCAGGCTCGATCCGTGAA
AGAAATCACTAATATTTATATTAGATTAGATCGTTTACCTAACTAAACAT
CCCTTGAAGTACTGCCCTTTCTCCAAACCATATGTGAACGTCAAATATTT
TATGCATCAACCTGTCTTTTTTATTTGGCCCCAACTAACTTCAATCCAC
ATAAATTATTAAATCTTGATATTAGTTGGAATAACATATCTCTTTTCTGA
GAAATTGAAAATAATGCCAGAACTATCATAATCTTTTTTTAAAAAATTG
TCTTGTTATTATCTTATTAATTTAAAATTTCTTTCTTCAGAGGAAATTT
AAGTCAATCTTTTTGTTCCTTAATTATTAATTAAACAAATAAATTCTTAT
ACATACTTTTTATGTGTTGATGCTATGAATTAATTATACAGGCATGGACA
AATGATAGATTGACATCTGCTCAACACAGGGTTGTAACAACAGGAGACAA
AGAAAGATTCTCTATTCAAGTTTTTTCCTTTCCAAATCCAGATTACACTG
TGAAGGTCCCACAAGAATTAGTGGATGAAGAACACCCTTTAATGTACAAG
CCTTTTAAGATGTCTGAATATAATAAATATATTATGTTAGGTGCTAAAAA
TGGATTGGGTGTCAAGAATTATTGTGGTCTTTAAAAATTTAGTAGCTATG
AAAATTTATTTATGTATTGTTTTGATGAATAAAATGTATCAGATGGC.
```

In one embodiment, a potato GAME31-like gene comprises the nucleic acid sequence of SEQ ID NO: 33. In another embodiment, a potato GAME31-like gene consists of the nucleic acid sequence of SEQ ID NO: 33. In another embodiment, SEQ ID NO: 33 comprises or consists of the following nucleic acid sequence:

"GAAACTTTGAAGTCTTTCTTGTTTCCTAAATATTCCTCAAATGGCATCT

ACCAAAGTTACGATTCCCACCATAGATTTTTGCGATTCTGAGCTTAAACC

AAACACTCCACAATGGGAATCAACAAAAGTTCAAGTTTTTGAAGCCTTAC

AAGAATTTGGTTGTTTGAAGCAATATATAACAAAGTTCCAAATGAAATT

AGAGAGGGCATGTTTGATACTTTAAAAGAAGTATTTGATTTTCCACTGCC

CAAATTGATAGAATATAGAGAGAAACCCTTTCATATATATGATGGGCAAA

TTCCAAGTGTACCACTCTTTGGTAGTGTGTACTCTGCTGATTTGGTCCTC

CCAAATAGTGTTGAAACATTTGCCAATACCTTTTGGTCTCATGGAAACCC

TAATTTTAGGTATGCATTACTTCTTTTTCATTAATTATAGGGAGTCACGA

TAGTGTAAGATGCATTAAAAGGAGAAACGTTTCCTAGTAGAATTGTTTCT

ATTCCTAGGGCTAGAATCAGGAACCTTTAGTTAAATTAATAGAGATAATA

TTCATTCCATCACTAAAGGTGAAAATTAAGTATCTTATATTGTCCATAAA

TTTTATATAGAAGAGATGTGAGAATTAATAAAATAAAAATTAAAACTCA

CGAGTAAACAAAATAATTATATCTAATTTATATTAATAAAGAAGAGTATT

TGATTATTATATTAAGTCAAATGATAAGCTAATAAATCAATATTAACAAT

CTAATCACATGATTTATATAAAATTGGTTATGGGTATGGGAAGGGAGGGA

GGGAAGTACATTTCATTGAGGAACAATGCAATAGTTAGACAGGATTTAAC

ATACTTGAACAAGATATCATAATCTAAAATGATTAAAAATAATTTTTTAA

TATTATCTACACATCGCGCGAATATATATATATATATATATTAAGTGTAT

TTCTTAAATAATATTGTATTACTATTTATATAAATTTTGTATGTTTTAAT

TTTGCAGCAATGTGGCAAAGTCCTACTTCAAGCAACTTATGGAATTAAAT

GACATGGTTAAAAGATGGTTTTGGAGAGTCTTGGGCTAAAAAATTACAT

TGATGAATTCTTGAATTCCAATGTTTATATGTCAAGATTTACTAATTACA

AGGTAATTAAAGGTGAAAATGAGAATAAATCAGGATTACCTTCCCACACA

GATAGTTCCTACTTGACCATAATTAAACAAATCAAAATGGATTGCAAGT

TCTCTACAAAAATGGAGAGTGGATTGAGCTCAATCGTCAAAATGGACTGC

AAGTTCTCTACAAAAATGGAGAGTGGATTGAGCTCAATCATACTTCACCA

AATTCCTATATTGTTTTATCAGAAGATGTTTTTATGGTAAGTTATTATTT

ATTTTTTATTACAGAAGTCAAAAATACACCTAAACTTTTTATTTATATGT

ATTTTTGACGCTTAACTCTTTATTTTTTTGTGTGTAGGCGTGGTTTGTTG

CTATAGTAGAGGAGAATAAAAGAAATAGATTTTTTTGTATGATTGATTA

TTCAAGCCCAACTAGAAGCTAAGATTAGAGGAGTTTTGAAGCAACGAAAA

AAAATGTTGTGTGATTTATAGATATTGATGCAGGCTCGATCCGTGAAA

GAAATCACTAATATTTATATTAGATTAGATCGTTTACCTAACTAAACATC

CCTTGAAGTACTGCCCTTTCTCCAAACCATATGTGAACGTCAAATATTTT

ATGCATCAACCTGTCTTTTTTATTTGGCCCCAACTAACTTCAATCCACA

TAAATTATTAAATCTTGATATTAGTTGGAATAACATATCTCTTTCTGAG

AAATTGAAAATAATGCCAGAACTATCATAATCTTTTTTAAAAAAATTGT

CTTGTTATTATCTTATTAATTTAAAATTTTCTTTCTTCAGAGGAAATTTA

AGTCAATCTTTTTGTTCCTTAATTATTAATTAAACAAATAAATTCTTATA

CATACTTTTTATGTGTTGATGCTATGAATTAATTATACAGGCATGGACAA

ATGATAGATTGACATCTGCTCAACACAGGGTTGTAACAACAGGAGACAAA

GAAAGATTCTCTATTCAAGTTTTTTCCTTTCCAAATCCAGATTACACTGT

GAAGGTCCCACAAGAATTAGTGGATGAAGAACACCCTTTAATGTACAAGC

CTTTTAAGATGTCTGAATATAATAAATATATTATGTTAGGTGCTAAAAAT

GGATTGGGTGTCAAGAATTATTGTGGTCTTTAAAAATTTAGTAGCTATGA

AAATTTATTTATGTATTGTTTTGATGAATAAAATGTATCAGATGGC (SEQ ID NO: 33; StGAME31-like1.

In one embodiment, a potato GAME31-like gene comprises the nucleic acid sequence of SEQ ID NO: 36. In another embodiment, a potato GAME31-like gene consists of the nucleic acid sequence of SEQ ID NO: 36. In another embodiment, SEQ ID NO: 36 comprises or consists of the following nucleic acid sequence:

TTATTATTTGCACAAAAAATACAAACAAAGCATGAATTCCCATCGAA

ATTACTCACTGTTACAACAATTCAAACATAAGATACACACTACTAAAGAA

ACACGAATTTCGACAAGCATTCTGTTAGAAATCCCATATATACTTACAGT

ATTCTAACAAGAACGTTCATAAAAAAATCACGTTTTTTTATTCTAGCATA

TATAAAACAAAGAACTCTAAAGCTAAAGATACACACTATTATAAAAACAC

GAATTCCAAATGAAATCCATTGGAAATGATGAAGACATTTTCGATGAATA

TTCTGTTAGAAATCCCAAATATACTAACAGTACTCTGACAAAAATGTTCA

TTAGAAATTCACGTTTATCATATCAAAGACCACAATAAGCCTTGAAAGCA

TCACTGGGAGCTGCATAGCCAGCTTGGGAAGTAACATACTCAGATAATCC

AACCATTTCAAATGGCTTGAAGAGTAAAGGGTGTTCTTCATCCACAAGTT

CTTTTGGGGCCTTTATAAAGTGACCTGGTTTTGAGAATGAAAATAATTGA

ATTGAGAATCTATCACTTTCACCAAATATTTTTACCTTGTGGATGGGAGA

ATGCAATCGACCATTTGTCCATGCCTGTATAAATTCACGTCGTCAGTGCA

TAAAACTCAAACACATTTATTTGAAGGATCCAACATTTTTAGAGATTCAA

AAAGCATAGACTCCAACAAATATCAAAATTCATTTTTCAGTTTTGCATGA

AAATATTAAATATGTAGGTAGTTCCATTTAATATTCGAGAAACATAGGTT

AATTCCAACAAATATGAAGATTCATTTTCAATTTTGCATCAAGATATTAA

ACCTAAATTTTGTTTGGTATATTCCAACCTTGGAAATATTCTTCACAAAT

ATCGTTAGGTATGCGTCAGATCCTCTAAAATCTATATTTTGTTTTTGAAG

GTGCAATAATAATATTTTTGAAGAGTTCGAGTAACATGGATTTCAACAAA

GTAATATGACTAGCTAAAAAAATAAAATGAGTAACACTTACTTTGAATGA

ATCACCAGACAAAACAACATAAGAATTTGGTGAAATATTGACATCAATCC

ACTCTCCATTTTTGTTGATTTGCAAACCATTGACTTGATTTTGTGATATA

AAAGTCAAGAAGTTACCATCTGTGTGGCCATTCAATCCATCTTGTTTAAT

ATTATTTTCATGATCTCCACTAATAATTGATGATCCCTTGTAATGTGTAA

ATCTAAATCTCATATAATTAATATCCAGCAATTCATCAATATGATTTTCT

AATCCCAAATTCTCCAAAATCATCTTTTTCAACATTTCATCCAATTCCAT

AAGTGGATTTGAGTAAGCTTTTACCAAATTGCTGCAAAAATTTATCACTA

TCTCAAAAATAACTTTCTCGCTACTCCACGACTCTAATCAATGCACAAAA

TAATTTTATTTTAAAAAATAAAATAAAGTAGACATACCAGAAATCAGGAT

TACCATGAGGCCAAAAGATATTAGCAAAAGTTTCAACATTTTGAGGATTA

AGCAAATCAGGAATACACAAACTCTCATAAAATGGCAAGTGTGGAATCAT

TCCTACATAGCCATGTAATGTTATATCTGAATAATTTTTCACTTTGGTCT

CTAAAGGAAATTGAAATATTTCTTTTGTAATACCAAAAATACCCTCTCTA

ATTTCATTTGGAATTTTATCATATGTTGCTTCAAAACAACCATATTCTTT

TAAAGCTTCAAAAACTTGAACTTTTGTGGATTCCCATAGTGGAGTGTTTG

GTTTTAGTTCTAGATTAGAAAAATCTATGGTGGGAATCTTAACTTTGGTA

GATGCCATTTGAAAGAAACAAAGAAGGAATTAAAGACTTCACAATGTGAA (SEQ ID NO: 36; StGAME31-like2).

In one embodiment, a potato GAME31-like gene comprises the nucleic acid sequence of SEQ ID NO: 39. In another embodiment, a potato GAME31-like gene consists of the nucleic acid sequence of SEQ ID NO: 39. In another embodiment, SEQ ID NO: 39 comprises or consists of the following nucleic acid sequence:

ATTTTTTAATAAAAATAATACAGTACAATACATTACAATACAACGCA

ACACAATACAATACGTTATGTAATCATATGCAATAACCATTCAAATATAA

ATTTTCAACCACCCATACATACGTACATTTTATTCATAAAGAAAATACA

CATATATAAATTTTCATACCCTACAAAAATTTTAAAGACCACAATAATTC

TTGAGATTAATTCCATTTTTATCACCTGACATAGTTTATTTATGAAATTC

AAGCAAGTTAAAAGGCTTGAAGAGTAAAGGGTGGTCTTCATCCACTAATT

CTTTTGGGGTCCTTCACAGTATAATCTGGATGTGGTATGGAAATAATTG

AATAGATAATCTATCTTTGTCTCCTGTTGGTACTACTCTGTGTTCAGCAG

ATGTCAAACTATTATTTGTCCATGCCTGTATAAATCCACAACATCGACAC

ATAAAAAGCATTAGTGATTTCTTTCACAGAGAAAGGGCAGCACCTCAAGG

GGATGTTAGGAAAACAATCTAATCTAATAGAAAATATTAGTGATTTTTTC

TCGATCAAGCCCGCATCGTAATCTATATATCACATACAAACAATCTTATC

GTTACTTCAAAACTGCTCTGATCTTAGCTTCTAGTTGGGCTTAAATAATC

AACCATACAAAAAAATCTCTATTTCTTTNNNNNNNNNNNNNNNNNNNNN

NNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNN

NNNNNNNNNNNNNNNNNNNNNNNNNNNNNNNNNNNNGGTGTGTTTGGTA

CGAAGGAAAATATTTTCTGGAAAATGTTTTTTAATTTCCCATGTTTGGTT

GACTTTAATTATTTGGAAAATGTTTTCCAAATCAACTTATTTTCCTCAAA

TTTAAGGAAATGATTTCCCTTAAAAATTAAGGAAAACATTTTCGAAACT

TCTACTTCATCCTTAAATTATAATATTTTTTACCCCTACTACCAAACCA

GCCCGCCACCCCTGTCAAATTTTATTTTATTTAAAAAATTACTTTTGAAA

AATATTTCAGGGTCGGAAGTTTGGCTGGGGTCCTAGGTCAGATCTCTAGG

TCGGATTTTGAACGGTCATCAAGGTCATGTCCTAGTTCGGGTGTTAGGGT

CGGGTCCTAGATTGATTATTGGGATTGATTTTCGAGTTAAAAGTTATTTT

CCTAAAGAGTATTTTCTAGTCTTAAGCGAAAAATAAAAGATATTTTCTGG

AAAAAAAATTCATTCACCAACCAAACATTAAAAAATAGTTTCTACTCATC

AACTAAATATGAGAAAATAAGTTAGAAATCCACTTGTTTTCCAAGAAAAC

ATTTTCCTTCATACCAAACACACCCTTAATATATATNNNNNNNNNNNNNN

NNNNTTATATATGTATAGATAGCTAGTATACATACTCGAGCGATGTGCGG

AAAATATTAATATGTTATTTTAATCTTACCCCTACCCATGCCCCTACCC

GACCTTCCCCATTCAAAAAATAAATTAAAATTTTTAAAATTTCAAATAT

ATTTTTATCACTACCACCAAACTAGCTCCCCGCCCCCCTCCCCTCAAAC

ATAAAAAAAAAAATTAAAATTATTTTTGAAAAATTTTTAAATCTTAAAT

TTTTTTTACCTCACCAACCCCTACCACCCCTACTCCCTTCCCCCTCATTT

TTAAATTTCCCATGTTTGGTTGACTTTAATGATTTGGAAAATGTTTTCCAA

ATCAACTTATTTTCCTCAAATTTAAGGAAAATGATTATCCTAAAAGTTAT

TTTCCTAAAGAGTATTTTCTAGTCTCAAGAGAAAATAAAAGATATTTTTT

CAGAAAATAATTTTCATTCACCAACCAAACATGAGAAAATAAGTTAGAAA

TCCACTTGTTTTCCAAGAAAACATTTTCCTTCATACCAAACACACCCTTA

ATATATAATGTATATATACCTAGTATACATACTCGCGTGATGTGTGAAAA

ATATTTAAATGTTATTTTAAATCATTTTAGATTGTGATATCTTGTTCGAG

CATGTTAAATCACGTCCAACTATTGCATTGTTACTCAATGAAATGTACTC

CCCTCCATCCCTTCACATACCCGTAACCAATTCTATATGAATAGCGACAA

TGAATCATGTGATTAGATTGTTAGTATTGATTTTATTAGCTTATCACTTG

GATATAATTATTAAATACTCTTCTAATTAATATAAATTAGATATATTTAT

TTTGTTTACTCGTGAGTTCTTAATTTTTATTTTATTAATGATCACATCTC

TTTTATATAAAATGTATGGACAATAAGATACTTAATTTTCACCTTTAGTG

ATGGAATGAATATTATCTCTATAATTTAACTAAAGATTCATGATTCTAGC

CTTAGGAATAAAAACAATTCTAGTAGGAAACGTTTCTCCTTTTAATGTGT

CTTACACTATCGTGACTCCATATTATTAATCTGAATCCCAAAATAAATAC

CGAATACATAATGAAAAAAAAAAATCTCCTACAAATATATGAGCAAGAA

TAATTGGTGTACTAACATGACTAAAACTAAATGATATCACCTACATAAAT

CTTATTCTTTCAAATATCATTAATGAAAAATGACTTTCATAATACCGAGC

ACATTATATGTAATTAAAAGAAGTAATACATACCTAAAGTTAGGGTTTCC

ATCAGACCAAAAGGTATTGGCAAATGTTTCAATACTATTTGGGAGGACCA

```
AATCAGCAGAGCTCACACTACCATAGAGTGGTATACTTGGAATTTTCCA

TCATATATATGAAAGGGTTTTTCTCTATATTCTATCAATTTGGACAATGG

AAAATCAAATACTTCTTTTAAATTATCAAACATGCCCTCTCTAATTTCAT

TTGGAACTTTGTCATATATTGCTTCAAAACAACCAAATTCTTTTAAGGCT

TCAAAAACTTGAACTTTTGTTGATTCCCATTGTGGAGTGTTTGGTTTTAG

CTCAAGATTGCAAAAATCTATGGTGGGAATCTTACCTTTAGTAGATGCCA

TTGATGAATAAATTAAAAGAGAGGAAATAGAAAGAAATAAAGAAGGAGA

AATACTTTACAATATGAAAATTAAAG (SEQ ID NO: 39; St.

GAME31-like3; N represents unknown nucleotide sequence).
```

In one embodiment, a potato GAME31-like gene comprises the nucleic acid sequence of SEQ ID NO: 42. In another embodiment, a potato GAME31-like gene consists of the nucleic acid sequence of SEQ ID NO: 42. In another embodiment, SEQ ID NO: 42 comprises or consists of the following nucleic acid sequence:

```
GAAACTTTGAAGTCTTTCTTGTTTCCTAAATATTCCTCAAATGGCATC

TACCAAAGTTACGATTCCCACCATAGATTTTTGCGATTCTGAGCTTAAAC

CAAACACTCCACAATGGGAATCAACAAAAGTTCAAGTTTTTGAAGCCTTA

CAAGAATTTGGTTGTTTTGAAGCAATATATAACAAAGTTCCAAATGAAAT

TAGAGAGGGCATGTTTGATACTTTAAAAGAAGTATTTGATTTTCCACTGC

CCAAATTGATAGAATATAGAGAGAAACCCTTTCATATATATGATGGGCAA

ATTCCAAGTGTACCACTCTTTGGTAGTGTGTACTCTGCTGATTTGGTCCT

CCCAAATAGTGTTGAAACATTTGCCAATACCTTTTGGTCTCATGGAAACC

CTAATTTTAGGTATGCATTACTTCTTTTTCATTAATTATAGGGAGTCACG

ATAGTGTAAGATGCATTAAAAGGAGAAACGTTTCCTAGTAGAATTGTTTC

TATTCCTAGGGCTAGAATCAGGAACCTTTAGTTAAATTAATAGAGATAAT

ATTCATTCCATCACTAAAGGTGAAAATTAAGTATCTTATATTGTCCATAA

ATTTTATATAGAAGAGATGTGAGAATTAATAAAATAAAAATTAAAAACTC

ACGAGTAAACAAATAATTATATCTAATTTATATTAATAAAGAAGAGTAT

TTGATTATTATATTAAGTCAAATGATAAGCTAATAAATCAATATTAACAA

TCTAATCACATGATTTATATAAAATTGGTTATGGGTATGGGAAGGGAGGG

AGGGAAGTACATTTCATTGAGGAACAATGCAATAGTTAGACAGGATTTAA

CATACTTGAACAAGATATCATAATCTAAAATGATTAAAAATAATTTTTTA

ATATTATCTACACATCGCGCGAATATATATATATATATATTAAGTGTA

TTTCTTAAATAATATTGTATTACTATTTATATAAATTTTGTATGTTTTAA

TTTTGCAGCAATGTGGCAAAGTCCTACTTCAAGCAACTTATGGAATTAAA

TGACATGGTTAAAAAGATGGTTTTGGAGAGTCTTGGGCTAAAAAATTACA

TTGATGAATTCTTGAATTCCAATGTTTATATGTCAAGATTTACTAATTAC

AAGGTAATTAAAGGTGAAAATGAGAATAAATCAGGATTACCTTCCCACAC

AGATAGTTCCTACTTGACCATAATTAAACAAAATCAAATGGATTGCAAG

TTCTCTACAAAAATGGAGAGTGGATTGAGCTCAATCGTCAAAATGGACTG

CAAGTTCTCTACAAAAATGGAGAGTGGATTGAGCTCAATCATACTTCACC

AAATTCCTATATTGTTTTATCAGAAGATGTTTTTATGGTAAGTTATTATT

TATTTTTTATTACAGAAGTCAAAAATACACCTAAACTTTTTATTTATATG

TATTTTTGACGCTTAACTCTTTATTTTTTTGTGTGTAGGGGTGGTTTGTT

GCTATAGTAGAGGAGAATAAAAGAAATAGATTTTTTTTGTATGATTGATT

ATTCAAGCCCAACTAGAAGCTAAGATTAGAGGAGTTTTGAAGCAACGAAA

AAAAATGTTGTGTGATTTATAGATATTGATGCAGGCTCGATCCGTGAA

AGAAATCACTAATATTTATATTAGATTAGATCGTTTACCTAACTAAACAT

CCCTTGAAGTACTGCCCTTTCTCCAAACCATATGTGAACGTCAAATATTT

TATGCATCAACCTGTCTTTTTTATTTGGCCCCAACTAACTTCAATCCAC

ATAAATTATTAAATCTTGATATTAGTTGGAATAACATATCTCTTTTCTGA

GAAATTGAAAATAATGCCAGAACTATCATAATCTTTTTTTAAAAAAATTG

TCTTGTTATTATCTTATTAATTTAAAATTTTCTTTCTTCAGAGGAAATTT

AAGTCAATCTTTTTGTTCCTTAATTATTAATTAAACAAATAAATTCTTAT

ACATACTTTTTATGTGTTGATGCTATGAATTAATTATACAGGCATGGACA

AATGATAGATTGACATCTGCTCAACACAGGGTTGTAACAACAGGAGACAA

AGAAAGATTCTCTATTCAAGTTTTTTCCTTTCCAAATCCAGATTACACTG

TGAAGGTCCCACAAGAATTAGTGGATGAAGAACACCCTTTAATGTACAAG

CCTTTTAAGATGTCTGAATATAATAAATATATTATGTTAGGTGCTAAAAA

TGGATTGGGTGTCAAGAATTATTGTGGTCTTTAAAAATTTAGTAGCTATG

AAAATTTATTTATGTATTGTTTTGATGAATAAAATGTATCAGATGGC (SEQ ID NO: 42; StGAME31-like4).
```

In one embodiment, a potato GAME31-like gene comprises the nucleic acid sequence of SEQ ID NO: 45. In another embodiment, a potato GAME31-like gene consists of the nucleic acid sequence of SEQ ID NO: 45. In another embodiment, SEQ ID NO: 45 comprises or consists of the following nucleic acid sequence:

```
                            (SEQ ID NO: 45; St.GAME31-like5)
GAAACTTTGAAGTCTTTCTTGTTTCCTAAATATTCCTCAAATGGCATCTA

CCAAAGTTACGATTCCCACCATAGATTTTTGCGATTCTGAGCTTAAACCA

AACACTCCACAATGGGAATCAACAAAAGTTCAAGTTTTTGAAGCCTTACA

AGAATTTGGTTGTTTTGAAGCAATATATAACAAAGTTCCAAATGAAATTA

GAGAGGGCATGTTTGATACTTTAAAAGAAGTATTTGATTTTCCACTGCCC

AAATTGATAGAATATAGAGAGAAACCCTTTCATATATATGATGGGCAAAT

TCCAAGTGTACCACTCTTTGGTAGTGTGTACTCTGCTGATTTGGTCCTCC

CAAATAGTGTTGAAACATTTGCCAATACCTTTTGGTCTCATGGAAACCCT

AATTTTAGGTATGCATTACTTCTTTTTCATTAATTATAGGGAGTCACGAT

AGTGTAAGATGCATTAAAAGGAGAAACGTTTCCTAGTAGAATTGTTTCTA

TTCCTAGGGCTAGAATCAGGAACCTTTAGTTAAATTAATAGAGATAATAT

TCATTCCATCACTAAAGGTGAAAATTAAGTATCTTATATTGTCCATAAAT

TTTATATAGAAGAGATGTGAGAATTAATAAAATAAAAATTAAAAACTCAC
```

GAGTAAACAAAATAATTATATCTAATTTATATTAATAAAGAAGAGTATTT
GATTATTATATTAAGTCAAATGATAAGCTAATAAATCAATATTAACAATC
TAATCACATGATTTATATAAAATTGGTTATGGGTATGGGAAGGGAGGGAG
GGAAGTACATTTCATTGAGGAACAATGCAATAGTTAGACAGGATTTAACA
TACTTGAACAAGATATCATAATCTAAAATGATTAAAAATAATTTTTTAAT
ATTATCTACACATCGCGCGAATATATATATATATATATATTAAGTGTATT
TCTTAAATAATATTGTATTACTATTTATATAAATTTTGTATGTTTTAATT
TTGCAGCAATGTGGCAAAGTCCTACTTCAAGCAACTTATGGAATTAAATG
ACATGGTTAAAAGATGGTTTTGGAGAGTCTTGGGCTAAAAAATTACATT
GATGAATTCTTGAATTCCAATGTTTATATGTCAAGATTTACTAATTACAA
GGTAATTAAAGGTGAAAATGAGAATAAATCAGGATTACCTTCCCACACAG
ATAGTTCCTACTTGACCATAATTAAACAAAATCAAATGGATTGCAAGTT
CTCTACAAAAATGGAGAGTGGATTGAGCTCAATCGTCAAAATGGACTGCA
AGTTCTCTACAAAAATGGAGAGTGGATTGAGCTCAATCATACTTCACCAA
ATTCCTATATTGTTTTATCAGAAGATGTTTTTATGGTAAGTTATTATTTA
TTTTTTATTACAGAAGTCAAAAATACACCTAAACTTTTTATTTATATGTA
TTTTTGACGCTTAACTCTTTATTTTTTGTGTGTAGGGGTGGTTTGTTGC
TATAGTAGAGGAGAATAAAAGAAATAGATTTTTTTTGTATGATTGATTAT
TCAAGCCCAACTAGAAGCTAAGATTAGAGGAGTTTTGAAGCAACGAAAAA
AAATGTTGTGTGTGATTTATAGATATTGATGCAGGCTCGATCCGTGAAAG
AAATCACTAATATTTATATTAGATTAGATCGTTTACCTAACTAAACATCC
CTTGAAGTACTGCCCTTTCTCCAAACCATATGTGAACGTCAAATATTTTA
TGCATCAACCTGTCTTTTTTATTTGGCCCCAACTAACTTCAATCCACAT
AAATTATTAAATCTTGATATTAGTTGGAATAACATATCTCTTTTCTGAGA
AATTGAAAATAATGCCAGAACTATCATAATCTTTTTTTAAAAAAATTGTC
TTGTTATTATCTTATTAATTTAAAATTTTCTTTCTTCAGAGGAAATTTAA
GTCAATCTTTTTGTTCCTTAATTATTAATTAAACAAATAAATTCTTATAC
ATACTTTTTATGTGTTGATGCTATGAATTAATTATACAGGCATGGACAAA
TGATAGATTGACATCTGCTCAACACAGGGTTGTAACAACAGGAGACAAAG
AAAGATTCTCTATTCAAGTTTTTTCCTTTCCAAATCCAGATTACACTGTG
AAGGTCCCACAAGAATTAGTGGATGAAGAACACCCTTTAATGTACAAGCC
TTTTAAGATGTCTGAATATAATAAATATATTATGTTAGGTGCTAAAAATG
GATTGGGTGTCAAGAATTATTGTGGTCTTTAAAAATTTAGTAGCTATGAA
AATTTATTTATGTATTGTTTTGATGAATAAAATGTATCAGATGGC.

In one embodiment, a potato GAME31-like gene comprises the nucleic acid sequence of SEQ ID NO: 48. In another embodiment, a potato GAME31-like gene consists of the nucleic acid sequence of SEQ ID NO: 48. In another embodiment, SEQ ID NO: 48 comprises or consists of the following nucleic acid sequence:

(SEQ ID NO: 48; StGAME31-like6)
CACTAATATATTTTTAATAAAAACAATACAGTACAATACATTACAATACA
ACGCAACACAACACAATACAATACGTTATGAAATCATATGCAATAACCAC
ACAAATATAAATTTTCAACCACCCATGCATACGATACATTGTATTCATAA
AGAAAATACACATAAATAAATACCCTACTAAATTTTTAAAGACCACAATA
ATTCTTGAGATTAATTCAATTTTTATTACCTGACATAGTTTATTTATGAA
ATTCAAGCAAGTTAAAAGGCTTGAAGAGTAAGGGTGGTCTTCATCCACTA
ATTATTTTGGGGCCTTCACAGCAAATCTTGATTTGGGAAAGGAAAATAA
TTGAATAGATAGTCTATCTTTGTCTCCTGTTGTTACTACTCTGTGTTCAG
CAGATGTCAAACTATCATTTGTCCATGCCTGTATAAATCCACAACATCGA
CACATAAAAGTATTAGTGATTTCTTTTCACAGAGAAAGGGCAACACCTC
AAGGGATGTTAGGAAAACAATCTAATCTAATACAAAATATTAGTGATTTT
TTCTCGATCAAGCCCGCATCGTAATCTATAAATCACATACAAACAATCTT
ATCGTTACTTCAAAACTGCTCTGATCTTAGCTTCTAGTTGGGCTTGAATA
ATCAACCATACAAAAAAATCTCTATTTCTTTTATTCTCCTCTTCTATAGC
ATCAACCCACCCCCTCACACACAAAATAATAAAGAGTTAAGCGTCAAAAA
TACACATAAATAAATAATTTAGGTGTATTTTTTACCTTGATACTCAAAAA
TAAATAATAACTTACCCTGAAAGCATCTGCTGATAAAACAATATAGGAAT
TTGGTGTTGTATTATTGAGCTCTATCCACTCTCCATTTTTGTAGAGAACT
TGCAATCCATTTTGATTTTGTTTAATTATAGTCAAGTAGCCACTATCTGT
GTGGGGAGGTAATTCTGATCTATTCTCATCTTCACCTTTAATTACCTTGT
AATTAGTAAATCTTGACACAAAAACATTGGAATTCAAGATTTCATCAATG
TAATTTGTTTTCCCAAGACTCTCCAAAACCATTTTTTCCACCATGTCATT
CAATTCCATAAGTTGCTTGAAGTAGGACTTTGCCACATTGCTGCCAAATT
AAAACATACAAAACTTATATAATGGTAATGCAATATTGTGATATTACTCA
AAATTATGTAAGAAATACACTTAGGGTGTGTTTGGTACGAAGGAAAATAT
TTTCTAGAAAATGTTTTTTAATTTCCCATGTTTGGTTGACTTTAATGATT
TGGAAAATGTTTTCCAAATCAACTTATTTTCCTCAAATTTAAGGAAAATG
ATTATCCTAAAAGTTATTTTCCTAAAGAGTATTTTCTAGTCTTAAGTGAA
AAATAAGTTAGAAATCCACTTGTTTTCCAAGAAAACATTTTCCTTCATAC
CAAACACACCCTTAATATATAATGTATATATACCTAGTATACATACTCGC
GCGATGTGAAAAATATTTAAATGTTATTTTAATCATTTTAGATTGTGA
TATCTTGTTCGAGCATGTTAAATCATGTCCAACTATTGCATTGTTACTCA
ATGAAATGTACTCCCCTCCATCCCTTCACATACCCGTAACCAATTCTATA
TGAATAGCGATGTGTGAAAAATATTTAAATGTTATTTTTAATCATTTTAG
ATTGTGATATCTTGTTCGAGCATGTTAAATCATGTCCAACTATTGCATTG
TTACTCAATGAAATGTACTCCCCTCCATCCCTTCACATACCCGTAACCAA
TTCTATATGAATAGCGACAATGAATCATGTGATTAGATTGTTAATATTGA
TTTTATTAGCTTATCACTTGGATATAATTATTAAATACTCTTCTAATTAA
TATAAATTAGATATATTTATTTTGTTTACTCGTGAGTTCTTAATTTTTAT
TTTATTAATGATCACATCTCTTTTATATAAAATGTATGGACAATAAGATA
CTTAATTTTCACCTTTAGTGATGGAATGAATATTATCTCTATAATTTAAC -continued
TAAAGATTCCTGATTCTAGCCTTAGGAATAAAAACAATTCTAGTAGGAAA

CGTTTCTCCTTTTAATGTGTCTTACACTATCGTGACTCCATATTATTAAA

TCTGAAATCCCAAAAATAAATACCGAATACATAATGAAAAAAAAAAATC

TCCTACAAAATATATGAGCAAGAATAATTGGTGTACTAACATGACTAAAC

TAAATGATATCACCTACATAAATCTTATTCTTTCAAATATCATTAATGAA

AAATAACTTTCATAATACCGAACACATTATATATAATTAAAAGAAGTAAT

ACATACCTAAAGTTAGGGTTTCCATCAGACCAAAAGGTATTGGCAAATGT

TTCAACACTATTTGGGAGGACCAAATCAGCAGAGCTCACACTACCATAGA

GTGGTATACTTGGAATTTGCCCATCATATAAATGGGGTTTTTCTCTATAT

TCTATCAATTTGGACACTGGAAAATCAAATACTTCTTTTAAAGTATCAAA

CATGCCCTCTCTAATTTCATTTGGAACTTTGTCATATATTGCTTCAAAAC

AACCAAATTCTTTTAAGGCTTCAAAAACTTGAACTTTTGTTGATTCCCAT

TGTGGAGTGTTTGGTTTTAGCTCAAGATTGCAAAAATCTATGGTGGGAAT

CTTAACTTTGGTAGATGCCATTGATGAATAAATTAAATAGAGAGGAAATA

GAAAGAAATAAA.

In one embodiment, a potato GAME31-like gene comprises the nucleic acid sequence of SEQ ID NO: 51. In another embodiment, a potato GAME31-like gene consists of the nucleic acid sequence of SEQ ID NO: 51. In another embodiment, SEQ ID NO: 51 comprises or consists of the following nucleic acid sequence:

(SEQ ID NO: 51; StGAME31-like7)
GCAGCAATGTGGCAAAGTCCTACTTCAAGCAACTTATGGAATTGAATGGC

ATGGTGGAAAAGATGGTTTTGGAGAGTCTTGGGCTAAAAAATTACATTGA

TGAATTCTTGAATTCCAATGTTTATATGTCAAGATTTACTAATTACAAGG

TAATTAAAGGTGAAAATGAGAATAAATCAGGATTACCTTCCCACACAGAT

AGTTCCTACTTGACCATAATTAAACAAAATCAAATGGATTGCAAGTTCT

TCTACAAAAATGGAGAGTGGATTGAGCTCAATCATACCTCACCAAATTCC

TATATTGTTTTATCAGCAGATGCTCTTATGGTAAGTTATTATTTATTTTT

GATTACAGCAGTCAAAAATACGCCTAAACTTCTAATTTATATGTATTTTT

GACGCTTTAACTCATTATTATTTTTGTGTGTGGGGTGGTTTGTTGCTAT

AGTAGAGGAGAATAAAAGAAATAGAGATTTTTTTGTATGATTGATTATT

CAAGCCCAACTAGAAGCTAAGATTAGAGGAGTTTTCAACCAACGAAAAAA

ATGTTTGTGTGATTTATATATCATGATGCAGGCTCAATCCGTAAAAGA

AATCACTAATATTTGTATTAGATTAGATTGTTTACCTAACTAACATCCCT

TGAAGTGTTGCCCTTTCTCCAAACCCTATGTGAACGTCAAATATTTTATG

CATCAACCTGTCTTATTTTATTTGACCTCAACTAACTTCAATCCACAAAA

AATATTAAATCTTGATATTATTTGGAATAACGTATCTCTTTTTCTGGAAA

ATTGAAAATGATACCAGAACTATCATAATAATTTTTTAAATTGTCTTGTT

ATTATCTTATTAATTTAAAATTTTCATTCTCCATAGGAAATTTAAGTCAA

TCTTTTTGTTCCTTAATTATTAATTAAACAAATAAATTCTTATACATACT

TTTTATGTGTTGATGATATGAATTAATTATACAGGCATGGACAAATGATA

GATTGACATCTGCTCAACATAGGGTTGTAACAACAGGAGACAAAGATAGA

TTCTCTGTTCAATTATTTTCCCTCGTAAATCCAGATTATACTTTGAAGGT

CCCAAAAGAATTAGTGGATGAAGAACACCCTTTAATGTACAAGCCTTTTA

AGATGCCTGAATATAATAAATATCTTATGTTAGGTGCTAAAAATGGATTG

GGTGTCAAGAATTATTGTGGTCTTTAAAAATTTAGTAGCTATGAAAATTT

ATTTATGTATTGTTTTGATGAATAAAATGTATCAGATGGCTGGTTGAATA

CTTTGAATTTATATTTGGATGGTTATTACGTATGATTGCGTAAAGTATTG

TATTGTATTTTATTTTGTTGTGTTGTTTTGTATTGTGTTGCGTTGTATAT

ATTGTTTTGATGAATAAAATATATGAGTG.

In one embodiment, a tomato GAME31 cDNA comprises the nucleic acid sequence of SEQ ID NO: 17. In another embodiment, a tomato GAME31 cDNA consists of the nucleic acid sequence of SEQ ID NO: 17. In another embodiment, SEQ ID NO: 17 comprises or consists of the following nucleic acid sequence:

(SEQ ID NO: 17)
TGACTATAATTGATACTCAATCTGTTGAAATATAATGAACCAATTCTTAT

CAAAACACAGTGGAGTACAAGTAATCACGTTGGTTCCTATGAAATGGTTC

ATCTATTTCCCATTATATATAGGCTACTTATTTCCTCACCTATAAAGTAA

AAAACTTTCTAGTGTTTTCTTCTTTCTTTTGTTTTTTTCTCTTTGCTCAT

ATTCTAAAAATATTTCATCAATGGCATCTATCAAATCAGTTAAAGTTCCT

ACTATAGATTTTTCCAATTATCAAGAGCTAAAACCAAACACTCCACTATG

GGAATCCACAAAAATTCAAGTTTTTGAAGCTTTACAAGAATATGGTTGTT

TTGAAGCAATATATGATAAAGTTTCAAAGGAAATTAGAGAGGAAACATTT

GATATGTCAAAAGAAATATTTGAATTTCCTTTAGAGACTAAAGTGAAAAA

TATCTCAGAAAAACCAATGCATGGCTATATGGGGATGATTCCACAATTGC

CATTGTATGAGAGTTTGTGTATTCCTGATTTGCTTAATCCTCAAAGTCTT

GAAAAATTTTCTAATATCTTTTGGCCTCAGGGTAATCAACATTTCTGCAA

TTTGATAAAATCTTATTCTAATCCACTTGTGGAATTGGATGGGATGTTGA

AAAGGATGATTTCGGAGAATTTGGGATTGAAAAATCACATTGATGAATTA

TTGAATGCCAATTACTTCCTATTTAGATTTACACATTATAAGGGATCATC

AATTGCTAGTGGAGATGAAAATAATAAAGCTGCTGGATTGGGTGGCCACA

CGGATGGTAACTTCTTGACTTTTATATCGCAAAATCAAGTTAATGGATTG

CAAATCAACAAAAATGGAGAATGGATTGATGTGATTATTTCACCAAATTC

TTACGTTGTTTTGGCCGGTGATTCCTCAAAGCTTGGACAAATGGTCGAT

TGCATTCACCTCTCCACAGAGTAACAATGTCCGGACAAAATGATAGACTC

TCCATTCAATTGTTTTCATTATCAAAGCCAGGTCACTTCATCCAGGCACC

AAAAGAACTAGTAGATGAAGAACACCCATTACTCTTCAAGCCATTTGAAA

TTCTTGAATTATTCAAGTATGGTACCACAGAAGCTGGCTATACAGCTCCT

CCAAGTGATCTTTTCAAGATTTATTGTGGTGTTTGATATGCTAATTGTTG

AATTTCCGCTTCAACAAGCAACTTTTCTAATGAGTTTCATCTTGTTTTTT

TAAGTAGTATGCATTTTATGTTTGAATTGTTGCAGTTGGCAATTCATGTT

```
TAATTTGTTTTTGTTTTTTTGAGAAAATATTTCCAATGGGTTTCGTTGGA

AATTCGTCTTGTTTTTTTTTTCAAGTAGTGTACATCTTATTTTTGGATT

GTTGATGTTGAGCGCTAATGTTTAATTTGTTTGTGTTTTGAAGAGGATGA

TTATACTCTTTAAGAGGATTCACCGTAATCTTTTAGTATTATTTG.
```

The start codon (ATG) for SEQ ID NO: 17 starts at nucleotide 221 of SEQ ID NO: 17. The coding sequence present within SEQ ID NO: 17 ends at nucleotide 1186. Therefore, the skilled artisan would recognize that the CDS comprised in SEQ ID NO: 17 comprises nucleotides 221-1186. In one embodiment, the tomato GAME31 CDS comprises the nucleic acid sequence of SEQ ID NO: 59. In another embodiment, the tomato GAME31 CDS consists of the nucleic acid sequence of SEQ ID NO: 59. In another embodiment, SEQ ID NO: 59 comprises or consists of the following nucleic acid sequence:

```
                              (SEQ ID NO: 59)
ATGGCATCTATCAAATCAGTTAAAGTTCCTACTATAGATTTTTCCAATTA

TCAAGAGCTAAAACCAAACACTCCACTATGGGAATCCACAAAAATTCAAG

TTTTTGAAGCTTTACAAGAATATGGTTGTTTTGAAGCAATATATGATAAA

GTTTCAAAGGAAATTAGAGAGGAAACATTTGATATGTCAAAAGAAATATT

TGAATTTCCTTTAGAGACTAAAGTGAAAAATATCTCAGAAAAACCAATGC

ATGGCTATATGGGGATGATTCCACAATTGCCATTGTATGAGAGTTTGTGT

ATTCCTGATTTGCTTAATCCTCAAAGTCTTGAAAAATTTTCTAATATCTT

TTGGCCTCAGGGTAATCAACATTTCTGCAATTTGATAAAATCTTATTCTA

ATCCACTTGTGGAATTGGATGGGATGTTGAAAAGGATGATTTCGGAGAAT

TTGGGATTGAAAAATCACATTGATGAATTATTGAATGCCAATTACTTCCT

ATTTAGATTTACACATTATAAGGGATCATCAATTGCTAGTGGAGATGAAA

ATAATAAAGCTGCTGGATTGGGTGGCCACACGGATGGTAACTTCTTGACT

TTTATATCGCAAAATCAAGTTAATGGATTGCAAATCAACAAAAATGGAGA

ATGGATTGATGTGATTATTTCACCAAATTCTTACGTTGTTTTGGCCGGTG

ATTCCTTCAAAGCTTGGACAAATGGTCGATTGCATTCACCTCTCCACAGA

GTAACAATGTCCGGACAAAATGATAGACTCTCCATTCAATTGTTTTCATT

ATCAAAGCCAGGTCACTTCATCCAGGCACCAAAAGAACTAGTAGATGAAG

AACACCCATTACTCTTCAAGCCATTTGAAATTCTTGAATTATTCAAGTAT

GGTACCACAGAAGCTGGCTATACAGCTCCTCCAAGTGATCTTTTCAAGAT

TTATTGTGGTGTTTGA
```

In one embodiment, a tomato GAME31 cDNA comprises the nucleic acid sequence of SEQ ID NO: 20. In another embodiment, a tomato GAME31 cDNA consists of the nucleic acid sequence of SEQ ID NO: 20. In another embodiment, SEQ ID NO: 20 comprises or consists of the following nucleic acid sequence:

```
                       (SEQ ID NO: 20; SlGAME31-like1)
ATGGCATCTACCAAATTAGTTAAAGTTCCCACAATAGATTTTTCAAATCA

TCAAGATCTAAAACCAAACACTCCACTATGGGAATCCAAAAAAATTCAAG

TTTTTGAAGCTTTGCAAGAATATGGTTGTTTTGAAGCAATTTATGATAAA

GTTCCAAAAGATATTAGAGAGGAAACATTTAGTATTTCAAAAGAAATATT

TGAATTTCCTTTAGAGACTAAATTGAAAAATATTTCAGAAAAACCAACGC

ATGGATATATGGGAATGATTCCACAATTGCCATTGTATGAGAGTTTGTGT

ATTCCTGATTTGCTTAATCCTAAAAGTCTTCAAAGTTTTGCTAATATCTT

TTGGCCTCAGGGTAACCAACATTTCTGGTATGTTTACTTATGTTTTTATT

TCGCCCTAGCAGAAGTGTTCAAAAGTACGACATTAGAAATTCTTAGTGAC

TTAATTGATTGA.
```

In one embodiment, a tomato GAME31 cDNA comprises the nucleic acid sequence of SEQ ID NO: 23. In another embodiment, a tomato GAME31 cDNA consists of the nucleic acid sequence of SEQ ID NO: 23. In another embodiment, SEQ ID NO: 23 comprises or consists of the following nucleic acid sequence:

```
                       (SEQ ID NO: 23; SlGAME31-like2)
TGAGATGTTGAAAAGGATGATTTCGGAGAATTTGGGATTAAAAAATCACA

TTGATGAATTATTGAATGCCAATTACATCCTATTTAGATTTACACAGTAT

AAGGGATCATCAATTGCTAGTGGAGATGAAAATAATAAAGCAGCTGGATT

GGGTGGCCACACAGATGGTAACTTCTTGTCTATTATATCACAAAATGAAG

TTAATGGATTGCAAATCAACAAAAATGGAGAGTGGATTGATGTCAACATT

TCGCCAAATTCTTATGTTGTTTTATCCGGTGATTCCTTCACAGCATGGAC

AAATGGCCGATTGCATTCTCCTGTTCATAGAGTTGAAATGCCCAGAGGAA

GTGATAGATATTCCATTCAATTATTTTCATTATCAAAACCAGGTCACTTC

ATCGAGGCACCAAAAGAAATGGTGGATGAAGAACACCCTTTGCTTTTCAA

GCCATTTGAAATTCTTGGATTACTTGGGTATGGTGCCACAGAAGCTGGCT

ATACAACTCCTCCCAGTGATCTTTTCAAGGCATATTGCGGTGTCTGA.
```

In one embodiment, a tomato GAME31 cDNA comprises the nucleic acid sequence of SEQ ID NO: 26. In another embodiment, a tomato GAME31 cDNA consists of the nucleic acid sequence of SEQ ID NO: 26. In another embodiment, SEQ ID NO: 26 comprises or consists of the following nucleic acid sequence: TGACTAGAAATAGA-CATAAAACCCTGTACTTTTTGACACACATGTAA TAGCACTTTCTCTATCTAATACGCAACTCTTTAT-TAATTTTGCGTAAATTTTGA GCTATTTCCCAT-TATATATAGGCTACTTATTTCCTCACCTCT-TAAGTAAAAAAC TTTCAAGTGTTTCTTCTTTCTTTTATTTCTCTTTGTT-CACATATTCTAAAAATAT TTCATCAATGGCATCTAT-CAAATCAGTTAAAGTTCCTACTATAGATTTTTCCA ATTATCAAGAGCTAAAACCAAACACTCCACTATGG-GAATCCACAAAAATTCA AGTTTTTGAAGCTTTT-CAAGAATATGGTTGTTTTGAAGCAATATATGA-TAAAG TTCCAAATGAAATTAGAGAGGAAACATTTGA-TATGTCAAAAGAAATATTTGA ATTTCCTTTAGA-TACTAAAGTGAAAAATATTTCAGAAAAACCAATG-CATGGAT ATATGGGAATGATTCCACAATTGCCATTGTAT-GAGAGTTTGTGTATTCCTGAT TTGCTTAATCCT-CAAAGTCTTCAAAAT-TTTGCTAATATCTTTTGGCCTCAGGGT AATCAACATTTCTGCAATTTGGTAAAGTCTTAT- TCTAATCCACTTGTGGAATT GGATGAGATTTT-GAAAAGGATGATTTCGGAGAATTTGAGAT-TAAAAATTCAC ATTGATGAATTGTTGAATGCCAATTATTTCCTATTTA-GATTTACACATTACAA GGGATCATCAAT-TACTGGTGGAGATGAGAATAACAAAGTTGCTGGAT-TGGGT GGCCACACAGATGGTAACTTCTTGACTTT-TATATCGCAAAATCAAGTCAATGG ATTGCAAAT-CAACAAAAATGGAGAATGGATTGATGTGAATATTT-CACCAAAT TCTTATGTTGTTTTGGCTGGTGATTCCTT-CAAAGCTTGGACAAATGGTCGATTG CAT-TCTCCTCTTCACAGAGTAACAATGTCCG-GAGAAAATGATAGACTCTCCAT TCAATTATTTTCATTATCAAAACCAGGTCACTT-CATCGAGGCACCAAAAGAAC TAGTGGAT-GAAGAACACCCTTTACTCTTCAAGCCATTTGAAAT-TATTGGATTA TTTGAGTATGGTACCACAGAAGCTGGCTATA-CAGCTCCTCCAAGTGATCTTCT CAAGAGTTAT-TGCGGTGTTTGATATGCTAATTGCGAAT-TTCCGCTTCAGCAAC CAACTTTTCTAATAAGTTTCGTCTGAAAT-TCGTGTTGTTTTAATTATTATGCAT TTTATGTTT-GAATTGTTGTAGTTGGCAATTCATGTTTAAT-TTGTTTGTGTTTTTT TTTTTTCTTTAGTGGAAATGAT (SEQ ID NO: 26; SlGAME31-like3). The start codon (ATG) for SEQ ID NO: 26 starts at nucleotide 217. The coding sequence present within SEQ ID NO: 26 ends at nucleotide 1182. Therefore, the skilled artisan would recognize that the CDS comprised in SEQ ID NO: 26 comprises nucleotides 21-1182.

In another embodiment, an aubergine GAME31 cDNA comprises the nucleic acid sequence of SEQ ID NO: 28. In another embodiment, an aubergine GAME31 cDNA consists of the nucleic acid sequence of SEQ ID NO: 28. In another embodiment, SEQ ID NO: 28 comprises or consists of the following nucleic acid sequence:

(SEQ ID NO: 28)
ATGGGATCTACCAAATCAATTAAAGTTCCCACTATCGATTTTTCCAA

CCATCAAGATCTAAAACCAAACACTCCACAATGGGAATCCACAAAAGATC

AAGTTTTTGAAGCTTTTCAAGAATTTGGTTGTTTTGAAGCAATATATGAT

AAAGTGCCAAATGAAATTAGAAAGGGCATGTTTGATGTTTCAAAAGAAAT

ATTTGAATTTCCCCTAGAGACCAAATTGAAAAACTTATCAGACAAACCAT

TACATGGCTACATGGGGATGATTCCAAACTTGCCTTTGTATGAGAGTTTG

TGTATTCCTGATTTGCTTAATCCTCAAAGTCTTCAAAATTTTGAAAATAT

CTTTTGGCCACATGGAAATCCTGATTTTTGCAATTTGGTAAAATGTTACT

CAAATCCACTTGTGGAATTGGATGAAATGTTGAAGAGGATGATTTTGGAG

AAATTGGGAGTAGAAAATCAGATTGATGAGTTATTGGATCCCAAATATGT

CCTATTTAGATTTACACACTACAAGGGGTCATCACCAACTAATGGAGATA

AAAATACTAAAAGTGAGGGACTAGGTGGCCACACTGATGGTAACTTCTTG

ACTTTTATAGCACAAAATCAAGTAAGTGGATTGCAAATTAATAAAAATGG

AGAGTGGATTGATGTCAACATCTCACCAAATTCTTTTGCTGTTTTGTCTG

CTGATTCCTTCAAAGCATGGACAAATGGTCGATTGCATTCTCCAATTCAC

AGAGTAACAATGGCTGGAGAAAATGATAGATTCTCCATTCAATTATTTTC

ACTATCCAAACCAGGTCACTTCATAGAGGCCCCAAAAGAACTTGTGGATG

AACAACACCCTTTACTCTTCAAACCATATGAAATGCTTGGATTATTTAAG

TATGTTACTTCACAAAGTGGATATGGAGCTCCTGGTGATGCTTTCAAGGC

TTATTGTGGTGTTTGA.

In another embodiment, a potato GAME31 cDNA comprises the nucleic acid sequence of SEQ ID NO: 31. In another embodiment, a potato GAME31 cDNA consists of the nucleic acid sequence of SEQ ID NO: 31. In another embodiment, SEQ ID NO: 31 comprises or consists of the following nucleic acid sequence:

(SEQ ID NO: 31)
ATGGCATCTACCAAAGTTAAGATTCCCACCATAGATTTTTCTAATCTAGA

ACTAAAACCAAACACTCCACTATGGGAATCCACAAAAGTTCAAGTTTTTG

AAGCTTTAAAAGAATATGGTTGTTTTGAAGCAACATATGATAAAATTCCA

AATGAAATTAGAGAGGGTATTTTTGGTATTACAAAAGAAATATTTCAATT

TCCTTTAGAGACCAAAGTGAAAAATTATTCAGATATAACATTACATGGCT

ATGTAGGAATGATTCCACACTTGCCATTTTATGAGAGTTTGTGTATTCCT

GATTTGCTTAATCCTCAAAATGTTGAAACTTTTGCTAATATCTTTTGGCC

TCATGGTAATCCTGATTTCTGCAATTTGGTAAAAGCTTACTCAAATCCAC

TTATGGAATTGGATGAAATGTTGAAAAAGATGATTTTGGAGAATTTGGGA

TTAGAAAATCATATTGATGAATTGCTGGATATTAATTATATGAGATTTAG

ATTTACACATTACAAGGGATCATCAATTATTAGTGGAGATCATGAAAATA

ATATTAAACAAGATGGATTGAATGGCCACACAGATGGTAACTTCTTGACT

TTTATATCACAAAATCAAGTCAATGGTTTGCAAATCAACAAAAATGGAGA

GTGGATTGATGTCAATATTTCACCAAATTCTTATGTTGTTTTGTCTGGTG

ATTCATTCAAAGCATGGACAAATGGTCGATTGCATTCTCCCATCCACAAG

GTAAAAATATTTGGTGAAAGTGATAGATTCTCAATTCAATTATTTTCATT

CTCAAAACCAGGTCACTTTATAAAGGCCCCAAAAGAACTTGTGGATGAAG

AACACCCTTTACTCTTCAAGCCATTTGAAATGGTTGGATTATCTGAGTAT

GTTACTTCCCAAGCTGGCTATGCAGCTCCCAGTGATGCTTTCAAGGCTTA

TTGTGGTCTTTGA.

In another embodiment, a potato GAME31 cDNA comprises the nucleic acid sequence of SEQ ID NO: 34. In another embodiment, a potato GAME31 cDNA consists of the nucleic acid sequence of SEQ ID NO: 34. In another embodiment, SEQ ID NO: 34 comprises or consists of the following nucleic acid sequence:

ATGGCATCTACCAAAGTTACGATTCCCACCATAGATTTTGCGATTCTGA

GCTTAAACCAAACACTCCACAATGGGAATCAACAAAAGTTCAAGTTTTTG

AAGCCTTACAAGAATTTGGTTGTTTTGAAGCAATATATAACAAAGTTCCA

AATGAAATTAGAGAGGGCATGTTTGATACTTTAAAAGAAGTATTTGATTT

TCCACTGCCCAAATTGATAGAATATAGAGAGAAACCCTTTCATATATATG

```
ATGGGCAAATTCCAAGTGTACCACTCTTTGGTAGTGTGTACTCTGCTGAT

TTGGTCCTCCCAAATAGTGTTGAAACATTTGCCAATACCTTTTGGTCTCA

TGGAAACCCTAATTTTAGCAATGTGGCAAAGTCCTACTTCAAGCAACTTA

TGGAATTAAATGACATGGTTAAAAAGATGGTTTTGGAGAGTCTTGGGCTA

AAAAATTACATTGATGAATTCTTGAATTCCAATGTTTATATGTCAAGATT

TACTAATTACAAGGTAATTAAAGGTGAAAATGAGAATAAATCAGGATTAC

CTTCCCACACAGATAGTTCCTACTTGACCATAATTAAACAAAATCAAAAT

GGATTGCAAGTTCTCTACAAAAATGGAGAGTGGATTGAGCTCAATCGTCA

AAATGGACTGCAAGTTCTCTACAAAAATGGAGAGTGGATTGAGCTCAATC

ATACTTCACCAAATTCCTATATTGTTTTATCAGAAGATGTTTTTATGGCA

TGGACAAATGATAGATTGACATCTGCTCAACACAGGGTTGTAACAACAGG

AGACAAAGAAAGATTCTCTATTCAAGTTTTTTCCTTTCCAAATCCAGATT

ACACTGTGAAGGTCCCACAAGAATTAGTGGATGAAGAACACCCTTTAATG

TACAAGCCTTTTAAGATGTCTGAATATAATAAATATATTATGTTAGGTGC

TAAAAATGGATTGGGTGTCAAGAATTATTGTGGTCTTTAA (SEQ ID

NO: 34; StGAME31-like1).
```

In another embodiment, a potato GAME31 cDNA comprises the nucleic acid sequence of SEQ ID NO: 37. In another embodiment, a potato GAME31 cDNA consists of the nucleic acid sequence of SEQ ID NO: 37. In another embodiment, SEQ ID NO: 37 comprises or consists of the following nucleic acid sequence:

```
ATGATTCCACACTTGCCATTTTATGGGAGTTTGTGTATTCCTGATTTGCT

TAATCCTCAAAATGTTGAAACTTTTGCTAATATCTTTTGGCCTCATGGTA

ATCCTGATTTCTGCAATTTGGTAAAAGCTTACTCAAATCCACTTATGGAA

TTGGATGAATTGTTGAAAAGGATGATTTTGGAGAATTTGGGATTAGAAAA

TCATATTGATGAATTGTTGGATCCTAATTATATGAGATTTAGATTTACAC

ATTACAAGGGATCATCAATTATTAGTGGAGATCATGAAAATAATATTAAA

CATGATGGATTGAATGCCACACAGATGGTAGCTTCTTGA (SEQ ID

NO: 37; StGAME31-like2).
```

In another embodiment, a potato GAME31 cDNA comprises the nucleic acid sequence of SEQ ID NO: 40. In another embodiment, a potato GAME31 cDNA consists of the nucleic acid sequence of SEQ ID NO: 40. In another embodiment, SEQ ID NO: 40 comprises or consists of the following nucleic acid sequence:

```
ATGGCATCTACTAAAGGTAAGATTCCCACCATAGATTTTGCAATCTTGAG

CTAAAACCAAACACTCCACAATGGGAATCAACAAAAGTTCAAGTTTTTGAA

GCCTTAAAAGAATTTGGTTGTTTTGAAGCAATATATGACAAAGTTCCAAAT

GAAATTAGAGAGGGCATGTTTGATAATTTAAAAGAAGTATTTGATTTTCCA

TTGTCCAAATTGATAGAATATAGAGAAAAACCCTTTCATATATATGATGGG

AAAATTCCAAGTATACCACTCTATGGTAGTGTGAGCTCTGCTGATTTGGTC

CTCCCAAATAGTGTTGAAACATTTGCCAATACCTTTTGGTCTGATGGAAAC

CCTAACTTTAGGTATGTATTACTTCTTTTAATTATATATAATGTGCTTGGT

ATTATGAAAGTCATTTTTCATTAA (SEQ ID NO: 40; StGAME31- like3).
```

In another embodiment, a potato GAME31 cDNA comprises the nucleic acid sequence of SEQ ID NO: 43. In another embodiment, a potato GAME31 cDNA consists of the nucleic acid sequence of SEQ ID NO: 43. In another embodiment, SEQ ID NO: 43 comprises or consists of the following nucleic acid sequence:

```
ATGGCATCTACCAAAGTTACGATTCCCACCATAGATTTTTGCGATTCTGAG

CTTAAACCAAACACTCCACAATGGGAATCAACAAAAGTTCAAGTTTTTGAA

GCCTTACAAGAATTTGGTTGTTTTGAAGCAATATATAACAAAGTTCCAAAT

GAAATTAGAGAGGGCATGTTTGATACTTTAAAAGAAGTATTTGATTTTCCA

CTGCCCAAATTGATAGAATATAGAGAGAAACCCTTTCATATATATGATGGG

CAAATTCCAAGTGTACCACTCTTTGGTAGTGTGTACTCTGCTGATTTGGTC

CTCCCAAATAGTGTTGAAACATTTGCCAATACCTTTTGGTCTCATGGAAAC

CCTAATTTTAGCAATGTGGCAAAGTCCTACTTCAAGCAACTTATGGAATTG

AATGACATGGTGGAAAAGATGGTTTTGGAGAGTCTTGGGCTAAAAAATTAC

ACTGATGAATTCTTGAATTCCAATGTTTATATGTCAAGATTTACTAATTAC

AAGGTAATTAAAGGTGAAAATGAGAATAAATCAGCATTACCTTCACACACA

GATAGTTCCTACTTGACCATAATTAAACAAAATCAAAATGGATTGCAAGCA

TGGACAAATGATAGATTGACATCTGCTCAACACAGGGTTGTAACAACAGGA

GACAAAGATAGATTCTCTGTTCAATTATTTTCCCTCCTAAATCCAGATTAT

ACTGTGAAGGTCCCAAAAGAATTAGTGGATGAAGAACACCCTTTAATGTAC

AAGCCTTTTAAGATGCCTGAATATAATAAATATCTTATGTTAGGTGCTAAA

AATGGATTGGGTGTCAAGAATTATTGTGGTCTTTAA (SEQ ID

NO: 43; StGAME31-like4).
```

In another embodiment, a potato GAME31 cDNA comprises the nucleic acid sequence of SEQ ID NO: 46. In another embodiment, a potato GAME31 cDNA consists of the nucleic acid sequence of SEQ ID NO: 46. In another embodiment, SEQ ID NO: 46 comprises or consists of the following nucleic acid sequence:

```
ATGATATCTTGTTCTGGGCTAAAAAATTACATTGATGAATTCTTGAATTC

CAATGTTTTTATGTCAAGATTTACTAATTACAGGGTAATTAAAGGTGAAA

ATGAGAATAAATCAGCACTACCTTCCCACACAGATAGTTCCTACTTGACC

ATAATTAAACAAAATCAAAATGGATTGCAAGTTCTCTACAAAAATGGAGA

GTGGATTGAGCTCAATCATACTTCACCAAATTCCTATATTGTTTTATCAG

AAGATGTTTTTATGGCATGGACAAATGATAGATTGACATCTGCTCAACAC

AGGGTTGTAACAACAGGAGACAAAGATAGATTCTCTATTCAAGTTTTTTC

CTTTCCAAATCCAGATTACACTGTGAAGGTCCCACAAGAATTAGTGGATG

AAGAACACCCTTTAATGTTCAAGCCTTTTAAGTTGCCTGAATTTAATAAA
```

-continued

TATATTAAGTTAGGTGCTAAAAATGGACCGGGTCTCAAGAATTATTGTGG

TTTTTAA (SEQ ID NO: 46; StGAME31-like5).

In another embodiment, a potato GAME31 cDNA comprises the nucleic acid sequence of SEQ ID NO: 49. In another embodiment, a potato GAME31 cDNA consists of the nucleic acid sequence of SEQ ID NO: 49. In another embodiment, SEQ ID NO: 49 comprises or consists of the following nucleic acid sequence:

(SEQ ID NO: 49; StGAME31-like6)
ATGGCATCTACCAAAGTTAAGATTCCCACCATAGATTTTTGCAATCTTGA

GCTAAAACCAAACACTCCACAATGGGAATCAACAAAAGTTCAAGTTTTTG

AAGCCTTAAAAGAATTTGGTTGTTTTGAAGCAATATATGACAAAGTTCCA

AATGAAATTAGAGAGGGCATGTTTGATACTTTAAAAGAAGTATTTGATTT

TCCAGTGTCCAAATTGATAGAATATAGAGAAAAACCCCATTTATATGATG

GGCAAATTCCAAGTATACCACTCTATGGTAGTGTGAGCTCTGCTGATTTG

GTCCTCCCAAATAGTGTTGAAACATTTGCCAATACCTTTTGGTCTGATGG

AAACCCTAACTTTAGCAATGTGGCAAAGTCCTACTTCAAGCAACTTATGG

AATTGAATGACATGGTGGAAAAAATGGTTTTGGAGAGTCTTGGGAAAACA

AATTACATTGATGAAATCTTGAATTCCAATGTTTTTGTGTCAAGATTTAC

TAATTACAAGGTAATTAAAGGTGAAGATGAGAATAGATCAGAATTACCTC

CCCACACAGATAGTGGCTACTTGACTATAATTAAACAAAATCAAAATGGA

TTGCAAGTTCTCTACAAAAATGGAGAGTGGATAGAGCTCAATAATACAAC

ACCAAATTCCTATATTGTTTTATCAGCAGATGCTTTCAGGGCATGGACAA

ATGATAGTTTGACATCTGCTGAACACAGAGTAGTAACAACAGGAGACAAA

GATAGACTATCTATTCAATTATTTTCCTTTCCCAAATCAAGATTTTGCTG

TGAAGGCCCCAAAATAATTAGTGGATGA.

In another embodiment, a potato GAME31 cDNA comprises the nucleic acid sequence of SEQ ID NO: 52. In another embodiment, a potato GAME31 cDNA consists of the nucleic acid sequence of SEQ ID NO: 52. In another embodiment, SEQ ID NO: 52 comprises or consists of the following nucleic acid sequence:

(SEQ ID NO: 52; StGAME31-like7)
ATGGATTGCAAGTTCTTCTACAAAAATGGAGAGTGGATTGAGCTCAATCA

TACCTCACCAAATTCCTATATTGTTTTATCAGCAGATGCTCTTATGGCAT

GGACAAATGATAGATTGACATCTGCTCAACATAGGGTTGTAACAACAGGA

GACAAAGATAGATTCTCTGTTCAATTATTTTCCCTCGTAAATCCAGATTA

TACTTTGAAGGTCCCAAAAGAATTAGTGGATGAAGAACACCCTTTAATGT

ACAAGCCTTTTAAGATGCCTGAATATAATAAATATCTTATGTTAGGTGCT

AAAAATGGATTGGGTGTCAAGAATTATTGTGGTCTTTAA.

In one embodiment, a tomato GAME31 polypeptide comprises the amino acid sequence set forth in SEQ ID NO: 18. In another embodiment, a tomato GAME31 polypeptide consists of the amino acid sequence set forth in SEQ ID NO: 18. In another embodiment, SEQ ID NO: 18 comprises or consists of the following amino acid sequence:

(SEQ ID NO: 18)
MASIKSVKVPTIDFSNYQELKPNTPLWESTKIQVFEALQEYGCFEAIYDK

VSKEIREETFDMSKEIFEFPLETKVKNISEKPMHGYMGMIPQLPLYESLC

IPDLLNPQSLEKFSNIFWPQGNQHFCNLIKSYSNPLVELDGMLKRMISEN

LGLKNHIDELLNANYFLFRFTHYKGSSIASGDENNKAAGLGGHTDGNFLT

FISQNQVNGLQINKNGEWIDVIISPNSYVVLAGDSFKAWTNGRLHSPLHR

VTMSGQNDRLSIQLFSLSKPGHFIQAPKELVDEEHPLLFKPFEILELFKY

GTTEAGYTAPPSDLFKIYCGV.

In one embodiment, a tomato GAME31 polypeptide comprises the amino acid sequence set forth in SEQ ID NO: 21. In another embodiment, a tomato GAME31 polypeptide consists of the amino acid sequence set forth in SEQ ID NO: 21. In another embodiment, SEQ ID NO: 21 comprises or consists of the following amino acid sequence:

(SEQ ID NO: 21; SlGAME31-like1)
MASTKLVKVPTIDFSNHQDLKPNTPLWESKKIQVFEALQEYGCFEAIYDK

VPKDIREETFSISKEIFEFPLETKLKNISEKPTHGYMGMIPQLPLYESLC

IPDLLNPKSLQSFANIFWPQGNQHFWYVYLCFYFALAEVFKSTTLEILSD

LID.

In one embodiment, a tomato GAME31 polypeptide comprises the amino acid sequence set forth in SEQ ID NO: 24. In another embodiment, a tomato GAME31 polypeptide consists of the amino acid sequence set forth in SEQ ID NO: 24. In another embodiment, SEQ ID NO: 24 comprises or consists of the following amino acid sequence:

(SEQ ID NO: 24; SlGAME31-like2)
EMLKRMISENLGLKNHIDELLNANYILFRFTQYKGSSIASGDENNKAAGL

GGHTDGNFLSIISQNEVNGLQINKNGEWIDVNISPNSYVVLSGDSFTAWT

NGRLHSPVHRVEMPRGSDRYSIQLFSLSKPGHFIEAPKEMVDEEHPLLFK

PFEILGLLGYGATEAGYTTPPSDLFKAYCGV.

In one embodiment, a tomato GAME31 polypeptide comprises the amino acid sequence set forth in SEQ ID NO: 27. In another embodiment, a tomato GAME31 polypeptide consists of the amino acid sequence set forth in SEQ ID NO: 27. In another embodiment, SEQ ID NO: 27 comprises or consists of the following amino acid sequence:

MASIKSVKVPTIDFSNYQELKPNTPLWESTKIQVFEAFQEYGCFEAIYDK

VPNEIREETFDMSKEIFEFPLDTKVIKNISEKPMHGYMGMIPQLPLYESL

CIPDLLNPQSLQNFANIFWPQGNQHFCNLVKSYSNPLVELDEILKRMISE

NLRLKIHIDELLNANYFLFRFTHYKGSSITGGDENNKVAGLGGHTDGNFL

TFISQNQVNGLQINKNGEWIDVNISPNSYVVLAGDSFKAWTNGRLHSPLH

RVTMSGENDRLSIQLFSLSKPGHFIEAPKELVDEEHPLLFKPFEIIGLFE

YGTTEAGYTAPPSDLLKSYCGV (SEQ ID NO: 27; SlGAME31- like3).

In another embodiment, an aubergine GAME31 polypeptide comprises the amino acid sequence set forth in SEQ ID NO: 29. In another embodiment, an aubergine GAME31 polypeptide consists of the amino acid sequence set forth in SEQ ID NO: 29. In another embodiment, SEQ ID NO: 29 comprises or consists of the following amino acid sequence:

```
                                            (SEQ ID NO: 29)
MGSTKSIKVPTIDFSNHQDLKPNTPQWESTKDQVFEAFQEFGCFEAWD

KVPNEIRKGMFDVSKEIFEFPLETKLKNLSDKPLHGYMGMIPNLPLYESL

CIPDLLNPQSLQNFENIFWPHGNPDFCNLVKCYSNPLVELDEMLKRMILE

KLGVENQIDELLDPKYVLFRFTHYKGSSPTNGDKNTKSEGLGGHTDGNFL

TFIAQNQVSGLQINKNGEWIDVNISPNSFAVLSADSFKAWTNGRLHSPIH

RVTMAGENDRFSIQLFSLSKPGHFIEAPKELVDEQHPLLFKPYEMLGLFK

YVTSQSGYGAPGDAFKAYCGV.
```

In another embodiment, a potato GAME31 polypeptide comprises the amino acid sequence set forth in SEQ ID NO: 32. In another embodiment, a potato GAME31 polypeptide consists of the amino acid sequence set forth in SEQ ID NO: 32. In another embodiment, SEQ ID NO: 32 comprises or consists of the following amino acid sequence:

```
                                            (SEQ ID NO: 32)
MASTKVKIPTIDFSNLELKPNTPLWESTKVQVFEALKEYGCFEATYDKIP

NEIREGIFGITKEIFQFPLETKVKNYSDITLHGYVGMIPHLPFYESLCIP

DLLNPQNVETFANIFWPHGNPDFCNLVKAYSNPLMELDEMLKKMILENLG

LENHIDELLDINYMRFRFTHYKGSSIISGDHENNIKQDGLNGHTDGNFLT

FISQNQVNGLQINKNGEWIDVNISPNSYVVLSGDSFKAWTNGRLHSPIHK

VKIFGESDRFSIQLFSFSKPGHFIKAPKELVDEEHPLLFKPFEMVGLSEY

VTSQAGYAAPSDAFKAYCGL.
```

In another embodiment, a potato GAME31 polypeptide comprises the amino acid sequence set forth in SEQ ID NO: 35 In another embodiment, a potato GAME31 polypeptide consists of the amino acid sequence set forth in SEQ ID NO: 35. In another embodiment, SEQ ID NO: 35 comprises or consists of the following amino acid sequence:

```
MASTKVTIPTIDFCDSELKPNTPQWESTKVQVFEALQEFGCFEAIYNKVP

NEIREGMFDTLKEVFDFPLPKLIEYREKPFHIYDGQIPSVPLFGSVYSAD

LVLPNSVETFANTFWSHGNPNFSNVAKSYFKQLMELNDMVKKMVLESLGL

KNYIDEFLNSNVYMSRFTNYKVIKGENENKSGLPSHTDSSYLTIIKQNQN

GLQVLYKNGEWIELNRQNGLQVLYKNGEWIELNHTSPNSYIVLSEDVFMA

WTNDRLTSAQHRVVTTGDKERFSIQVFSFPNPDYTVKVPQELVDEEHPLM

YKPFKMSEYNKYIMLGAKNGLGVKNYCGL (SEQ ID NO: 35;

StGAME31-like1).
```

In another embodiment, a potato GAME31 polypeptide comprises the amino acid sequence set forth in SEQ ID NO: 38 In another embodiment, a potato GAME31 polypeptide consists of the amino acid sequence set forth in SEQ ID NO: 38. In another embodiment, SEQ ID NO: 38 comprises or consists of the following amino acid sequence:

```
MIPHLPFYGSLCIPDLLNPQNVETFANIFVVPHGNPDFCNLVKAYSNPLM

ELDELLKRMILENLGLENHIDELLDPNYMRFRFTHYKGSSIISGDHENNI

KHDGLNATQMVAS (SEQ ID NO: 38; StGAME31-like2).
```

In another embodiment, a potato GAME31 polypeptide comprises the amino acid sequence set forth in SEQ ID NO: 41. In another embodiment, a potato GAME31 polypeptide consists of the amino acid sequence set forth in SEQ ID NO: 41. In another embodiment, SEQ ID NO: 41 comprises or consists of the following amino acid sequence:

```
MASTKGKIPTIDFCNLELKPNTPQWESTKVQVFEALKEFGCFEAIYDKVP

NEIREGMFDNLKEVFDFPLSKLIEYREKPFHIYDGKIPSIPLYGSVSSAD

LVLPNSVETFANTFWSDGNPNFRYVLLLLITYNVLGINIKVIFH (SEQ

ID NO: 41; StGAME31-like3).
```

In another embodiment, a potato GAME31 polypeptide comprises the amino acid sequence set forth in SEQ ID NO: 44. In another embodiment, a potato GAME31 polypeptide consists of the amino acid sequence set forth in SEQ ID NO: 44. In another embodiment, SEQ ID NO: 44 comprises or consists of the following amino acid sequence:

```
MISCSGLKNYIDEFLNSNVFMSRFTNYRVIKGENENKSALPSHTDSSYLT

IIKQNQNGLQVLYKNGEWIELNHTSPNSYIVLSEDVFMAWTNDRLTSAQH

RVVTTGDKDRFSIQVFSFPNPDYTVKVPQELVDEEHPLMFKPFKLPEFNK

YIKLGAKNGPGLKNYCGF (SEQ ID NO: 44; StGAME31- like4).
```

In another embodiment, a potato GAME31 polypeptide comprises the amino acid sequence set forth in SEQ ID NO: 47. In another embodiment, a potato GAME31 polypeptide consists of the amino acid sequence set forth in SEQ ID NO: 47. In another embodiment, SEQ ID NO: 47 comprises or consists of the following amino acid sequence:

```
MISCSGLKNYIDEFLNSNVFMSRFTNYRVIKGENENKSALPSHTDSSYLT

IIKQNQNGLQVLYKNGEWIELNHTSPNSYIVLSEDVFMAWTNDRLTSAQH

RVVTTGDKDRFSIQVFSFPNPDYTVKVPQELVDEEHPLMFKPFKLPEFNK

YIKLGAKNGPGLKNYCGF (SEQ ID NO: 47; StGAME31- like5).
```

In another embodiment, a potato GAME31 polypeptide comprises the amino acid sequence set forth in SEQ ID NO: 50 In another embodiment, a potato GAME31 polypeptide consists of the amino acid sequence set forth in SEQ ID NO: 50. In another embodiment, SEQ ID NO: 50 comprises or consists of the following amino acid sequence:

```
MASTKVKIPTIDFCNLELKPNTPQWESTKVQVFEALKEFGCFEAIYDKVP

NEIREGMFDTLKEVFDFPVSKLIEYREKPHLYDGQIPSIPLYGSVSSADL

VLPNSVETFANTFWSDGNPNFSNVAKSYFKQLMELNDMVEKMVLESLGKT

NYIDEILNSNVFVSRFTNYKVIKGEDENRSELPPHTDSGYLTIIKQNQNG

LQVLYKNGEWIELNNTTPNSYIVLSADAFRAWTNDSLTSAEHRVVTTGDK
```

-continued
DRLSIQLFSFPKSRFCCEGPKIISG (SEQ ID NO: 50;
StGAME31-like6).

In another embodiment, a potato GAME31 polypeptide comprises the amino acid sequence set forth in SEQ ID NO: 53. In another embodiment, a potato GAME31 polypeptide consists of the amino acid sequence set forth in SEQ ID NO: 53. In another embodiment, SEQ ID NO: 53 comprises or consists of the following amino acid sequence:

MDCKFFYKNGEWIELNHTSPNSYIVLSADALMAWTNDRLTSAQHRVVTTGD
KDRFSVQLFSLVNPDYTLKVPKELVDEEHPLMYKPFKMPEYNKYLMLGAKN
GLGVKNYCGL (SEQ ID NO: 53; StGAME31-like7).

In another embodiment, a 2-oxoglutarate-dependent dioxygenase enzyme (GAME31) comprises the amino acid sequence set forth in any one of SEQ ID NO: 18, SEQ ID NO: 21, SEQ ID NO: 24, SEQ ID NO: 27, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, and SEQ ID NO: 53, or a protein homologue thereof, wherein said protein homologue is at least 80% homologous to any of SEQ ID NO: 18, SEQ ID NO: 21, SEQ ID NO: 24, SEQ ID NO: 27, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, and SEQ ID NO: 53.

In one embodiment, homologues of the GAME31 enzyme comprise a 2-oxoglutarate-dependent dioxygenase enzyme activity. In some embodiments, a homologue also encompasses deletion, insertion, or substitution variants thereof and biologically active polypeptide fragments thereof. In one embodiment, the variant comprises conservative substitutions, or deletions, insertions, or substitutions that do not significantly alter the three dimensional structure of the GAME31 enzyme. In another embodiment, the deletion, insertion, or substitution does not alter the function of interest of the GAME31 enzyme, which in one embodiment wherein said plant is a tomato plant, is a step in the conversion of dehydrotomatine to hydroxy-dehydrotomatine, and a step in the conversion of α-tomatine to hydroxytomatine. In another embodiment, the deletion, insertion, or substitution does not alter the function of interest of the GAME31 enzyme, which in one embodiment wherein said plant is a potato plant, is a step in the conversion of α-solanine to leptinine II and a step in the conversion of α-chaconine to leptinine I. In another embodiment, the deletion, insertion, or substitution does not alter the function of interest of the GAME31 enzyme, which in one embodiment wherein said plant is an aubergine plant, is a step in the conversion of solasonine to hydroxysolasonine and a step in the conversion of α-solamargine to hydroxysolamargine.

In another embodiment, the disclosure includes a homologue of a GAME31 enzyme. In another embodiment, the disclosure includes a homologue of a GAME31 enzyme having a 2-oxoglutarate-dependent dioxygenase enzyme activity. In another embodiment, homologues comprise polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to a GAME31 enzyme as determined using BlastP software of the National Center of Biotechnology Information (NCBI) using default parameters.

In another embodiment, the amino acid sequence of a GAME31 enzyme homologue is at least 70% homologous to a GAME31 amino acid sequence or a peptide thereof, described herein. In another embodiment, the amino acid sequence of a GAME31 enzyme homologue is at least 80% homologous a GAME31 amino acid sequence or a peptide thereof, described herein. In another embodiment, the amino acid sequence of a GAME31 enzyme homologue is at least 90% homologous a GAME31 amino acid sequence or a peptide thereof, described herein. In another embodiment, the amino acid sequence of a GAME31 enzyme homologue is at least 95% homologous a GAME31 amino acid sequence or a peptide thereof, described herein. In another embodiment, the amino acid sequence of a GAME31 enzyme homologue is at least 98% homologous a GAME31 amino acid sequence or a peptide thereof, described herein.

In one embodiment, homologues of GAME31 enzyme are expressed in a plant, wherein said plant comprises a cultivated tomato, a wild tomato, a cultivated potato, a wild potato, or an aubergine plant.

In another embodiment, a 2-oxoglutarate-dependent dioxygenase comprises the amino acid sequence set forth in any one of SEQ ID NO: 18, SEQ ID NO: 21, SEQ ID NO: 24, SEQ ID NO: 27, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, and SEQ ID NO: 53.

In one embodiment, the 2-oxoglutarate-dependent dioxygenase (GAME31) polypeptide is encoded by a gene comprising the nucleotide sequence set forth in any one of SEQ ID NO: 16, SEQ ID NO: 19, SEQ ID NO: 22, SEQ ID NO: 25, SEQ ID NO: 30, SEQ ID NO: 33, SEQ ID NO: 36, SEQ ID NO: 39, SEQ ID NO: 42, SEQ ID NO: 45, SEQ ID NO: 48, and SEQ ID NO: 51, or a gene homologue thereof, wherein said gene homologue is at least 80% homologous to any of SEQ ID NO: 16, SEQ ID NO: 19, SEQ ID NO: 22, SEQ ID NO: 25, SEQ ID NO: 30, SEQ ID NO: 33, SEQ ID NO: 36, SEQ ID NO: 39, SEQ ID NO: 42, SEQ ID NO: 45, SEQ ID NO: 48, and SEQ ID NO: 51. In another embodiment, the 2-oxoglutarate-dependent dioxygenase (GAME31) polypeptide is encoded by a cDNA comprising the nucleotide sequence set forth in any one of SEQ ID NO: 17, SEQ ID NO: 20, SEQ ID NO: 23, SEQ ID NO: 26, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, and SEQ ID NO: 52, or a cDNA homologue thereof, wherein said cDNA homologue is at least 80% homologous to any of SEQ ID NO: 17, SEQ ID NO: 20, SEQ ID NO: 23, SEQ ID NO: 26, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, and SEQ ID NO: 52.

In one embodiment, the 2-oxoglutarate-dependent dioxygenase (GAME31) polypeptide is encoded by a gene comprising the nucleotide sequence set forth in any one of SEQ ID NO: 16, SEQ ID NO: 19, SEQ ID NO: 22, SEQ ID NO: 25, SEQ ID NO: 30, SEQ ID NO: 33, SEQ ID NO: 36, SEQ ID NO: 39, SEQ ID NO: 42, SEQ ID NO: 45, SEQ ID NO: 48, and SEQ ID NO: 51. In another embodiment, the 2-oxoglutarate-dependent dioxygenase (GAME31) polypeptide is encoded by a cDNA comprising the nucleotide sequence set forth in any one of SEQ ID NO: 17, SEQ ID NO: 20, SEQ ID NO: 23, SEQ ID NO: 26, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, and SEQ ID NO: 52.

In one embodiment, the 2-oxoglutarate-dependent dioxygenase (GAME31) polypeptide is encoded by a nucleic acid sequence set forth in any one of SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51 and SEQ ID NO: 52, or a nucleic acid homologue thereof, wherein said homologue is at least 80% homologous to any of SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51 and SEQ ID NO: 52.

In one embodiment, the 2-oxoglutarate-dependent dioxygenase (GAME31) polypeptide is encoded by a nucleic acid sequence set forth in any one of SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51 and SEQ ID NO: 52.

In some embodiment, the 2-oxoglutarate-dependent dioxygenase (GAME31) is encoded by a gene comprising the polynucleotide sequence set forth in any one of SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, or SEQ ID NO: 52, or a nucleic acid sequence having at least 80% identity to any of SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, or SEQ ID NO: 52.

In one embodiment, homologues of a GAME31 gene or a GAME31 cDNA encode a polypeptide comprising a 2-oxoglutarate-dependent dioxygenase enzyme activity. In some embodiments, a homologue also encompasses deletion, insertion, or substitution variants, thereof, and biologically active polynucleotide fragments thereof. In one embodiment, the variant comprises conservative substitutions, or deletions, insertions, or substitutions that do not significantly alter the three dimensional structure of the encoded GAME31 enzyme. In another embodiment, the deletion, insertion, or substitution does not alter the function of interest of the encoded GAME31 enzyme, which in one embodiment wherein said plant is a tomato plant, is a step in the conversion of dehydrotomatine to hydroxy-dehydrotomatine and/or a step in the conversion of α-tomatine to hydroxy tomatine. In another embodiment, the deletion, insertion, or substitution does not alter the function of interest of the encoded GAME31 enzyme, which in another embodiment wherein said plant is a potato plant, is a step in the conversion of α-solanine to leptinine II and/or conversion of α-chaconine to leptinine I. In another embodiment, the deletion, insertion, or substitution does not alter the function of interest of the encoded GAME31 enzyme, which in another embodiment wherein said plant is an aubergine plant, is a step in the conversion of solasonine to hydroxysolasonine and/or the conversion of solamargine to hydroxysolamargine.

In another embodiment, disclosed herein are GAME31 gene homologues. In another embodiment, disclosed herein are GAME31 cDNA homologues. In another embodiment, disclosed herein are GAME31 gene homologues encoding an enzyme having a 2-oxoglutarate-dependent dioxygenase enzyme activity. In another embodiment, the disclosure includes a homologue of a GAME31 cDNA encoding an enzyme having a 2-oxoglutarate-dependent dioxygenase enzyme activity. In another embodiment, homologues comprise a polynucleotide sequence which is at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to a GAME31 gene nucleic acid sequence.

In another embodiment, the nucleic sequence of a GAME31 gene homologue is at least 70% homologous to a GAME31 nucleic acid sequence or a fragment thereof, described herein. In another embodiment, the nucleic sequence of a GAME31 gene homologue is at least 80% homologous to a GAME31 nucleic acid sequence or a fragment thereof, described herein. In another embodiment, the nucleic sequence of a GAME31 gene homologue is at least 90% homologous to a GAME31 nucleic acid sequence or a fragment thereof, described herein. In another embodiment, the nucleic sequence of a GAME31 gene homologue is at least 95% homologous to a GAME31 nucleic acid sequence or a fragment thereof, described herein. In another embodiment, the nucleic sequence of a GAME31 gene homologue is at least 98% homologous to a GAME31 nucleic acid sequence or a fragment thereof, described herein.

In another embodiment, the nucleic sequence of a GAME31 cDNA homologue is at least 70% homologous to a GAME31 nucleic acid sequence or a fragment thereof, described herein. In another embodiment, the nucleic sequence of a GAME31 cDNA homologue is at least 80% homologous to a GAME31 nucleic acid sequence or a fragment thereof, described herein. In another embodiment, the nucleic sequence of a GAME31 cDNA homologue is at least 90% homologous to a GAME31 nucleic acid sequence or a fragment thereof, described herein. In another embodiment, the nucleic sequence of a GAME31 cDNA homologue is at least 95% homologous to a GAME31 nucleic acid sequence or a fragment thereof, described herein. In another embodiment, the nucleic sequence of a GAME31 cDNA homologue is at least 98% homologous to a GAME31 nucleic acid sequence or a fragment thereof, described herein.

In one embodiment, homologues of a GAME31 gene are expressed in a plant, wherein said plant includes a cultivated tomato, a wild tomato, a cultivated potato, a wild potato, a sweet or chili pepper, an aubergine plant, and a bittersweet plant. In one embodiment, homologues of a GAME31 cDNA are expressed in a plant, wherein said plant comprises a cultivated tomato, a wild tomato, a cultivated potato, a wild potato, a sweet or chili pepper, an aubergine plant, and a bittersweet plant.

In one embodiment, a genetically modified plant as disclosed herein comprises a Solanaceae crop plant. A skilled artisan would appreciate that the term "Solanaceae" refers to a family of plants that includes the genus *Solanum*. In some embodiments, a Solanaceae crop plant is selected from the group comprising *Solanum lycopersicum, Solanum pennellii, Solanum tuberosum, Solanum chacoense, Capiscum annuum, Solanum melongena,* and *Solanum dulcamara*. In some embodiments, a Solanaceae crop plant comprises any Solanaceae crop plant that produces a steroidal alkaloid or a glycosylated derivative thereof, or an unsaturated or saturated steroidal saponin or a glycoside derivative thereof, or any combination thereof.

Steroidal alkaloids (SAs), also known as "*Solanum* alkaloids" and the glycosylated derivatives thereof, are common constituents of numerous plants belonging to the Solanaceae family, particularly of the genus *Solanum*. Estimated in the order of 1350 species, *Solanum* is one of the largest genera of flowering plants, representing about a half of the species in the Solanaceae. SAs the glycosylated derivatives thereof have diverse structural composition and biological activity, and they occur in food plants included in the *Solanum* genus, including tomato (*Solanum lycopersicum*), wild-tomato (*Solanum pennellii*), potato (*Solanum tuberosum*), eggplant (*Solanum melongena*), and bittersweet plant (*Solanum dukamara*). In one embodiment, a plant disclosed herein is selected from the *Solanum* genus of plants comprising cultivated tomato (*Solanum lycopersicum*), wild-tomato (*Solanum pennellii*), cultivated potato (*Solanum tuberosum*), wild potato *Solanum chacoense*, eggplant (*Solanum melongena*), and bittersweet plant (*Solanum dulcamara*). In another embodiment, a plant disclosed herein is selected from the family of Solanaceae crop plants comprising a cultivated tomato plant (*Solanum lycopersicum*), a wild-tomato plant (*Solanum pennellii*), a cultivated potato plant (*Solanum tuberosum*), a wild potato plant *Solanum chacoense*, a sweet bell pepper plant (*Capsicum annuum*), a sweet or chili pepper plant (*Capsicum annuum*), an eggplant plant (*Solanum melongena*), and a bittersweet plant (*Solanum dulcamara*).

In one embodiment, an altered expression of said at least one gene comprising GAME25, or GAME31, or a combination thereof, comprises a reduced or inhibited expression of said at least one gene compared to its expression in a corresponding unmodified plant, and wherein said altered content comprises a reduced content of at least one cholesterol derived compound selected from the group comprising a steroidal alkaloid or a glycosylated derivative thereof and an unsaturated or saturated steroidal saponin or a glycoside derivative thereof compared to said corresponding unmodified plant.

In another embodiment, altered expression of said at least one gene is comprises reduced or inhibited expression of said gene. In another embodiment, altered expression of said at least one gene comprises reduced expression of said gene. In another embodiment, altered expression of said at least one gene comprises inhibited expression of said gene.

In another embodiment, altered expression of a GAME25 gene comprises reduced or inhibited expression of the GAME25 gene. In another embodiment, altered expression of said GAME25 gene comprises reduced expression of the GAME25 gene. In another embodiment, altered expression of said GAME25 gene comprises inhibited expression of the GAME25 gene.

In another embodiment, altered expression of a GAME31 gene comprises reduced or inhibited expression of the GAME31 gene. In another embodiment, altered expression of said GAME31 gene comprises reduced expression of the GAME31 gene. In another embodiment, altered expression of said GAME31 gene comprises inhibited expression of the GAME31 gene.

In another embodiment, altered expression of a GAME31 gene and a GAME25 gene comprises reduced or inhibited expression of the GAME31 gene and the GAME25 gene. In another embodiment, altered expression of said GAME31 gene and said GAME25 gene comprises reduced expression of both genes. In another embodiment, altered expression of said GAME31 gene and said GAME25 gene comprises inhibited expression of both genes. In another embodiment, altered expression of said GAME31 gene and said GAME25 gene comprises reduced expression of said GAME31 gene and inhibited expression of said GAME25 gene. Alternatively, in another embodiment, altered expression of said GAME31 gene and said GAME25 gene comprises reduced expression of said I gene and inhibited expression of said GAME31 gene.

In some embodiments, altered expression comprises a reduced or inhibited expression of said GAME25 gene, or GAME31 gene, or a combination thereof compared to its expression in a corresponding unmodified plant; or an increased expression of said GAME25 gene, or GAME31 gene, or a combination thereof compared to its expression in a corresponding unmodified plant; or a combination of reduced or inhibited expression of one of said GAME25 gene or said GAME31 gene, and increased expression the other of said GAME25 gene or said GAME31 gene of compared to their expression in a corresponding unmodified plant and increased expression of.

In one embodiment, gene expression of at least one gene is reduced by at least 5% compared to a corresponding unmodified plant. In another embodiment, gene expression of at least one gene is reduced by at least 10% compared to a corresponding unmodified plant. In another embodiment, gene expression of at least one gene is reduced by at least 15% compared to a corresponding unmodified plant. In another embodiment, gene expression of at least one gene is reduced by at least 20% compared to a corresponding unmodified plant. In another embodiment, gene expression of at least one gene is reduced by at least 25% compared to a corresponding unmodified plant. In another embodiment, gene expression of at least one gene is reduced by at least 30% compared to a corresponding unmodified plant. In another embodiment, gene expression of at least one gene is reduced by at least 35% compared to a corresponding unmodified plant. In another embodiment, gene expression of at least one gene is reduced by at least 40% compared to a corresponding unmodified plant. In another embodiment, gene expression of at least one gene is reduced by at least 45% compared to a corresponding unmodified plant. In another embodiment, gene expression of at least one gene is reduced by at least 50% compared to a corresponding unmodified plant. In another embodiment, gene expression of at least one gene is reduced by at least 55% compared to a corresponding unmodified plant. In another embodiment, gene expression of at least one gene is reduced by at least 60% compared to a corresponding unmodified plant. In another embodiment, gene expression of at least one gene is reduced by at least 65% compared to a corresponding unmodified plant. In another embodiment, gene expression of at least one gene is reduced by at least 70% compared to a corresponding unmodified plant. In another embodiment, gene expression of at least one gene is reduced by at least 75% compared to a corresponding unmodified plant. In another embodiment, gene expression of at least one gene is reduced by at least 80% compared to a corresponding unmodified plant. In another embodiment, gene expression of at least one gene is reduced by at least 85% compared to a corresponding unmodified plant. In another embodiment, gene expression of at least one gene is reduced by at least 90% compared to a corresponding unmodified plant. In another embodiment, gene expression of at least one gene is reduced by at least 95% compared to a corresponding unmodified plant. In another embodiment, gene expression of at least one gene is reduced by at least 98% compared to a corresponding unmodified plant. In another embodiment, gene expression of at least one gene is reduced by 100% compared to a corresponding unmodified plant.

In another embodiment, gene expression of at least two genes is reduced by at least 5% compared to a corresponding unmodified plant. In another embodiment, gene expression of at least two genes is reduced by at least 10% compared to a corresponding unmodified plant. In another embodiment, gene expression of at least two genes is reduced by at least 15% compared to a corresponding unmodified plant. In another embodiment, gene expression of at least two genes is reduced by at least 20% compared to a corresponding unmodified plant. In another embodiment, gene expression of at least two genes is reduced by at least 25% compared to a corresponding unmodified plant. In another embodiment, gene expression of at least two genes is reduced by at least 30% compared to a corresponding unmodified plant. In another embodiment, gene expression of at least two genes is reduced by at least 35% compared to a corresponding unmodified plant. In another embodiment, gene expression of at least two genes is reduced by at least 40% compared to a corresponding unmodified plant. In another embodiment, gene expression of at least two genes is reduced by at least 45% compared to a corresponding unmodified plant. In another embodiment, gene expression of at least two genes is reduced by at least 50% compared to a corresponding unmodified plant. In another embodiment, gene expression of at least two genes is reduced by at least 55% compared to a corresponding unmodified plant. In another embodiment, gene expression of at least two genes is reduced by at least 60% compared to a corresponding unmodified plant. In another embodiment, gene expression of at least two genes is reduced by at least 65% compared to a corresponding unmodified plant. In another embodiment, gene expression of at least two genes is reduced by at least 70% compared to a corresponding unmodified plant. In another embodiment, gene expression of at least two genes is reduced by at least 75% compared to a corresponding unmodified plant. In another embodiment, gene expression of at least two genes is reduced by at least 80% compared to a corresponding unmodified plant. In another embodiment, gene expression of at least two genes is reduced by at least 85% compared to a corresponding unmodified plant. In another embodiment, gene expression of at least two genes is reduced by at least 90% compared to a corresponding unmodified plant. In another embodiment, gene expression of at least two genes is reduced by at least 95% compared to a corresponding unmodified plant. In another embodiment, gene expression of at least two genes is reduced by at least 98% compared to a corresponding unmodified plant. In another embodiment, gene expression of at least two genes is reduced by 100% compared to a corresponding unmodified plant.

It would be appreciated by the skilled artisan that while the gene expression of more than one gene may be altered, the percent change of expression, for example reduction, may not be the same for both genes. That is one gene may have reduced expression of a percent greater than or less than the percent change in a second gene.

Altered gene expression in at least one cell of a genetically modified plant described herein, results in the genetically modified plant having an altered content of at least one steroidal alkaloids or a glycosylated derivative thereof, compared to a corresponding unmodified plant. In one embodiment, an at least one steroidal alkaloid or glycosylated derivative thereof a genetically modified plant described herein comprises a steroidal alkaloid or glycosylated derivative thereof selected from the group comprising solasodine, hydroxyl solasodine, α-solanine, α-chaconine, tomatidine, α-tomatine, hydroxytomatine, acetoxytomatine, acetoxy-hydroxytomatine, tomatidine+4 hexose, esculeoside A, esculeoside A+hexose, esculeoside B, acetoxyesculeoside B, demissidine, demissine, dehydrosolasodine, hydroxy-dehydrotomatine, acetoxy-hydroxy-dehydrotomatine, dehydrotomatidine, dehydroesculeosides, leptinine I, leptinine II, leptine I, leptine II, and hydroxysolamargine, or any derivatives thereof, or any combination thereof. In another embodiment, the altered content of at least one cholesterol derived compound selected from the group comprising a steroidal alkaloid or a glycosylated derivative thereof and an unsaturated or saturated steroidal saponin or a glycoside derivative thereof is altered in a part of the plant selected from the group comprising a peel, a leaf, a young leaf, a mature leaf, a bud, a petal, a root, and an edible part of the plant. In another embodiment, the altered content of at least one cholesterol derived compound selected from the group comprising a steroidal alkaloid or a glycosylated derivative thereof and an unsaturated or saturated steroidal saponin or a glycoside derivative thereof is altered in an edible plant part. In another embodiment, the altered content of at least one cholesterol derived compound selected from the group comprising a steroidal alkaloid or a glycosylated derivative thereof and an unsaturated or saturated steroidal saponin or a glycoside derivative thereof is altered in a non-edible plant part. In another embodiment, the altered content of at least one cholesterol derived compound selected from the group comprising a steroidal alkaloid or a glycosylated derivative thereof and an unsaturated or saturated steroidal saponin or a glycoside derivative thereof is altered in a leaf. In another embodiment, the altered content of at least one cholesterol derived compound selected from the group comprising a steroidal alkaloid or a glycosylated derivative thereof and an unsaturated or saturated steroidal saponin or a glycoside derivative thereof is altered in a young leaf. In another embodiment, the altered content of at least one cholesterol derived compound selected from the group comprising a steroidal alkaloid or a glycosylated derivative thereof and an unsaturated or saturated steroidal saponin or a glycoside derivative thereof is altered in a mature leaf. In another embodiment, the altered content of at least one cholesterol derived compound selected from the group comprising a steroidal alkaloid or a glycosylated derivative thereof and an unsaturated or saturated steroidal saponin or a glycoside derivative thereof is altered in a bud. In another embodiment, the altered content of at least one cholesterol derived compound selected from the group comprising a steroidal alkaloid or a glycosylated derivative thereof and an unsaturated or saturated steroidal saponin or a glycoside derivative thereof is altered in a petal. In another embodiment, the altered content of at least one cholesterol derived compound selected from the group comprising a steroidal alkaloid or a glycosylated derivative thereof and an unsaturated or saturated steroidal saponin or a glycoside derivative thereof is altered in a root. In another embodiment, the genetically modified plant has an altered content of a at least one cholesterol derived compound selected from the group comprising a steroidal alkaloid or a glycosylated derivative thereof and an unsaturated or saturated steroidal saponin or a glycoside derivative thereof is selected from the family of Solanaceae crop plants.

In some embodiments, altered content comprises an appearance of at least one steroidal alkaloid or a glycosylated derivative thereof compared to said corresponding unmodified plant that does not contain said at least one steroidal alkaloid or a glycosylated derivative thereof. In some embodiments, the appearance of at least one steroidal alkaloid or a glycosylated derivative thereof comprises a new appearance of said steroidal alkaloid or a glycosylated derivative thereof, wherein the plant does not naturally produce said steroidal alkaloid or a glycosylated derivative thereof.

In some embodiments, altered content comprises an appearance of at least one unsaturated or saturated steroidal saponin or a glycosylated derivative thereof compared to said corresponding unmodified plant that does not contain said at least one unsaturated or saturated steroidal saponin or a glycosylated derivative thereof. In some embodiments, the altered content comprises an appearance of said at least one unsaturated or saturated steroidal saponin or a glycosylated derivative thereof, wherein the plant does not naturally produce said unsaturated or saturated steroidal saponin or a glycosylated derivative thereof.

In another embodiment, the altered content of at least one steroidal alkaloid or a glycosylated derivative thereof comprises altering the content of an anti-nutritional steroidal alkaloid or glycosylated derivative thereof. In yet another embodiment, the altered content of at least one steroidal alkaloid or a glycosylated derivative thereof comprises altering the content of a steroidal alkaloid or glycosylated derivative thereof that provides plant resistance to pests or pathogens. In still a further embodiment, the altered content of at least one steroidal alkaloid or a glycosylated derivative thereof comprises altering the content of both an anti-nutritional steroidal alkaloid or glycosylated derivative thereof, and a steroidal alkaloid or glycosylated derivative thereof that provides plant resistance to pests or pathogens.

In another embodiment, the altered content of at least one steroidal alkaloid (SA) or a glycosylated derivative thereof (SGA) compared to a corresponding unmodified plant comprises reduction of said SA or SGA content by at least 5% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 10% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 15% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 20% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 25% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 30% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 35% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 40% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 45% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 50% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 55% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 60% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 65% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 70% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 75% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 80% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 85% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 90% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by at least 95% compared to the corresponding unmodified plant. In another embodiment, the altered content of at least one steroidal alkaloid (SA) or a glycosylated derivative thereof (SGA) compared to a corresponding unmodified plant comprises reduction of said SA or SGA content by 100% compared to the corresponding unmodified plant.

In some embodiments, the altered content of at least one cholesterol derived compound selected from the group comprising a steroidal alkaloid or a glycosylated derivative thereof and an unsaturated or saturated steroidal saponin or a glycoside derivative thereof comprises
  a reduced content of at least one steroidal alkaloid or a glycosylated derivative thereof compared to said corresponding unmodified plant, or
  an increased content of at least one steroidal alkaloid or a glycosylated derivative thereof compared to said corresponding unmodified plant, or
  a reduced content of at least one unsaturated or saturated steroidal saponin or a glycosylated derivative thereof compared to said corresponding unmodified plant, or
  an increased content of at least one unsaturated or saturated steroidal saponin or a glycosylated derivative thereof compared to said corresponding unmodified plant, or
  a combination of a reduced content of at least one steroidal alkaloid or a glycosylated derivative thereof, and an increased content of at least one steroidal alkaloid or a glycosylated derivative thereof,
  or any combination thereof,
compared to said corresponding unmodified plant.

In some embodiments, the reduced content of at least one steroidal alkaloid or a glycosylated derivative thereof comprises reduced content of at least one anti-nutritional steroidal alkaloid or a glycosylated derivative thereof, or reduced content of at least one toxic steroidal alkaloid or a glycosylated derivative thereof, or a combination thereof. In some embodiments, the increased content results in increased plant resistance to at least one plant pathogen, pest, or predator, or any combination thereof, and optionally generates precursor molecules for steroidal alkaloid molecules that provide resistance to at least one plant pathogen, pest, or predator, or any combination thereof.

In some embodiments, an altered steroidal alkaloid or a glycosylated derivative thereof is selected from the group comprising tomatidine, α-tomatine, α-tomatine isomer (1 and 2), α-tomatine isomer 1, α-tomatine isomer 2, hydroxytomatine, acetoxytomatine, dehydrotomatidine, dehydrotomatine, dehydrotomatine isomer 1, dehydrotomatine+4-hexose, acetoxy-hydroxytomatine, acetoxy-hydroxy-dehydrotomatine, tomatidine+4 hexose, esculeoside A, esculeoside A+hexose, esculeoside B, acetoxyesculeoside B, demissidine, demissine, dehydrosolasodine, hydroxy-dehydrotomatine, acetoxy-hydroxy-dehydrotomatine, dehydroesculeosides, dehydroesculeoside A, dehydroesculeoside A+hexose, leptinine I, leptinine II, leptine I, leptine II, soladulcidine, β-soladulcine, soladulcine A, solanidine, α-solanine, α-chaconine, solasoidine, α-solasonine, α-solamargine, hydroxysolasonine, and hydroxysolamargine, or any derivatives thereof, or any combination thereof.

In some embodiments, an altered unsaturated or saturated steroidal saponin or a glycosylated derivative thereof is selected from the group comprising dioscin, diosgenin, parillin, and sarasapogenin.

In some embodiments, an altered unsaturated or saturated steroidal saponin or a glycosylated derivative thereof is selected from the group comprising aescin, araloside A, astragaloside, bacopaside, bacoside, bacoside A, chaconine, charantin, daucosterol, esculeoside A, ginsenoside, glycyrrhizin, α-hederin, holothurin, momordicine, momordin, osladin, protodioscin, pseudoginsenoside F11, QS21, solanine, triterpenoid saponin, and ziziphin.

In some embodiments, the reduced content of at least one steroidal alkaloid or a glycosylated derivative thereof comprises reduced content of at least one anti-nutritional steroidal alkaloid or a glycosylated derivative thereof. In some embodiments, an anti-nutritional steroidal alkaloid or a glycosylated derivative thereof comprises a steroidal alkaloid or glycosylated derivative endogenous to the plant.

In some embodiments, an anti-nutritional steroidal alkaloid or a glycosylated derivative thereof comprises anti-nutritional properties towards a mammal. In some embodiments, an anti-nutritional steroidal alkaloid or a glycosylated derivative thereof comprises anti-nutritional properties towards a human subject. In some embodiments, an anti-nutritional steroidal alkaloid or a glycosylated derivative thereof comprises anti-nutritional properties towards a farm animal. In some embodiments, an anti-nutritional steroidal alkaloid or a glycosylated derivative thereof comprises anti-nutritional properties towards a domesticated animal A skilled artisan would appreciate that an anti-nutritional steroidal alkaloid, or a glycosylated derivative may encompass lethal toxins or compounds that disrupt digestion and nutrient absorption, or any combination thereof. In another embodiment, an anti-nutritional steroidal alkaloid or a glycosylated derivative comprises a toxin. In some embodiments, the reduced content of at least one steroidal alkaloid or a glycosylated derivative thereof comprises reduced content of at least one toxic steroidal alkaloid or a glycosylated derivative thereof.

In another embodiment, the altered content of at least one steroidal alkaloid (SA) or a glycosylated derivative thereof (SGA) compared to a corresponding unmodified plant comprises increase of said SA or SGA content by at least 5% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 10% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 15% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 20% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 25% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 30% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 35% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 40% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 45% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 50% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 55% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 60% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 65% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 70% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 75% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 80% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 85% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 90% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by at least 95% compared to the corresponding unmodified plant. In another embodiment, the altered content of at least one steroidal alkaloid (SA) or a glycosylated derivative thereof (SGA) compared to a corresponding unmodified plant comprises increase of said SA or SGA content by 100% compared to the corresponding unmodified plant.

In another embodiment, the altered content of at least one steroidal alkaloid (SA) or a glycosylated derivative thereof (SGA) comprises increased content of at least one steroidal alkaloid or glycosylated derivative thereof that provides resistance to a plant pathogen, pest, or predator compared to a corresponding unmodified plant.

In another embodiment, the altered content of at least one steroidal alkaloid (SA) or a glycosylated derivative thereof (SGA) comprises increased content of at least one precursor molecule for at least steroidal alkaloid or glycosylated derivative thereof that provides resistance to a plant pathogen, pest, or predator compared to a corresponding unmodified plant. In another embodiment the content of said at least one precursor is increased by at least 5% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 10% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 15% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 20% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 25% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 30% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 35% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 40% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 45% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 50% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 55% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 60% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 65% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 70% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 75% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 80% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 85% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 90% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by at least 95% compared to the corresponding unmodified plant. In another embodiment, the altered content of at least one precursor steroidal alkaloid (SA) or a glycosylated derivative thereof (SGA) compared to a corresponding unmodified plant comprises increase of said precursor SA or SGA content by 100% compared to the corresponding unmodified plant.

A skilled artisan would appreciate that the terms "plant pathogen" or "plant predator" or "plant pest" may encompass any organism that can infect and cause harm to a plant or any part thereof. In some embodiments, a plant can be harmed by an inhibition or slowing of the growth of a plant, by damage to a tissue or tissues of a plant, by a weakening of the defense mechanism of a plant, by a reduction in the resistance of a plant to abiotic stresses, by a premature death of the plant, and the like. Plant pathogens, pests, and or predators include, but are not limited to insects, fungi, oomycetes, viruses, and bacteria.

In another embodiment, a genetically modified potato plant comprises increased content of at least one steroidal alkaloid (SA) or a glycosylated derivative thereof (SGA) compared to a corresponding unmodified plant, wherein said SA or SGA is selected from the group comprising leptinine I, leptinine II, leptine I, or leptine II, or any combination thereof. In another embodiment, a genetically modified potato plant comprises increased content of at least one steroidal alkaloid (SA) or a glycosylated derivative thereof (SGA) compared to a corresponding unmodified plant, wherein said SA or SGA comprises a precursor of a compound selected from the group comprising leptinine I, leptinine II, leptine I, or leptine II, or any combination thereof. In some embodiments, a genetically modified potato plant comprises an altered content of at least one steroidal alkaloid (SA) or a glycosylated derivative thereof (SGA) compared to a corresponding unmodified plant, wherein said SA or SGA is selected from the group comprising α-solanine, α-chaconine, leptinine I, leptinine II, leptine I, and leptine II, or any combination thereof.

In one embodiment, disclosed herein are methods of enhancing the content of at least one cholesterol derived compound selected from the group comprising a steroidal alkaloid or a glycosylated derivative thereof and an unsaturated or saturated steroidal saponin or a glycoside derivative thereof in a plant, comprising transforming at least one plant cell within said plant with a nucleic acid sequence operably linked to a 2-oxoglutarate-dependent dioxygenase gene (GAME31), wherein said nucleic acid sequence operably linked to a GAME31 gene results in overexpression of said GAME31 gene, thereby producing a plant with an enhanced content of said at least one cholesterol derived compound selected from the group comprising a steroidal alkaloid or a glycosylated derivative thereof and an unsaturated or saturated steroidal saponin or a glycoside derivative thereof compared to a corresponding non-transformed plant. A non-limiting example of a nucleic acid sequence that could be operably linked to a GAME31 gene to achieve overexpression would be a 35S promotor. In another embodiment, an at least one steroidal alkaloid or a glycosylated derivative thereof comprises a leptin or a derivative thereof, or leptinine or a derivative thereof, or any combination thereof. In another embodiment, the increase of a leptin or a derivative thereof, or leptinine or a derivative thereof, or any combination thereof provides resistance to at least one plant pathogen, pest, or predator.

In some embodiments, a genetically modified plant comprising increased expression of GAME25 in at least one cell, comprises increased saturated steroidal alkaloids or steroidal glycoalkaloids, or derivatives thereof. In some embodiments, a genetically modified plant comprising increased expression of GAME25 in at least one cell, comprises decreased unsaturated steroidal alkaloids or steroidal glycoalkaloids, or derivatives thereof. In some embodiments, a genetically modified plant comprising increased expression of GAME25 in at least one cell, comprises increased saturated steroidal alkaloids or steroidal glycoalkaloids, or derivatives thereof, wherein said change in saturation is at a C5,C6 bond. In some embodiments, a genetically modified plant comprising increased expression of GAME25 in at least one cell, comprises decreased unsaturated steroidal alkaloids or steroidal glycoalkaloids, or derivatives thereof, wherein said change in saturation is at a C5,C6 bond.

In some embodiments, said increased SA, or SGA, or derivatives thereof occurs in a fruit. In some embodiments, the increased SA, or SGA, or derivatives thereof, occurs in a green fruit, a breaker fruit, a turning fruit, a pink fruit, a light red fruit, or a red fruit, or a combination thereof. In some embodiments, said decreased SA, or SGA, or derivatives thereof occurs in a fruit. In some embodiments, the decreased SA, or SGA, or derivatives thereof, occurs in a green fruit, a breaker fruit, a turning fruit, a pink fruit, a light red fruit, or a red fruit, or a combination thereof.

In some embodiments, a genetically modified plant comprising increased expression of GAME25 in at least one cell, comprises increased unsaturated or saturated steroidal saponins or a glycoside derivative thereof.

In some embodiments, a genetically modified tomato plant comprising increased expression of GAME25 in at least one cell, comprises increased saturated steroidal alkaloids or steroidal glycoalkaloids, or derivatives thereof in said at least one cell, said SA or SGA comprising increased α-tomatine, or hydroxytomatine, or acetoxytomatine, or α-tomatine isomers (2), or acetoxy-hydroxytomatine, or esculeosides, or lycoperosides, or derivatives thereof, or any combination thereof, compared to a non-modified tomato plant. In some embodiments, a genetically modified tomato plant comprising increased expression of GAME25 in at least one cell, comprises decreased unsaturated steroidal alkaloids or steroidal glycoalkaloids, or derivatives thereof, said SA or SGA comprising dehydrotomatine, or hydroxy-dehydrotomatine, or acetoxy-dehydrotomatine, or acetoxy-hydroxy-dehydrotomatine, or dehydroesculeosides, or dehydrolycoperosides, or any derivatives thereof, or any combination thereof, compared to a non-modified tomato plant.

A skilled artisan would appreciate that a genetically modified plant comprising a GAME25 enzyme having increased biological activity in at least one cell, would similarly comprises increased saturated steroidal alkaloids or steroidal glycoalkaloids, or derivatives thereof, compared to a non-modified plant. Similarly, a genetically modified plant comprising a GAME25 enzyme having increased biological activity in at least one cell, would similarly comprise decreased unsaturated steroidal alkaloids or steroidal glycoalkaloids, or derivatives thereof, compared to a non-modified plant.

In a further embodiment, the altered content of at least one steroidal alkaloid (SA) or a glycosylated derivative thereof (SGA) compared to a corresponding unmodified plant comprises an increase in at least one SA or SGA, and a reduction in at least one other SA or SGA, wherein the percent increase or reduction of said SAs or SGAs may independently be increased or reduced by different percentages. Alternatively, in another embodiment, the altered content of at least one steroidal alkaloid (SA) or a glycosylated derivative thereof (SGA) compared to a corresponding unmodified plant comprises an increase in at least one SA or SGA, and a reduction in at least one other SA or SGA, wherein the percent increase or reduction of said SAs or SGAs may be equal to equivalent percent increase and decrease. In another embodiment, the altered content of at least one SA or SGA comprises altered contented or multiple SA or SGA compounds, wherein the number of SA or SGA compounds increased or reduced is not equivalent, e.g., decrease of two SA or SGA compounds and increase of one SA or SGA compound. One of ordinary skill in the art would appreciate that there are many possible combinations of increased and/or decreased SA or SGA compounds, wherein each comprises an embodiment herein.

According to certain embodiments, a genetically modified plant described herein, comprises non-toxic amount of at least one steroidal alkaloid or a glycosylated derivative thereof. A skilled artisan would recognize that the term "non-toxic amount" encompasses less than 200 mg of anti-nutritional steroidal; alkaloids or glycoalkaloids per kilogram fresh weight of an edible plant part. According to certain embodiments, the genetically modified plant comprises non-detectable amount of anti-nutritional steroidal alkaloid or a glycosylated derivative thereof.

In another embodiment, a genetically modified plant comprises a Solanaceae crop plant and said altered content comprises reduction of at least one steroidal alkaloid or glycosylated derivative thereof selected from the group comprising solanidine, solasodine hydroxy solasodine, α-solanine, α-chaconine, tomatidine, α-tomatine, hydroxytomatine, acetoxytomatine, acetoxy-hydroxytomatine, tomatidine+4 hexose, esculeosides, esculeoside A, esculeoside A+hexose, esculeoside B, acetoxyesculeoside B, demissidine, demissine, dehydrosolasodine, dehydrotomatidine, hydroxy-dehydrotomatine, acetoxy-dehydrotomatine, acetoxy-hydroxy-dehydrotomatine, dehydroesculeosides, leptinine I, leptinine II, leptine I, leptine II, lycoperosides, and hydroxysolamargine, or any derivatives thereof, or any combination thereof.

In one embodiment, disclosed herein is a method of producing beneficial steroidal derivatives, said method comprising the steps of: incubating a recombinant GAME25 enzyme, as disclosed herein, or GAME31 enzyme, as disclosed herein, or a combination thereof with selected precursor molecules under biosynthetic conditions; and collecting and isolating the steroidal derivatives from the biosynthetic medium. In another embodiment, the recombinant GAME25 enzyme or GAME31 enzyme or the combination thereof are expressed in a microbial cell or an insect cell, and wherein said incubating comprises incubating said cell in media comprising necessary precursor molecules. In some embodiments, said beneficial steroidal derivatives comprise precursors of a steroidal alkaloid or glycosylated derivative thereof. In some embodiments, a beneficial steroidal derivative is selected from the group comprising demissidine, soladelucidine, leptin, leptinine 1, and leptinine 2.

In some embodiments, disclosed herein are uses of a recombinant protein disclosed herein having the amino acid sequence set forth in SEQ ID NO: 3, SEQ ID NO: 12, or SEQ ID NO: 15, or a protein homologue thereof, wherein said protein homolog is at least 50% homologous to any of SEQ ID NO: 3, SEQ ID NO: 12, or SEQ ID NO: 15 and has the same catalytic function as the protein set forth in SEQ ID NO: 3, SEQ ID NO: 12, or SEQ ID NO: 15, for the production of a cholesterol derived compound selected from the group comprising a steroidal alkaloid or a glycosylated derivative thereof and an unsaturated or saturated steroidal saponin or a glycoside derivative thereof or a biosynthetic product thereof. In some embodiment, disclosed herein are uses of a recombinant protein having the amino acid sequence set forth in SEQ ID NO: 18, SEQ ID NO: 21, SEQ ID NO: 24, SEQ ID NO: 27, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50 or SEQ ID NO: 53, or a protein homologue thereof, wherein said protein homolog is at least 50% homologous to any of SEQ ID NO: 18, SEQ ID NO: 21, SEQ ID NO: 24, SEQ ID NO: 27, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50 or SEQ ID NO: 53 and has the same catalytic function as the protein set forth in SEQ ID NO: 18, SEQ ID NO: 21, SEQ ID NO: 24, SEQ ID NO: 27, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50 or SEQ ID NO: 53, for the production of a cholesterol derived compound selected from the group comprising a steroidal alkaloid or a glycosylated derivative thereof, an unsaturated or saturated steroidal saponin or a glycoside derivative thereof, or a hydroxylated derivative thereof, or a biosynthetic product thereof. In some embodiments, uses disclosed herein are in vitro uses.

In some embodiments, disclosed herein are uses of a nucleic acid sequence encoding a 3-β-hydroxysteroid dehydrogenase/isomerase (GAME25) enzyme, said nucleic acid comprising the sequence set forth in SEQ ID NO: 1, SEQ ID NO: 2, SEQ ID NO: 11, SEQ ID NO: 13, or SEQ ID NO: 14, or a nucleic acid sequence having a sequence which is at least 50% identical to SEQ ID NO: 1, SEQ ID NO: 2, SEQ ID NO: 11, SEQ ID NO: 13, or SEQ ID NO: 14, wherein said encoded enzyme has the same catalytic function as the protein of SEQ ID NO:1, SEQ ID NO: 2, SEQ ID NO: 11, SEQ ID NO: 13, or SEQ ID NO: 14, for the production of a recombinant cholesterol derived compound selected from the group comprising a steroidal alkaloid or a glycosylated derivative thereof and an unsaturated or saturated steroidal saponin or a glycoside derivative thereof. In some embodiments, disclosed herein are uses of a nucleic acid sequence encoding a 3-β-hydroxysteroid dehydrogenase/isomerase (GAME25) enzyme, said nucleic acid comprising the sequence set forth in SEQ ID NO: 1, SEQ ID NO: 2, SEQ ID NO: 11, SEQ ID NO: 13, or SEQ ID NO: 14, or a nucleic acid sequence having a sequence which is at least 50% identical to SEQ ID NO: 1, SEQ ID NO: 2, SEQ ID NO: 11, SEQ ID NO: 13, or SEQ ID NO: 14, wherein said encoded enzyme has the same catalytic function as the protein of SEQ ID NO: 1, SEQ ID NO: 2, SEQ ID NO: 11, SEQ ID NO: 13, or SEQ ID NO: 14, for the production of a recombinant cell capable of biotransformation of a cholesterol derived compound selected from the group comprising a steroidal alkaloid or a glycosylated derivative thereof and an unsaturated or saturated steroidal saponin or a glycoside derivative thereof. In one embodiment, a use for production of a recombinant cholesterol derived compound selected from the group comprising a steroidal alkaloid or a glycosylated derivative thereof and an unsaturated or saturated steroidal saponin or a glycoside derivative thereof comprises an in vitro use. In one embodiment, a use for production of a recombinant cholesterol derived compound selected from the group comprising a steroidal alkaloid or a glycosylated derivative thereof and an unsaturated or saturated steroidal saponin or a glycoside derivative thereof comprises an in vivo use.

In some embodiments, uses disclosed herein comprise use of a nucleic acid sequence encoding a 2-oxoglutarate-dependent dioxygenase (GAME31) enzyme, said nucleic acid comprising the sequence set forth in SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, and SEQ ID NO: 52 or a nucleic acid sequence having a sequence which is at least 50% identical to SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, and SEQ ID NO: 52, wherein said encoded enzyme has the same catalytic function as the protein of SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, and SEQ ID NO: 52, for the production of a recombinant cholesterol derived compound selected from the group comprising a steroidal alkaloid or a glycosylated derivative thereof and an unsaturated or saturated steroidal saponin or a glycoside derivative thereof. In some embodiments, uses disclosed herein comprise use of a nucleic acid sequence encoding a 2-oxoglutarate-dependent dioxygenase (GAME31) enzyme, said nucleic acid comprising the sequence set forth in SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, and SEQ ID NO: 52 or a nucleic acid sequence having a sequence which is at least 50% identical to SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, and SEQ ID NO: 52, wherein said encoded enzyme has the same catalytic function as the protein of SEQ ID NO: 16, SEQ ID NO: 17, SEQ ID NO: 19, SEQ ID NO: 20, SEQ ID NO: 22, SEQ ID NO: 23, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, and SEQ ID NO: 52, for the production of a recombinant cell capable of biotransformation of a cholesterol derived compound selected from the group comprising a steroidal alkaloid or a glycosylated derivative thereof and an unsaturated or saturated steroidal saponin or a glycoside derivative thereof. In one embodiment, a use for production of a recombinant. In one embodiment, a use for production of a recombinant cholesterol derived compound selected from the group comprising a steroidal alkaloid or a glycosylated derivative thereof and an unsaturated or saturated steroidal saponin or a glycoside derivative thereof comprises an in vitro use. In one embodiment, a use for production of a recombinant cholesterol derived compound selected from the group comprising a steroidal alkaloid or a glycosylated derivative thereof and an unsaturated or saturated steroidal saponin or a glycoside derivative thereof comprises an in vivo use.

In another embodiment, a genetically modified plant comprises a Solanaceae crop plant and said altered content comprises increase of at least one steroidal alkaloid or glycosylated derivative thereof selected from the group comprising hydroxy solasodine, dehydrotomatine or an isomer thereof, hydroxy-dehydrotomatine, acetoxy-dehydrotomatine, acetoxy-hydroxy-dehydrotomatine, dehydrotomatidine+4 hexose, dehydroesculeoside A, dehydroesculeoside A+hexose, solanidine, α-solanine, α-chaconine, leptinine I, leptinine II, leptine I, leptine II, solasodine, α-solasonine, α-solamargine, hydroxysolasonine, and hydroxysolamargine, or any derivatives thereof, or any combination thereof.

In another embodiment, said Solanaceae crop plant comprises a tomato plant, said altered expression comprises altered expression of GAME25, and said altered content comprises reduction of at least tomatidine and α-tomatine, or derivatives thereof compared to a corresponding non-genetically modified plant. In another embodiment, said Solanaceae crop plant comprises a tomato plant, said altered expression comprises altered expression of GAME25, and said altered content comprises increase of at least dehydrotomatidine or derivatives thereof compared to a corresponding non-genetically modified plant. In another embodiment, said Solanaceae crop plant comprises a tomato plant, said altered expression comprises altered expression of GAME25, and said altered content comprises reduction of at least tomatidine and α-tomatine, or derivatives thereof compared to a corresponding non-genetically modified plant increase of at least dehydrotomatidine or derivatives thereof compared to a corresponding non-genetically modified plant.

In another embodiment, said Solanaceae crop plant comprises a potato plant, said altered expression comprises altered expression of GAME25, and said altered content comprises reduction of at least demissidine or derivatives thereof compared to a corresponding non-genetically modified plant. In another embodiment, said Solanaceae crop plant comprises a potato plant, said altered expression comprises altered expression of GAME25, and said altered content comprises increase of at least solanidine or derivatives thereof compared to a corresponding non-genetically modified plant. In another embodiment, said Solanaceae crop plant comprises a potato plant, said altered expression comprises altered expression of GAME25, and said altered content comprises reduction of at least demissidine or derivatives thereof compared to a corresponding non-genetically modified plant and increase of at least solanidine or derivatives thereof compared to a corresponding non-genetically modified plant.

In another embodiment, said Solanaceae crop plant comprises an aubergine plant, said altered expression comprises altered expression of GAME25, and said altered content comprises reduction of at least dihydrosolasodine or derivatives thereof compared to a corresponding non-genetically modified plant. In another embodiment, said Solanaceae crop plant comprises an aubergine plant, said altered expression comprises altered expression of GAME25, and said altered content comprises increase of at least solasoidine or derivatives thereof compared to a corresponding non-genetically modified plant. In another embodiment, said Solanaceae crop plant comprises an aubergine plant, said altered expression comprises altered expression of GAME25, and said altered content comprises reduction of at least dihydrosolasodine or derivatives thereof compared to a corresponding non-genetically modified plant and increase of at least solasoidine or derivatives thereof compared to a corresponding non-genetically modified plant.

In another embodiment, said Solanaceae crop plant comprises a tomato plant, said altered expression comprises altered expression of GAME31, and said altered content comprises reduction of at least hydroxy-dehydrotomatine, or hydroxytomatine, or any combination thereof, or derivatives thereof, compared to a corresponding non-genetically modified plant. In another embodiment, said Solanaceae crop plant comprises a tomato plant, said altered expression comprises altered expression of GAME31, and said altered content comprises increase of at least dehydrotomatine, or α-tomatine, or any combination thereof, or derivatives thereof compared to a corresponding non-genetically modified plant. In another embodiment, said Solanaceae crop plant comprises a tomato plant, said altered expression comprises altered expression of GAME31, and said altered content comprises reduction of at least hydroxy-dehydrotomatine, or hydroxytomatine, or any combination thereof, or derivatives thereof, compared to a corresponding non-genetically modified plant and increase of at least dehydrotomatine, or α-tomatine, or any combination thereof, or derivatives thereof compared to a corresponding non-genetically modified plant.

In another embodiment, said Solanaceae crop plant comprises a potato plant, said altered expression comprises altered expression of GAME31, and said altered content comprises reduction of at least leptinine II, leptinine I, or derivatives thereof or any combination thereof, compared to a corresponding non-genetically modified plant. In another embodiment, said Solanaceae crop plant comprises a potato plant, said altered expression comprises altered expression of GAME31, and said altered content comprises increase of at least α-solanine, α-chaconine, or derivatives thereof, or any combination thereof, compared to a corresponding non-genetically modified plant. In another embodiment, said Solanaceae crop plant comprises a potato plant, said altered expression comprises altered expression of GAME31, and said altered content comprises reduction of at least leptinine II, leptinine I, or derivatives thereof or any combination thereof, compared to a corresponding non-genetically modified plant and increase of at least α-solanine, α-chaconine, or derivatives thereof, or any combination thereof, compared to a corresponding non-genetically modified plant.

In another embodiment, said Solanaceae crop plant comprises an aubergine plant, said altered expression comprises altered expression of GAME31, and said altered content comprises reduction of at least hydroxysolasonine, hydroxysolamargine, or derivatives thereof, or any combination thereof compared to a corresponding non-genetically modified plant. In another embodiment, said Solanaceae crop plant comprises an aubergine plant, said altered expression comprises altered expression of GAME31, and said altered content comprises increase of at least solasonine, solamargine, or derivatives thereof, or any combination thereof compared to a corresponding non-genetically modified plant. In another embodiment, said Solanaceae crop plant comprises an aubergine plant, said altered expression comprises altered expression of GAME31, and said altered content comprises reduction of at least hydroxysolasonine, hydroxysolamargine, or derivatives thereof, or any combination thereof compared to a corresponding non-genetically modified plant and increase of at least solasonine, solamargine, or derivatives thereof, or any combination thereof compared to a corresponding non-genetically modified plant.

While being exemplified in a genetically modified plant, the disclosure herein may further enable manipulating the synthesis of steroidal alkaloids or glycosylated derivatives thereof in any organism naturally capable of steroidal alkaloid synthesis. Thus, according in another embodiment, a genetically modified organism comprising at least one cell having altered expression of at least one gene selected from the group comprising a gene encoding a 3-β-hydroxysteroid dehydrogenase/isomerase (GAME25) and a gene encoding 2-oxoglutarate-dependent dioxygenase (GAME31), or a combination thereof compared to an unmodified organism, wherein the genetically modified organism has an altered content of at least one compound selected from steroidal alkaloids and glycosylated derivatives thereof compared to a corresponding unmodified organism.

Down-regulation or inhibition of the gene expression can be affected on the genomic and/or the transcript level using a variety of molecules that interfere with transcription and/or translation (e.g., antisense, siRNA, Ribozyme, or DNAzyme), or on the protein level using, e.g., antagonists, enzymes that cleave the polypeptide, and the like. One of ordinary skill in the art would appreciate that molecules that interfere with transcription and/or translation may be termed "silencing molecules".

In one embodiment, the genetically modified plant described herein comprising at least one cell having an altered gene expression comprises at least one silencing molecule targeted to a gene selected from the group comprising GAME25 and GAME31, or a combination thereof.

In another embodiment, the genetically modified plant is a transgenic plant comprising at least one cell comprising at least one silencing molecule targeted to a gene selected from the group comprising GAME25 and GAME31, and a combination thereof.

A silencing molecule targeted to at least one of GAME25 and/or GAME31 can be designed as is known to a person skilled in the art (See below and Methods for Examples 3-9).

In one embodiment, a silencing molecule is selected from the group comprising an RNA interference molecule, a co-suppression molecule, and an antisense molecule.

In one embodiment, a silencing molecule comprises a polynucleotide having a nucleic acid sequence substantially complementary to a region of the GAME25 gene or a complementary sequence thereof. In another embodiment, the silencing molecule comprises a polynucleotide having a nucleic acid sequence substantially complementary to a region of the GAME25 gene, the gene having the nucleic acids sequence set forth in any one of SEQ ID 1, and SEQ ID NO: 13, In yet another embodiment, the silencing molecule comprises a polynucleotide having a nucleic acid sequence substantially complementary to a region of the GAME25 cDNA, the cDNA having the nucleic acids sequence set forth in any one of SEQ ID 2, SEQ ID NO: 11, and SEQ ID NO: 14.

In one embodiment, the nucleic acid sequence of a silencing molecule comprises the nucleic acid sequence set forth in SEQ ID NO: 8, or a fragment thereof.

In one embodiment, a silencing molecule comprises a polynucleotide having a nucleic acid sequence substantially complementary to a region of the GAME31 gene or a complementary sequence thereof. In another embodiment, the silencing molecule comprises a polynucleotide having a nucleic acid sequence substantially complementary to a region of the GAME31 gene, the gene having the nucleic acids sequence set forth in any one of SEQ ID NO: 16, SEQ ID NO: 19, SEQ ID NO: 22, SEQ ID NO: 25, SEQ ID NO: 30, SEQ ID NO: 33, SEQ ID NO: 36, SEQ ID NO: 39, SEQ ID NO: 42, SEQ ID NO: 45, SEQ ID NO: 48, and SEQ ID NO: 51. In yet another embodiment, the silencing molecule comprises a polynucleotide having a nucleic acid sequence substantially complementary to a region of the GAME31 cDNA, the cDNA having the nucleic acids sequence set forth in any one of SEQ ID NO: 17, SEQ ID NO: 20, SEQ ID NO: 23, SEQ ID NO: 26, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, and SEQ ID NO: 52.

In one embodiment, the nucleic acid sequence of a silencing molecule comprises the nucleic acid sequence set forth in SEQ ID NO: 58, or a fragment thereof. In one embodiment, the nucleic acid sequence of a silencing molecule comprises the nucleic acid sequence set forth in SEQ ID NO: 59, or a fragment thereof.

In some embodiments, a genetically modified plant comprising reduced expression of GAME25 in at least one cell, comprises decreased saturated steroidal alkaloids or steroidal glycoalkaloids, or derivatives thereof. In some embodiments, a genetically modified plant comprising reduced expression of GAME25 in at least one cell, comprises increased unsaturated steroidal alkaloids or steroidal glycoalkaloids, or derivatives thereof. In some embodiments, a genetically modified plant comprising reduced expression of GAME25 in at least one cell, comprises decreased saturated steroidal alkaloids or steroidal glycoalkaloids, or derivatives thereof, wherein said change in saturation is at a C5,C6 bond. In some embodiments, a genetically modified plant comprising reduced expression of GAME25 in at least one cell, comprises increased unsaturated steroidal alkaloids or steroidal glycoalkaloids, or derivatives thereof, wherein said change in saturation is at a C5,C6 bond. In some embodiments, said decreased SA, or SGA, or derivatives thereof occurs in a fruit. In some embodiments, the decreased SA, or SGA, or derivatives thereof, occurs in a green fruit, a breaker fruit, a turning fruit, a pink fruit, a light red fruit, or a red fruit, or a combination thereof. In some embodiments, said increased SA, or SGA, or derivatives thereof occurs in a fruit. In some embodiments, the increased SA, or SGA, or derivatives thereof, occurs in a green fruit, a breaker fruit, a turning fruit, a pink fruit, a light red fruit, or a red fruit, or a combination thereof.

In some embodiments, a genetically modified tomato plant comprising reduced expression of GAME25 in at least one cell, comprises decreased saturated steroidal alkaloids or steroidal glycoalkaloids, or derivatives thereof in said at least one cell, said SA or SGA comprising decreased α-tomatine, or hydroxytomatine, or acetoxytomatine, or α-tomatine isomers (1 and 2), or acetoxy-hydroxytomatine, or tomatidine+4 hexoses, or esculeoside A, or esculeosides, or lycoperosides, or any derivatives thereof, or any combination thereof, compared to a non-modified tomato plant. In some embodiments, a genetically modified tomato plant comprising reduced expression of GAME25 in at least one cell, comprises increased unsaturated steroidal alkaloids or steroidal glycoalkaloids, or derivatives thereof, said SA or SGA comprising dehydrotomatine, or hydroxy-dehydrotomatine, or dehydrotomatine isomer (1 and 2), or acetoxy-dehydrotomatine, or acetoxy-hydroxy-dehydrotomatine, or dehydrotomatidine+4 hexose, or dehydroesculeoside A, or dehydroesculeosides, or dehydrolycoperosides, or any derivatives thereof, or any combination thereof.

A skilled artisan would appreciate that a genetically modified plant comprising a GAME25 enzyme having decreased biological activity in at least one cell, would similarly comprises decreased saturated steroidal alkaloids or steroidal glycoalkaloids, or derivatives thereof, compared to a non-modified plant. Similarly, a genetically modified plant comprising a GAME25 enzyme having decreased biological activity in at least one cell, would similarly comprise increased unsaturated steroidal alkaloids or steroidal glycoalkaloids, or derivatives thereof, compared to a non-modified plant.

Antisense Molecules

Antisense technology is the process in which an antisense RNA or DNA molecule interacts with a target sense DNA or RNA strand. A sense strand is a 5' to 3' mRNA molecule or DNA molecule. The complementary strand, or mirror strand, to the sense is called an antisense. When an antisense strand interacts with a sense mRNA strand, the double helix is recognized as foreign to the cell and will be degraded, resulting in reduced or absent protein production. Although DNA is already a double stranded molecule, antisense technology can be applied to it, building a triplex formation.

One skilled in the art would appreciate that the terms "complementary" or "complement thereof" are used herein to encompass the sequences of polynucleotides which is capable of forming Watson & Crick base pairing with another specified polynucleotide throughout the entirety of the complementary region. This term is applied to pairs of polynucleotides based solely upon their sequences and not any particular set of conditions under which the two polynucleotides would actually bind.

RNA antisense strands can be either catalytic or non-catalytic. The catalytic antisense strands, also called ribozymes, cleave the RNA molecule at specific sequences. A non-catalytic RNA antisense strand blocks further RNA processing.

Antisense modulation of expression levels of GAME25, GAME31, or any combination thereof, in cells and/or tissues of an organisms may be effected by transforming the organism cells or tissues with at least one antisense compound, including antisense DNA, antisense RNA, a ribozyme, DNAzyme, a locked nucleic acid (LNA) and an aptamer. In some embodiments the molecules are chemically modified. In other embodiments the antisense molecule is antisense DNA or an antisense DNA analog. In some embodiment, an organism is a plant. In other embodiments, an organism is not a plant. In some embodiments, a cell is a plant cell. In other embodiments, a cell is not a plant cell.

RNA Interference (RNAi) Molecules

RNAi refers to the introduction of homologous double stranded RNA (dsRNA) to target a specific gene product, resulting in post transcriptional silencing of that gene. This phenomenon was first reported in *Caenorhabditis elegans* by Guo and Kemphues (1995, Cell, 81(4):611-620) and subsequently Fire et al. (1998, Nature 391:806-811) discovered that it is the presence of dsRNA, formed from the annealing of sense and antisense strands present in the in vitro RNA preps, that is responsible for producing the interfering activity.

In certain embodiments, disclosed herein altered gene expression comprises the use of RNA interference (RNAi) to down regulate the expression of GAME25, GAME31, or combination thereof to attenuate the level of steroidal alkaloids/glycoalkaloids in plants.

In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger. The short-nucleotide RNA sequences are homologous to the target gene that is being suppressed. Thus, the short-nucleotide sequences appear to serve as guide sequences to instruct a multicomponent nuclease, RISC, to destroy the specific mRNAs.

The dsRNA used to initiate RNAi, may be isolated from native source or produced by known means, e.g., transcribed from DNA. Plasmids and vectors for generating RNAi molecules against target sequence are now readily available from commercial sources.

The dsRNA can be transcribed from the vectors as two separate strands. In other embodiments, the two strands of DNA used to form the dsRNA may belong to the same or two different duplexes in which they each form with a DNA strand of at least partially complementary sequence. When the dsRNA is thus-produced, the DNA sequence to be transcribed is flanked by two promoters, one controlling the transcription of one of the strands, and the other that of the complementary strand. These two promoters may be identical or different. Alternatively, a single promoter can derive the transcription of single-stranded hairpin polynucleotide having self-complementary sense and antisense regions that anneal to produce the dsRNA.

One skilled in the art would appreciate that the terms "promoter element," "promoter," or "promoter sequence" may encompass a DNA sequence that is located at the 5' end (i.e. precedes) the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Inhibition is sequence-specific in that nucleotide sequences corresponding to the duplex region of the RNA are targeted for genetic inhibition. RNA molecules containing a nucleotide sequence identical to a portion of the target gene are preferred for inhibition. RNA sequences with insertions, deletions, and single point mutations relative to the target sequence have also been found to be effective for inhibition. Thus, sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript. The length of the identical nucleotide sequences may be at least 25, 50, 100, 200, 300 or 400 bases. There is no upper limit on the length of the dsRNA that can be used. For example, the dsRNA can range from about 21 base pairs (bp) of the gene to the full length of the gene or more.

The term "RNA interference" or "RNAi" refers to the silencing or decreasing of gene expression mediated by small double stranded RNAs. It is the process of sequence-specific, post-transcriptional gene silencing in animals and plants, initiated by inhibitory RNA (iRNA) that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

One of ordinary skill in the art would appreciate that the term RNAi molecule refers to single- or double-stranded RNA molecules comprising both a sense and antisense sequence. For example, the RNA interference molecule can be a double-stranded polynucleotide molecule comprising self-complementary sense and antisense regions, wherein the antisense region comprises complementarity to a target nucleic acid molecule. Alternatively the RNAi molecule can be a single-stranded hairpin polynucleotide having self-complementary sense and antisense regions, wherein the antisense region comprises complementarity to a target nucleic acid molecule or it can be a circular single-stranded polynucleotide having two or more loop structures and a stem comprising self-complementary sense and antisense regions, wherein the antisense region comprises complementarity to a target nucleic acid molecule, and wherein the circular polynucleotide can be processed either in vivo or in vitro to generate an active molecule capable of mediating RNAi.

According to some embodiments, the silencing molecule is RNAi targeted to the GAME25 gene, comprising the nucleic acid sequence set forth in SEQ ID NO:8 or a complementary sequence thereof.

According to some embodiments, the silencing molecule is RNAi targeted to the GAME31 gene, comprising the nucleic acid sequence set forth in SEQ ID NO: 58 or a complementary sequence thereof Co-Suppression Molecules Another agent capable of down-regulating the expression of GAME25, or GAME31, or a combination thereof is a Co-Suppression molecule. Co-suppression is a post-transcriptional mechanism where both the transgene and the endogenous gene are silenced.

Surprisingly, in some embodiments, overexpression of GAME25 results in suppression of the GAME25 gene. According to some embodiments, the co-suppression molecule is polynucleotide homologous to the GAME25 coding sequence. In some embodiments, the co-suppression molecule comprising a polynucleotide homologous to the GAME 25 coding sequence comprises a sequence selected from SEQ ID NO: 8, SEQ ID NO: 2, SEQ ID NO: 11, and SEQ ID NO: 14, or a fragment thereof, or a complementary sequence thereof.

Surprisingly, in some embodiments, overexpression of GAME31 results in suppression of the GAME31 gene. According to some embodiments, the co-suppression molecule is polynucleotide homologous to the GAME31 coding sequence. In some embodiments, the co-suppression molecule comprising a polynucleotide homologous to the GAME 31 coding sequence comprises a sequence selected from SEQ ID NO: 58, SEQ ID NO: 59, and SEQ ID NO: 30, or a fragment thereof, or a complementary sequence thereof. According to some embodiments, the co-suppression molecule is polynucleotide homologous to the GAME31 coding sequence, comprising the nucleic acid sequence set forth in SEQ ID NO: 59 or a complementary sequence thereof.

DNAzyme Molecules

Another agent capable of down-regulating the expression of GAME25, or GAME31, or a combination thereof is a DNAzyme molecule, which is capable of specifically cleaving an mRNA transcript or a DNA sequence of the GAME25, and/or GAME31. DNAzymes are single-stranded polynucleotides that are capable of cleaving both single- and double-stranded target sequences. A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (for review of DNAzymes, see: Khachigian, L. M. (2002) Curr Opin Mol Ther 4, 119-121).

Examples of construction and amplification of synthetic, engineered DNAzymes recognizing single- and double-stranded target cleavage sites are disclosed in U.S. Pat. No. 6,326,174, the disclosure of which is incorporated herein in its entirety.

Enzymatic Oligonucleotide

The terms "enzymatic nucleic acid molecule" or "enzymatic oligonucleotide" refers to a nucleic acid molecule which has complementarity in a substrate binding region to a specified gene target, and also has an enzymatic activity which is active to specifically cleave target RNA of GAME25, or GAME31, thereby silencing each of the genes. The complementary regions allow sufficient hybridization of the enzymatic nucleic acid molecule to the target RNA and subsequent cleavage. The term enzymatic nucleic acid is used interchangeably with for example, ribozymes, catalytic RNA, enzymatic RNA, catalytic DNA, aptazyme or aptamer-binding ribozyme, catalytic oligonucleotide, nucleozyme, DNAzyme, RNAenzyme. The specific enzymatic nucleic acid molecules described in the instant application are not limiting and an enzymatic nucleic acid molecule of this invention requires a specific substrate binding site which is complementary to one or more of the target nucleic acid regions, and that it have nucleotide sequences within or surrounding that substrate binding site which impart a nucleic acid cleaving and/or ligation activity to the molecule. U.S. Pat. No. 4,987,071 discloses examples of such molecules.

Mutagenesis

Altering the expression of endogenous or exogenous GAME25, or GAME31 genes or a combination thereof, can be also achieved by the introduction of one or more point mutations into a nucleic acid molecule encoding the corresponding proteins. Mutations can be introduced using, for example, site-directed mutagenesis (see, e.g. Wu Ed., 1993 Meth. In Enzymol. Vol. 217, San Diego: Academic Press; Higuchi, "Recombinant PCR" in Innis et al. Eds., 1990 PCR Protocols, San Diego: Academic Press, Inc). Such mutagenesis can be used to introduce a specific, desired amino acid insertion, deletion or substitution. Several technologies for targeted mutagenesis are based on the targeted induction of double-strand breaks (DSBs) in the genome followed by error-prone DNA repair. Mostly commonly used for genome editing by these methods are custom designed nucleases, including zinc finger nucleases and *Xanthomonas*-derived transcription activator-like effector nuclease (TALEN) enzymes.

In some embodiments, when the expression of the at least one gene or combination thereof is altered, said altering comprises mutagenizing the at least one gene, said mutation present within a coding region of said at least one gene, or a regulatory sequence of said at least one gene, or a combination thereof.

Various types of mutagenesis can be used to modify GAME25 or GAME31 and their encoded polypeptides in order to produce conservative or non-conservative variants. Any available mutagenesis procedure can be used. In some embodiments, the mutagenesis procedure comprises site-directed point mutagenesis. In some embodiments, the mutagenesis procedure comprises random point mutagenesis. In some embodiments, the mutagenesis procedure comprises in vitro or in vivo homologous recombination (DNA shuffling). In some embodiments, the mutagenesis procedure comprises mutagenesis using uracil-containing templates. In some embodiments, the mutagenesis procedure comprises oligonucleotide-directed mutagenesis. In some embodiments, the mutagenesis procedure comprises phosphorothioate-modified DNA mutagenesis. In some embodiments, the mutagenesis procedure comprises mutagenesis using gapped duplex DNA. In some embodiments, the mutagenesis procedure comprises point mismatch repair. In some embodiments, the mutagenesis procedure comprises mutagenesis using repair-deficient host strains. In some embodiments, the mutagenesis procedure comprises restriction-selection and restriction-purification. In some embodiments, the mutagenesis procedure comprises deletion mutagenesis. In some embodiments, the mutagenesis procedure comprises mutagenesis by total gene synthesis. In some embodiments, the mutagenesis procedure comprises double-strand break repair. In some embodiments, the mutagenesis procedure comprises mutagenesis by chimeric constructs. In some embodiments, the mutagenesis procedure comprises mutagenesis by CRISPR/Cas. In some embodiments, the mutagenesis procedure comprises mutagenesis by zinc-finger nucleases (ZFN). In some embodiments, the mutagenesis procedure comprises mutagenesis by transcription activator-like effector nucleases (TALEN). In some embodiments, the mutagenesis procedure comprises any other mutagenesis procedure known to a person skilled in the art.

In some embodiments, mutagenesis can be guided by known information about the naturally occurring molecule and/or the mutated molecule. By way of example, this known information may include sequence, sequence comparisons, physical properties, crystal structure and the like. In some embodiments, the mutagenesis is essentially random. In some embodiments the mutagenesis procedure is DNA shuffling.

A skilled artisan would appreciate that clustered regularly interspaced short palindromic repeats (CRISPR)/CRISPR associated protein (Cas) system comprises genome engineering tools based on the bacterial CRISPR/Cas prokaryotic adaptive immune system. This RNA-based technology is very specific and allows targeted cleavage of genomic DNA guided by a customizable small noncoding RNA, resulting in gene modifications by both non-homologous end joining (NHEJ) and homology-directed repair (HDR) mechanisms (Belhaj K. et al., 2013. Plant Methods 2013, 9:39), In some embodiments, a CRISPR/Cas system comprises a CRISPR/Cas9 system.

In some embodiments, a CRISPR/Cas system comprises a single-guide RNA (sgRNA) and/or a Cas protein known in the art. In some embodiments, a CRISPR/Cas system comprises a single-guide RNA (sgRNA) and/or a Cas protein newly created to cleave at a preselected site. The skilled artisan would appreciate that the terms "single-guide RNA", "sgRNA", and "gRNA" are interchangeable having all the same qualities and meanings, wherein an sgRNA may encompass a chimeric RNA molecule which is composed of a CRISPR RNA (crRNA) and trans-encoded CRISPR RNA (tracrRNA). In some embodiments, a crRNA is complementary to a preselected region of GAME25 or GAME31 DNA, wherein the crRNA "targets" the CRISPR associated polypeptide (Cas) nuclease protein to the preselected target site.

In some embodiments, the length of crRNA sequence complementary is 19-22 nucleotides long e.g., 19-22 consecutive nucleotides complementary to the target site. In another embodiment, the length of crRNA sequence complementary to the region of DNA is about 15-30 nucleotides long. In another embodiment, the length of crRNA sequence complementary to the region of DNA is about 15, 16, 17, 18, 19, 20, 21, 22, 23, 24, 25, 26, 27, 28, 29, or 30 nucleotides long. In another embodiment, the length of crRNA sequence complementary to the region of DNA is 20 nucleotides long. In some embodiments, the crRNA is located at the 5' end of the sgRNA molecule. In another embodiment, the crRNA comprises 100% complementation within the preselected target sequence. In another embodiment, the crRNA comprises at least 80% complementation within the preselected target sequence. In another embodiment, the crRNA comprises at least 85% complementation within the preselected target sequence. In another embodiment, the crRNA comprises at least 90% complementation within the preselected target sequence. In another embodiment, the crRNA comprises at least 95% complementation within the preselected target sequence. In another embodiment, the crRNA comprises at least 97% complementation within the preselected target sequence. In another embodiment, the crRNA comprises at least 99% complementation within the preselected target sequence. In another embodiment, a tracrRNA is 100-300 nucleotides long and provides a binding site for the Cas nuclease e.g., a Cas9 protein forming the CRISPR/Cas9 complex.

In one embodiment, a mutagenesis system comprises a CRISPR/Cas system. In another embodiment, a CRISPR/Cas system comprises a Cas nuclease and a gRNA molecule, wherein said gRNA molecule binds within said preselected endogenous target site thereby guiding said Cas nuclease to cleave the DNA within said preselected endogenous target site.

In some embodiments, a CRISPR/Cas system comprise an enzyme system including a guide RNA sequence ("gRNA" or "sgRNA") that contains a nucleotide sequence complementary or substantially complementary to a region of a target polynucleotide, for example a preselected endogenous target site, and a protein with nuclease activity.

In another embodiment, a CRISPR/Cas system comprises a Type I CRISPR-Cas system, or a Type II CRISPR-Cas system, or a Type III CRISPR-Cas system, or derivatives thereof. In another embodiment, a CRISPR-Cas system comprises an engineered and/or programmed nuclease system derived from naturally accruing CRISPR-Cas systems. In another embodiment, a CRISPR-Cas system comprises engineered and/or mutated Cas proteins. In another embodiment, a CRISPR-Cas system comprises engineered and/or programmed guide RNA.

A skilled artisan would appreciate that a guide RNA may contain nucleotide sequences other than the region complementary or substantially complementary to a region of a target DNA sequence, for example a preselected endogenous target site. In another embodiment, a guide RNA comprises a crRNA or a derivative thereof. In another embodiment, a guide RNA comprises a crRNA: tracrRNA chimera.

In another embodiment, a gRNA molecule comprises a domain that is complementary to and binds to a preselected endogenous target site on at least one homologous chromosome. In another embodiment, a gRNA molecule comprises a domain that is complementary to and binds to a polymorphic allele on at least one homologous chromosome. In another embodiment, a gRNA molecule comprises a domain that is complementary to and binds to a preselected endogenous target site on both homologous chromosomes. In another embodiment, a gRNA molecule comprises a domain that is complementary to and binds to polymorphic alleles on both homologous chromosomes.

Cas enzymes comprise RNA-guided DNA endonuclease able to make double-stranded breaks (DSB) in DNA. The term "Cas enzyme" may be used interchangeably with the terms "CRISPR-associated endonucleases" or "CRISPR-associated polypeptides" having all the same qualities and meanings. In one embodiment, a Cas enzyme is selected from the group comprising Cas1, Cas1B, Cas2, Cas3, Cas4, Cas5, Cas6, Cas7, Cas8, Cas9, Cas10, C2cl, CasX, NgAgo, Cpf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4, or homologs thereof, or modified versions thereof. In another embodiment, a Cas enzyme comprises Cas9. In another embodiment, a Cas enzyme comprises Cas1. In another embodiment, a Cas enzyme comprises Cas1B. In another embodiment, a Cas enzyme comprises Cas2. In another embodiment, a Cas enzyme comprises Cas3. In another embodiment, a Cas enzyme comprises Cas4. In another embodiment, a Cas enzyme comprises Cas5. In another embodiment, a Cas enzyme comprises Cas6. In another embodiment, a Cas enzyme comprises Cas7. In another embodiment, a Cas enzyme comprises Cas8. In another embodiment, a Cas enzyme comprises Cas10. In another embodiment, a Cas enzyme comprises Cpf1. In another embodiment, a Cas enzyme comprises Csy1. In another embodiment, a Cas enzyme comprises Csy2. In another embodiment, a Cas enzyme comprises Csy3. In another embodiment, a Cas enzyme comprises Cse1. In another embodiment, a Cas enzyme comprises Cse2. In another embodiment, a Cas enzyme comprises Csc1. In another embodiment, a Cas enzyme comprises Csc2. In another embodiment, a Cas enzyme comprises Csa5. In another embodiment, a Cas enzyme comprises Csn2. In another embodiment, a Cas enzyme comprises Csm2. In another embodiment, a Cas enzyme comprises Csm3. In another embodiment, a Cas enzyme comprises Csm4. In another embodiment, a Cas enzyme comprises Csm5. In another embodiment, a Cas enzyme comprises Csm6. In another embodiment, a Cas enzyme comprises Cmr1. In another embodiment, a Cas enzyme comprises Cmr3. In another embodiment, a Cas enzyme comprises Cmr4. In another embodiment, a Cas enzyme comprises Cmr5. In another embodiment, a Cas enzyme comprises Cmr6. In another embodiment, a Cas enzyme comprises Csb1. In another embodiment, a Cas enzyme comprises Csb2. In another embodiment, a Cas enzyme comprises Csb3. In another embodiment, a Cas enzyme comprises Csx17. In another embodiment, a Cas enzyme comprises Csx14. In another embodiment, a Cas enzyme comprises Csx10. In another embodiment, a Cas enzyme comprises Csx16, CsaX. In another embodiment, a Cas enzyme comprises Csx3. In another embodiment, a Cas enzyme comprises Csx1, Csx15, Csf1. In another embodiment, a Cas enzyme comprises Csf2. In another embodiment, a Cas enzyme comprises Csf3. In another embodiment, a Cas enzyme comprises Csf4. In another embodiment, a Cas enzyme comprises Cpf1. In another embodiment, a Cas enzyme comprises C2cl. In another embodiment, a Cas enzyme comprises CasX. In another embodiment, a Cas enzyme comprises NgAgo. In another embodiment, a Cas enzyme is Cas homologue. In another embodiment, a Cas enzyme is a Cas orthologue. In another embodiment, a Cas enzyme is a modified Cas enzyme. In another embodiment, a Cas enzyme is any CRISPR-associated endonucleases known in the art.

A skilled artisan would appreciate that the terms "zinc finger nuclease" or "ZFN" are interchangeable having all the same meanings and qualities, wherein a ZFN encompasses a chimeric protein molecule comprising at least one zinc finger DNA binding domain operatively linked to at least one nuclease capable of double-strand cleaving of DNA. In some embodiments, a ZFN system comprises a ZFN known in the art. In some embodiments, a ZFN system comprises a ZFN newly created to cleave a preselected site.

In some embodiments, a ZFN creates a double-stranded break at a preselected endogenous target site. In some embodiments, a ZFN comprises a DNA-binding domain and a DNA-cleavage domain, wherein the DNA binding domain is comprised of at least one zinc finger and is operatively linked to a DNA-cleavage domain. In another embodiment, a zinc finger DNA-binding domain is at the N-terminus of the chimeric protein molecule and the DNA-cleavage domain is located at the C-terminus of the molecule. In another embodiment, a zinc finger DNA-binding domain is at the C-terminus of the chimeric protein molecule and the DNA-cleavage domain is located at the N-terminus of the molecule. In another embodiment, a zinc finger binding domain encompasses the region in a zinc finger nuclease that is capable of binding to a target locus, for example a preselected endogenous target site as disclosed herein. In another embodiment, a zinc finger DNA-binding domain comprises a protein domain that binds to a preselected endogenous target site on at least one homologous chromosome. In another embodiment, a zinc finger DNA-binding domain comprises a protein domain that binds to a polymorphic allele on at least one homologous chromosome. In another embodiment, a zinc finger DNA-binding domain comprises a protein domain that binds to a preselected endogenous target site on both homologous chromosomes. In another embodiment, a zinc finger DNA-binding domain comprises a protein domain that binds to polymorphic alleles on both homologous chromosomes.

The skilled artisan would appreciate that the term "chimeric protein" is used to describe a protein that has been expressed from a DNA molecule that has been created by operatively joining two or more DNA fragments. The DNA fragments may be from the same species, or they may be from a different species. The DNA fragments may be from the same or a different gene. The skilled artisan would appreciate that the term "DNA cleavage domain" of a ZFN encompasses the region in the zinc finger nuclease that is capable of breaking down the chemical bonds between nucleic acids in a nucleotide chain. Examples of proteins containing cleavage domains include restriction enzymes, topoisomerases, recombinases, integrases and DNAses.

In some embodiments, a TALEN system comprises a TAL effector DNA binding domain and a DNA cleavage domain, wherein said TAL effector DNA binding domain binds within said preselected endogenous target site, thereby targeting the DNA cleavage domain to cleave the DNA within said preselected endogenous target site.

A skilled artisan would appreciate that the terms "transcription activator-like effector nuclease", "TALEN", and "TAL effector nuclease" may be used interchangeably having all the same meanings and qualities, wherein a TALEN encompasses a nuclease capable of recognizing and cleaving its target site, for example a preselected endogenous target site as disclosed herein. In another embodiment, a TALEN comprises a fusion protein comprising a TALE domain and a nucleotide cleavage domain. In another embodiment, a TALE domain comprises a protein domain that binds to a nucleotide in a sequence-specific manner through one or more TALE-repeat modules. A skilled artisan would recognize that TALE-repeat modules comprise a variable number of about 34 amino acid repeats that recognize plant DNA sequences. Further, repeat modules can be rearranged according to a simple cipher to target new DNA sequences. In another embodiment, a TALE domain comprises a protein domain that binds to a preselected endogenous target site on at least one homologous chromosome. In another embodiment, a TALE domain comprises a protein domain that binds to a polymorphic allele on at least one homologous chromosome. In another embodiment, a TALE domain comprises a protein domain that binds to a preselected endogenous target site on both homologous chromosomes. In another embodiment, a TALE domain comprises a protein domain that binds to polymorphic alleles on both homologous chromosomes.

In one embodiment, a TALE domain comprises at least one of the TALE-repeat modules. In another embodiment, a TALE domain comprises from one to thirty TALE-repeat modules. In another embodiment, a TALE domain comprises more than thirty repeat modules. In another embodiment, a TALEN fusion protein comprises an N-terminal domain, one or more of TALE-repeat modules followed by a half-repeat module, a linker, and a nucleotide cleavage domain.

Chemical mutagenesis using an agent such as Ethyl Methyl Sulfonate (EMS) can be employed to obtain a population of point mutations and screen for mutants of the GAME25, or GAME31 genes, or a combination thereof that may become silent or down-regulated. In plants, methods relaying on introgression of genes from natural populations can be used. Cultured and wild types species are crossed repetitively such that a plant comprising a given segment of the wild genome is isolated. Certain plant species, for example Maize (corn) or snapdragon have natural transposons. These transposons are either autonomous, i.e. the transposase is located within the transposon sequence or non-autonomous, without a transposase. A skilled person can cause transposons to "jump" and create mutations. Alternatively, a nucleic acid sequence can be synthesized having random nucleotides at one or more predetermined positions to generate random amino acid substituting.

In some embodiments, the expression of endogenous GAME25 or GAME31 genes can be altered by the introduction of one or more point mutations into their regulatory sequences. In some embodiments, the expression of exogenous GAME25 or GAME31 genes can be altered by the introduction of one or more point mutations into their regulatory sequences. A skilled artisan would appreciate that "regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. In some embodiments, regulatory sequences comprise promoters. In some embodiments, regulatory sequences comprise translation leader sequences. In some embodiments, regulatory sequences comprise introns. In some embodiments, regulatory sequences comprise polyadenylation recognition sequences. In some embodiments, regulatory sequences comprise RNA processing sites. In some embodiments, regulatory sequences comprise effector binding sites. In some embodiments, regulatory sequences comprise stem-loop structures.

A skilled artisan would appreciate that "promoter" refers to a DNA sequence capable of controlling the expression of a coding sequence or functional RNA. In some embodiments, a coding sequence is located 3' to a promoter sequence. It is understood by those skilled in the art that different promoters may direct the expression of a gene in different tissues or cell types, or at different stages of development, or in response to different environmental or physiological conditions. In some embodiments, the promoter comprises a constitutive promoter, i.e., a promoter that causes a gene to be expressed in most cell types at most times. In some embodiments, the promoter comprises a regulated promoter, i.e., a promoter that causes a gene to be expressed in response to sporadic specific stimuli. It is further recognized that in many cases the exact boundaries of regulatory sequences have not been completely defined yet.

A skilled artisan would appreciate that the term "3' non-coding sequences" or "transcription terminator" refers to DNA sequences located downstream of a coding sequence. In some embodiments, 3' non-coding sequences comprise polyadenylation recognition sequences. In some embodiments, 3' non-coding sequences comprise sequences encoding regulatory signals capable of affecting mRNA processing. In some embodiments, 3' non-coding sequences comprise sequences encoding regulatory signals capable of affecting gene expression. The polyadenylation signal is usually characterized by affecting the addition of polyadenylic acid tracts to the 3' end of the mRNA precursor. In some embodiments, mutations in the 3' non-coding sequences affect gene transcription. In some embodiments, mutations in the 3' non-coding sequences affect RNA processing. In some embodiments, mutations in the 3' non-coding sequences affect gene stability. In some embodiments, mutations in the 3' non-coding sequences affect translation of the associated coding sequence.

Biological Activity

In some embodiments, the biological activity of GAME25 or GAME31 is altered compared with a control GAME25 enzyme or a control GAME31 enzyme.

A skilled artisan would recognize that the term "biological activity" refers to any activity associated with a protein that can be measured by an assay. In some embodiments, the biological activity of GAME25 and/or GAME31 comprises biosynthesis of steroidal alkaloids and glycosylated derivatives thereof. In some embodiments, the biological activity of GAME25 and/or GAME31 affect the levels of steroidal alkaloids in at least a part of a plant. In some embodiments, an altered biological activity comprises increased enzyme activity. In some embodiments, an altered biological activity comprises decreased enzyme activity. In some embodiments, an altered biological activity comprises increased stability of the polypeptide. In some embodiments, an altered biological activity comprises decreased stability of the polypeptide.

In some embodiments, the altered biological activity comprises increased enzyme activity of said 3-β-hydroxysteroid dehydrogenase/isomerase (GAME25) or said 2-oxoglutarate-dependent dioxygenase (GAME31), or the combination thereof; or increased stability of said 3-β-hydroxysteroid dehydrogenase/isomerase (GAME25) or said 2-oxoglutarate-dependent dioxygenase (GAME31), or the combination thereof; or decreased enzyme activity of said 3-β-hydroxysteroid dehydrogenase/isomerase (GAME25) or said 2-oxoglutarate-dependent dioxygenase (GAME31), or the combination thereof; or decreased stability of said 3-β-hydroxysteroid dehydrogenase/isomerase (GAME25) or said 2-oxoglutarate-dependent dioxygenase (GAME31), or the combination thereof;

compared to the biological activity in an unmodified plant.

In some embodiments, the biological activity of a GAME25 enzyme is increased compared with a control GAME25 enzyme. In some embodiments, the biological activity of a GAME 25 enzyme is decreased compared with a control GAME25 enzyme. In some embodiments, a GAME25 enzyme has increased stability compared with a control GAME25 enzyme. In some embodiments, a GAME25 enzyme has decreased stability compared with a control GAME25 enzyme.

In some embodiments, the biological activity of a GAME31 enzyme is increased compared with a control GAME31 enzyme. In some embodiments, the biological activity of a GAME 31 enzyme is decreased compared with a control GAME31 enzyme. In some embodiments, a GAME31 enzyme has increased stability compared with a control GAME31 enzyme. In some embodiments, a GAME31 enzyme has decreased stability compared with a control GAME31 enzyme.

In some embodiments, the biological activity of a GAME25 enzyme is increased compared with a control GAME25 enzyme, and the biological activity of GAME 31 is unchanged. In some embodiments, the biological activity of a GAME25 enzyme is increased compared with a control GAME25 enzyme, and the biological activity of GAME 31 is also increased compared with a control GAME31. In some embodiments, the biological activity of a GAME25 enzyme is increased compared with a control GAME25 enzyme, and the biological activity of GAME 31 is decreased compared with a control GAME31. In some embodiments, the biological activity of a GAME 25 enzyme is decreased compared with a control GAME25 enzyme and the biological activity of GAME31 is unchanged. In some embodiments, the biological activity of a GAME 25 enzyme is decreased compared with a control GAME25 enzyme and the biological activity of GAME31 is also decreased compared with a control GAME31. In some embodiments, the biological activity of a GAME 25 enzyme is decreased compared with a control GAME25 enzyme and the biological activity of GAME31 is increased compared with a control GAME31.

In some embodiments, the stability of a GAME25 enzyme is increased compared with a control GAME25 enzyme, and the stability of GAME 31 is unchanged. In some embodiments, the stability of a GAME25 enzyme is increased compared with a control GAME25 enzyme, and the stability of GAME 31 is also increased compared with a control GAME31. In some embodiments, the stability of a GAME25 enzyme is increased compared with a control GAME25 enzyme, and the stability of GAME 31 is decreased compared with a control GAME31. In some embodiments, the stability of a GAME 25 enzyme is decreased compared with a control GAME25 enzyme and the stability of GAME31 is unchanged. In some embodiments, the stability of a GAME 25 enzyme is decreased compared with a control GAME25 enzyme and the stability of GAME31 is also decreased compared with a control GAME31. In some embodiments, the stability of a GAME 25 enzyme is decreased compared with a control GAME25 enzyme and the stability of GAME31 is increased compared with a control GAME31.

In some embodiment, the biological activity comprises biosynthesis of steroidal alkaloids and glycosylated derivatives thereof. Thus, the biological activity of GAME25 and/or GAME31 affect the levels of steroidal alkaloids in at least a part of a plant.

In some embodiments, a genetically modified plant comprising an altered the biological activity of GAME25 alters the content of at least one cholesterol derived compound selected from the group comprising a steroidal alkaloid or a glycosylated derivative thereof and an unsaturated or saturated steroidal saponin or a glycoside derivative thereof compared to a corresponding unmodified plant. In some embodiments, a genetically modified plant comprising an altered the biological activity of GAME31 alters the content of at least one steroidal alkaloid or a glycosylated derivative thereof compared to a corresponding unmodified plant. In some embodiments, a genetically modified plant comprising an altered the biological activity of GAME25 and GAME31 alters the content of at least one cholesterol derived compound selected from the group comprising a steroidal alkaloid or a glycosylated derivative thereof and an unsaturated or saturated steroidal saponin or a glycoside derivative thereof compared to a corresponding unmodified plant.

In some embodiments, disclosed herein is a method of altering the content of at least one cholesterol derived compound selected from the group comprising a steroidal alkaloid or a glycosylated derivative thereof and an unsaturated or saturated steroidal saponin or a glycoside derivative thereof in a plant, comprising altering the biological activity of at least one protein selected from the group comprising a 3-β-hydroxysteroid dehydrogenase/isomerase (GAME25) and a 2-oxoglutarate-dependent dioxygenase (GAME31), or a combination thereof. In some embodiments, altering the biological activity of at least one protein selected from the group comprising a 3-β-hydroxysteroid dehydrogenase/isomerase (GAME25) and a 2-oxoglutarate-dependent dioxygenase (GAME31), or a combination thereof, comprises introducing one or more point mutations into a DNA sequence coding GAME25, or GAME31, or a combination thereof, wherein said mutated DNA sequence is expressed in at least one plant cell within said plant. In some embodiments, altering the biological activity of at least one protein selected from the group comprising a 3-β-hydroxysteroid dehydrogenase/isomerase (GAME25) and a 2-oxoglutarate-dependent dioxygenase (GAME31), or a combination thereof, comprises introducing one or more point mutations into a DNA regulatory sequence that is operably linked to the DNA sequence encoding GAME25, or GAME31, or a combination thereof, wherein said mutated regulatory DNA sequence alters the expression of the DNA sequence encoding GAME25, or GAME31, or a combination thereof in at least one plant cell within said plant.

In some embodiments, a method of producing a plant with an altered content of at least one cholesterol derived compound selected from the group comprising a steroidal alkaloid or a glycosylated derivative thereof and an unsaturated or saturated steroidal saponin or a glycoside derivative thereof comprises altering the biological activity of a 3-β-hydroxysteroid dehydrogenase/isomerase (GAME25) and a 2-oxoglutarate-dependent dioxygenase (GAME31), or a combination thereof, as described herein, or altering the expression level of a 3-β-hydroxysteroid dehydrogenase/isomerase (GAME25) and a 2-oxoglutarate-dependent dioxygenase (GAME31), or a combination thereof as described herein, or altering the activity and expression level of a 3-β-hydroxysteroid dehydrogenase/isomerase (GAME25) and a 2-oxoglutarate-dependent dioxygenase (GAME31), or a combination thereof as described herein, compared to a corresponding non-transformed plant. In some embodiments, altering the content of at least one cholesterol derived compound selected from the group comprising a steroidal alkaloid or a glycosylated derivative thereof and an unsaturated or saturated steroidal saponin or a glycoside derivative thereof in a plant comprises increasing said content. In some embodiments, altering the content of at least one cholesterol derived compound selected from the group comprising a steroidal alkaloid or a glycosylated derivative thereof and an unsaturated or saturated steroidal saponin or a glycoside derivative thereof in a plant comprises decreasing said content. In some embodiments, altering the content of at least one cholesterol derived compound selected from the group comprising a steroidal alkaloid or a glycosylated derivative thereof and an unsaturated or saturated steroidal saponin or a glycoside derivative thereof in a plant comprises increasing the content of at least one cholesterol derived compound selected from the group comprising a steroidal alkaloid or a glycosylated derivative thereof and an unsaturated or saturated steroidal saponin or a glycoside derivative thereof and decreasing the content of at least one other cholesterol derived compound selected from the group comprising a steroidal alkaloid or a glycosylated derivative thereof and an unsaturated or saturated steroidal saponin or a glycoside derivative thereof.

In some embodiments, the biological activity of GAME25 comprises a 3-β-hydroxysteroid dehydrogenase/isomerase enzyme activity. In some embodiments, the biological activity of GAME25 comprises a step in the multi-step conversion of dehydrotomatidine to tomatidine. In some embodiments, the biological activity of GAME25 comprises a step in the multi-step conversion of solanidine to demissidine. In some embodiments, the biological activity of GAME25 comprises a step in the multi-step conversion of solasoidine to dihydrosolasodine.

In some embodiments, the biological activity of GAME31 comprises a 2-oxoglutarate-dependent dioxygenase enzyme activity. In some embodiments, the biological activity of GAME31 comprises a step in the conversion of dehydrotomatine to hydroxy-dehydrotomatine. In some embodiments, the biological activity of GAME31 comprises a step in the conversion of α-tomatine to hydroxytomatine. In some embodiments, the biological activity of GAME31 comprises a step in the conversion of α-solanine to leptinine II. In some embodiments, the biological activity of GAME31 comprises a step in the conversion of α-chaconine to leptinine I. In some embodiments, the biological activity of GAME31 comprises a step in the conversion of solasonine to hydroxysolasonine. In some embodiments, the biological activity of GAME31 comprises a step in the conversion of α-solamargine to hydroxysolamargine.

In some embodiments, the biological activity of GAME 25, GAME31, or a combination thereof, comprises altering the content of a steroidal alkaloid or a glycosylated derivative thereof selected from the group comprising: tomatidine, α-tomatine, α-tomatine isomer (1 and 2), hydroxytomatine, acetoxytomatine, acetoxy-hydroxytomatine, tomatidine+4 hexose, esculeosides, esculeoside A, esculeoside A+hexose, esculeoside B, acetoxyesculeoside B, demissidine, demissine, dehydrosolasodine, hydroxy-dehydrotomatine, acetoxy-hydroxy-dehydrotomatine, dehydroesculeosides, leptinine I, leptinine II, leptine I, leptine II, lycoperosides, and hydroxysolamargine, or any derivatives thereof, or any combination thereof.

In some embodiments, the biological activity of GAME 25, GAME31, or a combination thereof, comprises altering the content of a steroidal alkaloid or a glycosylated derivative thereof selected from the group comprising: dehydrotomatine or an isomer thereof, hydroxy-dehydrotomatine, acetoxy-dehydrotomatine, acetoxy-hydroxy-dehydrotomatine, dehydrotomatidine+4 hexose, dehydroesculeoside A, dehydroesculeoside A+hexose, solanidine, α-solanine, α-chaconine, leptinine I, leptinine II, leptine I, leptine II, solasoidine, α-solasonine, α-solamargine, hydroxysolasonine, and hydroxysolamargine, or any derivatives thereof, or any combination thereof.

In some embodiments, the biological activity of GAME 25, GAME31, or a combination thereof, comprises increasing plant resistance to at least one plant pathogen, pest, or predator, or any combination thereof. In some embodiments, the biological activity of GAME 25, GAME31, or a combination thereof, comprises generating precursor molecules for steroidal alkaloid molecules that provide resistance to at least one plant pathogen, pest, or predator, or any combination thereof.

In some embodiments, the biological activity of GAME 25, GAME31, or a combination thereof, comprises synthesizing anti-nutritional steroidal alkaloids or glycosylated derivatives thereof.

In some embodiments, the biological activity of GAME25 is enhanced by the introduction of one or more point mutations into its DNA coding sequences. In some embodiments, the biological activity of GAME25 is diminished by the introduction of one or more point mutations into its DNA coding sequences. In some embodiments, the biological activity of GAME31 is enhanced by the introduction of one or more point mutations into its DNA coding sequences. In some embodiments, the biological activity of GAME31 is diminished by the introduction of one or more point mutations into its DNA coding sequences. In some embodiments, the biological activity of GAME25, GAME31, or a combination thereof, is enhanced by increasing the stability of GAME25, GAME31, or a combination thereof, by the introduction of one or more point mutations into their DNA coding sequences. In some embodiments, the biological activity of GAME25, GAME31, or a combination thereof, is decreased by decreasing the stability of GAME25, GAME31, or a combination thereof, by the introduction of one or more point mutations into their DNA coding sequences.

Overexpression

According to yet additional embodiments, provided herein is a genetically modified plant having enhanced expression of at least one gene selected from the group comprising a gene encoding 3-β-hydroxysteroid dehydrogenase/isomerase (GAME25), and a gene encoding 2-oxoglutarate-dependent dioxygenase (GAME31), or a combination thereof, wherein the genetically modified plant has an increased amount of at least one cholesterol derived compound selected from the group comprising a steroidal alkaloid or a glycosylated derivative thereof and an unsaturated or saturated steroidal saponin or a glycoside derivative thereof compared to a corresponding unmodified plant. In plants, steroidal alkaloids play a role in protecting the plant from various pathogens. Steroidal alkaloids are referred to as phytoanticipins, i.e. low molecular weight anti-microbial compounds that are present in the plant before challenge by microorganisms or produced after infection solely from preexisting constituents. Over-expression of GAME25, or GAME31, or any combination thereof in non-edible parts of the plant can thus enhance the plant resistance to steroidal-alkaloid-sensitive pathogens.

Transgenic Plants

Cloning of a polynucleotide encoding a protein of the present invention selected from the group comprising of 3-β-hydroxysteroid dehydrogenase/isomerase (GAME25, 2-oxoglutarate-dependent dioxygenase (GAME31), and a combination thereof or a molecule that silences a gene encoding same may be performed by any method as is known to a person skilled in the art. Various DNA constructs may be used to express the desired gene or silencing molecule targeted to the gene in a desired organism.

In certain embodiments, the gene or a silencing molecule targeted thereto form part of an expression vector comprising all necessary elements for expression of the gene or its silencing molecule. In certain embodiments, the expression is controlled by a constitutive promoter. In certain embodiments, the constitutive promoter is specific to a plant tissue. According to these embodiments, the tissue specific promoter is selected from the group consisting of root, tuber, leaves and fruit specific promoter. Root specific promoters are described, e.g. in Martinez, E. et al. 2003. Curr. Biol. 13:1435-1441. Fruit specific promoters are described among others in Estornell L. H et al. 2009. Plant Biotechnol. J. 7:298-309 and Fernandez A. I. Et al. 2009 Plant Physiol. 151:1729-1740. Tuber specific promoters are described, e.g.

in Rocha-Sosa M, et al., 1989. EMBO J. 8:23-29; McKibbin R. S. et al., 2006. Plant Biotechnol J. 4(4):409-18. Leaf specific promoters are described, e.g. in Yutao Yang, Guodong Yang, Shijuan Liu, Xingqi Guo and Chengchao Zheng. Science in China Series C: Life Sciences. 46: 651-660.

In certain embodiments, the expression vector further comprises regulatory elements at the 3' non-coding sequence. A skilled artisan would appreciate that the term "3' non-coding sequences" encompasses DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht I L et al. (1989. Plant Cell 1:671-680).

Those skilled in the art would appreciate that the various components of the nucleic acid sequences and the transformation vectors described in the present invention are operatively linked, so as to result in expression of said nucleic acid or nucleic acid fragment. Techniques for operatively linking the components of the constructs and vectors of the present invention are well known to those skilled in the art. Such techniques include the use of linkers, such as synthetic linkers, for example including one or more restriction enzyme sites.

One skilled in the art would appreciate that the term "operably linked" may encompass the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation.

Methods for transforming a plant, described herein, are known to those skilled in the art. One skilled in the art would appreciate that the term "transformation" or "transforming" describes a process by which a foreign DNA, such as a DNA construct, including expression vector, enters and changes a recipient cell into a transformed, genetically altered or transgenic cell. Transformation may be stable, wherein the nucleic acid sequence is integrated into the organism genome and as such represents a stable and inherited trait, or transient, wherein the nucleic acid sequence is expressed by the cell transformed but is not integrated into the genome, and as such represents a transient trait. According to preferred embodiments the nucleic acid sequence of the present invention is stably transformed into the plant cell.

The genetically altered plants having altered content of the desired steroidal alkaloid(s) or steroidal glycoalkaloid(s), disclosed herein, are typically first selected based on the expression of the gene or protein. Plants having enhanced or aberrant expression of the gene or protein, are then analyzed for the content of steroidal alkaloids and steroidal glycoalkaloids.

Detection of mutated GAME25, or GAME31 genes, or a combination thereof and/or the presence of silencing molecule targeted to the gene is performed employing standard methods of molecular genetics, known to a person of ordinary skill in the art.

For measuring the gene(s) or silencing molecule(s) expression, cDNA or mRNA should be obtained from an organ in which the nucleic acid is expressed. The sample may be further processed before the detecting step. For example, the polynucleotides in the cell or tissue sample may be separated from other components of the sample, may be amplified, etc. All samples obtained from an organism, including those subjected to any sort of further processing are considered to be obtained from the organism.

Detection of the gene(s) or the silencing molecule(s) typically requires amplification of the polynucleotides taken from the candidate altered organism. Methods for DNA amplification are known to a person skilled in the art. Most commonly used method for DNA amplification is PCR (polymerase chain reaction; see, for example, PCR Basics: from background to Bench, Springer Verlag, 2000; Eckert et al., 1991. PCR Methods and Applications 1:17). Additional suitable amplification methods include the ligase chain reaction (LCR), transcription amplification and self-sustained sequence replication, and nucleic acid based sequence amplification (NASBA).

In certain embodiments, the nucleic acid sequence comprising the GAME25, or GAME31 genes or its silencing molecule further comprises a nucleic acid sequence encoding a selectable marker. In certain embodiments, the selectable marker confers resistance to antibiotic or to an herbicide; in these embodiments the transgenic plants are selected according to their resistance to the antibiotic or herbicide.

The content of steroidal alkaloids and/or steroidal glycoalkaloids is measured as exemplified hereinbelow and as is known to a person skilled in the art.

In one embodiment, the genetically modified plant disclosed herein comprising at least one cell having an altered expression, comprises at least one transcribable polynucleotide. In another embodiment, the genetically modified plant disclosed herein comprising at least one cell having an altered expression, comprises at least one transcribable polynucleotide encoding at least one protein, said at least one protein selected from the group comprising a GAME25 3-β-hydroxysteroid dehydrogenase/isomerase and a GAME31 2-oxoglutarate-dependent dioxygenase, or any combination thereof. In another embodiment, the genetically modified plant disclosed herein comprising at least one cell having an altered expression, comprises at least one transcribable polynucleotide complementary of anti-sense to a GAME25 gene or portion thereof. In another embodiment, the genetically modified plant disclosed herein comprising at least one cell having an altered expression, comprises at least one transcribable polynucleotide complementary or anti-sense to a GAME31 gene or portion thereof. In another embodiment, the genetically modified plant disclosed herein comprising at least one cell having an altered expression, comprises at least one transcribable polynucleotide complementary of anti-sense to a GAME25 gene or portion thereof, or complementary or anti-sense to a GAME31 gene or portion thereof, or any combination thereof.

In some embodiments, the at least one transcribable polynucleotide comprises the nucleic acid sequence set forth in SEQ ID NO: 8. In some embodiments, the at least one transcribable polynucleotide comprises the nucleic acid sequence set forth in SEQ ID NO: 58. In some embodiments, the at least one transcribable polynucleotide comprises the nucleic acid sequence set forth in SEQ ID NO: 59. In some embodiments, the at least one transcribable polynucleotide comprises the nucleic acid sequence set forth in any one of SEQ ID NO: 8, SEQ ID NO: 58, and SEQ ID NO: 59, or any combination thereof.

One skilled in the art would appreciate that edible components of plants may go through ripening stages. For example, for a tomato, six ripening stages may be identified:

Green, Breakers, Turning, Pink, Light Red, and Red. In one embodiment, Green—stage one—means that the surface of the tomato is completely green in color, wherein the shade of green may vary from light to dark. In one embodiment, Breakers—stage two—means there is a definite "break" in color from green to tannish-yellow, pink or red on not more than 10% of the surface. In one embodiment, Turning—stage 3—means that more than 10%, but not more than 30%, of the surface, in the aggregate, shows a definite change in color from green to tannish-yellow, pink, red, or a combination thereof. In one embodiment, Pink—stage four—means that more than 30%, but not more than 60%, of the surface, in the aggregate, shows pink or red in color. Light Red—stage 5—means that more than 60% of the surface, in the aggregate, shows pinkish-red or red, provided that not more than 90% of the surface is red. Red—stage 6—means that more than 90% of the surface, in the aggregate, is red.

In one embodiment, the at least one cell having altered expression is selected from the group consisting of an immature green tissue cell, a mature green tissue cell, an orange tissue cell, a breaker tissue cell, and a ripe tissue cell.

In another embodiment, the at least one cell having altered expression is selected from the group consisting of leaf cell, a bud cell, a petal cell, a root cell, a peal cell, a flower cell, a stem cell, a shoot cell, and a fruit cell. One skilled in the art would appreciate that it may be advantageous for a plant to have increased expressions of at least one SA/SGA in order to provide the plant with resistance to pathogens and pests during development and growth, wherein at the same time it would be advantageous for an edible part of the plant to have reduced SA/SGA, wherein the SA/SGA comprising anti-nutritional compounds. In some embodiments, a leaf cell comprises a young leaf cell. In some embodiments, a leaf cell comprises a mature leaf cell.

In one embodiment, an edible part of a plant is a fruit. In another embodiment, an edible part of a plant is a tuber. In another embodiment, an edible part of a plant is a leaf, a young leaf, or a mature leaf. In another embodiment, an edible part of a plant is a bud. In one embodiment, a fruit comprises a green fruit, a breaker fruit, a turning fruit, a pink fruit, a light red fruit, or a red ripe fruit. In another embodiment, a fruit comprises a green fruit, a breaker fruit, or a red ripe fruit.

In one embodiment, disclosed herein is a method of reducing the content of at least one cholesterol derived compound selected from the group comprising a steroidal alkaloid or a glycosylated derivative thereof and an unsaturated or saturated steroidal saponin or a glycoside derivative thereof in a plant, comprising transforming at least one plant cell within said plant with at least one silencing molecule targeted to a nucleic acid sequence encoding at least one protein selected from the group comprising a3-β-hydroxysteroid dehydrogenase/isomerase (GAME25) and a 2-oxoglutarate-dependent dioxygenase (GAME31), or a combination thereof, thereby producing a plant with a reduced content of said at least one cholesterol derived compound selected from the group comprising a steroidal alkaloid or a glycosylated derivative thereof and an unsaturated or saturated steroidal saponin or a glycoside derivative thereof compared to a corresponding non-transformed plant. In another embodiment, a method of reducing the content of at least one cholesterol derived compound selected from the group comprising a steroidal alkaloid or a glycosylated derivative thereof and an unsaturated or saturated steroidal saponin or a glycoside derivative thereof comprises reducing the content of at least one cholesterol derived compound selected from the group comprising a steroidal alkaloid or a glycosylated derivative thereof and an unsaturated or saturated steroidal saponin or a glycoside derivative thereof comprising an anti-nutritional compound.

In some embodiments, a method of reducing the content of at least one cholesterol derived compound selected from the group comprising a steroidal alkaloid or a glycosylated derivative thereof and an unsaturated or saturated steroidal saponin or a glycoside derivative thereof in a plant, said method comprising a step transforming at least one plant cell within said plant with at least one silencing molecule targeted to a nucleic acid sequence encoding at least one protein selected from the group comprising 3-β-hydroxysteroid dehydrogenase/isomerase (GAME25), 2-oxoglutarate-dependent dioxygenase (GAME31), or any combination thereof; or transforming at least one plant cell within said plant with at least one polynucleotide sequence encoding at least one protein selected from the group comprising 3-β-hydroxysteroid dehydrogenase/isomerase (GAME25), or a 2-oxoglutarate-dependent dioxygenase (GAME31), or any combination thereof, wherein said at least one polynucleotide sequence comprises a mutation in a coding region or a regulatory region; or a combination of (a) and (b);

thereby producing a plant with a reduced content of said at least one cholesterol derived compound selected from the group comprising a steroidal alkaloid or a glycosylated derivative thereof and an unsaturated or saturated steroidal saponin or a glycoside derivative thereof compared to a corresponding non-transformed plant.

In another embodiment, the method of reducing the content of at least one steroidal alkaloid or a glycosylated derivative thereof comprising reducing the content of at least one anti-nutritional compound, maintains or essentially maintains the resistance to at least one pathogen or predator in the plant, compared to a corresponding non-transformed plant. In an alternate embodiment, the plant resistance to at least one pathogen or predator is increased compared to a corresponding non-transformed plant.

In some embodiments, the reduced at least one steroidal alkaloid or a glycosylated derivative thereof comprises any of the SA or SGA disclosed herein. In some embodiments, the reduced at least one steroidal alkaloid or a glycosylated derivative thereof comprises a sub-set of the SA or SGA disclosed herein. In some embodiments, the sub-set of reduced at least one steroidal alkaloid or a glycosylated derivative thereof comprises α-tomatine, α-tomatine isomer (1 and 2), hydroxytomatine, acetoxytomatine, acetoxy-hydroxytomatine, esculeosides, lycoperosides, or derivatives thereof, or any combination thereof. In some embodiments, while a sub-set of SA or SGA are reduced, additionally at least one steroidal alkaloid or a glycosylated derivative thereof is increased, wherein the at least one steroidal alkaloid or a glycosylated derivative thereof comprising a dehydrotomatine, a dehydrotomatine isomer 1, a dehydrotomatidine+4-hexose, a hydroxy-dehydrotomatine, an acetoxy-dehydrotomatine, an acetoxy-hydroxy-dehydrotomatine, an dehydroesculeosides, an dehydrolycoperosides, or any derivatives thereof, or any combination thereof.

In some embodiments, the reduced at least one unsaturated or saturated steroidal saponin or a glycosylated derivative thereof comprises any unsaturated or saturated steroidal saponin or glycosylated derivative thereof. In some embodiments, the reduced at least one unsaturated or saturated steroidal saponin or a glycosylated derivative thereof comprises dioscin, diosgenin, parillin, or sarasapogenin. In some embodiments, the reduced at least one unsaturated or saturated steroidal saponin or a glycosylated derivative thereof comprises aescin, araloside A, astragaloside, bacopaside, bacoside, bacoside A, chaconine, charantin, daucosterol, esculeoside A, ginsenoside, glycyrrhizin, α-hederin, holothurin, momordicine, momordin, osladin, protodioscin, pseudoginsenoside F11, QS21, solanine, triterpenoid saponin, and ziziphin Breeding In some embodiments, disclosed herein is a method for breeding a plant having altered content of at least one cholesterol derived compound selected from the group comprising a steroidal alkaloid or a glycosylated derivative thereof and an unsaturated or saturated steroidal saponin or a glycoside derivative thereof; said method comprising providing a first plant, wherein the expression level of GAME25, GAME31, or a combination thereof, in said first plant is in a pre-determined range of values; providing a second plant; crossing said first and second plants to generate an offspring plant; and selecting an offspring plant that has a significantly different content of at least one cholesterol derived compound selected from the group comprising a steroidal alkaloid or a glycosylated derivative thereof and an unsaturated or saturated steroidal saponin or a glycoside derivative thereof compared to said second plant. In some embodiments, a method for breeding a plant having altered content of at least one cholesterol derived compound selected from the group comprising a steroidal alkaloid or a glycosylated derivative thereof and an unsaturated or saturated steroidal saponin or a glycoside derivative thereof; comprises (a) providing a first plant, wherein the expression level of a polynucleotide encoding a 3-β-hydroxysteroid dehydrogenase/isomerase (GAME25), a 2-oxoglutarate-dependent dioxygenase (GAME31), or a combination thereof is in a pre-determined range of values, or a biological activity of a 3-β-hydroxysteroid dehydrogenase/isomerase (GAME25), a 2-oxoglutarate-dependent dioxygenase (GAME31), or a combination thereof, is in a pre-determined range of values; (b) providing a second plant; (c) crossing said first and second plants to generate an offspring plant; and (d) selecting an offspring plant that has a significantly different content of at least one cholesterol derived compound selected from the group comprising a steroidal alkaloid or a glycosylated derivative thereof and an unsaturated or saturated steroidal saponin or a glycoside derivative thereof compared to said second plant.

In some embodiments, a pre-determined value of expression comprises under-expression or over-expression compared to a non-genetically modified plant. In some embodiments, a pre-determined value of expression comprises under-expression or over-expression compared to a wild-type plant. In some embodiments, a pre-determined value of expression comprises under-expression or over-expression compared to a different genetically modified plant.

In some embodiments, a pre-determine value of biological activity comprises increase enzyme activity, or decreased enzyme activity, or increased stability, or decreased stability of said GAME25 or GAME31, or the combination thereof, compared to a non-genetically modified plant. In some embodiments, a pre-determine value of biological activity comprises increase enzyme activity, or decreased enzyme activity, or increased stability, or decreased stability of said GAME25 or GAME31, or the combination thereof, compared to a wild-type plant. In some embodiments, a pre-determine value of biological activity comprises increase enzyme activity, or decreased enzyme activity, or increased stability, or decreased stability of said GAME25 or GAME31, or the combination thereof, compared to a different genetically modified plant.

In some embodiments, disclosed herein is a method for breeding a plant with decreased content of at least one cholesterol derived compound selected from the group comprising a steroidal alkaloid or a glycosylated derivative thereof and an unsaturated or saturated steroidal saponin or a glycoside derivative thereof; said method comprising providing a first plant, wherein the expression level of GAME25, GAME31, or a combination thereof, in said first plant is below a pre-determined value; providing a second plant; crossing said first and second plants to generate an offspring plant; and selecting an offspring plant that has decreased content of at least one cholesterol derived compound selected from the group comprising a steroidal alkaloid or a glycosylated derivative thereof and an unsaturated or saturated steroidal saponin or a glycoside derivative thereof compared to said second plant.

In some embodiments, disclosed herein is a method for breeding a plant with increased content of at least one cholesterol derived compound selected from the group comprising a steroidal alkaloid or a glycosylated derivative thereof and an unsaturated or saturated steroidal saponin or a glycoside derivative thereof; said method comprising providing a first plant, wherein the expression level of GAME25, GAME31, or a combination thereof, in said first plant is above a pre-determined value; providing a second plant; crossing said first and second plants to generate an offspring plant; and selecting an offspring plant that has increased content of at least one cholesterol derived compound selected from the group comprising a steroidal alkaloid or a glycosylated derivative thereof and an unsaturated or saturated steroidal saponin or a glycoside derivative thereof compared to said second plant.

In some embodiments, alternative methods may be used to breed a plant having an altered expression of at least one gene. For example, in some embodiments, a method for breeding a plant having an altered expression of at least one gene selected from the group comprising a gene encoding 3-β-hydroxysteroid dehydrogenase/isomerase (GAME25), a gene encoding a 2-oxoglutarate-dependent dioxygenase (GAME31), or a combination thereof, said method comprising:

providing a first transformed plant, wherein said first transformed plant is transformed with an expression vector comprising a polynucleotide comprising at least one silencing molecule targeted to a nucleic acid sequence encoding at least one protein selected from the group comprising a 3-β-hydroxysteroid dehydrogenase/isomerase (GAME25) and a 2-oxoglutarate-dependent dioxygenase (GAME31), or a combination thereof, wherein said at least one silencing molecule is operably linked to a promoter; or providing a first transformed plant, wherein said first transformed plant is transformed with an expression vector comprising at least one polynucleotide which overexpresses at least one protein selected from the group comprising a 3-β-hydroxysteroid dehydrogenase/isomerase (GAME25), a 2-oxoglutarate-dependent dioxygenase (GAME31), or a combination thereof; or providing a first transformed plant, wherein said first transformed plant is transformed with an expression vector comprising at least one polynucleotide which comprises a mutation in a gene encoding at least one protein selected from the group comprising a 3-β- hydroxysteroid dehydrogenase/isomerase (GAME25), a 2-oxoglutarate-dependent dioxygenase (GAME31), or a combination thereof;

providing a second non-transformed plant;

crossing said first transformed plant of (a) or (b) or (c) with a second plant to generate a hybrid plant, wherein the hybrid plant comprises the expression vector; and selecting a hybrid plant that has an altered expression of at least one of said genes compared with an unmodified plant. Further, said plant may, in certain embodiments comprise an altered content of at least one cholesterol derived compound selected from the group comprising a steroidal alkaloid or a glycosylated derivative thereof and an unsaturated or saturated steroidal saponin or a glycoside derivative thereof, compared to a corresponding unmodified plant.

In some embodiments, the at least one silencing molecule or said overexpressing polynucleotide is operably linked to a constitutive promoter, an inducible promoter, a tissue-specific promoter, or a developmental-stage specific promoter. In some embodiments, the at least one polynucleotide comprising a mutation is operably linked to a constitutive promoter, an inducible promoter, a tissue-specific promoter, or a developmental-stage specific promoter. In some embodiments, the expression level and/or biological activity of the 3-β-hydroxysteroid dehydrogenase/isomerase (GAME25), or the 2-oxoglutarate-dependent dioxygenase (GAME31), or a combination thereof, provide a biological marker for a plant comprising altered content of at least one cholesterol derived compound selected from the group comprising a steroidal alkaloid or a glycosylated derivative thereof and an unsaturated or saturated steroidal saponin or a glycoside derivative thereof. In some embodiments, the altered content comprises reduced content of an anti-nutritional or toxic steroidal alkaloid or a glycosylated derivative thereof. In some embodiments, the altered content comprises increased content of a steroidal alkaloid or a glycosylated derivative thereof that provides resistance to a plant pathogen, pest, or predator.

In some embodiments, increased content of at least one SA or SGA can be produced in a genetically modified plant. In some embodiments, a method of enhancing the content of at least one steroidal alkaloid or a glycosylated derivative thereof in a plant, comprising transforming at least one plant cell within said plant with a nucleic acid sequence encoding 3-β-hydroxysteroid dehydrogenase/isomerase (GAME25), 2-oxoglutarate-dependent dioxygenase (GAME31), or a combination thereof, wherein said transforming results in overexpression of said GAME25, GAME31, or a combination thereof; or transforming at least one plant cell with at least one polynucleotide sequence encoding at least one protein selected from the group comprising 3-β-hydroxysteroid dehydrogenase/isomerase (GAME25), or a 2-oxoglutarate-dependent dioxygenase (GAME31), or any combination thereof, wherein said at least one polynucleotide sequence comprises a mutation in a coding region or a regulatory region;

thereby producing a plant with an enhanced content of said at least one cholesterol derived compound selected from the group comprising a steroidal alkaloid or a glycosylated derivative thereof and an unsaturated or saturated steroidal saponin or a glycoside derivative thereof, compared to a corresponding non-transformed plant.

In some embodiments, increased content of at least one SA of SGA comprises any SA or SGA disclosed herein. In some embodiments, increased content of at least one SA of SGA comprises a subset of SA or SGA disclosed herein. In some embodiments, a sub-set of increased SA of SGA comprises at least one of a α-tomatine, α-tomatine isomer (1 and 2), hydroxytomatine, acetoxytomatine, soladulcidine, β-soladulcine, soladulcine A, an unsaturated or saturated steroidal saponin or a glycoside derivative thereof, a leptin, or a leptinine, or any combination thereof. In some embodiments, increased SA or SGA results in a plant, wherein said plant resistance to at least one plant pathogen, pests or predator is increased, compared to a corresponding non-transformed plant.

In some embodiments, provided herein is a method for selecting plant progenitors for plant breeding, said method comprising a step of determining the expression level of GAME25, GAME31, or a combination thereof, wherein expression levels of GAME25, GAME31, or a combination thereof, below a pre-determined value are predictive of low content of at least one cholesterol derived compound selected from the group comprising a steroidal alkaloid or a glycosylated derivative thereof and an unsaturated or saturated steroidal saponin or a glycoside derivative thereof in the offspring plants.

In some embodiments, provided herein is a method for selecting plant progenitors for plant breeding, said method comprising a step of determining the expression level of GAME25, GAME31, or a combination thereof, wherein expression levels of GAME25, GAME31, or a combination thereof, above a pre-determined value are predictive of high content of at least one cholesterol derived compound selected from the group comprising a steroidal alkaloid or a glycosylated derivative thereof and an unsaturated or saturated steroidal saponin or a glycoside derivative thereof in the offspring plants.

In some embodiments, a method for selecting plant progenitors, comprises a step of (a) determining the expression level of a gene encoding a 3-β-hydroxysteroid dehydrogenase/isomerase (GAME25), or a 2-oxoglutarate-dependent dioxygenase (GAME31), or a combination thereof, wherein expression levels of said GAME25 gene, or said GAME31 gene, or the combination thereof, is predictive of altered content of at least one cholesterol derived compound selected from the group comprising a steroidal alkaloid or a glycosylated derivative thereof and an unsaturated or saturated steroidal saponin or a glycoside derivative thereof in an offspring plant; or (b) determining the biological activity of a 3-β-hydroxysteroid dehydrogenase/isomerase (GAME25), or a 2-oxoglutarate-dependent dioxygenase (GAME31), or a combination thereof, wherein biological activity of said GAME25 enzyme, or said GAME31 enzyme, or the combination thereof, is predictive of altered content of at least one cholesterol derived compound selected from the group comprising a steroidal alkaloid or a glycosylated derivative thereof and an unsaturated or saturated steroidal saponin or a glycoside derivative thereof in an offspring plant.

In some embodiments, a method for determining the capacity of a plant to produce steroidal alkaloids or glycosylated derivatives thereof in at least a part of said plant, comprises a step of measuring the expression level of GAME25, or GAME31, or a combination thereof, in at least a part of said plant; or measuring the biological activity of a 3-β-hydroxysteroid dehydrogenase/isomerase (GAME25), or a 2-oxoglutarate-dependent dioxygenase (GAME31), or a combination thereof, in at least a part of said plant; or a combination thereof. In some embodiments, the steroidal alkaloids or glycosylated derivatives thereof are selected from the group comprising: tomatidine, α-tomatine, α-tomatine isomer (1 and 2), α-tomatine isomer 1, α-tomatine isomer 2, hydroxytomatine, acetoxytomatine, dehydrotomatidine, dehydrotomatine, dehydrotomatine isomer 1, dehydrotomatine 4-hexose, acetoxy-hydroxytomatine, acetoxy-hydroxy-dehydrotomatine, tomatidine+4 hexose, esculeosides, esculeoside A, esculeoside A+hexose, esculeoside B, acetoxyesculeoside B, demissidine, demissine, dehydrosolasodine, hydroxy-dehydrotomatine, acetoxy-hydroxy-dehydrotomatine, dehydroesculeosides, dehydroesculeoside A, dehydroesculeoside A+hexose, lycoperosides, leptinine I, leptinine II, leptine I, leptine II, soladulcidine, β-soladulcine, soladulcine A, an unsaturated or saturated steroidal saponin or a glycoside derivative thereof, solanidine, α-solanine, α-chaconine, solasoidine, α-solasonine, α-solamargine, hydroxysolasonine, and hydroxysolamargine, or any derivatives thereof, or any combination thereof.

In some embodiments, disclosed herein are methods for breeding a plant having an altered expression of at least one gene selected from the group comprising GAME25, GAME31, or a combination thereof, said method comprising providing a first transformed plant, wherein said first transformed plant is transformed with an expression vector comprising a polynucleotide comprising at least one silencing molecule targeted to a nucleic acid sequence encoding at least one protein selected from the group comprising GAME25, GAME31, or a combination thereof, wherein said at least one silencing molecule is operably linked to a promoter; providing a second non-transformed plant; crossing said first and second plants to generate an offspring hybrid plant, wherein the offspring hybrid plant comprises the expression vector; and selecting an offspring hybrid plant that has an altered content of at least one cholesterol derived compound selected from the group comprising a steroidal alkaloid or a glycosylated derivative thereof and an unsaturated or saturated steroidal saponin or a glycoside derivative thereof compared to a corresponding unmodified plant.

In some embodiments, an expression vector is operably linked to a different promoter so that the expression of the silencing molecule can be controlled under different conditions. In another embodiment, the silencing molecule is operably linked to a constitutive promoter. In another embodiment, the silencing molecule is operably linked to an inducible promoter. In another embodiment, the silencing molecule is operably linked to a tissue active or specific promoter. In another embodiment, the silencing molecule is operably linked to a developmental-stage active or specific promoter. When the silencing molecule is linked to a constitutive promoter, changes in expression of a gene will be observed in all tissues and at all times and a broad overview of the effects of the expression of the gene on a plant will be observed. When the silencing molecule is linked to a tissue specific promoter or an inducible promoter or developmental-stage promoter, the expression of the silencing molecule may be turned on or off in a particular tissue such as seed, roots, flowers, leaves, shoots, fruits or stems, during a particular period in development, such as early, middle or late stages in development, or under particular conditions, such as specific environmental or disease stresses. In some embodiments, a plant may be transformed with more than one expression vector. In one embodiment, the at least one silencing molecule is operably linked to a constitutive promoter, an inducible promoter, a tissue-specific promoter, or a developmental-stage specific promoter.

In some embodiments, a hybrid plant is then selected wherein said plant comprises the desired expression of GAME25, or GAME31, or a combination thereof. In some embodiment, the expression level of GAME25, GAME31, or a combination thereof, provide a marker for a plant comprising altered content of at least one cholesterol derived compound selected from the group comprising a steroidal alkaloid or a glycosylated derivative thereof and an unsaturated or saturated steroidal saponin or a glycoside derivative thereof. In some embodiments, use of GAME25 levels, or GAME31 levels, or a combination thereof as a marker provides the ability to select a plant breed to comprise a reduced content of an anti-nutritional or toxic cholesterol derived compound selected from the group comprising a steroidal alkaloid or a glycosylated derivative thereof and an unsaturated or saturated steroidal saponin or a glycoside derivative thereof, as compared to a control plant. In some embodiments, use of GAME25 levels, or GAME31 levels, or a combination thereof as a marker provides the ability to select a plant breed to comprise improved resistance to a plant pathogen, pest, or predator, as compared to a control plant.

In one embodiment, the method combines genomic and plant breeding techniques. In one embodiment, the method alters the expression level or levels of GAME25, GAME31, or a combination thereof. Expression levels may be altered constitutively, or altered selectively to monitor tissue specific expression, inducible expression, developmental-stage specific expression or the like in a high-throughput manner. In another embodiment, the expression of these known genes, or the enzymes they encode, act as markers for breeding plants having SA or SGA derivatives comprising beneficial properties, for example SA or SGA derivatives that provide increased resistance to pathogens, pests, or predators, plants having a decreased anti-nutritional content or decreased toxins, or any combination thereof.

In some embodiments, transformation techniques including breeding through transgene editing, use of transgenes, use of transient expression of a gene or genes, or use of molecular markers, or any combination thereof, may be used in the breeding of a plant having an altered expression. If transformation techniques require use of tissue culture, transformed cells may be regenerated into plants in accordance with techniques well known to those of skill in the art. The regenerated plants may then be grown and crossed with the same or different plant varieties using traditional breeding techniques to produce seed, which are then selected under the appropriate conditions.

In some embodiments, an offspring plant comprises decreased anti-nutritional contents or decreased toxins compared to at least one of the progenitor plants. In some embodiments, an offspring plant comprises improved resistance to a plant pathogen, pest, or predator compared to at least one of the progenitor plants.

In one embodiment, a plant as disclosed herein comprises a Solanaceae crop plant. In some embodiments, a Solanaceae crop plant is selected from the group comprising *Solanum lycopersicum, Solanum pennellii, Solanum tuberosum, Solanum chacoense, Capiscum annuum,* and *Solanum melongena*. In some embodiments, a Solanaceae plant is selected from the group comprising ground cherry, eggplant, potato, tomato, pepper, bell pepper, cayenne pepper, chili pepper, pimiento, tabasco pepper, tobacco, and bittersweet. In some embodiments, a Solanaceae plant comprises any Solanaceae plant that produces a steroidal alkaloid or a glycosylated derivative thereof, or an unsaturated or saturated steroidal saponin or a glycoside derivative thereof, or any combination thereof.

A skilled artisan would appreciate that plant breeding can be accomplished through many different techniques ranging from simply selecting plants with desirable characteristics for propagation, to methods that make use of knowledge of genetics and chromosomes, to more complex molecular techniques.

A skilled artisan would appreciate that the term "hybrid plant" may encompass a plant generated by crossing two plants of interest, propagating by seed or tissue and then growing the plants. When plants are crossed sexually, the step of pollination may include cross pollination or self-pollination or back crossing with an untransformed plant or another transformed plant. Hybrid plants include first generation and later generation plants. Disclosed herein is a method to manipulate and improve a plant trait, for a non limiting example—increasing plant resistance, decreasing anti-nutritional properties in a plant, or decreasing toxins in a plant, or any combination thereof.

Biomarkers

A skilled artisan would appreciate that the term "biomarker" comprises any measurable substance in an organism whose presence is indicative of a biological state or a condition of interest. In some embodiments, the presence of a biomarker is indicative of the presence of a compound or a group of compounds of interest. In some embodiments, the concentration of a biomarker is indicative of the concentration of a compound or a group of compounds of interest. In some embodiments, the concentration of a biomarker is indicative of an organism phenotype.

The enzymes GAME25 and GAME31, are hereby disclosed to have an essential role in the biosynthesis of steroidal alkaloids found in Solanaceae plants. Thus, in some embodiments, the expression levels of GAME25, GAME31, or a combination thereof, are indicative of the capacity of a plant to produce steroidal alkaloids or glycosylated derivatives thereof.

In some embodiments, disclosed herein is a method for determining the capacity of a plant to produce steroidal alkaloids or glycosylated derivatives thereof in at least a part of said plant, the method comprising a step of determining the expression level of GAME25, or GAME31, or a combination thereof, in at least a part of said plant. In some embodiments, said expression level is compared to a pre-determined value. In some embodiments, expression levels above a pre-determined value indicate a high capacity of a plant to produce steroidal alkaloids or glycosylated derivatives thereof. In some embodiments, expression levels below a pre-determined value indicate a low capacity of a plant to produce steroidal alkaloids or glycosylated derivatives thereof.

In some embodiments, the expression level of GAME25, or GAME31 are determined in at least a part of the plant, wherein said part of said plant is selected from the group comprising: a peel, a leaf, a bud, a petal, a root, an edible part of the plant, and any combination thereof. In some embodiments, the plant is a Solanaceae crop plant. In some embodiments, the steroidal alkaloids or glycosylated derivatives thereof are produced in at least a part of the plant, wherein said part of said plant is selected from the group comprising: a peel, a leaf, a bud, a petal, a root, an edible part of the plant, and any combination thereof. In some embodiments, a leaf comprises a young leaf. In some embodiments, a leaf comprises a mature leaf.

In some embodiments, said steroidal alkaloids or glycosylated derivatives thereof are selected from the group comprising: tomatidine, α-tomatine, α-tomatine isomer (1 and 2), hydroxytomatine, acetoxytomatine, acetoxy-hydroxytomatine, tomatidine+4 hexose, esculeoside A, esculeoside A+hexose, esculeoside B, acetoxyesculeoside B, demissidine, demissine, dehydrosolasodine, hydroxy-dehydrotomatine, acetoxy-hydroxy-dehydrotomatine, dehydroesculeosides, leptinine I, leptinine II, leptine I, leptine II, and hydroxysolamargine, or any derivatives thereof, or any combination thereof.

In some embodiments, disclosed herein is a method for determining the capacity of a plant to produce tomatidine in at least a part of said plant, said method comprising a step of determining the expression level of GAME25, or GAME31, or a combination thereof, in at least a part of said plant. In some embodiments, disclosed herein is a method for determining the capacity of a plant to produce α-tomatine in at least a part of said plant, said method comprising a step of determining the expression level of GAME25, or GAME31, or a combination thereof, in at least a part of said plant. In some embodiments, disclosed herein is a method for determining the capacity of a plant to produce hydroxytomatine in at least a part of said plant, said method comprising a step of determining the expression level of GAME25, or GAME31, or a combination thereof, in at least a part of said plant. In some embodiments, disclosed herein is a method for determining the capacity of a plant to produce acetoxytomatine in at least a part of said plant, said method comprising a step of determining the expression level of GAME25, or GAME31, or a combination thereof, in at least a part of said plant.

In some embodiments, disclosed herein is a method for determining the capacity of a plant to produce acetoxy-hydroxytomatine in at least a part of said plant, said method comprising a step of determining the expression level of GAME25, or GAME31, or a combination thereof, in at least a part of said plant. In some embodiments, disclosed herein is a method for determining the capacity of a plant to produce tomatidine+4 hexose in at least a part of said plant, said method comprising a step of determining the expression level of GAME25, or GAME31, or a combination thereof, in at least a part of said plant. In some embodiments, disclosed herein is a method for determining the capacity of a plant to produce esculeoside A in at least a part of said plant, said method comprising a step of determining the expression level of GAME25, or GAME31, or a combination thereof, in at least a part of said plant. In some embodiments, disclosed herein is a method for determining the capacity of a plant to produce esculeoside A+hexose in at least a part of said plant, said method comprising a step of determining the expression level of GAME25, or GAME31, or a combination thereof, in at least a part of said plant.

In some embodiments, disclosed herein is a method for determining the capacity of a plant to produce esculeoside B in at least a part of said plant, said method comprising a step of determining the expression level of GAME25, or GAME31, or a combination thereof, in at least a part of said plant. In some embodiments, disclosed herein is a method for determining the capacity of a plant to produce acetoxyesculeoside B in at least a part of said plant, said method comprising a step of determining the expression level of GAME25, or GAME31, or a combination thereof, in at least a part of said plant. In some embodiments, disclosed herein is a method for determining the capacity of a plant to produce demissidine in at least a part of said plant, said method comprising a step of determining the expression level of GAME25, or GAME31, or a combination thereof, in at least a part of said plant. In some embodiments, disclosed herein is a method for determining the capacity of a plant to produce demissine in at least a part of said plant, said method comprising a step of determining the expression level of GAME25, or GAME31, or a combination thereof, in at least a part of said plant. In some embodiments, disclosed herein is a method for determining the capacity of a plant to produce dehydrosolasodine in at least a part of said plant, said method comprising a step of determining the expression level of GAME25, or GAME31, or a combination thereof, in at least a part of said plant.

In some embodiments, disclosed herein is a method for determining the capacity of a plant to produce hydroxy-dehydrotomatine in at least a part of said plant, said method comprising a step of determining the expression level of GAME25, or GAME31, or a combination thereof, in at least a part of said plant. In some embodiments, disclosed herein is a method for determining the capacity of a plant to produce acetoxy-hydroxy-dehydrotomatine in at least a part of said plant, said method comprising a step of determining the expression level of GAME25, or GAME31, or a combination thereof, in at least a part of said plant. In some embodiments, disclosed herein is a method for determining the capacity of a plant to produce dehydroesculeosides in at least a part of said plant, said method comprising a step of determining the expression level of GAME25, or GAME31, or a combination thereof, in at least a part of said plant. In some embodiments, disclosed herein is a method for determining the capacity of a plant to produce leptinine I in at least a part of said plant, said method comprising a step of determining the expression level of GAME25, or GAME31, or a combination thereof, in at least a part of said plant.

In some embodiments, disclosed herein is a method for determining the capacity of a plant to produce leptinine II in at least a part of said plant, said method comprising a step of determining the expression level of GAME25, or GAME31, or a combination thereof, in at least a part of said plant. In some embodiments, disclosed herein is a method for determining the capacity of a plant to produce leptine I in at least a part of said plant, said method comprising a step of determining the expression level of GAME25, or GAME31, or a combination thereof, in at least a part of said plant. In some embodiments, disclosed herein is a method for determining the capacity of a plant to produce leptine II in at least a part of said plant, said method comprising a step of determining the expression level of GAME25, or GAME31, or a combination thereof, in at least a part of said plant. In some embodiments, disclosed herein is a method for determining the capacity of a plant to produce hydroxysolamargine in at least a part of said plant, said method comprising a step of determining the expression level of GAME25, or GAME31, or a combination thereof, in at least a part of said plant.

In some embodiments, disclosed herein is a method for selecting a plant with reduced content of an anti-nutritional or toxic cholesterol derived compound selected from the group comprising a steroidal alkaloid or a glycosylated derivative thereof and an unsaturated or saturated steroidal saponin or a glycoside derivative thereof, as compared to a control plant, said method comprising a step of determining the expression level of GAME25, or GAME31, or a combination thereof, in said plant, wherein expression level below a pre-determined value indicates reduced content of an anti-nutritional or toxic cholesterol derived compound selected from the group comprising a steroidal alkaloid or a glycosylated derivative thereof and an unsaturated or saturated steroidal saponin or a glycoside derivative thereof.

In some embodiments, disclosed herein is a method for selecting a plant with improved resistance to a plant pathogen, pest, or predator, as compared to a control plant, said method comprising a step of determining the expression level of GAME25, or GAME31, or a combination thereof, in said plant, wherein expression level above a pre-determined value indicates improved resistance to a plant pathogen, pest, or predator.

In some embodiments, disclosed herein is a method for selecting a plant with altered content of steroidal alkaloids or glycosylated derivatives thereof, as compared to a control plant, said method comprising a step of determining mutations in GAME25, or GAME31, or a combination thereof, in said plant, wherein mutations indicate altered content of steroidal alkaloids or glycosylated derivatives thereof. In some embodiments, disclosed herein is a method for selecting a plant with decreased content of steroidal alkaloids or glycosylated derivatives thereof, as compared to a control plant, said method comprising a step of determining mutations in GAME25, or GAME31, or a combination thereof, in said plant, wherein mutations indicate decreased content of steroidal alkaloids or glycosylated derivatives thereof.

Further, one skilled in the art would appreciate that the term "comprising" used throughout is intended to mean that the genetically modified plants disclosed herein, and methods of altering expression of genes, and altering production of SA and/or SGA within these genetically modified plants includes the recited elements, but not excluding others which may be optional. "Consisting of" shall thus mean excluding more than traces of other elements. The skilled artisan would appreciate that while, in some embodiments the term "comprising" is used, such a term may be replaced by the term "consisting of", wherein such a replacement would narrow the scope of inclusion of elements not specifically recited.

The following examples are presented in order to more fully illustrate embodiments described herein above. They should in no way be construed, however, as limiting.

EXAMPLES

Example 1

Expression of GAME25, a Short-Chain Dehydrogenases/Reductases Family Member Accords with the Accumulation of the Typical Green Tissue Steroidal Glycoalkaloids Objective:

GAME9 AP2-type transcription factor is associated with the regulation of steroidal glycoalkaloids (SGAs) biosynthesis in tomato and potato. Transcriptome analysis of GAME9 overexpressing (GAME9-Ox) and GAME9 silenced (GAME9-RNAi) tomato lines revealed a concise set of 27 genes that were common among up- and down-regulated genes. Among these genes, a putative 3-β-hydroxysteroid dehydrogenase/isomerase was identified and termed GAME25 (SEQ ID NO: 1). To understand the role of this gene, the expression pattern of GAME25 was examined in 14 different tomato tissue types.

Methods:

Plant Materials

Tomato (*Solanum lycopersicum*) cultivar (cv). MicroTom plants were grown in a climate-controlled greenhouse at 24° C. during the day and 18° C. during the night, with natural light.

The database SolGenomics (Fernandez-Pozo N, Menda N, Edwards J D, Saha S, Tecle I Y, Strickler S R, Bombarely A, Fisher-York T, Pujar A, Foerster H, Yan A, Mueller L A. The Sol Genomics Network (SGN) from genotype to phenotype to breeding. (2015) Nucleic Acids Res. Volume 43 (Database issue):D1036-41) was used for searching and analyzing sequences.

Quantitative Real-Time PCR (qPCR) Analysis

Total RNA was isolated from tomato (leaf, green fruit, breaker and red fruits) tissues using the Trizol method (Sigma-Aldrich). DNase I (Sigma-Aldrich)-treated RNA was reverse transcribed using a high-capacity cDNA reverse transcription kit (Applied Biosystems). Gene-specific oligonucleotides were designed with Primer Express 3 software (Applied Biosystems). The TIP41 gene was used as a reference gene for tomato samples.

```
GAME25 qRT Forward primer:
                                       (SEQ ID NO: 4)
GAAGCAATTTACGGTAATGGACAC GAME25 qRT Reverse primer:
                                       (SEQ ID NO: 5)
GAACTTAGTCCACCATCAACAGC
```

Figure 4A:
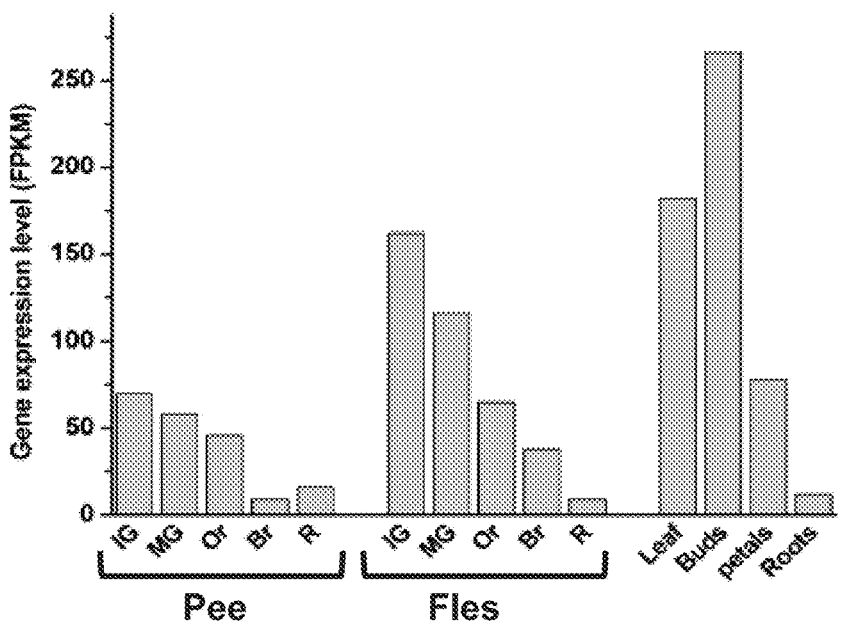
FIGS. 4A-4B show levels of major SGAs and expression profile of GAME25 in various tomato wild accessions.

Results:

GAME25 showed higher expression in flower buds and young leaves compared to fruit specific tissues. During fruit development highest expression of GAME25 was observed at the early stage of fruit development, i.e. immature green (IG) fruit (FIG. 4A).

Figure 4B:
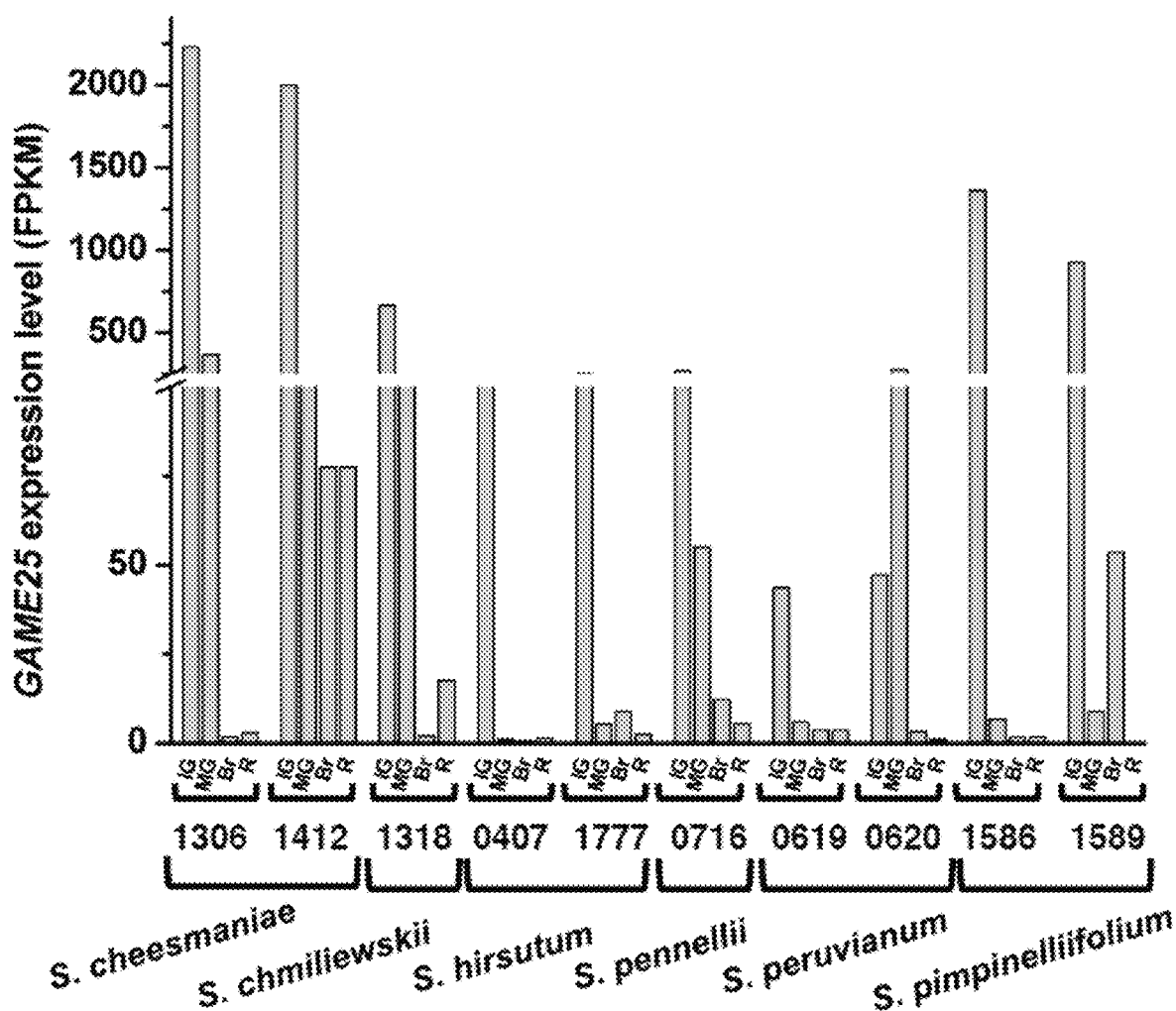

The expression pattern of GAME25 was similar to the profile of steroidal glycoalkaloids (SGAs) α-tomatine and dehydrotomatine that accumulate predominantly in green tissues (leaves, buds, peel and flesh of immature green fruit). For example, the reduced transcript levels of the GAME25 gene observed at later time points of fruit development correlates with the typical pattern of reduction of α-tomatine and dehydrotomatine levels observed during fruit development and ripening. Moreover, GAME25 expression in pattern during tomato fruit developmental stages was similar to the one observed in wild tomato accessions (FIG. 4B).

Conclusion:

The association between GAME25 transcript level and accumulation of α-tomatine and dehydrotomatine SGAs in the tissues examined suggests a possible role of GAME25 in steroidal glycoalkaloid metabolism.

Example 2

Characterization of GAME25 as a Short-Chain Dehydrogenases/Reductases Family Member Objective:

To characterize GAME25 structurally and functionally.

Methods:

Phylogenetic Analysis

GAME25 and its homologous sequences from various plants were obtained using the BLASTP program. Additionally, literature search was performed for known SDR family proteins that partake in secondary metabolism among various plant species. Amino acid sequences were aligned using ClustalOmega. The Maximum Likelihood tree was inferred in MEGA6 using 1000 bootstrap replications. Evolutionary distances are in units of number of amino acid substitutions per site. All positions containing gaps and missing data were eliminated. The amino acid sequences used in the phylogenetic analysis are provided in below.

```
S. lycopersicum GAME25:
                                       (SEQ ID NO: 3)
MANKLRLEGKVAIITGAASGIGEASARLFVEHGARVVVADIQDELGQKV

VDSIGSDKASYRHCDVTDEKQVEETVAYAVEKYGTLDIMFSNVGTLNFCSVLD

MDVLAFDETMAINVRGSALAVKHAAKVMVDKKIRGSIICNASLEGILAGAASL

AYIASKHAVVGIIKAAARELGPHGIRVNGVSPYGIATPLVTKAYGLDAALLEEAI

YGNGHLKGVKLSTMHVAQSALFLASDESAYTSGQNLAVDGGLSSILKLQ

S. pennellii GAME25:
                                       (SEQ ID NO: 12)
MANKLRLEGKVAIITGAASGIGEASARLFVEHGARVVVADIQDELGQKV

VDSIGADKASYRHCDVTDEKQVEETVAYAVEKYGTLDIMFSNVGTLNFCSVLD

MDVMAFDETMAINVRGSALAVKHAAKVMVDKKIRGSIICNASLEGILAGAASL

AYIASKHAVVGIIKAAARELGPHGIRVNGVSPYGIATPLVCKAYGLDAALLEEAI

YGNGHLKGVKLSTMHVAQSALFLASDESAYTSGQNLAVDGGLSSILKLQ

S. tuberosum GAME25:
                                       (SEQ ID NO: 15)
MANKLRLEGKVAIITGAASGIGEASARLFAEHGARIVVADIQDELGLKV

VESIGADKASYRHCDVTDEKQVEDTVAYTVEKYGTLDIMFSNVGTLNFCSVLD

MDVMVFDKTMAINARGSALAVKHAARFMVDKKIRGSIICNASLDGIVAGATSL

AYIASKHAVVGIVKAAARDLGPYGIRVNGVSPYGIATPLVCKAYGLDAGPLEA

AIYGNGNLKGVRLSTMHVAQSALFLASDESAYTSGQNLAVDGGLSSILKVQ
```

-continued

S. lycopersicum 3βHSD:
(SEQ ID NO: 66)
MASKLRLEGKVAIITGGASGIGEASARLFVQHGARVVVADIQDELGLQV

VQSIGIHKATYRHCDVTDEKQVEDTVAYAVQKYATLDIMFSNVGTLNFCSVLD

MDMTAFDETMTVNVRGSALAVKHAARVMVDKKIRGSIICNVSLEGILAGAASL

AYIASKHAVVGIVKAAARELGPYGIRVNGVSPYGIATPLVCKAYGLDAAPLEA

AINGNANLKGVTLSTMHVAQSALFLASDESAYTSGQNLAVDGGLSSILKLQ

S. pennellii 3βHSD:
(SEQ ID NO: 67)
MASKLRLEGKVAIITGGASGIGEASARLFVQHGARVVVADIQDELGLQV

VQSIGIHKATYRHCDVTDEKQVEDTVAYAVQKYATLDVMFSNVGTLNFCSVL

DMDMTAFDETMTVNVRGSALAVKHAARVMVDKKIRGSIICNVSLEGILAGAAS

LAYIASKHAVVGIVKAAARELGPYGIRVNGVSPYGIATPLVCKAYGLDAAPLEA

AINGNANLKGVTLSTMHVAQSALFLASDESAYTSGQNLAVDGGLSSILKLQ

C. annuum 3βHSD:
(SEQ ID NO: 68)
LEGKVAVITGAASGIGEASARLFVEHGARVVIADIQDELGLQIAASIGTD

KASYIHCDVTDEKQVEEAVAYAVENSVLDLDVKAFDETMVINARGSAVAVKH

AARVMVEKKIRGSIICTASLEGILAGAASLAYVSSKHAVVGLVKAAARELGVH

GIRVNGVSPYGIATPLVCKAYGLDAGPLETAIYGNAHLKGVTLSTMHVAQAAL

FLASDESAYISGQNLAVDGGLSSILKLE

N. benthamiana 3βHSD:
(SEQ ID NO: 69)
MANKLRLEGKVAVITGGASGIGEATARLFVEHGARVVIADIQDELGLQV

VASIGTDKASYRHCDVTDENKVEETVAYAVEKYGTLDIMFSNVGTLNFCSVLD

IDVTAFDKTMALNVRGTALAVKHAARVMVAKQVKGSIICNASIEAILAGAASL

AYVASKHAVVGIVKAAARELGLHGIRVNGVSPYGIATPLVCKAYGCEDAASLE

AGISVNAHLKGVTLSTEHIAQAALFLASDESAYISGHNLAVDGGLTSMLKLSY

S. melongena ADH1:
(SEQ ID NO: 70)
MANKLKLEGKVAVITGGASGIGEESARLFVEHGARVVIADIQDDLGLEV

VTSIGADKACYRHCDVSEEKQVKETVAYAVEKYGTLDIMFSNAGTLGTLGSVL

EMDMTAFDMTMAVNMRGSALAVKHAARVMVANKIRGSIICTASVEAILAGAA

PLAYVASKHAILGVMKAAARELGQYGIRVNCVSPYGIATPLVCKAYHSDAGSL

EASIYERAHLKGITLSTKHIANASLFLASDESAYVSGHNLAVDGALSSIMS

C. annuum ADH1:
(SEQ ID NO: 71)
MIFFFCGTRLEGKIAIITGAASGIGEASARLFVEHGAHVIIADIQDELGLQV

VSSIGTDKACYRHCDVTDEKQVEETVAYAVEKYGTLDIMFSNAGMLGTFGSLL

DMDVKEFDLTIAVNTRGAALAVKHAARVMVAKNIRGSIICTASVESILAGAAPL

AYIASKHGILGVVKAAARELGKNGIRVNCVSPFGIATPMVCKSYGAEASYIETS

VGGHANLKGVSLTTKHIAEAALFLASEESAYISGQNLAVDGGLSAIMRLD

S. melongena ADH2:
(SEQ ID NO: 72)
MANKLRLEGKVAVITGGASGIGEASARLFVEHGARVVIADIQDELSLQV

VSSIGGDKACYRRCDVSDEKQVEETVAYAVEKYGTLDIMFSNAGILGSFGSLLE

MDMTAFDRIMAVNTRGAALAVKHAARVMVANKIRGSIICTASVEAILAGEASL

-continued

AYIASKHAILGVVKAAARDLGQYGIRVNCVSPYGIATPMVCKSIGADAATIEAR

ICGNANLKGVSLNTKHIAEAALFLGSDESAYVSAHNLAVDGGLSSIMKLN

*S. tuberosum* ADH1:
(SEQ ID NO: 73)
MANKLRLEGKVAVITGGASGIGEATARLFVEHGAHVVIADIQDELALQV

VSSIGSDNVCYRRCDVTDEKQVDETVAFAVQKYGTLDIMFSNAGILGSSGSLLE

MDMAVFDRTMAVNTRGAALAVKHAAKVMVAKKIRGSIICTASVESILAGAAS

LAYIASKHAVLGVVKAAARELGQHGIRVNCVSPFGVATPMVCKSFGADAAAM

EATIRGNANLKGVSLTTMHIAEAALFLASDESAYISAHNLAIDGGLSSIMKINVN

*S. lycopersicum* ADH1:
(SEQ ID NO: 74)
MANKLRLEGKVAVITGGASGIGEAAARLFVEHGARVVIADIQDELALQV

ASSIGSDNVCYQRCDVSDEKQVNETVAFAVEKYGTLDIMFSNAGILNPFESILE

MDMTVFDRTIAVNARGAALAVKHAARVMVANKIRGSIICTASVESILAGAAPL

AYIASKHAVLGVVKAAARELGQHGIRVNCVSPFGIATPMVCKSFGADAAAIEA

KICGNANLKGVSLTTMHIAEAALFLASDESAYISAQNLAVDGGLSSMMKLM

*S. pennellii* ADH1:
(SEQ ID NO: 75)
MANKLRLEGKVAVITGGASGIGEAAARLFVEHGARVVIADIQDELALQV

ASSIGSVNVCCRRCDVSDEKQVNETVAFAVEKYGTLDIMFSNAGILNPFESILEM

DMTVFDRTIAVNARGAALAVKHAARVMVANKIRGSIICTASVESILAGAAPLA

YIASKHAVLGVVKAAARELGQHGIRVNCVSPFGIATPMVCKSFGADAAAIEAKI

CGNANLKGVSLTTMHIAEAALFLASDESAYISAQNLAVDGGLSSMMKLM

*N. benthamiana* ADH1:
(SEQ ID NO: 76)
MANKRRLEGKVAVITGAASGIGEATARLFVEHGARVVIADIQDELGHQV

VASIGTDKASYRHCDVTDEKQVEDTVVYTVEKYGTLDIMFSNAGTIGTLGSILD

MDMTVFDRTMAINARGSALAVKHAARVMVTKKIQGSIICTASLEATLAGAAPL

AYVTSKHAILGVVKAAARELGQHGIRVNCVSPYGIATPMVCKTFGGDAAPIEAS

ISGNANLKGITLSTKHIAEAALFLASDESAYVSAHNLAVDGGLSSIMKLD

*N. benthamiana* ADH2:
(SEQ ID NO: 77)
MANKLRLEGKVAVITGAASGIGEATARLFVEHGARVVIADIQDELGHQV

VASIGTDKASYRHCDVTDEKQVEDTVVYAVEKYGTLDIMFSNAGTIGTLSSILD

MDMTVFDRTMAINARGSALAVKHAARIMVTKKIQGSIICTASLEAILAGAAPLA

YVASKHAILGVVKAAARELGQHGIRVNCVSPYGIATPMVCKTFGGDAAPIEASI

SGNANLKGITLSTKHIAEAALFLASDESAY

*A. thaliana* ADH:
(SEQ ID NO: 78)
MSGKRLDGKIVIITGGASGIGAESVRLFTEHGARVVIVDVQDELGQNVA

VSIGEDKASYYHCDVTNETEVENAVKFTVEKYGKLDVLFSNAGVIEPFVSILDL

NLNELDRTIAINLRGTAAFIKHAARAMVEKGIRGSIVCTTSVAAEIAGTAPHGYT

TSKHGLLGLIKSASGGLGKYGIRVNGVAPFGVATPLVCNGFKMEPNVVEQNTS

ASANLKGIVLKARHVAEAALFLASDESAYVSGQNLAVDGGYSVVKP

*M. truncatula* ADH:
(SEQ ID NO: 79)
MSRKRLEGKVAIVTGGASGIGAETAKTFVENGAFVVIADINDELGHQVA

TSIGLDKVSYHHCDVRDEKQVEETVAFALEKYGTLDIMFSNAGIEGGMSSSILEF

DLNEFDNTMAINVRGSLAAIKHAARFMVERKIRGSIICTASVAASVAGNRGHDY

VTSKHGLLGLVRSTCGELGAYGIRVNSISPYGVATPLACRALNMEMSKVEANM

KDSANLKGITLKATHIAEAALFLASEESAYISGHNLVVDGGFSVINSCVPTTIKK

*C. annuum* ADH2:
(SEQ ID NO: 80)
MAVVMQKLKGKVAIVTGGASGIGEATVRLFAEHGARAVVIADIQDEKG

RAVAESIPLQVCSYVHCDVSDENQVKGLVDWTVKKYGQLDIMFSNAGTVGNS

GQKVLDLDLSEFDRVIRVNARGMAACVKHAARAMVEQGGRGSIICTGSVGAS

KGAAWRTDYTMSKHAVLGLVTSASRQLGKYGIRVNSISPSAVMTPLMSSAEAE

TSMKVLKMYGPLTSLKGITLTVKHLADAVLFLASDDSAFVNGHDLLVDGGLLH

LPDPMSSL

*S. tuberosum* ADH2:
(SEQ ID NO: 81)
MAEVTQKLKGKVAIVTGGASGIGEATARLFAQHGARAVVIADIQDGKG

RAVAVSIPSQICSYVQCDVSDENQVKAMVDWTVQKYGQLDIMFSNAGVVGNS

GQKVLDLDLSEFDRVMNVNARGMAACVKHAARAMVDKRVRGSIICTGSIGAS

RGGAWRTDYIMSKHAVLGLVRSACRQLGEYGIRVNSISPSAVMTPLMISAEPEV

SMKSLKRYGPQTSLKGITLTVKHLAEAALFLASDDSAFSSRSNEFIVKQREQPNL

SLFFF

*S. melongena* ADH3:
(SEQ ID NO: 82)
MSAITQKLNGKVAIVTGGASGIGEATVRLFAQHGARAVVIADIQDEKGR

AVAQSIPSQICIYVKCDVSDENQVKSMVDWTVQQYGQLDIMFSNAGTVGNSGQ

KILDLDLSEFDRVMNVNARGMAACVKHAARAMVEKRVRGSIICTGSIAASRAG

AWRTDYAMSKHAVLGLMRSASRQLGEYGIRVNSISPSAVMTPLMISAEAEASM

RVLKMYGSVTSLKGITLTVKHLADAVLFLASDDSVFVSGHDLAVDGGLISLPDP

MSSL

*O. sativa* MIS2:
(SEQ ID NO: 83)
MFTAMHRILSRGRRTPAASSSSVTAFATASDSQRLAGKVAVITGGASGIG

RATAEEFVRNGAKVILADVQDDLGHAVAAELGADAASYARCDVTDEAQVAA

AVDLAVARHGRLDVVFNNAGIPGDLTPTPVGALDLADFDRVMAVNTRAVVAG

VKHAARVMVPRRRGSIICTASTAGVIGGVAVPHYSVSKAAVLGLVRAVAGEM

ARSGVRVNAISPNYIWTPMAAVAFARWYPSRSADDHRRIVENDINEMDGVTLE

AEDVARAAVFLASDEAKYVNGHNLVVDGGYTVGKVPNMPVPDGH

*O. sativa* MIS3:
(SEQ ID NO: 84)
MFRAAQLLLRETNRALGAATSPAGFVSGFSTASNSAQRLAGKVAVITGG

ASGIGKATAKEFIENGAKVIMADVQDDLGHSTAAELGPDASYTRCDVTDEAQV

AAAVDLAVKRHGHLDILYNNAGVMGAMPQDDMASVDLANFDRMMAINARA

ALVGIKHAARVMSPRRSGVILCTASDTGVMPMPNIALYAVSKATTIAIVRAAAE

PLSRHGLRVNAISPHGTRTPMAMHVLSQMYPGVSKDDLEKMADAAMDAGEV

MEPKYVARAALYLASDEAKYVNGHNLVVDGGFTSHKGSDTRLN

*A. thaliana* ABA2:
(SEQ ID NO: 85)
MSTNTESSSYSSLPSQRLLGKVALITGGATGIGESIVRLFHKHGAKVCIVD

LQDDLGGEVCKSLLRGESKETAFFIHGDVRVEDDISNAVDFAVKNFGTLDILIN

NAGLCGAPCPDIRNYSLSEFEMTFDVNVKGAFLSMKHAARVMIPEKKGSIVSLC

SVGGVVGGVGPHSYVGSKHAVLGLTRSVAAELGQHGIRVNCVSPYAVATKLA

LAHLPEEERTEDAFVGFRNFAAANANLKGVELTVDDVANAVLFLASDDSRYIS

GDNLMIDGGFTCTNHSFKVFR

O. sativa MS3:
(SEQ ID NO: 86)
MAGSSYGDVHESARKLVGKVALITGGASGIGECTARLFVKHGAQVVVA

DIQDEAGARLCAELGSATASYVRCDVTSEDDVAAAVDHAVARYGKLDVMFN

NAGIGGAACHSILESTKADFDRVLAVNLTGPFLGTKHAARVMVAAGRGGCIIG

TASLASAVAGTASHAYTCAKRALVGLTENAAAELGRHGIRVNCVSPAAAATPL

ATGYVGLEGEAFEAAMEAVANLKGVRLRVEDIAAAVLFLASDDARYVSGHNL

LIDGGCSIVNPSFGIFKD

O. sativa MS1:
(SEQ ID NO: 87)
MAAGSSHVSADARKLVGKVAVITGGASGIGACTARLFVKHGARVVVA

DIQDELGASLVAELGPDASSYVHCDVTNEGDVAAAVDHAVARFGKLDVMFNN

AGVSGPPCFRMSECTKEDFERVLAVNLVGPFLGTKHAARVMAPARRGSIISTAS

LSSSVSGAASHAYTTSKHALVGFTENAAGELGRHGIRVNCVSPAGVATPLARA

AMGMDDEAIEAIMANSANLKGAGALKADDIAAAALFLASDDGRYVSGQNLRV

DGGLSVVNSSFGFFRD

O. sativa MS2:
(SEQ ID NO: 88)
MAGSSHVSADARKLVGKVAVITGGASGIGACTARLFVKHGARVVVADI

QDELGASLVAELGPDASSYVHCDVTNEGDVAAAVDHAVATFGKLDVMFNNA

GVTGPPCFRITESTKEDFERVLAVNLIGPFLGTKHAARVMAPARRGSIISTASLSS

SVSGTASHAYTTSKRALVGFTENAAGELGRHGIRVNCVSPAAVATPLARAAMG

MDMDDETIEAIMEKSANLKGVGLKVDDIAAAALFLASDDGRYVSGQNLRVDG

GVSVVNSSFGFFRD

A. thaliana 11/17-βHSD:
(SEQ ID NO: 89)
MELINDFLNLTAPFFTFFGLCFFLPPFYFFKFLQSIFSTIFSENLYGKVVLIT

GASSGIGEQLAYEYACRGACLALTARRKNRLEEVAEIARELGSPNVVTVHADV

SKPDDCRRIVDDTITHFGRLDHLVNNAGMTQISMFENIEDITRTKAVLDTNFWG

SVYTTRAALPYLRQSNGKIVAMSSSAAWLTAPRMSFYNASKAALLSFFETMRIE

LGGDVHITIVTPGYIESELTQGKYFSGEGELIVNQDMRDVQVGPFPVASASGCA

KSIVNGVCRKQRYVTEPSWFKVTYLWKVLCPELIEWGCRLLYMTGTGMSEDT

ALNKRIMDIPGVRSTLYPESIRTPEIKSD

A. thaliana TR:
(SEQ ID NO: 90)
METDKRWSLAGKTALVTGGTRGIGRAVVEELAKFGAKVHTCSRNQEEL

NACLNDWKANGLVVSGSVCDASVRDQREKLIQEASSAFSGKLNILINNVGTNV

RKPTVEYSSEEYAKIMSTNLESAFHLSQIAHPLLKASGVGSIVFISSVAGLVHLSS

GSIYGATKGALNQLTRNLACEWASDNIRTNCVAPWYIKTSLVETLLEKKEFVEA

VVSRTPLGRVGEPEEVSSLVAFLCLPASSYITGQVISVDGGFTVNGFSYAMKP

-continued

```
Z. mays SDR:
                                        (SEQ ID NO: 91)
MDAAAAAASPTSKRIALVTGGNKGIGLETCRQLASRGVRVVLTARNEA

RGLEAVERVRCARGDAEVYFHQLDVTDPCSAARLADFVRDQFGRLDILINNAG

ISGVHRDPVLSAAVKDKVDGMDVNQRVEWNIKENSKETYEEAVQCMKTNYYG

AKLVTEALLPLLQLSSSGRIVNVSSGFGLLRNFNSEDLRKEFEDIDNLTESRLEEL

MDKFLEDFKANLVEEHGWPTGGSSAYKVVKAALNAYTRILAKKYPTLRINCLT

PGYVKTDISMHMGVLTLEEGARNPVKVALLPDDGPTGAYFDLNGEASFV

A. thaliana SR:
                                        (SEQ ID NO: 92)
MAEETPRLFNGFCRYAVVTGANRGIGFEICRQLASEGIRVVLTSRDENRG

LEAVETLKKELEISDQSLLFHQLDVADPASITSLAEFVKTQFGKLDILVNNAGIG

GIITDAEALRAGAGKEGFKWDEIITETYELTEECIKINYYGPKRMCEAFIPLLKLS

DSPRIVNVSSSMGQLKNVLNEWAKGILSDAENLTEERIDQVINQLLNDFKEGTV

KEKNWAKFMSAYVVSKASLNGYTRVLAKKHPEFRVNAVCPGFVKTDMNFKT

GVLSVEEGASSPVRLALLPHQETPSGCFFSRKQVSEF

P. bracteatum SR:
                                        (SEQ ID NO: 93)
MPETCPNTVTKMRCAVVTGGNKGIGFEICKQLSSSGIMVVLTCRDVTRG

LEAVEKLKNSNHENVVFHQLDVTDPITTMSSLADFIKARFGKLDILVNNAGVAG

FSVDADRFKAMISDIGEDSEEVVKIYEKPEAQELMSETYELAEECLKINYYGVK

SVTEVLLPLLQLSDSPRIVNVSSSTGSLKYVSNETALEILGDGDALTEERIDMVV

NMLLKDFKENLIETNGWPSFGAAYTTSKACLNAYTRVLAKKIPKFQVNCVCPG

LVKTEMNYGIGNYTADEGAKHVVRIALFPDDGPSGFFYDCSELSAF

Z. mays LCR:
                                        (SEQ ID NO: 94)
MSTGGRKMRTACVTGGNGYIASALIKVLLEKGYAVKTTVRNPDDMEK

NSHLKDLQALGSLEVFRADLDEDGSFDDAVAGCDYAFLVAAPVNLHTKNPEEE

MIEPAVRGTLNVMRSCVKAGTVRRVVLTSSAAAVTTRPQLQGDGHVLDEESW

SDVEYLRAHKPAGPWGYPVSKVLLEKEASRFAEEHGIGLVTVCPGLTVGAAPA

PTARTSVPNCLSLLSGDEAAFAVLDAIESATGCLPLVHVDDVCRAELFAAEEGA

AARRYVCCGLNTTVAELARFLADKYPQYGVKTNLLSGERLEKPRVCLSSAKLV

KEGFEFRYRTLDDIYDDMVEYGKALGILPDL

A. thaliana ACR:
                                        (SEQ ID NO: 95)
MDQTLTHTGSKKACVIGGTGNLASILIKHLLQSGYKVNTTVRDPENEKK

IAHLRKLQELGDLKIFKADLTDEDSFESSFSGCEYIFHVATPINFKSEDPEKDMIK

PAIQGVINVLKSCLKSKSVKRVIYTSSAAAVSINNLSGTGIVMNEENWTDVEFLT

EEKPFNWGYPISKVLAEKTAWEFAKENKINLVTVIPALIAGNSLLSDPPSSLSLS

MSFITGKEMHVTGLKEMQKLSGSISFVHVDDLARAHLFLAEKETASGRYICCAY

NTSVPEIADFLIQRYPKYNVLSEFEEGLSIPKLTLSSQKLINEGFRFEYGINEMYD

QMIEYFESKGLIKAK

P. somniferum NOS:
                                        (SEQ ID NO: 96)
MHGQKNISERYQKFKEMEGTGKIVCVTGGAGYLASWLIMRLLERGYSV

RTTVRSDPKFREDVSHLKALPEATEKLQIFEADLENPESFDDAINGCVGVFLVA
```

-continued

QGMNFAEEYTLEKIIKTCVEGTLRILQSCLKSKTVKKVVYTSSADAAMMISNLK

AVKEIDETIWSEVDNFISKPEQVIPGLPSYVVSKVLTERACLKFSEEHGLDVVTIL

PPLVVGPFITPHPPPSVSIALSIISGDVSMMLGVRLENAVHIDDVALAHIFVFECE

KAKGRHICSSVDFPMHDLPKFISENYPEFNVPTDLLKDIEEQEPVHLSSDKLLSM

GFQFKYDFAEIFGDAIRCAKEKGFL

A. thaliana 4-DFR:
(SEQ ID NO: 97)
MVREEEEDDNNGGGGERKLPVADETVPSLLDGTGLVCVTGGTGFVAS

WLIMRLLQRGYSVRATVRTNPEGNKKDISYLTELPFASERLQIFTADLNEPESFK

PAIEGCKAVFHVAHPMDPNSNETEETVTKRTVQGLMGILKSCLDAKTVKRFFY

TSSAVTVFYSGKNGGGGGEVDESVWSDVEVFRNQKEKRVSSSYVVSKMAAET

AALEFGGKNGLEVVTLVIPLVVGPFISPSLPSSVFISLAMLFGNYKEKYLFDTYN

MVHIDDVARAMILLLEKPVAKGRYICSSVEMKIDEVFEFLSTKFPQFQLPSIDLK

NYKVEKRMSLSSKKLRSEGFEFKYGAEEIFGGAIRSCQARGFL

H. sapiens AKR:
(SEQ ID NO: 98)
MDPKYQRVELNDGHFMPVLGFGTYAPPEVPRNRAVEVTKLAIEAGFRHI

DSAYLYNNEEQVGLAIRSKIADGSVKREDIFYTSKLWCTFFQPQMVQPALESSL

KKLQLDYVDLYLLHFPMALKPGETPLPKDENGKVIFDTVDLSATWEVMEKCK

DAGLAKSIGVSNFNCRQLEMILNKPGLKYKPVCNQVECHPYLNQSKLLDFCKS

KDIVLVAHSALGTQRHKLWVDPNSPVLLEDPVLCALAKKHKRTPALIALRYQL

QRGVVVLAKSYNEQRIRENIQVFEFQLTSEDMKVLDGLNRNYRYVVMDFLMD

HPDYPFSDEY

M. musculus AKR:
(SEQ ID NO: 99)
MDSKQQTVRLSDGHFIPILGFGTYAPQEVPKSKATEATKIAIDAGFRHIDS

ASMYQNEKEVGLAIRSKIADGTVKREDIFYTSKVWCTFHRPELVRVCLEQSLKQ

LQLDYVDLYLIHFPMAMKPGENYLPKDENGKLIYDAVDICDTWEAMEKCKDA

GLAKSIGVSNFNRRQLEKILKKPGLKYKPVCNQVECHPYLNQGKLLDFCRSKDI

VLVAYSALGSHREKQWVDQSSPVLLDNPVLGSMAKKYNRTPALIALRYQLQR

GVVVLAKSFSEKRIKENMQVFEFQLTSEDMKVLDDLNKNIRYISGSSFKDHPDF

PFWDEY

S. lycopersicum AKR2:
(SEQ ID NO: 100)
MAEATEMPYIELNTGFSIPAVGLGTWQSDPGVVGKAVETAIKMGYRHID

CAQIYKNEKEIGEVLSRLFKDGVVKRRELFITSKLWNTNHAPEDVPVALDKTLQ

DLQLEYVDLYLIHWPVSMKPGSVDFKPENLMPTNIPRIWEAMEKVYDSGKARV

IGVSNFSTKKLEDLLQVARTPPAVNQVECHPSWQQAKLRELCKSNNVHLSAYS

PLGSPGTTWLKSDVLKQPAVISVAEKLGKTPAQVCLRWGIQMGQSVLPKSTHE

ARIKENLDVLNWSIPDDLLAKFSEIPQARLLKGASFAHETHGQYRTLEELWDGE

S. lycopersicum AKR1:
(SEQ ID NO: 101)
MTMNLIKQMLVPNVNLNSGHKMPLIGMGTAPSLPEHDQLVSTLIDAIEI

GYRHFDTAAVYGSEEALGQAVVEAIQRGLIKSREQVFITSKLWCTETHRHLVLP

ALKRTLGRLKMDYLDLYLIHLPVTMKKKVNSKDDEMRVDKEDIIPFDMRGTW

EAMEECCRLGLAKSIGVSNFTCTKISQILHYATILPAVNQVEMHVAWRQEKML

-continued

```
EFCKEKGIHVSAWSPLGANGLTPWGIHSVMESPVLKDIAIHKRKSVAQVALRW

VYEQGASVIVKSFNKERMKENLQILDWELSNEEIAQIQEIPPCTGFNVDMVLVH

PNGPYKSANQFWDGEI
```

M. truncatula AKR:

(SEQ ID NO: 102)
```
MGSVEIPTKVLTNTSSQLKMPVVGMGSAPDFTCKKDTKDAIIEAIKQGY

RHFDTAAAYGSEQALGEALKEAIELGLVTRQDLFVTSKLWVTENHPHLVIPALQ

KSLKTLQLDYLDLYLIHWPLSSQPGKFTFPIDVADLLPFDVKGVWESMEEGLKL

GLTKAIGVSNFSVKKLENLLSVATILPAVNQVEMNLAWQQKKLREFCNANGIV

LTAFSPLRKGASRGPNEVMENDMLKEIADAHGKSVAQISLRWLYEQGVTFVPK

SYDKERMNQNLCIFDWSLTKEDHEKIDQIKQNRLIPGPTKPGLNDLYDD
```

P. somniferum COR:

(SEQ ID NO: 103)
```
MESNGVPMITLSSGIRMPALGMGTAETMVKGTEREKLAFLKAIEVGYRH

FDTAAAYQTEECLGEAIAEALQLGLIKSRDELFITSKLWCADAHADLVLPALQN

SLRNLKLDYLDLYLIHHPVSLKPGKFVNEIPKDHILPMDYKSVWAAMEECQTL

GFTRAIGVCNFSCKRLQELMETANSPPVVNQVEMSPTLHQKNLREYCKANNIMI

TAHSVLGAVGAAWGTNAVMHSKVLHQIAVARGKSVAQVSMRWVYQQGASL

VVKSFNEARMKENLKIFDWELTAEDMEKISEIPQSRTSSAAFLLSPTGPFKTEEE

FWDEKD
```

A. thaliana AKR:

(SEQ ID NO: 104)
```
MSALTFPIGSVHHLMPVLALGTAASPPPEPIVLKRTVLEAIKLGYRHFDTS

PRYQTEEPLGEALAEAVSLGLIQSRSELFVTSKLWCADAHGGLVVPAIQRSLETL

KLDYLDLYLIHWPVSSKPGKYKFPIEEDDFLPMDYETVWSEMEECQRLGVAKC

IGVSNFSCKKLQHILSIAKIPPSVNQVEMSPVWQQRKLRELCKSKGIVVTAYSVL

GSRGAFWGTHKIMESDVLKEIAEAKGKTVAQVSMRWAYEEGVSMVVKSFRK

DRLEENLKIFDWSLTEEEKQRISTEISQSRIVDGEVYISEKGPIKSVTEMWDGEI
```

D. lanata 3βHSD:

(SEQ ID NO: 105)
```
MSSKPRLEGKVAIITGAASGIGEETARLFVEHGASVVVADVQDELGRQV

VASVNSDDKISYYHCDVRDEKQVAATVRYAVEKYGRLDIMLSNAGVFGALMT

NVIDLDMVDFENVLATNVRGVANTIKHAARAMVEGKVKGSIICTASVSASLGG

MGPPAYTASKHAVLGLVKGACAELGVHGIRVNSVAPYGVATPMPCSAYGMTP

SQMEEANNSRANLKGVVLKAKHVAEAALFLASDESAYVSGQNLAVDGGFTVV

R
```

Figure 6:
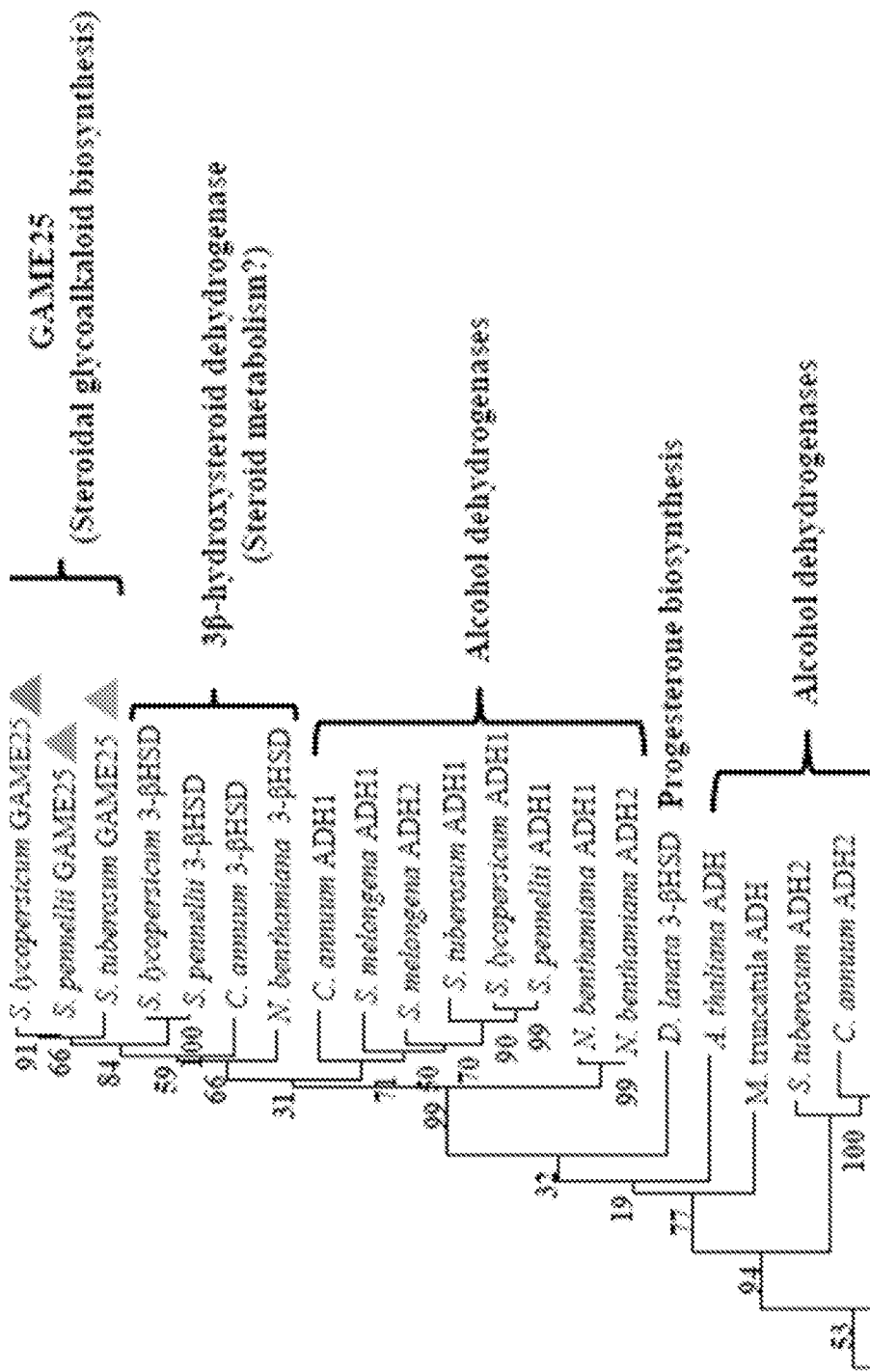
FIG. 6 shows that GAME25 proteins form a separate clade in the large short-chain dehydrogenases/reductases family. Tomato, potato and *S. pennellii* (wild tomato species) GAME25 proteins characterized in this disclosure are marked in red, blue and green triangles, respectively. Five large short-chain dehydrogenases/reductases families (SDR65C, SDR108E, SDR110C, SDR114C and SDR119C) were included in the phylogenetic analysis that comprises enzymes involved predominantly in secondary metabolism. TR-like, tropane alkaloids; ACR, anthocyanidins; 4-DFR, 4-dihydroflavonols; LCR, leucoanthocyanidins; NOS, narcotinehemeacetal precursors; ABA2, abscisic acid; MS and MIS, diterpenoid; SR, quinoline alkaloids; 11/17 β-hydroxysteroid dehydrogenase, steroid metabolism. Another separate clade, ADH ('alcohol dehydrogenase') comprises SDRs from various plant species whose functions are still unknown. Details of the amino acid sequences used are provided in below. The evolutionary history was inferred using the maximum-likelihood method in MEGA6.0. Numbers on branches indicate bootstrap values in percentage of 1,000 replicates.
Figure 6:
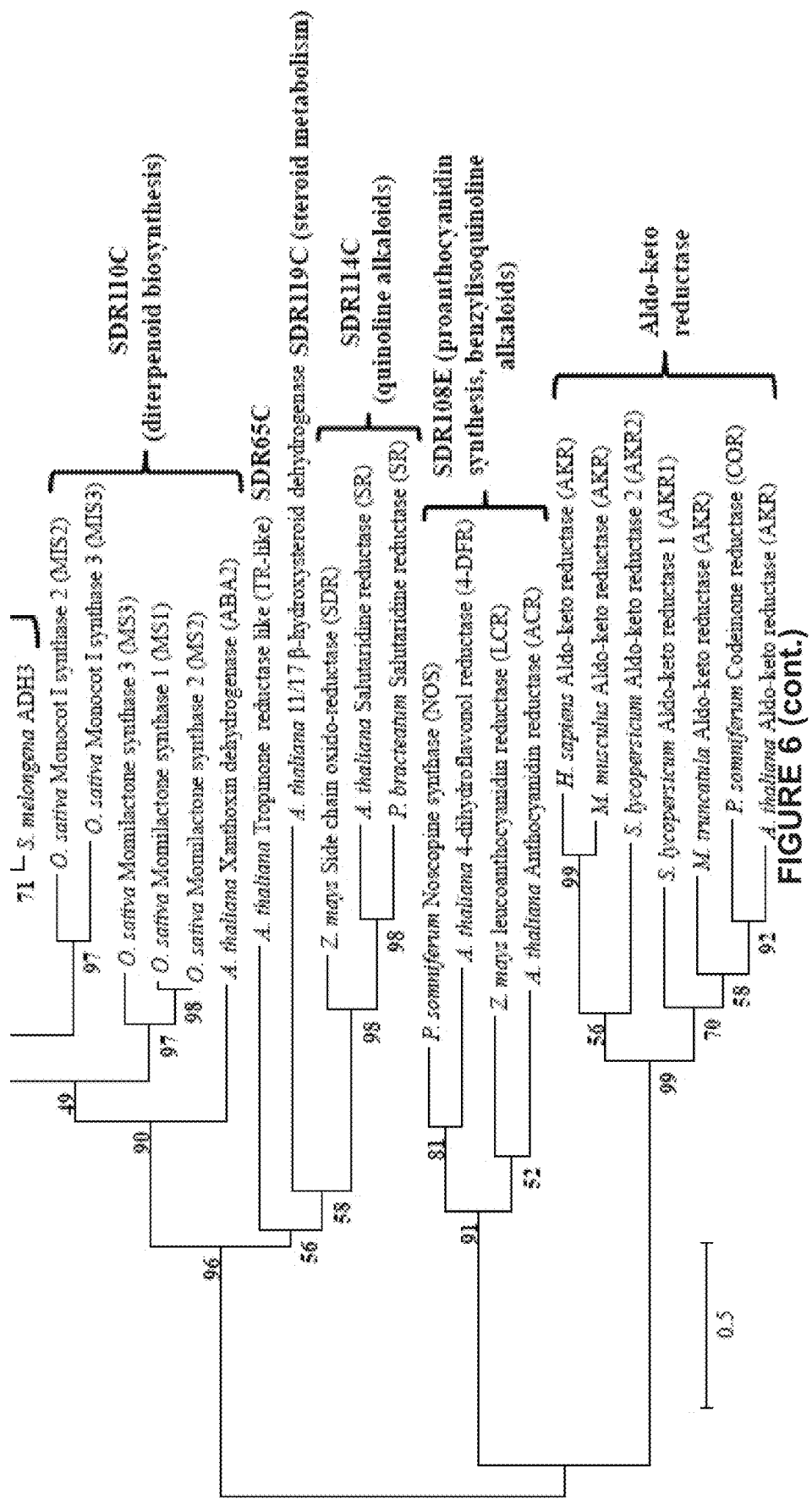

Results:

Short-chain dehydrogenases/reductases (SDR) represents one of the largest and most diverse NAD(P)(H)-dependent enzyme superfamilies' that have evolved in plants and were recently categorized into 49 sub-families. SDR is over-represented in plants and was recently categorized into sets of 49 sub-families. The 259 amino acid GAME25 protein sequence shows the characteristics of a classical SDR family member containing the TGxxxGxG cofactor binding and the YxxxK catalytic motifs (FIG. 5). The presence of a specific Asp residue ($40^{th}$ amino acid) indicated the likely preference of GAME25 for $NAD^+$ over $NADP^+$ cofactor (FIG. 5). Phylogenetic analysis showed that GAME25 homologs of certain Solanaceae species (i.e. tomato, potato, and *Solanum pennellii*) form a distinct sub-clade compared to other plant SDRs (FIG. 6). The most related sub-clade next to GAME25 proteins in the phylogenetic tree included 3β-hydroxysteroid dehydrogenase homologs from tomato and *Solanum pennellii* (3-βHSD, ~90% amino acid identity with GAME25 sub-clade proteins) that may possibly be involved in plant steroid metabolism. Phylogenetic analysis also suggested that there is no homolog of GAME25 protein in eggplant and *capsicum* (FIG. 6). Moreover, GAME25 proteins are clearly separated from *Digitalis lanata* 3-βHSD protein (showing ~75% amino acid identity with the GAME25 proteins) that is involved in removal of C-5,6 double bond from steroid derivatives during the progesterone and cardenolide biosynthesis (FIG. 6). The distinctiveness of the tomato GAME25 sub-clade suggested unique catalytic capabilities for this sub-clade that is most likely different even from the relatively similar 3-βHSD sub-clade members (FIG. 6).

Methods for Examples 3-9

Plant Materials

Tomato (*Solanum lycopersicum*) cv. Micro Tom, potato (*Solanum tuberosum*) cv. Desiree and eggplant (*Solanum melongena*) cv. Tudela plants were grown in a climate-controlled greenhouse at 24° C. during the day and 18° C. during the night, with natural light.

Analytical Standards

Analytical standards Tomatidine (the commercial standard of tomatidine also contains dehydrotomatidine as impurity, Sigma-Aldrich), solanidine (ChemFaces), solasodine (ChemFaces), α-tomatine (the commercial standard of α-tomatine also contains dehydrotomatine as impurity, Carbosynth USA), α-solanine (Sigma Aldrich), α-chaconine (Sigma-Aldrich) and α-solamargine (ChemFaces), solanid-4-en-3-one (Sigma-Aldrich) and diosgenin (Sigma-Aldrich) were dissolved in methanol at concentration of 1 mg/ml.

Generation of GAME25 Transgenic Tomato, Potato, Eggplant and *S. pennellii* Plants The GAME25 silencing construct (RNAi, GAME25i) for tomato was generated by introducing a 199 bp 3' UTR fragment to pENTR/D-TOPO (Invitrogen) (by NotI and AscI, Forward primer: GCGGCCGCATTGTCACGCTATTTGTGTTGG (SEQ ID NO: 6), Reverse primer: GGCGCGCCGAAATTTATATCTTTTTAAGTCACAACG (SEQ ID NO: 7) and further cloning of the GAME25 fragment to the pK7GWIWG2 (II) binary vector using the Gateway LR Clonase II enzyme mix (Invitrogen). The GAME25 silencing construct for *S. pennellii*(Forward primer: GCGGCCGCATTGTCACTCTATTGTGTTGGCGTG (SEQ ID NO: 106), Reverse primer: GGCGCGCCTAAATTTATATCTTTTCAAGTCACAATG (SEQ ID NO: 107) was prepared using the same methods described as above. For the over-expression (GAME25-Ox), corresponding GAME25 coding sequence from tomato and potato was cloned into pDONR221 using the Gateway BP Clonase II enzyme mix (Invitrogen) and then transferred to the pK2GW7 binary vector using Gateway LR Clonase II enzyme mix. Constructs were transformed into tomato cv. Micro Tom, potato, eggplant cv. Tudela and *S. pennellii* as described previously. Positive transgenic lines were selected by quantitative Real Time—PCR (qPCR) and further used for metabolite analysis.

Fragment Used for GAME25-RNAi Construction

The nucleic acid sequence of the GAME25-RNAi construct is set forth in SEQ ID NO: 8.

```
                                         (SEQ ID NO: 8)
ATTGTCACGCTATTTGTGTTGGCGTGCTGTGGCGTGGGCCTTAATCC

TCACTCTCTTGTGTCTGTACTTCTGTTTCATCTCGTTTCGTTTCAAAT
TTTCA

ACTTAATAATACTCTCATATTTTATGCGATATTTTTCAGATT
TATACTAAGTT

TTTTATAGATATTTTAAACGTTGTGACTTAAAAAGATATAAATTTC
```

Plants Extract Preparation and Targeted Profiling of Steroidal Metabolites

Preparation of extracts and the profiling of steroidal alkaloids (SAs) and steroidal glycoalkaloids (SGAs) in various tomato (leaves, green and red fruit), potato (leaves, tuber skin and flesh), eggplant (leaves), and *S. pennellii* (leaves) tissues were performed with same methods as described by Itkin et al. (2011) and Cardenas et al. (2016) Nat. Commun. 7:10654. Three biological replicates (n=3) from each genotype were used for metabolic analysis (e.g. #2, #3 and #4 are three independent GAME25-RNAi transgenic lines and each transgenic line represents three biological samples collected from three different plants). Briefly, 100 mg frozen powder of plant tissue was extracted with 80% methanol and 0.1% formic acid, and followed by brief vortex and sonication for 20 min at room temperature. Finally, the extracts were centrifuged for 15 min at 14,000×g and filtered through 0.22 µm filters.

Samples were analyzed using a high-resolution UPLC/qTOF system comprised of a UPLC (Waters Acquity) connected to a qTOF detector (tandem quadrupole/time-of-flight mass spectrometer, Waters). Separation of metabolites was performed on the 100×2.1-mm i.d., 1.7-um UPLC BEH C18 column (Waters Acquity). The mobile phase consisted of 0.1% formic acid in acetonitrile:water (5:95, v/v; phase A) and 0.1% formic acid in acetonitrile (phase B). The following linear gradient was used for steroidal alkaloids analysis and for the enzyme assays products: from 100 to 72% phase A over 22 min, from 72 to 0% phase A over 14 min, then held at 100% phase B for further 2 min; and then returned to the initial conditions (100% phase A) in 0.5 min and conditioning at 100% phase A for 1.5 min. For the separation of GAME25 enzyme assay product with dehydrotomatidine as a substrate, that is tomatid-4-en-3-one a different, shorter linear gradient was used: from 75 to 55% phase A over 10.5 min, from 55 to 0% phase A over 0.5 min, then held at 100% phase B for further 1.5 min; and then returned to the initial conditions (75% phase A) in 0.5 min and conditioning at 75% phase A for 1 min. The flow rate was 0.3 mL/min, and the column temperature was kept at 35° C. Masses of the eluted compounds were detected with two different qTOF detectors, equipped with an electrospray ionization source (ESI): either with a XEVO MS or with Synapt HDMS. The following settings were used for XEVO MS: capillary—1 kV; cone—27 V; source temperature was set to 140° C., desolvation—400° C., desolvation gas flow—800 Uh. The following settings were used for Synapt HDMS: capillary—3.4 kV; cone—24 V; source temperature was set to 125° C., desolvation—275° C., desolvation gas flow—650 L/h. Argon was used as a collision gas. ESI was used in positive ionization mode at the m/z range from 50 to 1600 Da. The MS system was calibrated using sodium formate, and Leu enkephalin was used as the lock mass. MassLynx software version 4.1 (Waters) was used to control the instrument and calculate accurate masses and elemental compositions. In addition, a mixture of 15 standard metabolites, injected after each 10 samples, was used for quality control. For steroidal alkaloids analysis, data acquisition was performed in the $MS^E$ mode with energy ramp that records an exact mass precursor and fragment ion information from every detectable component in a sample. $MS^E$ mode rapidly alternates between two functions: the first acquiring low-energy exact mass precursor ion spectra and the second acquiring elevated-energy exact mass fragment ion spectra. The collision energy was set to 4 eV for low-energy function, and for the high-energy function the collision energy was set either to 10-30 eV ramp for Synapt HDMS, or 15-45 eV for XEVO MS. Metabolites were identified using standard compounds (see the Analytical Standards section above) by comparison of their retention times and mass fragments. When the corresponding standards were not available, compounds were putatively identified by comparing their retention times, elemental composition and fragmentation pattern with those described in literature (see Itkin et al. (2011); Wu et al. (2013); Schwahn et al. (2015)). Relative quantification of the compounds was carried out using TargetLynx™ (Waters), which is a targeted analysis application.

For enzyme assay experiments, an additional MS-MS analysis with a collision energy ramp from 20 to 50 eV was performed to identify the structures of the enzymatic reaction products. The solanid-4-en-3-one product was identified based on the comparison of its retention time and MS-MS spectrum to those measured for its corresponding standard. Another three products (tomatid-4-en-3-one, solasod-4-en-3-one and diosgen-4-en-3-one) were putatively assigned as follows: first, elemental composition based on accurate masses and the isotopic pattern was calculated using the MassLynx software. Then the MS-MS fragmentation pattern was analyzed, and the fragments were assigned applying the fragmentation rules for steroid-based compounds.

Quantitative Real-Time PCR Analysis

Total RNA was isolated from wild type and transgenic tomato lines (leaf, green fruit, breaker fruit and red ripe fruit), transgenic potato (leaves, tuber skin and flesh), transgenic eggplant (leaves) and transgenic S. pennellii leaves with three biological replicates (n=3) using the Trizol method (Sigma-Aldrich). Three biological replicates (for each genotype) denote three separate tissue samples obtained from three different plants. DNase I (Sigma-Aldrich)-treated RNA was reverse transcribed using a high-capacity cDNA reverse transcription kit (Applied Biosystems). Gene-specific oligonucleotides were designed with the Primer Express 3 software (Applied Biosystems). The TIP41 gene was used as a reference gene for tomato and S. pennellii samples and the NAC gene was used as an endogenous control for potato. For eggplant, the cyclophilin gene was used as a reference for Real Time PCR analysis.

Example 3

Tomato Steroidal Glycoalkaloid Metabolism is Re-Routed from the Native, Predominant Saturated α-Tomatine Branch to the Unsaturated Dehydrotomatine Branch in GAME25-Silenced Leaves Objective:

To determine the role of GAME25 in SGA metabolism.

Figure 7:
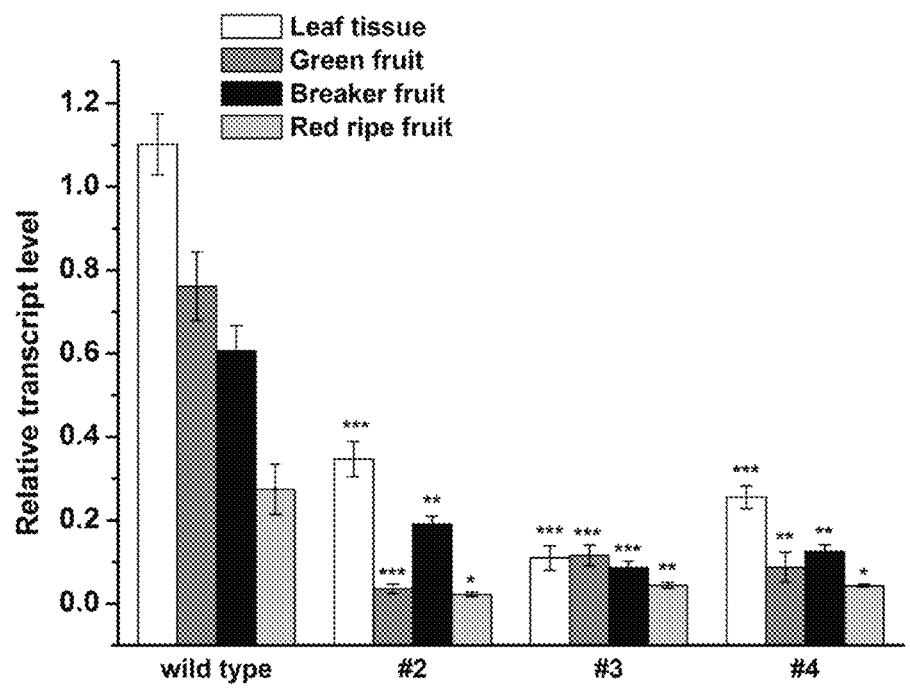
FIG. 7 shows the GAME25 expression levels in leaves and different fruit tissues (developmental stages) of GAME25-RNAi (#2, #3 and #4) transgenic tomato lines (qRT PCR assay). Briefly, RNA-Seq transcriptome data was obtained from different tomato tissues and organs (flesh, peel, roots, young leaf, flower buds and young flower petals) and five developmental stages for peel and flesh tissues (19 experiments in total). Values represent mean±standard error (n=3). Asterisks indicate significant changes from control samples (wild-type) as calculated by a Student's t-test (*P-value <0.05; P-value <0.01; *P-value <0.001).
Figure 8:
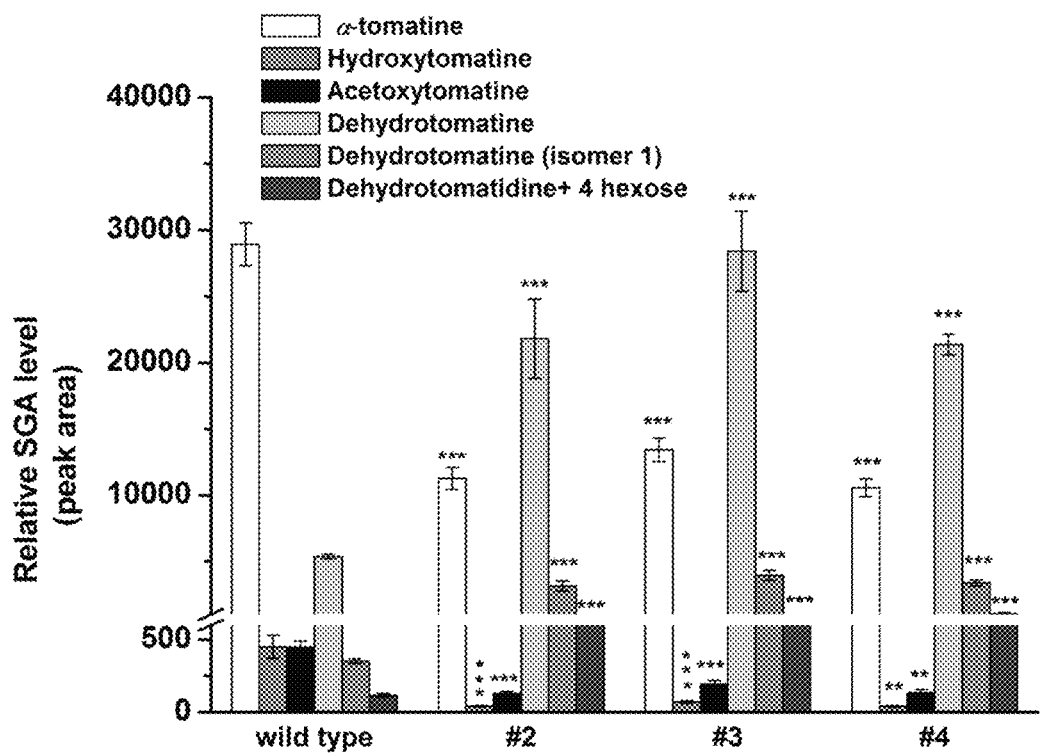
FIG. 8 shows the SGAs levels in leaves of wild-type (non-transformed) and GAME25-RNAi tomato lines determined by Liquid Chromatography-Mass Spectrometry (LC-MS). Samples #2, #3 and #4 are three independent GAME25-RNAi transgenic tomato lines. Values indicate means of three biological replicates±standard error. Asterisks indicate significant changes from wild-type samples as calculated by a Student's t-test (*P-value <0.05; P-value <0.01; *P-value <0.001).
Figure 9:
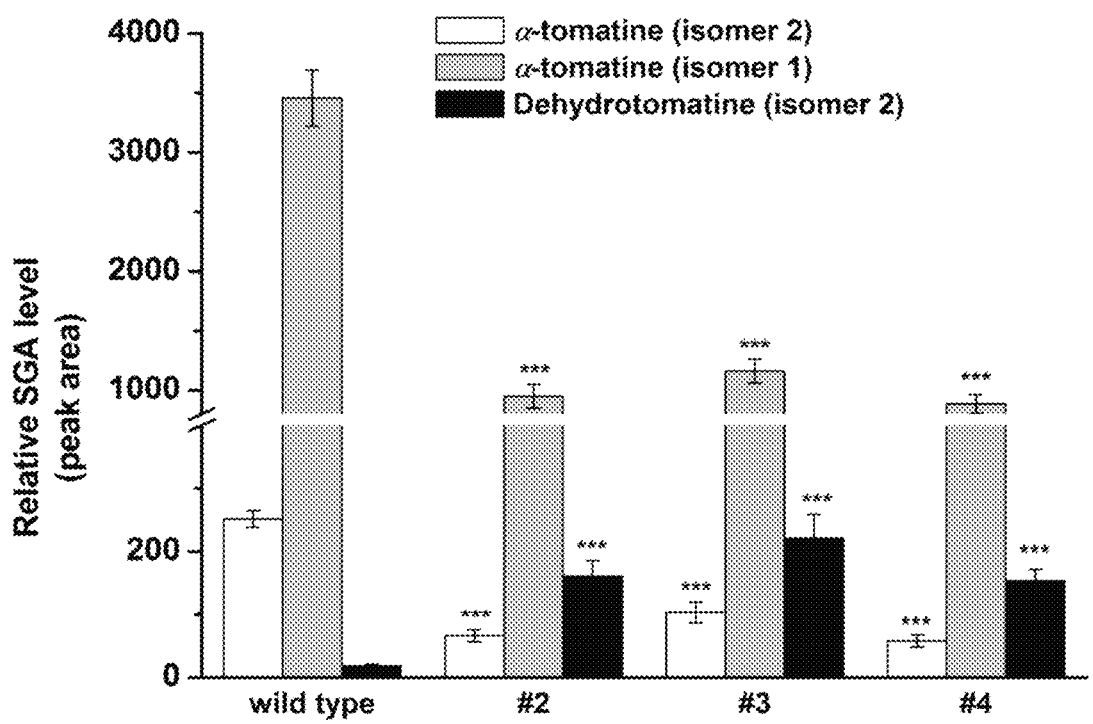
FIG. 9 shows levels of less abundant SGAs in GAME25 silenced tomato leaf tissues. Line #2, #3 and #4 are three independent GAME25-RNAi transgenic tomato lines. Values indicate means of three biological replicates±standard error. Asterisks indicate significant changes from wild-type samples as calculated by a Student's t-test (*P-value <0.05; P-value <0.01; *P-value <0.001).

Results:

3 independent GAME25-RNAi transgenic tomato lines (#2, #3 and #4) were generated as described above. GAME25 transcript level was significantly reduced in GAME25i leaves and various fruit tissues of developmental stages (green, breaker and red ripe fruit) (FIG. 7). GAME25-RNAi leaves showed significant reduction in α-tomatine (~2.5-3 fold), hydroxytomatine (~6-10 fold), acetoxytomatine (~2.5-3 fold), and α-tomatine isomers (1 and 2; ~3-4 fold) compared to wild-type leaves (FIG. 8). On the other hand, dehydrotomatine (~4-6 fold), dehydrotomatine isomer 1 (~9-11 fold) and dehyrotomatidine+4 hexose (~6-9 fold) were increased considerably compared to wild-type leaves (FIG. 8 and FIG. 9).

Conclusion:

Reduction in α-tomatine and its downstream metabolite levels, yet, accumulation of dehydrotomatine and its isomers in GAME25i lines suggest that either (i) GAME25 is involved in α-tomatine biosynthesis directly from the dehydrotomatine glycoside or (ii) it mediates tomatidine biosynthesis from dehydrotomatidine (also called tomatidenol)

No significant accumulation of dehydrotomatidine (tomatidenol), which is a dehydrotomatine precursor, was observed in GAME25i lines. This SGA appeared to be converted to its glycosylated derivative, dehydrotomatine that actually did show a major accumulation (FIGS. 1A-1C, and FIG. 8). The accumulation of dehyrotomatidine+4 hexoses metabolite derived from dehydrotomatidine (FIGS. 1A-1C, and FIG. 8) after GAME25 silencing indicate a role of GAME25 upstream of the SA aglycone glycosylation steps in SGA biosynthesis. Hence, it is hereby proposed that GAME25 is involved in the conversion dehydrotomatidine to tomatidine, rather than acting on dehydrotomatine.

Figure 10:
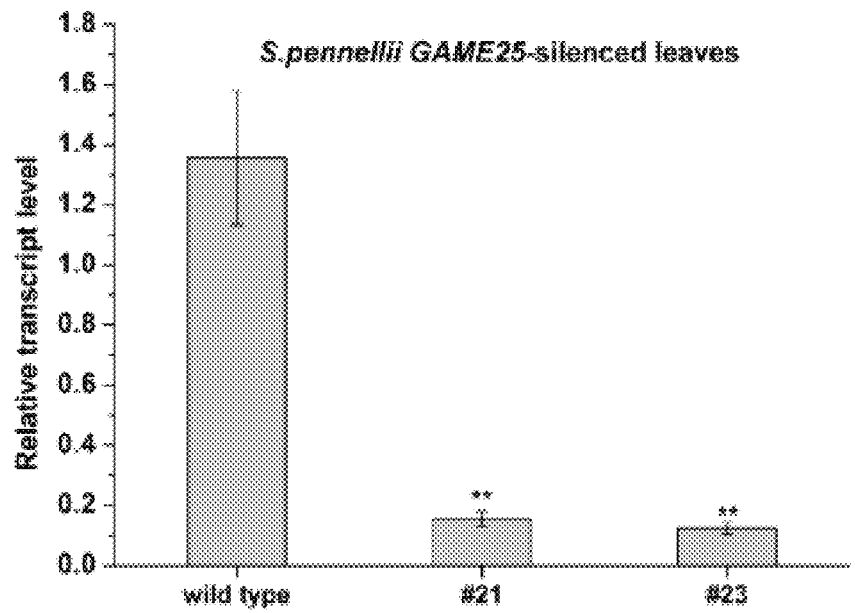
FIG. 10 shows the silencing of GAME25 in *S. pennellii*. Expression of GAME25 in leaves of GAME25i *S. pennellii* transgenic lines (qRT PCR assay). Line #21 and #23 are two independent GAME25-RNAi transgenic lines.

Subsequent in vitro enzyme assays confirmed that GAME25 could not act on glycosylated SAs (e.g. dehydrotomatine) Similar to the cultivated species, silencing of GAME25 in the wild tomato species, S. pennellii also resulted in reduced tomatine derived alkaloids levels, as α-tomatine and acetoxytomatine, while dehydro-alkaloids were enriched, i.e. dehydrotomatine and acetoxy-dehydrotomatine (FIG. 10).

Example 4

GAME25-Silencing Results in Gradual Loss of Saturated SGAs in Developing and Ripening Tomato Fruit and has a Major Impact on SGAs in Tomato Green Fruit Objective:

Observe the SGA profile in tomato green fruit when GAME25 expression is altered.

Figure 11A:
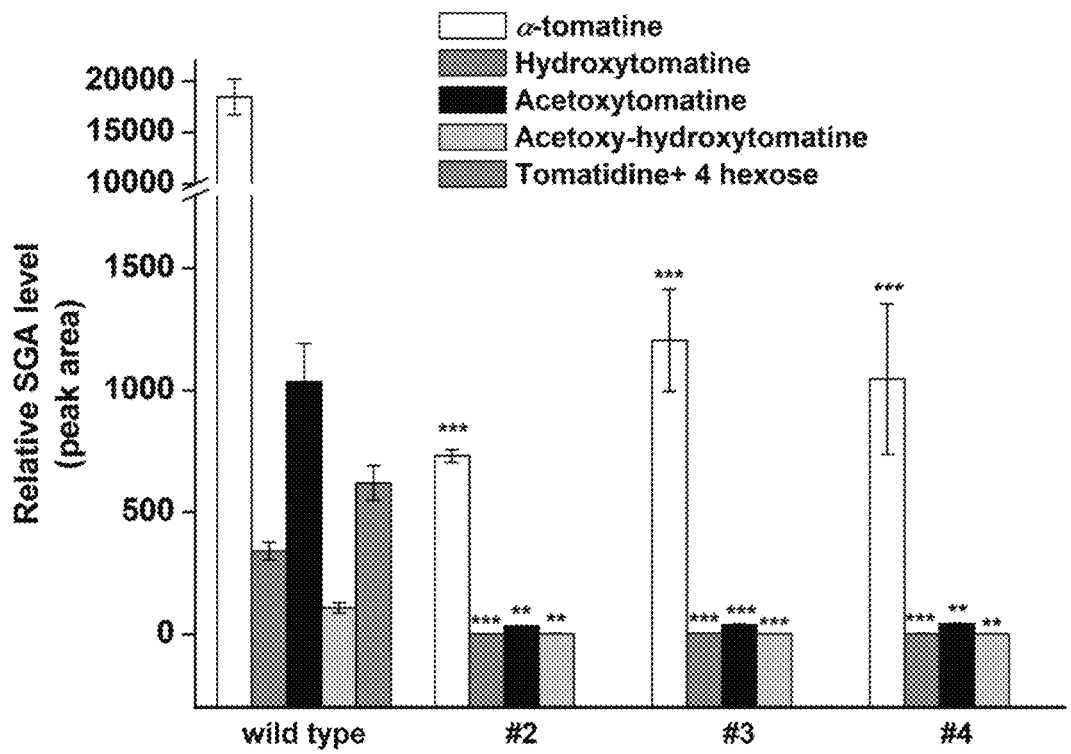
FIGS. 11A-11I show substantially altered SGA metabolism in fruit of GAME25-silenced tomato lines (#2, #3 and #4 are three independent lines). Values represent mean±standard error (n=3).
Figure 11B:
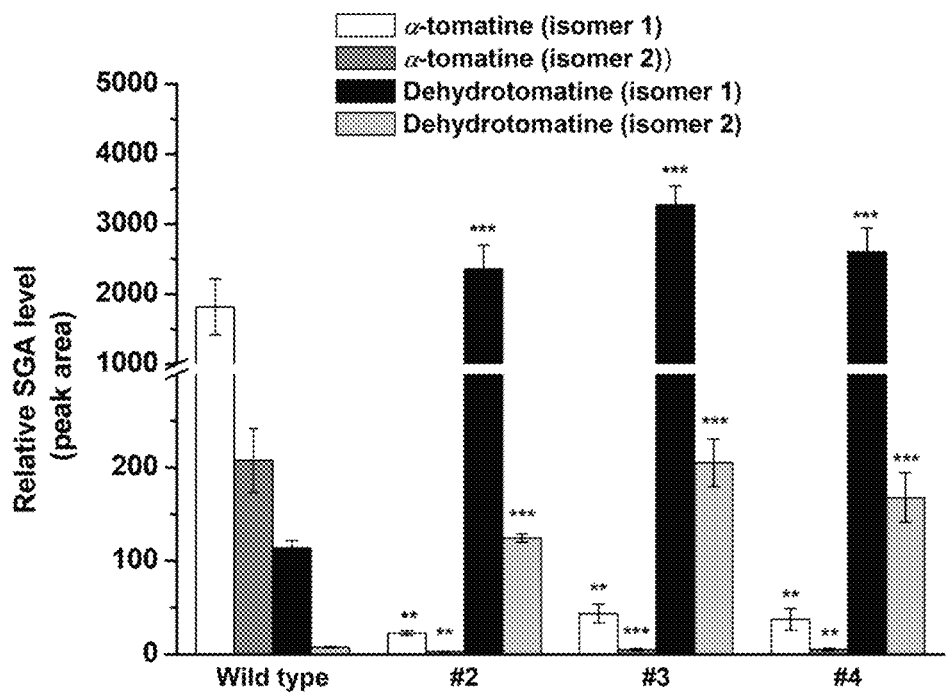

Results:

The SGAs profile of green fruit of GAME25i lines was compared to wild-type green fruits. During the transition from green to red fruit in tomato, α-tomatine is converted to esculeosides and lycoperosides (saturated SGAs), while dehydrotomatine is converted to dehydroesculeosides and dehydrolycoperosides (unsaturated SGAs) (FIGS. 1A-1C). Esculeoside A and its derivatives are the major SGAs found in tomato red ripe fruit, while dehydroesculeosides and dehydrolycoperosides are minor SGAs found in this tissue. GAME25i green fruits displayed drastic reduction in levels of α-tomatine (~15-25 fold), hydroxytomatine (~100 fold), acetoxytomatine (~30 fold), acetoxy-hydroxytomatine (~50 fold), α-tomatine isomer (1 and 2) and complete absence of tomatidine+4 hexose as compared to wild-type (FIGS. 11A-11B). Thus, α-tomatine and its downstream saturated SGA intermediates were severely affected in green fruit tissue due to GAME25 silencing.

Figure 11C:
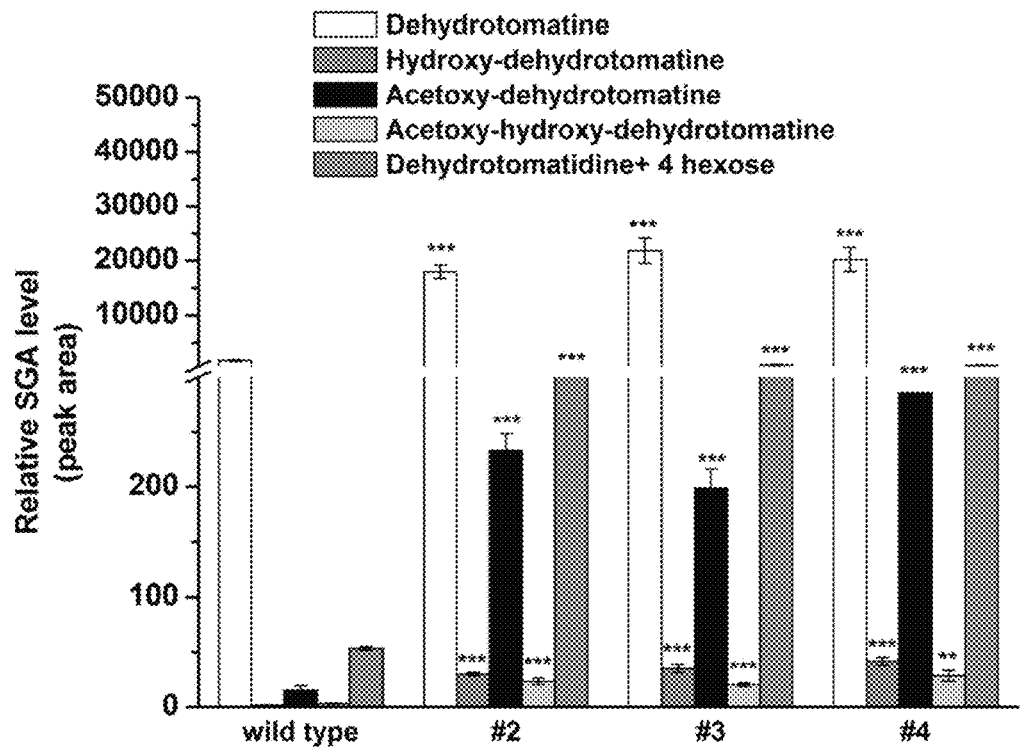

In contrast, unsaturated SGAs as dehydrotomatine (~10-12 fold), hydroxy-dehydrotomatine (~25 fold), dehydrotomatine isomer (1 and 2), acetoxy-dehydrotomatine (~12-15 fold), acetoxy-hydroxy-dehydrotomatine (~6-8 fold) and dehydrotomatidine+4 hexose (~12-18 fold) were increased significantly compared to wild-type suggesting redirection of the flux towards unsaturated dehydro-SGAs due to GAME25 silencing (FIGS. 11B-11C).

Conclusion:

Silencing of GAME25 diverted metabolic flux from the α-tomatine derived pathway to the dehydrotomatine dependent SGAs branch.

Example 5

GAME25i Breaker Fruit Accumulates Dehydrotomatine Derived SGAs

Objective:

To determine the SGAs in GAME25i breaker fruit.

Figure 11D:
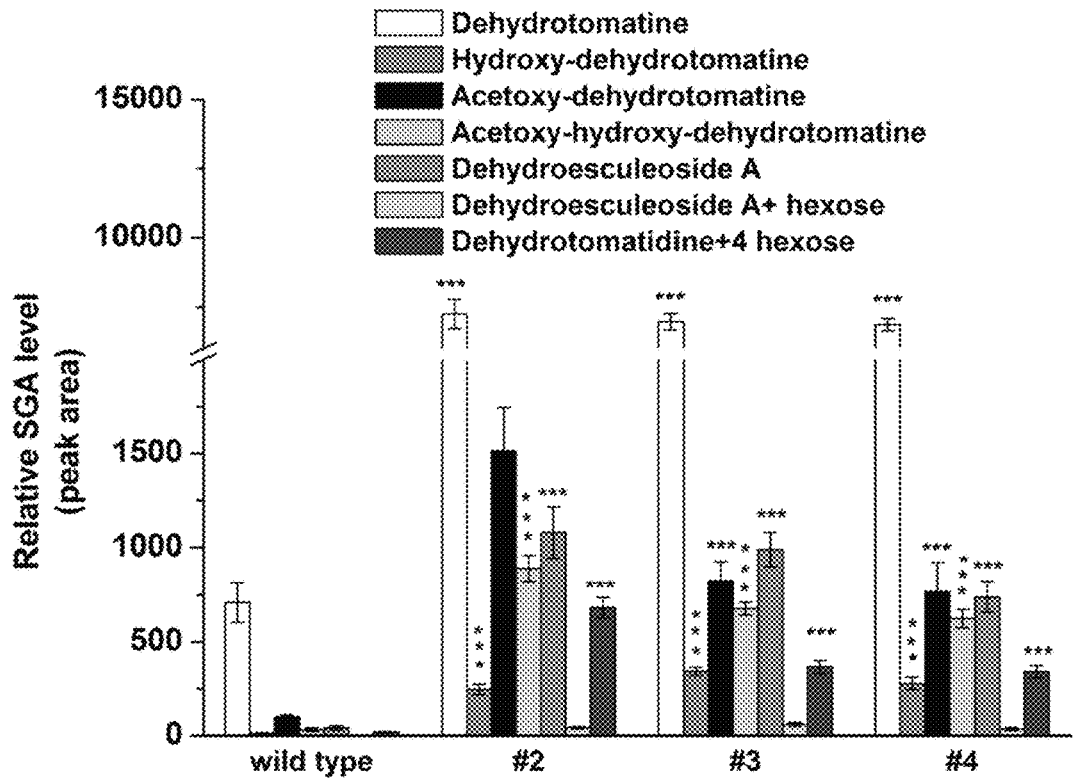
Figure 11E:
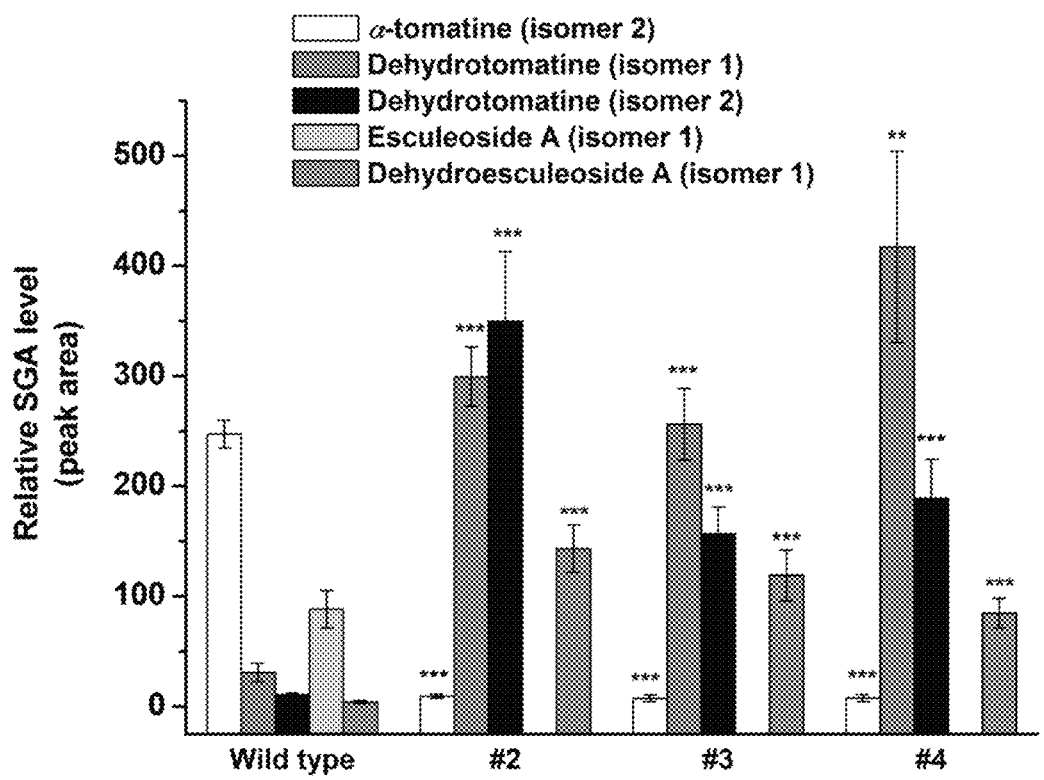
Figure 11F:
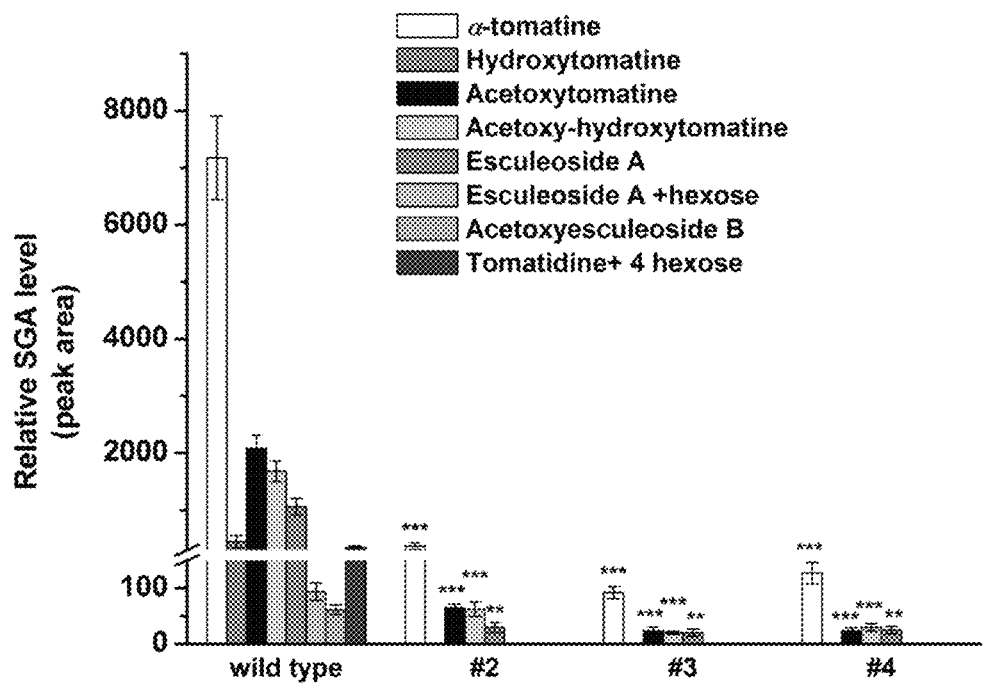

Results:

SGAs analysis was performed in breaker fruits from GAME25i lines and compared to wild-type breaker fruits. The metabolic flux from α-tomatine to the dehydro-SGAs pathway was further extended to dehydrotomatine and additional downstream SGAs. SGAs metabolites accumulated following GAME25-silencing included hydroxy-dehydrotomatine (~20-30 fold), acetoxy-dehydrotomatine (~7-15 folds), acetoxy-hydroxy-dehydrotomatine (~20-25 fold) as well as dehydroesculeoside A (~20-25 fold) and its derivatives (FIGS. 11D-11E). On the other hand, tomatine derived SGAs including hydroxytomatine, acetoxytomatine, acetoxy-hydroxytomatine and esculeoside A, were almost non-existent in GAME25i lines (FIGS. 11E-11F).

Example 6

Dehydroesculeoside A, is the Predominant SGA in GAME25i Red Ripe Fruit

Objective:

To determine the SGAs in GAME25i red ripe fruit.

Figure 11G:
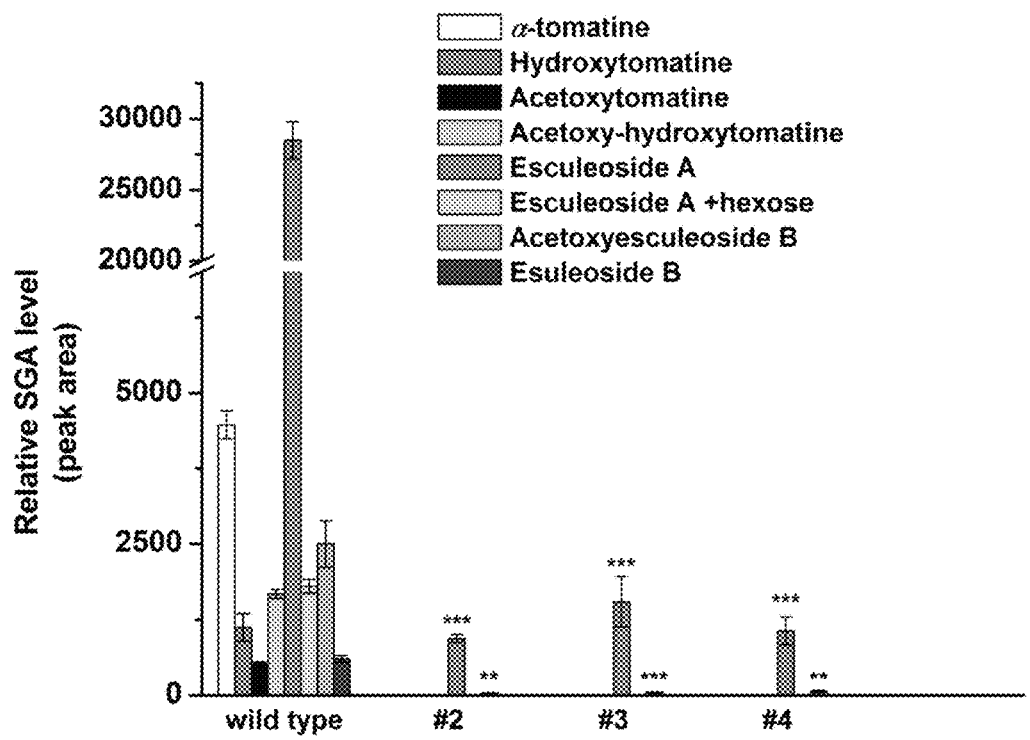
Figure 11H:
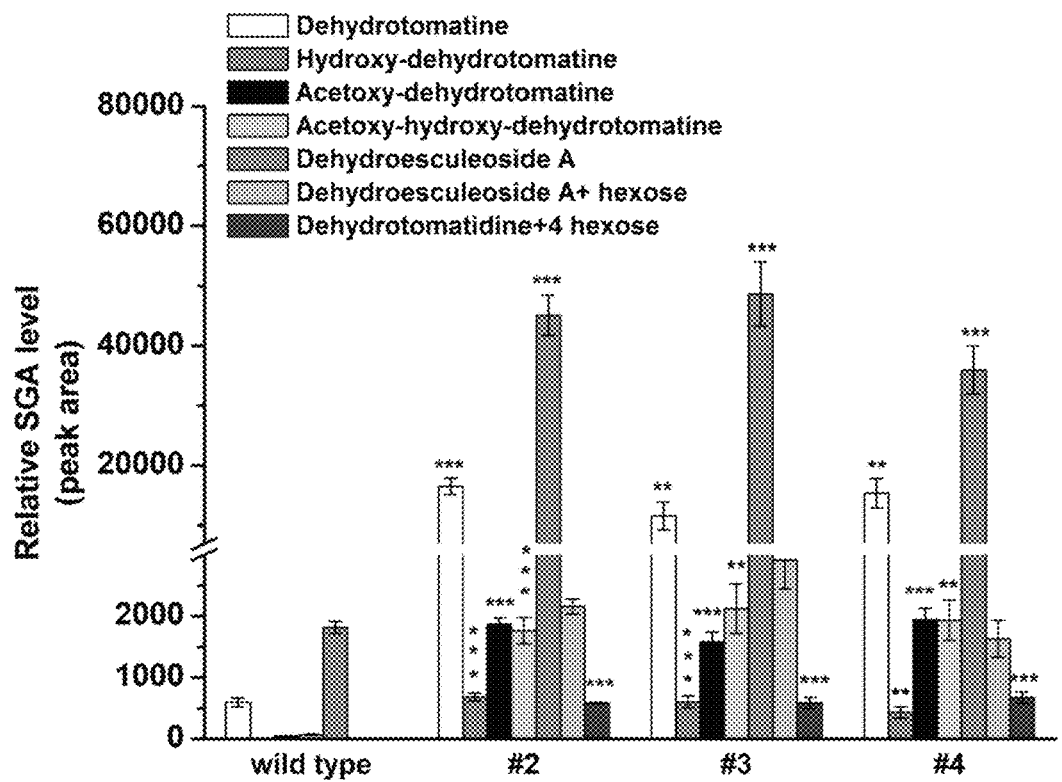
Figure 11I:
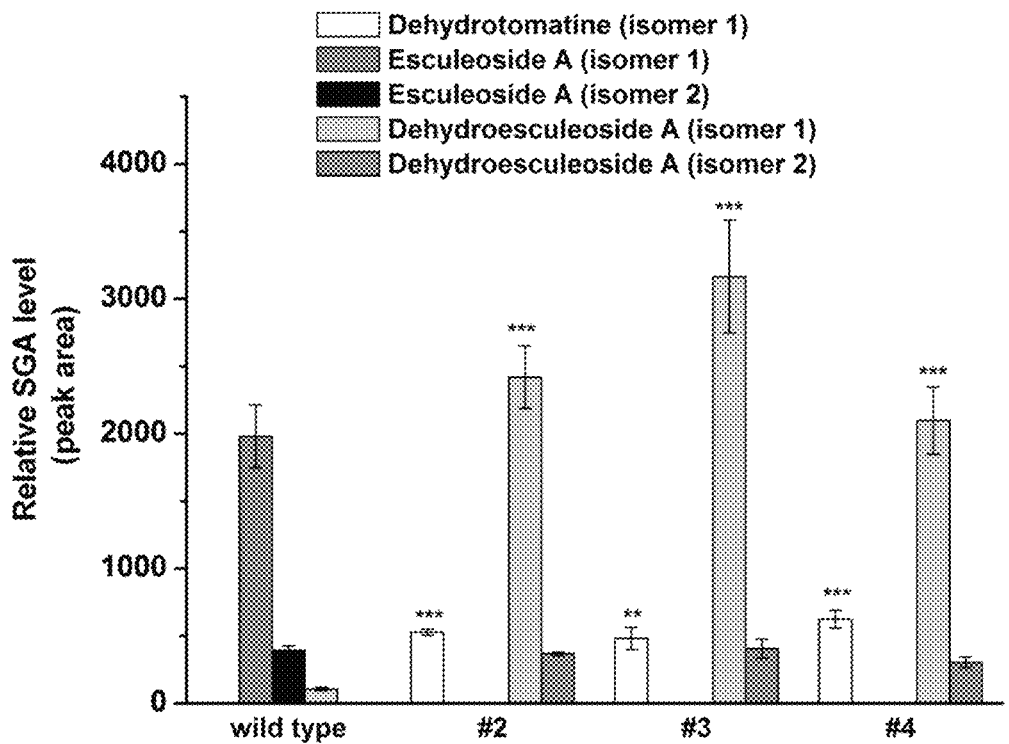
Figure 12:
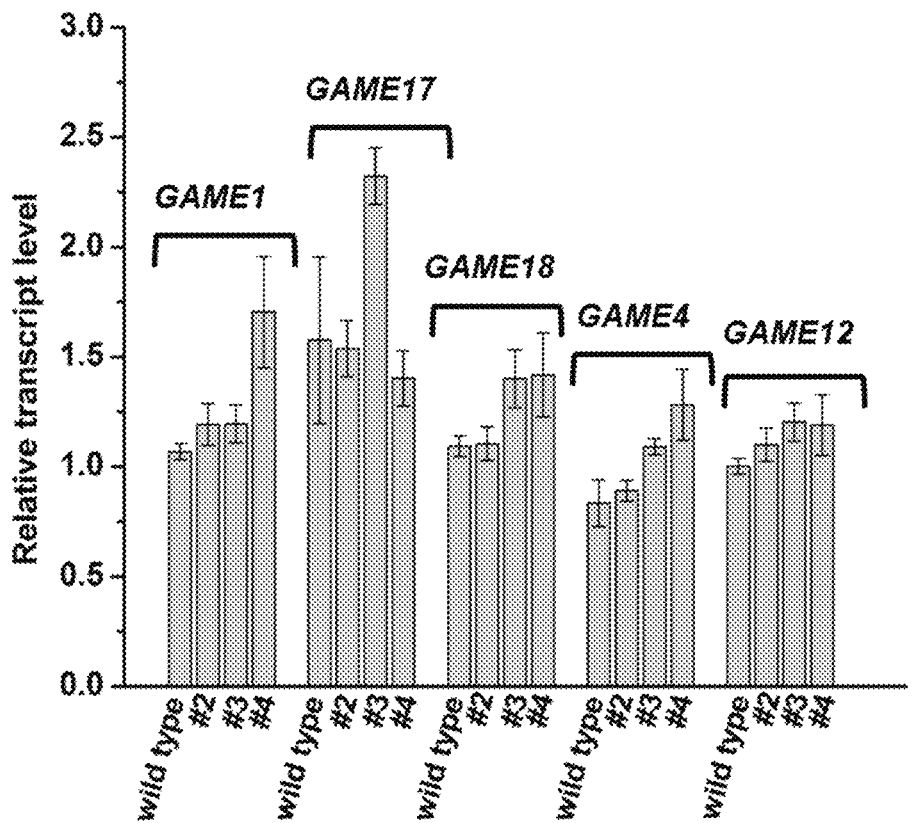
FIG. 12 shows that altering GAME25 expression does not affect other SGA biosynthetic genes in tomato. The figure shows the expression of selected genes involved in SGA biosynthesis from leaves of GAME25i tomato transgenic lines (qRT PCR assay). Line #2, #3 and #4 are three independent GAME25-RNAi transgenic tomato lines. Values represent mean±standard error (n=3). Asterisks indicate significant changes from control samples (wild-type) as calculated by a Student's t-test (*P-value <0.05; P-value <0.01; *P-value <0.001).

Results:

Esculeoside A and its derivatives are the predominant SGAs found in wild-type tomato red ripe fruits. The drastic reduction in α-tomatine levels at the green stage fruit in GAME25i lines resulted in severe decline of esculeoside A and lycoperosides (~20-25 folds) in red ripe fruit stage (FIG. 11G). On the other hand, the significant accumulation of dehydrotomatine in green fruit in GAME25i lines resulted in a massive accumulation of dehydroesculeoside A (~20-25) and derivatives in red ripe fruit (FIGS. 11G-11I), providing additional evidence regarding the role of GAME25 in the early divergence of the saturated (α-tomatine) and unsaturated (dehydrotomatine) SGA biosynthesis branches. It appeared that GAME25 silencing did not affect expression of core SGA biosynthesis genes including GAME4 and GAME12 involved in the formation of the dehydrotomatidine aglycone and GAME1, GAME17 and GAME18 performing the glycosylation of the SA-aglycones (FIG. 12).

Example 7

GAME25 Over-Expression in Tomato Resulted in the Accumulation of Saturated α-Tomatine and its Downstream SGAs

Objective:

To examine the role of GAME25 in SGA biosynthesis.

Figure 13A:
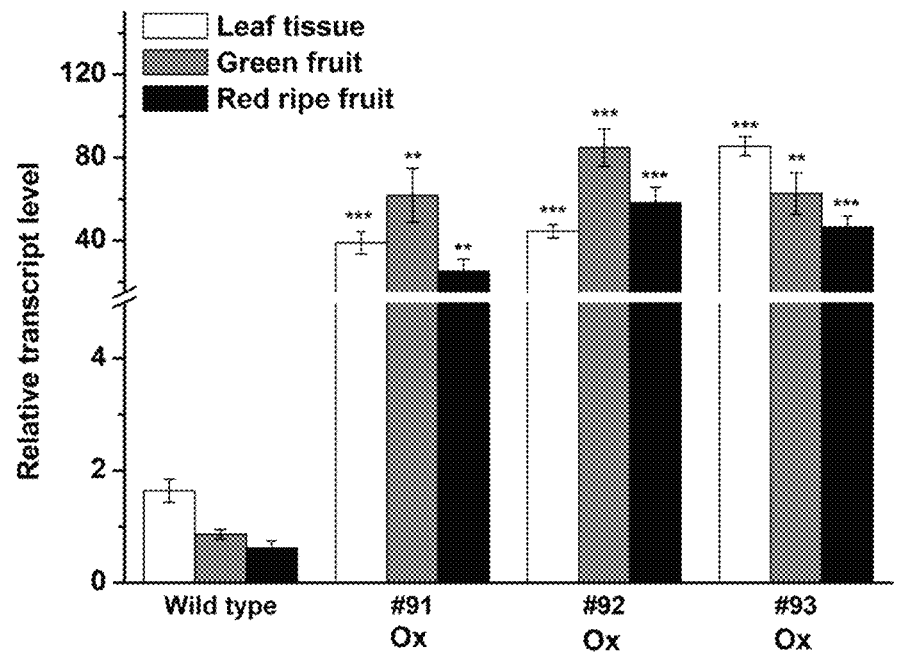
FIGS. 13A-13E show that overexpression of GAME25 in tomato enhances the levels of the α-tomatine branch in the SGA pathway.
Figure 13B:
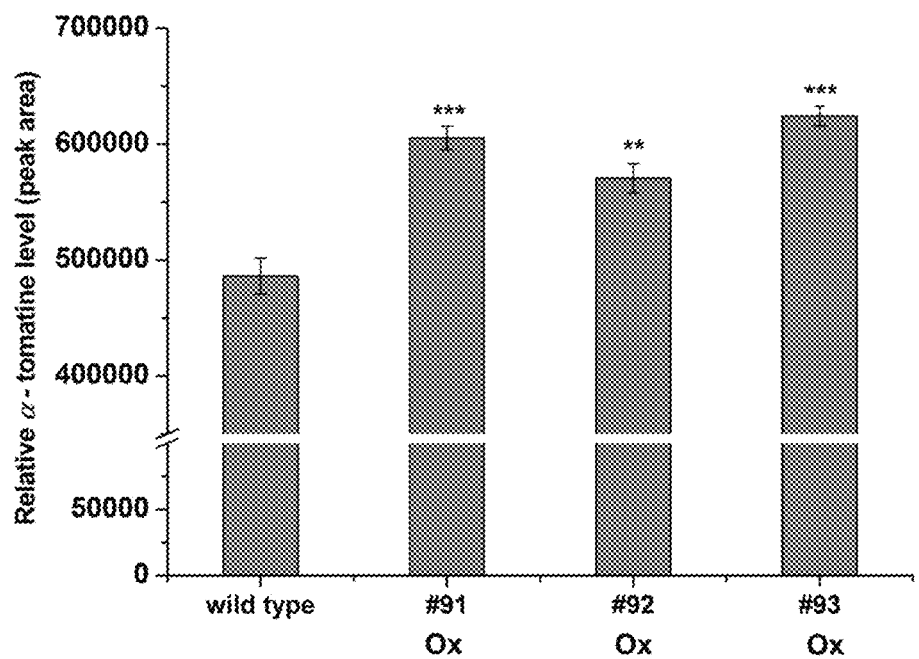
Figure 13C:
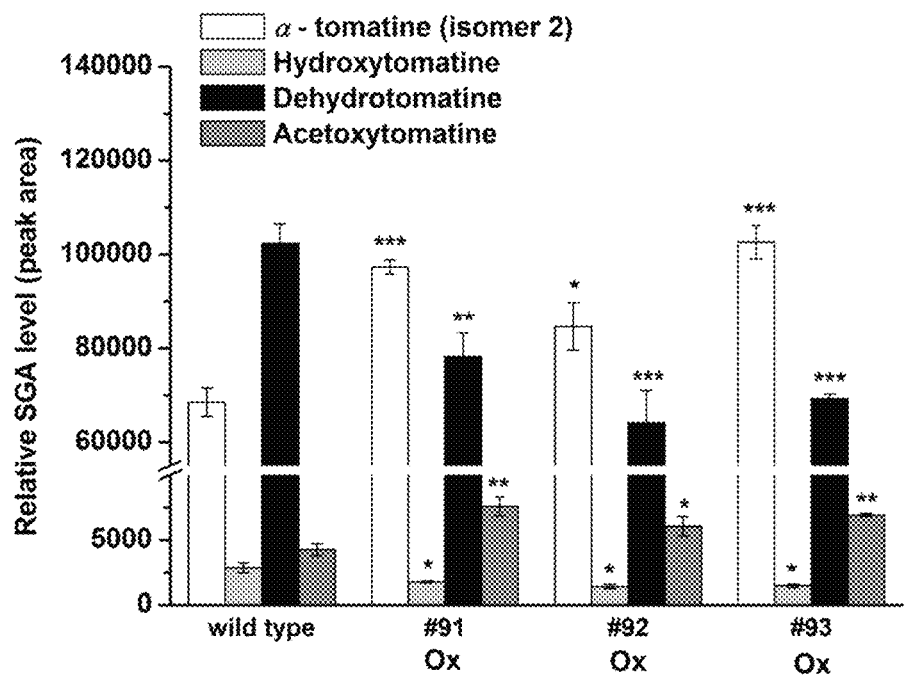
Figure 13D:
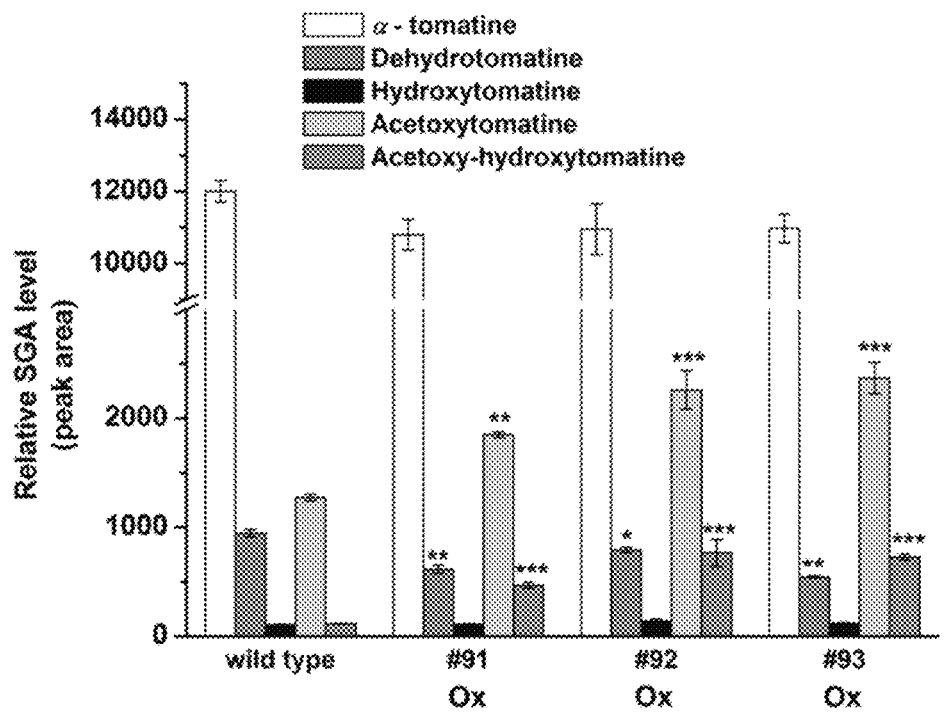
Figure 13E:
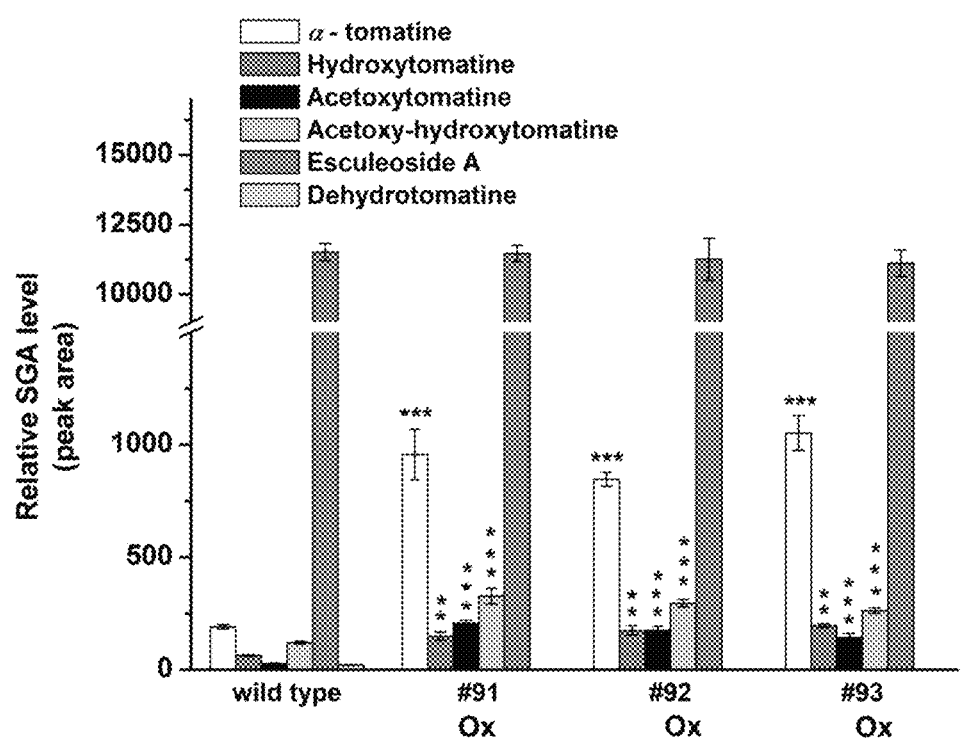

Results:

3 independent transgenic tomato lines over-expressing GAME25 (GAME25-Ox; lines #91, #92 and #93) were generated as described above. GAME25 expression in leaves and fruit tissues (green and red fruit) of transgenic tomato lines was significantly higher than in wild-type tomato plants as determined by qRT PCR (FIG. 13A). In leaves of GAME25-Ox lines, levels of α-tomatine, α-tomatine (isomer 2) and acetoxytomatine increased significantly with simultaneous reduction of dehydrotomatine compared to wild-type leaves (FIGS. 13B-13C). GAME25-Ox tomato green fruits displayed a significant reduction in dehydrotomatine levels, whereas no change in α-tomatine content was observed in the same tissues (FIG. 13D). However, significant increase in acetoxytomatine and acetoxy-hydroxytomatine (α-tomatine derived SGAs) was detected when compared to wild-type green fruits (FIG. 13D). Analysis of red fruit derived from GAME25-Ox lines clearly showed accumulation of α-tomatine (~4-6 fold) and its downstream saturated derivatives (i.e. hydroxytomatine (~2-3 fold), acetoxytomatine (~5-7 fold), and acetoxy-hydroxytomatine (~2-3 fold)) (FIG. 13E). Yet, red fruit of the GAME25-Ox plants did not show a change in esculeoside A content suggesting that the glycosylation step of the SGA steroidal backbone (likely of acetoxy-hydroxytomatine) is a limiting factor (FIGS. 1A-1C, and 13E).

Example 8

Tomato GAME25 Overexpression in Cultivated Eggplant Results in Newly Produced Saturated SGAs and Steroidal Saponins

Figure 3A:
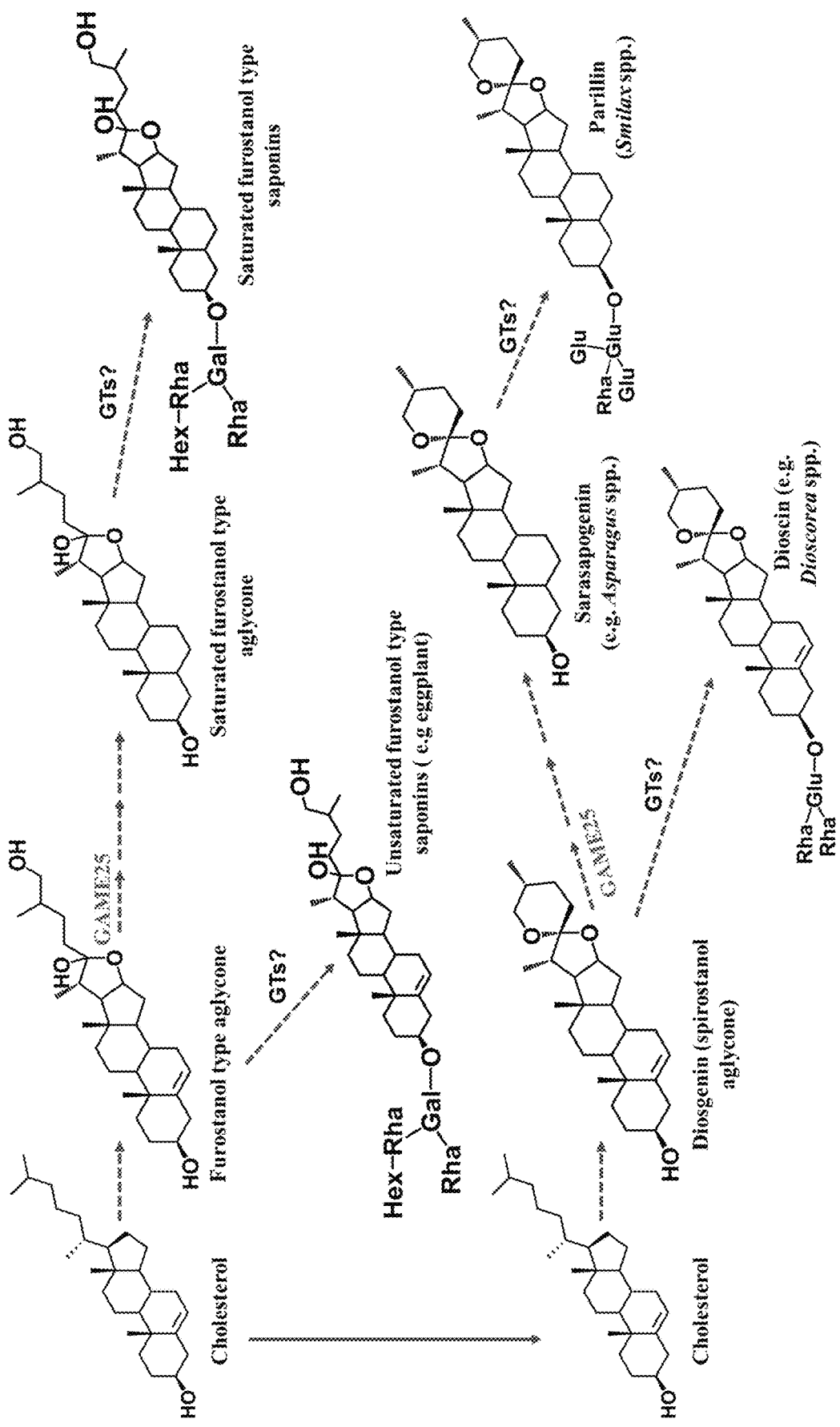
FIGS. 3A-3C shows the proposed biosynthetic pathway for steroidal saponin glycosides in steroidal saponin producing plant species and steroidal glycoalkaloids in eggplant.
Figure 3B:
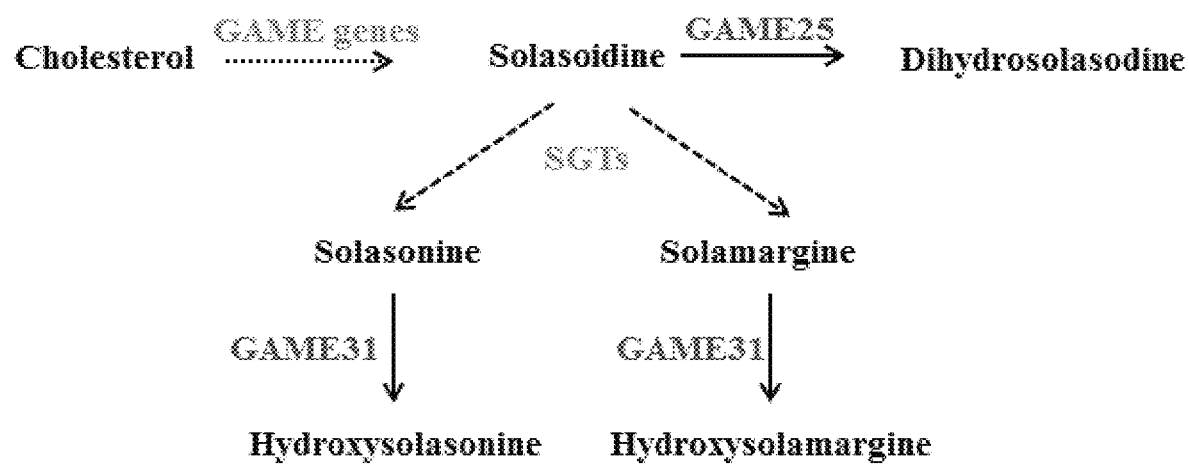
Figure 14:
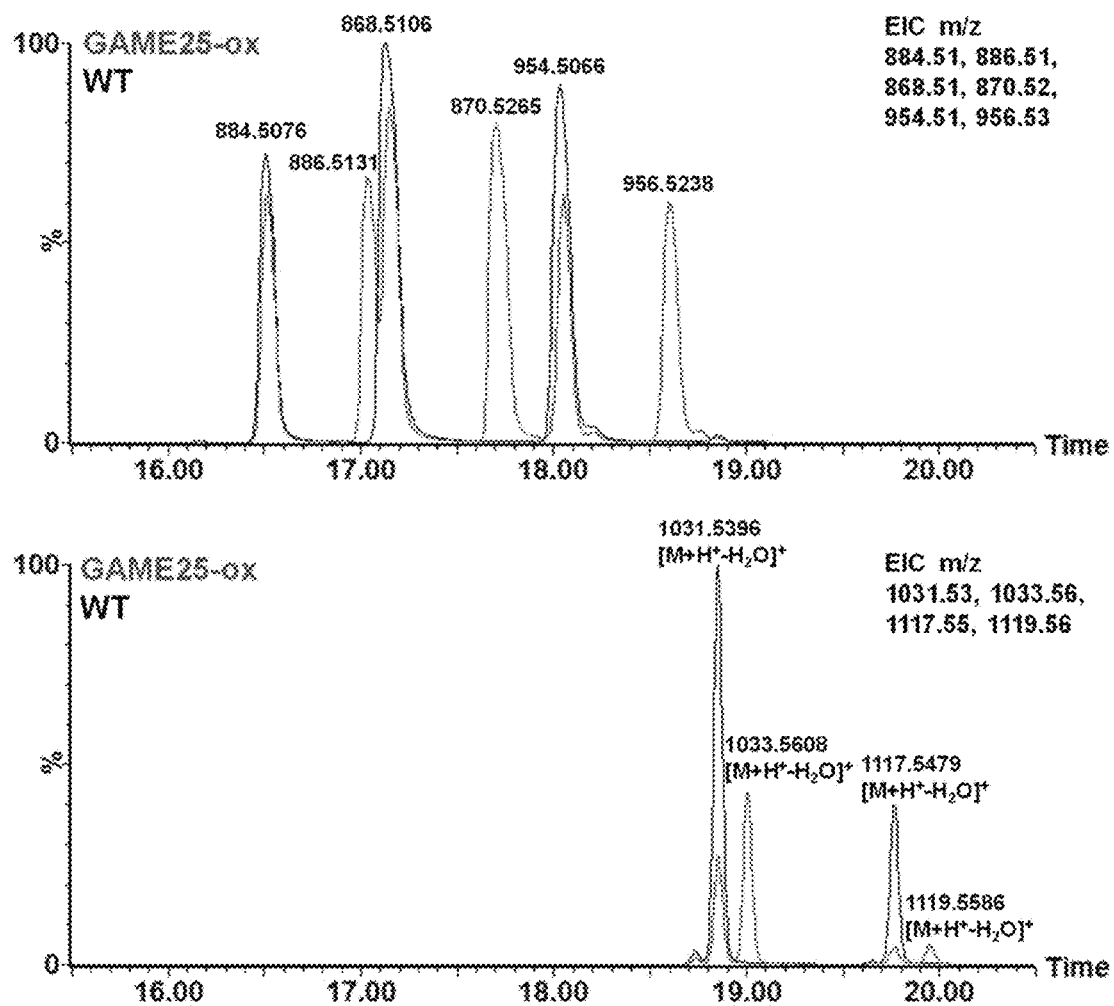
FIG. 14 shows that overexpression of tomato GAME25 results in accumulation of new saturated SGAs and steroidal saponins in eggplant. Comparison of SGA (upper panel) and steroidal saponin (lower panel) profile of wild-type (WT) and GAME25 overexpression transgenic eggplant lines; the naturally occurring unsaturated steroidal alkaloids (Solmargine, m/z 868.5106; Solasonine, m/z 884.5076 and malonyl-solamargine, m/z 954.5066) are reduced in the overexpression lines compared to the WT, while the saturated derivatives (lacking the 5-6 double bond) accumulate soladulcine A (m/z 870.5265), β-soladulcine (m/z 886.5131) & saturated malonyl-solamargine (m/z 956.5238); similarly the steroidal saponins (m/z 1031.5396 & m/z 1117.5479) are reduced, while their saturated forms (m/z 1033.5608 & 1119.5586) accumulate in GAME25 overexpression transgenic eggplants.
Figure 15:
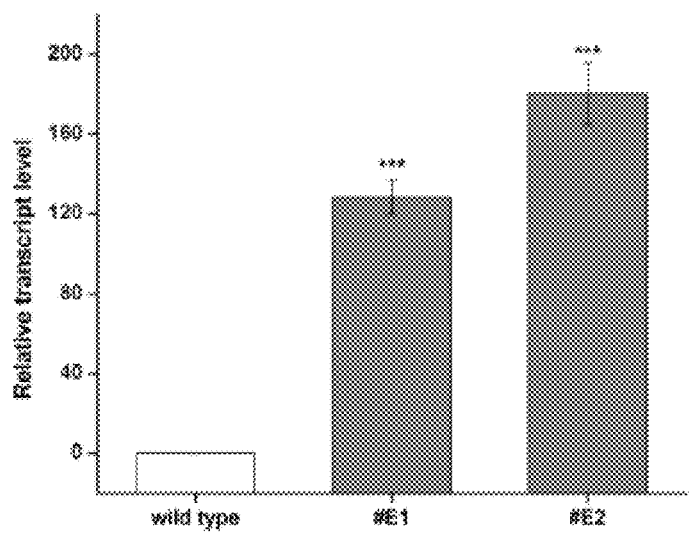
FIG. 15 shows the relative expression level of tomato GAME25 gene in leaves of GAME25-Ox eggplant (cv. Tudela) as compared to wild-type plants determined by quantitative real-time PCR (qRT-PCR). Tomato GAME25 gene was overexpressed in eggplant. #E1 and #E2 are two independent GAME25-Ox eggplant transgenic lines. Values indicate means of three biological replicates±standard error. Asterisks indicate significant changes from wild-type samples as calculated by a Student's t-test (*P-value <0.05; P-value <0.01; *P-value <0.001).

Unlike tomato, saturated SGAs (without C5,6-double bond) are normally not present in cultivated eggplant suggesting the absence of GAME25 activity in this species. This is further supported by the absence of a GAME25 homolog in eggplant as observed in phylogenetic analysis of GAME25 proteins (FIG. 6). In cultivated eggplant (wild type), α-solasonine [m/z 884.5, M+H$^+$], α-solamargine [m/z 868.5, M+H$^+$] and malonyl-solamargine [m/z 954.5, M+H$^+$] are the major unsaturated SGAs (with C-5,6 double bond) derived from the solasodine aglycone (FIG. 14). Moreover, cultivated eggplant also produces unsaturated furostanol type steroidal saponin glycosides [m/z 1031.5, (M+H$^+$-H$_2$O)$^+$ and m/z 1117.5, (M+H$^+$-H$_2$O)$^+$] from unsaturated furostanol type saponin aglycone (FIG. 14). Henceforth, the impact of tomato GAME25 activity in eggplant was examined in order to see whether GAME25 can shift SGA metabolism in eggplant from predominant unsaturated SGA branch to normally not occurring saturated SGA branch. Transgenic eggplant lines were generated overexpressing the tomato GAME25 gene (#E1 and #E2 are two independent transgenic eggplant lines; FIG. 15). Surprisingly, in eggplant leaves, GAME25 overexpression resulted in reduction of the unsaturated α-solasonine, α-solamargine, malonyl-solamargine SGAs as well as unsaturated furostanol saponin glycosides (FIG. 14). Conversely, major accumulation of β-soladulcine [m/z 886.5, M+H$^+$], soladulcine A [m/z 870.5, M+H$^+$] and saturated form of malonyl-solamargine [m/z 956.5, M+H$^+$] (FIG. 14) was observed in GAME25-Ox eggplant leaves. Both β-soladulcine and soladulcine A (lacking the C-5,6 double bond) are SGAs derived from the saturated soladulcidine aglycone and are typically found in S. dulcamara (FIG. 3A). Thus, S. dulcamara must have an active GAME25 homolog that mediates the formation of above mentioned saturated SGAs. Surprisingly, saturated furostanol type steroidal saponin glycosides (m/z 1033.5, (M+H$^+$-H$_2$O)$^+$ and m/z 1119.5, (M+H$^+$-H$_2$O)$^+$ in FIG. 14) were also found in GAME25 overexpressing transgenic eggplant lines that were completely absent in wild type. Thus, tomato GAME25 drives the formation of saturated soladulcidine (SA aglycone) from solasodine and saturated saponin aglycone from unsaturated ones respectively in eggplant that further produce their respective glycosylated forms.

Figure 16A:
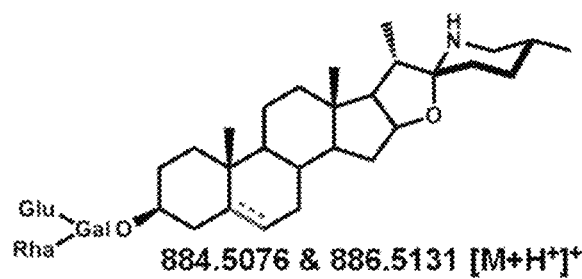
FIGS. 16A-16F show the structures of detected steroidal alkaloids and saponins in leaves of GAME25-Ox eggplant (cv. Tudela). Chemical structures were putatively assigned by calculating elemental compositions from the accurate mass and interpretation of mass fragmentation patterns, loss of water in positive ionization mode from steroidal saponins is typical for furostanol-type compounds (Heinig & Aharoni, 2014).
Figure 16B:
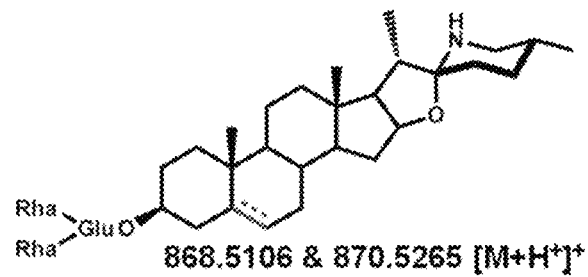
Figure 16C:
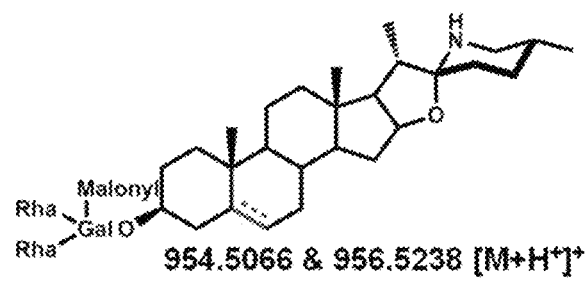
Figure 16D:
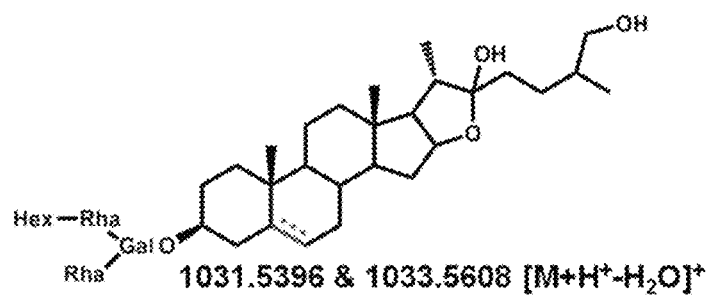
Figure 16E:
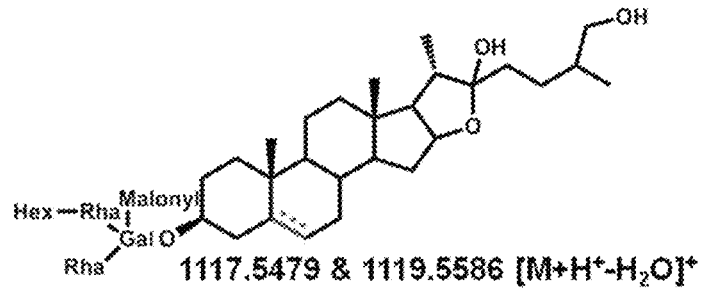
Figure 16F:
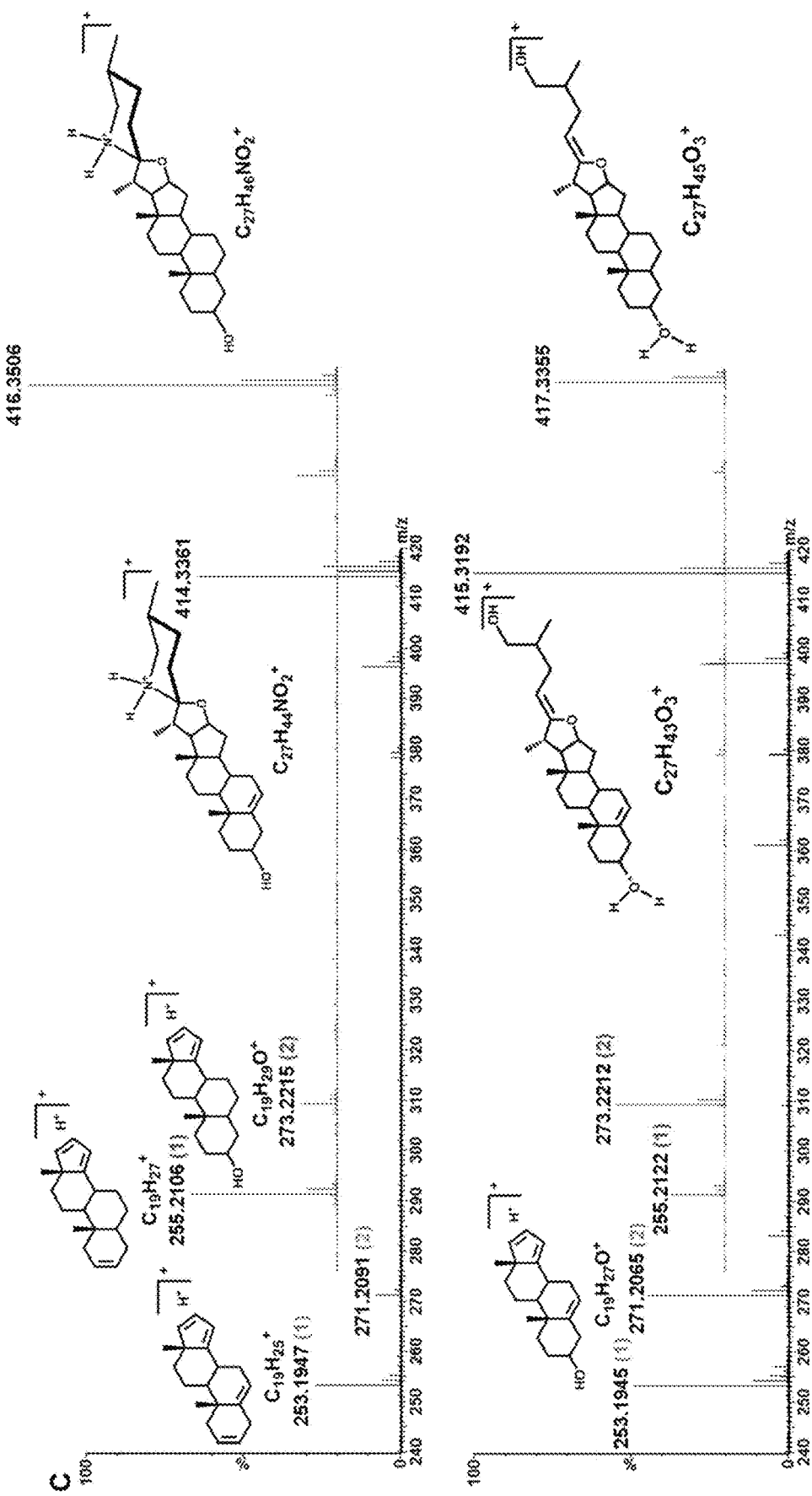

The chemical structures of unsaturated and saturated, SGAs as well unsaturated and saturated steroidal saponins metabolites identified here are provided in FIGS. 16A-16E. The identification of metabolites was based on Mass fragmentation pattern. Loss of C-3 sugar moieties in unsaturated SGAs led to the formation of the fragment ion with m/z 414.3 that corresponds to unsaturated steroidal aglycone backbone (FIG. 16F). Further loss of E and F ring in unsaturated steroidal backbone resulted in the fragment ion m/z 271.2 which further produced ion with m/z 253.19 after dehydration (FIG. 16F, upper panel). On the other hand, due to absence of C-5,6 double bond, saturated SGAs formed the fragment ion with m/z 416.3 corresponding to saturated steroidal aglycone that further produced the fragment ions m/z 273.2 and 255.2 after loss of E/F rings and dehydration respectively (FIG. 16F, upper panel) Similarly, unsaturated furostanol type steroidal saponins showed m/z 415.3, 271.2 and 253.19 fragment ions whereas saturated furostanol type steroidal saponins displayed m/z 417.3, 273.2 and 255.2 fragment ions after MS-fragmentation analysis (FIG. 16F, lower panel).

In tomato, it is hereby predicted that GAME25 catalyzes conversion of unsaturated dehydrotomatidine aglycone to saturated tomatidine aglycone. As tomato GAME25 induces the formation of saturated SGAs (e.g. β-soladulcine and soladulcine A) from solasodine aglycone as well as saturated saponins from unsaturated furostanol saponin aglycone in eggplant, it is possible that GAME25 might have broad preference for unsaturated SA aglycone and saponin substrates in *Solanum* plants.

Example 9

Figure 17A:
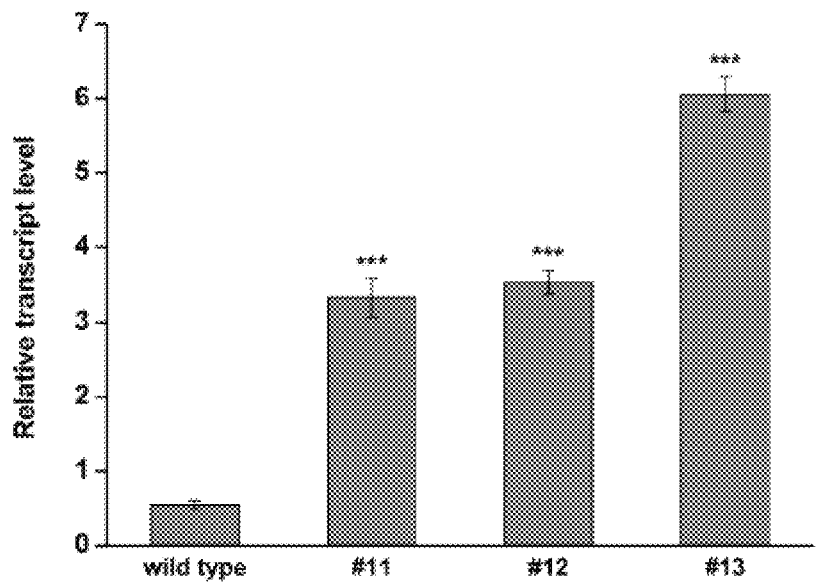
FIGS. 17A-17C show overexpression of GAME25 in potato.

GAME25 Overexpression Results in Reduced Levels of α-Solanine and α-Chaconine, the Major SGAs in Potato
Objective:
  To examine the impact of GAME25 activity on SGAs metabolism in potato.
Results:
  Potato plants overexpressing GAME25 (GAME25-Ox) were generated as described above (FIG. 17A). The pathway from the aglycone solanidine to demissidine and its glycosylated form (i.e. demissine) in potato corresponds to the tomato pathway in which the C-5,6 double bond is eliminated from dehydrotomatidine towards tomatidine and the glycosylated α-tomatine (FIGS. 2A and 2B). While α-tomatine and its derivatives accumulate to high levels in tomato, the domesticated potato does not accumulate demissidine or demissine SGAs in any plant part (while wild potato species do). In contrast to tomato, the potato GAME25 showed very low expression in green and vegetative potato tissues. Yet, a GAME25 transcript is abundant in various potato tuber tissues (i.e. skin and cortex).

Figure 17B:
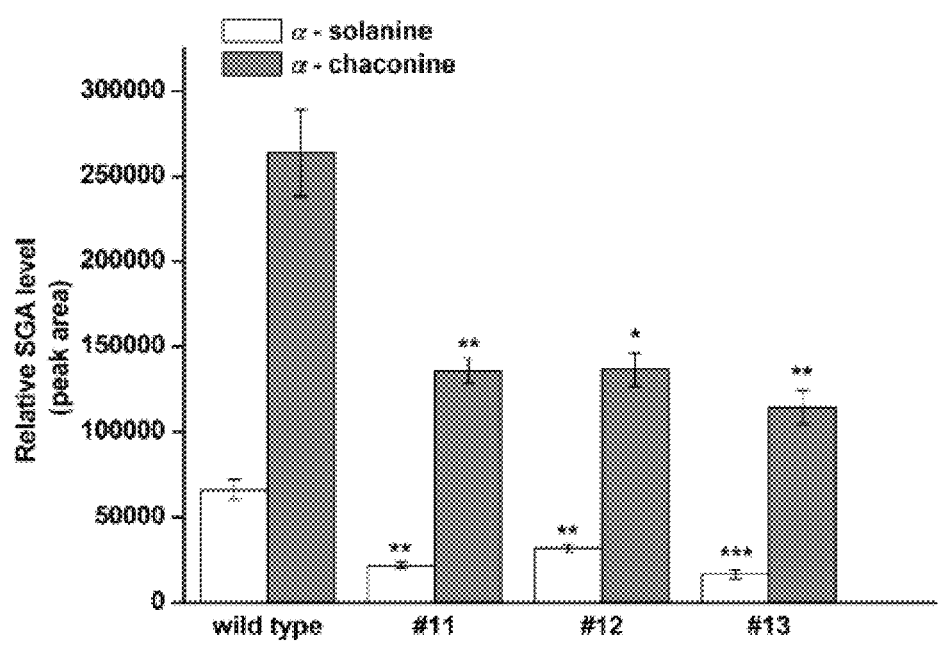
Figure 17C:
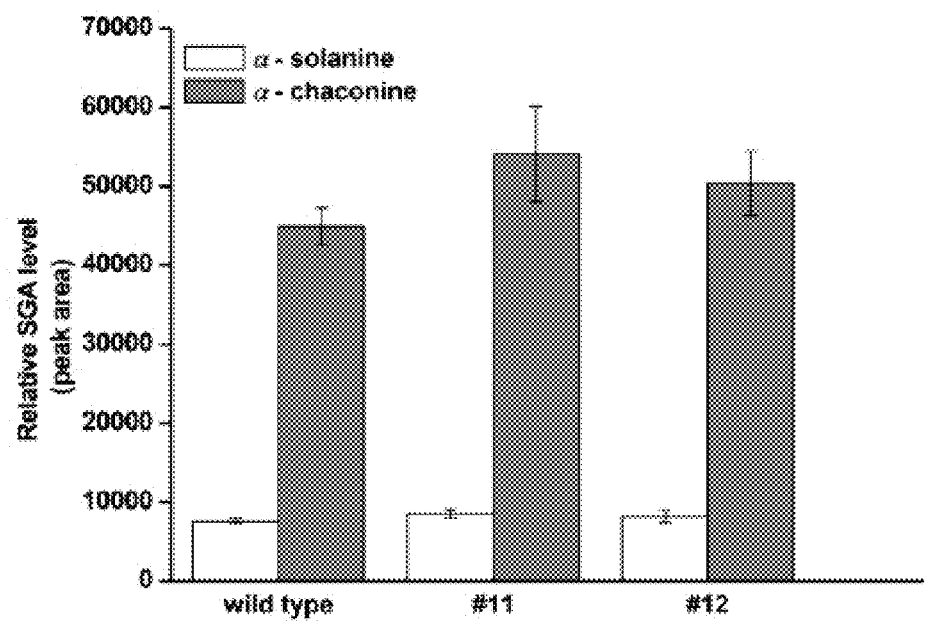

Over-expression of GAME25 in potato leaves resulted in a significant reduction in levels of α-solanine and α-chaconine, the major SGAs in potato (FIG. 17B). Yet, accumulation of demissidine or demissine was not detected in these leaves. Moreover, analysis of tuber skin tissue in GAME25-Ox potato plants showed no accumulation of demissidine or demissine along with no major change in α-solanine and α-chaconine SGAs (FIG. 17C).

Example 10

Functional Characterization of the *S. lycopersicum* GAME25 Encoded Recombinant Enzyme Produced in Sf9 Insect Cells and *E. coli*
Objective:
  To functionally characterize the enzyme activity encoded by GAME25.
Methods:
  The recombinant tomato and potato GAME25 enzymes were produced in Sf9 insect cells and examined for activity with dehydrotomatidine, solanidine and solasodine as substrates (the major SGAs aglycones in tomato, potato and eggplant, respectively).

Heterologous Expression of the *S. lycopersicum* GAME25 Encoded Enzyme in Baculovirus Infected Sf9 Insect Cells
  The GAME25 gene was cloned into the pVL1393 baculovirus expression vector using the following primers.

```
GAME25 baculo Forward primer:
                                     (SEQ ID NO: 9)
CCCGGGATGGCAAATAAGCTCAGGTTGG.

GAME25 baculo Reverse primer:
                                     (SEQ ID NO: 10)
TCTAGATTACAGATCTTCTTCAGAAATAAGTTTTTGTTCTTGTAGCTT-
CAAA
ATAGAACTTAGTCC.
```

Each expression vector construct was co-transfected with the ProGreen GFP linearized baculovirus DNA (AB vector) to generate the recombinant viruses in *Spodoptera frugiperda* (Sf9) insect cells. Infection efficiency was monitored by fluorescence of recombinant GFP viruses infected cells. Sf9 cells were grown in ESF921, protein free culture medium (Expression Systems). Three days post-infection cells were collected and washed twice in PBS. Microsomal fractions were isolated by suspending the cell pellet in 20 mM potassium phosphate buffer pH 7.25, 20% (v/v) glycerol, 1 mM EDTA and 1 mM DTT. The resuspended cells were sonicated, and the cell debris was removed by centrifugation at 10,000×g for 15 min. The supernatant was further centrifuged at 100,000×g for 60 min. The pellet containing the microsomal fractions was homogenized in lysis buffer. GAME25 was expressed with a myc-tag at the C-terminus. The isolated microsomal fractions were analyzed by SDS-PAGE and immune-blot with c-myc antibodies (A2S Technologies Ltd.).

GAME25 and GAME35 Expression in *E. coli* BL21 (DE3) Cells and their Protein Purification
  GAME25 and GAME35 genes were cloned into pET28 vector separately and expressed in *E. coli* BL21 (DE3). Bacterial cells were grown in LB medium at 37° C. When cultures reached A600=0.6, protein expression was induced with 200 µM of isopropyl-1-thio-β-d-galactopyranoside (IPTG) at 15° C. for 24 h. Bacterial cells were lysed by sonication in 50 mM Tris-HCl pH 7.5, 500 mM NaCl, 1 mM PMSF and protease inhibitor cocktail (Calbiochem). An aliquot of whole cell extract was kept for further analysis. Soluble protein was purified using Ni-NTA agarose beads (Adar Biotech) and eluted with 500 mM imidazole in buffer containing 50 mM NaH$_2$PO$_4$ pH-7.5 and 300 mM NaCl. The whole cell extract and the eluted fractions were analyzed by SDS-PAGE staining with InstatBlue and by Western blot with HRP conjugated anti-His antibodies (Sigma).

In Vitro Assays of the Recombinant GAME25 Enzyme(s) Expressed in Insect Cells
  The steroidal alkaloid aglycones dehydrotomatidine, solanidine and solasodine as well as their glycosylated forms (i.e. SGAs) α-tomatine, α-solanine, α-chaconine and α-solamargine were used as substrates for GAME25 enzyme assays. In vitro assays for the tomato and potato recombinant GAME25 enzymes were performed as follows: Briefly, microsomal fractions of Sf9 cells expressing tomato or potato GAME25 proteins (0.2 mg total protein was used per reaction) were separately incubated in sodium phosphate buffer (pH 7.4) with 100 µM of each individual substrate (details are mentioned above), DTT (5 mM) and NAD$^+$ (150 µM) at 37° C. for 4 hrs. The reactions were stopped by addition of 300 µl of 80% methanol and 0.1% formic acid, followed by brief vortex and sonication for 15 min. Finally, the extracts were centrifuged for 15 min at 14,000×g, filtered through 0.22 µm filters, and analyzed by LC-MS (see Plant extracts preparation and targeted profiling of steroidal metabolites section above). Sf9 cells (without the baculovirus vector) microsomes were used in control enzyme reactions.

In Vitro Assays of the Recombinant Tomato GAME25 Enzyme Expressed in E. coli

Assay for purified recombinant tomato GAME25 enzyme (5 µg) from E. coli cells using solanidine (steroidal alkaloid aglycone) and diosgenin (steroidal saponin aglycone) substrates was performed under standard assay conditions similarly as described above.

In Vitro Assays of the Recombinant Tomato GAME25 Enzyme Expressed in E. coli

Assay for purified recombinant tomato GAME25 enzyme (5 µg) from E. coli cells using solanidine (steroidal alkaloid aglycone) and diosgenin (steroidal saponin aglycone) substrates was performed under standard assay conditions similarly as described above.

GAME35 Enzyme Assay

Purified GAME35 protein (5 µg) was incubated with solanid-4-en-3-one substrate (150 µM), DTT (1 mM), NADH or NADPH (500 µM) in sodium phosphate buffer (pH 7.4) at 30° C. for 3 hrs. The reactions were stopped by addition of 250 µl of 80% methanol and 0.1% formic acid, and followed by brief vortex and sonication for 15 min. Finally, the extracts were centrifuged for 10 min at 13,000×g and filtered through 0.22 µm filters, and analyzed by LC-MS, as described in the section above (plant extracts preparation and targeted profiling of steroidal metabolites). Fractions from pET28 vector (empty) transformed into BL21 (DE3) cells was used as a control in enzyme reaction.

Figure 18A:
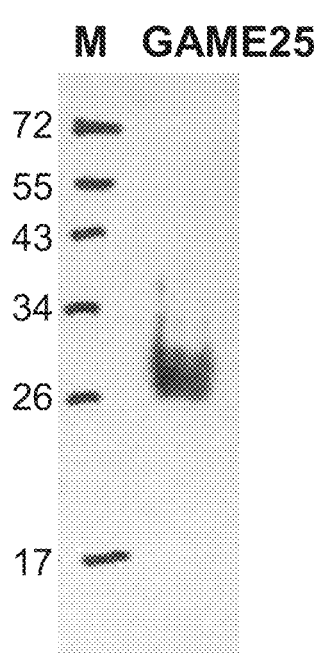
FIGS. 18A-18B show expression of tomato and potato GAME25 protein in the microsomal fraction of Sf9 cells. Recombinant GAME25 proteins were expressed in Sf9 cells and analyzed by immunoblot with anti-myc antibodies.
Figure 18B:
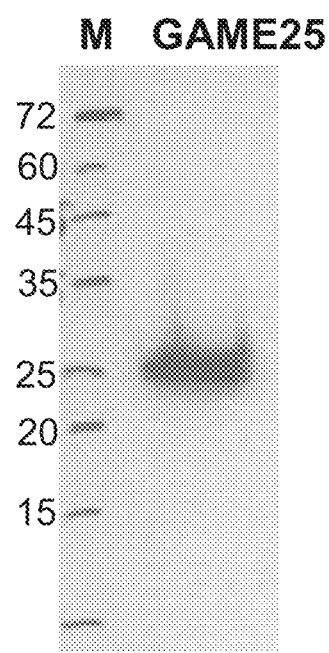
Figure 19A:
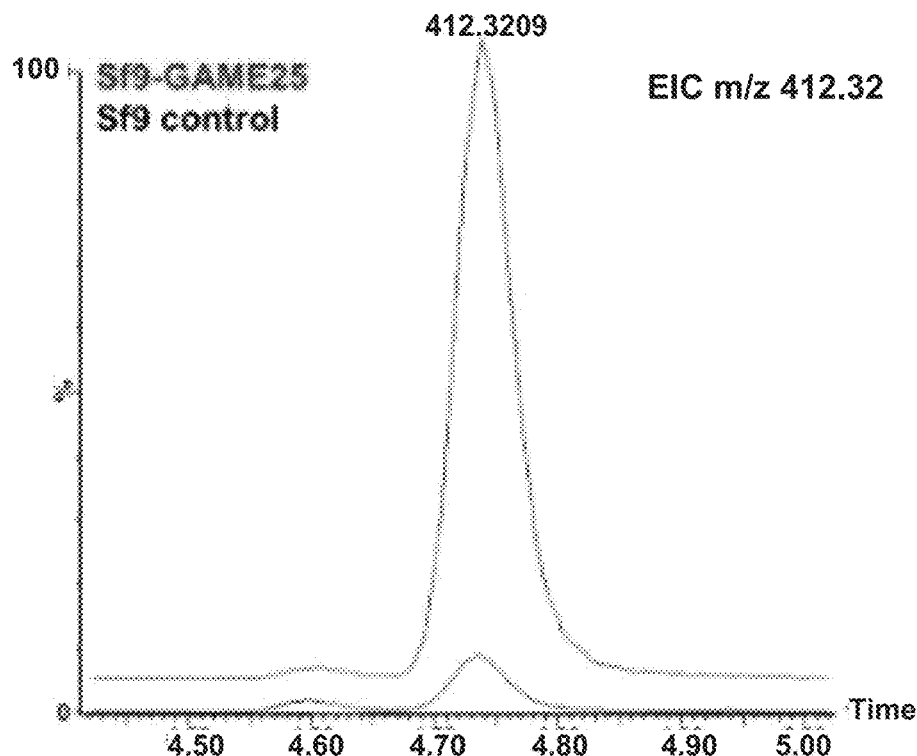
FIGS. 19A-19L show the activity of the recombinant tomato and potato GAME25 produced in Sf9 insect cells with dehydrotomatidine and solanidine as substrates.
Figure 19B:
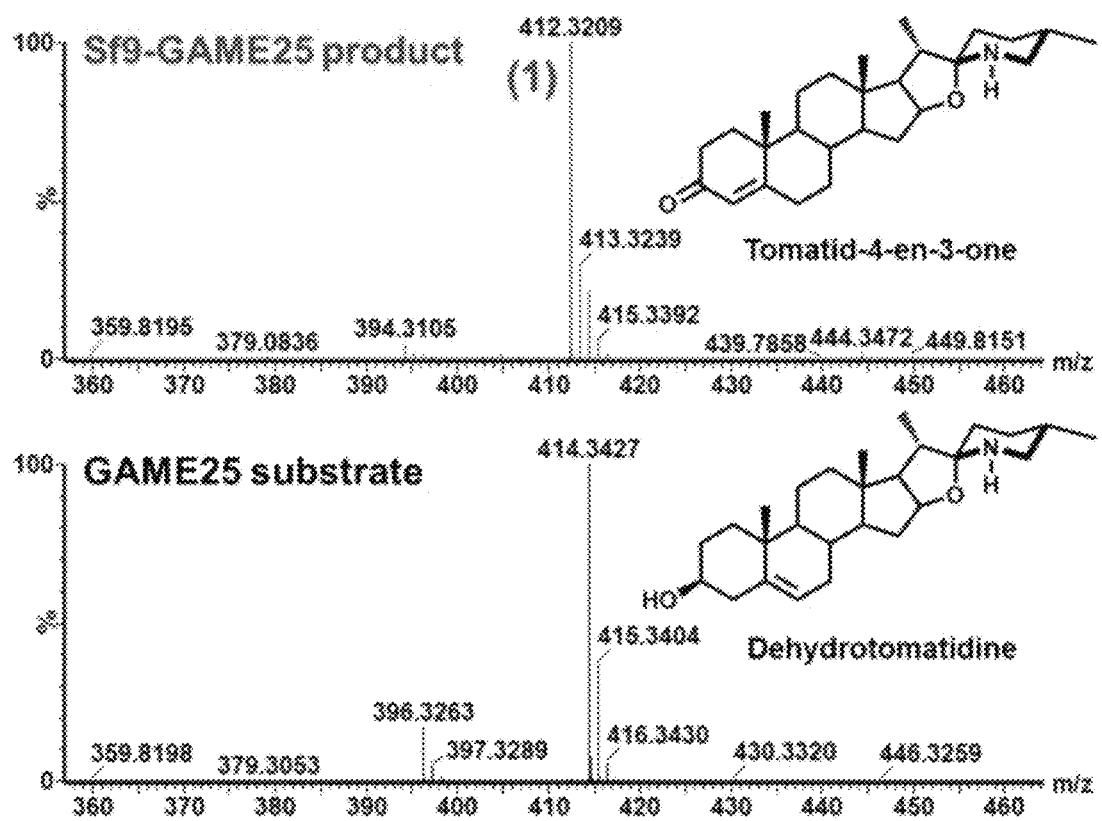
Figure 19C:
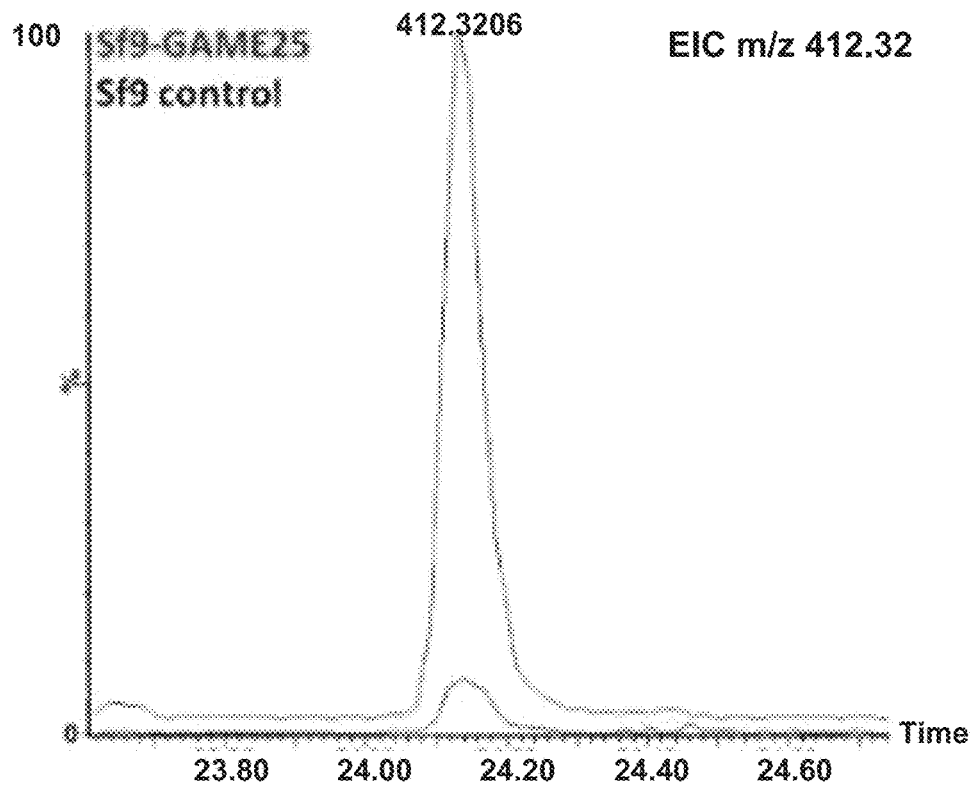
Figure 19D:
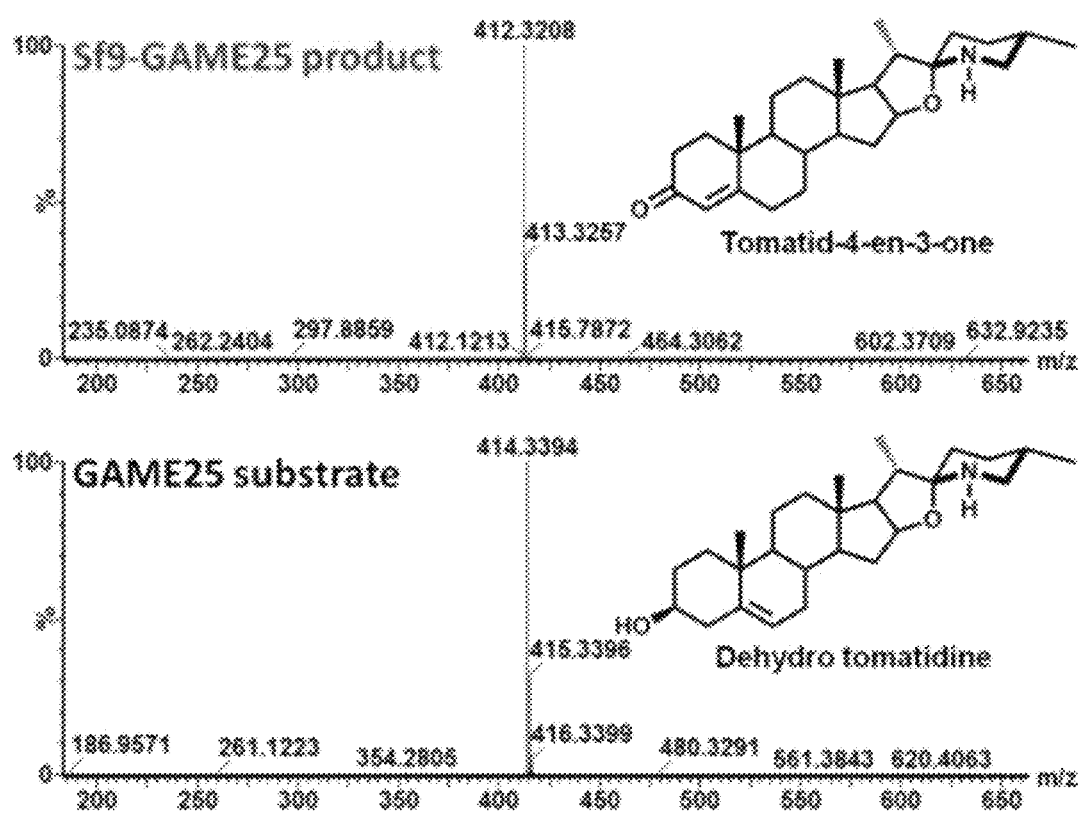
Figure 19E:
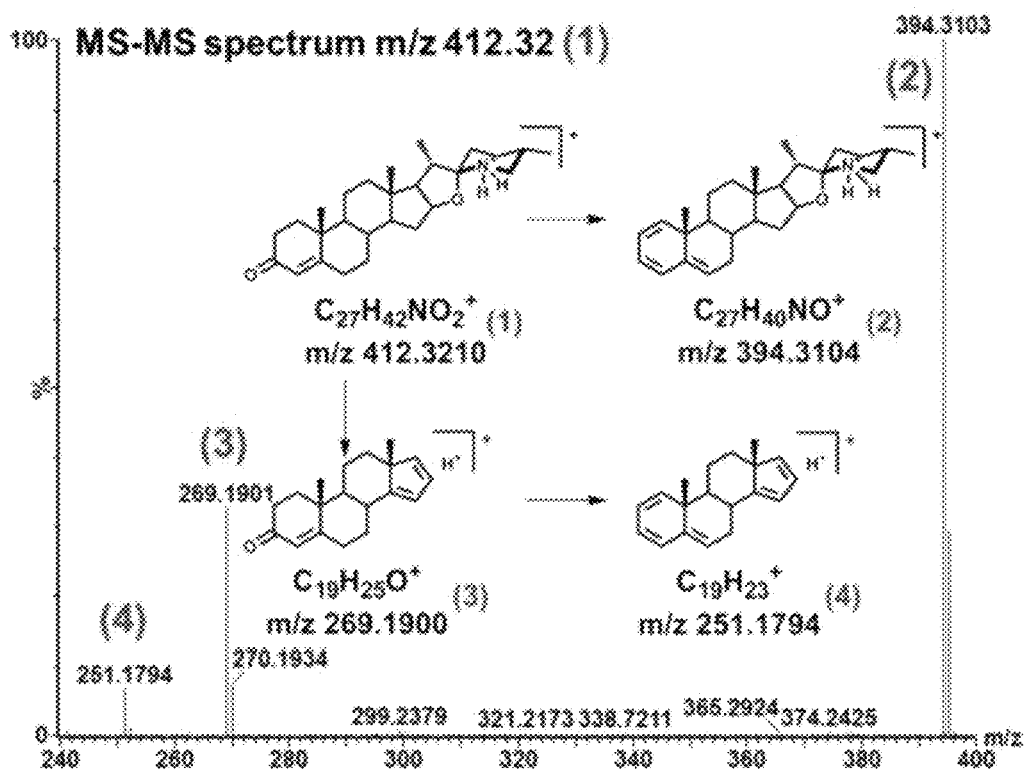

Results:

The suggested role of GAME25 in conversion of dehydrotomatidine to tomatidine was examined by expressing the recombinant tomato and potato enzymes in sf9 insect cells and testing microsomal fractions for activity with dehydrotomatidine, solanidine and solasodine (SA aglycones) as substrates respectively. The expression of potato and tomato GAME25 recombinant proteins in sf9 cell microsomes was confirmed by western blot using c-myc antibody (FIGS. 18A and 18B). Enzymatic assays were performed in the presence of NAD$^+$ as a cofactor. Assays with either tomato or potato recombinant GAME25 did not result in the formation of tomatidine, demissidine and soladulcidine (saturated steroidal alkaloid aglycones), the expected reaction products. However, assay of both recombinant GAME25 enzymes with dehydrotomatidine (m/z 414.3, M+H$^+$) resulted in the formation of a novel compound with the mass m/z 412.3 (M+H$^+$) in tomato (FIGS. 19A and 19B) and potato (FIGS. 19C and 19D) GAME25 assay. To identify the newly formed compounds, MS-MS fragmentation pattern analysis was employed (FIGS. 19A, 19B and 19E). The observed fragmentation pattern contains three major fragment ions from 2 parallel fragmentation routes. Loss of the carbonyl-oxygen and formation of an additional double bond leads to the fragment ion with m/z 394.3. Loss of the E and F ring of the steroidal skeleton leads to the fragment ion m/z 269.2 which afterwards gets dehydrated to form fragment m/z 251.17 (FIG. 19E). In conclusion, the newly formed compound was putatively assigned as tomatid-4-en-3-one.

Figure 19F:
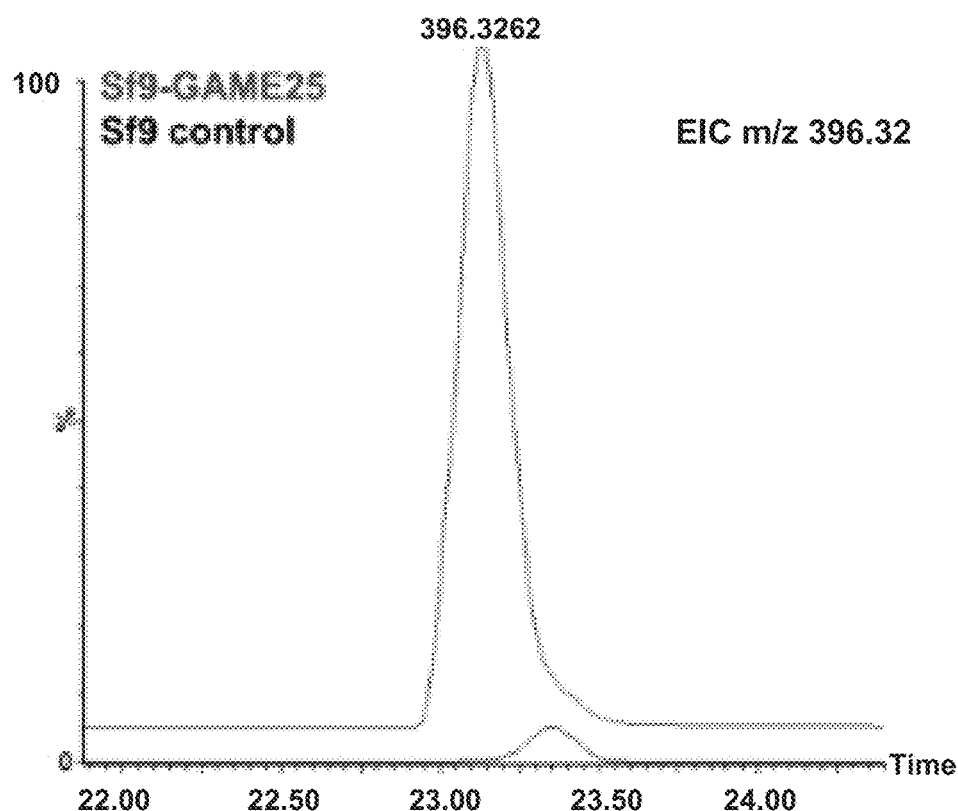
Figure 19G:
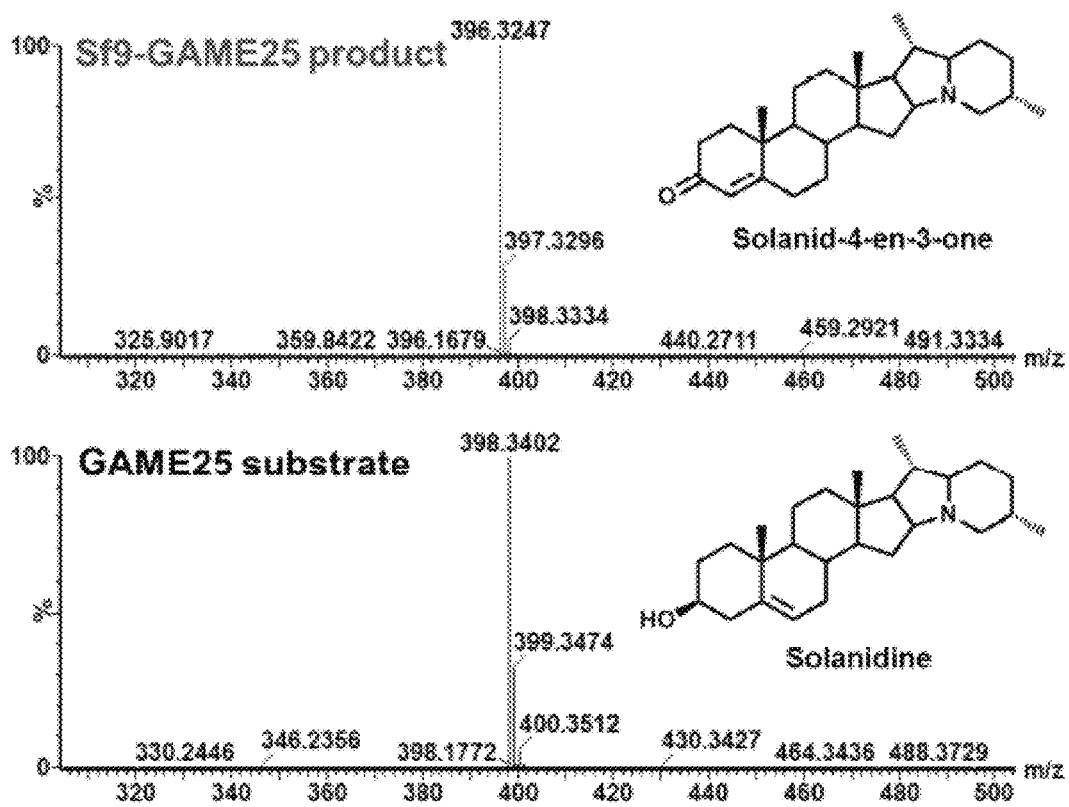
Figure 19H:
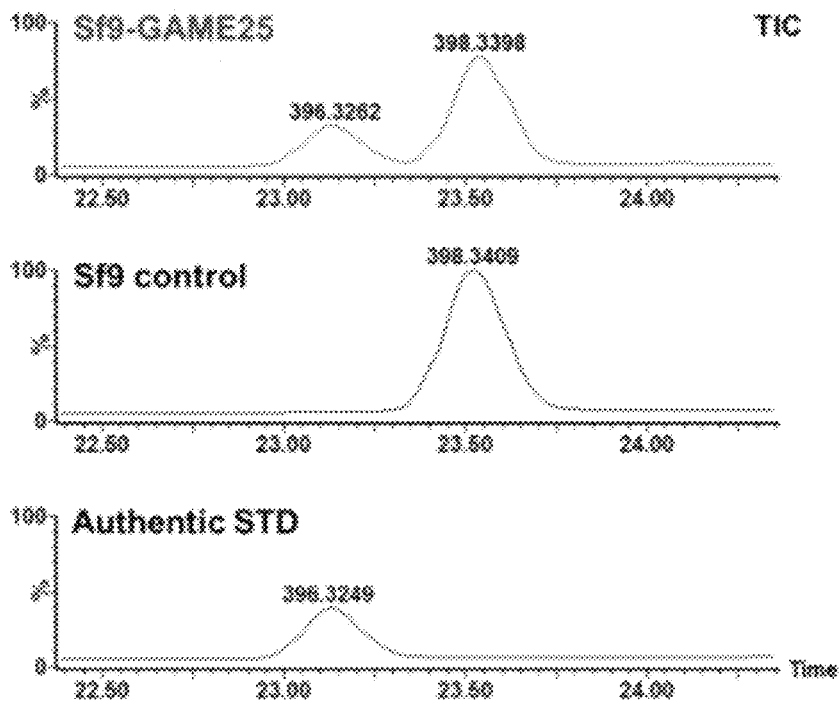
Figure 19I:
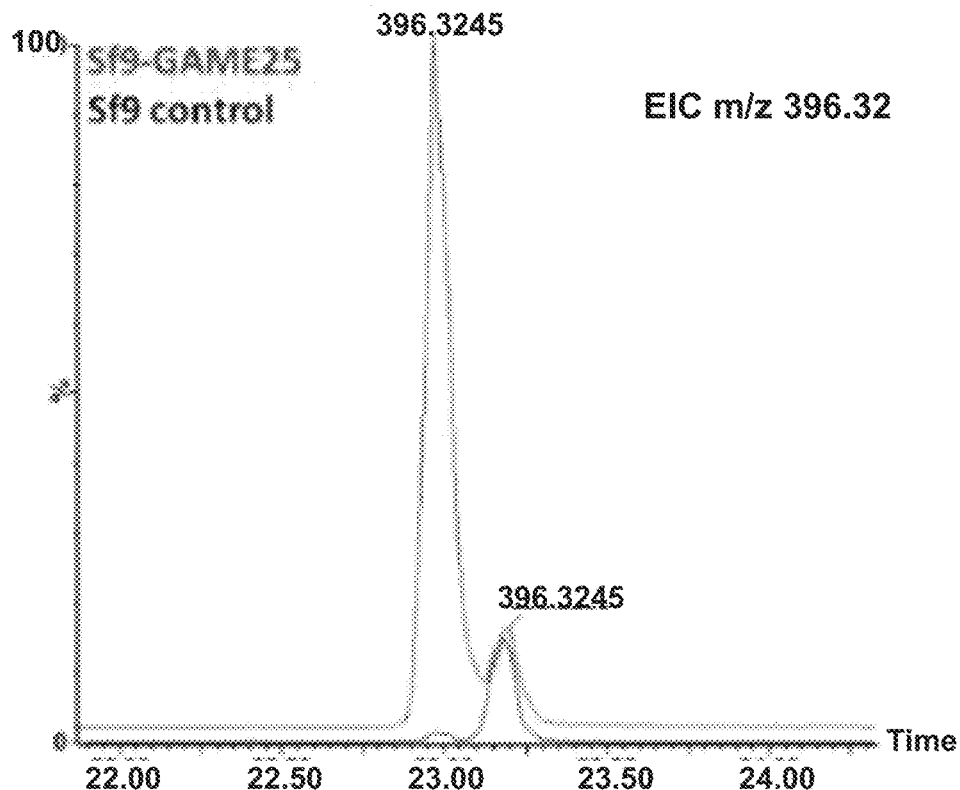
Figure 19J:
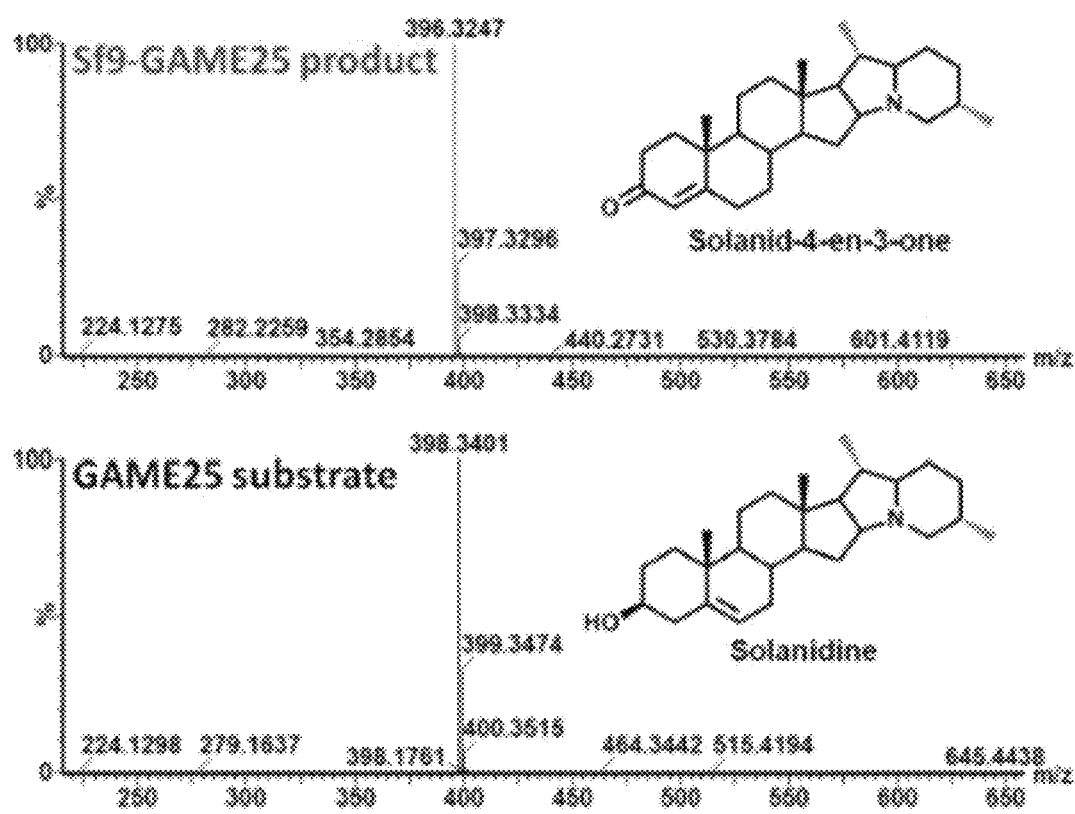
Figure 19K:
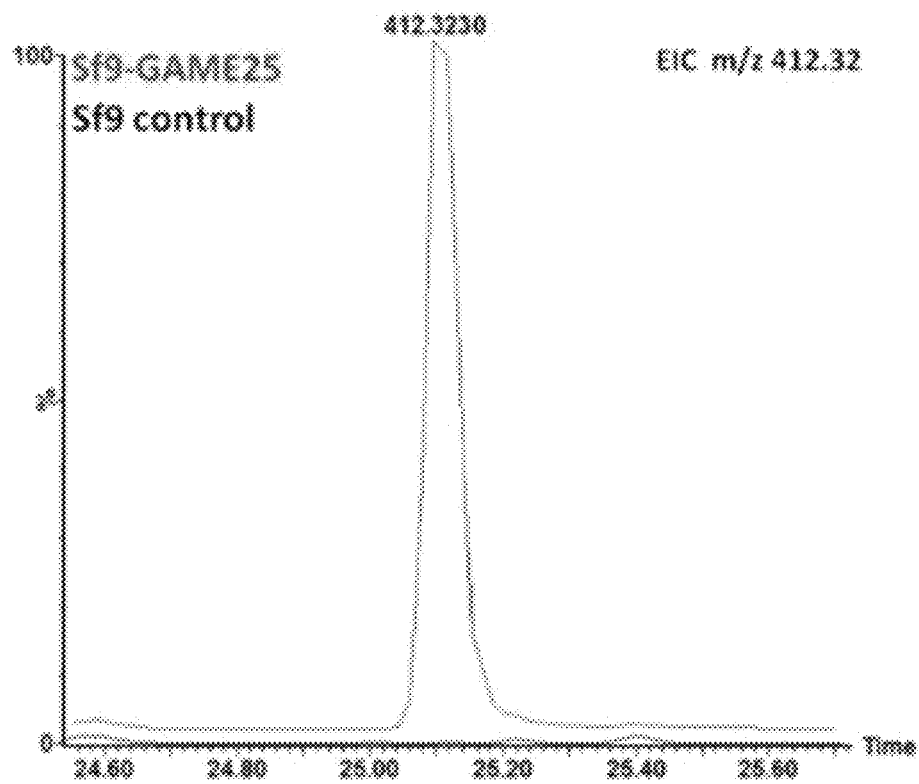
Figure 19L:
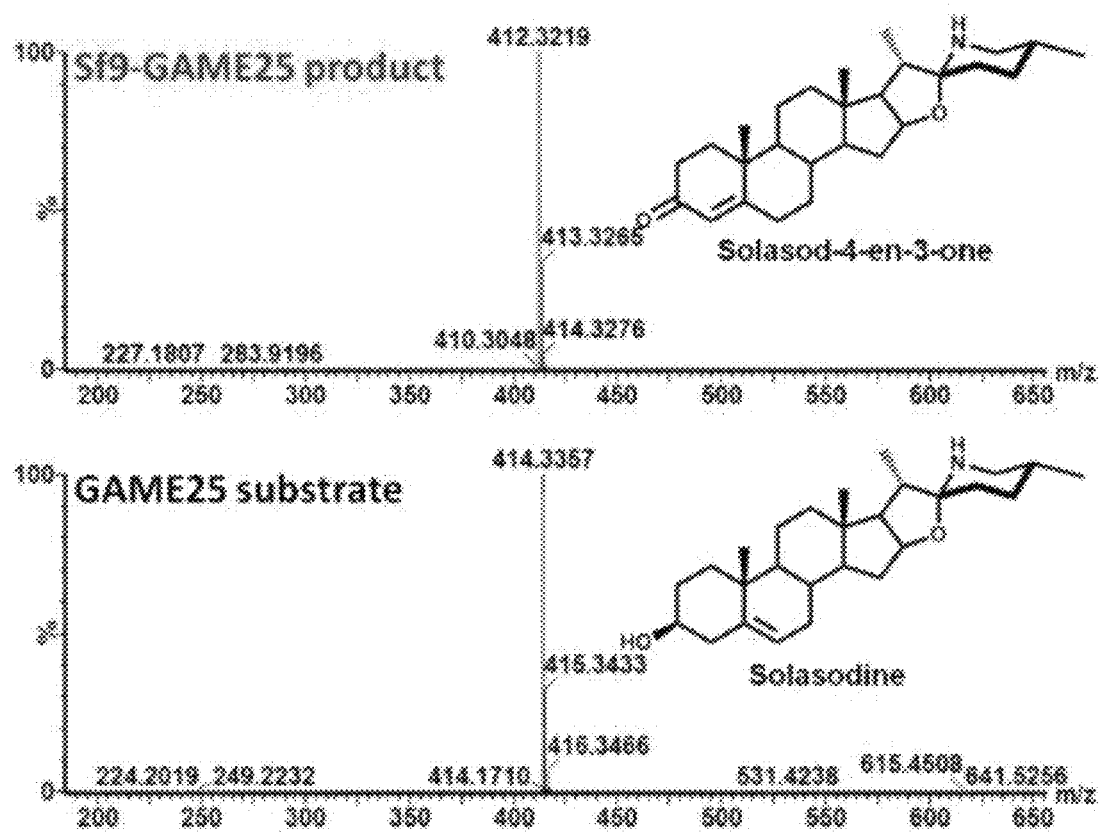
Figure 20A:
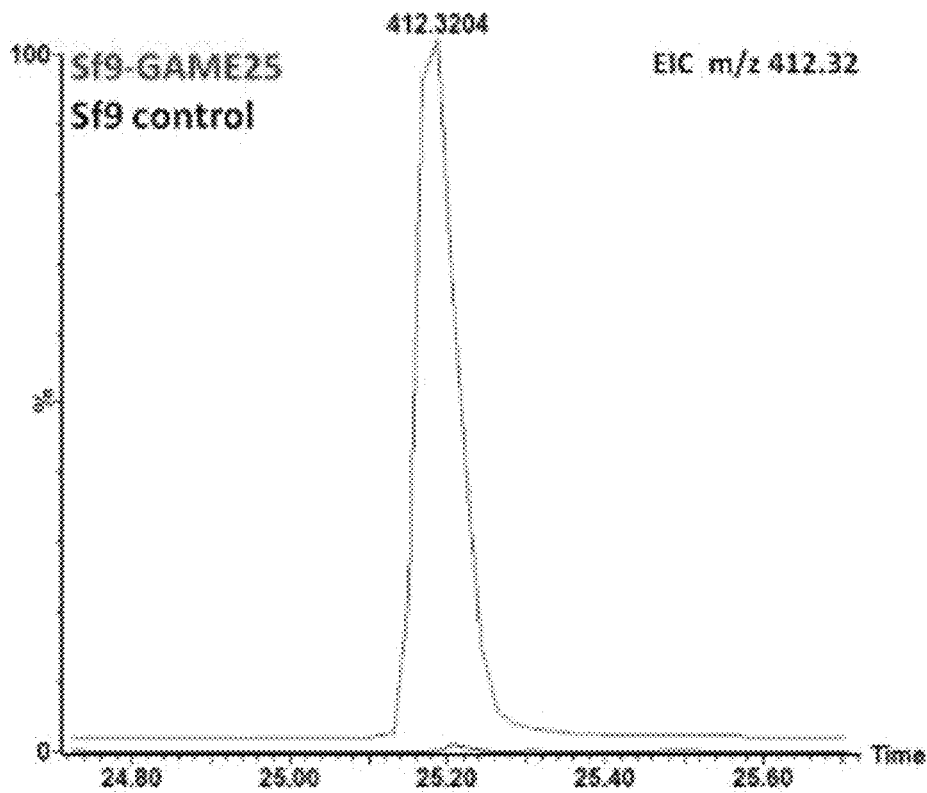
FIGS. 20A-20D show a characterization of GAME25 (tomato) by in vitro enzyme activity assay. GAME25 (tomato) was expressed in Sf9 insect cells.
Figure 20B:
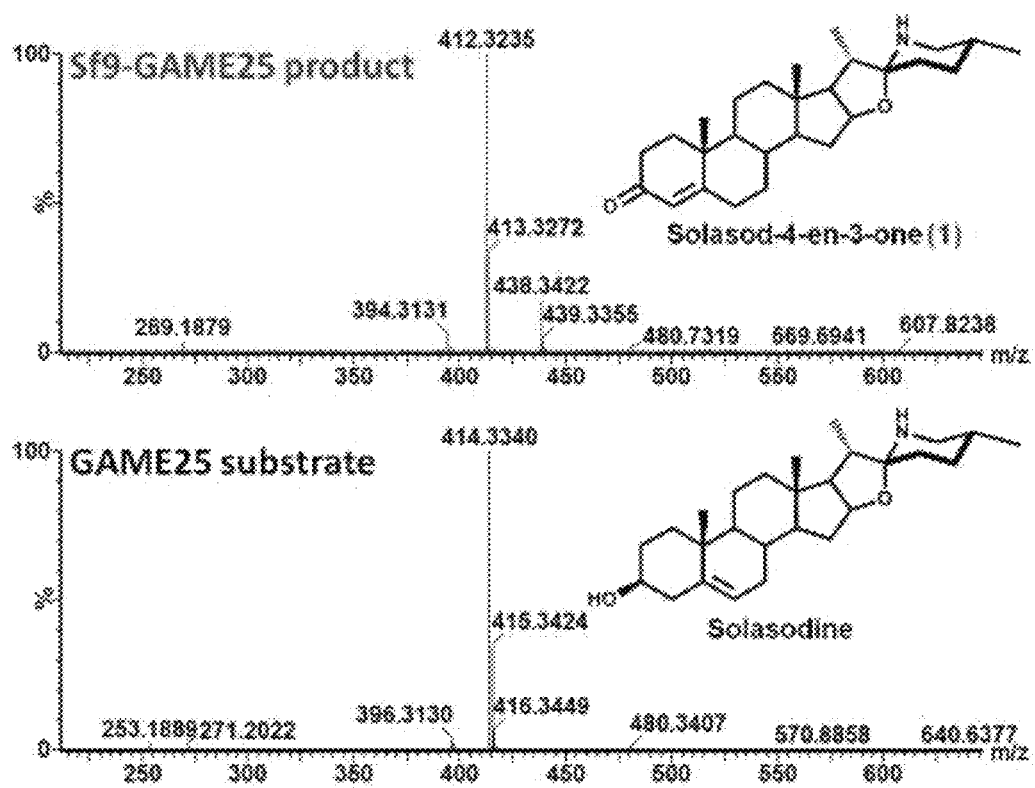
Figure 20C:
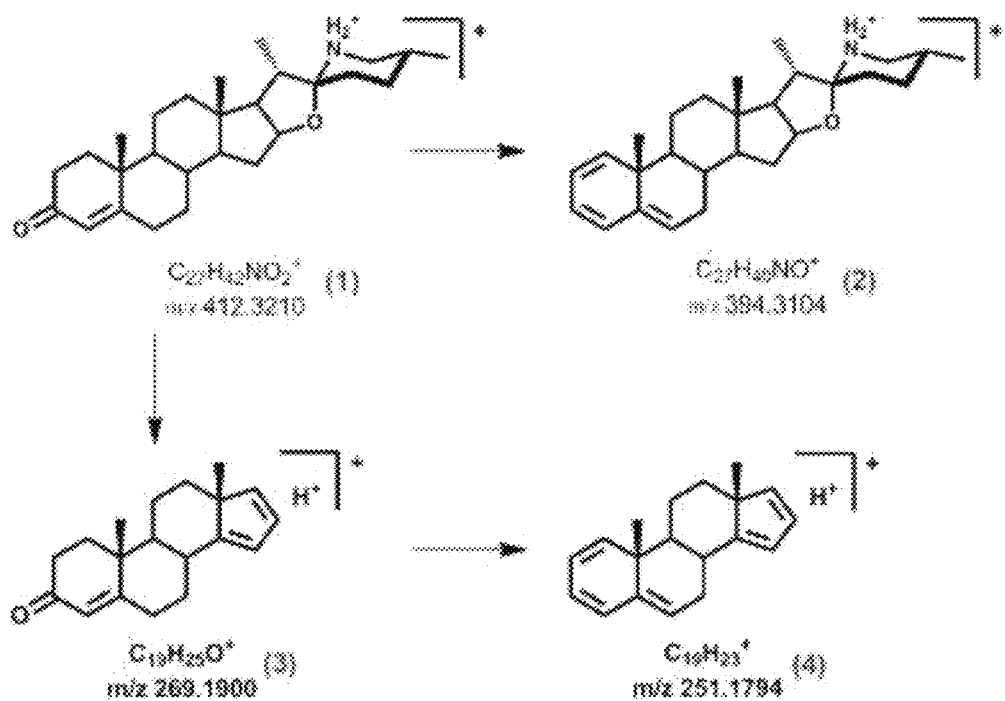
Figure 20D:
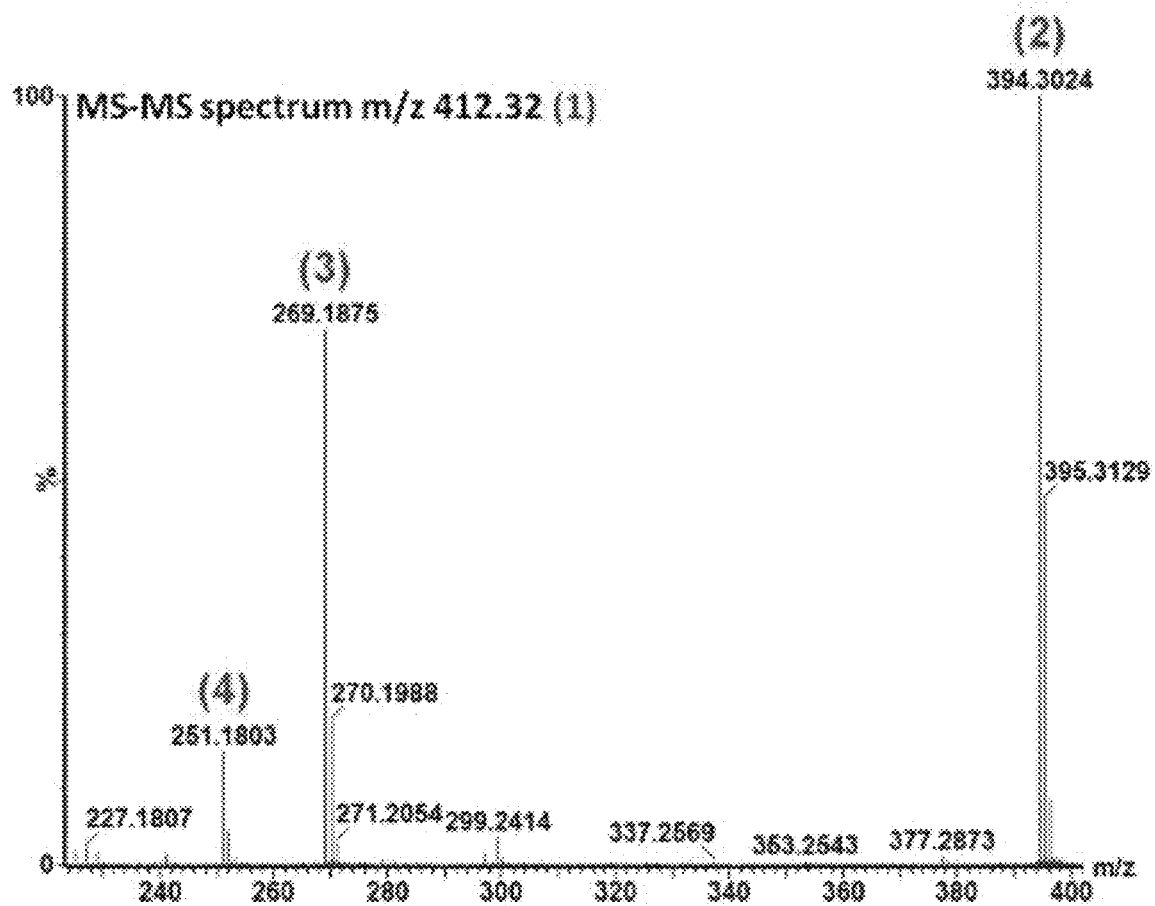

Using solanidine as a substrate (M+H$^+$, m/z 398.3), GAME25 enzyme assay (with both tomato and potato GAME25 enzymes) led to formation of a new product with an apparent molecular ion of m/z 396.3 (M+H$^+$). This product was identified as solanid-4-en-3-one by comparing retention time and mass spectrum to the authentic commercially available solanid-4-en-3-one standard both for tomato GAME25 (FIGS. 19F-19H) and for tomato GAME25 (FIGS. 17B, 19I, and 19J) assay. The recombinant GAME25 enzymes (both from tomato and potato) were also able to convert solasodine, the eggplant aglycone (M+H$^+$, m/z 414.3) to the putative solasod-4-en-3-one compound (M+H$^+$, m/z 412.3) identified based on MS-MS fragmentation pattern analysis similarly as described above for assignment of tomadid-4-en-3-one for potato GAME25 (FIGS. 19K and 19L) and for tomato GAME25 (FIG. 20A-20D) assay.

Tomato and potato recombinant GAME25 enzymes were also tested with glycosylated SAs; α-tomatine, dehydrotomatine, α-solanine, α-chaconine and α-solamargine, however, no activity was observed with these substrates. These results suggest that GAME25 catalyzes the oxidation of the 3β-hydroxyl group (3β-hydroxysteroid dehydrogenase activity) and the isomerization of double bond from the C-5,6 to the C-4,5 position (3-oxosteroid $\Delta^{5,4}$ isomerase activity) in SA aglycone substrates to form the 3-oxo-$\Delta^{5,4}$ SA aglycone intermediates that have been identified here (tomatid-4-en-3-one, solanid-4-en-3-one and solasod-4-en-3-one) (FIGS. 19B, 19D, 19E, 19G, 19J, 19L, and 20B-20D). Furthermore, these results show that GAME25 has activity on various SA aglycones and possibly possesses a novel 3β-hydroxysteroid dehydrogenase/$\Delta^{5,4}$ isomerase activity.

Figure 21A:
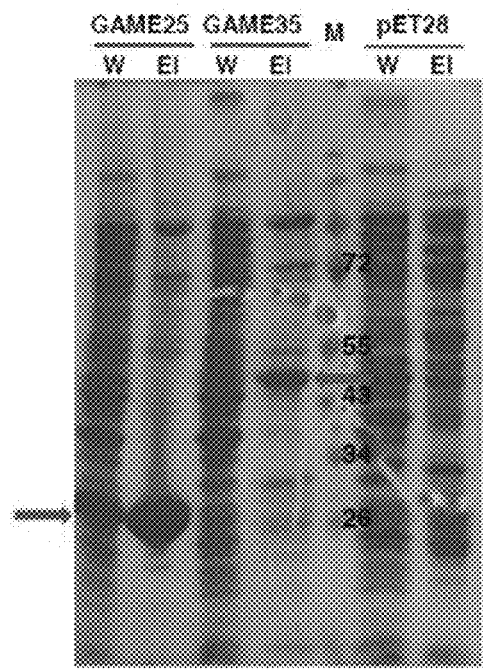
FIGS. 21A-21C show GAME25 and GAME35 protein expression in BL21(DE3).
Figure 21B:
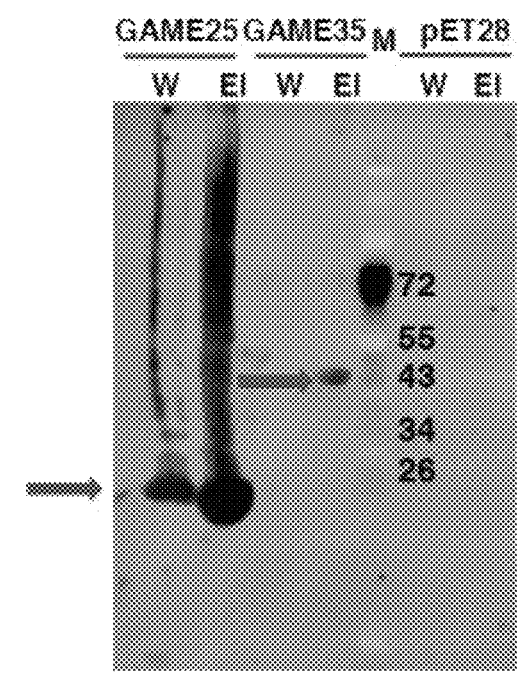
Figure 21C:
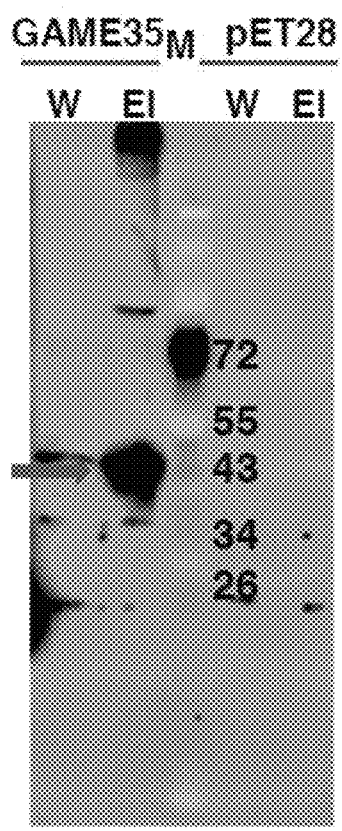

The observed 3β-hydroxysteroid dehydrogenase/$\Delta^{5,4}$ isomerase activity for tomato and potato recombinant GAME25 enzymes is rather uncommon since other SDR family enzymes partaking in secondary metabolism typically possess 3β-hydroxysteroid dehydrogenase activity only. For example, in Digitalis, the oxidation (3β-hydroxyl group) and isomerization (C-5,6 to the C-4,5 position) steps which are required during the conversion of pregnenolone to progesterone are carried out successively by two separate enzymes, the 3-βHSD (3β-hydroxysteroid dehydrogenase activity) and the 3-KSI ($\Delta^5$-3-ketosteroid isomerase activity), In order to confirm that the $\Delta^{5,4}$ isomerase activity observed previously for recombinant GAME25 enzymes produced in insect cells came originally from GAME25 enzymes and not from any endogenous enzymes of insect cells, tomato GAME25 protein was expressed in E. coli and purified by Ni-NTA chromatography (FIGS. 21A-21C). Enzyme assay with the purified GAME25 recombinant enzyme using solanidine substrate and NAD$^+$ as a cofactor resulted in the formation of the same solanid-4-en-3-one product (FIG. 22A) as described before. The solanid-4-en-3-one product's identity was confirmed by comparison of retention time and mass spectrum with authentic solanid-4-en-3-one standard as described above (FIGS. 17B and 19F-19H). Thus, it is hereby shown doubtlessly that the recombinant GAME25 enzyme possesses both the 3β-hydroxysteroid dehydrogenase and the $\Delta^{5,4}$ isomerase activities. These results also indicate that the removal of C-5,6 double bond in the SA aglycones is not a single step reaction as suggested previously.

A Putative 5β-Progesterone Reductase Homolog Doesn't Act as Second Enzyme Following GAME25 Reaction in Tomato Recombinant enzyme assay of GAME25 with various SA aglycones clearly shows that GAME25 alone is not sufficient to catalyze the entire $\Delta^5$ reduction (removal of C-5,6 double bond) in SA aglycone substrates and thus additional enzymes are required to form saturated SA aglycone and further saturated SGAs. In *Digitalis*, following the reactions of 3-βHSD and 3-KSI, conversion of progesterone to 5β-pregnan-3,20-dione (removal of C-4,5 bond) is catalyzed by 5β-progesterone reductase (5β-POR). Thus, it was hypothesized that a 5β-POR homolog in tomato might act as a second enzyme and catalyzing a similar reduction with the various 3-oxo-$\Delta^{5,4}$ steroidal alkaloid aglycone intermediates (e.g. solanid-4-en-3-one). Sequence homology search with *Digitalis* 5β-POR against the tomato genome resulted in two candidates; Solyc10g049600 (71% identity) and Solyc10g049620 (78% identity). Among these two genes, only Solyc10g049620 (termed here GAME35) was found to be expressed in different tomato tissues (Cárdenas et al. (2016), Tomato RNA seq data in NCBI Sequence Read Archive with BioProject ID PRJNA307656). In order to examine whether GAME35 catalyzes the enzymatic reaction following GAME25, GAME35 was expressed in *E. coli* and purified by Ni-NTA chromatography (FIGS. 21A-21C). For GAME35 activity assay, solanid-4-en-3-one was used as a substrate. GAME35 did not react with the solanid-4-en-3-one substrate, suggesting its minimal role in the reduction of the C-4,5 double bond in SA aglycone substrates (FIG. 22B). Thus, a different reductase enzyme might be required to carry out second reaction (removal of C-4,5 bond) during the biosynthesis of saturated SA aglycone from unsaturated one in *Solanum* plants.

Example 11

The Presence of the C-5,6 Double Bond in SGAs is Significant to Pathogenicity and Growth of Tomato Fungi Objective:

Given the finding that silencing of GAME25 in tomato redirects SGA metabolism towards the dehydro-SGAs branch instead of its typical tomatine derived SGAs, it was examined whether dehydro-SGAs levels affect pathogenicity or growth of disease causing fungi.

Methods:

Fungal Inhibition Assay

Methanolic extracts from 2.5 g wild-type leaves and three independent GAME25i transgenic plant leaves (#2, #3 and #4 are three independent GAME25i transgenic lines, and for each transgenic line, three separate tissue samples (weighing 0.8, 0.8 and 0.9 g each) were collected from three different plants respectively) were evaporated to dryness and redissolved in 700 µl of methanol. Fungal inhibition activity of the GAME25i and wild-type methanolic extracts was determined by the disc diffusion method. *Botrytis cinerea* (B05.10) and *Colletotrichum gloeosporioides* (Cg14) were grown on PDA (potato dextrose agar) plates for 10 days at 28° C. After 10 days, a conidial suspension was prepared and $4 \times 10^4$ conidia were spread in each petri dish containing PDA medium. Whatman filter paper (13 mm) was soaked with 100 µL of extract and allowed it to dry. Furthermore, the loaded Whatman filter paper was placed on the pre-inoculated petri dishes. Discs soaked with methanol were used as a control. The plates were then incubated at 28° C. for 2 days. Fungal inhibition activity was evaluated as the area of inhibition of mycelium growth subtracted by the area of the disc. Inhibition of conidia germination by GAME25i and wild-type extracts was tested as described earlier. Briefly, fungal conidia were collected from respective PDA plates and adjusted to the final conidia concentration of $1 \times 10^5$ conidia/ml using sterile distilled water. A drop of conidia suspension was incubated with GAME25i and wild-type methanol extracts (diluted by 5 times) on glass slides with 5 replicates and incubated in a humid chamber for 19 hrs. After incubation, slides were examined under microscope (×40) and each slide was evaluated in three different fields for recording the percentage of conidia germination. This experiment was repeated three times.

Results:

The predominant SGA α-tomatine in tomato green tissues is renowned to affect the growth of many pathogenic fungi, including *Botrytiscinerea*, *Fusariumoxysporum* and *Colletotrichumgloeosporioides*. As it normally produced in small amounts in tomato tissues, the role of dehydrotomatine in phytopathogenicity was not examined. Analysis of GAME25i leaf extracts (producing predominantly dehydrotomatine and downstream SGAs) showed a clear and significant mycelial growth inhibition of the pathogenic fungi *B. cinerea* and *C. gloeosporioides* as compared to wild-type extracts (accumulating α-tomatine and derived SGAs) (FIGS. 23A-23D). In addition, fungal conidia germination was severely affected in treatments with GAME25i extracts as compared to wild-type ones (FIGS. 23E-23J).

Example 12

Figure 24A:
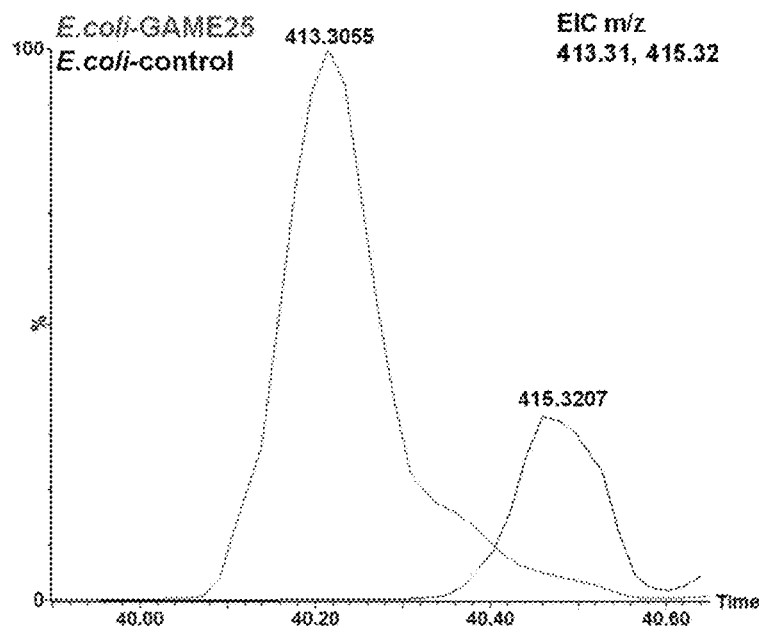
FIGS. 24A-24B show the conversion of Diosgenin, a steroidal saponin to Diosgen-4-en-3-one by tomato GAME25 enzyme.
Figure 24B:
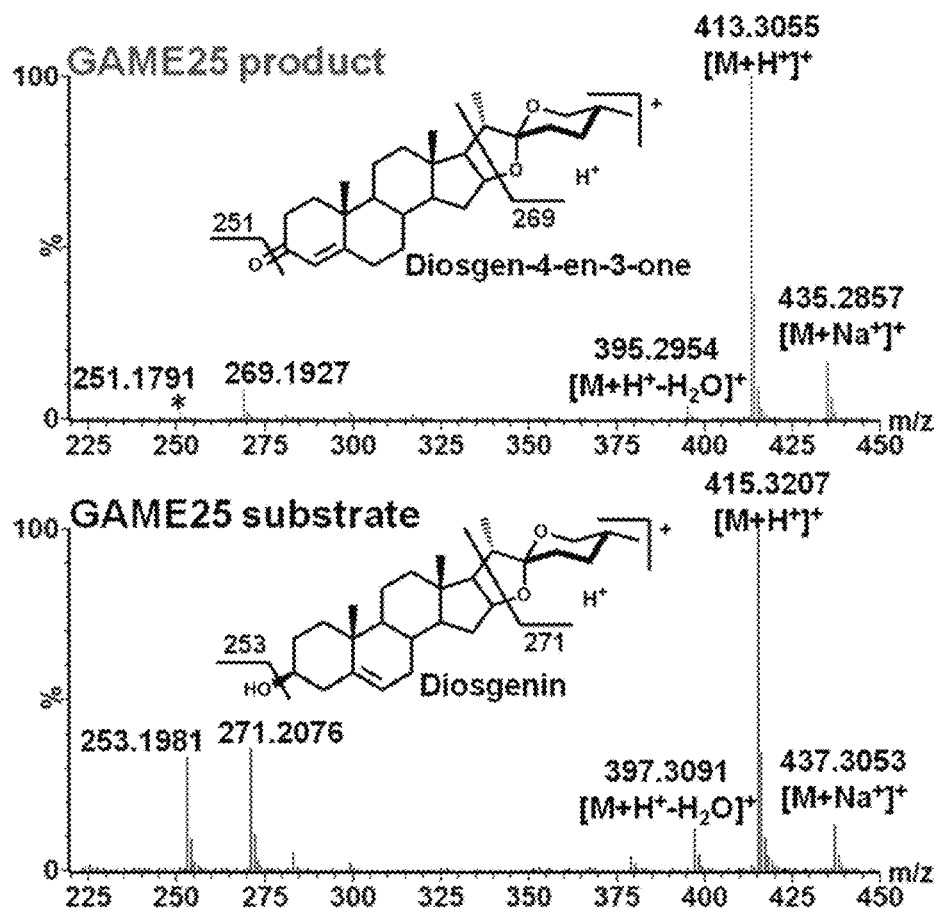

The Tomato Recombinant GAME25 Enzyme Also Converts Diosgenin, a Spirostanol Type Saponin Aglycone to Diosgen-4-En-3-One, 3-Oxo-$\Delta^{5,4}$ Steroidal Saponin Intermediate Similar to SGAs, steroidal saponins also display two structural forms, unsaturated or saturated based on C-5,6 double bond position in saponin aglycone (that is either furostanol or spirostanol type) (FIG. 3A). Formation of new saturated furostanol type saponins by GAME25 overexpression in eggplant suggests its possible role also in removal of C-5,6 double bond from steroidal saponin metabolites. Furthermore, recombinant GAME25 enzyme exhibits the 3β-hydroxysteroid dehydrogenase and $\Delta^{5,4}$ isomerase activities on various SA aglycone substrates to form the 3-oxo-$\Delta^{5,4}$ SA aglycone intermediates. To examine whether GAME25 can catalyze similar reactions but on steroidal saponin aglycone substrate, a recombinant enzyme assay was performed using diosgenin [(M+H$^+$, m/z 415.3); a major spirostanol type steroidal saponin aglycone produced by *Dioscorea* species] as substrate. Interestingly, GAME25 assay resulted in the formation of novel compound with molecular ion m/z 413.3 (M+H$^+$) representing oxidation of 3β-hydroxyl group and isomerization of double bond from C-5,6 position to C-4,5 position (FIGS. 24A-24B). While unsaturated diosgenin substrate produce three major fragment ions with m/z 415.3, 271.2 and 253.2, the newly formed compound (m/z 413.3) showed fragment ions with m/z 413.3, 269.2 and 251.2 respectively. Based on mass fragmentation analysis and assignment described as above for SA aglycones (e.g. dehydrotomatidine), this newly formed compound was putatively assigned as diosgen-4-en-3-one (FIGS. 24A-24B). Thus, similar to SA aglycones, GAME25 also catalyzes oxidation of the 3β-hydroxyl group and the isomerization of double bond from the C-5,6 to the C-4,5 position in steroidal saponin aglycone substrates to form the 3-oxo-$\Delta^{5,4}$ steroidal saponin aglycone intermediates. The results also suggest that formation of saturated steroidal saponin aglycone (removal of C-5,6 double bond) from unsaturated saponin aglycone is also not a single step reaction and GAME25 is catalyzing the first of them.

Summary for Examples 1-12

GAME25 is a Key Branch Point Enzyme that Determines the Diversity of SGAs Produced in *Solanum* Species and Modulates their Level of Toxicity The enormous diversity of chemical structures produced by plants are often due to what seems to be a minor change in one or more of the core scaffolds that are consequently metabolized by various downstream modifications. This occurs in steroidal glycoalkaloids; a renowned class of secondary metabolites that likely evolved separately in the Solanaceae and Liliaceae families. In *Solanum* species investigated here, the presence or absence of a double bond at the C-5,6 in the core scaffolds is a major source of structural diversity. More specifically, in tomato, two SA aglycones, namely, dehydrotomatidine and tomatidine, differing in the presence or absence of the C-5,6 double bond, are similarly glycosylated to their corresponding glycoalkaloids dehydrotomatine and α-tomatine, respectively. Both dehydrotomatidine and tomatidine aglycones are highly toxic to plant cells and likely undergo glycosylation to prevent self-toxicity. Studies in animal models demonstrated that SGAs deficient in the C-5,6 double bond, e.g. α-tomatine, are much less toxic to animals and humans as compared to those possessing it (e.g. α-chaconine and α-solanine from potato). This suggests that dehydrotomatine is likely a more toxic SGA when compared to α-tomatine.

Although less toxic to humans and animals, α-tomatine is a highly active molecule that is involved in a range of host-plant resistance mechanisms in tomato plants. Yet, the contribution of dehydrotomatine, typically produced to lower levels in tomato, to the plant resistance against pathogens was not clear. In the present disclosure, severe growth and conidia germination inhibition of the pathogenic fungi *B. cinerea* and *C. gloeosporioides* pointed towards enhanced toxicity of extracts enriched with dehydro-derivatives (due to GAME25 silencing) as compared to those (wild-type) predominantly containing α-tomatine and related metabolites (FIG. 23). Thus, in planta, α-tomatine and dehydrotomatine SGAs could be acting synergistically against pathogens and both of these SGAs might have co-evolved in order to exert synergistic effect against a broad range of diseases. GAME25 reported here, catalyzes the first step in the conversion of dehydrotomatidine to tomatidine in which the double bond at the C-5,6 position is reduced (FIG. 22). This reaction is therefore a key branch point that not only determines the diversity of SGAs produced in more than hundreds of *Solanum* species known to date but also modulates the toxic effects of these molecules in planta, animals and likely also in pathogens and herbivores.

The Formation of Tomatidine from Dehydrotomatidine in Tomato Involves the Reaction Catalyzed by GAME25 and Further Requires Additional Biochemical Reactions.

During the past decades the biosynthesis of dehydrotomatine and α-tomatine was hypothesized to occur through several different pathways. In one scenario, dehydrotomatidine was proposed to be derived from cholesterol which contains a C-5,6 double bond while tomatidine from cholestanol lacking the C-5,6 double bond. Thus, conversion of cholesterol to cholestanol might be responsible for formation of tomatidine. An alternative pathway suggested that teneimine having the double bond, an intermediate derived from cholesterol, is partitioned, leading to tomatidine through the action of a hypothetical hydrogenase reducing the double bond while a portion of it is converted to dehydrotomatidine. In another hypothesis, tomatidine was proposed to be partly dehydrogenated to form dehydrotomatidine by a hypothetical dehydrogenase. In another case, the formation of tomatidine from dehydrotomatidine was hypothesized as a single step reaction catalyzed by a hypothetical hydrogenase. The present disclosure functionally characterizes GAME25 through in planta and in vitro assays and rules out these previous hypotheses. Instead, it is suggested that the formation of tomatidine from dehydrotomatidine, i.e. the reduction of $\Delta^5$ (C-5,6 position) bond in the SA aglycones, is carried out in multiple steps and GAME25 catalyzes the first of them.

Furthermore, the examples above show that, unexpectedly, SA/SGA levels can be severely reduced in a tomato plant by modifying expression of an enzyme involved in the steroidal alkaloids biosynthetic pathway.

GAME25 Exhibits a Novel Dual-Function Activity in *Solanum* Plants

Figure 22A:
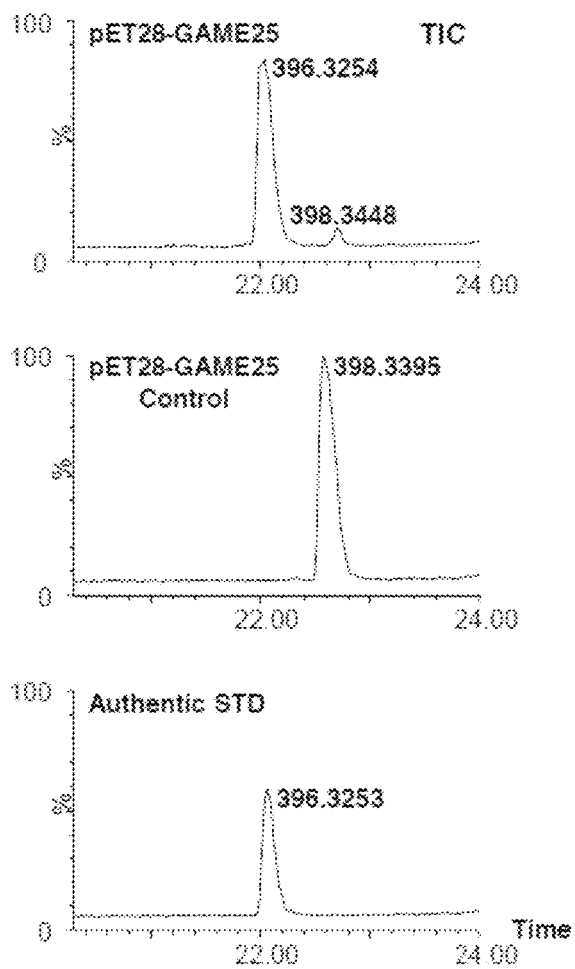
FIGS. 22A-22B show enzyme assays of the purified recombinant tomato GAME25 and GAME 25 produced in E. coli BL21 (DE3) cells.
Figure 22B:
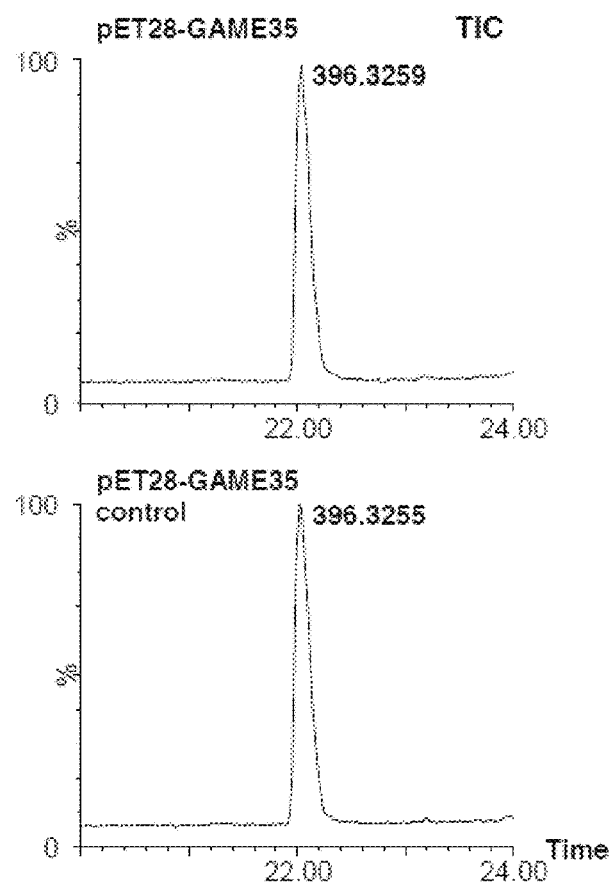
Figure 23A:
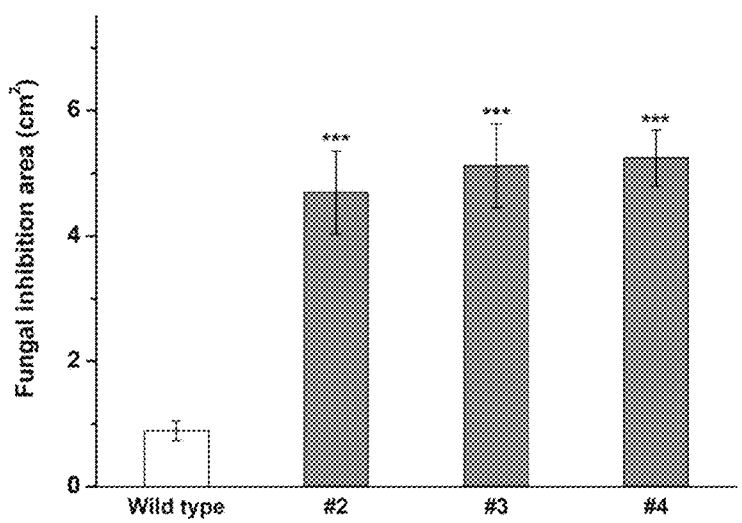
FIGS. 23A-23J show inhibition of growth and spore germination of Colletotrichum gloeosporioides and Botrytis cinereal fungi on medium containing leaf extracts derived from GAME25 silenced tomato plants. Methanol extracts of tomato leaves from wild-type (WT) and GAME25 silenced lines (i.e. GAME25i, #2, #3 and #4 are three independent GAME25i transgenic lines) were used for fungal inhibition assays.
Figure 23B:
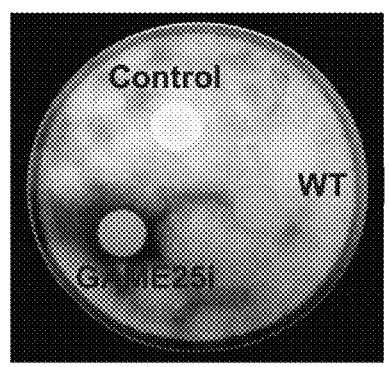
Figure 23C:
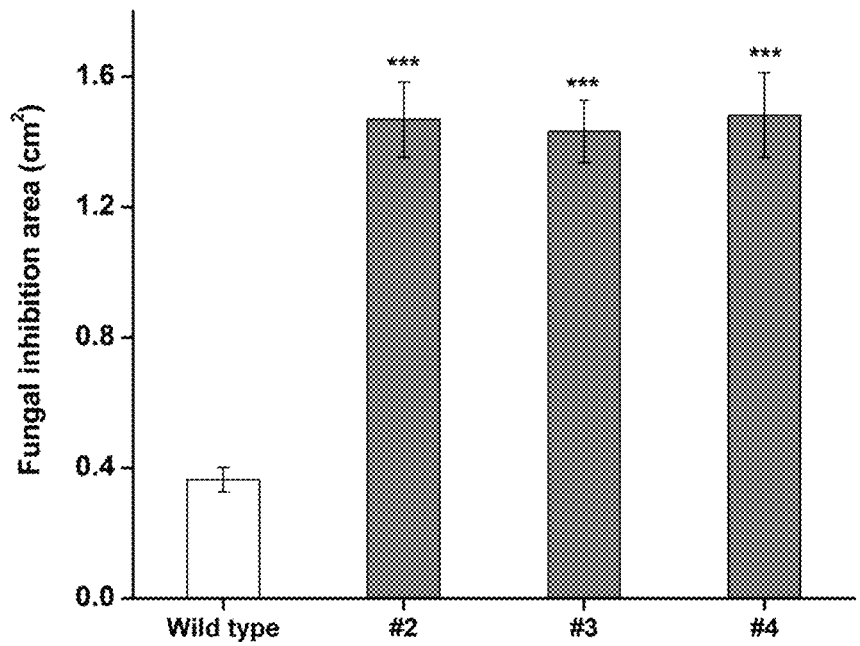
Figure 23D:
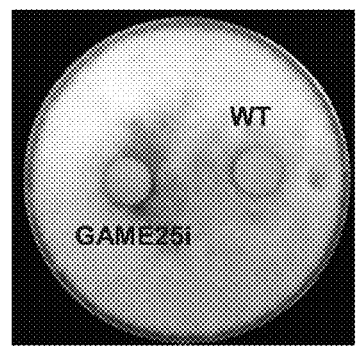
Figure 23E:
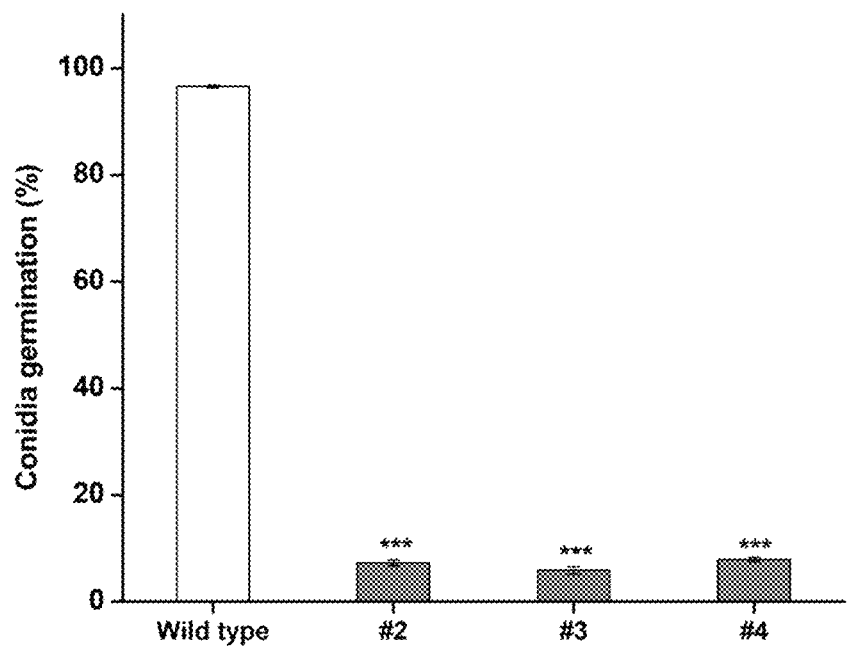
Figure 23F:
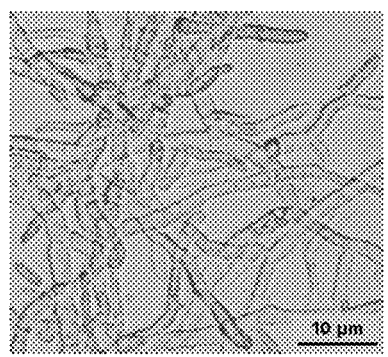
Figure 23G:
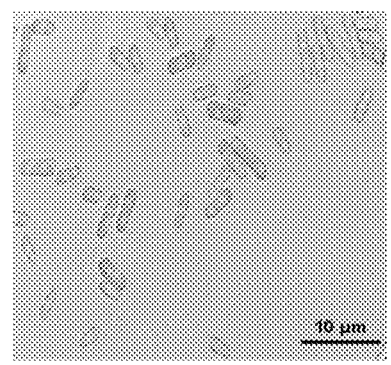
Figure 23H:
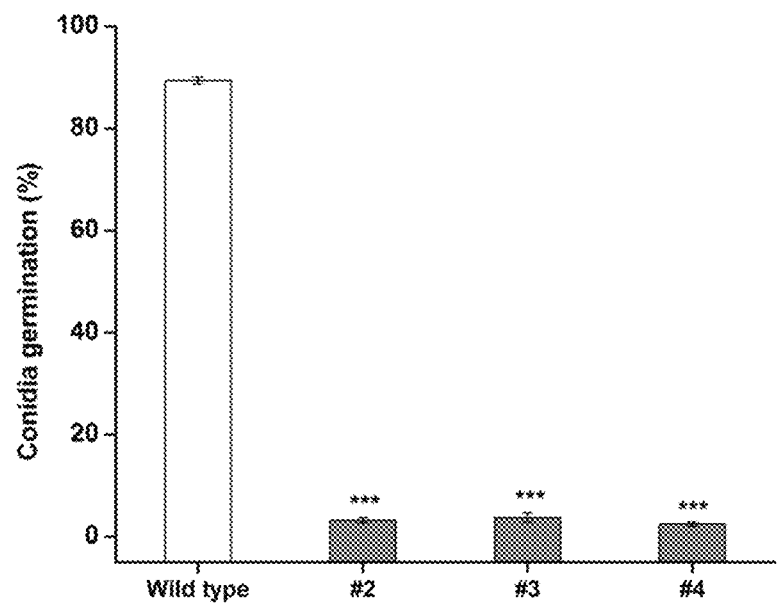
Figure 23I:
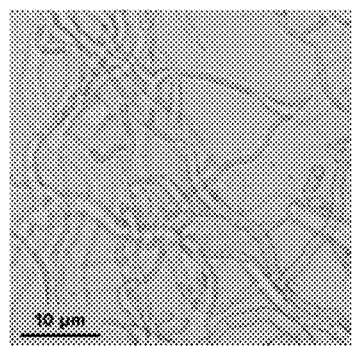
Figure 23J:
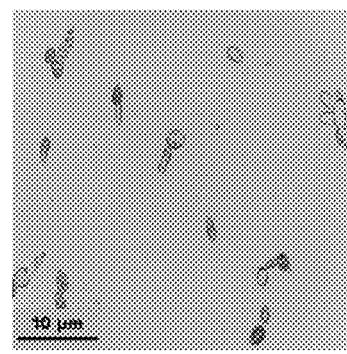

In vitro enzyme assays with the recombinant tomato and potato GAME25 enzyme pointed towards its dual activity, i.e., (i) oxidation of the 3β-hydroxyl group (3β-hydroxysteroid dehydrogenase activity) and (ii) isomerization of the double bond from the C-5,6 position to the C-4,5 position (3-oxosteroid $\Delta^{5,4}$ isomerase activity) in SA and steroidal saponin aglycone substrates (FIGS. 19, 20, and 22A). The dual activity reported here for GAME25 is apparently novel as most if not all 3-βHSD enzymes participating in plant secondary metabolism (i.e. members of the 3-βHSD and SDR family) possess only 3β-hydroxysteroid dehydrogenase activity but not isomerase activity; for example, the 3-βHSD enzyme from *Digitalis*, Noscapine synthase (NOS) from poppy and momilactone synthase (MS) in rice. Interestingly, in mammals' steroid hormone metabolism, the conversion of pregnenolone to progesterone includes a 3βHSD enzyme that is similar to GAME25 and possesses a dual dehydrogenase and isomerase activity.

Additional results obtained in these assays showed that GAME25 is active with steroidal aglycones produced by tomato (dehydrotomatidine), potato (solanidine) and eggplant (solasodine) but not with the glycosylated steroidal alkaloids forms (e.g. α-tomatine, dehydrotomatine, α-solanine, α-chaconine and α-solamargine). The latter, more bulky structures that contain multi-glycoside residues might not be able to bind to the active site pocket in the GAME25 enzyme. The GAME25 enzyme was also not reactive with cholesterol and cholestenol that were predicted in the past to be precursor molecules for dehydrotomatidine and tomatidine, respectively. Furthermore, a similar three-step enzymatic conversion in wild potato species producing demissidine and further demissine SGAs as well as additional *Solanum* species like *S. dulcamara* that produce both the more toxic double bond containing SGAs and the less toxic, saturated ones (FIG. 22) is predicted.

Absence of GAME25 Activity in Cultivated Potato and Eggplants is Responsible for Lack of Saturated SGAs in them The pathway from the unsaturated SA aglycone solanidine to saturated SA aglycone demissidine and its glycosylated form (i.e. demissine) in wild potato species corresponds to the tomato pathway in which the C-5,6 double bond is eliminated from dehydrotomatidine towards tomatidine and the glycosylated α-tomatine (FIG. 2B). While α-tomatine and its derivatives accumulate to high levels in tomato, the domesticated potato does not accumulate saturated demissidine or demissine SGAs in any plant part (while wild potato species do). The absence of the saturated SGAs demissidine or demissine in cultivated potato tubers albeit GAME25 gene in it suggests that these SGAs were selected against and lost during the domestication process (possibly through altered GAME25 activity). In addition, even if GAME25 is considered to be active in vivo, additional enzymes required for further conversion of solanid-4-en-3-one (3-oxo-$\Delta^{5,4}$ SA aglycone intermediate formed after GAME25 activity) might be absent or inactive in potato. Although recombinant GAME25 enzyme from potato showed in vitro activity with various SA aglycone substrates tested, the involvement of GAME25 gene in SGA metabolism in cultivated potato remains unclear (FIG. 19).

Figure 3C:
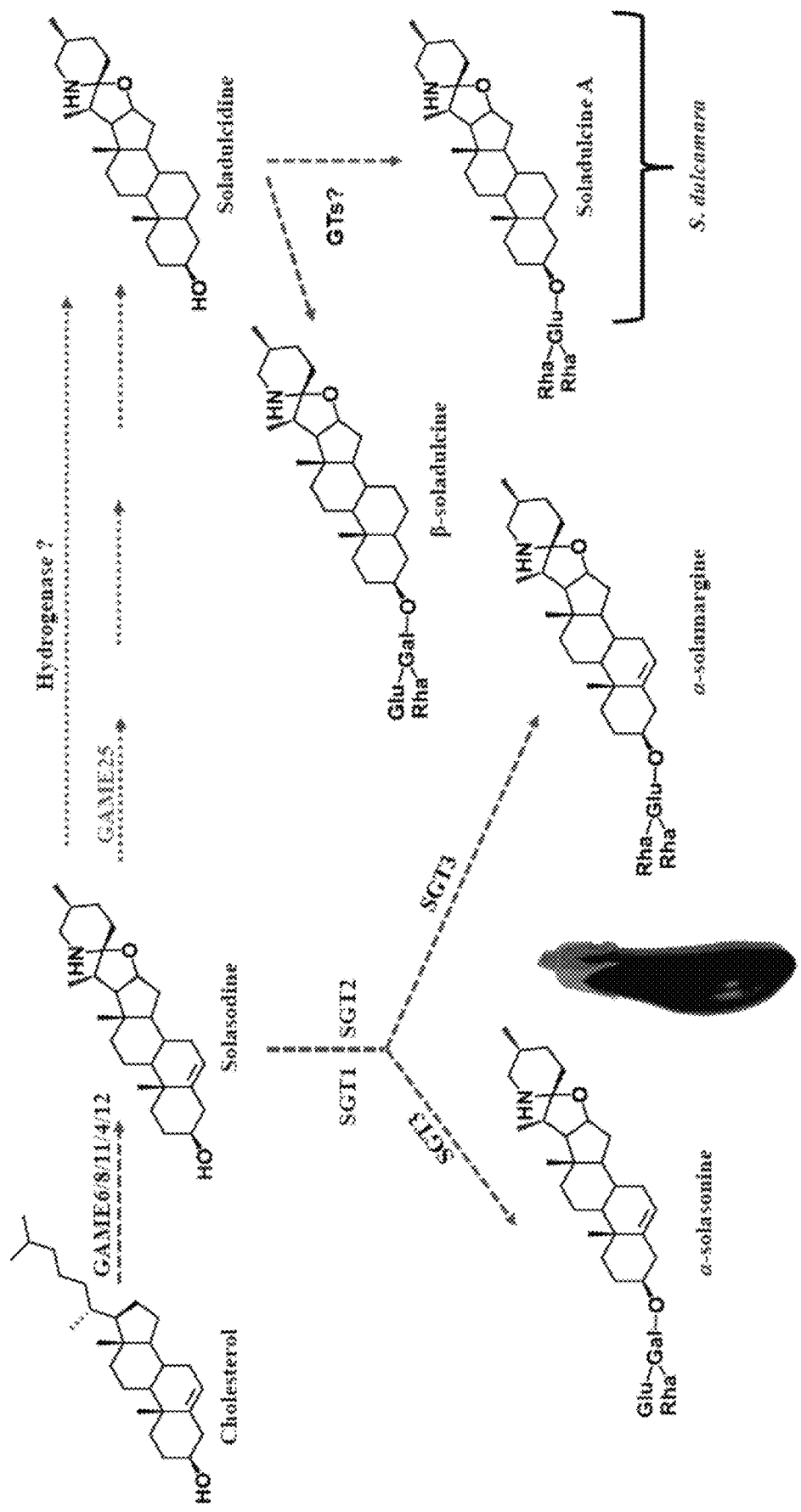

In the case of eggplant, merely GAME25 activity might be lacking as overexpression of the tomato GAME25 gene resulted in the production of saturated SGAs, suggesting the availability of the additional enzymes that are required to produce final saturated forms of SGAs after GAME25 action. In addition to saturated SGAs, novel saturated steroidal saponins were also formed in GAME25-Ox eggplant transgenic lines underscoring its crucial role in steroidal saponin biosynthesis in *solanum* plants. Based on these results, for other plant species that produce steroidal saponins, it is hereby predicted the existence of a GAME25-like enzyme and other additional enzymes in them that are required for eliminating the C-5,6 double bond from unsaturated steroidal saponin aglycone substrates and further to form saturated steroidal saponin aglycone and saponin glycosides (FIG. 3C).

GAME25 is a Unique Classical SDR Family Member for Specialized Metabolism in *Solanum* Plants In plants, more than 3000 known SDR enzymes catalyze NAD(P)(H)-dependent oxidation/reduction reactions on a wide range of substrates including alcohols, sugars, steroids, aromatic compounds and xenobiotics and thus contribute to a wide array of biochemical processes. As found in other eukaryotes, the majority of plant SDRs is either classical or extended types SDRs, yet, high number of SDRs in plants could not be classified to a particular functional category. With respect to distribution, the number of SDRs in land plants varies significantly, e.g. 126 in *P. patens* to around 315 in *G. max*. Members of SDR family have been reported to participate in the metabolism of various specialized metabolites including cardiac glycosides in *Digitalis* spp. (3βHSD), tropane-like alkaloids (SDR65C), terpenoids like xanthoxin, menthone and zerumbone (SDR110C, SDR114C), benzylisoquinoline alkaloids in poppy (NOS), oryzalexin diterpenoids in rice (MSI and MI1-3) and phenolic substrates, e.g. 4-dihydroflavanol, anthocyanidin, cinnamoyl-CoA and phenylacetaldehyde (SDR108E). The present disclosure shows that GAME25 is a key enzyme in the biosynthesis of saturated SGAs and unsaturated and saturated steroidal saponins, renowned classes of specialized metabolites in the *Solanum* genus. Phylogenetic analysis of SDR family proteins from plants partaking in specialized metabolism suggested that GAME25 proteins of the Solanaceae family have undergone significant diversification as compared to other family proteins that are known to be involved in plant secondary metabolism (FIG. 6). This can be supported by novel dual enzyme activities (dehydrogenase and isomerase) of GAME25 proteins in Solanaceae plants which could be acquired during the evolution over other SDR members that has evolved only with a single classic activity (e.g. only dehydrogenase).

Three Steps Enzymatic Conversion is Required for Formation of Saturated SA and Saponin Aglycones from Respective Unsaturated Forms

Figure 25:
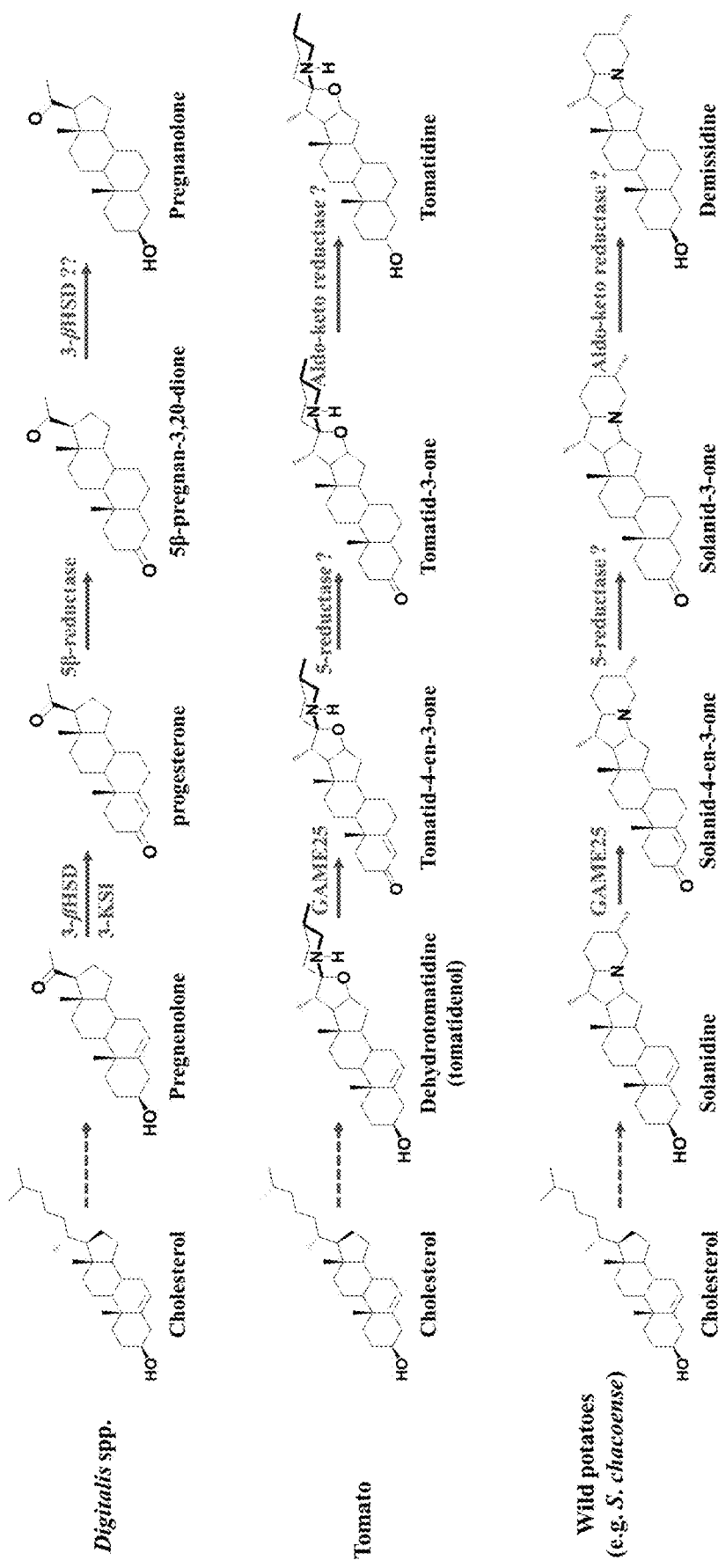
FIG. 25 shows that GAME25 enzymes plays a key role in the formation of saturated (elimination of the C-5,6 double bond) SA and steroidal saponin aglycones produced in different plant species in a sequence of three reactions. A three step reaction sequence for the conversion of dehydrotomatidine to tomatidine in tomato, solanidine to demissidine in wild potatoes (S. chacoense) and solasodine to soladulcidine in certain solanum species (e.g. S. dulcamara) is proposed. Additionally, it suggests three step reactions for the conversion of unsaturated steroidal saponin aglycone to saturated steroidal saponin aglycone in steroidal saponin producing plant species. GAME25, a novel 3β-hydroxysteroid dehydrogenase/isomerase perform the first step in this reaction sequence and produce 3-oxo-$\Delta^{5,4}$ steroidal alkaloid/saponin aglycone derivatives from the respective unsaturated steroidal alkaloid/saponin aglycone substrates (e.g. dehydrotomatidine or diosgenin) which are further converted to saturated ($C_5$-$C_6$ deficient) products by successive actions of putative 5-reductases and aldo-keto reductases respectively. This three step conversion partly resembles to steroid metabolism (e.g. progesterone formation and further catabolism) in plant species such as Digitalis spp. that produce cardiac glycoside secondary metabolites. Dashed arrows indicate multi-step reactions.
Figure 25:
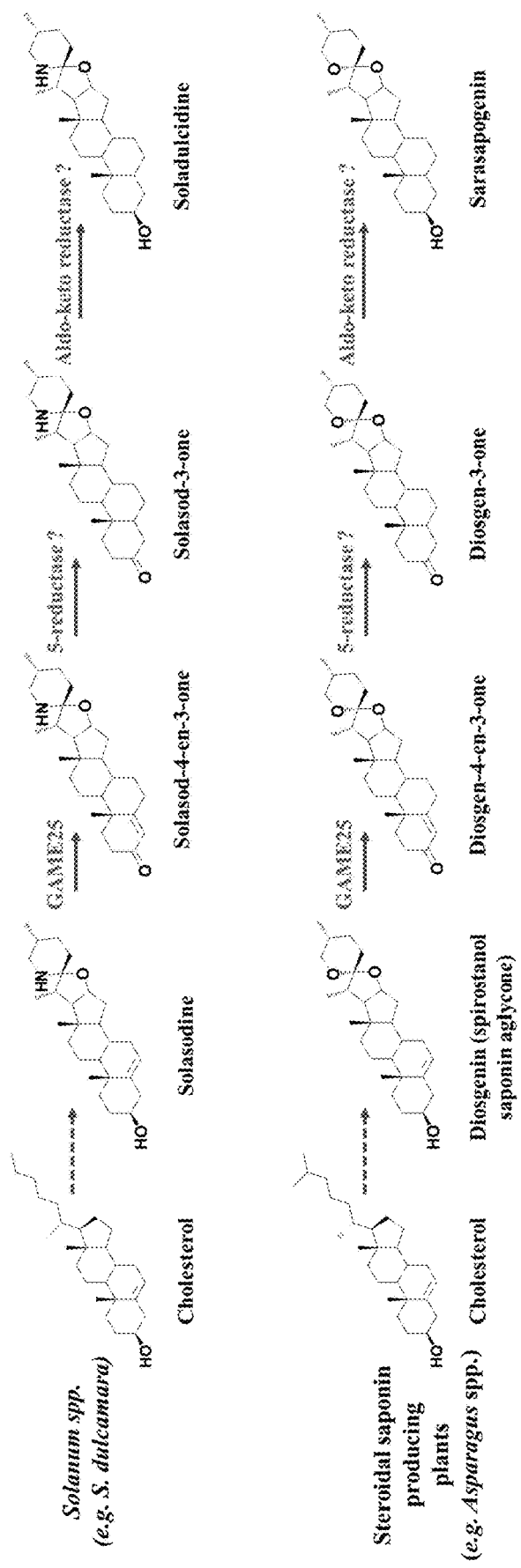
Figure 26A:
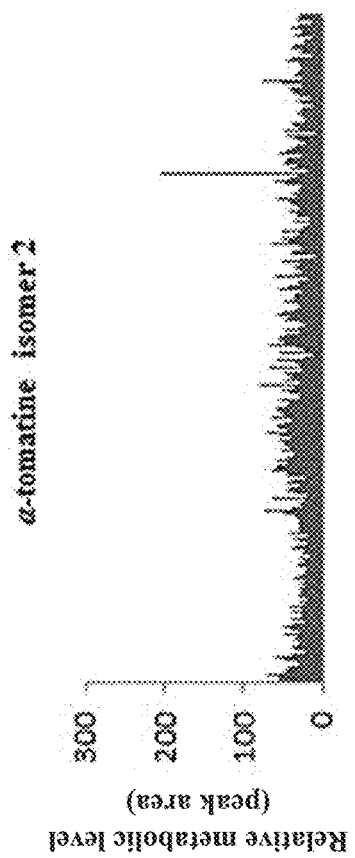
Figure 26B:
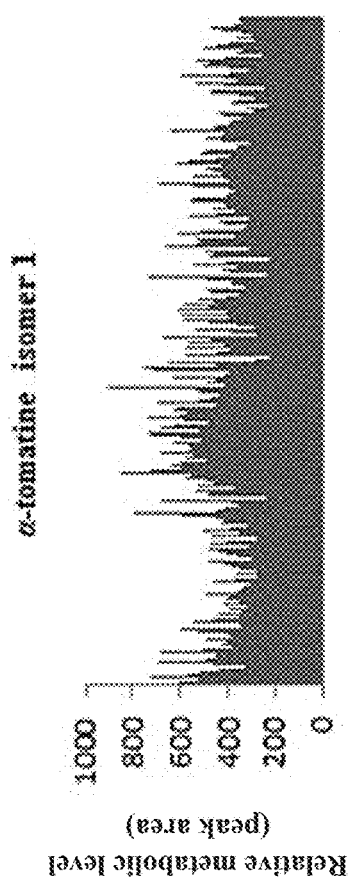
Figure 26C:
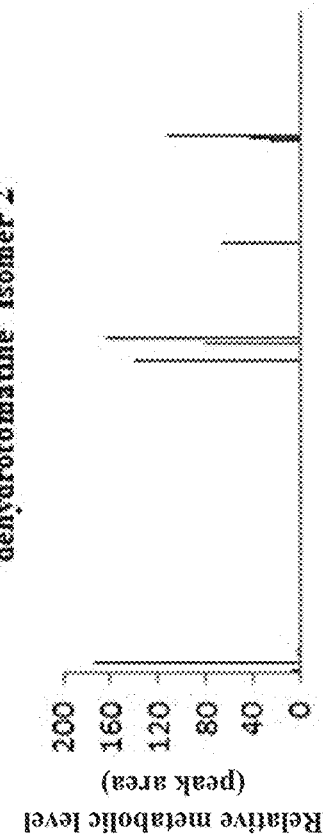
Figure 26D:
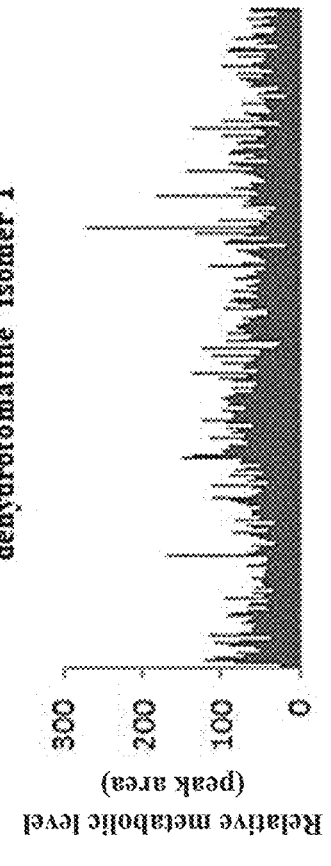
Figures 27A, 27B:
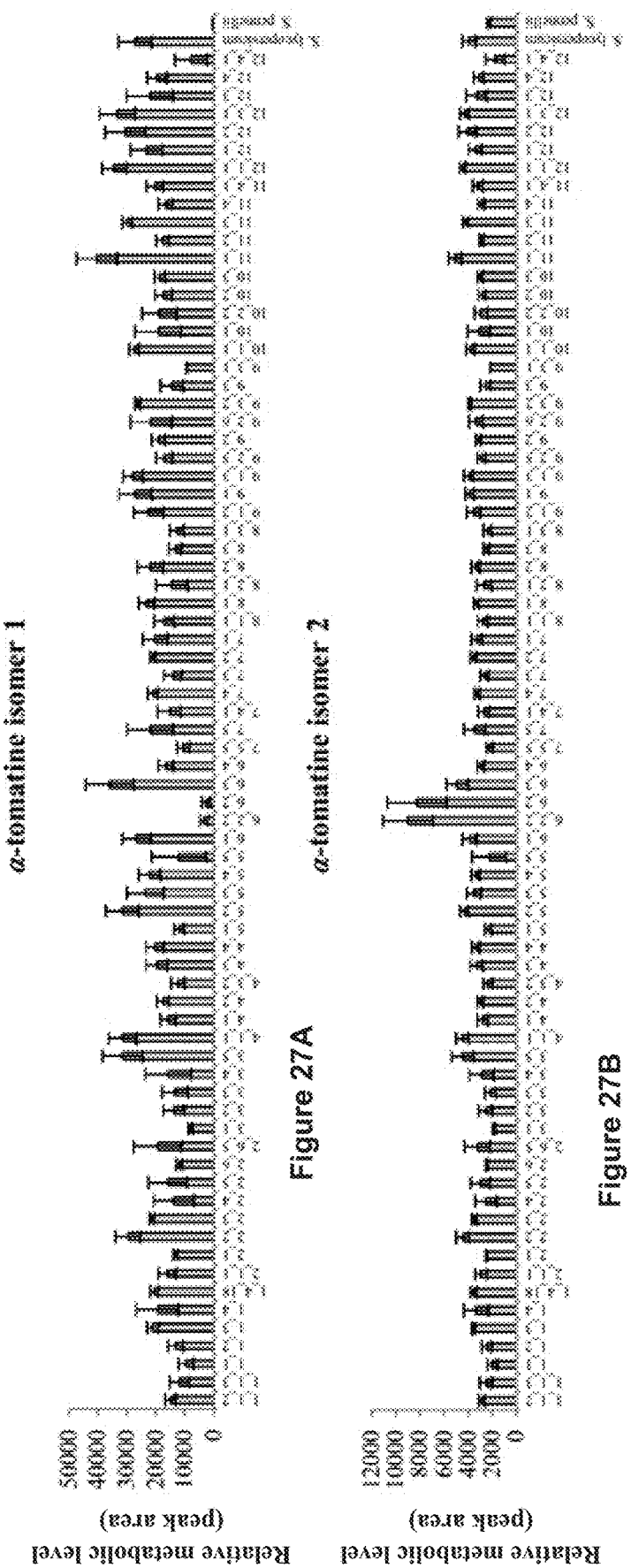
Figures 27C, 27D:
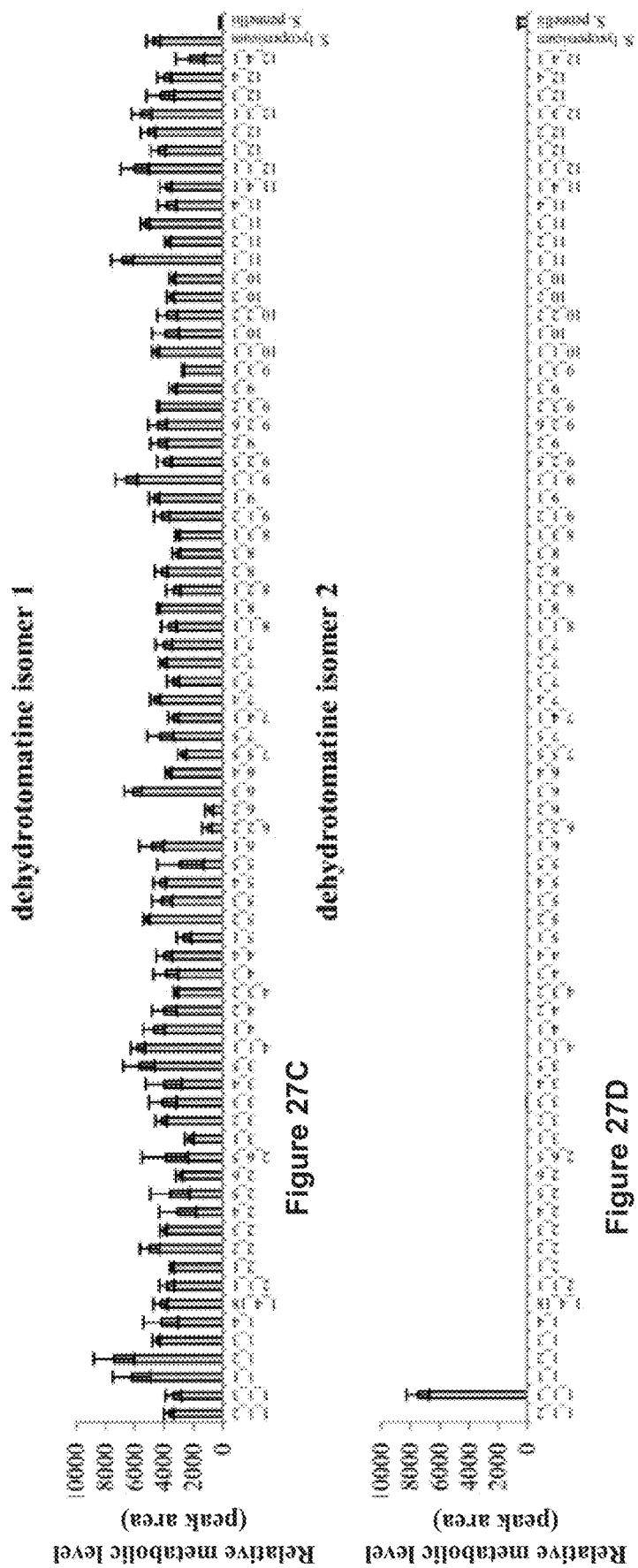

*Digitalis* species are known to produce an important class of specialized metabolites, the cardenolides or cardiac glycosides. During the biosynthesis of cardenolides, pregnenolone is converted to pregnanolone. Both pregnenolone and pregnanolone are steroid derivatives which differ only by the presence or absence of the double bond at the C-5,6 position (FIG. 25). The conversion of pregnenolone to pregnanolone (reduction of $\Delta^5$ bond) occurs in four steps: (i) oxidation of (3β-hydroxyl group) pregnenolone by 3βHSD enzyme followed by (ii) isomerization of double bond from the C-5,6 to the C-4,5 position by 3-KSI enzyme to form progesterone, (iii) In the third step, progesterone is converted to 5β-pregnan-3,20-dione (removal of C-4,5 bond) by 5β-progesterone reductase (5β-POR) which is subsequently converted to pregnanolone by 3βHSD enzyme. Thus, the conversion of pregnenolone to pregnanolone resembles to formation of tomatidine from dehydrotomatidine aglycone in tomato, or demissidine from solanidine aglycone in wild potato plants where C-5,6 double bond is also removed (FIG. 25). Interestingly, formation of saturated SA aglycone (e.g. tomatidine or demissidine) in Solanaceae plants was predicted to occur in single step by hypothetical hydrogenase enzyme. The present disclosure clearly demonstrates that the removal of C-5,6 bond of steroid derivatives in *Digitalis* spp. and SA aglycones in Solanaceae plants is strikingly different because of a novel dual activity of GAME25 enzyme that catalyzes first step in *Solanum* plants as compared to two separate enzyme activities required for same first step in *Digitalis* spp. (FIG. 25). In addition, 5β-progesterone reductase (5β-POR) homolog in tomato doesn't seem to be appropriate enzyme for catalyzing second step following GAME25 activity in saturated SGA biosynthesis. Based on further requirement of analogous enzymes after GAME25 reaction step that has been characterized extensively here in various Solanaceae plants, it is hereby proposed that the conversion of dehydrotomatidine to tomatidine in tomato is a three step reaction sequence with GAME25 catalyzing the first step, converting dehydrotomatidine to tomatid-4-en-3-one (3-oxo-$\Delta^{5,4}$ SA aglycone intermediate (FIG. 25). Tomatid-4-en-3-one is subsequently reduced to tomatidine by the successive action of a putative 5-reductase and an aldo-keto reductase (FIG. 25). The possible steroidal glycoalkaloids pathway reactions from the unsaturated aglycone solanidine to saturated demissidine and its glycosylated form (i.e. demissine) in wild potato species (e.g. *S. chacoense*) corresponds to the tomato SGA pathway reactions where the C-5,6 double bond is eliminated from dehydrotomatidine towards tomatidine in three steps (FIG. 25). A similar three-step conversion in wild potato species producing saturated demissidine from solanidine aglycone is predicted hereby. In addition, tomato GAME25 overexpression in cultivated eggplants generated saturated SGAs (soladulcidine and its glycosylated derivatives) from solasodine aglycone that are actually native to certain *solanum* species (e.g. *S. dulcamara*), thus indicating presence of active GAME25 in them. Based on this, it is hereby suggested that three step conversion reactions in those *solanum* species (e.g. *S. dulcamara*) produce saturated soladulcidine from solasodine aglycone (FIG. 25). Finally, based on in vivo (GAME25-Ox in eggplant) and in vitro (enzyme activity) results, it is hereby proposed three step reactions in the hundreds of steroidal saponin producing plant species that produce saturated saponin aglycones from their unsaturated forms and further saturated steroidal saponin glycosides (FIG. 25).

The characterization of GAME25 activity in the SGAs and biosynthesis pathway is a significant step towards resolving the complete core SGAs pathway in Solanaceae species. Likewise, it further contributes to the understanding of how a large portion of the structural diversity in the SGAs steroidal saponin producing Solanaceae species is formed. Nevertheless, the enzymes completing the elimination of the C-5,6 double bond from the core SGAs aglycones succeeding GAME25, are yet to be identified. The dramatic shift from saturated (without C-5,6 double bond) to unsaturated SGAs (with C-5,6 double bond) in GAME25 silenced tomato plants including the dominance of dehydroesculeosides in ripening fruit make these genetic materials an excellent resource for future investigation. It will allow probing the significance of this structural variance to the potency of these molecules with respect to plant pathogens and herbivores. Ripe fruit accumulating α-tomatine on behalf of the typical esculeosides as a result of GAME25 overexpression will also be of value for carrying out similar interaction studies in tomato. The presence of the double bond at the C-5,6 position is not merely an issue of structural variation, but ample evidence suggests its relevance to the level of toxicity these molecules possess to humans. SGAs, largely the unsaturated ones, prevalent in potato tubers are renowned 'anti-nutritionals' and their levels in cultivated potato are tightly regulated. Together with the previously reported structural and regulatory genes, overexpression of GAME25 affords a valuable strategy to reduce the levels of these substances in commercial potato varieties.

Methods for Examples 12-17

Plant Material

The tomato Introgression Line (IL) and Backcross Inbred Line (BIL) populations derived from crosses of the M82 tomato cultivar and *Solanum pennellii* were obtained from publicly available collections of inbred lines as described in Ofner, I et al., (2016) *Solanum pennellii* backcross inbred lines (BILs) link small genomic bins with tomato traits. Plant J. 87(2):151-160; and Eshed and Zamir (1995) An introgression line population of *Lycopersicon pennellii* in the cultivated tomato enables the identification and fine mapping of yield-associated QTL. Genetics 141: 1147-1162. These populations (IL and BIL) consist of 671 lines, including the two parental lines M82 and *S. pennellii*, F1, 132 ILs and 536 BILs. The plants were grown in a climate-controlled greenhouse at 24° C. during the day and 18° C. during night, with natural light.

The GAME31-RNAi construct was created by introducing a GAME31 fragment to pENTR/D-TOPO (Invitrogen) (by NotI and AscI) and further transfer of the resulting cloned fragment to the pK7GWIWG2 (II) binary vector (Karimi et al., (2002) GATEWAY™ vectors for *Agrobacterium*-mediated plant transformation. Trends Plant Sci. 7: 193-195) using Gateway LR Clonase II enzyme mix (Invitrogen). The GAME31-Cosup (co-suppression) construct was generated by introducing the corresponding tomato GAME31 coding sequences into pDONR221 using the Gateway BP Clonase II enzyme mix (Invitrogen) and then transferred to the pK2GW7 binary vector using Gateway LR Clonase II enzyme mix. Constructs were transformed into tomato (cv. Microtom) as described previously (Itkin et al., 2011, ibid, 2013, ibid). Primers used in this work are listed in Table I, below

TABLE 1

Primers used for Examples 12-17.

| Name | Sequence | SEQ ID NO: | Use |
| --- | --- | --- | --- |
| RF-Tomato-GAME31-Fw | tccgcgggtgaaaacctgtacttccaggg tgcatctatcaaatcagttaaagttc | 54 | RF cloning |
| RF-Tomato-GAME31-Rv | gtggtggtgctcgagtgcggccgcaagc tttcaaacaccacaataaatcttgaaaag | 55 | RF cloning |
| RF-Eggplant-GAME31-Fw | tccgcgggtgaaaacctgtacttccaggg tggatctaccaaatcaattaaagttc | 56 | RF cloning |
| RF-Eggplant-GAME31-Rv | gtggtggtgctcgagtgcggccgcaagc tttcaaacaccacaataagccttt | 57 | RF cloning |
| Diox460-Fw | agtacaagtaatcacgttggttcctatga | 60 | qRT-PCR |
| Diox460-Rv aaa | cactagaaagttttttactttataggtgagg | 61 | qRT-PCR |
| Dioxy-NotI-RNAi-Fw | aaaaagcggccgcgggatcgaggaaat tcgtct | 62 | Cloning SlGAME31 for RNAi |
| Dioxy-AscI-RNAi-Rv | aaaaaggcgcgccctaaaagattacggt gaatcctctt | 63 | Cloning SlGAME31 for RNAi |
| Dioxy-attB1-Fw | ggggacaagtagtacaaaaaagcaggct atggcatctatcaaatcagttaaagt | 64 | Cloning SlGAME31 for co-suppression |
| Dioxy-attB2-Rv | ggggaccactttgtacaagaaagctgggt tcaaacaccacaataaatcttgaaa | 65 | Cloning SlGAME31 for co-suppression |

Screening of SGAs in Tomato BIL and IL Populations

For screening experiments for SGAs, a rapid extraction method and a short 10-min run in the UPLC-qTOF-MS (Xevo, Waters) was developed. For the extraction, the leaflet next to the youngest leaf was selected (about ~1-month old plants). The leaflet was dipped in 1 ml of isopropanol: acetonitrile:water (3:3:2 v/v) containing 0.1% formic acid (in a 2 ml Eppendorf tube) and gently rocked for 1 min. Then the solvent was transferred to a LC vial for injection. The leaflets were dried in an oven to obtain their weight (mg).

Data from UPLC-qTOF-MS analyses were manually inspected in order to determine the major SGA metabolites present in the populations. Elemental composition and MS/MS fragmentation patterns were used for putative identification of SGAs previously reported (Itkin et al., 2011, ibid). A list of peaks was generated using retention time (RT) and m/z as identifiers for each compound. Peak area quantification was performed by the program TargetLynx (Waters). The resulting values were normalized to dry leaf weights and considered to be the amount of metabolite present in each sample. For ground-tissue, preparation of plant extracts and metabolite analysis by UPLC-qTOF-MS was carried out as described previously (Cárdenas et al., (2016) GAME9 regulates the biosynthesis of steroidal alkaloids and upstream isoprenoids in the plant mevalonate pathway. Nat. Commun. 7: 10654).

Briefly, tomato plant tissues were frozen in liquid nitrogen and ground to a fine powder using an analytical mill or mortar and pestle. Then, frozen tissue (100 mg) was extracted with 80% methanol:water (v/v) containing 0.1% formic acid [the solid:liquid ratio was kept at 1:3 (w/v)]. The mixture was vortexed for 30 s, sonicated for 30 min at room temperature, vortexed again for 30 s, centrifuged (20,000×g, 10 min), and filtered through a 0.22-mm polytetrafluoroethylene membrane filter. Metabolite targeted analysis was performed using the targeted analysis program, TargetLynx program (Waters).

Genotyping and Mapping of QTL

The BIL/IL populations were constructed and genotyped as previously described (Ofner et al., 2016, ibid).

Generation of Recombinant GAME31 Enzyme

GAME31 was amplified from cDNA (SEQ ID NO: 17) and cloned into pET28 vector by restriction free (RF) cloning as described previously (Unger et al., 2010, J Struct Biol. 172:34-44). The primers used for the cloning of GAME31 are listed in Table 1 above.

The resulting plasmids were verified by sequencing and transformed to E. coli BL21 DE3. For isolation of the GAME31-His tagged enzymes, fresh overnight cultures were diluted 1:100 in 1000 ml of LB medium (Formedium) with 50 μg/ml kanamycin and incubated at 37° C. and 250 rpm until an $A_{600\,nm}$ of 0.5 was reached. Subsequently, for induction of expression of the recombinant proteins, IPTG was added to a final concentration of 0.2 μM and the incubation was continued overnight at 16° C. and 250 rpm. Then cells were harvested by centrifugation at 10,000×g and bacteria were lysed by sonication in a buffer (pH 7.4) containing 0.02 M $NaH_2PO_4$ 0.02 M, 0.5 M NaCl, and SIGMAFAST protease inhibitor tablets (Sigma-Aldrich) and benzonase nuclease (Sigma-Aldrich) according to manufacturer's instructions. Lysed cultures were centrifuged, and the soluble fraction was purified by nickel affinity chromatography which was operated with an AKTA liquid chromatography system (AKTA avant, GE Healthcare) according to the manufacturer's instructions. Proteins were stored at −80° C. until further analysis.

Enzymatic Activity Assays for GAME31 Enzymes

All the SA/SGAs substrates were prepared at a concentration of 1 mg/ml, dissolved in methanol, except dehydrotomatine that was prepared in DMSO. The enzymatic activity was performed according to Kawai et al. (2014) Evolution and diversity of the 2-oxoglutarate-dependent dioxygenase superfamily in plants. Plant J. 78: 328-43. Briefly, the standard full reaction (100 μL) consisted of 10 mM L-ascorbic acid, 10 mM α-ketoglutaric acid, 500 μM $FeSO_4$, 20 μM substrate, 50 mM potassium phosphate buffer (pH 7.5) and purified enzyme. All the components, except the enzyme, were pre-incubated for 10 min at 30° C., after which the reaction was started by addition of the enzyme. After incubation at 30° C. for 1 h, the reaction was stopped by freezing in liquid nitrogen Finally, the reaction was mixed with 300 μL methanol, extracted and analyzed by UPLC-qTOF-MS as described above.

Quantitative Real-Time PCR

Gene expression analysis was performed with three biological replicates (n=3) for each genotype. RNA isolation was performed by the Trizol method (Sigma-Aldrich). DNase I (Sigma-Aldrich)-treated RNA was reverse transcribed using a high-capacity cDNA reverse transcription kit (Applied Biosystems). Gene-specific oligonucleotides were designed with Primer Express 2 software (Applied Biosystems). The TIP41 gene (Expósito-Rodríguez et al., (2008) Selection of internal control genes for quantitative real-time RT-PCR studies during tomato development process. BMC Plant Biol. 8: 131-142) was used as an endogenous control for tomato samples. Oligonucleotides used are listed in Table 1, above.

SGA Targeted Analysis

Preparation of plant extracts and metabolite analysis by UPLC-qTOF-MS was carried out as described previously (Cárdenas et al., 2016, Nat. Commun. 7:10654). Briefly, tomato plant tissues were frozen in liquid nitrogen and ground to a fine powder using an analytical mill or mortar and pestle. Then, frozen tissue (100 mg) was extracted with 80% methanol:water (v/v) containing 0.1% formic acid (the solid:liquid ratio was kept at 1:3 [w/v]). The mixture was vortexed for 30 s, sonicated for 30 min at room temperature, vortexed again for 30 s, centrifuged (20,000 g, 10 min), and filtered through a 0.22-mm polytetrafluoroethylene membrane filter. Metabolite targeted analysis was performed using the TargetLynx program (Waters).

Constructs

The GAME31-RNAi construct was created by introducing a GAME31 fragment into pENTR/D-TOPO (Invitrogen) (by NotI and AscI) and further transferring the resulting plasmid to the pK7GWIWG2 (II) binary vector (Karimi et al., 2002, Trends Plant Sci. 7:193-195) using Gateway LR Clonase II enzyme mix (Invitrogen).

The GAME31-Cosup (co-suppression) construct was generated by introducing the corresponding tomato GAME31 coding sequences (SEQ ID NO: 59) into pDONR221 using the Gateway BP Clonase II enzyme mix (Invitrogen) and then transferred to the pK2GW7 binary vector using Gateway LR Clonase II enzyme mix.

Constructs were transformed into tomato (cv. Microtom) as described previously (Itkin et al., 2011, Plant Cell 23:4507-45-25; Itkin et al., 2013, Science 341:175-179). Primers used in this work are listed in Table 1.

Example 12

Screening of SGAs in Backcross Inbred Line (BIL) and Introgression Line (IL) Populations Objective:

To find new candidate genes involved in the metabolism of steroidal glycoalkaloids (SGAs). FIGS. 1-3 provide the core genes (GLYCOALKALOID METABOLISM genes; GAMEs) required for synthesis of SA aglycones, starting from the precursor cholesterol, and its glycosylation in tomato have been elucidated (Itkin et al., 2011 ibid., 2013, ibid). In tomato, cholesterol is generated from the cytosolic mevalonic acid pathway and further modified by GLYCOALKALOID METABOLISM (GAME) enzymes (in blue) through hydroxylation, oxidation and transamination to generate the aglycone tomatidine. Then, tomatidine is glycosylated generating α-tomatine, the major SGA in green tissues along with dehydrotomatine. Subsequently, hydroxyand acetoxy-derivatives accumulate at the fruit breaker stage. In the red ripe tomato fruit, the most abundant SGA correspond to esculeoside A. SGAs detected in the leaf-dip screening of the BIL/IL populations are shown in green. Dashed arrows represent multiple biosynthetic reactions whereas solid arrows represent a single step.

Results:

In the search for new candidate genes involved in the metabolism of steroidal glycoalkaloids (SGAs), SGA levels were screened in tomato Introgression Line (IL) and Backcross Inbred Line (BIL) populations derived from crosses of the M82 tomato cultivar and *Solanum pennellii* LA0716. This whole set consisted of 671 lines, including the two parental lines M82 and *S. pennellii*, F1, 132 ILs and 536 BILs. In these lines, single (in the case of the ILs) or multiple (for the BILs) regions from the wild species *S. pennellii*, replaced the homologous counterpart of the cultivated M82 variety. In order to analyze alkaloid content in the large number of lines in a high-throughput manner, metabolite analysis was performed using a leaf-dip method (Schilmiller et al., (2010) Mass spectrometry screening reveals widespread diversity in trichome specialized metabolites of tomato chromosomal substitution lines. Plant J. 62: 391-403), instead of extracting the metabolites from ground tissues. Leaflets from ~1-month old plants were harvested and immediately extracted by dipping in the extraction solvent and gentle agitation. This method offers information on a relatively low number of SGAs as compared to the number of SGAs detected in ground-tissue extracts; however, it provided a more efficient screening procedure.

For profiling of SGAs, a rapid method using a short 10-minute run in the Ultra Performance Liquid Chromatography coupled to Quadrupole Time-Of-Flight Mass Spectrometry (UPLC-qTOF-MS) was developed. This allowed screening 7 different SGAs: 2 isomers of α-tomatine, 2 isomers of dehydrotomatine and 1 isomer of di-dehydrotomatine, acetoxytomatine and hydroxytomatine (FIGS. 1A-1C, 2A-2B, 3A-3C, and FIGS. 26A-26G). Under tested conditions, it was found that the α-tomatine isomers 1 and 2 and dehydrotomatine isomer 1 were the most abundant SGAs found in the population. Detailed inspection of the chromatograms revealed a second early-eluting isomer of dehydrotomatine present only in few samples. Similarly, hydroxytomatine, acetoxytomatine and di-dehydrotomatine were either absent or present at very low levels across the population and few lines accumulated them in larger quantities (FIGS. 26A-26G). These results were validated in ground-tissue extracts derived from the IL population and the relevant BILs (FIGS. 27A-27G).

Example 13

Mapping of GAME31 in Tomato and Identification in Other *Solanum* Species

Objective:

To identify chromosomal areas linked to the variation of each SGA.

Results:

Using the SGA content information from the screened lines, chromosomal areas linked to the variation of each SGA were identified. For instance, a region in chromosome 1 (covering 146 genes) associated to accumulation of dehydrotomatine isomer 2 in IL1-1-3 was identified (FIGS. 28A and 28B). This region has been previously reported from the IL population, and it has been suggested that this accumulating metabolite could be converted to α-tomatine by the action of a reductase, and that this activity was deficient in the ILs accumulating dehydrotomatine isomer 2 (Schilmiller et al., (2010), ibid). A detailed examination of the 146 genes in the region (FIGS. 29A and 29B), allowed us to point a candidate reductase (Solyc01g009310) and several cytochrome P450 enzymes as the most likely responsible enzymes for the observed metabolic change (FIGS. 28A and 28B).

Figure 29A:
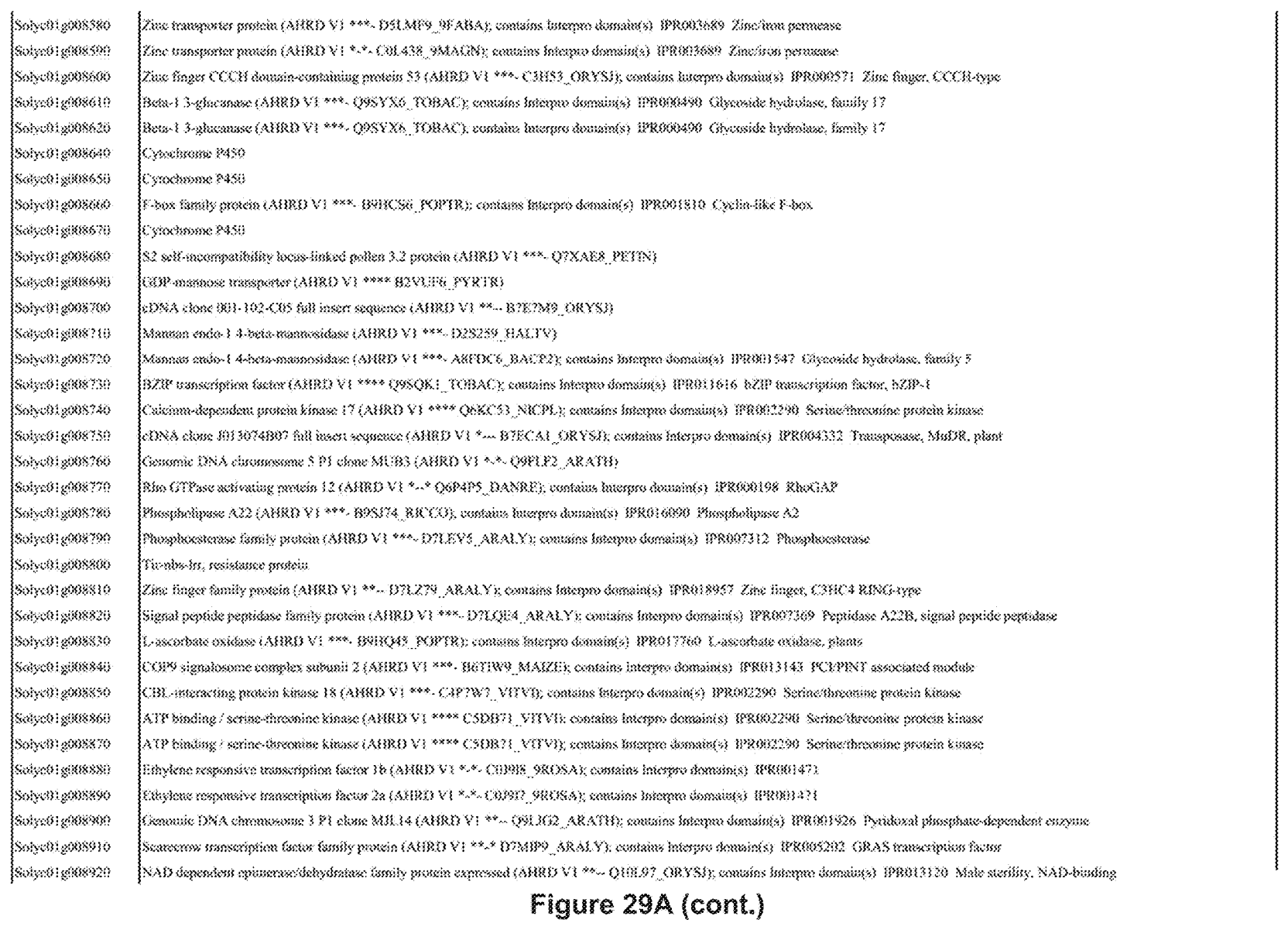
Figure 30A:
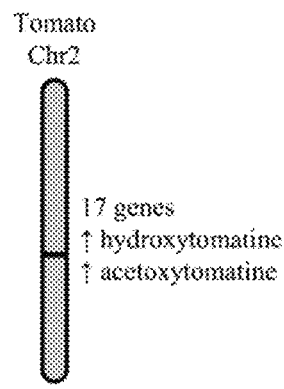
FIGS. 30A-30C present figures supporting the finding that a region in tomato chromosome 2 is linked to hydroxytomatine and acetoxytomatine content.
Figure 30B:
Figure 30C:
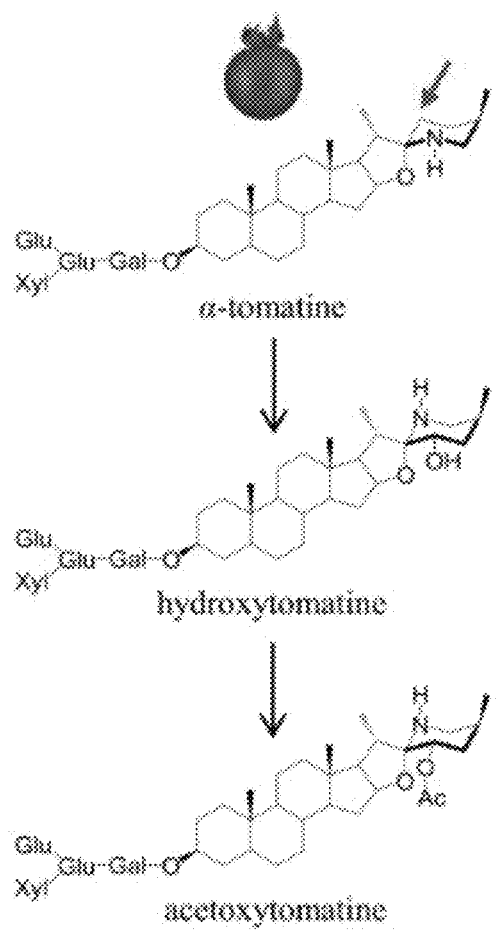

A region spanning ~250 Kbp in chromosome 2 of tomato (*Solanum lycopersicum*) was also identified as associated with an increase in hydroxytomatine and acetoxytomatine content (FIGS. 30A-30C). The increased amounts of these compounds in leaf tissues suggested the presence of an active hydroxylating enzyme in these BIL/IL populations. An examination of the 17 genes found in the QTL region revealed the presence of four 2-oxoglutarate-dependent dioxygenases (FIGS. 29A and 29B). The gene annotation provided the first indication that these enzymes may be acting in the hydroxylation of α-tomatine into hydroxytomatine. The genes were named GLYCOALKALOID METABOLISM 31 (SlGAME31; Solyc02g062460; SEQ ID NO: 16), SlGAME31-like1 (Solyc02g062470), SlGAME31-like2 (Solyc02g062490) and SlGAME31-like3 (Solyc02g062500) (FIG. 30B). Two of them are full length 2-oxoglutarate-dependent dioxygenase coding proteins (i.e. SlGAME31 and SlGAME31-like3), while the two others are partial (i.e. SlGAME31-like1 and SlGAME31-like2).

The annotation as a dioxygenase provided the first indication of the GAME31 enzyme (SEQ ID NO: 18) as the putative enzyme responsible for hydroxylating α-tomatine to form hydroxytomatine.

Hydroxylated SGAs are also found in other *Solanum* species. In eggplant (*S. melongena*), α-solamargine is hydroxylated generating hydroxysolamargine. In cultivated potato (*S. tuberosum*), hydroxylated SGAs are found in minor amounts. However, in wild relatives, like *S. chacoense*, SGAs are accumulated in higher amounts. When hydroxylated, α-chaconine and α-solanine are converted into leptinine I and leptinine II, respectively. Furthermore, these two potato SGAs could be further acetylated into leptine I and leptine II, respectively.

In the tomato chromosomal region harboring GAME31, as described above and in FIGS. 30A-30C, three additional SlGAME31-like genes were found (Table 2).

TABLE 2

Sequence IDs for GAME31 and GAME31-like genes in *Solanum* spp.

| *Solanum* spp | Sequence ID** | | SEQ ID NO: |
|---|---|---|---|
| *S. lycopersycum* | SlGAME31 | Solyc02g062460 | 16 |
| | SlGAME31-like1 | Solyc02g062470 | 17 |
| | SlGAME31-like2 | Solyc02g062490 | 22 |
| | SlGAME31-like3 | Solyc02g062500 | 25 |
| *S. melongena* | SmGAME31 | Sme2.5_04260.1_g00001.1 | 28 |
| *S. tuberosum* | StGAME31 (CDS) | Sotub01g007080 | 30 |
| | StGAME31-like1 | Sotub01g007070 | 33 |
| | StGAME31-like2 | Sotub01g007090 | 36 |
| | StGAME31-like3 | Sotub01g007100 | 39 |
| | StGAME31-like4 | Sotub01g007110 | 42 |
| | StGAME31-like5 | Sotub01g007120 | 45 |

TABLE 2-continued

Sequence IDs for GAME31 and GAME31-like genes in *Solanum* spp.

| *Solanum* spp | Sequence ID** | SEQ ID NO: |
|---|---|---|
| StGAME31-like6 | Sotub01g007130 | 48 |
| StGAME31-like7 | Sotub01g007150 | 53 |

**Sol Genomics Network (for tomato and eggplant) and Spud DB (for potato) - (Fernandez-Pozo N, Menda N, Edwards JD, Saha S, Tecle IY, Strickler SR, Bombarely A, Fisher-York T, Pujar A, Foerster H, Yan A, Mueller LA. The Sol Genomics Network (SGN)-from genotype to phenotype to breeding. (2015) Nucleic Acids Res. Volume 43 (Database issue): D1036-41.)

The knowledge of hydroxylated SGAs in eggplant and potato, led to an investigation of the presence of GAME31-like homologous genes in these species. In eggplant, one gene sitting on chromosome 1 (named SmGAME31) was found which has 88% similarity to SlGAME31 (78% identity), while in potato a region in chromosome 1 containing seven GAME31-like genes was found, with the closest gene having 86% similarity (77% identity) (Table 2).

Example 14

Figure 31A:
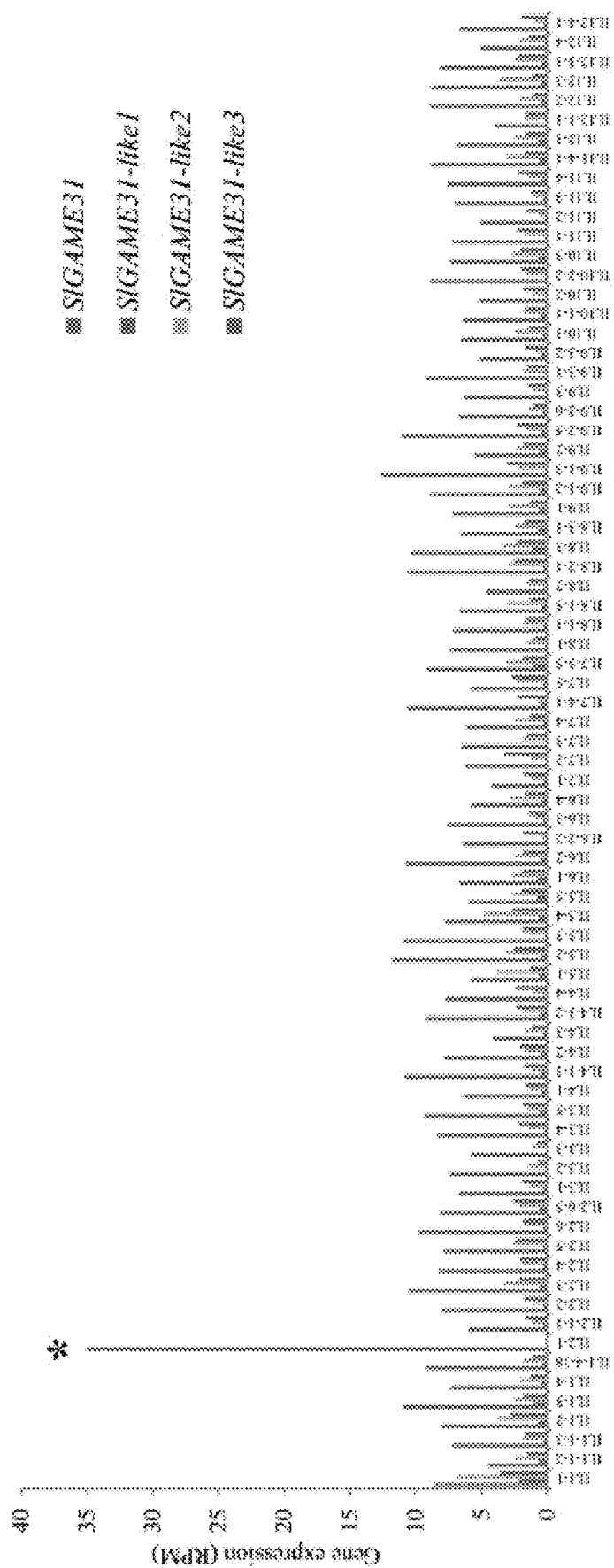
FIGS. 31A and 31B present graphs of SlGAME31 and SlGAME31-like gene expression.

Association of GAME31 with SGA Hydroxylation
Objective:
To examine the function of GAME31 enzyme.
Results:
The expression of genes found in the chromosome 2 region associated with higher hydroxytomatine and acetoxytomatine content in the BIL and IL lines was examined. RNA-Sequencing (RNA-Seq) gene expression data from vegetative apex, which had previously been reported for the IL population (Chitwood et al., (2013), A quantitative genetic basis for leaf morphology in a set of precisely defined tomato introgression lines. Plant Cell 25: 2465-2481), was used. By analyzing this dataset, expression of 12 out the 17 genes contained in the QTL region was detected. Excluding SlGAME31, all of the genes presented similar expression levels across the IL lines (<20 normalized Reads Per Million, RPM; data not shown). SlGAME31 showed 4.6-fold increased expression in IL2-1 (35 RPM) in comparison with the rest of the IL population (average 7.6 RPM) (FIG. 31A). SlGAME31-like1, SlGAME31-like2 and SlGAME31-like3 showed relatively low expression (<7 RPM) which appeared similar in all IL lines (FIG. 31A). The expression pattern of SlGAME31 in the ILs and increased accumulation of hydroxytomatine in IL2-1 (FIG. 27E) strongly suggested the role of this enzyme in hydroxylation of α-tomatine.

Figure 31B:
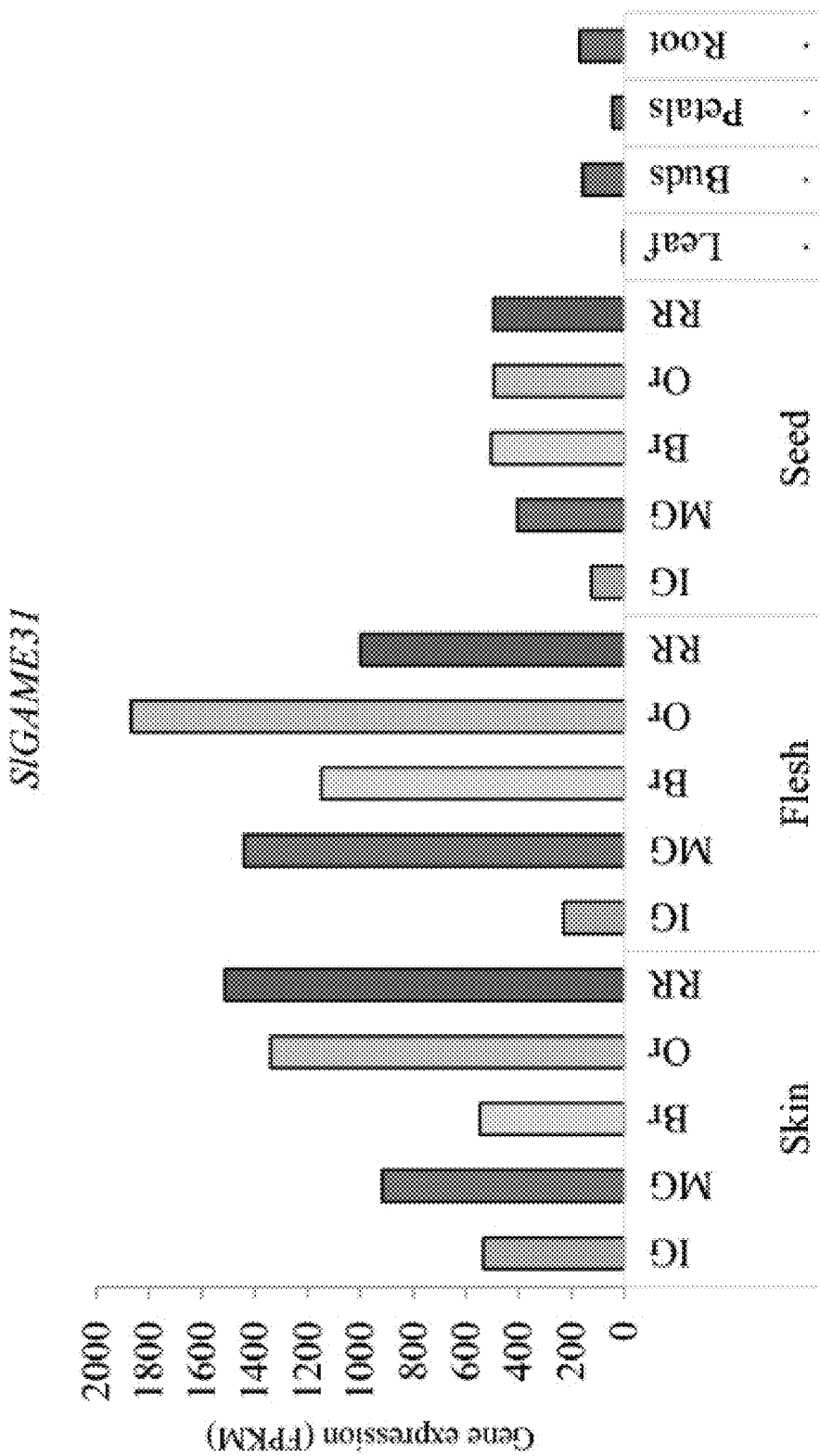

To provide additional evidence regarding the involvement of GAME31 in the hydroxylation of SGAs, the gene expression of GAME31 in RNA-Seq data covering various tissues and developmental stages of tomato (Cárdenas et al., (2016), ibid) was examined. It was found that SlGAME31 was highly expressed in fruit tissues among 19 different tomato tissues (FIG. 31B). In skin, flesh and seeds of tomato fruit the expression of GAME31 positively correlated with ripening, being less expressed in early immature stages of development. In other tissues, including leaf, flower buds, petals and roots S/GAME31 displayed lower expression levels. SlGAME31-like3 was found to be expressed at very low levels (<1.2 RPM), while SlGAME31-like1 and SlGAME31-like2 were not detected in this RNA-Seq dataset. The expression of SlGAME31 correlated with the previously reported accumulation of hydroxytomatine during tomato fruit ripening (Mintz-Oron et al., (2008) Gene expression and metabolism in tomato fruit surface tissues. Plant Physiol. 147: 823-851) supporting the hypothesis that SlGAME31 encodes an enzyme that potentially hydroxylates SGAs.

Example 15

Identification of SlGAME31 Homologs in Eggplant and Potato

Figures 32A, 32B:
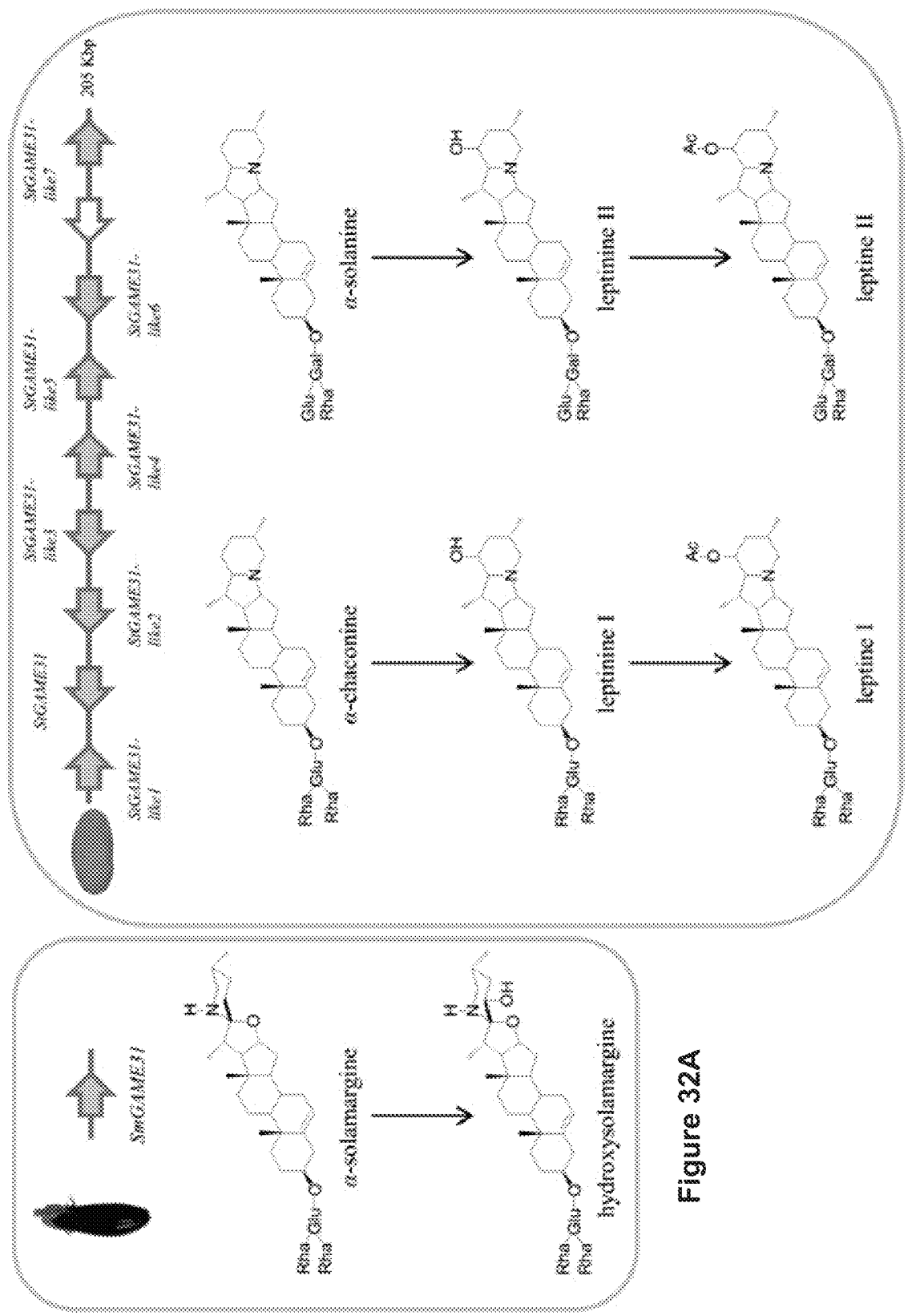
FIGS. 32A and 32B present the results of sequence searches for SlGAME31 homologs in eggplant and potato.

Objective:
To examine the genomes of other species of Solanaceae plants for homologs to SlGAME31 The knowledge of hydroxylated SGAs in other Solanaceae species like eggplant and potato led to the investigation of the presence of GAME31 homologous genes in these species.
Results:
Using sequence similarity searches in the Sol Genomics Network database, a single gene in eggplant (*Solanum melongena*) was identified located in chromosome 1 (SmGAME31; Sme2.5_04260.1_g00001.1) with 88% similarity (78% identity) at the protein level to SlGAME31 (FIGS. 32A-32B). In eggplant, SmGAME31 was predicted to catalyze the hydroxylation of α-solamargine to hydroxysolamargine.

In potato (*Solanum tuberosum*) a region was found in chromosome 1, spanning ~205 Kbp and containing eight GAME31 homologs. One of these (StGAME31) displayed 86% similarity (77% identity) to SlGAME31 at the protein sequence level (FIGS. 32A-32B). Out of the eight homologs, four represented full length 2-oxoglutarate-dependent dioxygenase coding sequences [StGAME31 (Sotub01g007080), StGAME31-like1 (Sotub01g007070), StGAME31-like4 (Sotub01g007110) and StGAME31-like6 (Sotub01g007130)] and four possessed only partial coding sequences [StGAME31-like2 (Sotub01g007090), StGAME31-like3 (Sotub01g007100), StGAME31-like5 (Sotub01g007120) and StGAME31-like7 (Sotub01g007150)]. In potato, StGAME31 is predicted to hydroxylate α-chaconine and α-solanine into leptinine I and II, respectively. These compounds are found in minor amounts in cultivated potatoes (Itkin et al., (2013), ibid); however, they are major relatively abundant in wild species like *Solanum chacoense*. Leptinine I and II can be further acetylated to produce leptine I and II, respectively (FIG. 32B).

Example 16

In Vitro Hydroxylation of SGAs by GAME31

Objective:
To examine the enzyme activity of GAME31 in vitro.
Results:
The in vitro function of the recombinant SlGAME31 produced in *Escherichia coli* was examined for hydroxylation activity with 8 SA/SGAs. From tomato α-tomatine and its aglycone tomatidine, dehydrotomatine were tested; from eggplant α-solamargine and its aglycone solasodine were tested; and in potato α-chaconine, α-solanine and its aglycone solanidine were tested.

Figure 33A:
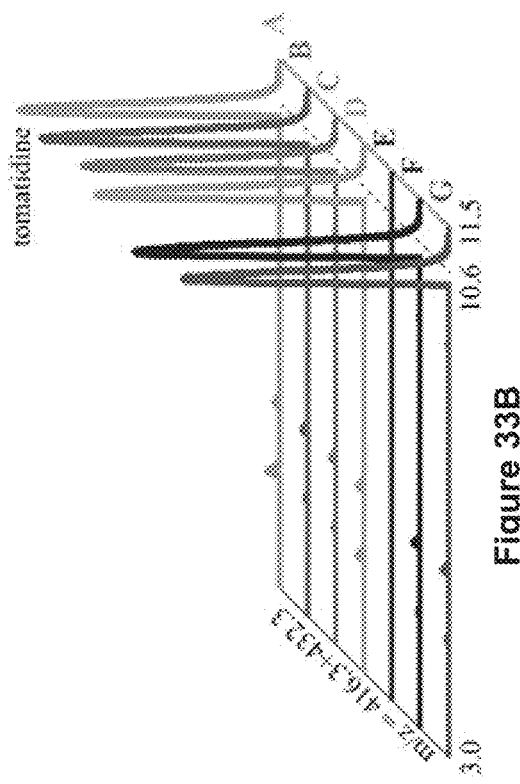
FIGS. 33A-33H shows the hydroxylation of SA/SGAs by recombinant SlGAME31. Enzymatic reactions were performed with SlGAME31 using multiple SA/SGA substrates: α-tomatine (FIG. 33A), tomatidine (FIG. 33B), dehydrotomatine (FIG. 33C), α-solamargine (FIG. 33D), solasodine (FIG. 33E), α-chaconine (FIG. 33F), α-solanine (FIG. 33G) and solanidine (FIG. 33H). The enzymatic reaction was carried out in multiple conditions (FIGS. 33A-33G-see box) and formation of hydroxy-derivatives was assessed by UPLC-qTOF-MS. For each compound its m/z and the m/z of its hydroxylated derivatives are shown. The x-axes show the retention time (RT).
Figure 33B:
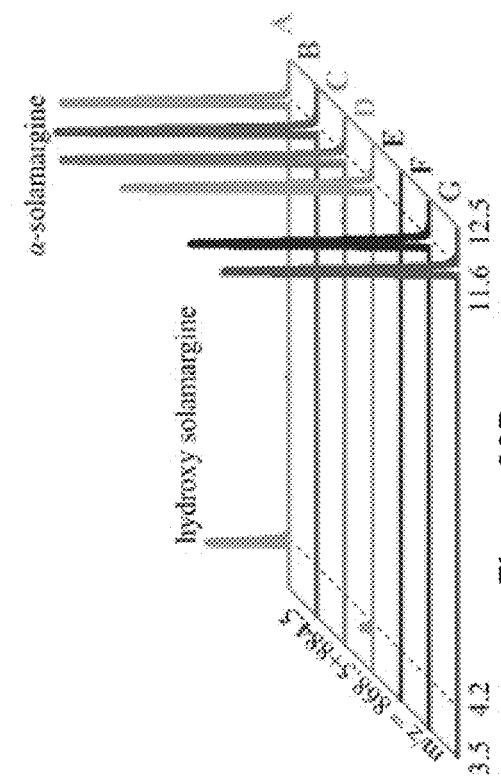
Figure 33C:
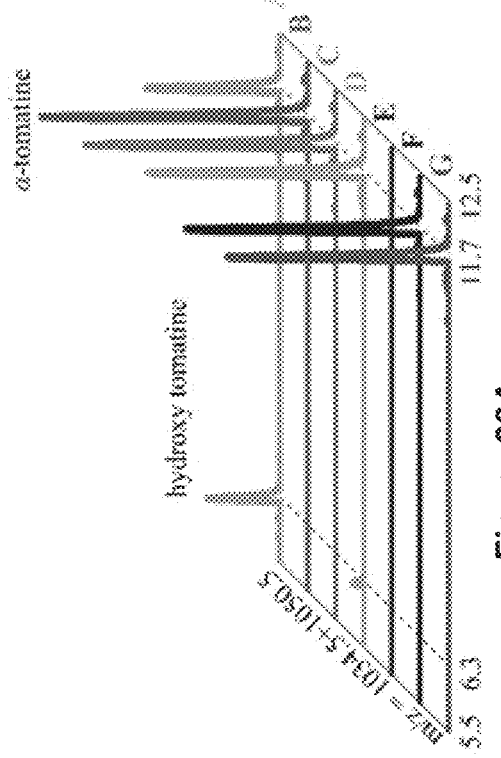
Figures 34A, 34B:
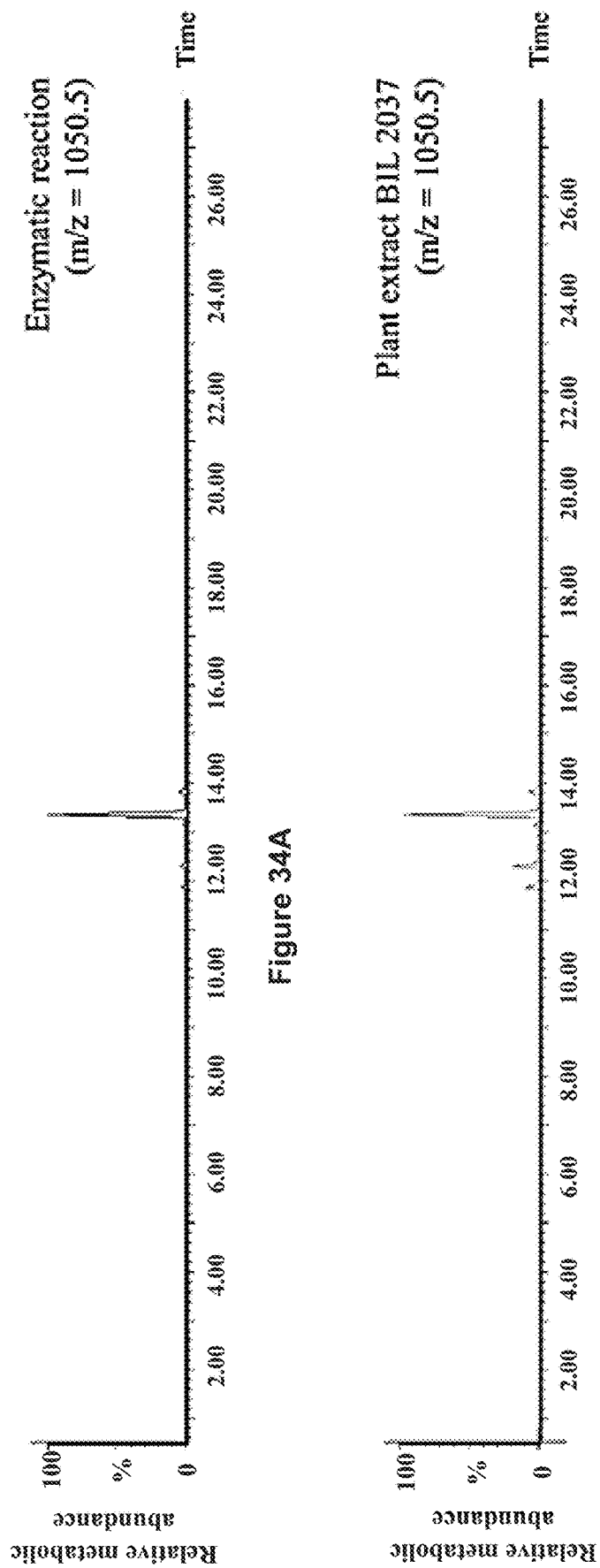
FIGS. 34A-34B show SlGAME31 in vitro enzyme activity. SlGAME31 expressed and purified from *E. coli* produced the same isomer (FIG. 34A) found in plants (FIG. 34B) (e.g. tomato line BIL 2037). The chromatogram shows the specific m/z=1050.5 for hydroxytomatine.

The recombinant SlGAME31 catalyzed the hydroxylation of α-tomatine forming hydroxytomatine (FIG. 33A) in the presence of the cofactors ketoglutaric and ascorbic acid. Removal of either cofactors resulted in lack of activity. Nevertheless, when the reaction was carried out in the absence of iron, minor amounts of hydroxytomatine were still generated. This is likely due to trace amounts of iron found in the reagents used; additionally previous reports have shown that the absence of iron had no effect in reactions catalyzed by a 2-oxoglutarate-dependent dioxygenase from *Catharanthus roseus* (De Carolis et al., (1990) Isolation and characterization of a 2-oxoglutarate dependent dioxygenase involved in the second-to-last step in vindoline biosynthesis. Plant Physiol. 94: 1323-1329). Interestingly, SlGAME31 generated the same hydroxytomatine isomer accumulating in the BIL lines containing the *S. pennellii* introgression on chromosome 2 (FIGS. 34A-34B). SlGAME31 did not show activity when the aglycone tomatidine was used as substrate, but it did perform hydroxylation of dehydrotomatine (FIGS. 33B-33C).

Figure 33D:
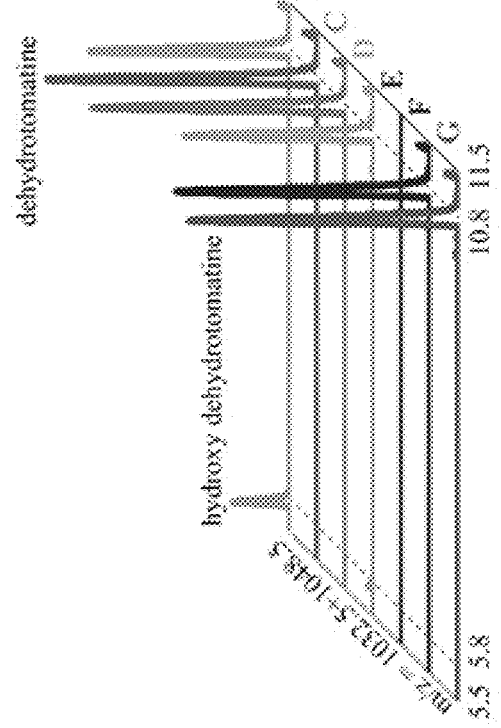
Figure 33E:
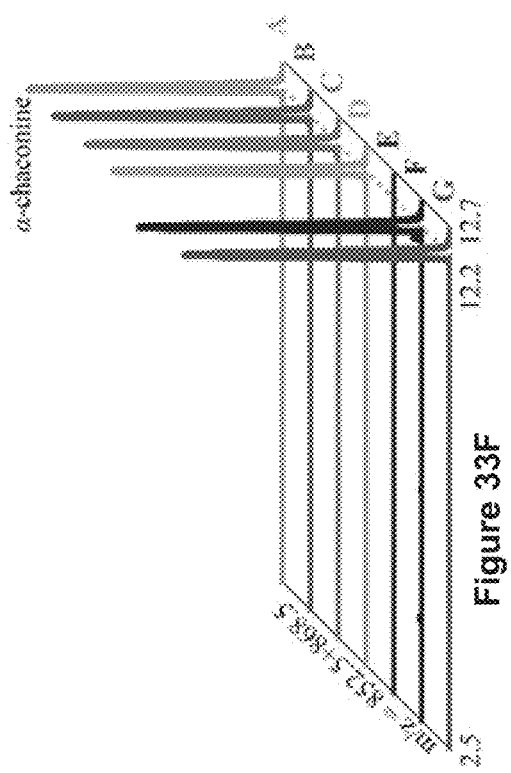
Figure 33F:
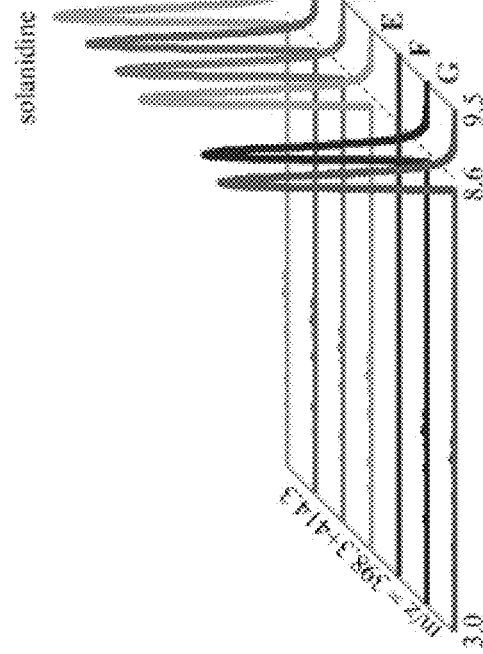
Figure 33G:
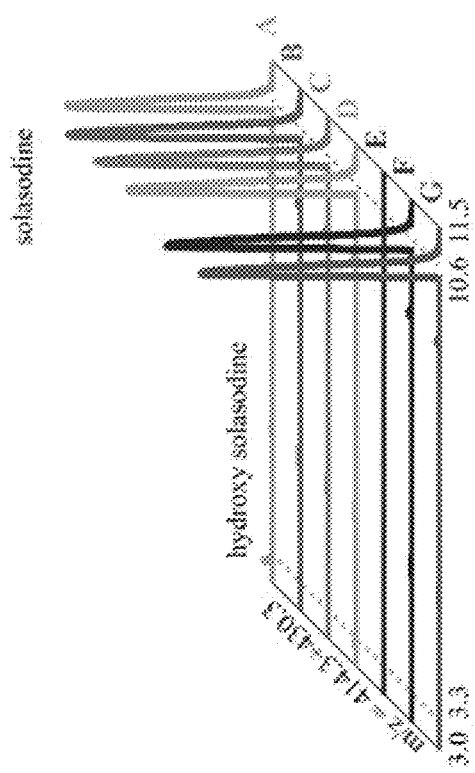
Figure 33H:
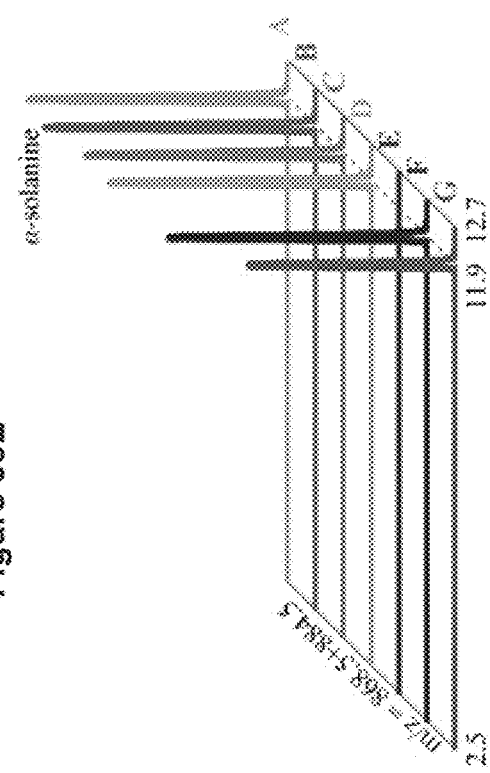

When SlGAME31 was tested with eggplant steroidal alkaloids, it hydroxylated α-solamargine generating hydroxysolamargine, and to a lesser extent the aglycone solasodine (FIGS. 33D and 33E). However, SlGAME31 did not hydroxylate any potato SA/SGA (FIGS. 33F-33H).

In the same way, enzymatic activity assays were performed using the recombinant enzyme cloned from eggplant, SmGAME31, and the same set of SA/SGAs used previously. Similar to the tomato enzyme, SmGAME31 performed hydroxylation of α-solamargine and to a lesser extent of solasodine, α-tomatine and dehydrotomatine (FIGS. 35A-35D). Conversely, SmGAME31 did not hydroxylate the aglycone tomatidine or potato SA/SGAs.

Conclusion:

The preference of both tomato and eggplant GAME31 for glycosylated substrates (see FIGS. 33A-33H and 35A-35D) indicates that these enzymes act preferably after glucosyltransferases have added the sugar moiety to the 3-OH position on the A ring of the SA aglycone.

Example 17

Altering SlGAME31 Expression Impacts SGA Profile in Tomato Fruit During Ripening Objective:

To characterized in more detail the role of GAME31 enzyme and observe the SGA profile in tomato fruit when GAME31 expression is altered.

Figure 36B:
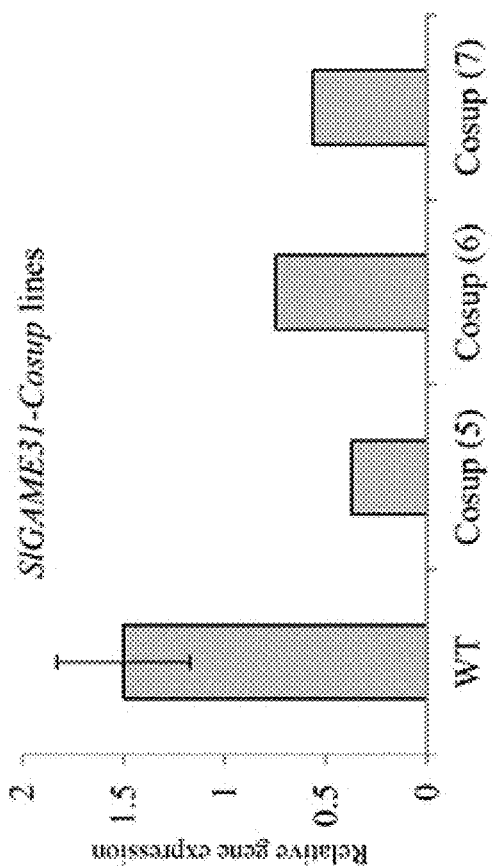
FIGS. 36A-36D present data showing SlGAME31 downregulation alters SGA profile in red ripe tomato fruit. The figures show SlGAME31 gene expression (qRT-PCR) in SlGAME31-RNAi (silencing) (FIG. 36A) and SlGAME31-Cosup (co-suppression) (FIG. 36B) tomato lines. WT: wild-type. Tomato independent $T_0$ primary transgenic plants, SlGAME31-RNAi (#17, #18, #19) and SlGAME31-Cosup (#5, #6, #7).
Figure 36A:
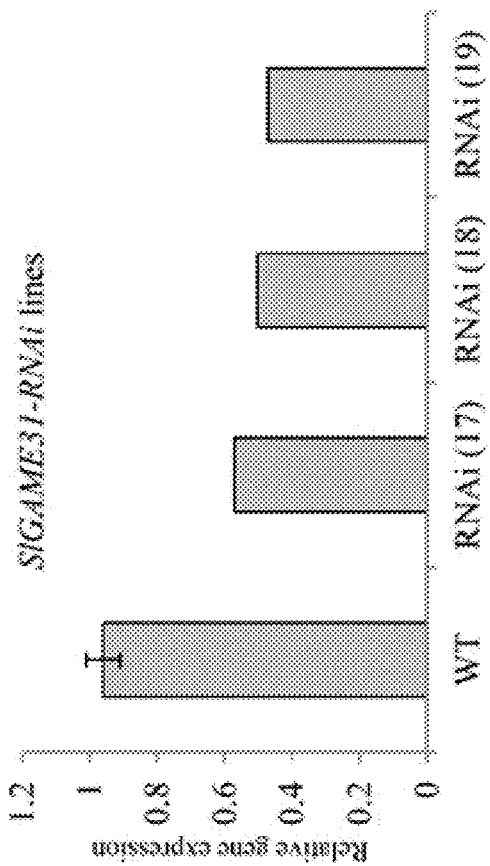

Results:

To further understand the role of SlGAME31 in hydroxylation of SGAs, transgenic tomato lines in which SlGAME31 was silenced by RNA interference (Sl-GAME31-RNAi) were generated. Also, lines constitutively expressing the tomato GAME31 were generated but these turned to be co-suppressed (SlGAME31-Cosup). Thus, although these plants were generated as plants having overexpression of GAME31, co-suppression is a post-transcriptional mechanism where both the transgene and the endogenous gene are silenced. Quantitative Real-Time PCR (qRT-PCR) analyses of independent $T_0$ primary transgenic plants showed that expression of SlGAME31 was reduced in SlGAME31-RNAi and strongly decreased in SlGAME31-Cosup tomato leaves, allowing selection of those lines for further metabolic analyses (FIG. 36A).

To further understand the role of SlGAME31 in hydroxylation of SGAs, transgenic tomato lines in which SlGAME31 was silenced by RNA interference (Sl-GAME31-RNAi) were generated. Also, lines constitutively expressing the tomato GAME31 were generated but these turned to be co-suppressed (SlGAME31-Cosup). Quantitative Real-Time PCR (qRT-PCR) analyses of independent $T_0$ primary transgenic plants showed that expression of SlGAME31 was reduced in SlGAME31-RNAi and strongly decreased in SlGAME31-Cosup tomato leaves, allowing selection of those lines for further metabolic analyses (FIG. 36A).

To further understand the role of SlGAME31 in hydroxylation of SGAs, transgenic tomato lines in which SlGAME31 was silenced by RNA interference (Sl-GAME31-RNAi) were generated. Also, lines constitutively expressing the tomato GAME31 were generated but these turned to be co-suppressed (SlGAME31-Cosup). Quantitative Real-Time PCR (qRT-PCR) analyses of independent $T_0$ primary transgenic plants showed that expression of SlGAME31 was reduced in SlGAME31-RNAi and strongly decreased in SlGAME31-Cosup tomato leaves, allowing selection of those lines for further metabolic analyses (FIG. 36B).

Figure 36C:
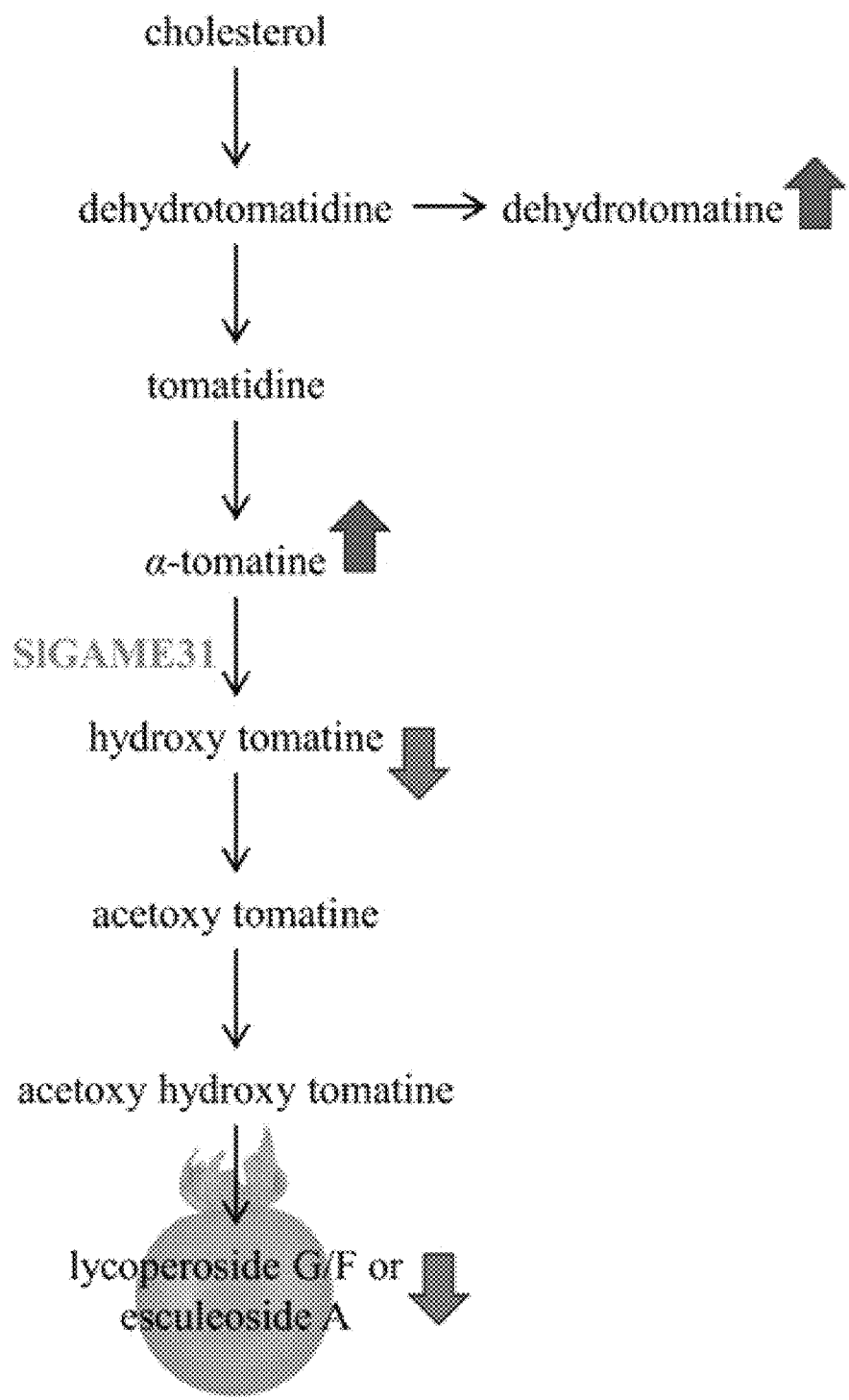
Figure 36D:
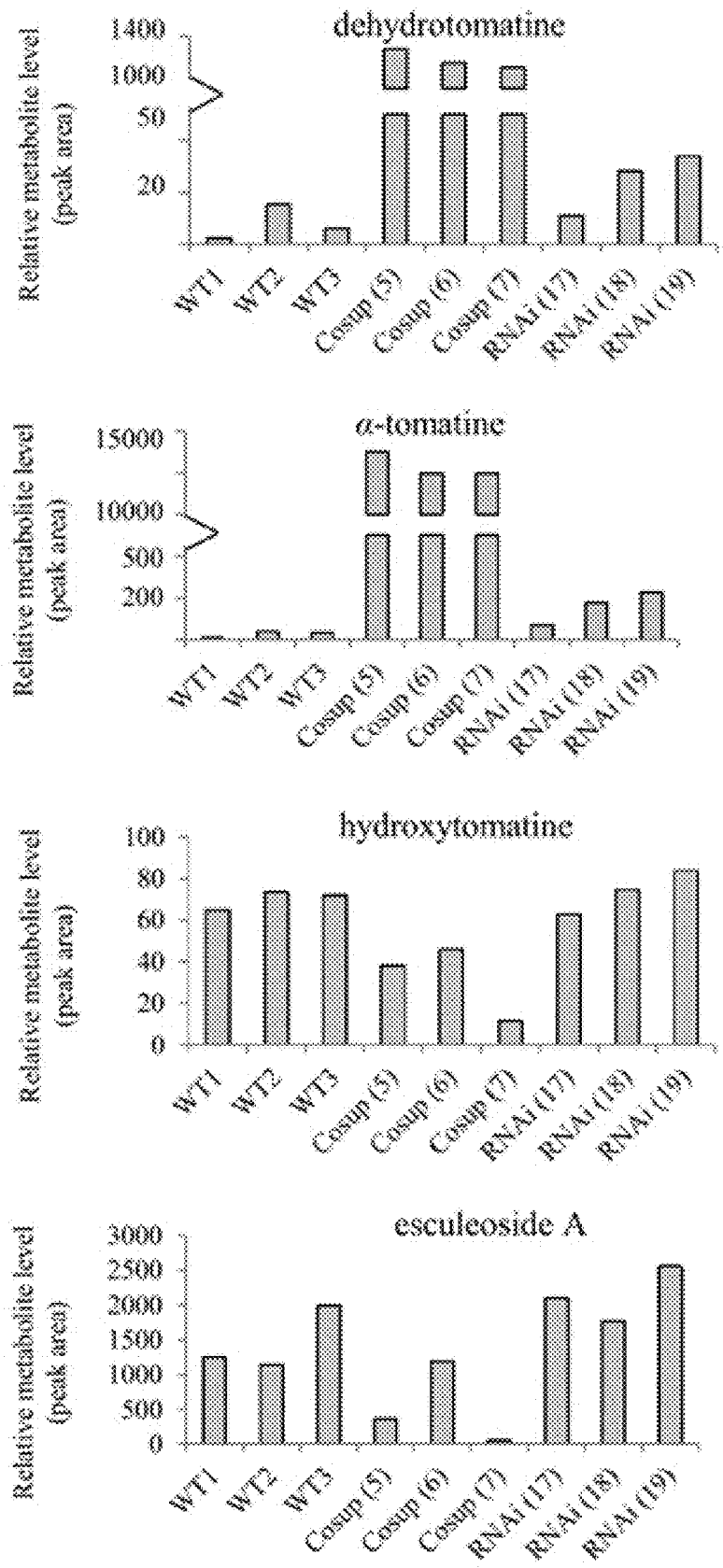

FIG. 36C presents a schematic representation of the SGA biosynthetic pathway and GAME31 role in it. SGA profiling was carried out on extracts of skin and flesh of red ripe tomato fruit of these lines by UPLC-qTOF-MS (FIG. 33D). In fruit of SlGAME31-RNAi lines, the levels of α-tomatine increased 2.6-8.4 fold as compared to wild-type (WT) plants, while in the SlGAME31-Cosup lines, where the silencing was stronger, α-tomatine increased more than 340-520 fold relative to WT plants. Similarly, dehydrotomatine increased 1.4-4.3 fold in SlGAME31-RNAi and 105-177 fold in SlGAME31-Cosup as compared with WT plants. On the other hand, hydroxytomatine and esculeoside A remained in similar levels in SlGAME31-RNAi and WT tomato fruit. However, in the co-suppression lines, SlGAME31-Cosup, a strong decrease in hydroxytomatine (1.8-6 fold, lines #7, #5) and esculeoside A (4-29 fold, lines #7, #5) was observed when compared to WT tomato fruit (FIG. 36D).

Conclusion:

Enzymatic activity assays using recombinant GAME31 and transgenic plants suppressing this gene, confirmed the role of SlGAME31 in hydroxylation of α-tomatine, the first step in the pathway leading to esculeoside A.

Summary for Examples 12-17

Examples 12-17 above describe the identification of a gene (GAME31) that encodes a 2-oxoglutarate-dependent dioxygenase (GAME31), where the dioxygenase activity hydroxylates α-tomatine in the first step leading to fruit-related SGAs (esculeosides and derivatives) in tomato. Recombinant tomato GAME31 enzyme produced in *E. coli* could catalyze the formation of the same hydroxytomatine isomer accumulating in tomato fruit. Additionally, homologs of GAME31 were identified in potato and eggplant, which are the putative genes responsible for the production of hydroxylated alkaloids in these species. Further, reduction of GAME31 expression resulted in altered SGA content in tomato fruit.

While certain features disclosed herein have been illustrated and described herein, many modifications, substitutions, changes, and equivalents will now occur to those of ordinary skill in the art. It is, therefore, to be understood that the appended claims are intended to cover all such modifications and changes as fall within the true spirit of the genetically modified plants and methods disclosed herein.

What is claimed is:

1. A genetically modified plant comprising an altered content of at least one cholesterol derived compound selected from a steroidal alkaloid or a glycosylated derivative thereof, said plant comprising at least one cell having a gene encoding a glycoalkaloid metabolism 31 (GAME31) polypeptide selected from a *Solanum* (*S.*) *lycopersicum* GAME31 (SlGAME31) polypeptide comprising the amino acid sequence set forth in SEQ ID NO: 18 and a *S. melongena* GAME31 (SmGAME31) polypeptide comprising the amino acid sequence as set forth in SEQ ID NO: 29;
wherein said GAME 31 comprises an enhanced expression, compared to GAME31 expression in a corresponding unmodified plant;
wherein the at least one cell of said genetically modified plant has an increased content of said at least one cholesterol derived compound compared to a corresponding unmodified plant;
and
wherein said plant is a cultivated tomato plant or an aubergine plant.

2. The genetically modified plant according to claim 1, wherein
said SlGAME31 polypeptide is encoded by the polynucleotide sequence set forth in SEQ ID NO: 16 or SEQ ID NO: 17, and said SmGAME31 polypeptide is encoded by the polynucleotide sequence set forth in SEQ ID NO: 28.

3. The genetically modified plant according to claim 1, wherein said at least one steroidal alkaloid or glycosylated derivative thereof is selected from the group consisting of hydroxytomatine, acetoxytomatine, and esculeoside A, or any derivatives thereof, or any combination thereof.

4. The genetically modified plant according to claim 1, wherein when said plant is a cultivated tomato plant, and said at least one steroidal alkaloid or glycosylated derivative thereof is selected from the group comprising esculeosides, lycoperoside, or any derivatives thereof, or any combination thereof, or
wherein when said plant is an aubergine plant, and said at least one steroidal alkaloid or glycosylated derivative thereof is selected from the group comprising soladulcidine, β-soladulcine, soladulcine A, or any derivatives thereof.

5. The genetically modified plant according to claim 1, wherein said at least one cell having altered expression, is selected from the group consisting of a leaf cell, a young leaf cell, a mature leaf cell, a bud cell, a petal cell, a flower cell, a stem cell, a shoot cell, a peel cell, a root cell, a green fruit cell, a breaker fruit cell, a red ripe fruit cell, a tuber cell, and a vegetable cell.

6. A method of enhancing the content of at least one cholesterol derived compound selected from a steroidal alkaloid or a glycosylated derivative thereof in a cultivated tomato plant or an aubergine plant, comprising
(a) transforming at least one plant cell within said plant with a nucleic acid sequence encoding glycoalkaloid metabolism 31 (GAME31), wherein said transforming results in overexpression of said GAME31; or
(b) transforming at least one plant cell with at least one polynucleotide sequence encoding a glycoalkaloid metabolism 31 (GAME31), wherein said at least one polynucleotide sequence comprises a mutation in a coding region or a regulatory region of the GAME31 gene;
wherein said GAME31 is selected from a *Solanum* (*S.*) *lycopersicum* GAME31 (SlGAME31) comprising an amino acid sequence as set forth in SEQ ID NO: 18 and a *S. melongena* GAME31 (SmGAME31) comprising an amino acid sequence as set forth in SEQ ID NO: 29,
thereby producing a cultivated tomato plant or an aubergine plant with an enhanced content of said at least one cholesterol derived compound compared to a corresponding non-transformed plant;

wherein said at least one steroidal alkaloid or a glycosylated derivative thereof comprises a hydroxytomatine, acetoxytomatine, soladulcidine, β-soladulcine, soladulcine A, a leptin, or a leptinine.

7. The method of claim 6, wherein said nucleic acid sequence encoding SlGAME31 comprises the polynucleotide sequence set forth in SEQ ID NO: 16 or SEQ ID NO: 17, and said nucleic acid sequence encoding SlGAME31 comprises the polynucleotide sequence set forth in SEQ ID NO: 28.

8. The method according to claim 6, wherein said at least one cell is selected from the group consisting of a leaf cell, a young leaf cell, a mature leaf cell, a bud cell, a petal cell, a flower cell, a stem cell, a shoot cell, a peel cell, a root cell, a green fruit cell, a breaker fruit cell, a red ripe fruit cell, a tuber cell, and a vegetable cell.

9. The genetically modified plant of claim 1, wherein said modification in said plant comprises transforming the at least one plant cell with a nucleic acid encoding said GAME31.

\* \* \* \* \*